(12) United States Patent
Dubensky, Jr. et al.

(10) Patent No.: US 7,842,289 B2
(45) Date of Patent: Nov. 30, 2010

(54) RECOMBINANT NUCLEIC ACID MOLECULES, EXPRESSION CASSETTES, AND BACTERIA, AND METHODS OF USE THEREOF

(75) Inventors: Thomas W. Dubensky, Jr., Piedmont, CA (US); Daniel A. Portnoy, Albany, CA (US); William S. Luckett, Jr., Richmond, CA (US); David N. Cook, Lafayette, CA (US)

(73) Assignee: Aduro BioTech, Berkeley, CA (US)

( * ) Notice: Subject to any disclaimer, the term of this patent is extended or adjusted under 35 U.S.C. 154(b) by 1331 days.

(21) Appl. No.: 11/021,441

(22) Filed: Dec. 23, 2004

(65) Prior Publication Data

US 2005/0249748 A1    Nov. 10, 2005

Related U.S. Application Data

(63) Continuation-in-part of application No. PCT/US2004/23881, filed on Jul. 23, 2004, and a continuation-in-part of application No. 10/883,599, filed on Jun. 30, 2004, now Pat. No. 7,695,725, and a continuation-in-part of application No. 10/773,618, filed on Feb. 6, 2004, and a continuation-in-part of application No. 10/773,792, filed on Feb. 6, 2004, now Pat. No. 7,691,393.

(60) Provisional application No. 60/616,750, filed on Oct. 6, 2004, provisional application No. 60/615,287, filed on Oct. 1, 2004, provisional application No. 60/599,377, filed on Aug. 5, 2004, provisional application No. 60/556,744, filed on Mar. 26, 2004, provisional application No. 60/541,515, filed on Feb. 2, 2004, provisional application No. 60/532,598, filed on Dec. 24, 2003.

(51) Int. Cl.
*A61K 48/00* (2006.01)
*A61K 39/29* (2006.01)
*A61K 39/00* (2006.01)
*C12N 1/20* (2006.01)
*C12N 15/00* (2006.01)
*C07H 21/04* (2006.01)
*C07H 21/02* (2006.01)

(52) U.S. Cl. .................... 424/93.2; 424/93.1; 424/93.4; 424/234.1; 424/235.1; 424/184.1; 424/225.1; 424/277.1; 435/252.1; 435/252.3; 435/320.1; 435/440; 435/441; 435/443; 536/23.1; 536/23.4; 536/23.7

(58) Field of Classification Search ................. None
See application file for complete search history.

(56) References Cited

U.S. PATENT DOCUMENTS

| 4,546,771 | A | 10/1985 | Eggleton et al. |
|---|---|---|---|
| 5,171,568 | A | 12/1992 | Burke et al. |
| 5,180,819 | A | 1/1993 | Cayre |
| 5,192,549 | A | 3/1993 | Barenolz et al. |
| 5,488,954 | A | 2/1996 | Sleva et al. |
| 5,504,005 | A | 4/1996 | Bloom et al. |
| 5,547,871 | A * | 8/1996 | Black et al. .................. 435/348 |
| 5,643,599 | A | 7/1997 | Lee et al. |
| 5,655,537 | A | 8/1997 | Crowley |
| 5,830,702 | A | 11/1998 | Portnoy et al. |
| 5,844,140 | A | 12/1998 | Seale |
| 5,871,900 | A * | 2/1999 | Wollowitz et al. .............. 435/2 |
| 5,879,305 | A | 3/1999 | Yock et al. |
| 5,921,931 | A | 7/1999 | O'Donnell et al. |
| 6,004,815 | A | 12/1999 | Portnoy et al. |
| 6,051,237 | A | 4/2000 | Paterson |
| 6,093,725 | A | 7/2000 | Cook et al. |
| 6,099,848 | A | 8/2000 | Frankel et al. |
| 6,143,490 | A | 11/2000 | Cook et al. |
| 6,143,551 | A | 11/2000 | Goebel |
| 6,153,430 | A | 11/2000 | Pastan et al. |
| 6,171,777 | B1 | 1/2001 | Cook et al. |
| 6,177,441 | B1 | 1/2001 | Cook et al. |

(Continued)

FOREIGN PATENT DOCUMENTS

EP    0 790 835 B1    8/2004

(Continued)

OTHER PUBLICATIONS

Fuglsang, Anders (Protein Expression and Purification vol. 31, Oct. 2003 247-249).*

(Continued)

*Primary Examiner*—Robert Mondesi
*Assistant Examiner*—Oluwatosin Ogunbiyi
(74) *Attorney, Agent, or Firm*—Michael A. Whittaker; Biotechnology Law Group

(57) ABSTRACT

The present invention provides recombinant nucleic acid molecules, expression cassettes, and vectors useful for expression of polypeptides, including heterologous polypeptides, such as antigens, in bacteria. Some of the recombinant nucleic acid molecules, expression cassettes and vectors comprise codon-optimized sequences encoding the polypeptides and/or signal peptides. Some of the recombinant nucleic acid molecules, expression cassettes, and expression vectors comprise sequences encoding non-Listerial and/or non-secA1 signal peptides for secretion of the polypeptides. The invention also provides bacteria comprising the nucleic acid molecules, expression cassettes, and expression vectors, as well as compositions such as vaccines comprising the bacteria. Methods of making and using the bacteria, recombinant nucleic acid molecules, and expression cassettes are also provided.

36 Claims, 71 Drawing Sheets

U.S. PATENT DOCUMENTS

| | | |
|---|---|---|
| 6,270,776 B1 | 8/2001 | Bloom et al. |
| 6,270,952 B1 | 8/2001 | Cook et al. |
| 6,287,556 B1 | 9/2001 | Portnoy et al. |
| 6,403,080 B1 | 6/2002 | Segal |
| 6,410,219 B1 | 6/2002 | Cook et al. |
| 6,440,735 B1 | 8/2002 | Gaeta |
| 6,497,876 B1 | 12/2002 | Maraskovsky et al. |
| 6,514,987 B1 | 2/2003 | Cook et al. |
| 6,565,852 B1 | 5/2003 | Paterson |
| 6,566,121 B1 | 5/2003 | Jacobs, Jr. et al. |
| 6,599,502 B2 | 7/2003 | Portnoy et al. |
| 6,679,845 B2 | 1/2004 | Ritter et al. |
| 6,709,810 B2 | 3/2004 | Cook et al. |
| 6,767,542 B2 | 7/2004 | Paterson et al. |
| 6,855,320 B2 | 2/2005 | Paterson |
| 2001/0023072 A1 | 9/2001 | Crawford et al. |
| 2002/0025323 A1 | 2/2002 | Paterson et al. |
| 2002/0028206 A1 | 3/2002 | Paterson |
| 2002/0028432 A1 | 3/2002 | Cook et al. |
| 2002/0039588 A1 | 4/2002 | Collier et al. |
| 2002/0045587 A1 | 4/2002 | Goebel |
| 2002/0136738 A1 | 9/2002 | Agrewala et al. |
| 2002/0141977 A1 | 10/2002 | Collins et al. |
| 2002/0142007 A1 | 10/2002 | Portnoy et al. |
| 2002/0150588 A1 | 10/2002 | Allison et al. |
| 2002/0155108 A1 | 10/2002 | Barbera-Guillem |
| 2002/0182581 A1 | 12/2002 | Cook et al. |
| 2002/0192193 A1 | 12/2002 | Chokri et al. |
| 2003/0077263 A1 | 4/2003 | Maraskovsky et al. |
| 2003/0092177 A1 | 5/2003 | Belardelli et al. |
| 2003/0119187 A1 | 6/2003 | De Santis |
| 2003/0166139 A1* | 9/2003 | Choi et al. ............... 435/69.1 |
| 2003/0190682 A1 | 10/2003 | Law et al. |
| 2003/0202985 A1 | 10/2003 | Paterson |
| 2003/0203472 A1 | 10/2003 | Portnoy et al. |
| 2004/0009194 A1 | 1/2004 | Andrieu et al. |
| 2004/0013690 A1 | 1/2004 | Portnoy et al. |
| 2004/0022761 A1 | 2/2004 | Banchereau et al. |
| 2004/0029897 A1 | 2/2004 | Cook et al. |
| 2004/0037807 A1 | 2/2004 | Goldman |
| 2004/0038398 A1 | 2/2004 | Crawford et al. |
| 2004/0115221 A1 | 6/2004 | Portnoy et al. |
| 2004/0180321 A1 | 9/2004 | Cook et al. |
| 2004/0197343 A1 | 10/2004 | Dubensky et al. |
| 2004/0228877 A1 | 11/2004 | Dubensky et al. |
| 2005/0118184 A1 | 6/2005 | Paterson et al. |
| 2005/0129715 A1 | 6/2005 | Paterson et al. |
| 2005/0175625 A1 | 8/2005 | Jaffee et al. |
| 2005/0281783 A1 | 12/2005 | Kinch et al. |

FOREIGN PATENT DOCUMENTS

| | | | |
|---|---|---|---|
| FR | | 2 686 896 A1 | 8/1993 |
| WO | WO-89/04669 A1 | | 6/1989 |
| WO | WO-90/11089 A1 | | 10/1990 |
| WO | WO-90/14436 A1 | | 11/1990 |
| WO | WO-93/15212 A1 | | 8/1993 |
| WO | WO-96/14087 A1 | | 5/1996 |
| WO | WO-97/22349 A1 | | 6/1997 |
| WO | WO-98/30545 A1 | | 7/1998 |
| WO | WO-98/33386 A1 | | 8/1998 |
| WO | WO-99/25376 A1 | | 5/1999 |
| WO | WO-99/29884 A2 | | 6/1999 |
| WO | WO-99/47646 A1 | | 9/1999 |
| WO | WO-00/09156 A1 | | 2/2000 |
| WO | WO-01/27295 A1 | | 4/2001 |
| WO | WO-01/72329 A1 | | 10/2001 |
| WO | WO 01/77358 A2 | | 10/2001 |
| WO | WO-01/77358 A3 | | 10/2001 |
| WO | WO-02/33109 A2 | | 4/2002 |
| WO | WO-02/33109 A3 | | 4/2002 |
| WO | WO-02/40046 A1 | | 5/2002 |
| WO | WO-02/083879 A2 | | 10/2002 |
| WO | WO-02/083879 A3 | | 10/2002 |
| WO | WO-03/065787 A2 | | 8/2003 |
| WO | WO-03/065787 A3 | | 8/2003 |
| WO | WO-03/065787 C1 | | 8/2003 |
| WO | WO-03/083056 A2 | | 10/2003 |
| WO | WO-03/083056 A3 | | 10/2003 |
| WO | WO-03/092600 A2 | | 11/2003 |
| WO | WO-03/092600 A3 | | 11/2003 |
| WO | WO-03/102168 A1 | | 12/2003 |
| WO | WO-2004/006837 A2 | | 1/2004 |
| WO | WO-2004/011492 A1 | | 2/2004 |
| WO | WO-2004/062597 A2 | | 7/2004 |
| WO | WO-2004/062597 A3 | | 7/2004 |
| WO | WO-2004/084936 A2 | | 10/2004 |
| WO | WO-2004/110481 A2 | | 12/2004 |
| WO | WO-2005/009463 A2 | | 2/2005 |
| WO | WO-2005/009463 A3 | | 2/2005 |
| WO | WO-2005/037233 A2 | | 4/2005 |
| WO | WO-2005-037233 A3 | | 4/2005 |
| WO | WO-2005/067460 A1 | | 7/2005 |
| WO | WO-2005/071088 A2 | | 8/2005 |
| WO | WO-2005/071088 A3 | | 8/2005 |
| WO | WO-2005/092372 A2 | | 10/2005 |
| WO | WO-2006/045110 A2 | | 4/2006 |

OTHER PUBLICATIONS

Nakamura et al (Nucleic Acids Research, 2000, vol. 28 p. 292 and supplemental material pp. 1-2).*

Ellis, R.W. (Chapter 29 of "Vaccines" [Plotkin, S.A. et al. (eds) published by W. B. Saunders company (Philadelphia) 1988.*

Koff et al (International Journal for Parasitology 33 (2003) 517-523, see section under hepatitis C virus vaccine.*

Definition of Vaccine: The Dictionary of Immunology, Herbert et al eds, Academic Press, 1995.*

Riggs, Paul (Current Protocols in Molecular Biology, 1994, 16.6.1-16.6.14).*

Hehl et al. Infection and Immunity, Dec. 2000, p. 7078-7086.*

Aggarwal, A. et al. (Oct. 1990). "Oral Salmonella: Malaria Circumsporozoite Recombinants Induce Specific CD8+ Cytotoxic T Cells," *J. Exp. Med.* 172:1083-1090.

Anderson, R.J. et al. (Apr. 28, 2000). "∆guaBA Attenuated *Shigella flexneri* 2a Strain CVD 1204 as a *Shigella* Vaccine and as a Live Mucosal Delivery System for Fragment C of Tetanus Toxin," *Vaccine* 18(21):2193-2202.

Angelakopolous, H. et al. (Jul. 2002). "Safety and Shedding of an Attenuated Strain of *Listeria monocytogenes* with a Deletion of actA/plcB in Adult Volunteers: A Dose Escalation Study of Oral Inoculation," *Infection and Immunity* 70(7):3592-3601.

Anonymous. (Feb. 4, 2003). "Cerus Corporation Starts Vaccine Trial for Epstein-Barr Virus," *Press Release, Cerus Corporation*, located at <http://www.cerus.com/pages/PR/2003/PRO20403.html> last visited on Nov. 8, 2004, two pages.

Anonymous. (Mar. 29, 2004). "MedImmune and Cerus to Present Data on Novel Vaccine Technology's Potential to Help Treat and Prevent Cancers," *Cerus Corporation Press Release*, located at <http://www/cerus.com/index.cfm/News/Press_Release_Archive?Year=2006&NID=25...>, last visited Apr. 28, 2006, three pages.

Anonymous. (Apr. 21, 2004). "MedImmune and Cerus Enter Agreement to Co-Develop Therapeutic Vaccine for Cancer," *Cerus Corporation Press Release*, located at <http://www/cerus.com/index.cfm/News/Press_Release_Archive?Year=2006&NID=24...>, last visited Apr. 28, 2006, three pages.

Anonymous. (Mar. 2005). "Recombinant *Listeria monocytogenes*-Based Immunotherapy Targeting the Receptor Tyrosine Kinase EphA2," presented at *American Association for Cancer Research (AACR), 95th Annual Meeting*, Mar. 27-31, 2004, as posted on <http://www.cerus.com/index.cfm/abstracts/2004/RecombinantListeriamonocytogenesBasedImmunotherapyTarg...>, last visited on Apr. 28, 2006, one page.

Antelmann, H. et al. (Sep. 2001). "A Proteomic View on Genome-Based Signal Peptide Predictions," *Genome Res.* 11(9):1484-1502.

Appelberg, R. et al. (Feb. 2000). "Mutants of *Listeria monocytogenes* Defective in In Vitro Invasion and Cell-to-Cell Spreading Still Invade and Proliferate in Hepatocytes of Neutropenic Mice," *Infection and Immunity* 68(2):912-914.

Argani, P. et al. (Dec. 2001). "Mesothelin Is Overexpressed in the Vast Majority of Ductal Adenocarcinomas of the Pancreas: Indentification of a New Pancreatic Cancer Marker by Serial Analysis of Gene Expression (SAGE),"*Clin. Cancer Res.* 7:3862-3868.

Auerbuch, V. et al. (Sep. 2001). "Development of a Competitive Index Assay to Evaluate the Virulence of *Listeria monocytogenes actA* Mutants during Primary and Secondary Infection of Mice," *Infection and Immunity* 69(9):5953-5957.

Auerbuch, V. et al. (Aug. 16, 2004). "Mice Lacking the Type I Interferon Receptor are Resistant to *Listeria monocytogenes,*" *Journal of Experimental Medicine* 200(4):527-533.

Badovinac, V.P. et al. (2000). "Adaptive Immunity and Enhanced CD8+ T Cell Response to *Listeria monocytogenes* in the Absence of Perforin and IFN-γ," *J. Immunol.* 164:6444-6452.

Baer, R. et al. (Jul. 19, 1984). "DNA Sequence and Expression of the B95-8 Epstein-Barr Virus Genome," *Nature* 310:207-211.

Bakardjiev, A. et al. (Jan. 2004). "Listeriosis in the Pregnant Guinea Pig: A Model of Vertical Transmission," *Infection and Immunity* 72(1):489-497.

Bao, L. et al. (Apr. 2003). "Virulence, Immunogenicity, and Protective Efficacy of Two Recombinant *Mycobacterium bovis* Bacillus Calmette-Guérin Strains Expressing the Antigen ESAT-6 from *Mycobacterium tuberculosis,*" *Infect. Immuno.* 71(4):1656-1661.

Barry, R.A. et al. (Apr. 1992). "Pathogenicity and Immunogenicity of *Listeria monocytogenes* Small-Plaque Mutants Defective for Intracellular Growth and Cell-to-Cell Spread," *Infection and Immunity* 60(4):1625-1632.

Bendtsen, J.D. et al. (Jul. 16, 2004). "Improved Prediction of Signal Peptides: SignalP 3.0," *J. Mol. Biol.* 340(4):783-795.

Bensing, B.A. et al. (May 2002). "An Accessory *sec* locus of *Streptococcus gordonii* is Required for Export of the Surface Protein GspB and for Normal Levels of Binding to Human Platelets," *Mol. Microbiology* 44(4):1081-1094.

Bergmann, B. et al. (Feb. 2002). "InIA- but not InIB-mediated Internalization of *Listeria monocytogenes* by Non-Phagocytic Mammalian Cells Needs the Support of Other Internalins," *Molecular Microbiology* 43(3):557-570.

Berks, B.C. et al. (2000). "The Tat Protein Export Pathway," *Mol. Microbiology* 35(2):260-274.

Berks, B.C. et al. (2000). "The Tat Protein Translocation Pathway and its Role in Microbial Physiology," In *Advances in Microbial Physiology*, Poole, R.K. ed., Academic Press, Inc. 47:187-254.

Bhasin, M. et al. (Mar. 22, 2003). "MHCBN: A Comprehensive Database of MHC Binding and Non-Binding Peptides,"*Bioinformatics* 19(5):665-666.

Bhasin, M. et al. (Aug. 13, 2004). "Prediction of CTL Epitopes Using QM, SVM and ANN Techniques," *Vaccine* 22:3195-3204.

Bielecki, J. et al. (May 10, 1990). "*Bacillus subtilis* Expressing a Haemolysin Gene from *Listeria monocytogenes* Can Grow in Mammalian Cells," *Nature* 345(6271):175-176.

Bierne, H. et al. (Sep. 2002). "InIB, A Surface Protein of *Listeria monocytogenes* that Behaves as an Invasin and a Growth Factor," *Journal of Cell Science* 115:3357-3367.

Biet, F. et al. (May 2003). "Immune Response Induced by Recombinant *Mycobacterium bovis* BCG Producing the Cholera Toxin B Subunit," *Infect. Immun.* 71(5):2933-2937.

Bishop, D.K. et al. (Sep. 15, 1987). "Adoptive Transfer of Immunity to *Listeria monocytogenes*: The Influence of In Vitro Stimulation on Lymphocyte Subset Requirements," *J. Immunol.* 139(6):2005-2009.

Biswas, I. et al. (Jun. 1993). "High-Efficiency Gene Inactivation and Replacement System for Gram-Positive Bacteria," *J. Bacteriol.* 175(11):3628-3635.

Black, C.G. et al. (Feb. 16, 1998). "Absence of an SOS-like System in *Neisseria gonorrhoeae,*" *Gene* 208:61-66.

Bouwer, H.G.A. et al. (Apr. 14, 2003). "Recombinant *L. monocytogenes* as a Vaccine for Stimulation of Anti-Tumor Responses," (Abstract for the 90th Anniversary Meeting of the American Association of Immunologists, Denver, Co, May 6-10, 2003) *FASEB Journal*, 17(7):C330-331, Abstract 162.17.

Bouwer, H.G.A. et al. (May 6, 2003). "Recombinant *L. monocytogenes* as a Vaccine for Stimulation of Anti-Tumor Responses," Poster, *presented at the American Association of Immunologists 90th Anniversary Meeting*, Denver, CO, May 6-10, 2003. one page.

Braun, L. et al. (Oct. 1999). "The 213-amino-acid Leucine-rich Repeat Region of the *Listeria monocytogenes* InIB Protein is Sufficient for Entry into Mammalian Cells, Stimulation of PI 3-Kinase and Membrane Ruffling," *Molecular Microbiology* 34(1)10-23.

Braunstein, M. et al. (Dec. 2001). "Two Nonredundant SecA Homologues Function in Mycobacteria," *J. Bacteriology* 183(24):6979-6990.

Braunstein, M. et al. (Apr. 2003). "SecA2 Functions in the Secretion of Superoxide Dismutase A and in the Virulence of *Mycobacterium tuberculosis,*" *Mol. Microbiology* 48(2):453-64.

Brinkmann, U. et al. (Apr. 1, 1999). "Novel Genes in the PAGE and GAGE Family of Tumor Antigens Found by Homoly Walking in the dbEST Database," *Cancer Research* 59:1445-1448.

Brockstedt, D. et al. (Feb. 19, 2003). "Recombinant Attenuated *Listeria Monocytogenes* Elicits Striking Antigen-Specific CD8+ T-Cell Responses that Correlate with Prolonged Survival in a Murine Transplant Model of Melanoma," *presented at Keystone Symposia Meeting*, Keystone, CO, Feb. 17-23, 2003, one page.

Brockstedt, D. et al. (Mar. 2003). "Recombinant Attenuated *Listeria monocytogenes* Elicits Robust Cellular Immune Response to Tumor-Associated Antigen in *Listeria Immune* Mice," *Proceedings of the American Association for Cancer Research, 94th Annual Meeting*, Apr. 5-9, 2003, Toronto, Ontario, Canada, 44:194, Abstract No. 851, one page.

Brockstedt, D. et al. (Jul. 2003). "Recombinant Attenuated *Listeria monocytogenes* Elicits Robust Cellular Immune Response to Tumor-Associated Antigen in *Listeria Immune* Mice," (Abstract for the 94th Annual Meeting of the American Association for Cancer Research, Washington DC, USA, Jul. 11-14, 2003) *Proceedings of the American Association for Cancer Research Annual Meeting* 44(2):168, Abstract No. 851.

Brockstedt, D. et al. (Oct. 3, 2003). "Novel Strategies to Develop *Listeria monocytogenes* Vaccine Strains for Cancer Immunotherapy Applications," Poster, presented at *Cancer Vaccines 2003*, Oct. 1-3, 2003, one page.

Brockstedt, D. et al. (Mar. 2004). "The Living Dead: Psoralen-killed Metabolically Active *Listeria* DNA Repair Mutant-based Vaccines Induce Therapeutic Anti-tumor Efficacy Targeted Against an Endogenous Antigen," abstract *presented at the American Association for Cancer Research (AACR)*, Mar. 27-31, 2004, as posted on <http://www.cerus.com/pages/solution/abs156.html>, last visited on Aug. 26, 2004, two pages.

Brockstedt, D. et al. (Jul. 2004). "The Living Dead: Psoralen-killed Metabolically Active *Listeria* DNA Repair Mutant-based Vaccines Induce Therapeutic Anti-tumor Efficacy Targeted Against an Endogenous Antigen," abstract *presented at the Gordon Research Conference on Microbial Toxins and Pathogenicity*, Jul. 18-23, 2004, Andover, NH, as posted on <http://www.cerus.com/pages/solution/04_GordonResearchConf_Brockstedt.html>, last visited on Aug. 26, 2004, two pages.

Brockstedt, D.G. (Date Unknown). "Listeria-CEA Vaccine-Infected DC for Cancer Therapy," Abstract for Grant No. 1R43CA108026-01 located at <http://crisp.cit.nih.gov/crisp/CRISP_LIB.getdoc?testkey=6787426&,p_grant_num=1R43C...>, last visited Jun. 27, 2004, two pages.

Brockstedt, D.G. (Date Unknown). "Listeria-CEA Vaccine-Infected DC for Cancer Therapy," Abstract for Grant No. 1R43CA108026-01 located at <http://crisp.cit.nih.gov/crisp/CRISP_LIB.getdoc?testkey=6787426&p_grant_num=1R43C...>, last visited Apr. 28, 2006, two pages.

Brockstedt, D.G. et al. (Sep. 21, 2004). "*Listeria*-based Cancer Vaccines That Segregate Immunogenicity From Toxicity," *Proc. Natl. Acad. Sci. USA* 101(38):13832-13837.

Brockstedt, D.G. et al. (Nov. 16, 2004). "Killed but Metabolically Active Recombinant *Listeria monocytogenes* as an Antigen Delivery and Activation Platform for Human Dendritic Cell-Based Cancer Immunotherapy," Poster, *presented at the 46th Annual Meeting of the American Society of Hematology (ASH)*, Dec. 4-7, 2004, San Diego, CA, *Blood* 104(11-pt. 1):939A.

Brockstedt, D.G. et al. (Nov. 16, 2004). "Killed but Metabolically Active Recombinant *Listeria monocytogenes* as an Antigen Delivery and Activation Platform for Human Dendritic Cell-Based Cancer Immunotherapy," Poster Board No./Session No. 717-III , Abstract No. 3447, *46th Annual Meeting Program and Abstracts presented at the American Society of Hematology*, Dec. 4-7, 2004, San Diego, CA, *Blood* 104(11-pt. 1):939A.

Brockstedt, D.G. et al. (Dec. 2004). "Killed but Metabolically Active Recombinant *Listeria monocytogenes* as an Antigen Delivery and Activation Platform for Human Dendritic Cell-Based Cancer Immunotherapy," Abstract presented at *American Society of Hematology(ASH), 46th Annual Meeting* Dec. 4-7, 2004, located at <http://www.cerus.com/index.cfm/abstracts/2004/KilledbutMetabolicallyActiveRecombina...>, last visited on Apr. 28, 2006, one page.

Brockstedt, D.G. et al. (Dec. 6, 2004). "Killed but Metabolically Active Recombinant *Listeria monocytogenes* as an Antigen Delivery and Activation Platform for Human Dendritic Cell-Based Cancer Immunotherapy," Abstract No. 3447, *46th Annual Meeting of the American Society of Hematology*, San Diego, CA, Dec. 4-7, 2004, located at <http://www.abstracts2view.com/hem_sandiego2004/view.php?nu=HEM4L1_5352>, last visited on Apr. 28, 2006, one page.

Brockstedt, D.G. et al. (Aug. 2005). "Killed but Metabolically Active Microbes: A New Vaccine Paradigm for Eliciting Effector T-Cell Responses and Protective Immunity," *Nature Medicine* 11(8):853-860.

Brockstedt, D.G. et al. (Nov./Dec. 2005). "Characterization of Mesothelin-Specific T cell Responses in Healthy Individuals," *Journal of Immunotherapy* 28(6):631, Abstract.

Brown, D.P. et al. (May 1988). "Site-Specific Integration in *Saccharopolyspora erythraea* and Multisite Integration in *Streptomyces lividans* of Actinomycete Plasmid pSE101," *J. Bacteriology* 170(5):2287-2295.

Brusic, V. et al. (1998). "MHCPEP, A Database of MHC-binding Peptides: Update 1997," *Nucleic Acids Res.* 26(1):368-371.

Bumann, D. (Dec. 2001). "Regulated Antigen Expression in Live Recombinant *Salmonella enterica* Serovar typhimurium Strongly Affects Colonization Capabilities and Specific CD4(+)-T-cell Responses," *Infect. Immun.* 69(12):7493-7500.

Burns, D.M. et al. (Sep. 1985). "Rare Codons in *E. coli* and *S. typhimurium* Signal Sequences," *FEBS Letters* 189(2):318-324.

Camilli, A. et al. (Jul. 1990). "Insertional Mutagenesis of *Listeria monocytogenes* with a Novel Tn917 Derivative That Allows Direct Cloning of DNA Flanking Transposon Insertions," *Journal of Bacteriology* 172(7):3738-3744.

Camilli, A. et al. (1993). "Dual Roles of *plcA* in *Listeria monocytogenes* Pathogenesis," *Molecular Microbiology* 8(1):143-157.

Carles-Kinch, K. et al. (May 15, 2002). "Antibody Targeting of the EphA2 Tyrosine Kinase Inhibits Malignant Cell Behavior," *Cancer Research* 62:2840-2847.

CBS. (Date Unknown). SignalP 3.0 Server located at <http://www.cbs.dtu.dk/services/SignalP/>, last visited Jun. 1, 2006, two pages.

Chee, M.S. et al. (1990). "Analysis of the Protein-Coding Content of the Sequence of Human Cytomegalovirus Strain AD169" In *Cytomegaloviruses* McDougall, J.K. ed., Springer-Verlag, pp. 125-169.

Cheo, D.L. et al. (Sep. 1993). "Elucidation of Regulatory Elements That Control Damage Induction and Competence Induction of the *Bacillus subtilis* SOS System," *J. Bacteriol.* 175(18):5907-5915.

Chou, K.C. (Dec. 2002). "Prediction of Protein Signal Sequences," *Curr. Protein Pept. Sci.* 3(6):615-622.

Codon Usage Table: *Listeria monocytogenes* [gbbct]: 3262 CS's (1029006 codons) located at <http://www.kazusa.or.jp/codon/cgi-bin/showcondon.cgi?species=Listeria+monocytogenes...>, last visited Dec. 11, 2003, one page.

Cossart, P. et al. (1998). "Interactions of *Listeria monocytogenes* With Mammalian Cells During Entry and Actin-Based Movement: Bacterial Factors, Cellular Ligands and Signaling," *The EMBO Journal* 17(14):3797-3806.

Cossart, P. et al. (2001). "The Use of Host Cell Machinery in the Pathogenesis of *Listeria monocytogenes*," *Current Opinion in Immunology* 13:96-103.

Cossart, P. et al. (Jan. 2003). "Invasion of Mammalian Cells by *Listeria monocytogenes*: Functional Mimicry to Subvert Cellular Functions," *TRENDS in Cell Biology* 13(1):23-31.

Davison, A.J. et al. (1986). "The Complete DNA Sequence of Varicella-Zoster Virus," *J. Gen. Virol.* 67:1759-1816.

Decatur, A.L. et al. (Nov. 3, 2000). "A PEST-Like Sequence in Listeriolysin O Essential for *Listeria monocytogenes* Pathogenicity," *Science* 290:992-995.

Dilks, K. et al. (Feb. 2003). "Prokaryotic Utilization of the Twin-Arginine Translocation Pathway: a Genomic Survey," *J. of Bacteriology* 185(4):1478-1483.

Dönnes, P. et al. (Sep. 11, 2002). "Prediction of MHC Class I Binding Peptides, Using SVMHC," *BMC Bioinformatics* 3(1):25.

Dramsi, S. et al. (1995). "Entry of *Listeria monocytogenes* Into Hepatocytes Requires Expression of InIB, a Surface Protein of the Internalin Multigene Family," *Molecular Microbiology* 16(2):251-261.

Dramsi, S. et al. (May 1997). "Identification of Four New Members of the Internalin Multigene Family of *Listeria monocytogenes* EGD," *Infection and Immunity* 65(5):1615-1625.

Dubensky, T. (Feb. 22, 2003). "Cancer Vaccines Derived from Selected Attenuated Strains of *Listeria monocytogenes*," Presented at *Keystone Symposia Meeting*, Keystone, CO, Feb. 17-23, 2003, 22 pages.

Dubensky, T. (Mar. 14, 2003). "Cancer Vaccines Derived From Selected Attenuated Strains of *Listeria monocytogenes*," *presented at Days of Molecular Medicine—Immunotherapy*, 24 pages.

Dubensky, T. (Dec. 4, 2003). "Listeria-Based Therapeutic Vaccines for Infectious Disease and Cancer: Vaccines Disguised as an Invading Pathogen," *presented at Johns Hopkins University*, 57 pages.

Dubensky, T.W. (Date Unknown). "Listeria Immunotherapy for Pancreatic and Ovarian Cancer," Abstract for Grant No. 2R44CA101421-02 located at <http://crisp.cit.nih.gov/crisp/CRISP_LIB.getdoc?testkey=6992210&p=_grant_num=2R44C...>, last visited Dec. 7, 2005, two pages.

Dubensky, T.W. (Date Unknown). "Listeria Immunotherapy for Pancreatic and Ovarian Cancer," Abstract for Grant No. 2R44CA101421-02 located at <http://crisp.cit.nih.gov/crisp/CRISP_LIB.getdoc?testkey=6992210&p_grant_num=2R44C...>, last visited Apr. 28, 2006, two pages.

Dubensky, T.W. (Date Unknown). "Listeria-Based Vaccines for Ovarian Cancer Therapy," Abstract for Grant No. 1R43CA101421-01 located at <http://crisp.cit.nih.gov/crisp/CRISP_LIB.getdoc?testkey=6645288&p_grant_num=1R43CA...>, last visited Nov. 3, 2004, two pages.

Dubensky, T.W. (Date Unknown). "Listeria-Based Vaccines for Ovarian Cancer Therapy," Abstract for Grant No. 1R43CA101421-01 located at <http://crisp.cit.nih.gov/crisp/CRISP_LIB.getdoc?testkey=6645288&p_grant_num=1R43CA...>, last visited Apr. 28, 2006, two pages.

Egel-Mitani, M. et al. (1988). "Competitive Expression of Two Heterologous Genes Inserted Into One Plasmid in *Saccharomyces cerevisiae*," *Gene* 73:113-120.

Ferguson, L.R. et al. (1987). "Frameshift Mutagenesis by Nitracrine Analogues in Wild-Type uvrB polA and recA Strains of *Salmonella typhimurium* With and Without Plasmid pKM101," *Mutation Research* 184:13-21.

Fong, L. et al. (Mar. 15, 2001). "Dendritic Cells Injected Via Different Routes Induce Immunity in Cancer Patients," *Journal of Immunology* 166:4254-4259.

Fong, L. et al. (Jul. 17, 2001). "Altered Peptide Ligand Vaccination with Flt3 Ligand Expanded Dendritic Cells for Tumor Immunotherapy," *Proc. Natl. Acad. Sci. USA* 98(15):8809-8814.

Foon, K.A. et al. (Nov. 1995). "Immune Responses in Patients with T-Cell Lymphoma Treated with an Anti-Idiotype Antibody Mimicking a Highly Restricted T-Cell Antigen," *Clin. Cancer Res.* 1(11):1285-1294.

Frankel, F.R. et al. (Oct. 1994). "Delivery of HIV Antigens Using *Listeria monocytogenes* as a Live Vaccine Vector," Abstracts of Papers *Presented at the 1994 Meeting on Molecular Approaches to the Control of Infectious Diseases*, Oct. 5-9, 1994, Cold Spring Harbor Laboratory Press: Cold Spring Harbor, NY, p. 56.

Frankel, F.R. et al. (1995). "Induction of Cell-Mediated Immune Responses to Human Immunodeficiency Virus Type 1 Gag Protein by Using *Listeria monocytogenes* as a Live Vaccine Vector," *The Journal of Immunology* 155:4775-4782.

Franklin, W.A. et al. (Jun. 1984). "Removal of UV Light-Induced Pyrimidine-Pyrimidone (6-4) Products from *Escherichia coli* DNA Requires the *uvrA, uvrB,* and *urvC* Gene Products," *Proc. Natl. Acad. Sci. USA* 81:3821-3824.

Friedman, R.S. et al. (Nov. 2000). "Induction of Human Immunodeficiency Virus (HIV)-Specific CD8 T-Cell Responses by *Listeria monocytogenes* and a Hyperattenuated *Listeria* Strain Engineered to Express HIV Antigens," *Journal of Virology* 74(21):9987-9993.

Gaillard, J.-L: et al. (Jun. 28, 1991). "Entry of *L. monocytogenes* into Cells Is Mediated by Internalin, a Repeat Protein Reminiscent of Surface Antigens From Gram-Positive Cocci," *Cell* 65:1127-1141.

Gaillard, J-L. et al. (Feb. 1996). "The *inlAB* Locus Mediates the Entry of *Listeria monocytogenes* into Hepatocytes in Vivo," *Journal of Experimental Medicine* 183(2):359-369.

Garmory, H.S. et al. (2003). "The Use of Live Attenuated Bacteria as a Delivery System for Heterologous Antigens," *J. Drug Target* 11(8-10):471-479.

Garmory, H.S. et al. (Jun. 20, 2003). "Oral Immunisation with Live *aroA* Attenuated *Salmonella enterica* Serovar *typhimurium* Expressing the *Yersinia pestis* V Antigen Protects Mice Against Plague," *Vaccine* 21(21-22):3051-3057.

Gat, O. et al. (Feb. 2003). "Use of a Promoter Trap System in *Bacillus anthracis* and *Bacillus subtilis* for the Development of Recombinant Protective Antigen-Based Vaccines," *Infection and Immunity* 71(2):801-813.

Gedde, M.M. et al. (Feb. 2000). "Role of Listeriolysin O in Cell-To-Cell Spread of *Listeria monocytogenes*," *Infection and Immunity* 68(2):999-1003.

GenBank Accession No. AF043498 created Jan. 19, 1998, located at <http://www.ncbi.nlm.nih.gov>, last visited on Jun. 1, 2006, two pages.

GenBank Accession No. AL591824 created on Jul. 18, 2002, located at <http://www.ncbi.nlm.nih.gov>, last visited on Apr. 19, 2004, one page.

GenBank Accession No. AL591974 created on Jun. 6, 2001, located at <http://www.ncbi.nlm.nih.gov>, last visited on Jun. 21, 2006, 91 pages.

GenBank Accession No. AL591975 created on Jun. 6, 2001, located at <http://www.ncbi.nlm.nih.gov>, last visited on Jun. 21, 2006, 164 pages.

GenBank Accession No. BC009272 created Jun. 12, 2001, located at <http://www.ncbi.nlm.nih.gov>, last visited Jun. 1, 2006, three pages.

GenBank Accession No. K00654 created May 10, 2002, located at <http://www.ncbi.nlm.nih.gov>, last visited Jun. 1, 2006, two pages.

GenBank Accession No. M29540 created Nov. 1, 1994, located at <http://www.ncbi.nlm.nih.gov>, last visited Jun. 1, 2006, two pages.

GenBank Accession No. M54968 created Feb. 4, 1997, located at <http://www.ncbi.nlm.nih.gov>, last visited Jun. 1, 2006, three pages.

GenBank Accession No. M54969, created Apr. 5, 1995, located at <http://www.ncbi.nlm.nih.gov>, last visited Jun. 1, 2006, one page.

GenBank Accession No. M67471 created Apr. 26, 1993, located at <http://www.ncbi.nlm.nih.gov>, last visited on Apr. 19, 2004, four pages.

GenBank Accession No. NC_007322, created May 17, 2004, located at <http://www.ncbi.nlm.nih.gov>, last visited on Jun. 1, 2006, 104 pages.

GenBank Accession No. NM_001327 updated Jan. 29, 2006, located at <http://www.ncbi.nlm.nih.gov>, last visited on Jun. 1, 2006, six pages.

GenBank Accession No. NP_463897 [gi /16802412/ref/NP-_463897.1], created Jun. 6, 2001, located at <http://www.ncbi.nlm.nih.gov>, last visited on Jun. 1, 2006, two pages.

GenBank Accession No. NP_464110, created Nov. 23, 2004, located at <http://www.ncbi.nlm.nih.gov>, last visited Dec. 12, 2004, two pages.

GenBank Accession No. NP_466213, created Nov. 23, 2004, located at <http://www.ncbi.nlm.nih.gov>, last visited Dec. 12, 2004, two pages.

GenBank Accession No. NP_469731 [gi /16799463/ref/NP-_469731.1], created Jul. 9, 2001, located at <http://www.ncbi.nlm.nih.gov>, last visited Jun. 1, 2006, two pages.

GenBank Accession No. NP_471636 [gi /16801368/ref/NP-_471636.1], created Jul. 9, 2001, locate at <http://www.ncbi.nlm.nih.gov>, last visited Jun. 1, 2006, two pages.

GenBank Accession No. P01012, created Jul. 21, 1986, located at <http://www.ncbi.nlm.nih.gov>, last visited Jun. 1, 2006, ten pages.

GenBank Accession No. P01111, created Jul. 21, 1986, located at <http://www.ncbi.nlm.nih.gov>, last visited Jun. 1, 2006, six pages.

GenBank Accession No. P01112, created Jul. 21, 1986, located at <http://www.ncbi.nlm.nih.gov>, last visited Jun. 1, 2006, ten pages.

GenBank Accession No. P01116, created Jul. 21, 1986, located at <http://www.ncbi.nlm.nih.gov>, last visited Jun. 1, 2006, eight pages.

GenBank Accession No. P01117, created Jul. 21, 1986, located at <http://www.ncbi.nlm.nih.gov>, last visited Jun. 1, 2006, three pages.

GenBank Accession No. U40434, created Nov. 9, 1995, located at <http://www.ncbi.nlm.nih.gov>, last visited Jun. 1, 2006, three pages.

GenBank Accession No. U75285, created Oct. 17, 1996, located at <http://www.ncbi.nlm.nih.gov>, last visited Jun. 1, 2006, six pages.

GenBank Accession No. X55668, created Sep. 24, 1990, located at <http://www.ncbi.nlm.nih.gov>, last visited Jun. 1, 2006, two pages.

Genbank/Embl Accession No. CAB12056 [gi/2632548/emb/CAB12056.1/], created Jun. 27, 2003, located at <http://www.ncbi.nlm.nih.gov>, last visited Jun. 1, 2006, two pages.

Genbank/Embl Accession No. CAB12081 [gi/2632573/emb/CAB12081.1/], created Jun. 27, 2003, located at <http://www.ncbi.nlm.nih.gov>, last visited Jun. 1, 2006, two pages.

Genbank/Embl Accession No. CAB13278 [gi/2633776/emb/CAB13278.1/], created Jun. 27, 2003, located at <http://www.ncbi.nlm.nih.gov>, last visited Jun. 1, 2006, two pages.

Genbank/Embl Accession No. CAB14172 [gi/2634674/emb/CAB14172.1/], created Jun. 27, 2003, located at <http://www.ncbi.nlm.nih.gov>, last visited Jun. 1, 2006, two pages.

Genbank/Embl Accession No. CAB15017 [gi /2635523/emb/CAB15017.1/], created Jun. 27, 2003, located at <http://www.ncbi.nlm.nih.gov>, last visited Jun. 1, 2006, two pages.

Genbank/Embl Accession No. CAB15089 [gi/2635595/emb/CAB15089.1/], created Jun. 27, 2003, located at <http://www.ncbi.nlm.nih.gov>, last visited Jun. 1, 2006, two pages.

Genbank/Embl Accession No. CAB15852 [gi/2636361/emb/CAB15852.1/], created Jun. 27, 2003, located at <http://www.ncbi.nlm.nih.gov>, last visited Jun. 1, 2006, two pages.

Gentschev, I. et al. (Sep. 29, 2000). "Delivery of Protein Antigens and DNA by Virulence-Attenuated Strains of *Salmonella typhimurium* and *Listeria monocytogenes*," *Journal of Biotechnology* 83:19-26.

Gentschev, I. et al. (Feb. 2002). "Delivery of Protein Antigens and DNA by Attenuated Intracellular Bacteria," *Int. J. Med. Microbiol.* 291:577-582.

Giedlin, M. et al. (Date Unknown). "The Living Dead: Vaccines Against Microbial Pathogens Based on Psoralen-Killed Metabolically Active DNA Repair Mutants," Abstract 189 (H) located at <http://www.asmbiodefense.org/2004tueabs.asp>, last visited Nov. 5, 2004, one page.

Giedlin, M. et al. (Mar. 2004). "The Living Dead: Vaccines Against Microbial Pathogens Based on Psoralen-Killed Metabolically Active DNA Repair Mutants," abstract *presented at the American Society for Microbiology (ASM) Biodefense Research Meeting*, Mar. 7-10, 2004, as posted on <http://www.cerus.com/pages/solution/abs158.html>, last visited Jul. 18, 2004, two pages.

Giedlin, M. et al. (Mar. 9, 2004). "The Living Dead: Vaccines Against Microbial Pathogens Based on Psoralen-Killed Metabolically Active DNA Repair Mutants," Poster, *presented at American Society for Microbiology Biodefense Research Meeting*, Mar. 7-10, 2004, Baltimore, MD, one page.

Giedlin, M.A. (Date Unknown). "Listeria-Based Ovarian Cancer Polyepitope Vaccines," Abstract for Grant No. 1R43CA109868-01A1 located at <http://crisp.cit.nih.gov/crisp/CRISP_LIB.getdoc?testkey=6932934&p_grant_num=1R43C...>, last visited Dec. 7, 2005, two pages.

Giedlin, M.A. (Date Unknown). "Listeria-Based Ovarian Cancer Polyepitope Vaccines," Abstract for Grant No. 1R43CA109868-01A1 located at <http://crisp.cit.nih.gov/crisp/CRISP_LIB.getdoc?testkey=6932934&p_grant_num=1R43C...>, last visited Apr. 28, 2006, two pages.

Giedlin, M.A. (Date Unknown). "Use of Listeria as Colon Cancer Vaccine Adjuvants," Abstract for Grant No. 1R43CA101378-01 located at <http://crisp.cit.nih.gov/crisp/CRISP_LIB.getdoc?testkey=6645212&p_grant_num=1R43CA...>, last visited Nov. 3, 2004, two pages.

Giedlin, M.A. et al. (Mar. 2003). "Therapeutic Immunization with Attenuated Recombinant *Listeria monocytogenes* Prolongs Survival in a Murine Transplant Model of Melanoma," *Proceedings of the American Association for Cancer Research, 94th Annual Meeting*, Apr. 5-9, 2003,Toronto, Ontario, CA, 44:194, Abstract No. 850, one page.

Giedlin, M.A. et al. (Jul. 2003). "Therapeutic Immunization with Attenuated Recombinant *Listeria monocytogenes* Prolongs Survival in a Murine Transplant Model of Melanoma," (Abstract for the 94th Annual Meeting of the American Association for Cancer Research, Washington DC, USA, Jul. 11-14, 2003) *Proceedings of the American Association for Cancer Research Annual Meeting* 44(2):167-168, Abstract No. 850.

Glaser, P. et al. (Oct. 26, 2001). "Comparative Genomics of *Listeria* Species," *Science* 294:849-852.

Glomski, I.J. et al. (Mar. 18, 2002). "The *Listeria monocytogenes* Hemolysin Has an Acidic pH Optimum to Compartmentalize Activity and Prevent Damage to Infected Host Cells," *Journal of Cell Biology* 156(6):1029-1038.

Glomski, I.J. et al. (Dec. 2003). "*Listeria monocytogenes* Mutants That Fail to Compartmentalize Listeriolysin O Activity Are Cytotoxic, Avirulent, and Unable to Evade Host Extracellular Defenses," *Infect. Immun.* 71(12):6754-6765.

Goonetilleke, N.P. et al. (Aug. 1, 2003). "Enhanced Immunogenicity and Protective Efficacy Against *Mycobacterium tuberculosis* of Bacille Calmette-Guérin Vaccine Using Mucosal Administration and Boosting with a Recombinant Modified Vaccinia Virus Ankara," *J. Immunol.* 171(3):1602-1609.

Gregory, S.H. et al. (Oct. 1996). "Expression of the *inlAB* Operon by *Listeria monocytogenes* Is Not Required for Entry into Hepatic Cells in Vivo," *Infection and Immunity* 64(10):3983-3986.

Gregory, S.H. et al. (Dec. 1997). "Internalin B Promotes the Replication of *Listeria monocytogenes* in Mouse Hepatocytes," *Infection and Immunity* 65(12):5137-5141.

Greiffenberg, L. et al. (Dec. 1, 1997). "*Listeria monocytogenes*-infected Human Umbilical Vein Endothelial Cells: Internalin-Independent Invasion, Intracellular Growth, Movement, and Host Cell Responses," *FEMS Microbiology Letters* 157:163-170.

Guan, P. et al (2003). "MHCPred: A Server for Quantitative Prediction of Peptide—MHC Binding," *Nucleic Acids Res.* 31(13):3621-3624.

Gunn, G.R. et al. (2001). "Two *Listeria monocytogenes* Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16," *The Journal of Immunology* 167:6471-6479.

Gunn, G.R. et al. (Oct. 2002). "Recombinant Intra-Cellular Bacteria as Carriers for Tumor Antigens" Chapter 14 in *Vaccine Delivery Strategies*, Dietrich, G. et al. eds., Horizon Scientific Press: UK., pp. 315-348.

Guzmán, C.A. et al. (Jun. 1998). "Attenuated *Listeria monocytogenes* Carrier Strains Can Deliver an HIV-1 gp120 T Helper Epitope to MHC Class II-Restricted Human CD4$^+$ T Cells," *European Journal of Immunology* 28(6):1807-1814.

Hammarström, S. (1999). "The Carcinoembryonic Antigen (CEA) Family: Structures, Suggested Functions and Expression in Normal and Malignant Tissues," *Seminars in Cancer Biology* 9:67-81.

Harth, G. et al. (Jul. 2004). "A Two-Plasmid System for Stable, Selective-Pressure-Independent Expression of Multiple Extracellular Proteins in Mycobacteria," *Microbiology* 150(Pt. 7):2143-2151.

Henderson, R.A. et al. (Jul. 15, 1997). "Activation of Human Dendritic Cells Following Infection with *Mycobacterium tuberculosis*," *The Journal of Immunology* 159(2):635-643.

Hess, J. et al. (May 1995). "*Listeria monocytogenes* p60 Supports Host Cell Invasion by and in Vivo Survival of Attenuated *Salmonella typhimurium*," *Infection and Immunity* 63(5):2047-2053.

Higgins, D.E. et al. (1999). "Delivery of Protein to the Cytosol of Macrophages using *Escherichia coli* K-12," *Molecular Microbiology* 31(6):1631-1641.

Higgins, D.E. et al. (1999). "Delivery of Protein to the MHC Class I Processing Pathway Using *Escherichia coli* K-12 Expressing Listeriolysin O," Abstract B/D-109, *Abstracts of the 99th General Meeting of the American Society for Microbiology*, Chicago, IL, May 30-Jun. 3, 1999, 99:50.

Higgins, D.E. et al. (Sep. 1999). "Delivery of Protein to the Conventional MHC Class I Pathway for Antigen Processing Using *Escherichia coli* Expressing Listeriolysin O," *Abstracts of Papers Presented at the 1999 Meeting on Microbial Pathogenesis and Host Response*, Sep. 22-26, 1999, p. 197.

Hiller, K. et al. (Jul. 1, 2004). "PrediSi: Prediction of Signal Peptides and Their Cleavage Positions," *Nucleic Acids Res.* 32(Web Server Issue):W375-W379.

Hopp, T.P. (Jul./Aug. 1993). "Retrospective: 12 Years of Antigenic Determinant Predictions, and More," *Pept. Res.* 6(4):183-190.

Hopp, T.P. et al. (Jun. 1981). "Prediction of Protein Antigenic Determinants from Amino Acid Sequences," *Proc. Natl. Acad. Sci.* 78(6):3824-3828.

Horwitz, M.A. et al. (Dec. 5, 2000). "Recombinant Bacillus Calmette-Guérin (BCG) Vaccines Expressing the *Mycobacterium tuberculosis* 30-kDa Major Secretory Protein Induce Greater Protective Immunity Against Tuberculosis than Conventional BCG Vaccines in a Highly Susceptible Animal Model," *Proc. Natl. Acad. Sci. USA* 97(25):13853-13858.

Houghton, M. et al. (1991). "Molecular Biology of the Hepatitis C Viruses: Implications for Diagnosis, Development and Control of Viral Disease," *Hepatology* 14(2):381-388.

Huang, A.T.C. et al. (May 13, 1994). "Role of Bone Marrow-Derived Cells in Presenting MHC' Class I-Restricted Tumor Antigens," *Science* 264:961-965.

Huang, E.H. et al. (Jun. 2002). "CEA-Based Vaccines," *Exper. Rev. Vaccines* 1(1):49-63.

Humphreys, D.P. et al. (Nov. 2000). "High-Level Periplasmic Expression in *Escherichia coli* Using a Eukaryotic Signal Peptide: Importance of Codon Usage at the 5' end of the Coding Sequence," *Protein Expression and Purification* 20(2):252-264.

Ikonomidis, G. et al. (May 1994). "Delivery of a Viral Antigen to the Class I Pathway by *Listeria monocytogenes*: A Potential Vaccine Vector," Abstract No. E-90, *Abstracts of the 94th General Meeting of the American Society for Microbiology*, Las Vegas Convention Center: Las Vegas, NV, May 23-27, 1994, p. 159.

Ikonomidis, G. et al. (Dec. 1994). "Delivery of a Viral Antigen to the Class I Processing and Presentation Pathway by *Listeria monocytogenes*," *J. Exp. Med.* 180:2209-2218.

Ikonomidis, G. et al. (1995). "*Listeria monocytogenes*: A Novel Live Vaccine Vector" in *Vaccines 95*, Chanock, R.M. et al. eds., Cold Spring Harbor Laboratory Press: New York, 95:317-326.

Ikonomidis, G. et al. (Mar. 1997). "Influenza-Specific Immunity Induced by Recombinant *Listeria monocytogenes* Vaccines," *Vaccine* 15(4):433-440.

International Search Report issued for PCT Application No. PCT/US2004/044080, filed Dec. 23, 2004, mailed Aug. 19, 2005, 10 pages.

Ireton, K. et al. (Jun. 11, 1999). "The *Listeria monocytogenes* Protein InlB Is an Agonist of Mammalian Phosphoinositide 3-Kinase," *The Journal of Biological Chemistry* 274(24):17025-17032.

Jones, S. et al. (Dec. 1994). "Characterization of *Listeria monocytogenes* Pathogenesis in a Strain Expressing Perfringolysin O in Place of Listeriolysin O," *Infection and Immunity* 62(12):5608-5613.

Jones, S. et al. (Sep. 1996). "Conversion of an Extracellular Cytolysin into a Phagosome-Specific Lysin Which Supports the Growth of an Intracellular Pathogen," *Molecular Microbiology* 21(6):1219-1225.

Jongbloed, J.D.H. et al. (Dec. 29, 2000). "TatC Is a Specificity Determinant for Protein Secretion via the Twin-Arginine Translocation Pathway," *J. Biol. Chem.* 275(52):41350-41357.

Jongbloed, J.D.H. et al. (Nov. 15, 2002). "Selective Contribution of the Twin-Arginine Translocation Pathway to Protein Secretion in *Bacillus subtilis*," *J. Biol. Chem.* 277(48):44068-44078.

Kang, H.Y. et al. (Apr. 2002). "Immune Responses to Recombinant Pneumococcal PspA Antigen Delivered by Live Attenuated *Salmonella enterica* Serovar *Typhimurium* Vaccine," *Infect. Immun.* 70(4):1739-1749.

Kang, H.Y. et al. (Jul. 15, 2003). "Immune Responses Dependent on Antigen Location in Recombinant Attenuated *Salmonella typhimurium* Vaccines Following Oral Immunization," *FEMS Immunol. Med. Microbiol.* 37(2-3):99-104.

Kawahara, M. et al. (Dec. 2002). "Oral Recombinant *Mycobacterium bovis* Bacillus Calmette-Guérin Expresssing HIV-1 Antigens as a Freeze-Dried Vaccine Induces Long-Term, HIV-Specific Mucosal and Systemic Immunity," *Clin. Immunol.* 105(3):326-331.

Kawakami, Y. et al. (Jul. 1994). "Identification of a Human Melanoma Antigen Recognized by Tumor-Infiltrating Lymphocytes Associated with in vivo Tumor Rejection," *Proc. Natl. Acad. Sci. USA* 91:6458-6462.

Kiessling, A. et al. (Dec. 1, 2002). "Prostate Stem Cell Antigen: Identification of Immunogenic Peptides and Assessment of Reactive CD8+ T Cells in Prostate Cancer Patients," *Int. J. Cancer* 102(4):390-397.

Kim, C.H. et al. (Oct. 15, 1997). "Codon Optimization for High-Level Expression of Human Erythropoietin (EPO) in Mammalian Cells," *Gene* 199(1-2):293-301.

Kocks, C. et al. (Feb. 7, 1992). "L. monocytogenes-Induced Actin Assembly Requires the *actA* Gene Product, a Surface Protein," *Cell* 68:521-531.

Kolb-Maurer, A. et al. (Jun. 2000). "*Listeria monocytogenes*-Infected Human Dendritic Cells: Uptake and Host Cell Response," *Infection and Immunity* 68(6):3680-3688.

Lakey, D.L. et al. (Jan. 2000). "Enhanced Production of Recombinant *Mycobacterium tuberculois* Antigens in *Escherichia coli* by Replacement of Low-Usage Codons," *Infection and Immunity* 68(1):233-238.

Lampson, L.A. et al. (Jan. 1, 1993). "Exploiting the *lacZ* Reporter Gene for Quantitative Analysis of Disseminated Tumor Growth within the Brain: Use of the *lacZ* Gene Product as a Tumor Antigen, for Evaluation of Antigenic Modulation, and to Facilitate Image Analysis of Tumor Growth in Situ," *Cancer Research* 53(1):176-182.

Lauer, P. et al. (Nov. 1999). "Scanning Alanine Mutagenesis Reveals Multiple Functions for the N-Terminal Region of *Listeria monocytogenes* ActA in Actin-Based Motility," *Molecular Biology of the Cell* 10(Supp.):159a.

Lauer, P. et al. (Dec. 1999). "Scanning Alanine Mutagenesis Reveals Multiple Functions for the N-Terminal Region of *Listeria monocytogenes* ActA in Actin-Based Motility," Abstract 919, *Abstracts presented at the 39th Annual Meeting of the American Soceity for Cell Biology*, Washington, DC, Dec. 11-15, 1999, p. 159a.

Lauer, P. et al. (Dec. 2001). "Systematic Mutational Analysis of the Amino-Terminal Domain of the *Listeria monocytogenes* ActA Protein Reveals Novel Functions in Actin-Based Motility," *Molecular Microbiology* 42(5):1163-1177.

Lauer, P. et al. (Aug. 2002). "Construction, Characterization, and Use of Two *Listeria monocytogenes* Site-Specific Phage Integration Vectors," Journal of Bacteriology 184(15):4177-4186.

Lauer, P. et al. (Feb. 2003). "Construction, Characterization, and Use of Two *Listeria monocytogenes* Site-Specific Phage Integration Vectors," Author's Correction, *Journal of Bacteriology* 185(4):1484.

Lebrun, M. et al. (Aug. 1996). "Internalin Must be on the Bacterial Surface to Mediate Entry of *Listeria monocytogenes* into Epithelial Cells," *Molecular Microbiology* 21(3):579-592.

Lee, K-D. et al. (Mar. 29, 1996). "Delivery of Macromolecules into Cytosol using Liposomes Containing Hemolysin from *Listeria monocytogenes*," *Journal of Biological Chemistry* 271(13):7249-7252.

Lenz, L.L. et al. (May 23, 2002). "Mutations in a Second, Non-Essential, *secA* Gene Confer the Phase-Variable Rough Phenotype of *Listeria monocytogenes*," Abstract B-380, *Abstracts of the American Society for Microbiology 102nd General Meeting*, Salt Lake City, UT, May 19-23, 2002, 102:97.

Lenz, L.L. et al. (Aug. 2002). "Identification of a Second *Listeria secA* Gene Associated with Protein Secretion and the Rough Phenotype," *Molecular Microbiology* 45(4):1043-1056.

Lenz, L.L. et al. (Oct. 14, 2003). "SecA2-Dependent Secretion of Autolytic Enzymes Promotes *Listeria monocytogenes* Pathogenesis," *Proc. Natl. Acad. Sci. USA* 100(21):12432-12437.

Leong, M. et al. (Feb. 3, 2004). "Recombinant Attenuated *Listeria monocytogenes* Elicit Functional Immune Response Specific to a Heterologous Antigen in the Presence of Listeria-Specific Cellular and Humoral Immunity," *Gordon Research Conference on Immunochemistry & Immunobiology Conference*, Feb. 1-6, 2004, Buellton, CA, 20 pages.

Liau, L.M. et al. (Apr. 15, 2002). "Tumor Immunity Within the Central Nervous System Stimulated by Recombinant *Listeria monocytogenes* Vaccination," *Cancer Research* 62:2287-2293.

Lim, S.H. et al. (Mar. 1, 2001). "Sperm Protein 17 is a Novel Cancer-Testis Antigen in Multiple Myeloma," *Blood* 97(5):1508-1510.

Lu, J. et al. (Sep. 15, 2000). "Use of Two Predictive Algorithms of the World Wide Web for the Identification of Tumor-Reactive T-cell Epitopes," *Cancer. Res.* 60(18):5223-5227.

Makrides, S.C. (Sep. 1996). "Strategies for Achieving High-Level Expression of Genes in *Escherichia coli*," *Microbiological Reviews* 60(3):512-538.

Mallois, R.R. (Oct. 2001). "Predicting Class II MHC/Peptide Multi-Level Binding with an Iterative Stepwise Discriminant Analysis Meta-Algorithm," *Bioinformatics* 17(10):942-948.

Mansell, A. et al. (Nov. 23, 2001). "Internalin B Activates Nuclear Factor-κB via Ras, Phosphoinositide 3-Kinase, and Akt," *The Journal of Biological Chemistry* 276(47):43597-43603.

Maru, G. B. et al. (1987). "Formation and Persistence of Isoniazid-DNA Adducts in Mouse Tissues," *BIOSIS Database, Biosciences Information Service*, Database Accession No. PREV198783117667, Abstract, one page.

Maru, G. B. et al. (1987). "Formation and Persistence of Isoniazid-DNA Adducts in Mouse Tissues," *Human Toxicology* 6(2):153-158.

Mata, M. et al. (Jan. 8, 2001). "Evaluation of a Recombinant *Listeria monocytogenes* Expressing an HIV Protein that Protects Mice Against Viral Challenge," *Vaccine* 19(11-12):1435-1445.

Mayordomo, J.I. et al. (Dec. 1995). "Bone Marrow-Derived Dendritic Cells Pulsed With Synthetic Tumour Peptides Elicit Protective and Therapeutic Antitumour Immunity," *Nat. Med.* 1(12):1297-1302.

McCloy, E.W. (1951). "Studies on a Lysogenic *Bacillus* Strain. I. A Bacteriophage Specific for *Bacillus anthracis*," *J. Hyg.* 49:114-125.

McGeoch, D.J. et al. (1988). "The Complete DNA Sequence of the Long Unique Region in the Genome of Herpes Simplex Virus Type 1," *J. Gen Virol.* 69:1531-1574.

McSorley, S.J. et al. (Jan. 1997). "Vaccine Efficacy of *Salmonella* Strains Expressing Glycoprotein 63 with Different Promoters," *Infect. Immun.* 65(1):171-178.

Menne, K.M.L. et al. (Aug. 2000). "A Comparison of Signal Sequence Prediction Methods Using a Test Set of Signal Peptides," *Bioinformatics* 16(8):741-742.

Mérino, D. et al. (May 2002). "A Hypermutator Phenotype Attenuates the Virulence of *Listeria monocytogenes* in a Mouse Model," *Molecular Microbiology* 44(3):877-887.

Molldrem, J. et al. (Oct. 1, 1996). "Targeted T-cell Therapy for Human Leukemia: Cytotoxic T Lymphocytes Specific for a Peptide Derived from Proteinase 3 Preferentially Lyse Human Myeloid Leukemia Cells," *Blood* 88(7):2450-2457.

Molldrem, J.J. et al. (Oct. 1, 1997). "Cytotoxic T Lymphocytes Specific for a Nonpolymorphic Proteinase 3 Peptide Preferentially Inhibit Chronic Myeloid Leukemia Colony-Forming Units," *Blood* 90(7):2529-2534.

Molldrem, J.J. et al. (Jun. 1, 1999). "A PR1-Human Leukocyte Antigen-A2 Tetramer Can Be Used to Isolate Low-Frequency Cytotoxic T Lymphocytes From Healthy Donors That Selectively Lyse Chronic Myelogenous Leukemia," *Cancer Research* 59:2675-2681.

Molldrem, J.J. et al. (Sep. 2000). "Evidence That Specific T Lymphocytes May Participate in the Elimination of Chronic Myelogenous Leukemia," *Nature Medicine* 6(8):1018-1023.

Molldrem, J.J. et al. (Dec. 2002). "The Basis of T-Cell-Mediated Immunity to Chronic Myelogenous Leukemia," *Oncogene* 21:8668-8673.

Mollet, B. et al. (Jul. 1993). "Directed Genomic Integration, Gene Replacement, and Integrative Gene Expression in *Streptococcus thermophilus*," *J. Bacteriology* 175(14):4315-4324.

Moody, G. et al. (Mar. 2004). "Recombinant *Listeria monocytogenes*-Based Immunotherapy Targeting the Receptor Tyrosine Kinase EphA2," Abstract *presented at the American Association for Cancer Research (AACR)*, Mar. 27-31, 2004, as posted on <http://www.cerus.com/pages/solution/abs155.html>, last visited on Aug. 26, 2004, two pages.

Morgan, D.J. et al. (1998). "Activation of Low Avidity CTL Specific for a Self Epitope Results in Tumor Rejection But Not Autoimmunity," *J. Immunol.* 160:643-651.

Morse, M.A. et al. (Jun. 1999). "A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen," *Clin. Cancer Res.* 5:1331-1338.

Muller-Bérat, N. et al. (Jan. 1994). "The Phylogeny of Proteinase 3/Myeloblastin, The Autoantigen in Wegener's Granulomatosis, and Myeloperoxidase as Shown by Immunohistochemical Studies on Human Leukemic Cell Lines," *Clin. Immunol. Immunopath.* 70(1):51-59.

Nagata, T. et al. (Aug. 2, 1999). "Codon Optimization Effect on Translational Efficiency of DNA Vaccine in Mammalian Cells: Analysis of Plasmid DNA Encoding a CTL Epitope Derived from Microorganisms," *Biochem. Biophys. Res. Commun.* 261(2):445-451.

Nakamura, Y. et al. (Jan. 1, 2000). "Codon Usage Tabulated from International DNA Sequence Databases: Status for the Year 2000," *Nucleic Acids Research* 28(1):292.

Nielsen, H. et al. (Jan. 1997). "Identification of Prokaryotic and Eukaryotic Signal Peptides and Prediction of the Cleavage Sites," *Protein Engineering* 10(1):1-6.

Nielsen, M. et al. (Jun. 12, 2004). "Improved Prediction of MHC Class I and Class II Epitopes Using a Novel Gibbs Sampling Approach," *Bioinformatics* 20(9):1388-1397.

Nishiyama, T. et al. (Jan. 2001). "Immunotherapy of Bladder Cancer Using Autologous Dendritic Cells Pulsed with Human Lymphocyte Antigen-A24-Specific MAGE-3 Peptide," *Clinical Cancer Research* 7:23-31.

Nussbaum, A.K. et al. (Mar. 2001). "PAProC: A Prediction Algorithm for Proteasomal Cleavages Available on the WWW," *Immunogenetics* 53(2):87-94.

Ochsner, U.A. et al. (Jun. 11, 2002). "Effects of the Twin-Arginine Translocase on Secretion of Virulence Factors, Stress Response, and Pathogenesis," *Proc. Natl. Acad. Sci.* 99(12):8312-8317.

Pace, J.L. et al. (1998). "Inactivated Whole-Cell Bacterial Vaccines: Current Status and Novel Strategies," *Vaccine* 16(16):1563-1574.

Paglia, P. et al. (Jun. 1997). "The Defined Attenuated *Listeria monocytogenes* Δmpl2 Mutant is an Effective Oral Vaccine Carrier to Trigger a Long-Lasting Immune Response Against a Mouse Fibrosarcoma," *Eur. J. Immunol.* 27(6):1570-1575.

Pan, Z-K. et al. (May 1995). "A Recombinant *Listeria monocytogenes* Vaccine Expressing a Model Tumour Antigen Protects Mice Against Lethal Tumour Cell Challenge and Causes Regression of Established Tumours," *Nature Medicine* 1(5):471-477.

Pan, Z-K. et al. (Nov. 1, 1995). "Regression of Established Tumors in Mice Mediated by the Oral Administration of a Recombinant *Listeria monocytogenes* Vaccine," *Cancer Research* 55:4776-4779.

Pan, Z-K. et al. (Oct. 15, 1999). "Regression of Established B16F10 Melanoma with a Recombinant *Listeria monocytogenes* Vaccine," *Cancer Research* 59:5264-5269.

Parida, S.K. et al. (Apr. 1998). "Internalin B is Essential for Adhesion and Mediates the Invasion of *Listeria monocytogenes* into Human Endothelial Cells," *Molecular Microbiology* 28(1):81-93.

Parker, J.M.R. et al. (Sep. 23, 1986). "New Hydrophilicity Scale Derived from High-Performance Liquid Chromatography Peptide Retention Data: Correlation of Predicted Surface Residues with Antigenicity and X-ray-Derived Accessible Sites," *Biochemistry* 25(19):5425-5432.

Parker, K.C. et al. (Jan. 1, 1994). "Scheme for Ranking Potential HLA-A2 Binding Peptides Based on Independent Binding of Individual Peptide Side-Chains," *J. Immunol.* 152(1):163-175.

Peters, C. et al. (Jan. 2003). "Tailoring Host Immune Responses to *Listeria* by Manipulation of Virulence Genes— The Interface Between Innate and Acquired Immunity," *FEMS Immunology and Medical Microbiology* 35:243-253.

Pop, O. et al. (Feb. 1, 2002). "The Twin-Arginine Signal Peptide of PhoD and the $TatA_d/C_d$ Proteins of *Bacillus subtilis* Form an Autonomous Tat Translocation System," *J. Biol. Chem.* 277(5):3268-3273.

Portnoy, D.A. (Sep. 2000). "Unique Features of Listeriolysin O That are Essential for *L. monocytogenes* Pathogenesis," *Medical Microbiology and Immunology* 189(1):44.

Portnoy, D.A. et al. (Aug. 5, 2002). "The Cell Biology of *Listeria monocytogenes* Infection: The Intersection of Bacterial Pathogenesis and Cell-Mediated Immunity," *The Journal of Cell Biology* 158(3):409-414.

Raffelsbauer, D. et al. (1988). "The Gene Cluster *inIC2DE* of *Listeria monocytogenes* Contains Additional New Internalin Genes and Is Important for Virulence in Mice," *Mol. Gen. Genet.* 260:144-158.

Rammensee, H. et al. (Nov. 1999). "SYFPEITHI: Database for MHC Ligands and Peptide Motifs," *Immunogenetics* 50(3-4):213-219.

Reche, P.A. et al. (Sep. 2002). "Prediction of MHC Class I Binding Peptides Using Profile Motifs," *Hum. Immunol.* 63(9):701-709.

Reiter, R.E. et al. (Feb. 1998). "Prostate Stem Cell Antigen: A Cell Surface Marker Overexpressed in Prostate Cancer," *Proc. Natl. Acad. Sci.* 95:1735-1740.

Renkvist, N. et al. (2001). "A Listing of Human Tumor Antigens Recognized by T Cells," *Cancer Immunol. Immunother.* 50:3-15.

Rescigno, M. et al. (Mar. 2001). "Dendritic Cells, Loaded with Recombinant Bacteria Expressing Tumor Antigens, Induce a Protective Tumor-Specific Response," *Clinical Cancer Research* 7(Suppl.):865s-870s.

Rescigno, M. et al. (Mar. 2001). "Dendritic Cells, Loaded with Recombinant Bacteria Expressing Tumor Antigens, Induce a Protective Tumor-Specific Response," *Medline Database, U.S. National Library of Medicine (NLM)*, Database Accession No. NLM11300484. Abstract, one page.

Roback, J.D. et al. (Nov. 16, 2004). "Immunization with Live-Attenuated Listeria Encoding CMV Antigen Induces Extensive Expansion of CMV-Specific CD8+t-Cells Following HSCT: An Alternative to Adoptive Antiviral Immunotherapy," Abstract No. 2129, Poster Board—Session No. 342-11, *46th Annual Meeting of the American Society of Hematology*, San Diego, CA, Dec. 4-7, 2004, *Blood* 104(11-pt. 1):586A.

Roback, J.D. et al. (Dec. 5, 2004). "Immunization with Live-Attenuated *Listeria* Encoding CMV Antigen Induces Extensive Expansion of CMV-Specific CD8+t-Cells Following HSCT: An Alternative to Adoptive Antiviral Immunotherapy," Abstract No. 2129, Poster Session 342-II, *46th Annual Meeting of the American Society of Hematology*, San Diego, CA, Dec. 4-7, 2004, located at <http://www.abstracts2view.com/hem_sandiego2004/view.php?nu=HEM4L1_4025> last visited Apr. 28, 2006, one page.

Rüssman, H. et al. (Jul. 1, 2001). "Protection Against Murine Listeriosis by Oral Vaccination with Recombinant *Salmonella* Expressing Hybrid *Yersinia* Type III Proteins," *J. Immunol.* 167(1):357-365.

Salazar, E. et al. (2000). "Agonist Peptide From a Cytotoxic T-Lymphocyte Epitope of Human Carcinoembryonic Antigen Stimulates Production of TC1-Type Cytokines and Increases Tyrosine Phosphorylation More Efficiently Than Cognate Peptide," *Int. J. Cancer* 85:829-838.

Sander, P. et al. (Jun. 2001). "*Mycobacterium bovis* BCG *recA* Deletion Mutant Shows Increased Susceptibility to DNA-Damaging Agents but Wild-Type Survival in a Mouse Infection Model," *Infection and Immunity* 69(6):3562-3568.

Sashinami, H. et al. (Jan. 2003). "Effective Induction of Acquired Resistance to *Listeria monocytogenes* by Immunizing Mice With in Vivo-Infected Dendritic Cells," *Infection and Immunity* 71(1):117-125.

Schafer, R. et al. (Mar. 1992). "Induction of a Cellular Immune Response to a Foreign Antigen by a Recombinant *Listeria monocytogenes* Vaccine," Abstract O 447, *Journal of Cellular Biochemistry— Keystone Symposia on Antigen Presentation Functions of the MHC (Major Histocompatibility Complex)*, Taos, NM, Mar. 5-27, 1992, Supplement 16(pt. D):70.

Schafer, R. et al. (Jul. 1, 1992). "Induction of a Cellular Immune Response to a Foreign Antigen by a Recombinant *Listeria monocytogenes* Vaccine," *Journal of Immunology* 149:53-59.

Scheirlinck, T. et al. (Sep. 1989). "Integration and Expression of α-Amylase and Endoglucanase Genes in the *Lactobacillus plantarum* Chromosome," *Applied and Environmental Microbiology* 55(9):2130-2137.

Schirle, M. et al. (Nov. 1, 2001). "Combining Computer Algorithms with Experimental Approaches Permits the Rapid and Accurate Identification of T Cell Epitopes from Defined Antigens," *J. Immunol. Methods* 257(1-2):1-16.

Schneider, G. et al. (Jun. 2004). "Advances in the Prediction of Protein Targeting Signals," *Proteomics* 4(6):1571-1580.

Schönbach. C. et al. (Jan. 1, 2002). "FIMM, a Database of Functional Molecular Immunology: Update 2002," *Nucleic Acids Res.* 30(1):226-229.

Shah, M. et al. (Oct. 12, 2003). "A Computational Pipeline for Protein Structure Prediction and Analysis at Genome Scale," *Bioinformatics* 19(15):1985-96.

Sharkov, N.A. et al. (Feb. 22, 2002). "Discovery of Substrate for Type I Signal Peptidase SpsB From *Staphylococcus aureus*," *J. Biol. Chem.* 277(8):5796-5803.

Sharma, N. et al. (Jul. 1, 2004). "Potent Role of Vaccines Prepared from Macrophages Infected with Live Bacteria in Protection against *Mycobacterium tuberculosis* and *Salmonella typhimurium* Infections," *Journal of Infectious Diseases* 190(1):107-114.

Sharp, P.M. et al. (Feb. 11, 1987). "The Codon Adaptation Index—A Measure of Directional Synonymous Codon Usage Bias, and its Potential Applications," *Nucleic Acids Res.* 15(3):1281-1295.

Shastri, N. et al. (Apr. 1, 1993). "Endogenous Generation and Presentation of the Ovalbumin Peptide/$K^b$ Complex to T Cells," *J. Immunol.* 150(7):2724-2736.

Shen, H. et al. (Apr. 25, 1995). "Recombinant *Listeria monocytogenes* as a Live Vaccine Vehicle for the Induction of Protective Anti-Viral Cell-Mediated Immunity," *Proc. Natl. Acad. Sci. USA* 92:3987-3991.

Sijts, A.J.A.M. et al. (Aug. 1, 1997). "The *Listeria monocytogenes*-Secreted p60 Protein Is an N-end Rule Substrate in the Cytosol of Infected Cells," *J. Biol. Chem.* 272(31):19261-19268.

Simmons, L.C. et al. (May 1996). "Translational Level is a Critical Factor for the Secretion of Heterologous Proteins in *Escherichia coli*," *Nature Biotechnology* 14:629-634.

Simon, R. et al. (Nov. 1983). "A Broad Host Range Mobilization System for in Vivo Genetic Engineering: Transposon Mutagenesis in Gram Negative Bacteria," *Bio/Technology* pp. 784-791.

Singh, H. et al. (Dec. 2001). "ProPred: Prediction of HLA-DR Binding Sites," *Bioinformatics* 17(12):1236-1237.

Singh, H. et al. (May 22, 2003). "ProPred1: Prediction of Promiscuous MHC Class-I Binding Sites," *Bioinformatics* 19(8):1009-1014.

Skoble, J. et al. (Aug. 7, 2000). "Three Regions Within ActA Promote Arp2/3 Complex-Mediated Actin Nucleation and *Listeria monocytogenes* Motility," *The Journal of Cell Biology* 150(3):527-537.

Skoble, J. et al. (Nov. 1999). "Identification of Regions in ActA Involved in Arp2/3 Complex-Mediated Actin Nucleation," Abstract 918, (*Abstracts presented at the 39th Annual Meeting of the American Society for Cell Biology*, Washington, DC, Dec. 11-15, 1999), *Molecular Biology of the Cell* 10(Supp):158a.

Skoble, J. et al. (Dec. 1999). "Identification of Regions in ActA Involved in Arp2/3 Complex-Mediated Actin Nucleation," Abstract 918, *Abstracts presented at the 39th Annual Meeting of the American Society for Cell Biology*, Washington, DC, Dec. 11-15, 1999, p. 158a.

Slansky, J.E. et al. (Oct. 2000). "Enhanced Antigen-Specific Antitumor Immunity with Altered Peptide Ligands that Stabilize the MHC-Peptide-TCR Complex," *Immunity* 13:529-538.

Smith, G.A. et al. (Sep. 1995). "Asymmetric Distribution of the *Listeria monocytogenes* ActA Protein is Required and Sufficient to Direct Actin-Based Motility," *Molecular Microbiology* 17(5):945-951.

Stahl, M.L. et al. (May 1984). "Replacement of the *Bacillus subtilis* Subtilisin Structural Gene with an in Vitro-Derived Deletion Mutation," *J. Bacteriology* 158(2):411-418.

Starks, H. et al. (Jul. 1, 2004). "*Listeria Monocytogenes* as a Vaccine Vector: Virulence Attenuation or Existing Antivector Immunity Does Not Diminish Therapeutic Efficacy," *Journal of Immunology* 173:420-427.

Steidler, L. et al. (Jul. 2003). "Biological Containment of Genetically Modified *Lactococcus lacti* for Intestinal Delivery of Human Interleukin 10," *Nature Biotechnology* 21(7):785-789.

Strugnell, R.A. et al. (1990). "Stable Expression of Foreign Antigens from the Chromosome of *Salmonella typhimurium* Vaccine Strains," *Gene* 88(1):57-63.

Suárez, M. et al. (Dec. 2001). "A Role for ActA in Epithelial Cell Invasion by *Listeria monocytogenes*," *Cellular Microbiology* 3(12):853-864.

Sun, A. et al. (Nov. 1990). "Isolation of *Listeria monocytogenes* Small-Plaque Mutants Defective for Intracellular Growth and Cell-To-Cell Spread," *Infect. Immun.* 58(11):3770-3778.

Svensson, M. (Jun. 1996). "Dendritic Cells Can Process Viable Bacteria and Present Bacterial Antigens on MHC-1 Molecules," Abstract No. 121, *Scandinavian Journal of Immunology* 43(6):723.

Svensson, M. et al. (May 1, 1997). "Bone Marrow-Derived Dendritic Cells Can Process Bacteria for MHC-I and MHC-II Presentation to T Cells," *The Journal of Immunology* 158(9):4229-4236.

Tatsumi, T. et al. (Aug. 1, 2003). "Disease Stage Variation in CD4+ and CD8+ T-Cell Reactivity to the Receptor Tyrosine Kinase EphA2 in Patients with Renal Cell Carcinoma," *Cancer Res.* 63(15):4481-4489.

Tjalsma, H. et al. (Sep. 2000). "Signal Peptide-Dependent Protein Transport in *Bacillus subtilis*: A Genome-Based Survey of the Secretome," *Microbiology and Molecular Biology Reviews* 64(3):515-547.

Todar, K. (2002). "Mechanisms of Bacterial Pathogenicity: Bacterial Defense Against Phagocytes," Todar's Online Textbook of Bacteriology located at <http://testbookofbacteriology.net/antiphago.html>, last visited Nov. 30, 2004, eight pages.

Tsang, K.Y. et al. (Jul. 5, 1995). "Generation of Human Cytotoxic T Cells Specific for Human Carcinoembryonic Antigen Epitopes From Patients Immunized With Recombinant Vaccinia-CEA Vaccine," *J. Natl. Cancer Inst.* 87(13):982-990.

Uchijima, M. et al. (1998). "Optimization of Codon Usage of Plasmid DNA Vaccine Is Required for the Effective MHC Class I-Restricted T Cell Responses Against an Intracellular Bacterium," *Journal of Immunology* 161:5594-5599.

Uno-Furuta, S. et al. (Jul. 4, 2003). "Immunization with Recombinant Calmette-Guerin bacillus (BCG)-hepatitis C Virus (HCV) Elicits HCV-Specific Cytotoxic T Lympocytes in Mice," *Vaccine* 21(23):3149-3156.

Van Dijl, J.M. et al. (Sep. 25, 2002). "Functional Genomic Analysis of the *Bacillus subtilis* Tat Pathway for Protein Secretion," *J. of Biotechnology* 98(2/3):243-254.

Van Regenmortel, M.H.V. et al. (Jul./Aug. 1994). "Predicting Antigenic Determinants in Proteins: Looking for Unidimensional Solutions to a Three-Dimensional Problem?" *Pept. Res.* 7(4):224-228.

Varaldo, P.B. et al. (Jun. 2004). "Recombinant *Mycobacterium bovis* BCG Expressing the Sm14 Antigen of *Schistosoma mansoni* Protects Mice from Cercarial Challenge," *Infect. Immun.* 72(6):3336-3343.

Vazquez-Boland, J-A. et al. (Jan. 1992). "Nucleotide Sequence of the Lecithinase Operon of *Listeria monocytogenes* and Possible Role of Lecithinase in Cell-to-Cell Spread," *Infection and Immunity* 60(1):219-230.

Vázquez-Boland, J.A. et al. (Jul. 2001)."*Listeria* Pathogenesis and Molecular Virulence Determinants," *Clinical Microbiology Reviews* 14(3):584-640.

Wang, H. et al. (Jun. 1993). "Optimization of the Synthesis of Porcine Somatotropin in *Escherichia coli*," *Appl. Microbiol. Biotechnol.* 39(3):324-328.

Wang, J. et al. (Jan. 1999). "Immunogenicity of Viral B-cell Epitopes Inserted into Two Surface Loops of the *Escherichia coli* K12 LamB Protein and Expressed in an Attenuated *aro A* Strain of *Salmonella typhimurium*," *Vaccine* 17(1):1-12.

Weiskirch, L.M. et al. (1997). "*Listeria monocytogenes*: A Potent Vaccine Vector for Neoplastic and Infectious Disease," *Immunological Reviews* 158:159-169.

Welch, M.D. et al. (Jul. 3, 1998). "Interaction of Human Arp2/3 Complex and the *Listeria monocytogenes* ActA Protein in Actin Filament Nucleation," *Science* 281:105-108.

Welling, G.W. et al. (Sep. 1985). "Prediction of Sequential Antigenic Regions in Proteins," *FEBS Letters* 188(2):215-218.

Wirth, R. et al. (Mar. 1986). "Highly Efficient Protoplast Transformation System for *Streptococcus faecalis* and a New *Escherichia coli-S. faecalis* Shuttle Vector," *J. Bacteriol.* 165(3):831-836.

Wolfgang, C.D. et al. (Aug. 15, 2000). "TARP: A Nuclear Protein Expressed in Prostate and Breast Cancer Cells Derived from an Alternate Reading Frame of the T Cell Receptor γ Chain Locus," *Proc. Natl. Acad. Sci. USA* 97(17):9437-9442.

Worgall, S. et al. (Jul. 2001). "Protection Against Pulmonary Infection with *Pseudomonas aeruginosa* Following Immunization with *P. aeruginosa*-Pulsed Dendritic Cells," *Infection and Immunity* 69(7):4521-4527.

Written Opinion issued for PCT Application No. PCT/US2004/044080 filed Dec. 23, 2004, mailed Aug. 19, 2005, 9 pages.

Yuan, Z. et al. (Dec. 26, 2003). "Computational Differentiation of N-Terminal Signal Peptides and Transmembrane Helices," *Biochem. Biophys. Red. Commun.* 312(4):1278-1283.

Zantek, N. D. et al. (Sep. 1999). "E-Cadherin Regulates the Function of the EphA2 Receptor Tyrosine Kinase," *Cell Growth Differ.* 10:629-638.

Zaremba, S. et al. (Oct. 15, 1997). "Identification of an Enhancer Agonist Cytotoxic T Lymphocyte Peptide From Human Carcinoembryonic Antigen," *Cancer Res.* 57:4570-4577.

Zhang, Z. et al. (Oct. 2004). "Signal Peptide Prediction Based on Analysis of Experimentally Verified Cleavage Sites," *Protein Sci.* 13(10):2819-24.

Zhou, Y. et al. (Jul. 2002). "Current Methods for Loading Dendritic Cells With Tumor Antigen for the Induction of Antitumor Immunity," *The Journal of Immunology* 25(4):289-303.

Alonso, J.C. et al. (1991). "Characterization of *recF* Suppressors in *Bacillus subtilis*," *Biochimie* 73:277-280.

Armstrong, A.C. et al. (2002). "Cellular Vaccine Therapy for Cancer," *Expert. Rev. Vaccines* 1(3):303-316.

Asano, K. et al. (May 8, 1998). "Structural Basis for Binding of the Plasmid ColIb-P9 Antisense Inc RNA to Its Target RNA with the 5'-rUUGGCG-3' Motif in the Loop Sequence," *J. Biol. Chem.* 273(19):11826-11838.

Atalla, A. et al. (Aug. 2003). "The *pst* Operon of *Bacillus subtilis* Is Specifically Induced by Alkali Stress," *J. Bacteriol.* 185(16):5019-5022.

Bahjat, K.S. et al. (Nov. 2006). "Cytosolic Entry Controls CD8$^+$-T-Cell Potency During Bacterial Infection," *Infection and Immunity* 74(11):6387-6397.

Baillie, L.W.J. et al. (Jun. 1, 1998). "A Heat-Inducible *Bacillus subtilis* Bacteriophage Φ105 Expression System for the Production of the Protective Antigen of *Bacillus anthracis*" *FEMS Microbiol. Lett.* 163(1):43-47.

Banchereau, J. et al. (Mar. 19, 1998). "Dendritic Cells and the Control of Immunity," *Nature* 392(6673):245-252.

Banchereau, J. et al. (Sep. 1, 2001). "Immune and Clinical Responses in Patients with Metastatic Melanoma to CD34$^+$ Progenitor-Derived Dendritic Cell Vaccine," *Cancer Res.* 61:6451-6458.

Belitsky, B.R. et al. (Jul. 2002). "GabR, A Member of a Novel Protein Family, Regulates the Utilization of γ-Aminobutyrate in *Bacillus subtilis*," *Mol. Microbiol.* 45(2):569-583.

Bierne, H. et al. (Nov. 1997). "*uvrD* Mutations Enhance Tandem Repeat Deletion in the *Escherichia coli* Chromosome via SOS Induction of the RecF Recombination Pathway," *Mol. Microbiol.* 26(3):557-567.

Brockstedt, D.G. et al. (Sep. 21, 2004). "*Listeria*-based Cancer Vaccines That Segregate Immunogenicity From Toxicity," Supporting Information, Table and Figures cited in *Proc. Natl. Acad. Sci. USA Data Supplement* located at <http://www.pnas.org/cgi/content/full/0406035101/DC1>, last visited on Jul. 22, 2007, 9 pages.

Campoy, S. et al. (Nov. 2002). "A New Regulatory DNA Motif of the Gamma Subclass *Proteobacteria*: Identification of the LexA Protein Binding Site of the Plant Pathogen *Xylella fastidiosa*," *Microbiology* 148:3583-3597.

Carrasco, B. et al. (2002). "Effect of the *recU* Suppressors *sms* and *subA* on DNA Repair and Homologous Recombination in *Bacillus subtilis*," *Mol. Genet. Genomics* 266:899-906.

Chan, A.Y. et al. (Oct. 10, 2003). "Interaction of a Putative Transcriptional Regulatory Protein and the Thermo-Inducible *cts*-52 Mutant Repressor in the *Bacillus subtilis* Phage φ 105 Genome," *J. Mol. Biol.* 333(1):21-31.

Chang, D.H. et al. (Jun. 2003). "Dendritic Cells and Immunotherapy for Cancer," *Int. J. Hematol.* 77(5):439-443.

Clark, A.J. (1991). "*rec* Genes and Homologous Recombination Proteins in *Escherichia coli*," *Biochemie* 73:523-532.

Coote, J.G. et al. (Jan. 1996). "A Rapid, Colourimetric Assay for Cytotoxin Activity in *Campylobacter jejuni*," *FEMS Immunol. Med. Microbiol.* 13(1):65-70.

Courcelle, J. et al. (Jul. 17, 2001). "Participation of Recombination Proteins in Rescue of Arrested Replication Forks in UV-Irradiated *Escherichia coli* Need Not Involve Recombination," *Proc. Natl. Acad. Sci. USA* 98(15):8196-8202.

Crowley, D.J. et al. (May 10, 2001). "The SOS-Dependent Upregulation of *uvrD* is not Required for Efficient Nucleotide Excision Repair of Ultraviolet Light Induced DNA Photoproducts in *Escherichia coli*," *Mutat. Res.* 485(4):319-329.

Davis, E.O. et al. (Jun. 2002). "Definition of the Mycobacterial SOS Box and Use to Identify LexA-Regulated Genes in *Mycobacterium tuberculosis*," *J. Bacteriol.* 184(12):3287-3295.

Deuerling, E. et al. (Jul. 1995). "The *ftsH* Gene of *Bacillus subtilis* Is Transiently Induced after Osmotic and Temperature Upshift," *J. Bacteriol.* 177(14):4105-4112.

Dhodapkar, M.V. et al. (May 2000). "Active Immunization of Humans with Dendritic Cells," *J. Clin. Immunol.* 20(3):167-174.

Dullaghan, E.M. et al. (Nov. 2002). "The Role of Multiple SOS Boxes Upstream of the *Mycobacterium tuberculosis lexA* Gene—Identification of a Novel DNA-Damage-Inducible Gene," *Microbiology* 148(11):3609-3615.

Esche, C. et al. (Feb. 1999). "The Use of Dendritic Cells for Cancer Vaccination," *Curr. Opin. Mol. Ther.* 1(1):72-81.

Fisher, S.H. (Apr. 1999). "Regulation of Nitrogen Metabolism in *Bacillus subtilis*: Vive La Différence!" *Mol. Microbiol.* 32(2):223-232.

Fuangthong, M. et al. (Jun. 2002). "Regulation of the *Bacillus subtilis fur* and *perR* Genes by PerR: Not All Members of the PerR Regulon Are Peroxide Inducible," *J. Bacteriol.* 184(12):3276-3286.

GenBank Accession No. AJ271621, created Nov. 14, 2006, located at <http://www.ncbi.nlm.nih.gov/entrez/viewer.fcgi?db=nuccore&id=27527038>, last visited on Jun. 30, 2007, four pages.

Genbank Accession No. NC_007530, created Apr. 3, 2006, located at <http://www.ncbi.nlm.nih.gov/entrez/viewer.fcgi?db=nucleotide&val=50196905>, last visited on May 16, 2007, 163 pages.

GenBank Accession No. V00328, created Apr. 18, 2005, located at <http://www.ncbi.nlm.nih.gov/entrez/viewer.fcgi?db=nucleotide&val=42672>, last visited on May 16, 2007, three pages.

GenBank Accession No. X81135, created Nov. 30, 2006, located at <http://www.ncbi.nlm.nih.gov/entrez/viewer.fcgi?563492:EMBL:10735862>, last visited on Jul. 22, 2007, three pages.

Haddad, E.E. et al. (Oct.-Dec. 1994). "Adaptation of the MTT (3-(4,5-Dimethylthiazol-2-y1)-2,5-Diphenyl Tetrazolium Bromide) Assay for the Determination of Virus-Neutralizing Antibodies Using the Virus-Neutralization Assay," *Avian Dis.* 38(4):755-761.

Hall, J.D. et al. (Mar. 1975). "Temperature-Sensitive *recA* Mutant of *Escherichia coli* K-12: Deoxyribonucleic Acid Metabolism After Ultraviolet Irradiation," *J. Bacteriol.* 121(3):892-900.

Hanna, M.N. et al. (Oct. 2001). "*uvrA* Is an Acid-Inducible Gene Involved in the Adaptive Response to Low pH in *Streptococcus mutans*," *J. Bacteriol.* 183(20):5964-5973.

Hecker, M. et al. (Feb. 1996). "Heat-Shock and General Stress Response in *Bacillus subtilis*," *Mol. Microbiol.* 19(3):417-428.

Hering, D. et al. (Mar. 2004). "Validation of the Anthrax Lethal Toxin Neutralization Assay," *Biologicals* 32(1):17-27.

Humrich, J. et al. (2003). "Viral Vectors for Dendritic Cell-Based Immunotherapy," Chapter 11 in *Dendritic Cells and Virus Infection*, Steinkasserer, A. ed., Springer-Verlag: Berlin, Germany, 276:241-259.

Ivánovics, G. (1962). "The Pathogenicity of *Bacillus anthracis* Lysogenic with Mutants of Phage W," *J. Gen. Microbiol.* 28:87-101.

Johansson, J. et al. (Jun. 2003). "RNA-Mediated Control of Virulence Gene Expression in Bacterial Pathogens," *Trends Microbiol.* 11(6):280-285.

Johnston, J.L. et al. (Mar. 1997). "The *RecA* Gene from *Clostridium perfringens* is Induced by Methyl Methanesulphonate and Contains an Upstream Cheo Box," *Microbiology* 143(3):885-890.

Kaan, T. et al. (Nov. 2002). "Genome-Wide Transcriptional Profiling of the *Bacillus subtilis* Cold-Shock Response," *Microbiol.* 148(11):3441-3455.

Kawai, Y. et al. (Feb. 2003). "Identification of a Protein, YneA, Responsible for Cell Division Suppression During the SOS Response in *Bacillus subtilis*," *Mol. Microbiol.* 47(4):1113-1122.

Kuzminov, A. (Dec. 1999). "Recombinational Repair of DNA Damage in *Escherichia coli* and Bacteriophage λ," *Microbiol. Mol. Biol. Rev.* 63(4):751-813.

Lecuit, M. (Dec. 1997). "Internalin of *Listeria monocytogenes* with an Intact Leucine-Rich Repeat Region Is Sufficient to Promote Internalization," *Infection and Immunity* 65(12):5309-5319.

Lin, J-J. et al. (Dec. 5, 1990). "Reconstitution of Nucleotide Excision Nuclease with UvrA and UvrB Proteins from *Escherichia coli* and UvrC Protein from *Bacillus subtilis*," *J. Biol. Chem.* 265(34):21337-21341.

Lin, L. et al. (May 1, 1994). "Photochemical Inactivation of Pathogenic Bacteria in Human Platelet Concentrates," *Blood* 83(9):2698-2706.

Lin, L. (Jan./Feb. 1998). "Psoralen Photochemical Treatment of Platelets," *Science and Medicine* pp. 2-11.

Lingnau, A. et al. (Oct. 1995). "Expression of the *Listeria monocytogenes* EGD *inlA* and *inlB* Genes, Whose Products Mediate Bacterial Entry into Tissue Culture Cell Lines, by PrfA-Dependent and -Independent Mechanisms," *Infection and Immunity* 63(10):3896-3903.

Lipman, D.J. (Sep. 15, 1997). "Making (Anti)Sense of Non-Coding Sequence Conservation," *Nucleic Acids Res.* 25(18):3580-3583.

Lovett, C.M. Jr. et al. (Nov. 1993). "Purification of an SOS Repressor from *Bacillus subtilis*," *J. Bacteriol.* 175(21):6842-6849.

Lovett, C.M. Jr. et al. (Aug. 1994). "Analysis of the SOS Inducing Signal in *Bacillus subtilis* using *Escherichia coli* LexA as a Probe," *J. Bacterial.* 176(16):4914-4923.

Lu, W. et al. (Jan. 2003). "Therapeutic Dendritic-Cell Vaccine for Simian AIDS," *Nature Medicine* 9(1):27-32.

Mao, J-R. et al. (Aug. 25, 1995). "Gene Regulation by Antisense DNA Produced in Vivo," *J. Biol. Chem.* 270(34):19684-19687.

McGuire, A.M. et al. (May 2000). "Conservation of DNA Regulatory Motifs and Discovery of New Motifs in Microbial Genomes," *Genome Res.* 10(5):744-757.

Meletiadis, J. et al. (Aug. 2000). "Comparison of NCCLS and 3-(4,5-Dimethyl-2-Thiazy1)-2,5-Diphenyl-2H-Tetrazolium Bromide (MTT) Methods of in Vitro Susceptibility Testing of Filamentous Fungi and Development of a New Simplified Method," *J. Clin. Microbiol.* 38(8):2949-2954.

Mengaud, J. et al. (Mar. 22, 1996). "E-Cadherin Is the Receptor for Internalin, a Surface Protein Required for Entry of *L. monocytogenes* into Epithelial Cells," *Cell* 84:923-932.

Miller, M.C. et al. (Dec. 27, 1996). "The *Bacillus subtilis dinR* Gene Codes for the Analogue of *Escherichia coli* LexA," *J. Biol. Chem.* 271(52):33502-33508.

Mongkolsuk, S. et al. (Jul. 2002). "Regulation of Inducible Peroxide Stress Responses," *Mol. Microbiol.* 45(1):9-15.

Mota, L.J. et al. (Jul. 2001). "Control of the Arabinose Regulon in *Bacillus subtilis* by AraR in Vivo: Crucial Roles of Operators, Cooperativity, and DNA Looping," *J. Bacteriol.* 183(14):4190-4201.

Movahedzadeh, F. et al. (Mar. 1997). "Characterization of *Mycobacterium tuberculosis* LexA: Recognition of a Cheo (*Bacillus*-type SOS) Box," *Microbiology* 143(3):929-936.

Mu, D. et al. (1997). "DNA Excision Repair Assays" in *Progress in Nucleic Acid Research and Molecular Biology*, Cohn, W.E. et al. eds., Academic Press, Inc.: San Diego, CA, 56:63-81.

Munakata, N. et al. (Nov. 1991). "Inactivation Action Spectra of *Bacillus subtilis* Spores in Extended Ultraviolet Wavelengths (50-300 nm) Obtained with Synchrotron Radiation," *Photochem. Photobiol.* 54(5):761-768.

Nickel, M. et al. (Aug. 2004). "Cold Induction of the *Bacillus subtilis bkd* Operon is Mediated by Increased mRNA Stability," *Mol. Genet. Genomics* 272(1):98-107.

Noone, D. et al. (Mar. 2000). "Expression of *ykdA*, Encoding a *Bacillus subtilis* Homologue of HtrA, Is Heat Shock Inducible and Negatively Autoregulated," *J. Bacterial.* 182(6):1592-1599.

Office Action mailed Aug. 29, 2006, for U.S. Appl. No. 10/883,599, filed Jun. 30, 2004, 7 pages.

Office Action mailed Jan. 26, 2007, for U.S. Appl. No. 10/773,618, filed Feb. 6, 2004, 22 pages.

Office Action mailed Jan. 31, 2007, for U.S. Appl. No. 10/773,792, filed Feb. 6, 2004, 20 pages.

Office Action mailed Mar. 8, 2007, for U.S. Appl. No. 10/883,599, filed Jun. 30, 2004, 6 pages.

Palucka, A.K. et al. (Sep./Oct. 2003). "Single Injection of CD34+ Progenitor-Derived Dendritic Cell Vaccine Can Lead to Induction of T-Cell Immunity in Patients With Stage IV Melanoma," *J. Immunother.* 26(5):432-439.

Ramaswamy, M. et al. (Jan. 7, 1994). "Sequence-Specific Interactions of UvrABC Endonuclease with Psoralen Interstrand Cross-Links," *J. Biol. Chem.* 269(1):485-492.

Repoila, F. et al. (Nov. 2003). "Temperature Sensing by the *dsrA* Promoter," *J. Bacteriol.* 185(22):6609-6614.

Sakamoto, T. et al. (Feb. 2002). "Regulation of the Desaturation of Fatty Acids and its Role in Tolerance to Cold and Salt Stress," *Curr. Opin. Microbiol.* 5(1):206-210.

Sancar, A. (1996). "DNA Excision Repair," *Annu. Rev. Biochem.* 65:43-81.

Santini, S.M. et al. (2003). "Advances in the Use of Dendritic Cells and New Adjuvants for the Development of Therapeutic Vaccines," *Stem Cells* 21(4):495-505.

Schofield, D.A. et al. (Jun. 2003). "Development of a Thermally Regulated Broad-Spectrum Promoter System for Use in Pathogenic Gram-Positive Species," *Appl. Environ Microbiol.* 69(6):3385-3392.

Schönert, S. et al. (Apr. 1999). "Properties of Maltose-Inducible α-Glucosidase MalL (Sucrase-Isomaltase-Maltase) in *Bacillus subtilis*: Evidence for its Contribution to Maltodextrin Utilization," *Res. Microbiol.* 150(3):167-177.

Schuler, G. et al. (Apr. 2003). "The Use of Dendritic Cells in Cancer Immunotherapy," *Curr. Opin. Immunol.* 15(2):138-147.

Stülke, J. et al. (Jul. 1997). "Induction of the *Bacillus subtilis ptsGHI* Operon by Glucose is Controlled by a Novel Antiterminator, GlcT," *Mol. Microbiol.* 25(1):65-78.

Wagner, E.G.H. et al. (1994). "Antisense RNA Control in Bacteria, Phages, and Plasmids," *Ann. Rev. Microbiol.* 48:713-742.

Walsh, S.R. et al. (Apr. 2003). "Dendritic Cells and the Promise of Therapeutic Vaccines for Human Immunodeficiency Virus (HIV)-1," *Curr. HIV Res.* 1:205-216.

Wang, B. et al. (Mar. 28, 2003). "Assessment of the Utilization of the Antisense RNA Strategy to Identify Essential Genes in Heterologous Bacteria," *FEMS Microbiol. Lett.* 220(2):171-176.

Winterling, K.W. et al. (Mar. 1997). "Characterization of DinR, the *Bacillus subtilis* SOS Repressor," *J. Bacteriol.* 179(5):1698-1703.

Wong, K.K.Y. et al. (2004). "Evidence Implicating the 5' Untranslated Region of *Listeria monocytogenes actA* in the Regulation of Bacterial Actin-Based Motility," *Cellular Microbiology* 6(2):155-166.

Yansura, D.G. et al. (Jan. 1984). "Use of the *Escherichia coli lac* Repressor and Operator to Control Gene Expression in *Bacillus subtilis*," *Proc. Natl. Acad. Sci USA* 81(2):439-443.

Yasbin, R.E. et al. (May 1992). "Inducible DNA Repair and Differentiation in *Bacillus subtilis*: Interactions Between Global Regulons," *Mol. Microbiol.* 6(10):1263-1270.

Zhang, X. et al. (Nov. 6, 2002). "Advances in Dendritic Cell-Based Vaccine of Cancer," *Cancer Biother. Radiopharm.* 17(6):601-619.

Angelakopoulos et al., "Safety and Shedding of an Attenuated Strain of *Listeria monocytogenes* with a Deletion of actA/plcB in Adult Volunteers: a Dose Escalation Study of Oral Inoculation," Infection and Immunity, Jul. 2002, pp. 3592-3601.

Blattman, Joseph N. and Philip D. Greenberg, "Cancer Immunotherapy: A Treatment for the Masses," Science 2004, vol. 305, pp. 200-205.

Friedman et al., "Induction of Human Immunodeficiency Virus (HIV)-Specific CD8 T-Cell Responses by *Listeria monocyogenes* and a Hyperattenuated *Listeria* Strain Engineered to Express HIV Antigens," Journal of Virology, Nov. 2000, pp. 9987-9993.

Gustafsson et al., "Codon bias and heterologous protein expression," TRENDS in Biotechnology, Jul. 2004, vol. 22, pp. 346-353.

Ikonomidis et al., "Delivery of a Viral Antigen to the Class I Processing and Presentation Pathway by *Listeria monocytogenes*," J. Exp. Med., Dec. 1994, vol. 180, pp. 2209-2218.

Lara-Tejero, Maria and Eric g. Pamer, "T cell responses to *Listeria monocytogenes*," Current Opinion in Microbiology, 2004, vol. 7, pp. 45-50.

Pan et al., "Regression of Established Tumors in Mice Mediated by the Oral Administration of a Recombinant *Listeria monocytogenes* Vaccine," Cancer Research, Nov. 1995, vol. 55, pp. 4776-4779.

Pardoll, Drew M., "Spinning Molecular Immunology into Successful Immunotherapy," Nature Reviews, Apr. 2002, vol. 2, pp. 227-238.

Eyre-Walker, Adam and Michael Bulmer, Nucleic Acids Research, 21(19):4599-4603 (1993).

* cited by examiner

Listeria hly DP-L4056 and EGD Alignment

Query: Listeria EGD
Subject: DP-L4056 (wild-type, Portnoy strain)

```
                                                            prfA Box
Query:   1  ggtacctccttgattagtatattcctatcttaaagtgactttatgtgttgaggcattaac  60
            ||||||||||||||||||||||||||||||||||||||||||||||||||||||||||||
Sbjct:   1  ggtacctccttgattagtatattcctatcttaaagtgactttatgtggaggcattaac   60

Query:  61  atttgttaacgacgataaagggacagcaggactagaataaagctataaagcaagcatata  120
            ||||||||  ||||| ||||||||||||||||||||||||||||||||||||||||||||
Sbjct:  61  atttgttaatgacgtcaaaaggatagcaagacaagactagaataaagctataaagcaagcatata  120

Query: 121  atattgcgtttcatctttagaagcgaattcgccaatattataattatcaaaagagaggg  180
            |||||||||||||||||||||||||||||||||||||||||||||||||||||||||||
Sbjct: 121  atattgcgtttcatctttagaagcgaattcgccaatattataattatcaaaagagaggg  180

Shine-Dalgarno      LLO start
Query: 181  gtggcaaacggtatttggcattattaggttaaaaaatgtagaaggagagtgaaacccatg  240
            ||||||||||||||||||||||||||||||||||||||||||||||||||||||||||||
Sbjct: 181  gtggcaaacggtatttggcattattaggttaaaaaatgtagaaggagagtgaaacccatg  240
```

FIGURE 1

Construct: LLO@ss-PEST-hEphA2
Native LLO signal peptide + PEST fused to full-length human EphA2
Not Codon optimized
No epitope tags (e.g., myc or FLAG used in this construct)
Fusion protein coding sequence shown

```
ATGAAAAAAATAATGCTAGTTTTTATTACACTTATATTAGTTAGTCTACCAATTGCGCAACAAACTGAA
GCAAAGGATGCATCTGCATTCAATAAAGAAAATTCAATTTCATCCATGGCACCACCAGCATCTCCGCC
TGCAAGTCCTAAGACGCCAATCGAAAAGAAACACGCGGATCTCGAGCTCCAGGCAGCCCGCGCCTGC
TTCGCCCTGCTGTGGGGCTGTGCGCTGGCCGCGGCCGCGGCGGCGCAGGGCAAGGAAGTGGTACTGCT
GGACTTTGCTGCAGCTGGAGGGGAGCTCGGCTGGCTCACACACCCGTATGGCAAAGGGTGGGACCTG
ATGCAGAACATCATGAATGACATGCCGATCTACATGTACTCCGTGTGCAACGTGATGTCTGGCGACCA
GGACAACTGGCTCCGCACCAACTGGGTGTACCGAGGAGAGGCTGAGCGTATCTTCATTGAGCTCAAGT
TTACTGTACGTGACTGCAACAGCTTCCCTGGTGGCGCCAGCTCCTGCAAGGAGACTTTCAACCTCTACT
ATGCCGAGTCGGACCTGGACTACGGCACCAACTTCCAGAAGCGCCTGTTCACCAAGATTGACACCATT
GCGCCCGATGAGATCACCGTCAGCAGCGACTTCGAGGCACGCCACGTGAAGCTGAACGTGGAGGAGC
GCTCCGTGGGGCCGCTCACCCGCAAAGGCTTCTACCTGGCCTTCCAGGATATCGGTGCCTGTGTGGCG
CTGCTCTCCGTCCGTGTCTACTACAAGAAGTGCCCCGAGCTGCTGCAGGGCCTGGCCCACTTCCCTGAG
ACCATCGCCGGCTCTGATGCACCTTCCCTGGCCACTGTGGCCGGCACCTGTGTGGACCATGCCGTGGTG
CCACCGGGGGGTGAAGAGCCCCGTATGCACTGTGCAGTGGATGGCGAGGTGGCTGGTGCCCATTGGGC
AGTGCCTGTGCCAGGCAGGCTACGAGAAGGTGGAGGATGCCTGCCAGGCCTGCTCGCCTGGATTTTTT
AAGTTTGAGGCATCTGAGAGCCCCTGCTTGGAGTGCCCTGAGCACACGCTGCCATCCCCTGAGGGTGC
CACCTCCTGCGAGTGTGAGGAAGGCTTCTTCCGGGCACCTCAGGACCCAGCGTCGATGCCTTGCACAC
GACCCCCCTCCGCCCCACACTACCTCACAGCCGTGGGCATGGGTGCCAAGGTGGAGCTGCGCTGGACG
CCCCCTCAGGACAGCGGGGGCCGCGAGGACATTGTCTACAGCGTCACCTGCGAACAGTGCTGGCCCGA
GTCTGGGGAATGCGGGCCGTGTGAGGCCAGTGTGCGCTACTCGGAGCCTCCTCACGGACTGACCCGCA
CCAGTGTGACAGTGAGCGACCTGGAGCCCCACATGAACTACACCTTCACCGTGGAGGCCCGCAATGGC
GTCTCAGGCCTGGTAACCAGCCGCAGCTTCCGTACTGCCAGTGTCAGCATCAACCAGACAGAGCCCCC
CAAGGTGAGGCTGGAGGGCCGCAGCACCACCTCGCTTAGCGTCTCCTGGAGCATCCCCCCGCCGCAGC
AGAGCCGAGTGTGGAAGTACGAGGTCACTTACCGCAAGAAGGGAGACTCCAACAGCTACAATGTGCG
CCGCACCGAGGGTTTCTCCGTGACCCTGGACGACCTGGCCCCAGACACCACCTACCTGGTCCAGGTGC
AGGCACTGACGCAGGAGGGCCAGGGGGCCGGCAGCAGGGTGCACGAATTCCAGACGCTGTCCCCGGA
GGGATCTGGCAACTTGGCGGTGATTGGCGGCGTGGCTGTCGGTGTGGTCCTGCTTCTGGTGCTGGCAG
GAGTTGGCTTCTTTATCCACCGCAGGAGGAAGAACCAGCGTGCCCGCCAGTCCCCGGAGGACGTTTAC
TTCTCCAAGTCAGAACAACTGAAGCCCCTGAAGACATACGTGGACCCCCACACATATGAGGACCCCAA
CCAGGCTGTGTTGAAGTTCACTACCGAGATCCATCCATCCTGTGTCACTCGGCAGAAGGTGATCGGAG
CAGGAGAGTTTGGGGAGGTGTACAAGGGCATGCTGAAGACATCCTCGGGGAAGAAGGAGGTGCCGGT
GGCCATCAAGACGCTGAAAGCCGGCTACACAGAGAAGCAGCGAGTGGACTTCCTCGGCGAGGCCGGC
ATCATGGGCCAGTTCAGCCACCACAACATCATCCGCCTAGAGGGCGTCATCTCCAAATACAAGCCCAT
GATGATCATCACTGAGTACATGGAGAATGGGGCCCTGGACAAGTTCCTTCGGGAGAAGGATGGCGAG
TTCAGCGTGCTGCAGCTGGTGGGCATGCTGCGGGGCATCGCAGCTGGCATGAAGTACCTGGCCAACAT
GAACTATGTGCACCGTGACCTGGCTGCCCGCAACATCCTCGTCAACAGCAACCTGGTCTGCAAGGTGT
CTGACTTTGGCCTGTCCCGCGTGCTGGAGGACGACCCCGAGGCCACCTACACCACCAGTGGCGGCAAG
ATCCCCATCCGCTGGACCGCCCCGGAGGCCATTTCCTACCGGAAGTTCACCTCTGCCAGCGACGTGTG
GAGCTTTGGCATTGTCATGTGGGAGGTGATGACCTATGGCGAGCGGCCCTACTGGGAGTTGTCCAACC
ACGAGGTGATGAAAGCCATCAATGATGGCTTCCGGCTCCCCACACCCATGGACTGCCCCTCCGCCATC
TACCAGCTCATGATGCAGTGCTGGCAGCAGGAGCGTGCCCGCCGCCCCAAGTTCGCTGACATCGTCAG
CATCCTGGACAAGCTCATTCGTGCCCCTGACTCCCTCAAGACCCTGGCTGACTTTGACCCCCGCGTGTC
TATCCGGCTCCCCAGCACGAGCGGCTCGGAGGGGGTGCCCTTCCGCACGGTGTCCGAGTGGCTGGAGT
CCATCAAGATGCAGCAGTATACGGAGCACTTCATGGCGGCCGGCTACACTGCCATCGAGAAGGTGGTG
CAGATGACCAACGACGACATCAAGAGGATTGGGGTGCGGCTGCCCGGCCACCAGAAGCGCATCGCCT
ACAGCCTGCTGGGACTCAAGGACCAGGTGAACACTGTGGGGATCCCCATC
```

FIGURE 2

Construct: LLOss-PEST-hEphA2
Native LLO signal peptide + PEST fused to full-length human EphA2
Not Codon optimized
No epitope tags (e.g., myc or FLAG used in this construct)
Predicted fusion protein shown

EphA2 EX2 domain
Native nucleotide sequence

```
CAGGGCAAGGAAGTGGTACTGCTGGACTTTGCTGCAGCTGGAGGGGAGCTCGGCTG
GCTCACACACCCGTATGGCAAAGGGTGGGACCTGATGCAGAACATCATGAATGACA
TGCCGATCTACATGTACTCCGTGTGCAACGTGATGTCTGGCGACCAGGACAACTGGC
TCCGCACCAACTGGGTGTACCGAGGAGAGGCTGAGCGTATCTTCATTGAGCTCAAGT
TTACTGTACGTGACTGCAACAGCTTCCCTGGTGGCGCCAGCTCCTGCAAGGAGACTT
TCAACCTCTACTATGCCGAGTCGGACCTGGACTACGGCACCAACTTCCAGAAGCGCC
TGTTCACCAAGATTGACACCATTGCGCCCGATGAGATCACCGTCAGCAGCGACTTCG
AGGCACGCCACGTGAAGCTGAACGTGGAGGAGCGCTCCGTGGGGCCGCTCACCCGC
AAAGGCTTCTACCTGGCCTTCCAGGATATCGGTGCCTGTGTGGCGCTGCTCTCCGTC
CGTGTCTACTACAAGAAGTGCCCCGAGCTGCTGCAGGGCCTGGCCCACTTCCCTGAG
ACCATCGCCGGCTCTGATGCACCTTCCCTGGCCACTGTGGCCGGCACCTGTGTGGAC
CATGCCGTGGTGCCACCGGGGGGTGAAGAGCCCCGTATGCACTGTGCAGTGGATGG
CGAGTGGCTGGTGCCCATTGGGCAGTGCCTGTGCCAGGCAGGCTACGAGAAGGTGG
AGGATGCCTGCCAGGCCTGCTCGCCTGGATTTTTTAAGTTTGAGGCATCTGAGAGCC
CCTGCTTGGAGTGCCCTGAGCACACGCTGCCATCCCCTGAGGGTGCCACCTCCTGCG
AGTGTGAGGAAGGCTTCTTCCGGGCACCTCAGGACCCAGCGTCGATGCCTTGCACAC
GACCCCCCTCCGCCCCACACTACCTCACAGCCGTGGGCATGGGTGCCAAGGTGGAG
CTGCGCTGGACGCCCCCTCAGGACAGCGGGGGCCGCGAGGACATTGTCTACAGCGT
CACCTGCGAACAGTGCTGGCCCGAGTCTGGGGAATGCGGGCCGTGTGAGGCCAGTG
TGCGCTACTCGGAGCCTCCTCACGGACTGACCCGCACCAGTGTGACAGTGAGCGAC
CTGGAGCCCCACATGAACTACACCTTCACCGTGGAGGCCCGCAATGGCGTCTCAGG
CCTGGTAACCAGCCGCAGCTTCCGTACTGCCAGTGTCAGCATCAACCAGACAGAGC
CCCCCAAGGTGAGGCTGGAGGGCCGCAGCACCACCTCGCTTAGCGTCTCCTGGAGC
ATCCCCCCGCCGCAGCAGAGCCGAGTGTGGAAGTACGAGGTCACTTACCGCAAGAA
GGGAGACTCCAACAGCTACAATGTGCGCCGCACCGAGGGTTTCTCCGTGACCCTGG
ACGACCTGGCCCCAGACACCACCTACCTGGTCCAGGTGCAGGCACTGACGCAGGAG
GGCCAGGGGGCCGGCAGCAGGGTGCACGAATTCCAGACG
```

FIGURE 4

EphA2 EX2 domain
Nucleotide sequence for optimal codon usage in Listeria

```
CAAGGTAAAGAAGTTGTTTTATTAGATTTTGCAGCAGCAGGTGGTGAATTAGGTTGG
TTAACACATCCATATGGTAAAGGTTGGGATTTAATGCAAAATATTATGAATGATATG
CCAATTTATATGTATAGTGTTTGTAATGTTATGAGTGGTGATCAAGATAATTGGTTAC
GTACAAATTGGGTTTATCGTGGTGAAGCAGAACGTATTTTTATTGAATTAAAATTTA
CAGTTCGTGATTGTAATAGTTTTCCAGGTGGTGCAAGTAGTTGTAAAGAAACATTTA
ATTTATATTATGCAGAAAGTGATTTAGATTATGGTACAAATTTTCAAAAACGTTTATT
TACAAAAATTGATACAATTGCACCAGATGAAATTACAGTTAGTAGTGATTTTGAAGC
ACGTCATGTTAAATTAAATGTTGAAGAACGTAGTGTTGGTCCATTAACACGTAAAGG
TTTTTATTTAGCATTTCAAGATATTGGTGCATGTGTTGCATTATTAAGTGTTCGTGTTT
ATTATAAAAAATGTCCAGAATTATTACAAGGTTTAGCACATTTTCCAGAAACAATTG
CAGGTAGTGATGCACCAAGTTTAGCAACAGTTGCAGGTACATGTGTTGATCATGCAG
TTGTTCCACCAGGTGGTGAAGAACCACGTATGCATTGTGCAGTTGATGGTGAATGGT
TAGTTCCAATTGGTCAATGTTTATGTCAAGCAGGTTATGAAAAAGTTGAAGATGCAT
GTCAAGCATGTAGTCCAGGTTTTTTTAAATTTGAAGCAAGTGAAAGTCCATGTTTAG
AATGTCCAGAACATACATTACCAAGTCCAGAAGGTGCAACAAGTTGTGAATGTGAA
GAAGGTTTTTTTCGTGCACCACAAGATCCAGCAAGTATGCCATGTACACGTCCACCA
AGTGCACCACATTATTTAACAGCAGTTGGTATGGGTGCAAAAGTTGAATTACGTTGG
ACACCACCACAAGATAGTGGTGGTCGTGAAGATATTGTTTATAGTGTTACATGTGAA
CAATGTTGGCCAGAAAGTGGTGAATGTGGTCCATGTGAAGCAAGTGTTCGTTATAGT
GAACCACCACATGGTTTAACACGTACAAGTGTTACAGTTAGTGATTTAGAACCACAT
ATGAATTATACATTTACAGTTGAAGCACGTAATGGTGTTAGTGGTTTAGTTACAAGT
CGTAGTTTTCGTACAGCAAGTGTTAGTATTAATCAAACAGAACCACCAAAAGTTCGT
TTAGAAGGTCGTAGTACAACAAGTTTAAGTGTTAGTTGGAGTATTCCACCACCACAA
CAAAGTCGTGTTTGGAAATATGAAGTTACATATCGTAAAAAAGGTGATAGTAATAG
TTATAATGTTCGTCGTACAGAAGGTTTTAGTGTTACATTAGATGATTTAGCACCAGA
TACAACATATTTAGTTCAAGTTCAAGCATTAACACAAGAAGGTCAAGGTGCAGGTA
GTCGTGTTCATGAATTTCAAACA
```

FIGURE 5

EphA2 EX2 domain
Primary Amino Acid Sequence

Construct: LLOss-PEST-EX2_hEphA2
Native LLO signal peptide + PEST fused to external domain of human EphA2
Not Codon optimized
No epitope tags (e.g., myc or FLAG used in this construct)
Fusion protein coding sequence shown ATGAAAAAAATAATGCTAGTTTTTATTACACTTATATTAGTTAGTCTACCAATTGCGC
AACAAACTGAAGCAAAGGATGCATCTGCATTCAATAAAGAAAATTCAATTTCATCC
ATGGCACCACCAGCATCTCCGCCTGCAAGTCCTAAGACGCCAATCGAAAAGAAACA
CGCGGATCTCGAGCAGGGCAAGGAAGTGGTACTGCTGGACTTTGCTGCAGCTGGAG
GGGAGCTCGGCTGGCTCACACACCCGTATGGCAAAGGGTGGGACCTGATGCAGAAC
ATCATGAATGACATGCCGATCTACATGTACTCCGTGTGCAACGTGATGTCTGGCGAC
CAGGACAACTGGCTCCGCACCAACTGGGTGTACCGAGGAGAGGCTGAGCGTATCTT
CATTGAGCTCAAGTTTACTGTACGTGACTGCAACAGCTTCCCTGGTGGCGCCAGCTC
CTGCAAGGAGACTTTCAACCTCTACTATGCCGAGTCGGACCTGGACTACGGCACCA
ACTTCCAGAAGCGCCTGTTCACCAAGATTGACACCATTGCGCCCGATGAGATCACCGT
CAGCAGCGACTTCGAGGCACGCCACGTGAAGCTGAACGTGGAGGAGCGCTCCGTGG
GGCCGCTCACCCGCAAAGGCTTCTACCTGGCCTTCCAGGATATCGGTGCCTGTGTGG
CGCTGCTCTCCGTCCGTGTCTACTACAAGAAGTGCCCCGAGCTGCTGCAGGGCCTGG
CCCACTTCCCTGAGACCATCGCCGGCTCTGATGCACCTTCCCTGGCCACTGTGGCCG
GCACCTGTGTGGACCATGCCGTGGTGCCACCGGGGGGTGAAGAGCCCCGTATGCAC
TGTGCAGTGGATGGCGAGTGGCTGGTGCCCATTGGGCAGTGCCTGTGCCAGGCAGG
CTACGAGAAGGTGGAGGATGCCTGCCAGGCCTGCTCGCCTGGATTTTTTAAGTTTGA
GGCATCTGAGAGCCCCTGCTTGGAGTGCCCTGAGCACACGCTGCCATCCCCTGAGGG
TGCCACCTCCTGCGAGTGTGAGGAAGGCTTCTTCCGGGCACCTCAGGACCCAGCGTC
GATGCCTTGCACACGACCCCCTCCGCCCCACACTACCTCACAGCCGTGGGCATGGG
TGCCAAGGTGGAGCTGCGCTGGACGCCCCCTCAGGACAGCGGGGGCCGCGAGGACA
TTGTCTACAGCGTCACCTGCGAACAGTGCTGGCCCGAGTCTGGGGAATGCGGGCCGT
GTGAGGCCAGTGTGCGCTACTCGGAGCCTCCTCACGGACTGACCCGCACCAGTGTG
ACAGTGAGCGACCTGGAGCCCCACATGAACTACACCTTCACCGTGGAGGCCCGCAA
TGGCGTCTCAGGCCTGGTAACCAGCCGCAGCTTCCGTACTGCCAGTGTCAGCATCAA
CCAGACAGAGCCCCCCAAGGTGAGGCTGGAGGGCCGCAGCACCACCTCGCTTAGCG
TCTCCTGGAGCATCCCCCCGCCGCAGCAGAGCCGAGTGTGGAAGTACGAGGTCACT
TACCGCAAGAAGGGAGACTCCAACAGCTACAATGTGCGCCGCACCGAGGGTTTCTC
CGTGACCCTGGACGACCTGGCCCCAGACACCACCTACCTGGTCCAGGTGCAGGCAC
TGACGCAGGAGGGCCAGGGGGCCGGCAGCAGGGTGCACGAATTCCAGACG

FIGURE 7

Construct: LLOss-PEST-EX2_hEphA2
Native LLO signal peptide + PEST fused to external domain of human EphA2
Not Codon optimized
No epitope tags (e.g., myc or FLAG used in this construct)
Predicted fusion protein shown M K K I M L V F I T L I L V S L P I A Q Q T E A K D A S A F N K E N
S I S S M A P P A S P P A S P K T P I E K K H A D L E Q G K E V V L
L D F A A A G G E L G W L T H P Y G K G W D L M Q N I M N D M P I
Y M Y S V C N V M S G D Q D N W L R T N W V Y R G E A E R I F I E
L K F T V R D C N S F P G G A S S C K E T F N L Y Y A E S D L D Y G
T N F Q K R L F T K I D T I A P D E I T V S S D F E A R H V K L N V E
E R S V G P L T R K G F Y L A F Q D I G A C V A L L S V R V Y Y K K
C P E L L Q G L A H F P E T I A G S D A P S L A T V A G T C V D H A
V V P P G G E E P R M H C A V D G E W L V P I G Q C L C Q A G Y E
K V E D A C Q A C S P G F F K F E A S E S P C L E C P E H T L P S P
E G A T S C E C E E G F F R A P Q D P A S M P C T R P P S A P H Y L
T A V G M G A K V E L R W T P P Q D S G G R E D I V Y S V T C E Q
C W P E S G E C G P C E A S V R Y S E P P H G L T R T S V T V S D L
E P H M N Y T F T V E A R N G V S G L V T S R S F R T A S V S I N Q
T E P P K V R L E G R S T T S L S V S W S I P P P Q Q S R V W K Y E
V T Y R K K G D S N S Y N V R R T E G F S V T L D D L A P D T T Y
L V Q V Q A L T Q E G Q G A G S R V H E F Q T

FIGURE 8

NativeLLOss-PEST-FLAG-EX2_EphA2-myc-CodonOp
(Native L. monocytogenes LLO signal peptide + PEST-Codon optimized -FLAG-EX-2 EphA2-Myc)
Nucleotide Sequence (including *hly* promoter)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAAAAAAATAATGCTAGTTTTTATTACACTTATATTAGTTAGTCTA
CCAATTGCGCAACAAACTGAAGCAAAGGATGCATCTGCATTCAATAAAGAAAATTC
AATTTCATCCATGGCACCACCAGCATCTCCGCCTGCAAGTCCTAAGACGCCAATCGA
AAAGAAACACGCGGATGGATCCGATTATAAAGATGATGATGATAAACAAGGTAAAG
AAGTTGTTTTATTAGATTTTGCAGCAGCAGGTGGTGAATTAGGTTGGTTAACACATC
CATATGGTAAAGGTTGGGATTTAATGCAAAATATTATGAATGATATGCCAATTTATA
TGTATAGTGTTTGTAATGTTATGAGTGGTGATCAAGATAATTGGTTACGTACAAATT
GGGTTTATCGTGGTGAAGCAGAACGTATTTTTATTGAATTAAAATTTACAGTTCGTG
ATTGTAATAGTTTTCCAGGTGGTGCAAGTAGTTGTAAAGAAACATTTAATTTATATT
ATGCAGAAAGTGATTTAGATTATGGTACAAATTTTCAAAAACGTTTATTTACAAAAA
TTGATACAATTGCACCAGATGAAATTACAGTTAGTAGTGATTTTGAAGCACGTCATG
TTAAATTAAATGTTGAAGAACGTAGTGTTGGTCCATTAACACGTAAAGGTTTTTATT
TAGCATTTCAAGATATTGGTGCATGTGTTGCATTATTAAGTGTTCGTGTTTATTATAA
AAAATGTCCAGAATTATTACAAGGTTTAGCACATTTTCCAGAAACAATTGCAGGTAG
TGATGCACCAAGTTTAGCAACAGTTGCAGGTACATGTGTTGATCATGCAGTTGTTCC
ACCAGGTGGTGAAGAACCACGTATGCATTGTGCAGTTGATGGTGAATGGTTAGTTCC
AATTGGTCAATGTTTATGTCAAGCAGGTTATGAAAAAGTTGAAGATGCATGTCAAGC
ATGTAGTCCAGGTTTTTTTAAATTTGAAGCAAGTGAAAGTCCATGTTTAGAATGTCC
AGAACATACATTACCAAGTCCAGAAGGTGCAACAAGTTGTGAATGTGAAGAAGGTT
TTTTTCGTGCACCACAAGATCCAGCAAGTATGCCATGTACACGTCCACCAAGTGCAC
CACATTATTTAACAGCAGTTGGTATGGGTGCAAAAGTTGAATTACGTTGGACACCAC
CACAAGATAGTGGTGGTCGTGAAGATATTGTTTATAGTGTTACATGTGAACAATGTT
GGCCAGAAAGTGGTGAATGTGGTCCATGTGAAGCAAGTGTTCGTTATAGTGAACCA
CCACATGGTTTAACACGTACAAGTGTTACAGTTAGTGATTTAGAACCACATATGAAT
TATACATTTACAGTTGAAGCACGTAATGGTGTTAGTGGTTTAGTTACAAGTCGTAGT
TTTCGTACAGCAAGTGTTAGTATTAATCAAACAGAACCACCAAAAGTTCGTTTAGAA
GGTCGTAGTACAACAAGTTTAAGTGTTAGTTGGAGTATTCCACCACCACAACAAAGT
CGTGTTTGGAAATATGAAGTTACATATCGTAAAAAAGGTGATAGTAATAGTTATAAT
GTTCGTCGTACAGAAGGTTTTAGTGTTACATTAGATGATTTAGCACCAGATACAACA
TATTTAGTTCAAGTTCAAGCATTAACACAAGAAGGTCAAGGTGCAGGTAGTCGTGTT
CATGAATTTCAAACAGAACAAAAATTAATTAGTGAAGAAGATTTATGAGAGCTC

FIGURE 9

NativeLLOss-PEST-FLAG-EX2_EphA2-myc-CodonOp
(Native L. monocytogenes LLO signal peptide + PEST-Codon optimized -FLAG-EX-2 EphA2-Myc)
Primary Amino Acid Sequence M K K I M L V F I T L I L V S L P I A Q Q T E A K D A S A F N K E N
S I S S M A P P A S P P A S P K T P I E K K H A D G S D Y K D D D D
K Q G K E V V L L D F A A A G G E L G W L T H P Y G K G W D L M
Q N I M N D M P I Y M Y S V C N V M S G D Q D N W L R T N W V Y
R G E A E R I F I E L K F T V R D C N S F P G G A S S C K E T F N L
Y Y A E S D L D Y G T N F Q K R L F T K I D T I A P D E I T V S S D
F E A R H V K L N V E E R S V G P L T R K G F Y L A F Q D I G A C V
A L L S V R V Y Y K K C P E L L Q G L A H F P E T I A G S D A P S L
A T V A G T C V D H A V V P P G G E E P R M H C A V D G E W L V P
I G Q C L C Q A G Y E K V E D A C Q A C S P G F F K F E A S E S P C
L E C P E H T L P S P E G A T S C E C E E G F F R A P Q D P A S M P
C T R P P S A P H Y L T A V G M G A K V E L R W T P P Q D S G G R
E D I V Y S V T C E Q C W P E S G E C G P C E A S V R Y S E P P H G
L T R T S V T V S D L E P H M N Y T F T V E A R N G V S G L V T S R
S F R T A S V S I N Q T E P P K V R L E G R S T T S L S V S W S I P P
P Q Q S R V W K Y E V T Y R K K G D S N S Y N V R R T E G F S V T
L D D L A P D T T Y L V Q V Q A L T Q E G Q G A G S R V H E F Q T
E Q K L I S E E D L

FIGURE 10

Codon Optimized LLOss-PEST-FLAG-EX2_EphA2-myc-CodonOp
(Codon Optimized L. monocytogenes LLO signal peptide + PEST-Codon optimized -FLAG-EX-2 EphA2-Myc)
Nucleotide Sequence (including *hly* promoter)

```
GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAAAAAAATTATGTTAGTTTTTATTACATTAATTTTAGTTAGTTTAC
CAATTGCACAACAAACAGAAGCAAAAGATGCAAGTGCATTTAATAAAGAAAATAGT
ATTAGTAGTATGGCACCACCAGCAAGTCCACCAGCAAGTCCAAAAACACCAATTGA
AAAAAAACATGCAGATGGATCCGATTATAAAGATGATGATGATAAACAAGGTAAAG
AAGTTGTTTTATTAGATTTTGCAGCAGCAGGTGGTGAATTAGGTTGGTTAACACATC
CATATGGTAAAGGTTGGGATTTAATGCAAAATATTATGAATGATATGCCAATTTATA
TGTATAGTGTTTGTAATGTTATGAGTGGTGATCAAGATAATTGGTTACGTACAAATT
GGGTTTATCGTGGTGAAGCAGAACGTATTTTTATTGAATTAAAATTTACAGTTCGTG
ATTGTAATAGTTTTCCAGGTGGTGCAAGTAGTTGTAAAGAAACATTTAATTTATATT
ATGCAGAAAGTGATTTAGATTATGGTACAAATTTTCAAAAACGTTTATTTACAAAAA
TTGATACAATTGCACCAGATGAAATTACAGTTAGTAGTGATTTTGAAGCACGTCATG
TTAAATTAAATGTTGAAGAACGTAGTGTTGGTCCATTAACACGTAAAGGTTTTTATT
TAGCATTTCAAGATATTGGTGCATGTGTTGCATTATTAAGTGTTCGTGTTTATTATAA
AAAATGTCCAGAATTATTACAAGGTTTAGCACATTTTCCAGAAACAATTGCAGGTAG
TGATGCACCAAGTTTAGCAACAGTTGCAGGTACATGTGTTGATCATGCAGTTGTTCC
ACCAGGTGGTGAAGAACCACGTATGCATTGTGCAGTTGATGGTGAATGGTTAGTTCC
AATTGGTCAATGTTTATGTCAAGCAGGTTATGAAAAAGTTGAAGATGCATGTCAAGC
ATGTAGTCCAGGTTTTTTTAAATTTGAAGCAAGTGAAAGTCCATGTTTAGAATGTCC
AGAACATACATTACCAAGTCCAGAAGGTGCAACAAGTTGTGAATGTGAAGAAGGTT
TTTTTCGTGCACCACAAGATCCAGCAAGTATGCCATGTACACGTCCACCAAGTGCAC
CACATTATTTAACAGCAGTTGGTATGGGTGCAAAAGTTGAATTACGTTGGACACCAC
CACAAGATAGTGGTGGTCGTGAAGATATTGTTTATAGTGTTACATGTGAACAATGTT
GGCCAGAAAGTGGTGAATGTGGTCCATGTGAAGCAAGTGTTCGTTATAGTGAACCA
CCACATGGTTTAACACGTACAAGTGTTACAGTTAGTGATTTAGAACCACATATGAAT
TATACATTTACAGTTGAAGCACGTAATGGTGTTAGTGGTTTAGTTACAAGTCGTAGT
TTTCGTACAGCAAGTGTTAGTATTAATCAAACAGAACCACCAAAAGTTCGTTTAGAA
GGTCGTAGTACAACAAGTTTAAGTGTTAGTTGGAGTATTCCACCACCACAACAAAGT
CGTGTTTGGAAATATGAAGTTACATATCGTAAAAAAGGTGATAGTAATAGTTATAAT
GTTCGTCGTACAGAAGGTTTTAGTGTTACATTAGATGATTTAGCACCAGATACAACA
TATTTAGTTCAAGTTCAAGCATTAACACAAGAAGGTCAAGGTGCAGGTAGTCGTGTT
CATGAATTTCAAACAGAACAAAAATTAATTAGTGAAGAAGATTTATGAGAGCTC
```

FIGURE 11

Codon Optimized LLOss-PEST-FLAG-EX2_EphA2-myc-CodonOp
(Codon Optimized L. monocytogenes LLO signal peptide + PEST-Codon optimized -FLAG-EX-2 EphA2-Myc)
Primary Amino Acid Sequence MKKIMLVFITLILVSLPIAQQTEAKDASAFNKEN
SISSMAPPASPPASPKTPIEKKHADGSDYKDDDD
KQGKEVVLLDFAAAGGELGWLTHPYGKGWDLM
QNIMNDMPIYMYSVCNVMSGDQDNWLRTNWVY
RGEAERIFIELKFTVRDCNSFPGGASSCKETFNL
YYAESDLDYGTNFQKRLFTKIDTIAPDEITVSSD
FEARHVKLNVEERSVGPLTRKGFYLAFQDIGACV
ALLSVRVYYKKCPELLQGLAHFPETIAGSDAPSL
ATVAGTCVDHAVVPPGGEEPRMHCAVDGEWLVP
IGQCLCQAGYEKVEDACQACSPGFFKFEASESPC
LECPEHTLPSPEGATSCECEEGFFRAPQDPASMP
CTRPPSAPHYLTAVGMGAKVELRWTPPQDSGGR
EDIVYSVTCEQCWPESGECGPCEASVRYSEPPHG
LTRTSVTVSDLEPHMNYTFTVEARNGVSGLVTSR
SFRTASVSINQTEPPKVRLEGRSTTSLSVSWSIPP
PQQSRVWKYEVTYRKKGDSNSYNVRRTEGFSVT
LDDLAPDTTYLVQVQALTQEGQGAGSRVHEFQT
EQKLISEEDL

FIGURE 12

PhoD-FLAG-EX2_EphA2-myc-CodonOp
(Codon optimized B. subtilis phoD Tat signal peptide-FLAG-EX-2 EphA2-Myc)
Nucleotide Sequence (including *hly* promoter)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGGCATACGACAGTCGTTTTGATGAATGGGTACAGAAACTGAAAGA
GGAAAGCTTTCAAAACAATACGTTTGACCGCCGCAAATTTATTCAAGGAGCGGGGA
AGATTGCAGGACTTTCTCTTGGATTAACGATTGCCCAGTCGGTTGGGGCCTTTGGAT
CCGATTATAAAGATGATGATGATAAACAAGGTAAAGAAGTTGTTTTATTAGATTTTG
CAGCAGCAGGTGGTGAATTAGGTTGGTTAACACATCCATATGGTAAAGGTTGGGATT
TAATGCAAAATATTATGAATGATATGCCAATTTATATGTATAGTGTTTGTAATGTTAT
GAGTGGTGATCAAGATAATTGGTTACGTACAAATTGGGTTTATCGTGGTGAAGCAGA
ACGTATTTTTATTGAATTAAAATTTACAGTTCGTGATTGTAATAGTTTTCCAGGTGGT
GCAAGTAGTTGTAAAGAAACATTTAATTTATATTATGCAGAAAGTGATTTAGATTAT
GGTACAAATTTTCAAAAACGTTTATTTACAAAAATTGATACAATTGCACCAGATGAA
ATTACAGTTAGTAGTGATTTTGAAGCACGTCATGTTAAATTAAATGTTGAAGAACGT
AGTGTTGGTCCATTAACACGTAAAGGTTTTTATTTAGCATTTCAAGATATTGGTGCAT
GTGTTGCATTATTAAGTGTTCGTGTTTATTATAAAAAATGTCCAGAATTATTACAAG
GTTTAGCACATTTTCCAGAAACAATTGCAGGTAGTGATGCACCAAGTTTAGCAACAG
TTGCAGGTACATGTGTTGATCATGCAGTTGTTCCACCAGGTGGTGAAGAACCACGTA
TGCATTGTGCAGTTGATGGTGAATGGTTAGTTCCAATTGGTCAATGTTATGTCAAG
CAGGTTATGAAAAAGTTGAAGATGCATGTCAAGCATGTAGTCCAGGTTTTTTTAAAT
TTGAAGCAAGTGAAAGTCCATGTTTAGAATGTCCAGAACATACATTACCAAGTCCAG
AAGGTGCAACAAGTTGTGAATGTGAAGAAGGTTTTTTTCGTGCACCACAAGATCCAG
CAAGTATGCCATGTACACGTCCACCAAGTGCACCACATTATTTAACAGCAGTTGGTA
TGGGTGCAAAAGTTGAATTACGTTGGACACCACCACAAGATAGTGGTGGTCGTGAA
GATATTGTTTATAGTGTTACATGTGAACAATGTTGGCCAGAAAGTGGTGAATGTGGT
CCATGTGAAGCAAGTGTTCGTTATAGTGAACCACCACATGGTTTAACACGTACAAGT
GTTACAGTTAGTGATTTAGAACCACATATGAATTATACATTTACAGTTGAAGCACGT
AATGGTGTTAGTGGTTTAGTTACAAGTCGTAGTTTTCGTACAGCAAGTGTTAGTATT
AATCAAACAGAACCACCAAAAGTTCGTTTAGAAGGTCGTAGTACAACAAGTTTAAG
TGTTAGTTGGAGTATTCCACCACCACAACAAAGTCGTGTTTGGAAATATGAAGTTAC
ATATCGTAAAAAAGGTGATAGTAATAGTTATAATGTTCGTCGTACAGAAGGTTTTAG
TGTTACATTAGATGATTTAGCACCAGATACAACATATTTAGTTCAAGTTCAAGCATT
AACACAAGAAGGTCAAGGTGCAGGTAGTCGTGTTCATGAATTTCAAACAGAACAAA
AATTAATTAGTGAAGAAGATTTATGAGAGCTC

FIGURE 13

PhoD-FLAG-EX2_EphA2-myc-CodonOp
(Codon optimized B. subtilis phoD Tat signal peptide-FLAG-EX-2 EphA2-Myc)
Amino acid sequence MAYDSRFDEWVQKLKEESFQNNTFDRRKFIQGA
GKIAGLSLGLTIAQSVGAFGSDYKDDDDKQGKE
VVLLDFAAAGGELGWLTHPYGKGWDLMQNIMN
DMPIYMYSVCNVMSGDQDNWLRTNWVYRGEAE
RIFIELKFTVRDCNSFPGGASSCKETFNLYYAES
DLDYGTNFQKRLFTKIDTIAPDEITVSSDFEARH
VKLNVEERSVGPLTRKGFYLAFQDIGACVALLSV
RVYYKKCPELLQGLAHFPETIAGSDAPSLATVAG
TCVDHAVVPPGGEEPRMHCAVDGEWLVPIGQCL
CQAGYEKVEDACQACSPGFFKFEASESPCLECPE
HTLPSPEGATSCECEEGFFRAPQDPASMPCTRPP
SAPHYLTAVGMGAKVELRWTPPQDSGGREDIVY
SVTCEQCWPESGECGPCEASVRYSEPPHGLTRTS
VTVSDLEPHMNYTFTVEARNGVSGLVTSRSFRTA
SVSINQTEPPKVRLEGRSTTSLSVSWSIPPPQQSR
VWKYEVTYRKKGDSNSYNVRRTEGFSVTLDDLA
PDTTYLVQVQALTQEGQGAGSRVHEFQTEQKLIS
EEDL

FIGURE 14

EphA2 CO domain
Native nucleotide sequence

CACCGCAGGAGGAAGAACCAGCGTGCCCGCCAGTCCCCGGAGGACGTTTACTTCTC
CAAGTCAGAACAACTGAAGCCCCTGAAGACATACGTGGACCCCCACACATATGAGG
ACCCCAACCAGGCTGTGTTGAAGTTCACTACCGAGATCCATCCATCCTGTGTCACTC
GGCAGAAGGTGATCGGAGCAGGAGAGTTTGGGGAGGTGTACAAGGGCATGCTGAA
GACATCCTCGGGGAAGAAGGAGGTGCCGGTGGCCATCAAGACGCTGAAAGCCGGCT
ACACAGAGAAGCAGCGAGTGGACTTCCTCGGCGAGGCCGGCATCATGGGCCAGTTC
AGCCACCACAACATCATCCGCCTAGAGGGCGTCATCTCCAAATACAAGCCCATGAT
GATCATCACTGAGTACATGGAGAATGGGGCCCTGGACAAGTTCCTTCGGGAGAAGG
ATGGCGAGTTCAGCGTGCTGCAGCTGGTGGGCATGCTGCGGGGCATCGCAGCTGGC
ATGAAGTACCTGGCCAACATGAACTATGTGCACCGTGACCTGGCTGCCCGCAACATC
CTCGTCAACAGCAACCTGGTCTGCAAGGTGTCTGACTTTGGCCTGTCCCGCGTGCTG
GAGGACGACCCCGAGGCCACCTACACCACCAGTGGCGGCAAGATCCCCATCCGCTG
GACCGCCCCGGAGGCCATTTCCTACCGGAAGTTCACCTCTGCCAGCGACGTGTGGAG
CTTTGGCATTGTCATGTGGGAGGTGATGACCTATGGCGAGCGGCCCTACTGGGAGTT
GTCCAACCACGAGGTGATGAAAGCCATCAATGATGGCTTCCGGCTCCCCACACCCAT
GGACTGCCCCTCCGCCATCTACCAGCTCATGATGCAGTGCTGGCAGCAGGAGCGTGC
CCGCCGCCCCAAGTTCGCTGACATCGTCAGCATCCTGGACAAGCTCATTCGTGCCCC
TGACTCCCTCAAGACCCTGGCTGACTTTGACCCCGCGTGTCTATCCGGCTCCCCAG
CACGAGCGGCTCGGAGGGGGTGCCCTTCCGCACGGTGTCCGAGTGGCTGGAGTCCA
TCAAGATGCAGCAGTATACGGAGCACTTCATGGCGGCCGGCTACACTGCCATCGAG
AAGGTGGTGCAGATGACCAACGACGACATCAAGAGGATTGGGGTGCGGCTGCCCGG
CCACCAGAAGCGCATCGCCTACAGCCTGCTGGGACTCAAGGACCAGGTGAACACTG
TGGGGATCCCCATC

FIGURE 15

EphA2 CO domain
Nucleotide sequence for optimal codon usage in Listeria

CACAGACGTAGAAAAAATCAACGTGCTCGACAATCCCCAGAAGATGTGTATTTTCG
AAAAGTGAACAATTAAAACCATTAAAAACTTATGTTGATCCGCATACGTACGAAGA
CCCAAATCAAGCAGTATTAAAATTTACAACAGAAATACACCCAAGTTGTGTTACAA
GACAAAAAGTTATTGGAGCAGGTGAATTCGGAGAGGTATATAAAGGTATGTTAAAA
ACATCATCAGGTAAAAAAGAAGTTCCGGTTGCAATTAAAACCTTAAAGGCAGGATA
TACAGAAAACAGCGAGTTGATTTTTAGGTGAAGCAGGAATTATGGGTCAATTTAG
CCATCATAATATTATTCGTTTGGAAGGAGTAATAAGTAAATATAAACCAATGATGAT
TATTACAGAATACATGGAAAACGGTGCTTTAGATAAATTTTACGTGAAAAGGATGG
TGAATTTAGTGTTTTACAATTGGTTGGTATGTTAAGAGGAATTGCTGCAGGTATGAA
ATATTTAGCTAATATGAATTATGTTCACCGTGATTTGGCAGCAAGAAATATCCTAGT
CAATTCCAATTTAGTATGTAAAGTTAGTGATTTTGGTTTAAGCAGAGTATTAGAAGA
CGATCCAGAGGCAACCTATACAACATCGGGAGGTAAAATTCCTATTCGTTGGACAG
CACCAGAAGCTATCAGTTACCGTAAATTTACAAGTGCATCAGACGTGTGGAGTTTTG
GGATTGTAATGTGGGAAGTTATGACATATGGAGAAAGACCATATTGGGAATTAAGT
AATCATGAAGTTATGAAAGCAATTAACGATGGATTTAGATTACCAACTCCGATGGAT
TGTCCATCTGCCATTTATCAACTAATGATGCAATGTTGGCAACAAGAAAGAGCACGA
CGTCCAAAATTTGCAGATATTGTTAGTATTTTAGACAAATTAATTCGTGCACCAGAT
AGTTTAAAAACTTTAGCAGACTTTGATCCTCGTGTTAGTATTCGATTACCAAGTACGT
CAGGTTCCGAAGGAGTTCCATTTCGCACAGTCTCCGAATGGTTGGAATCAATTAAAA
TGCAACAATACACCGAACACTTTATGGCAGCAGGTTACACAGCAATCGAAAAAGTT
GTTCAAATGACAAATGATGATATTAAACGTATTGGAGTTAGATTACCAGGCCACCAG
AAACGTATTGCATATTCTTTATTAGGTTTAAAAGATCAAGTTAATACCGTGGGAATT
CCAATT

FIGURE 16

EphA2 CO domain
Primary Amino Acid Sequence

Construct: LLOss-PEST-CO-huEphA2
Native LLO signal peptide + PEST fused to cytoplasmic domain of human EphA2
Not Codon optimized
No epitope tags (e.g., myc or FLAG used in this construct)
Fusion protein coding sequence shown

```
ATGAAAAAAATAATGCTAGTTTTTATTACACTTATATTAGTTAGTCTACCAATTGCGC
AACAAACTGAAGCAAAGGATGCATCTGCATTCAATAAAGAAAATTCAATTTCATCC
ATGGCACCACCAGCATCTCCGCCTGCAAGTCCTAAGACGCCAATCGAAAAGAAACA
CGCGGATCTCGAGCACCGCAGGAGGAAGAACCAGCGTGCCCGCCAGTCCCCGGAGG
ACGTTTACTTCTCCAAGTCAGAACAACTGAAGCCCCTGAAGACATACGTGGACCCC
ACACATATGAGGACCCCAACCAGGCTGTGTTGAAGTTCACTACCGAGATCCATCCAT
CCTGTGTCACTCGGCAGAAGGTGATCGGAGCAGGAGAGTTTGGGGAGGTGTACAAG
GGCATGCTGAAGACATCCTCGGGGAAGAAGGAGGTGCCGGTGGCCATCAAGACGCT
GAAAGCCGGCTACACAGAGAAGCAGCGAGTGGACTTCCTCGGCGAGGCCGGCATCA
TGGGCCAGTTCAGCCACCACAACATCATCCGCCTAGAGGGCGTCATCTCCAAATACA
AGCCCATGATGATCATCACTGAGTACATGGAGAATGGGGCCCTGGACAAGTTCCTTC
GGGAGAAGGATGGCGAGTTCAGCGTGCTGCAGCTGGTGGGCATGCTGCGGGGCATC
GCAGCTGGCATGAAGTACCTGGCCAACATGAACTATGTGCACCGTGACCTGGCTGC
CCGCAACATCCTCGTCAACAGCAACCTGGTCTGCAAGGTGTCTGACTTTGGCCTGTC
CCGCGTGCTGGAGGACGACCCCGAGGCCACCTACACCACCAGTGGCGGCAAGATCC
CCATCCGCTGGACCGCCCCGGAGGCCATTTCCTACCGGAAGTTCACCTCTGCCAGCG
ACGTGTGGAGCTTTGGCATTGTCATGTGGGAGGTGATGACCTATGGCGAGCGGCCCT
ACTGGGAGTTGTCCAACCACGAGGTGATGAAAGCCATCAATGATGGCTTCCGGCTCC
CCACACCCATGGACTGCCCCTCCGCCATCTACCAGCTCATGATGCAGTGCTGGCAGC
AGGAGCGTGCCCGCCGCCCCAAGTTCGCTGACATCGTCAGCATCCTGGACAAGCTC
ATTCGTGCCCCTGACTCCCTCAAGACCCTGGCTGACTTTGACCCCCGCGTGTCTATCC
GGCTCCCCAGCACGAGCGGCTCGGAGGGGGTGCCCTTCCGCACGGTGTCCGAGTGG
CTGGAGTCCATCAAGATGCAGCAGTATACGGAGCACTTCATGGCGGCCGGCTACAC
TGCCATCGAGAAGGTGGTGCAGATGACCAACGACGACATCAAGAGGATTGGGGTGC
GGCTGCCCGGCCACCAGAAGCGCATCGCCTACAGCCTGCTGGGACTCAAGGACCAG
GTGAACACTGTGGGGATCCCCATC
```

FIGURE 18

Construct: LLOss-PEST-CO-huEphA2
Native LLO signal peptide + PEST fused to cytoplasmic domain of human EphA2
Not Codon optimized
No epitope tags (e.g., myc or FLAG used in this construct)
Predicted fusion protein shown M K K I M L V F I T L I L V S L P I A Q Q T E A K D A S A F N K E N
S I S S M A P P A S P P A S P K T P I E K K H A D L E H R R R K N Q
R A R Q S P E D V Y F S K S E Q L K P L K T Y V D P H T Y E D P N Q
A V L K F T T E I H P S C V T R Q K V I G A G E F G E V Y K G M L K
T S S G K K E V P V A I K T L K A G Y T E K Q R V D F L G E A G I M
G Q F S H H N I I R L E G V I S K Y K P M M I I T E Y M E N G A L D
K F L R E K D G E F S V L Q L V G M L R G I A A G M K Y L A N M N
Y V H R D L A A R N I L V N S N L V C K V S D F G L S R V L E D D P
E A T Y T T S G G K I P I R W T A P E A I S Y R K F T S A S D V W S
F G I V M W E V M T Y G E R P Y W E L S N H E V M K A I N D G F R
L P T P M D C P S A I Y Q L M M Q C W Q Q E R A R R P K F A D I V
S I L D K L I R A P D S L K T L A D F D P R V S I R L P S T S G S E G
V P F R T V S E W L E S I K M Q Q Y T E H F M A A G Y T A I E K V
V Q M T N D D I K R I G V R L P G H Q K R I A Y S L L G L K D Q V N
T V G I P I

FIGURE 19

NativeLLOss-PEST-FLAG-CO_EphA2-myc-CodonOp
(Native L. monocytogenes LLO signal peptide + PEST-Codon optimized -FLAG-CO_EphA2-Myc)
Nucleotide Sequence (including *hly* promoter)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAAAAAAATAATGCTAGTTTTTATTACACTTATATTAGTTAGTCTA
CCAATTGCGCAACAAACTGAAGCAAAGGATGCATCTGCATTCAATAAAGAAAATTC
AATTTCATCCATGGCACCACCAGCATCTCCGCCTGCAAGTCCTAAGACGCCAATCGA
AAAGAAACACGCGGATGGATCCGATTATAAAGATGATGATGATAAACACAGACGTA
GAAAAAATCAACGTGCTCGACAATCCCCAGAAGATGTGTATTTTCGAAAAGTGAA
CAATTAAAACCATTAAAAACTTATGTTGATCCGCATACGTACGAAGACCCAAATCAA
GCAGTATTAAAATTTACAACAGAAATACACCCAAGTTGTGTTACAAGACAAAAAGT
TATTGGAGCAGGTGAATTCGGAGAGGTATATAAAGGTATGTTAAAAACATCATCAG
GTAAAAAAGAAGTTCCGGTTGCAATTAAAACCTTAAAGGCAGGATATACAGAAAAA
CAGCGAGTTGATTTTTTAGGTGAAGCAGGAATTATGGGTCAATTTAGCCATCATAAT
ATTATTCGTTTGGAAGGAGTAATAAGTAAATATAAACCAATGATGATTATTACAGAA
TACATGGAAAACGGTGCTTTAGATAAATTTTTACGTGAAAAGGATGGTGAATTTAGT
GTTTTACAATTGGTTGGTATGTTAAGAGGAATTGCTGCAGGTATGAAATATTTAGCT
AATATGAATTATGTTCACCGTGATTTGGCAGCAAGAAATATCCTAGTCAATTCCAAT
TTAGTATGTAAAGTTAGTGATTTTGGTTTAAGCAGAGTATTAGAAGACGATCCAGAG
GCAACCTATACAACATCGGGAGGTAAAATTCCTATTCGTTGGACAGCACCAGAAGC
TATCAGTTACCGTAAATTTACAAGTGCATCAGACGTGTGGAGTTTTGGGATTGTAAT
GTGGGAAGTTATGACATATGGAGAAAGACCATATTGGGAATTAAGTAATCATGAAG
TTATGAAAGCAATTAACGATGGATTTAGATTACCAACTCCGATGGATTGTCCATCTG
CCATTTATCAACTAATGATGCAATGTTGGCAACAAGAAAGAGCACGACGTCCAAAA
TTTGCAGATATTGTTAGTATTTTAGACAAATTAATTCGTGCACCAGATAGTTTAAAA
ACTTTAGCAGACTTTGATCCTCGTGTTAGTATTCGATTACCAAGTACGTCAGGTTCCG
AAGGAGTTCCATTTCGCACAGTCTCCGAATGGTTGGAATCAATTAAAATGCAACAAT
ACACCGAACACTTTATGGCAGCAGGTTACACAGCAATCGAAAAAGTTGTTCAAATG
ACAAATGATGATATTAAACGTATTGGAGTTAGATTACCAGGCCACCAGAAACGTATT
GCATATTCTTTATTAGGTTTAAAAGATCAAGTTAATACCGTGGGAATTCCAATTGAA
CAAAAATTAATTTCCGAAGAAGACTTATAAGAGCTC

FIGURE 20

NativeLLOss-PEST-FLAG-CO_EphA2-myc-CodonOp
(Native L. monocytogenes LLO signal peptide + PEST-Codon optimized -FLAG-CO_EphA2-Myc)
Primary Amino Acid Sequence

Codon Optimized LLOss-PEST-FLAG-CO_EphA2-myc-CodonOp
(Codon Optimized L. monocytogenes LLO signal peptide + PEST-Codon optimized -FLAG-
CO_EphA2-Myc)
Nucleotide Sequence (including *hly* promoter)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAAAAAAATTATGTTAGTTTTATTACATTAATTTTAGTTAGTTTAC
CAATTGCACAACAAACAGAAGCAAAAGATGCAAGTGCATTTAATAAAGAAAATAGT
ATTAGTAGTATGGCACCACCAGCAAGTCCACCAGCAAGTCCAAAAACACCAATTGA
AAAAAAACATGCAGATGGATCCGATTATAAAGACGATGATGATAAACACAGACGTA
GAAAAAATCAACGTGCTCGACAATCCCCAGAAGATGTGTATTTTCGAAAAGTGAA
CAATTAAAACCATTAAAAACTTATGTTGATCCGCATACGTACGAAGACCCAAATCAA
GCAGTATTAAAATTTACAACAGAAATACACCCAAGTTGTGTTACAAGACAAAAAGT
TATTGGAGCAGGTGAATTCGGAGAGGTATATAAAGGTATGTTAAAAACATCATCAG
GTAAAAAAGAAGTTCCGGTTGCAATTAAAACCTTAAAGGCAGGATATACAGAAAAA
CAGCGAGTTGATTTTTAGGTGAAGCAGGAATTATGGGTCAATTTAGCCATCATAAT
ATTATTCGTTTGGAAGGAGTAATAAGTAAATATAAACCAATGATGATTATTACAGAA
TACATGGAAAACGGTGCTTTAGATAAATTTTTACGTGAAAAGGATGGTGAATTTAGT
GTTTTACAATTGGTTGGTATGTTAAGAGGAATTGCTGCAGGTATGAAATATTTAGCT
AATATGAATTATGTTCACCGTGATTTGGCAGCAAGAAATATCCTAGTCAATTCCAAT
TTAGTATGTAAAGTTAGTGATTTTGGTTTAAGCAGAGTATTAGAAGACGATCCAGAG
GCAACCTATACAACATCGGGAGGTAAAATTCCTATTCGTTGGACAGCACCAGAAGC
TATCAGTTACCGTAAATTTACAAGTGCATCAGACGTGTGGAGTTTTGGGATTGTAAT
GTGGGAAGTTATGACATATGGAGAAAGACCATATTGGGAATTAAGTAATCATGAAG
TTATGAAAGCAATTAACGATGGATTTAGATTACCAACTCCGATGGATTGTCCATCTG
CCATTTATCAACTAATGATGCAATGTTGGCAACAAGAAAGAGCACGACGTCCAAAA
TTTGCAGATATTGTTAGTATTTTAGACAAATTAATTCGTGCACCAGATAGTTTAAAA
ACTTTAGCAGACTTTGATCCTCGTGTTAGTATTCGATTACCAAGTACGTCAGGTTCCG
AAGGAGTTCCATTTCGCACAGTCTCCGAATGGTTGGAATCAATTAAAATGCAACAAT
ACACCGAACACTTTATGGCAGCAGGTTACACAGCAATCGAAAAAGTTGTTCAAATG
ACAAATGATGATATTAAACGTATTGGAGTTAGATTACCAGGCCACCAGAAACGTATT
GCATATTCTTTATTAGGTTTAAAAGATCAAGTTAATACCGTGGGAATTCCAATTGAA
CAAAAATTAATTTCCGAAGAAGACTTATAAGAGCTC

FIGURE 22

Codon Optimized LLOss-PEST-FLAG-CO_EphA2-myc-CodonOp
(Codon Optimized L. monocytogenes LLO signal peptide + PEST-Codon optimized -FLAG-CO_EphA2-Myc)
Primary Amino Acid Sequence MKKIMLVFITLILVSLPIAQQTEAKDASAFNKEN
SISSMAPPASPPASPKTPIEKKHADGSDYKDDDD
KHRRRKNQRARQSPEDVYFSKSEQLKPLKTYVD
PHTYEDPNQAVLKFTTEIHPSCVTRQKVIGAGEF
GEVYKGMLKTSSGKKEVPVAIKTLKAGYTEKQR
VDFLGEAGIMGQFSHHNIIRLEGVISKYKPMMIIT
EYMENGALDKFLREKDGEFSVLQLVGMLRGIAA
GMKYLANMNYVHRDLAARNILVNSNLVCKVSDF
GLSRVLEDDPEATYTTSGGKIPIRWTAPEAISYR
KFTSASDVWSFGIVMWEVMTYGERPYWELSNHE
VMKAINDGFRLPTPMDCPSAIYQLMMQCWQQER
ARRPKFADIVSILDKLIRAPDSLKTLADFDPRVSI
RLPSTSGSEGVPFRTVSEWLESIKMQQYTEHFMA
AGYTAIEKVVQMTNDDIKRIGVRLPGHQKRIAYS
LLGLKDQVNTVGIPIEQKLISEEDL

FIGURE 23

PhoD-FLAG-CO_EphA2-myc-CodonOp
(Codon optimized B. subtilis phoD Tat signal peptide-FLAG-CO_EphA2-Myc)
Nucleotide Sequence (including *hly* promoter)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGGCATACGACAGTCGTTTTGATGAATGGGTACAGAAACTGAAAGA
GGAAAGCTTTCAAAACAATACGTTTGACCGCCGCAAATTTATTCAAGGAGCGGGGA
AGATTGCAGGACTTTCTCTTGGATTAACGATTGCCCAGTCGGTTGGGGCCTTTGGAT
CCGATTATAAAGATGATGATGATAAACACAGACGTAGAAAAAATCAACGTGCTCGA
CAATCCCCAGAAGATGTGTATTTTCGAAAGTGAACAATTAAAACCATTAAAAACT
TATGTTGATCCGCATACGTACGAAGACCCAAATCAAGCAGTATTAAAATTTACAACA
GAAATACACCCAAGTTGTGTTACAAGACAAAAAGTTATTGGAGCAGGTGAATTCGG
AGAGGTATATAAAGGTATGTTAAAAACATCATCAGGTAAAAAGAAGTTCCGGTTG
CAATTAAAACCTTAAAGGCAGGATATACAGAAAAACAGCGAGTTGATTTTTTAGGT
GAAGCAGGAATTATGGGTCAATTTAGCCATCATAATATTATTCGTTTGGAAGGAGTA
ATAAGTAAATATAAACCAATGATGATTATTACAGAATACATGGAAAACGGTGCTTT
AGATAAATTTTTACGTGAAAAGGATGGTGAATTTAGTGTTTTACAATTGGTTGGTAT
GTTAAGAGGAATTGCTGCAGGTATGAAATATTTAGCTAATATGAATTATGTTCACCG
TGATTTGGCAGCAAGAAATATCCTAGTCAATTCCAATTTAGTATGTAAAGTTAGTGA
TTTTGGTTTAAGCAGAGTATTAGAAGACGATCCAGAGGCAACCTATACAACATCGG
GAGGTAAAATTCCTATTCGTTGGACAGCACCAGAAGCTATCAGTTACCGTAAATTTA
CAAGTGCATCAGACGTGTGGAGTTTTGGGATTGTAATGTGGGAAGTTATGACATATG
GAGAAAGACCATATTGGGAATTAAGTAATCATGAAGTTATGAAAGCAATTAACGAT
GGATTTAGATTACCAACTCCGATGGATTGTCCATCTGCCATTTATCAACTAATGATG
CAATGTTGGCAACAAGAAAGAGCACGACGTCCAAAATTTGCAGATATTGTTAGTATT
TTAGACAAATTAATTCGTGCACCAGATAGTTTAAAAACTTTAGCAGACTTTGATCCT
CGTGTTAGTATTCGATTACCAAGTACGTCAGGTTCCGAAGGAGTTCCATTTCGCACA
GTCTCCGAATGGTTGGAATCAATTAAAATGCAACAATACACCGAACACTTTATGGCA
GCAGGTTACACAGCAATCGAAAAGTTGTTCAAATGACAAATGATGATATTAAACG
TATTGGAGTTAGATTACCAGGCCACCAGAAACGTATTGCATATTCTTTATTAGGTTT
AAAAGATCAAGTTAATACCGTGGGAATTCCAATTGAACAAAAATTAATTTCCGAAG
AAGACTTATAAGAGCTC

FIGURE 24

PhoD-FLAG-CO_EphA2-myc-CodonOp
(Codon optimized B. subtilis phoD Tat signal peptide-FLAG-CO_EphA2-Myc)
Amino acid sequence M A Y D S R F D E W V Q K L K E E S F Q N N T F D R R K F I Q G A
G K I A G L S L G L T I A Q S V G A F G S D Y K D D D D K H R R R
K N Q R A R Q S P E D V Y F S K S E Q L K P L K T Y V D P H T Y E
D P N Q A V L K F T T E I H P S C V T R Q K V I G A G E F G E V Y K
G M L K T S S G K K E V P V A I K T L K A G Y T E K Q R V D F L G
E A G I M G Q F S H H N I I R L E G V I S K Y K P M M I I T E Y M E
N G A L D K F L R E K D G E F S V L Q L V G M L R G I A A G M K Y
L A N M N Y V H R D L A A R N I L V N S N L V C K V S D F G L S R
V L E D D P E A T Y T T S G G K I P I R W T A P E A I S Y R K F T S
A S D V W S F G I V M W E V M T Y G E R P Y W E L S N H E V M K
A I N D G F R L P T P M D C P S A I Y Q L M M Q C W Q Q E R A R R
P K F A D I V S I L D K L I R A P D S L K T L A D F D P R V S I R L P
S T S G S E G V P F R T V S E W L E S I K M Q Q Y T E H F M A A G Y
T A I E K V V Q M T N D D I K R I G V R L P G H Q K R I A Y S L L G
L K D Q V N T V G I P I E Q K L I S E E D L

FIGURE 25

Codon Optimized LLOss-PEST-NYESO1-CodonOp
(Codon Optimized L. monocytogenes LLO signal peptide + PEST-Codon optimized -NYESO1)
Nucleotide Sequence (including *hly* promoter)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAAAAAAATTATGTTAGTTTTTATTACATTAATTTTAGTTAGTTTAC
CAATTGCACAACAAACAGAAGCAAAAGATGCAAGTGCATTTAATAAAGAAAATAGT
ATTAGTAGTATGGCACCACCAGCAAGTCCACCAGCAAGTCCAAAAACACCAATTGA
AAAAAAACATGCAGATGGATCCCAAGCAGAAGGTCGCGGAACAGGAGGAAGTACA
GGAGATGCAGACGGACCAGGAGGACCAGGAATACCAGACGGACCAGGAGGAAATG
CAGGAGGCCCAGGCGAAGCAGGCGCAACAGGAGGAAGAGGACCAAGAGGAGCAG
GAGCAGCACGAGCATCAGGACCAGGAGGCGGAGCACCAAGAGGACCACATGGCGG
AGCGGCAAGCGGATTAAATGGATGTTGTAGATGTGGAGCACGCGGACCAGAATCAA
GACTTTTAGAATTTTATTTAGCCATGCCATTTGCAACCCCAATGGAAGCAGAATTAG
CACGAAGATCATTAGCACAAGATGCCCCACCATTACCAGTACCAGGAGTTTTATTAA
AAGAGTTTACAGTATCAGGCAATATTTTAACAATACGTTTAACAGCAGCAGACCATC
GTCAATTACAACTATCTATCAGTTCATGTTTACAACAATTATCCTTATTAATGTGGAT
TACACAATGTTTTTTACCAGTTTTTTTAGCACAACCACCATCAGGACAAAGAAGATA
AGAGCTC

FIGURE 26

Codon Optimized LLOss-PEST-NYESO1-CodonOp
(Codon Optimized L. monocytogenes LLO signal peptide + PEST-Codon optimized -NYESO1)
Primary amino acid sequence M K K I M L V F I T L I L V S L P I A Q Q T E A K D A S A F N K E N
S I S S M A P P A S P P A S P K T P I E K K H A D G S Q A E G R G T
G G S T G D A D G P G G P G I P D G P G G N A G G P G E A G A T G
G R G P R G A G A A R A S G P G G G A P R G P H G G A A S G L N G
C C R C G A R G P E S R L L E F Y L A M P F A T P M E A E L A R R S
L A Q D A P P L P V P G V L L K E F T V S G N I L T I R L T A A D H
R Q L Q L S I S S C L Q Q L S L L M W I T Q C F L P V F L A Q P P S
G Q R R

FIGURE 27

Phly(10403S)-Usp45-CodOp
(330 nts.)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAAAAAAAAAATTATTAGTGCAATTTTAATGAGTACAGTTATTTTA
AGTGCAGCAGCACCATTAAGTGGTGTTTATGCAGATACAGGATCC

FIGURE 28

Phly(10403S)-p60SP-Native
(330 nts.)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAATATGAAAAAAGCAACTATCGCGGCTACAGCTGGGATTGCGGT
AACAGCATTTGCTGCGCCAACAATCGCATCCGCAAGCACTGGATCC

FIGURE 29

Phly(10403S)-p60SP-CodOp
330 nts.

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAATATGAAAAAAGCAACAATTGCAGCAACAGCAGGTATTGCAGT
TACAGCATTTGCAGCACCAACAATTGCAAGTGCAAGTACAGGATCC

FIGURE 30 hlyP-p60 (KpnI-BamHI)

```
GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAATATGAAAAAAGCAACTATCGCGGCTACAGCTGGGATTGCGGT
AACAGCATTTGCTGCGCCAACAATCGCATCCGCAAGCACTGTAGTAGTCGAAGCTG
GTGATACTCTTTGGGGTATCGCACAAAGTAAAGGGACTACTGTTGACGCAATTAAAA
AAGCAAACAATTTAACAACAGATAAAATCGTACCAGGTCAAAAATTACAAGTAAAT
AATGAGGTTGCTGCTGCTGAAAAAACAGAGAAATCTGTTAGCGCAACTTGGTTAAA
CGTCCGTAGTGGCGCTGGTGTTGATAACAGTATTATTACGTCCATCAAAGGTGGAAC
AAAAGTAACTGTTGAAACAACCGAATCTAACGGCTGGCACAAAATTACTTACAACG
ATGGAAAAACTGGTTTCGTTAACGGTAAATACTTAACTGACAAAGCAGTAAGCACT
CCAGTTGCACCAACACAAGAAGTGAAAAAAGAAACTACTACTCAACAAGCTGCACC
TGCTGCAGAAACAAAAACTGAAGTAAAACAAACTACACAAGCAACTACACCTGCGC
CTAAAGTAGCAGAAACGAAAGAAACTCCAGTAGTAGATCAAAATGCTACTACACAC
GCTGTTAAAAGCGGTGACACTATTTGGGCTTTATCCGTAAAATACGGTGTTTCTGTTC
AAGACATTATGTCATGGAATAATTTATCTTCTTCTTCTATTTATGTAGGTCAAAAGCT
TGCTATTAAACAAACTGCTAACACAGCTACTCCAAAAGCAGAAGTGAAAACGGAAG
CTCCAGCAGCTGAAAAACAAGCAGCTCCAGTAGTTAAAGAAAATACTAACACAAAT
ACTGCTACTACAGAGAAAAAAGAAACAGCAACGCAACAACAAACAGCACCTAAAG
CACCAACAGAAGCTGCAAAACCAGCTCCTGCACCATCTACAAACACAAATGCTAAT
AAAACAAATACAAATACAAATACAAATACAAATACAAACAATACTAATACAAATAC
ACCATCTAAAAATACTAATACAAACTCAAATACTAATACGAATACAAACTCAAATA
CGAATGCTAATCAAGGTTCTTCCAACAATAACAGCAATTCAAGTGCAAGTGCTATTA
TTGCTGAAGCTCAAAAACACCTTGGAAAAGCTTATTCATGGGGTGGTAACGGACCA
ACTACATTTGATTGCTCTGGTTACACTAAATATGTATTTGCTAAAGCGGGAATCTCCC
TTCCACGTACTTCTGGCGCACAATACGCTAGCACTACAAGAATCTCTGAATCTCAAG
CAAAACCTGGTGATTTAGTATTCTTTGACTATGGTAGCGGAATTTCTCACGTTGGTAT
CTACGTTGGTAATGGTCAAATGATTAACGCGCAAGACAATGGCGTTAAATACGATA
ACATCCACGGCTCTGGCTGGGGTAAATATCTAGTTGGCTTCGGTCGCGTATAATTAA
GGATCC
```

Construct: pAM401-MCS
Plasmid pAM401 containing multiple cloning site (MCS) from pPL2 vector
Insertion of small *Aat II* MCS fragment from pPL2 inserted into pAM401 plasmid between blunted *Xba I* and *Nru I* sites.
Complete pAM401-MCS plasmid sequence shown

```
CTTTAAACGTGGATCATTTTCTTTAAATTTATGCTGACGACCTTTGAATTTGCCTTTTTTCTTAGCAATT
TCGATTCCTTGTGCCTGACGTTCCTTAATTTTTTTTCGTTCTGATTCTGCTTGATACTTGTACAATTCAAT
GACAAGGCTATTAATCAAACGCCTTAAATTTTCATCTTCAATACCATTCATTGAGGGTAAATTTAAGAC
TTCCAGGGTTGCCCCCTTAATTTGAATTTGATTCATCAATTCTGTTAATTCTTTATTATTTCGTCCTAATC
GATCTAATTCAGTAACAATAACAATATCCCCTTCACGAATATAGTTAAGCATAGCTTGTAATTGTGGGC
GTTCGACCGATTGACCGCTTAATTTGTCTGAAAAGACCTTAGAAACGCCCTGTAACGCTTGTAATTGCC
GATCTAAGTTCTGTTCTTTGCTACTGACACGTGCATAACCAATTTTAGCCATTTTCAACCAACCTCTAA
AATTCTCTCGGTTGCAATAACCAATCAGCAATATCTACTTTTTCAATTTCAAATTGCTTATCAGAAATT
GTCTTTTCGTAAGCGATAAAATCTTGCGCATATTGTTGCTCATTAAAAATAGCCACCACTTCGTCATTT
TCTAAAACTCGATAAATAAATTTTTTCATTTTACTCCTCCTATTATGCCCAACTTAAATGACCTATTCAC
CAAGTCAATTATACTGCTAAAATCATATTAGGACAAATAGGTATACTCTATTGACCTATAAATGATAG
CAACTTAAAAGATCAAGTGTTCGCTTCGCTCTCACTGCCCCTCGACGTTTTAGTAGCCTTTCCCTCACTT
CGTTCAGTCCAAGCCAACTAAAAGTTTTCGGGCTACTCTCTCCTTCTCCCCCTAATAATTAATTAAAAT
CTTACTCTGTATATTTCTGCTAATCATTCACTAAACAGCAAAGAAAAACAAACACGTATCATAGATAT
AAATGTAATGGCATAGTGCGGGTTTTATTTTCAGCCTGTATCGTAGCTAAACAAATCGAGTTGTGGGTC
CGTTTTGGGGCGTTCTGCCAATTTGTTTAGAGTTTCTTGAATAAATGTACGTTCTAAATTAAACGAAGC
TGTCAGCGCCTTTATATAGCTTTCTCGTTCTTCTTTTTTTAATTTAATGATCGATAGCAACAATGATTTA
ACACTAGCAAGTTGAATGCCACCATTTCTTCCTGGTTTAATCTTAAAGAAAATTTCCTGATTCGCCTTC
AGTACCTTCAGCAATTTATCTAATGTCCGTTCAGGAATGCCTAGCACTTCTCTAATCTCTTTTTTGGTCG
TCGCTAAATAAGGCTTGTATACATCGCTTTTTTCGCTAATATAAGCCATTAAATCTTCTTTCCATTCTGA
CAAATGAACACGTTGACGTTCGCTTCTTTTTTTCTTGAATTTAAACCACCCTTGACGGACAAATAAATC
TTTACTGGTTAAATCACTTGATACCCAAGCTTTGCAAAGAATGGTAATGTATTCCCTATTAGCCCCTTG
ATAGTTTTCTGAATAGGCACTTCTAACAATTTTGATTACTTCTTTTTCTTCTAAGGGTTGATCTAATCGA
TTATTAAACTCAAACATATTATATTCGCACGTTTCGATTGAATAGCCTGAACTAAAGTAGGCTAAAGA
GAGGGTAAACATAACGCTATTGCGCCCTACTAAACCCTTTTCTCCTGAAAATTTCGTTTCGTGCAATAA
GAGATTAAACCAGGGTTCATCTACTTGTTTTTTGCCTTCTGTACCGCTTAAAACCGTTAGACTTGAACG
AGTAAAGCCCTTATTATCTGTTTGTTTGAAAGACCAATCTTGCCATTCTTTGAAAGAATAACGGTAATT
GGGATCAAAAAATTCTACATTGTCCGTTCTTGGTATACGAGCAATCCCAAAATGATTGCACGTTAGAT
CAACTGGCAAAGACTTTCCAAAATATTCTCGGATATTTGCGAGATTATTTTGGCTGCTTTGACAGATT
TAAATTCTGATTTTGAAGTCACATAGACTGGCGTTTCTAAAACAAAATATGCTTGATAACCTTTATCAG
ATTTGATAATTAACGTAGGCATAAAACCTAAATCAATAGCTGTTGTTAAAATATCGCTTGCTGAAATA
GTTTCTTTTTCCGTGTGAATATCAAAATCAATAAAGAAGGTATTGATTTGTCTTAAATTGTTTTCAGAA
TGTCCTTTAGTGTATGAACGGTTTTCGTCTGCATACGTACCATAACGATAAACGTTTGGTGTCCAATGC
GTAAATGTATCTTGATTTTCGTGAATCGCTTCTTCGGAAGTCAGAACAACGCCACGTCCGCCAATCATG
CTTTTTTTTGAGCGATACGCAAAAATAGCCCCTTTACTTTTACCTGGCTTGGTAGTGATTGAGCGAATT
TTACTATTTTTAAATTTGTACTTTAACAAGCCGTCATGAAGCACAGTTTCTACAACAAAAGGGATATTC
ATTCAGCTGTTCTCCTTTCTTACGAAAATTAATTAGTTAGAAGCTACGATCAAAGTTGAATCACAACAA
AAAAGGCAATCAACTAAGTTTTTCTTAATTGATTGCCTGGTATCTTCTTAAAGACTTGAAATCCCCTCA
AAAACCCGATATAATGGGTTTACAGATATTTAAGTATCTGATTAATAAAGTAATTAAATACTTTACCA
AATTTTGGGTCTCGACTTCTTTAATTGATTGGTGGTAATCAATTAAGGCTCGCAGTTAAAATTTCTCAG
GCTTTAACTGGTCGTGGCTCTTTTTTTGTATTCTTTATTCAGTTCGTTGTTTCGTTATATCTAGTATATCG
CTTTTTAAAAAAATAAGCAATGATTTCGTGCATTATTCACACGAAATCATTGCTTTTTTCTTCTTCCATT
TCTAACTCCAATGTTACTTGTTCTGTTTCTGGTTCTGGTTCTGTTGGCTCATTTGGGATTAAATCCACTA
CTAGCGTTGAGTTAGTTCCGTCTCTAATAGCCGGTTAAGTAATAGCCGGTTAAGTGGTCAAACTTTGGG
AAAATCTCAACCCGCATTAAGTTTTGATGCCATGACAATCGTTGGAAATTTGAACAAAACTAATGCTA
AAAAGCTATCTGACTTTATGAGTGTAGAGCCACAAATACGACTTTGGGATATACTTCAAACAAAGTTT
```

FIGURE 32B (sequence continued from Figure 32A)

```
AAAGCTAAGGCACTTCAAGAAAAAGTTTATATCGAATATGACAAAGTAAAAGCAGATACTTGGGATA
GACGTAATATGCGTGTTGAATTTAATCCCAATAAACTCACACATGAAGAAATGATTTGGTTAAAACAA
AATATTATCGACTACATGGAAGATGACGGTTTTACAAGATTAGACTTAGCTTTTGATTTTGAAGATGAT
TTGAGCGATTACTATGCAATGACTGATAAAGCAGTTAAGAAAACTGTTTTTTATGGTCGTAATGGCAA
GCCAGAAACAAAATATTTTGGTGTCCGTGATAGTGATAGATTTATTAGAATTTATAATAAAAAACAAG
AACGTAAAGATAACGCAGATGTTGAAGTTGTGTTTGAACATTTATGGCGTGTAGAAGTTGAATTAAAA
AGAGATATGGTTGATTACTGGAATGATTGTTTTAATGATTTACACATCTTTGAAACCTGCGTGGGCTAC
TTTAGAAAAAATTAATGAGCAAGCTATGGTTTATACTTTGTTGCATGAAGAAAGTATGTGGGGAAAGC
TAAGTAAGAATACTAAGACTAAATTTAAAAAATTGATTAGAGAAATATCTCCAATTGATTTAACGGAA
TTAATGAAATCGACTTTAAAAGCGAACGAAAAACAATTGCAAAAGCAGATTGATTTTTGGCAACGTGA
ATTTAGGTTTTGGAAGTAAAATAAGTTTTATTTGATAAAAATTGCTAATTCAGTATAATTAATATTTAC
GAGGTGACATAACGTATGAAAAAATCAGAGGATTATTCCTCCTAAATATAAAAATTTAAAATTTAGGA
GGAAGTTATATATGACTTTTAATATTATTGAATTAGAAAATTGGGATAGAAAAGAATATTTTGAACAC
TATTTTAATCAGCAAACTACTTATAGCATTACTAAAGAAATTGATATTACTTTGTTTAAAGATATGATA
AAAAAGAAAGGATATGAAATTTATCCCTCTTTAATTTATGCAATTATGGAAGTTGTAAATAAAAATAA
AGTGTTTAGAACAGGAATTAATAGTGAGAATAAATTAGGTTATTGGGATAAGTTAAATCCTTTGTATA
CAGTTTTTAATAAGCAAACTGAAAAATTTACTAACATTTGGACTGAATCTGATAAAAACTTCATTTCTT
TTTATAATAATTATAAAAATGACTTGCTTGAATATAAAGATAAAGAAGAAATGTTTCCTAAAAAACCG
ATACCTGAAAACACCATACCGATTTCAATGATTCCTTGGATTGATTTTAGTTCATTTAATTTAAATATT
GGTAACAATAGCAGCTTTTTATTGCCTATTATTACGATAGGTAAATTTTATAGTGAGAATAATAAAATT
TATATACCAGTTGCTCTGCAACTTCATCATTCTGTATGTGATGGTTACCATGCTTCACTATTTATGAATG
AATTTCAAGATATAATTCATAGGGTAGATGATTGGATTTAGTTTTTAGATTTTGAAAGTGAATTTAATT
TTATACACGTAAGTGATCATAAAATTTATGAACGTATAACAACCACATTTTTTGGTTGCTTGTGGTTTT
GATTTTGAATTTGGTTTTGAACTTATGGACTGATTTATTCAGTCCATTTTTTGTGCTTGCACAAAAACTA
GCCTCGCAGAGCACACGCATTAATGACTTATGAAACGTAGTAAATAAGTCTAGTGTGTTATACTTTACT
TGGAAGATGCACCGAATAAAAAATATTGAAGAACAACTAGCAAAAGATTTTAAAGAGTTATTTTATTT
TAAGTCTTTATAACATGAGTGAAGCGAATTTTTAAATTTCGATAGAAATTTTTACATCAAAAAGCCCCC
TGTCAAAATTGACGAAGGGGGTTTTTGGCGCACGCTTTTCGTTAGAAATATACAAGATTGAAAATCG
TGTATAAGTGCGCCCTTTGTTTTGAACTTAGCACGTTACATCAATTTTTTAAAATGATGTATAAGTGCG
CCCTTTTAAATTTTGAGTGATTATATTTTTTGAGTTAGAAAAAGGGATTGGGAAAATTTCCCAAAATAA
TTTAAAAAATAAGCAAAAATTTTCGATAGAGAATGTGCTATTTTTTGTCAAAGGTGTATACCTTGACTG
TGCTTGCTGTTACATTAAGTTTATTTTTAAGTTATTAAAAAAGAAATAGCTTTTAAAGTTTGGCTCGCT
GTCGCTTTATAAAGCTGATTGACTTTTGATTGCAAACTACTTAAAGAAAACAAACTCGGACTATTCGTT
TTCTTCTCTTTGGTTTGAACATCAGCAATTATCCCTCTTGATTGCCTATTTTAGCTTGTTTAGAAGAAA
CAAAAGCTAAAAGCTCCTCTTGGGTTTTAAAACGCTGTGTGGGGCTTAGAACGCCCTTAAACGACCCT
TGGTTTACTTTTATACTAGCTTCCACCTCGAAAAAAGGTTCTTTTTTAAAATTCTCTATGGCTTCCTGGC
GCTGAAAAAATAAGGTATAAGGTGGGCGTTTGAACACGTCCTAGTGAAAATGTACCTTGTACGCCCCT
TCTGTTGTAAATTTAACGTATACAAAGGGCTTGCGTTCATGCCGATCAACCAATCGGCAATTTGGCGTG
TTTGCGCTTCTTGATAAAAGGGATAGTAATTCATTCCAGGTTGCAAATTTTGAAAACCGCTTCGGATTA
CATCTTTTTCTAAGCTATTGATCCATAGTCTTTTAAATGTTTTATCTTTTGAAAAGGCATTTGCTTTATG
GATAATCGACCAGGCGATATTTTCACCTTCTCTGTCGCTATCTGTTGCAACAATAATTGTATTTGCCTTT
TTGAGAAGTTCTGCAACAATTTTAAACTGCTTTCCCTTATCTTTTGCAACTTCAAAATCGTATCGATCA
GGAAAAATCGGCAAAGATTCAAGTTTCCAATTTTGCCACTTTTCGTCATAATGACCTGGTTCTGCTAAT
TCCACTAAATGCCCAAAACCAAAGGTGATAAACGTTTCATCTGTAAATAGTGGGTCTTTGATCTCAAA
ATAACCGTCTTTTTGGTGCTTTGTTTTAAAGCACTTGCGTAGGCTAATGCCTGGCTTGGTTTTTCAGCT
AAAATAACCGTACTCATTAACTATCCCTCTTTTCATTGTTTTTTCTTTGATCGACTGTCACGTTATATCT
TGCTCGATACCTTCTAAACGTTCGGCGATTGATTCCAGTTTGTTCTTCAACTTCTTTATCGGATAAACCA
TTCAAAAACAAATCGAAAGCATGGATGCGCCGCGTGCGGCTGCTGGAGATGGCGGACGCGATGGATA
TGTTCTGCCAAGGGTTGGTTTGCGCATTCACAGTTCTCCGCAAGAATTGATTGGCTCCAATTCTTGGAG
TGGTGAATCCGTTAGCGAGGTGCCGCCGGCTTCCATTCAGGTCGAGGTGGCCCGGCTCCATGCACCGC
GACGCAACGCGGGGAGGCAGACAAGGTATAGGGCGGCGCCTACAATCCATGCCAACCCGTTCCATGT
GCTCGCCGAGGCGGCATAAATCGCCGTGACGATCAGCGGTCCAGTGATCGAAGTTAGGCTGGTAAGA
```

FIGURE 32C (sequence continued from Figure 32B)

```
GCCGCGAGCGATCCTTGAAGCTGTCCCTGATGGTCGTCATCTACCTGCCTGGACAGCATGGCCTGCAA
CGCGGGCATCCCGATGCCGCCGGAAGCGAGAAGAATCATAATGGGGAAGGCCATCCAGCCTCGCGTC
GCAATACGACTCACTATAGGGCGAATTGGGTACCGGGCCCCCCCTCGAGGTCGACGGTATCGATAAGC
TTGATATCGAATTCCTGCAGCCCGGGGGATCCACTAGTTCTAGAGCGGCCGCCACCGCGGTGGAGCTC
CAGCTTTTGTTCCCTTTAGTGAGGGTTAATGCTAGAAATATTTTATCTGATTAATAAGATGATCTTCTTG
AGATCGTTTTGGTCTGCGCGTAATCTCTTGCTCTGAAAACGAAAAAACCGCCTTGCAGGGCGGTTTTTC
GAAGGTTCTCTGAGCTACCAACTCTTTGAACCGAGGTAACTGGCTTGGAGGAGCGCAGTCACCAAAAC
TTGTCCTTTCAGTTTAGCCTTAACCGGCGCATGACTTCAAGACTAACTCCTCTAAATCAATTACCAGTG
GCTGCTGCCAGTGGTGCTTTTGCATGTCTTTCCGGGTTGGACTCAAGACGATAGTTACCGGATAAGGCG
CAGCGGTCGGACTGAACGGGGGGTTCGTGCATACAGTCCAGCTTGGAGCGAACTGCCTACCCGGAACT
GAGTGTCAGGCGTGGAATGAGACAAACGCGGCCATAACAGCGGAATGACACCGGTAAACCGAAAGGC
AGGAACAGGAGAGCGCACGAGGGAGCCGCCAGGGGGAAACGCCTGGTATCTTTATAGTCCTGTCGGG
TTTCGCCACCACTGATTTGAGCGTCAGATTTCGTGATGCTTGTCAGGGGGGCGGAGCCTATGGAAAAA
CGGCTTTGCCGCGGCCCTCTCACTTCCCTGTTAAGTATCTTCCTGGCATCTTCCAGGAAATCTCCGCCCC
GTTCGTAAGCCATTTCCGCTCGCCGCAGTCGAACGACCGAGCGTAGCGAGTCAGTGAGCGAGGAAGC
GGAATATATCCTGTATCACATATTCTGCTGACGCACCGGTGCAGCCTTTTTCTCCTGCCACATGAAGC
ACTTCACTGACACCCTCATCAGTGCCAACATAGTAAGCCAGTATACACTCCGCTAGCGCTGATGTCCG
GCGGTGCTTTTGCCGTTACGCACCACCCCGTCAGTAGCTGAACAGGAGGGACAGCTGATAGAAACAGA
AGCCACTGGAGCACCTCAAAAACACCATCATACACTAAATCAGTAAGTTGGCAGCATCACCCGACGCA
CTTTGCGCCGAATAAATACCTGTGACGGAAGATCACTTCGCAGAATAAATAAATCCTGGTGTCCCTGT
TGATACCGGGAAGCCCTGGGCCAACTTTTGGCGAAAATGAGACGTTGATCGGCACGTAAGAGGTTCCA
ACTTTCACCATAATGAAATAAGATCACTACCGGGCGTATTTTTGAGTTATCGAGATTTTCAGGAGCTA
AGGAAGCTAAAATGGAGAAAAAAATCACTGGATATACCACCGTTGATATATCCCAATGGCATCGTAA
AGAACATTTTGAGGCATTTCAGTCAGTTGCTCAATGTACCTATAACCAGACCGTTCAGCTGGATATTAC
GGCCTTTTTAAAGACCGTAAAGAAAAATAAGCACAAGTTTTATCCGGCCTTTATTCACATTCTTGCCCG
CCTGATGAATGCTCATCCGGAATTCCGTATGGCAATGAAAGACGGTGAGCTGGTGATATGGGATAGTG
TTCACCCTTGTTACACCGTTTTCCATGAGCAAACTGAAACGTTTTCATCGCTCTGGAGTGAATACCACG
ACGATTTCCGGCAGTTTCTACACATATATTCGCAAGATGTGGCGTGTTACGGTGAAAACCTGGCCTATT
TCCCTAAAGGGTTTATTGAGAATATGTTTTTCGTCTCAGCCAATCCCTGGGTGAGTTTCACCAGTTTTG
ATTTAAACGTGGCCAATATGGACAACTTCTTCGCCCCCGTTTTCACCATGGGCAAATATTATACGCAAG
GCGACAAGGTGCTGATGCCGCTGGCGATTCAGGTTCATCATGCCGTCTGTGATGGCTTCCATGTCGGC
AGAATGCTTAATGAATTACAACAGTACTGCGATGAGTGGCAGGGCGGGGCGTAATTTTTTTAAGGCAG
TTATTGGTGCCCTTAAACGCCTGGTGCTACGCCTGAATAAGTGATAATAAGCGGATGAATGGCAGAAA
TTCGAAAGCAAATTCGACCCGGTCGTCGGTTCAGGGCAGGGTCGTTAAATAGCCGCTTATGTCTATTG
CTGGTTTACCGGTTTATTGACTACCGGAAGCAGTGTGACCGTGTGCTTCTCAAATGCCTGAGGCCAGTT
TGCTCAGGCTCTCCCCGTGGAGGTAATAATTGACGATATGATCATTTATTCTGCCTCCCAGAGCCTGAT
AAAAACGGTTAGCGCTTCGTTAATACAGATGTAGGTGTTCCACAGGGTAGCCAGCAGCATCCTGCGAT
GCAGATCCGGAACATAATGGTGCAGGGCGCTTGTTTCGGCGTGGGTATGGTGGCAGGCCCGTGGCCG
GGGGACTGTTGGGCGCTGCCGGCACCTGTCCTACGAGTTGCATGATAAAGAAGACAGTCATAAGTGCG
GCGACGATAGTCATGCCCCGCGCCCACCGGAAGGAGCTACCGGACAGCGGTGCGGACTGTTGTAACTC
AGAATAAGAAATGAGGCCGCTCATGGCGTTGACTCTCAGTCATAGTATCGTGGTATCACCGGTTGGTT
CCACTCTCTGTTGCGGGCAACTTCAGCAGCACGTAGGGGACTTCCGCGTTTCCAGACTTTACGAAACA
CGGAAACCGAAGACCATTCATGTTGTTGCTCAGGTCGCAGACGTTTTGCAGCAGCAGTCGCTTCACGT
TCGCTCGCGTATCGGTGATTCATTCTGCTAACCAGTAAGGCAACCCCGCCAGCCTAGCCGGGTCCTCA
ACGACAGGAGCACGATCATGCGCACCCGTGGCCAGGACCCAACGCTGCCCGA
```

Human Mesothelin Gene
Codon-Optimized for Expression in Listeria

ATGGCATTGCCAACTGCACGTCCATTACTAGGTAGTTGCGGTACACCAGCACTAGGT
TCTTTATTATTTTTGTTATTTTCTCTAGGTTGGGTTCAACCAAGTCGTACATTAGCAG
GTGAAACAGGTCAAGAAGCAGCACCACTTGACGGTGTATTAACGAATCCACCAAAT
ATATCAAGTTTAAGTCCACGTCAATTATTAGGTTTTCCATGTGCAGAAGTTTCAGGTT
TAAGTACAGAACGTGTCCGTGAGTTAGCAGTTGCATTAGCACAAAAAAACGTTAAA
TTATCTACAGAACAGTTACGTTGTTTAGCCCATAGATTAAGCGAACCACCAGAAGAC
TTAGATGCACTTCCTTTAGACCTTCTTTTATTCTTAAATCCAGATGCATTTTCAGGAC
CACAAGCATGTACACGTTTTTTAGTCGAATTACAAAAGCCAATGTTGATTTATTAC
CTCGTGGGGCTCCTGAAAGACAACGTTTATTACCTGCTGCATTAGCATGCTGGGGTG
TTCGCGGTAGCTTATTAAGTGAAGCCGATGTTCGTGCTTTAGGGGGTTTAGCATGTG
ATTTACCTGGTCGTTTCGTTGCAGAATCAGCAGAAGTGTTATTACCGAGATTAGTTTC
ATGCCCAGGACCTTTAGATCAAGATCAACAAGAGGCAGCTAGAGCAGCTCTTCAAG
GAGGAGGCCCACCATATGGCCCACCAAGTACATGGAGTGTTTCTACAATGGATGCG
TTAAGAGGTTTATTACCGGTTTAGGACAACCAATTATTCGTAGTATTCCACAAGGC
ATTGTAGCAGCATGGCGTCAACGTAGTTCTCGTGATCCGTCTTGGCGACAACCAGAA
CGTACAATTCTACGTCCAAGATTTCGTAGAGAAGTAGAAAAAACGGCGTGTCCTAGT
GGCAAAAAAGCACGTGAAATTGATGAAAGTTTAATTTTTTATAAAAAATGGGAATT
AGAAGCATGTGTCGATGCAGCATTACTAGCTACACAAATGGATCGTGTTAATGCTAT
TCCATTCACATATGAACAATTAGATGTTTTAAAGCATAAATTAGACGAATTATATCC
ACAAGGTTATCCAGAATCAGTTATTCAACATTTAGGTTACTTATTTTAAAAATGAG
TCCAGAAGACATACGCAAATGGAATGTTACAAGTTTAGAAACATTAAAAGCGCTTTT
AGAAGTTAACAAAGGTCATGAAATGAGTCCACAAGTTGCTACGTTAATTGATAGATT
CGTTAAAGGCCGTGGTCAATTAGATAAAGATACTTTAGATACATTAACAGCATTTTA
TCCTGGCTACTTATGCAGTTTATCACCAGAAGAATTAAGTTCCGTTCCACCGAGTAG
TATCTGGGCAGTTCGTCCGCAAGATTTAGATACATGCGACCCACGTCAATTAGATGT
TTTATATCCAAAAGCAAGATTAGCTTTCCAAAATATGAACGGTAGTGAATATTTCGT
AAAAATTCAATCCTTTTTAGGTGGTGCACCAACTGAAGATCTAAAAGCATTAAGCCA
ACAAAATGTAAGTATGGATTTAGCTACGTTTATGAAATTACGTACAGATGCAGTTCT
ACCATTAACAGTTGCAGAAGTTCAAAAATTATTAGGTCCACACGTAGAAGGATTAA
AAGCAGAAGAACGTCACCGTCCAGTTCGCGATTGGATTTTACGTCAACGTCAAGATG
ATTTAGATACATTAGGTTTAGGTTTACAAGGCGGTATTCCGAATGGATATTTAGTGT
TAGATTTATCTGTTCAAGAAGCATTAAGTGGTACACCGTGTTTATTAGGTCCAGGTC
CAGTTTTAACAGTGTTAGCATTATTATTAGCCAGTACATTAGCTTAA

Murine Mesothelin Gene
Codon-Optimized for Expression in Listeria

ATGGCATTACCAACGGCTCGCCCATTATTAGGTTCTTGTGGTTCACCAATTTGTAGTC
GCAGTTTTTTATTATTATTACTATCTTTAGGTTGGATTCCGCGTTTACAAACACAAAC
CACTAAAACAAGTCAAGAAGCTACATTATTGCATGCAGTCAATGGCGCAGCAGATT
TTGCAAGTTTACCAACAGGCTTATTTCTTGGTCTTACATGTGAAGAAGTTAGTGATTT
AAGTATGGAACAAGCAAAAGGTTTAGCGATGGCGGTTCGCCAAAAAAATATTACAT
TACGTGGTCATCAATTACGTTGTTTAGCACGTCGTTTACCACGACATTTAACAGATG
AAGAATTAAATGCTCTACCATTAGACTTATTATTATTTTAAATCCAGCAATGTTTCC
AGGTCAACAAGCATGTGCCCATTTTTTCAGTTTAATTTCGAAAGCAAATGTAGATGT
TTTACCGAGACGTAGCTTAGAACGTCAACGTCTTTTAATGGAAGCATTAAAATGTCA
AGGTGTTTATGGTTTCCAAGTTAGTGAAGCAGATGTTCGTGCACTTGGTGGTTTAGC
TTGTGATTTACCAGGGAAATTTGTAGCACGTTCTAGTGAAGTATTATTACCATGGTT
AGCAGGTTGTCAAGGTCCATTAGATCAAAGTCAAGAAAAGCAGTTCGTGAAGTCT
TACGTAGTGGTCGTACTCAATATGGCCCACCTAGCAAATGGAGTGTTAGTACGTTAG
ATGCATTACAAAGTTTAGTAGCTGTTTTAGATGAAAGTATTGTTCAGAGTATTCCAA
AAGATGTGAAAGCAGAGTGGTTACAACATATTTCCCGTGACCCATCTCGTTTAGGTA
GTAAATTAACAGTTATTCATCCACGTTTTCGCCGCGACGCAGAACAAAAAGCATGTC
CACCAGGTAAAGAACCATATAAAGTAGATGAAGATTTAATTTTTTATCAGAATTGGG
AATTAGAAGCCTGTGTTGATGGTACAATGTTAGCACGTCAAATGGATTTAGTTAATG
AAATTCCATTTACATATGAACAATTAAGTATCTTTAAACATAAATTAGATAAAACAT
ATCCACAAGGTTATCCAGAATCGTTAATTCAACAATTAGGTCATTTTTTCGTTATGT
TAGTCCAGAAGACATTCATCAATGGAATGTTACAAGTCCAGATACAGTTAAAACTTT
ATTAAAAGTTAGTAAAGGTCAAAAAATGAATGCTCAAGCAATTGCATTAGTCGCAT
GTTATTTACGTGGAGGTGGTCAATTAGATGAAGATATGGTTAAAGCATTAGGGGATA
TTCCATTATCATATTTATGTGATTTCTCCCCACAAGACTTACATTCAGTTCCAAGTAG
TGTTATGTGGTTAGTTGGTCCACAAGGTTTAGATAAATGTAGTCAACGTCATTTAGG
TTTACTTTATCAAAAAGCATGTAGTGCGTTTCAAAATGTTAGTGGTTTAGAATATTTT
GAAAAAATCAAAACATTTTTAGGAGGTGCATCTGTAAAAGATTTACGCGCATTAAGT
CAACATAATGTAAGTATGGATATCGCAACATTTAAACGTTTACAAGTCGATAGTCTA
GTTGGTCTTAGTGTAGCAGAAGTTCAAAAATTATTAGGGCCGAATATTGTAGATTTA
AAAACAGAAGAAGATAAAAGTCCAGTTCGTGACTGGTTATTTCGACAACATCAGAA
AGACTTAGATCGTCTTGGATTAGGTTTACAAGGTGGTATTCCAAATGGTTATTTAGTT
TTAGATTTTAATGTACGTGAAGCATTTAGTTCAAGAGCGAGTTTATTAGGTCCAGGT
TTTGTGTTAATTTGGATTCCAGCATTACTACCAGCACTTCGTTTATCATAA

FIGURE 35

Murine Mesothelin Primary Amino Acid Sequence

*hly* promoter-codon optimized Ba PA signal peptide sequence
(Unique 5' and 3' *Kpn I* and *Bam HI* sites underlined)

<u>GGTACC</u>TCCTTGATTAGTATATTCCTATCTTAAAGTTACTTTTATGTGGA
GGCATTAACATTTGTTAATGACGTCAAAAGGATAGCAAGACTAGAATAAA
GCTATAAAGCAAGCATATAATATTGCGTTTCATCTCTTAGAAGCGAATTTC
GCCAATATTATAATTATCAAAAGAGAGGAAGGAGAGTGAAACCCATGAAAAAACGTA
TATTAGGTAAAAATGTAGAAGGCATTAATGGCATTAAGTACAATTTAGTTAGTAGTACAG
AAGTTTAATTCCATTAAGTTATTCAAGCAGAAGTT<u>GGATCC</u>

FIGURE 47

Coding sequences of phEphA2KD:

```
GGATCCCAAGGAAAAGAAGTCGTACTTTAGATTTCGCAGCAGCAGGAGGAGAATTAGGATGGTTAACTCATCCATATGGC
AAAGGCTGGGATTTAATGCAAAACATTATGAACGATATGCCAATTTATATGTACTCCGTATGTAATGTAATGAGCGGTGATC
AAGATAACTGGTTACGTACTGAGGGGCCTCATCAGTGAAAGAAACATTCAATCTATATTATGCGAAAGCGATCTGATTATGGT
CTGTAATAGTTTTCCAGGAGGGCCTCATCAGTGAAAGAAACATTCAATCTATATTATGCGAAAGCGATCTGATTATGGT
ACAAATTTCCAAAAACGTTTATTACTAGAAGAACGCAGTGTTGGTCCACTAAGCTCCACTAGAAAATGTCCAGAACTACTTCAAGGCTAGCACATTTTCCAGAA
GTCATGTGCGTAGCATTGTATCCGTTCGTGTATACTATAAAAATGTCCAGAACTACTTCAAGGCTAGCACATTTTCCAGAA
GGCTTGCGTAGCATTGTATCCGTTCGTGCCATCACTTGCAACTGTGGCGGTTAGTTCCTTATGTTCATGTCAAGCCGGTTATGAAA
ACAATTGGGGCTCAGATGCGCATGCACTGTCAAGTAGATGCTCCCCAGTTTTTTAAATTCGAAGAAGGTTTTTTCGTGCCCACAAGATCCAGCCTCAA
CACACATTACCAAGTCCAGAAGGTGCAACATGCTCTGCTCGTGAAGATATTGTTAATTCGAAGAAGGTTTTTTCGTGCCCACAAGATCCAGCCTCAA
TGCCTTGTACACGACCGCCTCGTGAAGATATTGTTAATTCGGAACAATGTGTAACTAGAACTAGTGTCACAGTATCAGATTAGAACC
GCCCTCAAGATAGTGGAGGCCGTGAAGATATTGGAACAATGTAACTAGAACTAGTGTCACAGTATCAGATTAGAACC
GCCCTCAAGATAGTGGAGGCCGTGAAGATATTGGAACAATGTAACTAGAACTAGTGTCACAGTATCAGATTAGAACC
ACACATGAAGCATCAGTTAGATATTCGGAACCATGATGGCACGTAATGGAGCGCTTGAGTATCTGGTTTAGTTACCACGCTCTTTGCACAGCATCG
GTCTCTATTAACCAAACTGAACCGCCAAAGTTAAGATTAGAAGGGCGTTCGACAACACTACTTTCCGTAAGTTGGTCAATTC
CACCACCACAATCACGCGTTGAAATATGAAGTTACATACAGAAAAAAGGAGATTCGAATAGTTATATGTATAATGTTAGAC
GTACGAAGGATTCAGTGTAACCCTAGATTGATTTAGCTCCAGATACACACATATTAGTACAGGTGCAAGCATTAACAAGAC
AGGACAAGGGCGGCTCACGAGTTCAACAGTGAAATTCAAACCATGAAAGATCCAAAGTATGGGAGCACCACATATATAGCAAAG
CCAGAAGATATTTTTCAAATTACAGGCATGTTCAAGTCTGAAACCTCAGTGGAAAACCTCAGTAGACCATCATGCTGCTCAAAAAGTCATGGAATATTTCTAGTCATATTAATTAGACTTGAA
GGAGGTATACAAGCATGTTTGATTTTTAGGCAGCATGTTATTACTGAATGATTATTACTGAATATATGGAAAAATATCTTGCCAACATGAAT
TACAGAAAAACGTGATAGTTCTCTAAATATAAACCAATGATTGTATCAAGCATGATGATTATTACTGAATATATGGAAAAATATCTTGCCAACATGAAT
AAGATGGTAATTTTCTTGTCCTTCAATTGTTGGTATGTACTAGCTACTACTTCTTGTAAATTCCAATTAGTGTCAAGTTTAGTGTATTCGGTTTTTAGTTCG
AGTATGTACATAGAGATTTAGCGCTCGAAATTCTGCCGAATTCGATGGACGAGTCCTGCATCGATCGTTGGACACATACGGCGAAGCAAT
TTCATATCGTAAATTTACATCGTCAAGCGATGTTTGGAGTTTCGGAGTTGGAAGTGAATGACATACGGCGAAGCAAT
CCATATGGAATTGCTAAACCATGAAGTCAAGCCATGTAATGACAAGTAACGGATTAACGAGGCATTACCAACCCCAATGGACTGTCCAT
CAGCAATTTATCCAATGATGTCAATGCTGGCAACAAGAAGCTAAATTTGCAGACATTGTTCAATTTT
AGACAAACTAATTCGTGCGCCAGATAGTCTTAAACCCTGATTCGATTTGAATCGATTAAAGCAACAGTATACAGAACATTTTA
TCGGGATCTGAAGCCGGATACACAGGTGTTCCTTTAGAACGTAAGCGAGTGGTTGCAAATGACAAGTAACGTATTGGAGTGCGTCTACCTG
GCCACCAAAAAACGTATTGCTTACTCCCTTTTAAAAGACCAAGTAATACAGTCGAATTCGAATTCCAATATGAGAGCTC
```

FIGURE 49

*Mlu I* sub-fragment of codon-optimized human EphA2 containing the actA-plcB intergenic region:

ACGCGTTTGGAAATATGAAGTTACATACAGAAAAAAAGGAGATTCGAATAGTTATAATGTTAGAC
GTACAGAAGGATTCAGCGTAACCCTAGATGATTTAGCTCCAGATACAACATATTTAGTACAGGTGC
AAGCATTAACACAAGAAGGACAAGGGGCGGGCTCACGAGTTCATGAATTTCAAACATTATAAAAA
CACAGAACGAAAGAAAAAGTGAGGTGAATGATATGGCATATGATAGTCGTTTTGATGAATGGGT
TCAAAAATTAAAAGAAGAAAGTTTTCAAAATAATACATTTGATCGTCGTAAATTTATTCAAGGTGC
AGGTAAAATTGCAGGTTTAAGTTTAGGTTTAACAATTGCACAAAGTGTTGGTGCATTTCATAGAAG
AAGAAAGAATCAAAGAGCACGTCAATCACCAGAAGATGTTTATTTTTCAAAGTCTGAACAGTTGAA
ACCATTGAAAACCTATGTTGATCCACACACATACGAAGACCCAAACCAAGCGGTCCTTAAATTTAC
AACCGAAATTCATCCATCATGCGTAACTCGTCAAAAAGTGATCGGAGCTGGAGAATTCGGGGAGG
TATACAAAGGCATGTTGAAAACCTCAAGTGGTAAAAAAGAAGTTCCTGTAGCAATTATGACTCTTA
AAGCAGGGTATACAGAAAAACAACGAGTTGATTTTTTAGGCGAAGCTGGTATCATGGGACAATTTT
CGCATCATAATATAATTAGACTTGAAGGTGTTATCTCTAAATATAAACCAATGATGATTATTACTGA
ATATATGGAAAACGGTGCTTTAGATAAATTTCTACGCGAAAAAGATGGTGAATTTTCTGTCCTTCA
ATTAGTTGGTATGTTACGTGGCATCGCTGCAGGTATGAAATATCTTGCCAACATGAATTATGTACAT
AGAGATTTAGCGGCTCGAAATATTCTTGTAAATTCCAATTTAGTGTGCAAAGTTAGTGATTTCGGTT
TAAGTCGAGTATTAGAAGATGATCCAGAAGCAACCTATACTACTTCGGGGGGTAAAATTCCGATCC
GTTGGACAGCACCGGAAGCAATTTCATATCGTAAATTTACATCTGCAAGCGATGTTTGGAGTTTCG
GAATTGTGATGTGGGAAGTAATGACATACGGCGAACGTCCATATTGGGAATTGTCAAACCATGAA
GTAATGAAAGCGATTAACGATGGTTTCAGATTACCAACCCCAATGGACTGTCCATCAGCAATTTAT
CAACTAATGATGCAATGCTGGCAACAAGAAAGAGCTAGAAGACCTAAATTTGCAGACATTGTTTCA
ATTTAGACAAACTAATTCGTGCGCCAGATAGTCTTAAAACCCTAGCTGATTTCGATCCACGCGT

FIGURE 50

*hly* promoter-70 N-terminal p60 amino acids:

GGTACCCTCCTTTGATTAGTATATTCCTATCTTAAAGTTACTTTT
ATGTGGAGGCATTAACATTTGTTAATGACGTCAAAAGGATAG
CAAGACTAGAATAAAGCTATAAAGCAAGCATATATATTGCG
TTTCATCTTTAGAAGCGAATTTCGCCAATATTATATTATCAA
AAGAGAGGGGTGGCAAACGGTATTGGCATTATTAGGTTAAA
AAATGTAGAAGGAGAGTG

*KpnI-BamHI* sub-fragment of pPL2-hlyP-Np60 CodOp(1-77):

```
GGTACCTCCTTGATTAGTATATTCCTATCTTAAAGTTACTTTTATGTGGAGGCATTAACATTTG
TTAATGACGTCAAAGGATAGCAAGACTAGATAAAGCTATAAAGAGCAAGCATATAATATGC
GTTTCATCTTAGAAGCGAATTTCGCCAATATTATTATCAAAAGAGAGGGGTGGCAAACG
GTATTGGCATTATTAGTTAAAAATGTAGAAGGAGAGTGAAACCCATGCACCAACTATGCCTCA
GCTACGATTGCAGCTACAGCCGGCATTGCCGTAACAGCTTTTGCAGCACCAACTATTGCCTCA
GCCCTCTACAGTTGTTGTCGAAGCAGGAGACACATTATGGGGAATCGCACAAAGGTACA
ACGGTTGATGTATTAAAAAGCGAATAATTAACACAGATAAATCGTGCCAGTCAAAA
ACTGCAGGTAAATAATGAGGTTGCTGCTGTGTTGATAACAGGTATTATTACGTCCATCAAGGTGGAAC
GTTAAACGTCCGTACTGGCGCTGGAAACAACCGAATCTAACTTACGACAAGTAAGCAGTGGAA
AAAGTAACTGTTCGTTAAACGTAAATAAACTACTCAACAACCTGCGCTGTCAAAGCAGTTGCCACCAG
CACAAGAAGTAAAAACAAACTACCAAGCAACTACACACACGCTGTCAAAGCGGTGACACTATTGGGCTTT
GAAGTAAACAAATACAAATGGTGTTCTGTTCAAGACATTATGTCATGGAATCATTTATCTTCTTCT
ATCCGTAAAATACGGTGTTCTGTTCAAGACATTATGTCATGGAATCATTTATCTTTCTTCT
ATTTATGTAGGTCAAAGCTTGCTATTAAACAACTGCTAACACAGTCCCAGTAGTTAAGAAAATACTAA
GTGAAAAACGGAAGCTCCAGCAGCTGAAAACAACAGCAGCTCCAGTAGTTAAGAAAATACTAA
CACAAATACTGCTACTACAGAGAAAACAGAAAACAACAACAAACAGCACCTAAAG
CACCAACAGAAGCTGCAAATACAAATACAAACCAGTCCACCATCTAAAATATCTAAAAACG
AATACAAATACGAATACAAACTCAAATACGAAGTCTTCCAACAATAACAGCAAT
ACTAATAACGAATACAAACTCAAATACGAAGTCGAAGTCTTCCAACAATAACAGCAAT
TCAAGTGCAAGTGCTATTATTGCTGAAGCTAAAAACACCTTGGAAAAGCTTATTCATGGGGT
GGTAACGGACCAACTACATTGATTGCTGGGCACAATATTGCTACTACAGAATTCTGAATCTCAAG
ATCTCCCTTCCACGTACATCTGGGCACATCTGACTATGGTAGCGCAGACAATGGCGTTAATATGT
CAAACCTGGTGTCAAATGATTAGTATTCTGACTATGGTAGGCGCAGACAATGGCGTTAAATCTCAAG
TGGTAATGTCAAATATCTAGTTGGCTTCGGTCGGTATAATAAGGATCC
```

FIGURE 52

*KpnI-BamHI* sub-fragment of plasmid pPL2-hlyP-Np60 CodOp(1-77)-Mesothelin:

FIGURE 53

*KpnI-BamHI* sub-fragment of plasmid pPL2-hlyP-Np60 CodOp(1-77)-Mesothelin ΔSP/ ΔGPI:

GGTACCTCCTTGATTAGTATATTCCTATCTTAAAGTTACTTTTATGTGGAGGCATTAACATTTGTTAATGACGTCAAAAGGATAGCAAG
ACTAGAATAAAGCTATAAAGCAAGCATATAATTGCGTTTCATCTTTAGAAGCGAATTTGCCAATATATTGTTAATTATCAAAAGAGAGG
GGTGGCAAACGGTATTTGCATTATTAGGTTAAAAATGTAGAAGGAGAGTTAAAACCCATGAAATCGAATTGAAAAAGCTACGATTGCAGCT
ACAGCCGGCAATCCGT

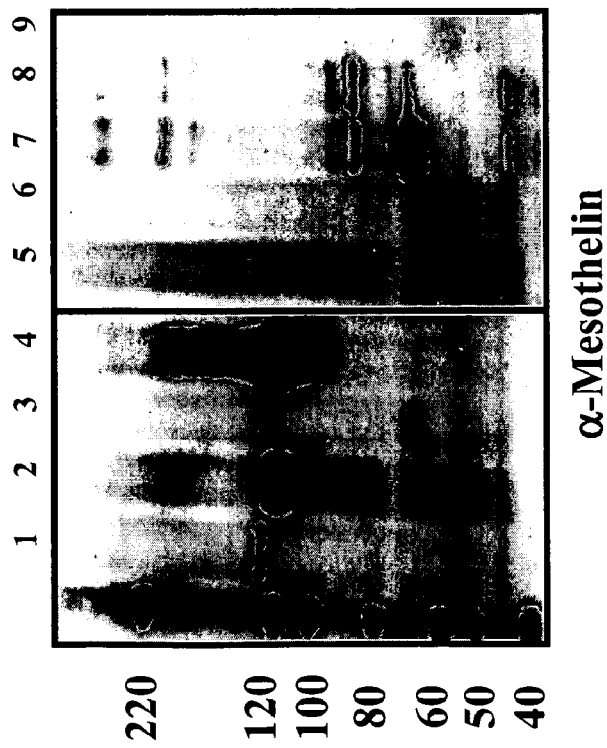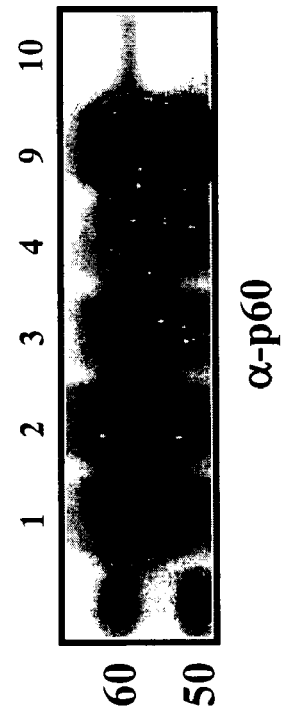
FIGURE 55

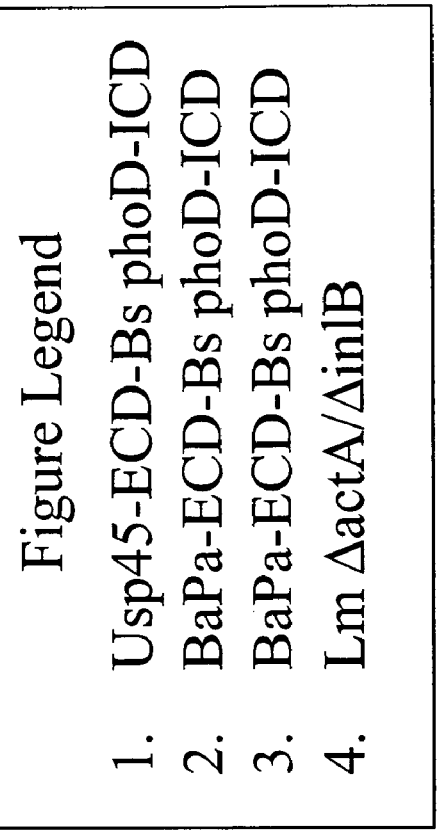
Figure Legend
1. Usp45-ECD-Bs phoD-ICD
2. BaPa-ECD-Bs phoD-ICD
3. BaPa-ECD-Bs phoD-ICD
4. Lm ΔactA/ΔinlB
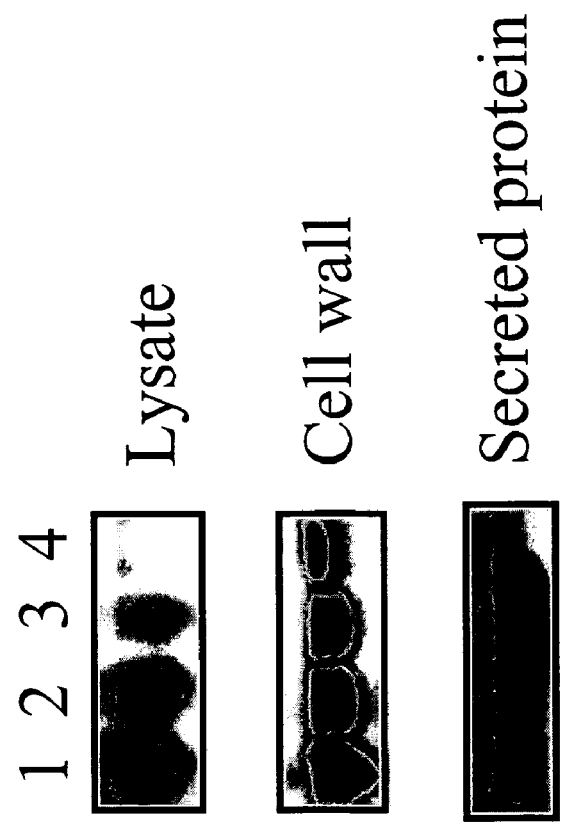
FIGURE 56

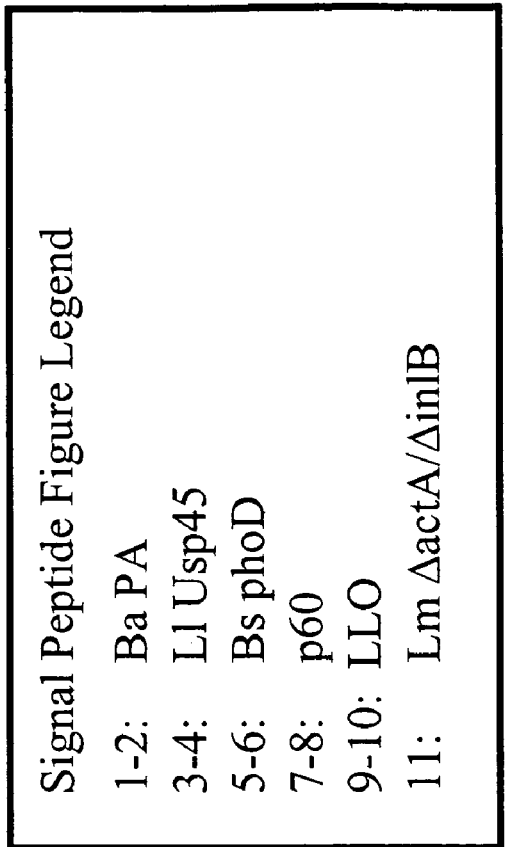
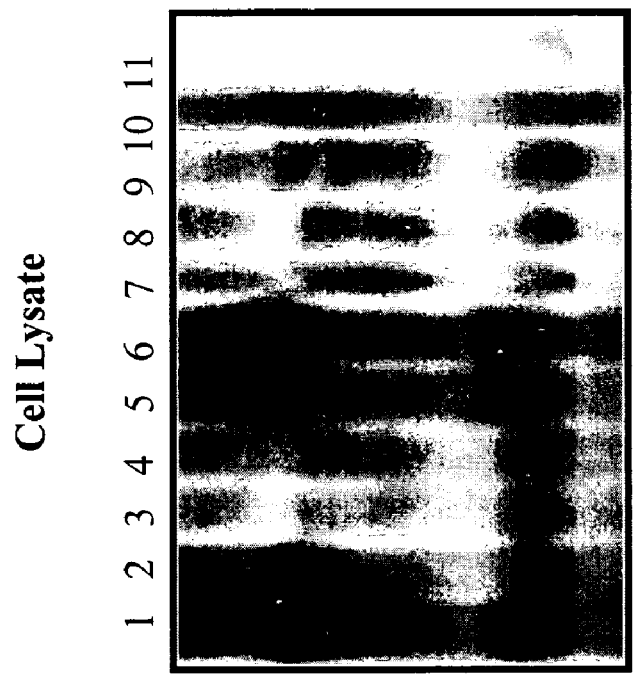
FIGURE 57C

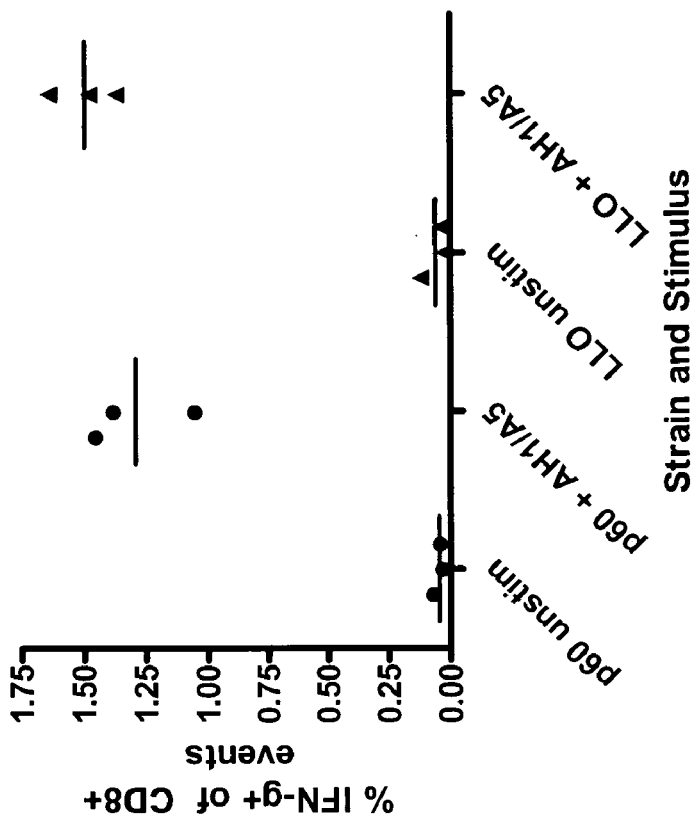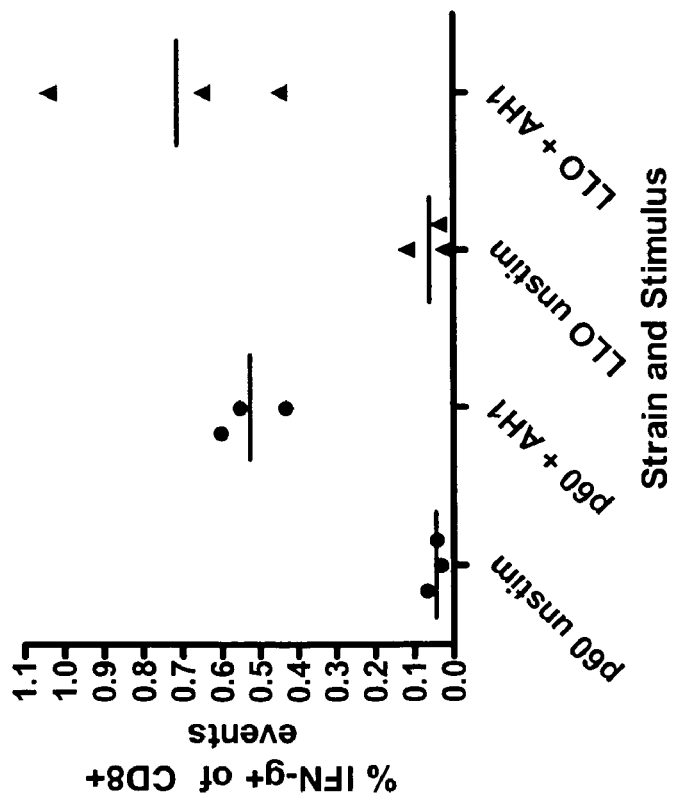
FIGURE 59

RECOMBINANT NUCLEIC ACID MOLECULES, EXPRESSION CASSETTES, AND BACTERIA, AND METHODS OF USE THEREOF

CROSS-REFERENCE TO RELATED APPLICATIONS

This application claims the priority benefit under 35 U.S.C. §119(e) of each of the following U.S. provisional applications, the disclosures of each of which are hereby incorporated by reference in their entirety herein: U.S. provisional application Ser. No. 60/616,750, entitled "Bacterial Expression Cassettes, Bacterial Vaccine Compositions, and Methods of Use Thereof," by Thomas W. Dubensky, Jr. et al., filed Oct. 6, 2004; U.S. provisional application Ser. No. 60/615,287, entitled "Bacterial Expression Cassettes, Bacterial Vaccine Compositions, and Methods of Use Thereof," by Thomas W. Dubensky, Jr. et al., filed Oct. 1, 2004; U.S. provisional application Ser. No. 60/599,377, filed Aug. 5, 2004; U.S. provisional application Ser. No. 60/556,744, filed Mar. 26, 2004; U.S. provisional application Ser. No. 60/541,515, filed Feb. 2, 2004; and U.S. provisional application Ser. No. 60/532,598, filed Dec. 24, 2003. In addition, this application is a continuation-in-part of each of the following prior applications, the disclosures of each of which are hereby incorporated by reference in their entirety herein: International Application No. PCT/US2004/23881, filed Jul. 23, 2004; U.S. patent application Ser. No. 10/883,599, filed Jun. 30, 2004 now U.S. Pat. No. 7,695,725 issued Apr. 13, 2010; U.S. patent application Ser. No. 10/773,618, filed Feb. 6, 2004; and U.S. patent application Ser. No. 10/773,792, filed Feb. 6, 2004 now U.S. Pat. No. 7,691,393 issued Apr. 6, 2010.

STATEMENT REGARDING FEDERALLY SPONSORED RESEARCH OR DEVELOPMENT

This invention was made, in part, with government support under SBIR Grant No. 1 R43 CA 101421-01, awarded by the National Institutes of Health. The government may have certain rights in the invention.

FIELD OF THE INVENTION

The field of this invention relates generally to novel polynucleotides and expression cassettes useful for expression of polypeptides, including heterologous polypeptides, in recombinant bacteria. In particular, this invention relates to recombinant bacteria comprising the novel expression cassettes and/or nucleic acid molecules which are useful in vaccine compositions.

BACKGROUND OF THE INVENTION

Microbes have begun to be developed for use as vaccines that deliver heterologous antigens. Heterologous antigen delivery is provided by microbes that have been modified to contain nucleic acid sequences encoding a protein or antigen originating from a different species. Heterologous antigen delivery is especially advantageous for treating or preventing diseases or conditions that result from especially virulent or lethal sources, such as cancer and pathogenic agents (for example, HIV or Hepatitis B), wherein injection of a native infectious agent or cancer cell is potentially deleterious to the recipient organism, and administration of attenuated or killed agent or cell has proven unsuccessful in eliciting an effective immune response, or where sufficient attenuation of the infectious agent or cancer cell cannot be assured with acceptable certainty. Recently, certain bacterial strains have been developed as recombinant vaccines. For instance, an oral vaccine of attenuated *Salmonella* modified to express *Plasmodium berghei* circumsporozite antigen has been shown to protect mice against malaria (Aggarwal et al. 1990. J. Exp. Med. 172:1083).

*Listeria monocytogenes* (*Listeria*) is a Gram-positive facultative intracellular bacterium that is being developed for use in antigen-specific vaccines due to its ability to prime a potent CD4+/CD8+ T-cell mediated response via both MHC class I and class II antigen presentation pathways. See, for instance, U.S. Pat. Nos. 6,051,237, 6,565,852, and 5,830,702.

*Listeria* has been studied for a number of years as a model for stimulating both innate and adaptive T cell-dependent antibacterial immunity. The ability of *Listeria* to effectively stimulate cellular immunity is based on its intracellular lifecycle. Upon infecting the host, the bacterium is rapidly taken up by phagocytes including macrophages and dendritic cells (DC) into a phagolysosomal compartment. The majority of the bacteria are subsequently degraded. Peptides resulting from proteolytic degradation of pathogens within phagosomes of infected APCs are loaded directly onto MHC class II molecules, and the processed antigens are expressed on the surface of the antigen presenting cell via the class II endosomal pathway, and these MHC II-peptide complexes activate CD4+ "helper" T cells that stimulate the production of antibodies. Within the acidic compartment, certain bacterial genes are activated including the cholesterol-dependent cytolysin, LLO, which can degrade the phagolysosome, releasing the bacterium into the cytosolic compartment of the host cell, where the surviving *Listeria* propagate. Efficient presentation of heterologous antigens via the MHC class I pathway requires de novo endogenous protein expression by *Listeria*. Within the cytoplasm of antigen presenting cells (APC), proteins synthesized and secreted by *Listeria* are sampled and degraded by the proteosome. The resulting peptides are shuttled into the endoplasmic reticulum by TAP proteins and loaded onto MHC class I molecules. The MHC I-peptide complex is delivered to the cell surface, which in combination with sufficient co-stimulation (signal 2) activates and stimulates cytotoxic T lymphocytes (CTLs) having the cognate T cell receptor to expand and subsequently recognize the MHC I-peptide complex displayed on, for example tumor cells. In the appropriate microenvironment, the activated T cell targets and kills the cancerous cell.

Given the mechanisms by which *Listeria* programs the presentation of heterologous antigens via the MHC class I pathway, the efficiency of both expression of heterologous genes and secretion of the newly synthesized protein from the bacterium into the cytoplasm of the infected (antigen presenting) cell is directly related to the potency of CD8+ T cell priming and/or activation. Since the level of Ag-specific T cell priming is directly related to vaccine efficacy, the efficiency of heterologous protein expression and secretion is linked directly to vaccine potency.

Thus, novel methods are needed in the art to optimize the efficiency of heterologous protein expression and secretion to maximize the potency of *Listeria*-based vaccines and other bacteria-based vaccines. It would also be beneficial to optimize the efficiency of heterologous protein expression and secretion in bacterial host expression systems where expression and secretion of large quantities of heterologous protein is desired.

BRIEF SUMMARY OF THE INVENTION

The present invention generally provides novel polynucleotides including novel recombinant nucleic acid molecules, expression cassettes, and vectors for use in expressing and/or secreting polypeptides (e.g. heterologous polypeptides) in bacteria, especially *Listeria*. In some embodiments, these polynucleotides provide enhanced expression and/or secretion of polypeptides in bacteria. The present invention also generally provides bacteria comprising the recombinant nucleic acid molecules, expression cassettes, or vectors, as well as pharmaceutical, immunogenic, and vaccine compositions comprising the bacteria. These bacteria and compositions are useful in the induction of immune responses and in the treatment and/or prevention of a wide array of diseases or other conditions, including cancer, infections and autoimmunity.

In one aspect, the invention provides a recombinant nucleic acid molecule, comprising a first polynucleotide encoding a signal peptide, wherein the first polynucleotide is codon-optimized for expression in a bacterium, and a second polynucleotide encoding a polypeptide (e.g., an antigen), wherein the second polynucleotide is in the same translational reading frame as the first polynucleotide, and wherein the recombinant nucleic acid molecule encodes a fusion protein comprising the signal peptide and the polypeptide. In some embodiments, the second polynucleotide is also codon-optimized for expression in bacteria, such as *Listeria*. The invention also provides expression cassettes comprising this recombinant nucleic acid molecule and further comprising a promoter operably linked to the recombinant nucleic acid molecule. Vectors and bacteria comprising the recombinant nucleic acid molecules and/or expression cassette are also provided, as are pharmaceutical compositions, immunogenic compositions, and vaccines comprising the bacteria. Methods of using the bacteria or compositions comprising the bacteria to induce immune responses and/or to prevent or treat a condition such as a disease in a host are also provided.

In another aspect, the invention provides a recombinant nucleic acid molecule, comprising (a) a first polynucleotide encoding a signal peptide native to a bacterium, wherein the first polynucleotide is codon-optimized for expression in the bacterium, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the polypeptide encoded by the second polynucleotide is heterologous to the signal peptide. In some embodiments, the polypeptide encoded by the second polynucleotide is foreign to the bacterium. The invention also provides expression cassettes comprising this recombinant nucleic acid molecule and further comprising a promoter operably linked to the recombinant nucleic acid molecule. Vectors and bacteria comprising the recombinant nucleic acid molecule and/or expression cassette are also provided, as are pharmaceutical compositions, immunogenic compositions, and vaccines comprising the bacteria. Methods of using the bacteria or compositions comprising the bacteria to induce an immune response and/or to prevent or treat a condition (e.g., a disease) in a host are also provided.

In another aspect, the invention provides a recombinant *Listeria* bacterium comprising a recombinant nucleic acid molecule, wherein the recombinant nucleic acid molecule comprises (a) a first polynucleotide encoding a signal peptide, wherein the first polynucleotide is codon-optimized for expression in *Listeria*, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the polypeptide encoded by the second polynucleotide is heterologous to the signal peptide. In some embodiments, the polypeptide is foreign to the *Listeria* bacterium. In some embodiments, the signal peptide is native to *Listeria*. Pharmaceutical compositions, immunogenic compositions, and vaccines, comprising the *Listeria* are also provided. Methods of using the *Listeria* (or compositions comprising the *Listeria*) to induce an immune response and/or to prevent or treat a condition (e.g., a disease) in a host are also provided.

In another aspect, the invention provides a recombinant nucleic acid molecule, comprising a first polynucleotide encoding a non-secA1 bacterial signal peptide, and a second polynucleotide encoding a polypeptide (such as an antigen), wherein the second polynucleotide is in the same translational reading frame as the first polynucleotide, and wherein the recombinant nucleic acid molecule encodes a fusion protein comprising the signal peptide and the polypeptide. In some embodiments, the polypeptide is heterologous to the signal peptide. In some embodiments, the first and/or second polynucleotides are codon-optimized for expression in bacteria, such as *Listeria*. The invention also provides expression cassettes comprising this recombinant nucleic acid molecule and further comprising a promoter operably linked to the recombinant nucleic acid molecule. Vectors and bacteria comprising the recombinant nucleic acid molecule and/or expression cassette are also provided, as are pharmaceutical compositions, immunogenic compositions, and vaccines comprising the bacteria. Methods of using the bacteria or compositions comprising the bacteria to induce immune responses and/or to treat a condition such as a disease in a host are also provided.

In still another aspect, the invention provides a recombinant *Listeria* bacterium comprising a recombinant nucleic acid molecule, wherein the recombinant nucleic acid molecule comprises (a) a first polynucleotide encoding a non-secA1 bacterial signal peptide, and (b) a second polynucleotide encoding a polypeptide either heterologous to the signal peptide or foreign to the bacterium, wherein the second polynucleotide is in the same translational reading frame as the first polynucleotide, wherein the recombinant nucleic acid molecule encodes a fusion protein comprising the signal peptide and the polypeptide. In some embodiments, the polypeptide encoded by the second polynucleotide is heterologous to the signal peptide or foreign to the bacterium (i.e., heterologous to the bacterium), or both. Pharmaceutical compositions, immunogenic compositions, and vaccines comprising the *Listeria* are also provided. Methods of using the *Listeria* (or compositions comprising the *Listeria*) to induce an immune response and/or to prevent or treat a condition (e.g., a disease) in a host are also provided.

In another aspect, the invention provides a recombinant nucleic acid molecule, wherein the recombinant nucleic acid molecule comprises a polynucleotide encoding a polypeptide foreign to *Listeria* (e.g., a cancer or non-Listerial infectious disease antigen), wherein the polynucleotide encoding the foreign polypeptide is codon-optimized for expression in *Listeria*. In some embodiments, the recombinant nucleic acid molecule further comprises a polynucleotide that encodes a signal peptide in the same translational reading frame as the polynucleotide encoding the polypeptide foreign to *Listeria*. In some embodiments, the signal peptide is native to the *Listeria* bacterium. In other embodiments, the signal peptide is foreign to the *Listeria* bacterium. In some embodiments, the polynucleotide encoding the signal peptide is also codon-optimized for expression in *Listeria*. *Listeria* comprising the recombinant nucleic acid molecule are also provided. Pharmaceutical compositions, immunogenic compositions, and vaccines comprising the *Listeria* are also provided. In addition, the invention provides methods of using the recombinant *Listeria* bacteria to induce immune responses and/or to prevent or treat a condition (such as, but not limited to, a disease) in a host.

In another aspect, the invention provides a recombinant *Listeria* bacterium comprising an expression cassette, wherein the expression cassette comprises a polynucleotide encoding a polypeptide foreign to *Listeria* (e.g., a cancer or non-Listerial infectious disease antigen), wherein the polynucleotide encoding the foreign polypeptide is codon-optimized for expression in *Listeria*, and a promoter, operably linked to the polynucleotide encoding the foreign polypeptide. In some embodiments, the expression cassette further comprises a polynucleotide that encodes a signal peptide (a signal peptide either native or foreign to the *Listeria* bacterium) in the same translational reading frame as the polynucleotide encoding the polypeptide foreign to *Listeria* and operably linked to the promoter so that the expression cassette expresses a fusion protein comprising the signal peptide and the foreign polypeptide. In some embodiments, the polynucleotide encoding the signal peptide is also codon-optimized for expression in *Listeria*. Pharmaceutical compositions, immunogenic compositions, and vaccines comprising the *Listeria* are also provided. In addition, the invention provides methods of using the recombinant *Listeria* bacteria to induce immune responses and/or to prevent or treat a condition (e.g., a disease) in a host.

In another aspect, the invention provides a recombinant nucleic acid molecule, wherein the recombinant nucleic acid molecule comprises (a) a first polynucleotide encoding a non-Listerial signal peptide, and (b) a second polynucleotide encoding a polypeptide that is in the same translational reading frame as the first polynucleotide, wherein the recombinant nucleic acid molecule encodes a fusion protein comprising both the non-Listerial signal peptide and the polypeptide. The invention also provides an expression cassette comprising the recombinant nucleic acid molecule, wherein the expression cassette further comprises a promoter operably linked to the first and second polynucleotides of the recombinant nucleic acid molecule. Vectors comprising the recombinant nucleic acid molecule and/or the expression cassette are also provided. In addition, a *Listeria* bacterium comprising the recombinant nucleic acid molecule and/or the expression cassette is also provided. Pharmaceutical compositions, immunogenic compositions, and vaccines, comprising the *Listeria* bacterium are also provided. Methods of using the *Listeria* bacterium (or compositions comprising the *Listeria* bacterium) to induce an immune response and/or to prevent or treat a condition (e.g., a disease) in a host are also provided.

In a further aspect, the invention provides a recombinant *Listeria* bacterium comprising a recombinant nucleic acid molecule, wherein the recombinant nucleic acid molecule comprises (a) a first polynucleotide encoding a non-Listerial signal peptide, and (b) a second polynucleotide encoding a polypeptide that is in the same translational reading frame as the first polynucleotide, wherein the recombinant nucleic acid molecule encodes a fusion protein comprising both the non-Listerial signal peptide and the polypeptide. Pharmaceutical compositions, immunogenic compositions, and vaccines, comprising the *Listeria* are also provided. Methods of using the *Listeria* (or compositions comprising the *Listeria*) to induce an immune response and/or to prevent or treat a condition (e.g., a disease) in a host are also provided.

In still another aspect, the invention provides a *Listeria* bacterium (for instance, from the species *Listeria monocytogenes*) comprising an expression cassette which comprises a first polynucleotide encoding a non-Listerial signal peptide, a second polynucleotide encoding a polypeptide (e.g., an antigen) that is in the same translational reading frame as the first polynucleotide, and a promoter operably linked to both the first and second polynucleotides. The expression cassette encodes a fusion protein comprising both the non-Listerial signal peptide and the polypeptide. In some embodiments, the first and/or second polynucleotides are codon-optimized for expression in *Listeria*. Pharmaceutical compositions, immunogenic compositions, and vaccines comprising the *Listeria* are also provided. In addition, the invention provides methods of using the recombinant *Listeria* bacteria to induce immune responses and/or to prevent or treat a condition (e.g., a disease) in a host.

The invention also provides a recombinant nucleic acid molecule, comprising (a) a first polynucleotide encoding a bacterial autolysin, or a catalytically active fragment or catalytically active variant thereof, and (b) a second polynucleotide encoding a polypeptide, wherein the second polynucleotide is in the same translational reading frame as the first polynucleotide, wherein the recombinant nucleic acid molecule encodes a protein chimera comprising the polypeptide encoded by the second polynucleotide and the autolysin, or catalytically active fragment or catalytically active variant thereof, wherein, in the protein chimera, the polypeptide is fused to or is positioned within the autolysin, or catalytically active fragment or catalytically active variant thereof. Vectors and bacteria comprising the recombinant nucleic acid molecule and/or expression cassette are also provided, as are pharmaceutical compositions, immunogenic compositions, and vaccines, comprising the bacteria. Methods of using the bacteria or compositions comprising the bacteria to induce immune responses and/or to treat a condition such as a disease in a host are also provided.

In another aspect, the invention provides a recombinant nucleic acid molecule, wherein the nucleic acid molecule encodes at least two discrete non-Listerial polypeptides. The invention further provides an expression cassette comprising the recombinant nucleic acid molecules and further comprising a promoter, wherein the promoter is operably linked to the recombinant nucleic acid molecule. Vectors comprising the recombinant nucleic acid molecule and/or expression cassette are further provides. In addition a recombinant *Listeria* bacterium comprising the recombinant nucleic acid molecule (and/or the expression cassette) is also provided. Pharmaceutical compositions, immunogenic compositions, and vaccines, comprising the *Listeria* are also provided. Methods of using the *Listeria* (or compositions comprising the *Listeria*) to induce an immune response and/or to prevent or treat a condition (e.g., a disease) in a host are also provided.

In an additional aspect, the invention provides a recombinant *Listeria* bacterium comprising a polycistronic expression cassette, wherein the polycistronic expression cassette encodes at least two discrete non-Listerial polypeptides. Pharmaceutical compositions, immunogenic compositions, and vaccines, comprising the *Listeria* are also provided. Methods of using the *Listeria* (or compositions comprising the *Listeria*) to induce an immune response and/or to prevent or treat a condition (e.g., a disease) in a host are also provided.

In other aspects, the invention provides a recombinant nucleic acid molecule, comprising (a) a first polynucleotide encoding a signal peptide, (b) a second polynucleotide encoding a secreted protein, or a fragment thereof, wherein the second polynucleotide is in the same translational reading frame as the first polynucleotide, and (c) a third polynucleotide encoding a polypeptide heterologous to the secreted protein, or fragment thereof, wherein the third polynucleotide is in the same translational reading frame as the first and second polynucleotides, wherein the recombinant nucleic acid molecule encodes a protein chimera comprising the signal peptide, the polypeptide encoded by the third polynucleotide, and the secreted protein, or fragment thereof, and wherein the polypeptide encoded by the third polynucleotide is fused to the secreted protein, or fragment thereof, or is positioned within the secreted protein, or fragment thereof, in the protein chimera. An expression cassette comprising the recombinant nucleic acid molecule and further comprising a promoter operably linked to the first, second, and third polynucleotides of the recombinant nucleic acid molecule is also provided. Vectors and bacteria comprising the recombinant nucleic acid molecule and/or expression cassette are also provided, as are pharmaceutical compositions, immunogenic compositions, and vaccines, comprising the bacteria. Methods of using the bacteria or compositions comprising the bacteria to induce an immune response and/or to prevent or treat a condition in a host are also provided.

In some embodiments, the methods of inducing an immune response in a host to an antigen comprise administering to the host an effective amount of a composition comprising a recombinant bacterium described herein (e.g., in any of the aspects above, or in the Detailed Description of the Invention or Examples, below) to the host, wherein a polypeptide encoded by the recombinant nucleic acid molecule, expression cassette, and/or vector in the bacterium comprises the antigen. In some embodiments, the methods of preventing or treating a condition, such as a disease, in a host comprise administering to the host an effective amount of a composition comprising a recombinant bacterium described herein to the host.

The invention further provides the use of a recombinant bacterium described herein (e.g., in any of the aspects above, or in the Detailed Description of the Invention or Examples, below) in the manufacture of a medicament for inducing an immune response in a host to an antigen, wherein a polypeptide encoded by the recombinant nucleic acid molecule, expression cassette, and/or vector in the bacterium comprises the antigen. In some embodiments, the antigen is a heterologous antigen. The invention also provides the use of a recombinant bacterium described herein in the manufacture of a medicament for preventing or treating a condition in a host (e.g., a disease such as cancer or an infectious disease). The invention further provides the recombinant bacteria described herein for use in inducing an immune response in a host to an antigen, wherein a polypeptide encoded by the recombinant nucleic acid molecule, expression cassette, and/or vector in the bacterium comprises the antigen. The invention further provides the recombinant bacteria described herein for use in the prevention or treatment of a condition (such as a disease) in a host.

In further aspects, the invention provides improved methods of expressing and secreting heterologous proteins in host bacteria.

Methods of making bacteria comprising each of the recombinant nucleic acid molecules and expression cassettes described above are also provided. Methods of using the bacteria to produce vaccines are also provided.

The invention further provides a variety of polynucleotides encoding signal peptides and/or antigens, including the polynucleotides which have been codon-optimized for expression in *Listeria monocytogenes*.

DRAWINGS

FIG. 1 shows the hly promoter alignment for the *Listeria monocytogenes* DP-L4056 (SEQ ID NO:1) (bottom sequence) and EGD strains (SEQ ID NO:2) (top sequence).

FIG. 2 shows the sequence (SEQ ID NO:3) of a polynucleotide encoding a fusion protein comprising the LLO signal peptide, LLO PEST sequence, and the full-length human EphA2 antigen.

FIG. 3 shows the sequence (SEQ ID NO:4) of the fusion protein encoded by the polynucleotide shown in FIG. 2.

FIG. 4 shows the native nucleotide sequence (SEQ ID NO:5) that encodes the human EphA2 extracellular domain (EX2).

FIG. 5 shows a nucleotide sequence (SEQ ID NO:6) encoding the human EphA2 extracellular domain that has been codon-optimized for expression in *Listeria monocytogenes*.

FIG. 6 shows the amino acid sequence (SEQ ID NO:7) of the human EphA2 extracellular domain (EX2).

FIG. 7 shows a non-codon optimized polynucleotide sequence (SEQ ID NO:8) encoding a fusion protein comprising an LLO signal peptide, LLO PEST sequence and the extracellular domain of human EphA2.

FIG. 8 shows the sequence (SEQ ID NO:9) of the fusion protein encoded by the coding sequence shown in FIG. 7.

FIG. 9 shows an expression cassette (SEQ ID NO:10) comprising the hly promoter and encoding a fusion protein comprising an LLO signal peptide, LLO PEST sequence and the extracellular domain of human EphA2. In this sequence, the sequence encoding the human EphA2 extracellular domain is codon-optimized for expression in *Listeria monocytogenes*.

FIG. 10 shows the amino acid sequence (SEQ ID NO:11) encoded by the expression cassette of FIG. 9.

FIG. 11 shows an expression cassette (SEQ ID NO:12) comprising the hly promoter and encoding a fusion protein comprising an LLO signal peptide, LLO PEST sequence and the extracellular domain of human EphA2. In this sequence, the sequences encoding the LLO signal peptide, LLO PEST, and human EphA2 extracellular domain have all been codon-optimized for expression in *Listeria monocytogenes*.

FIG. 12 shows the amino acid sequence (SEQ ID NO:13) encoded by the expression cassette of FIG. 11.

FIG. 13 shows an expression cassette (SEQ ID NO:14) comprising the hly promoter and encoding a fusion protein comprising the phoD Tat signal peptide and the extracellular domain of human EphA2. In this sequence, the sequences encoding the phoD Tat signal peptide and human EphA2 extracellular domain have both been codon-optimized for expression in *Listeria monocytogenes*.

FIG. 14 shows the amino acid sequence (SEQ ID NO:15) encoded by the expression cassette of FIG. 13.

FIG. 15 shows the native nucleotide sequence (SEQ ID NO:16) that encodes the human EphA2 intracellular domain (CO).

FIG. 16 shows a nucleotide sequence (SEQ ID NO:17) encoding the human EphA2 intracellular domain that has been codon-optimized for expression in *Listeria monocytogenes*.

FIG. 17 shows the amino acid sequence (SEQ ID NO:18) of the human EphA2 intracellular domain (EX2).

FIG. 18 shows a non-codon optimized polynucleotide sequence (SEQ ID NO:19) encoding a fusion protein comprising an LLO signal peptide, LLO PEST sequence and the intracellular domain of human EphA2.

FIG. 19 shows the sequence (SEQ ID NO:20) of the fusion protein encoded by the coding sequence shown in FIG. 18.

FIG. 20 shows an expression cassette (SEQ ID NO:21) comprising the hly promoter and encoding a fusion protein comprising an LLO signal peptide, LLO PEST sequence and the intracellular domain of human EphA2. In this sequence, the sequence encoding the human EphA2 intracellular domain is codon-optimized for expression in *Listeria monocytogenes*.

FIG. 21 shows the amino acid sequence (SEQ ID NO:22) encoded by the expression cassette of FIG. 20.

FIG. 22 shows an expression cassette (SEQ ID NO:23) comprising the hly promoter and encoding a fusion protein comprising an LLO signal peptide, LLO PEST sequence and the intracellular domain of human EphA2. In this sequence, the sequences encoding the LLO signal peptide, LLO PEST, and human EphA2 intracellular domain have all been codon-optimized for expression in *Listeria monocytogenes*.

FIG. 23 shows the amino acid sequence encoded (SEQ ID NO:24) by the expression cassette of FIG. 22.

FIG. 24 shows an expression cassette (SEQ ID NO:25) comprising the hly promoter and encoding a fusion protein comprising a phoD Tat signal peptide and the intracellular domain of human EphA2. In this sequence, the sequences encoding both the phoD Tat signal peptide and human EphA2 intracellular domain have been codon-optimized for expression in *Listeria monocytogenes*.

FIG. 25 shows the amino acid sequence (SEQ ID NO:26) encoded by the expression cassette of FIG. 24.

FIG. 26 shows a codon-optimized expression cassette (SEQ ID NO:27) comprising the hly promoter and encoding a fusion protein comprising an LLO signal peptide and the NY-ESO-1 antigen. Both the sequences encoding the signal peptide and the antigen are codon-optimized for expression in *Listeria monocytogenes*.

FIG. 27 shows the amino acid sequence (SEQ ID NO:28) encoded by the expression cassette of FIG. 26.

FIG. 28 shows a polynucleotide (SEQ ID NO:29) comprising the hly promoter operably linked to a codon-optimized sequence encoding a Usp45 signal peptide.

FIG. 29 shows a polynucleotide (SEQ ID NO:30) comprising the hly promoter operably linked to a native sequence encoding a p60 signal peptide.

FIG. 30 shows a polynucleotide (SEQ ID NO:31) comprising the hly promoter operably linked to a codon-optimized sequence encoding a p60 signal peptide.

FIG. 31 shows the sequence (SEQ ID NO:32) of an hlyP-p60 gene fragment.

FIG. 32 (includes FIGS. 32A, 32B, and 32C) shows the sequence (SEQ ID NO:33) of pAM401-MCS, the pAM401 plasmid containing a multiple cloning site (MCS) from pPL2 vector.

FIG. 33 shows the coding sequence (SEQ ID NO:34) for human mesothelin which has been codon-optimized for expression in *Listeria monocytogenes*.

FIG. 34 shows the amino acid sequence of human mesothelin (SEQ ID NO:35).

FIG. 35 shows the coding sequence (SEQ ID NO:36) for murine mesothelin which has been codon-optimized for expression in *Listeria monocytogenes*.

Figure 36:
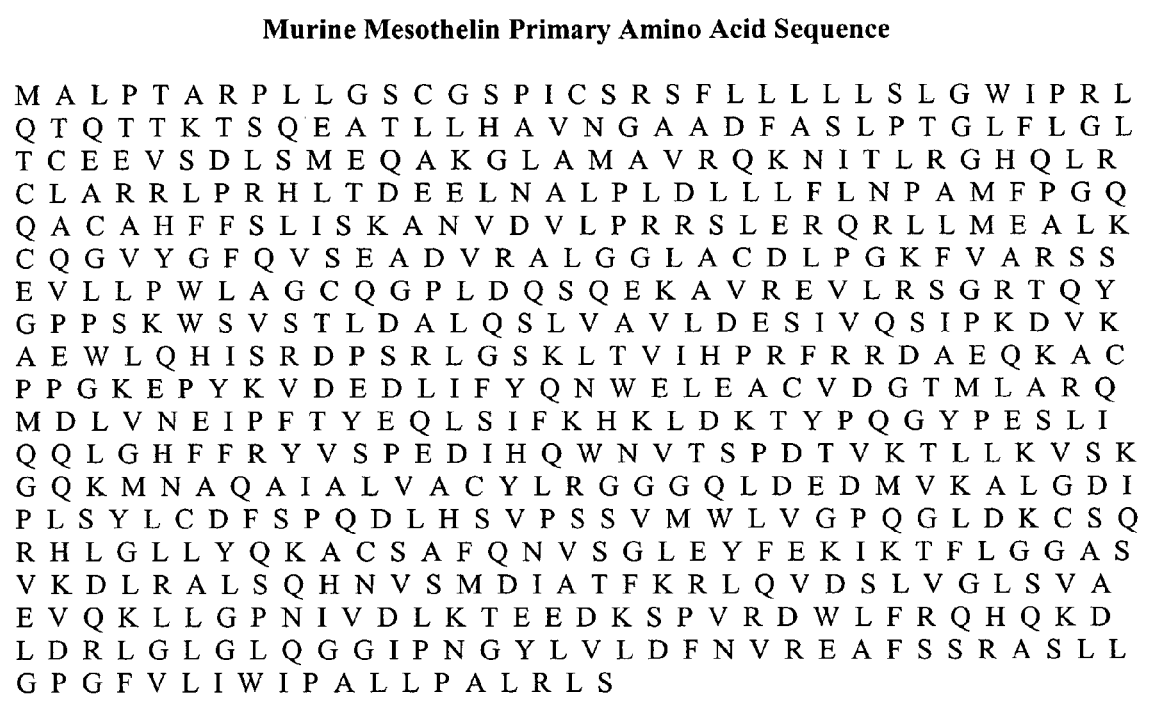

FIG. 36 shows the amino acid sequence (SEQ ID NO:37) of murine mesothelin.

Figure 37:
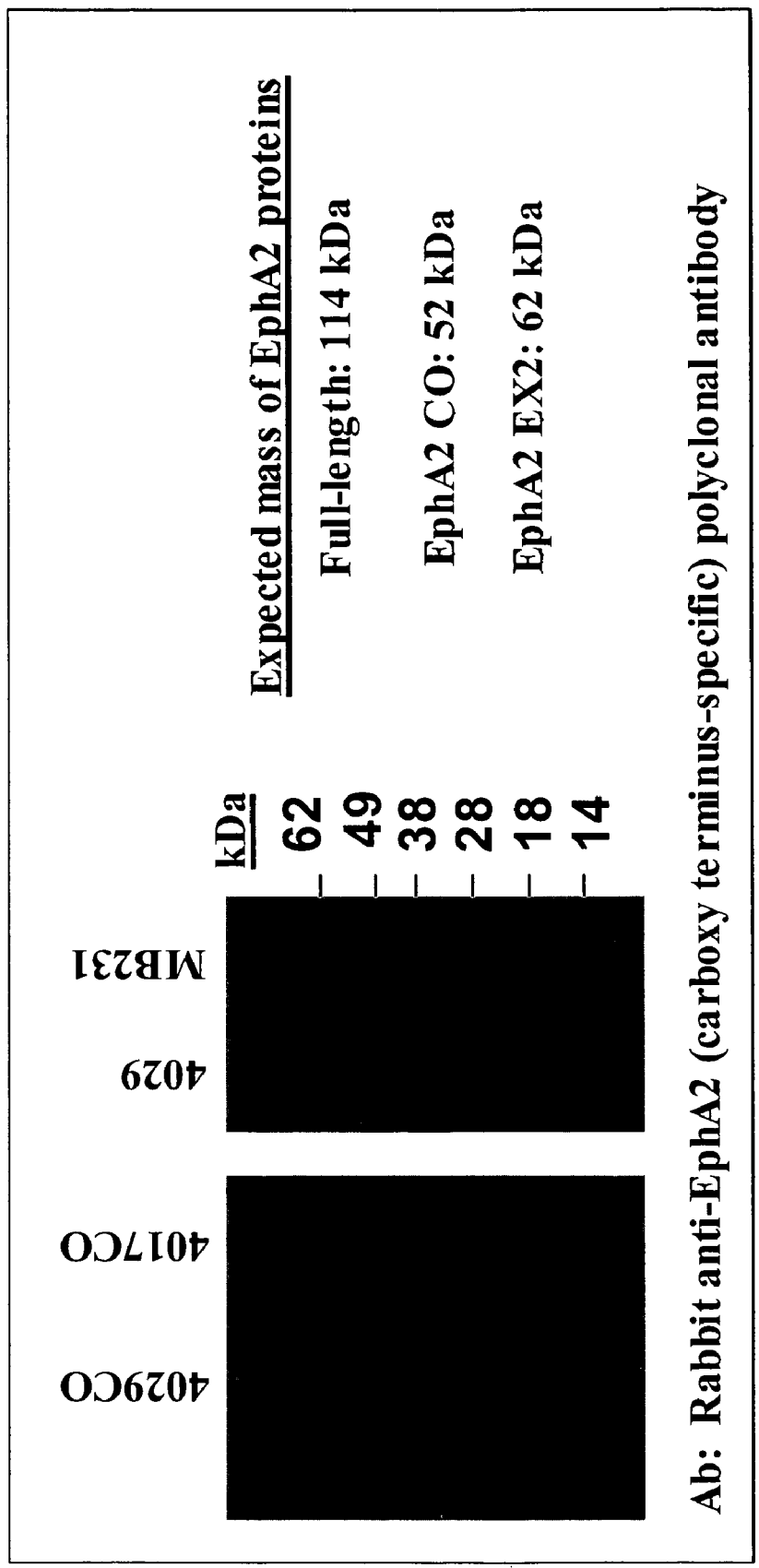

FIG. 37 shows a Western blot analysis of secreted protein from recombinant *Listeria* encoding a native EphA2 CO domain sequence.

Figure 38:
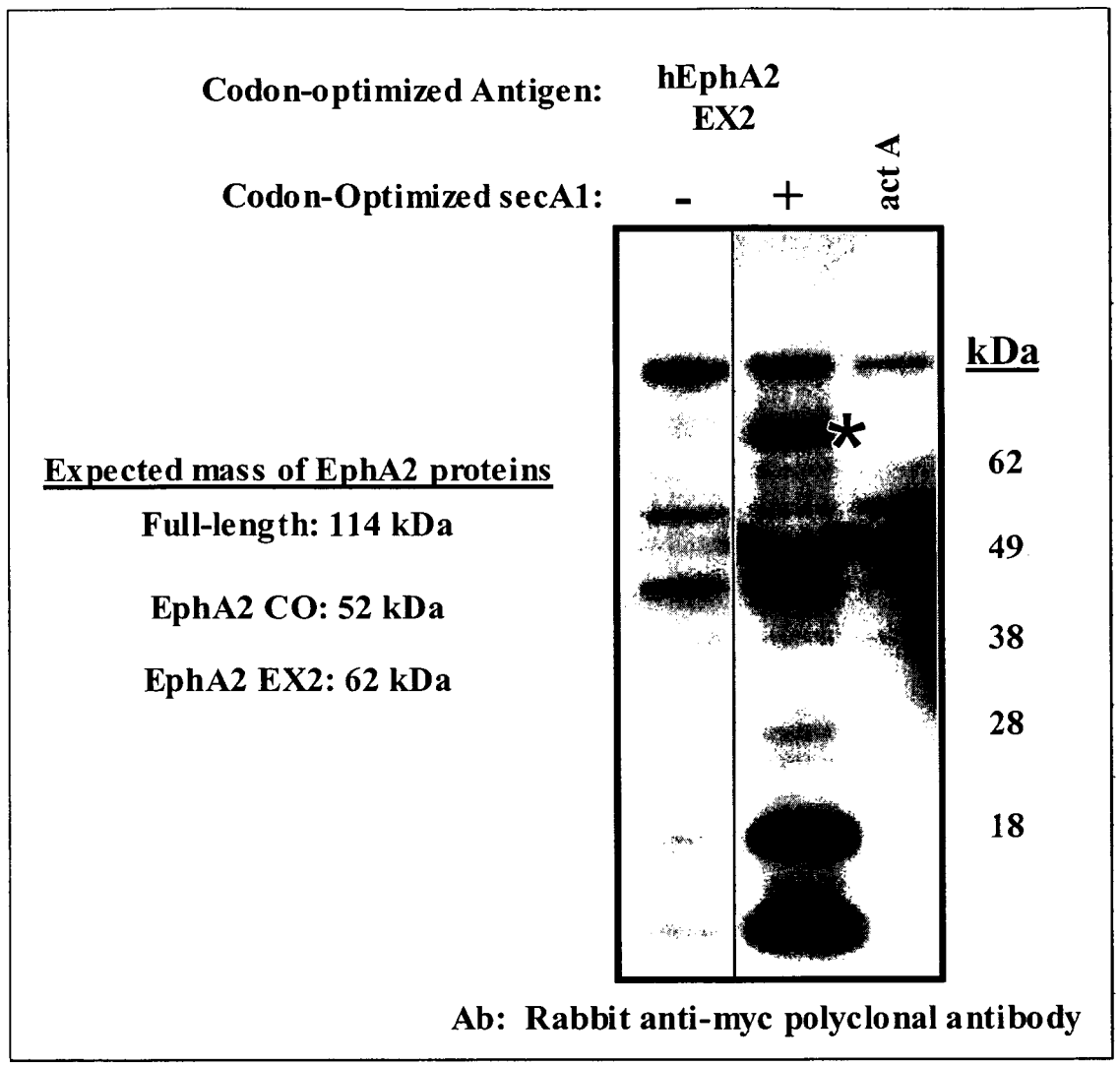

FIG. 38 shows a Western blot analysis of secreted protein from recombinant *Listeria* encoding native or codon-optimized LLO secA1 signal peptide fused with codon-optimized EphA2 EX2 domain sequence.

Figure 39:
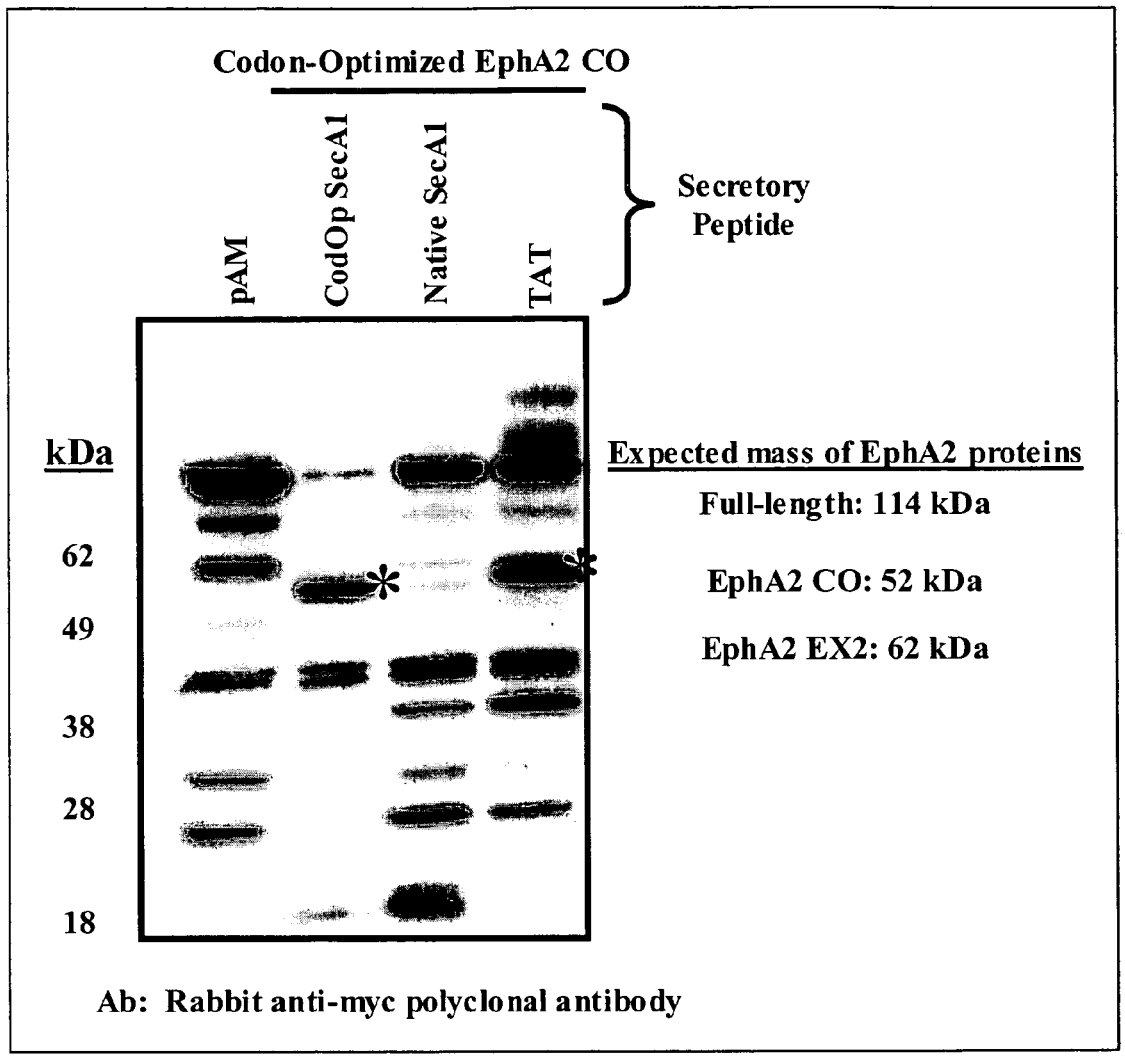

FIG. 39 shows a Western blot analysis of secreted protein from recombinant *Listeria* encoding native or codon-optimized LLO secA1 signal peptide or codon-optimized Tat signal peptide fused with codon-optimized EphA2 CO domain sequence.

Figure 40:
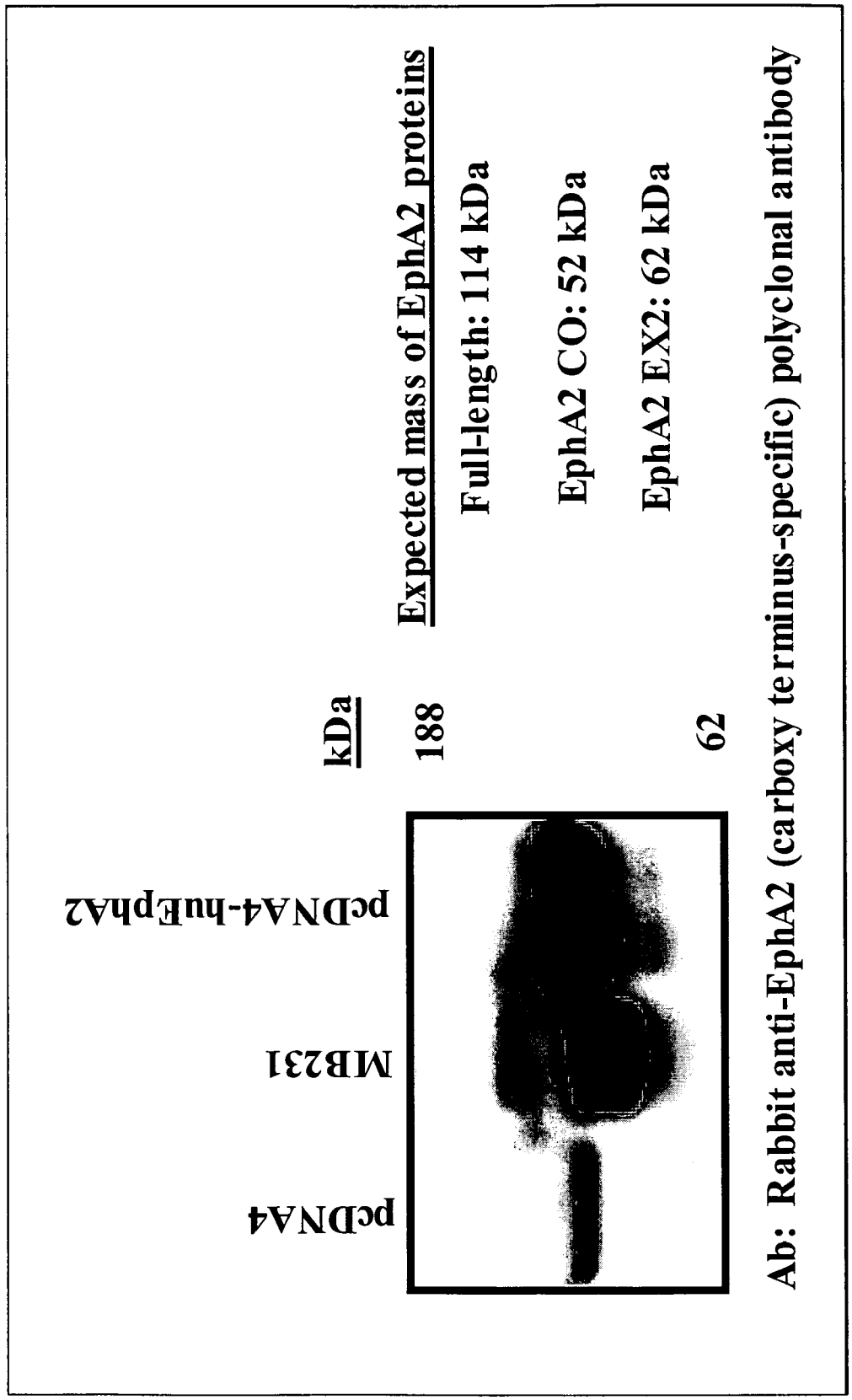

FIG. 40 shows a Western blot analysis of lysate from 293 cells 48 hr following transfection with pCDNA4 plasmid DNA encoding full-length native EphA2 sequence.

Figure 41:
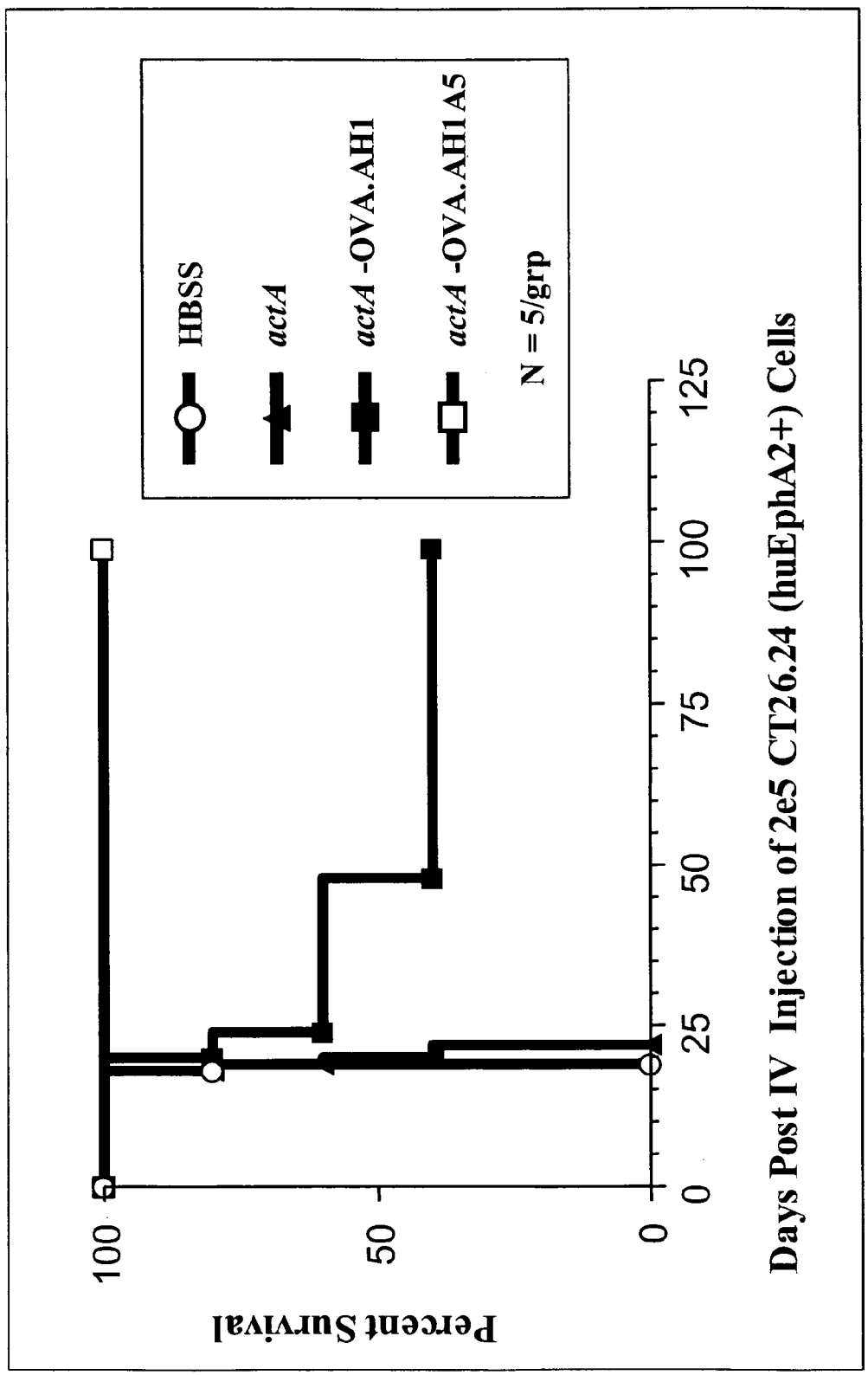

FIG. 41 is a graph showing that immunization of Balb/C mice bearing CT26.24 (huEphA2+) lung tumors with recombinant *Listeria* encoding OVA.AH1 or OVA.AH1-A5 confers long-term survival.

Figure 42:
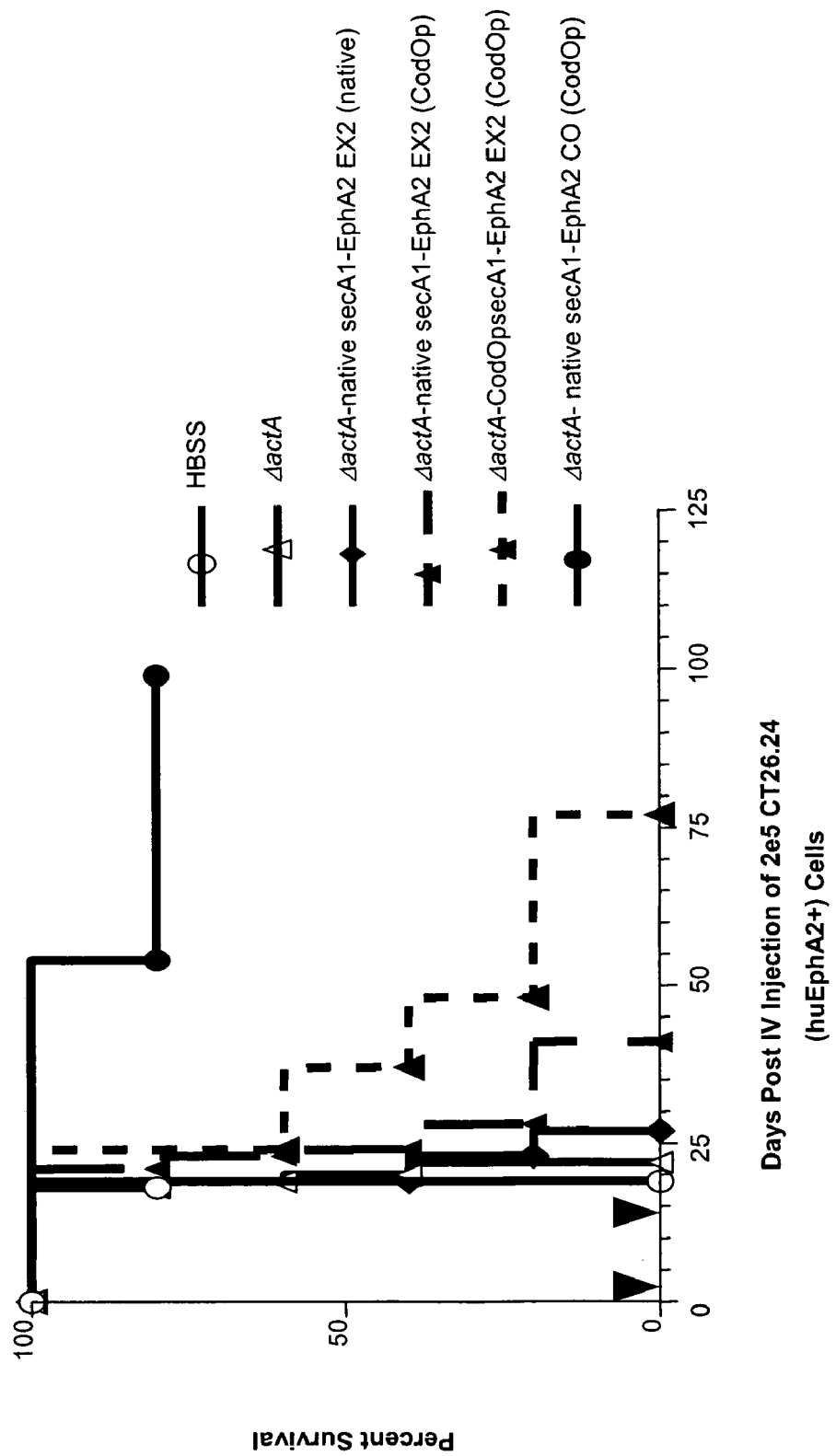

FIG. 42 is a graph showing the increased survival of Balb/C mice bearing CT26.24 (huEphA2+) lung tumors when immunized with recombinant *Listeria* encoding codon-optimized secA1 signal peptide fused with codon-optimized EphA2 EX2 domain sequence.

Figure 43:
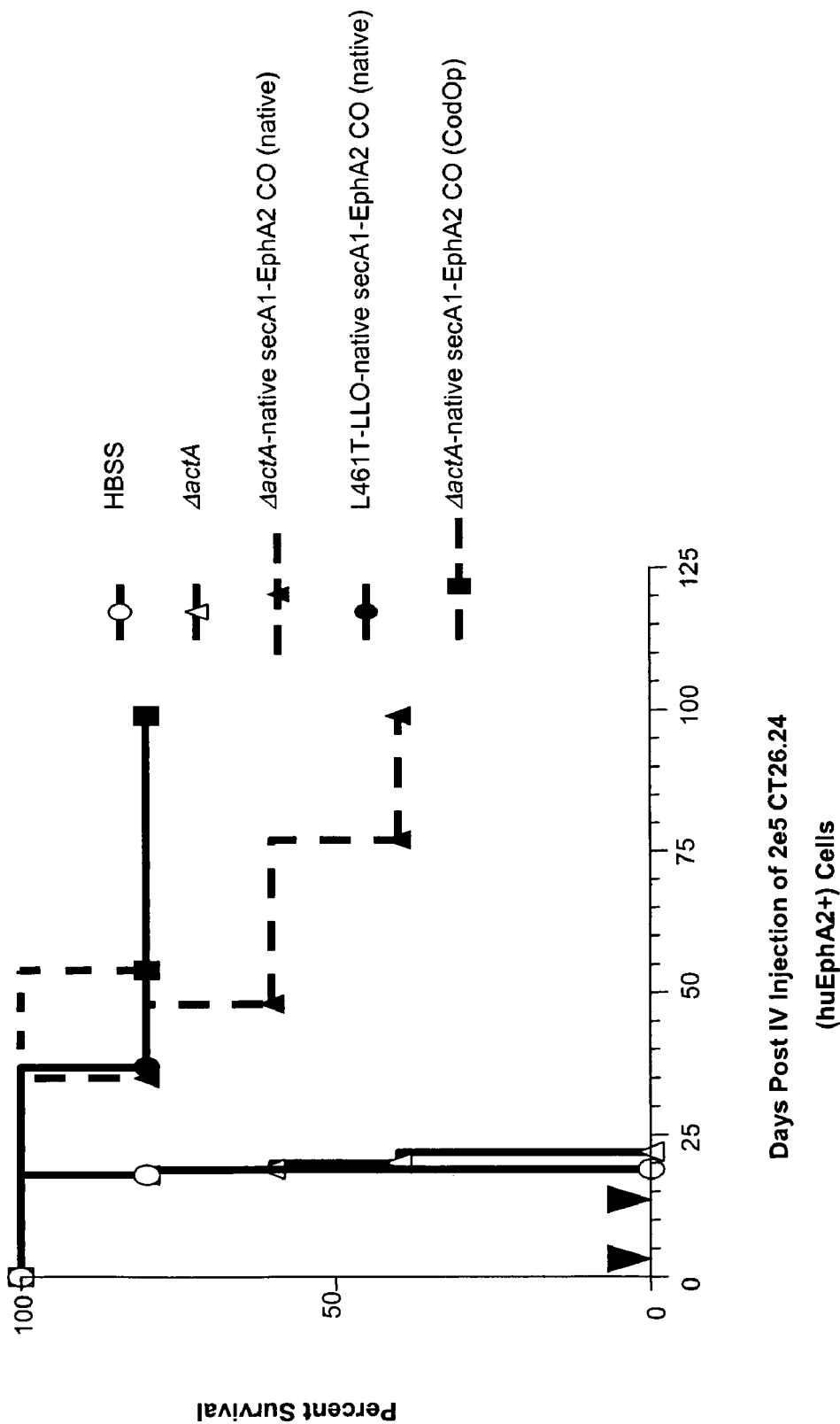

FIG. 43 is a graph showing that immunization of Balb/C mice bearing CT26.24 (huEphA2+) lung tumors with recombinant *Listeria* encoding EphA2 CO domain confers long-term survival.

Figure 44:
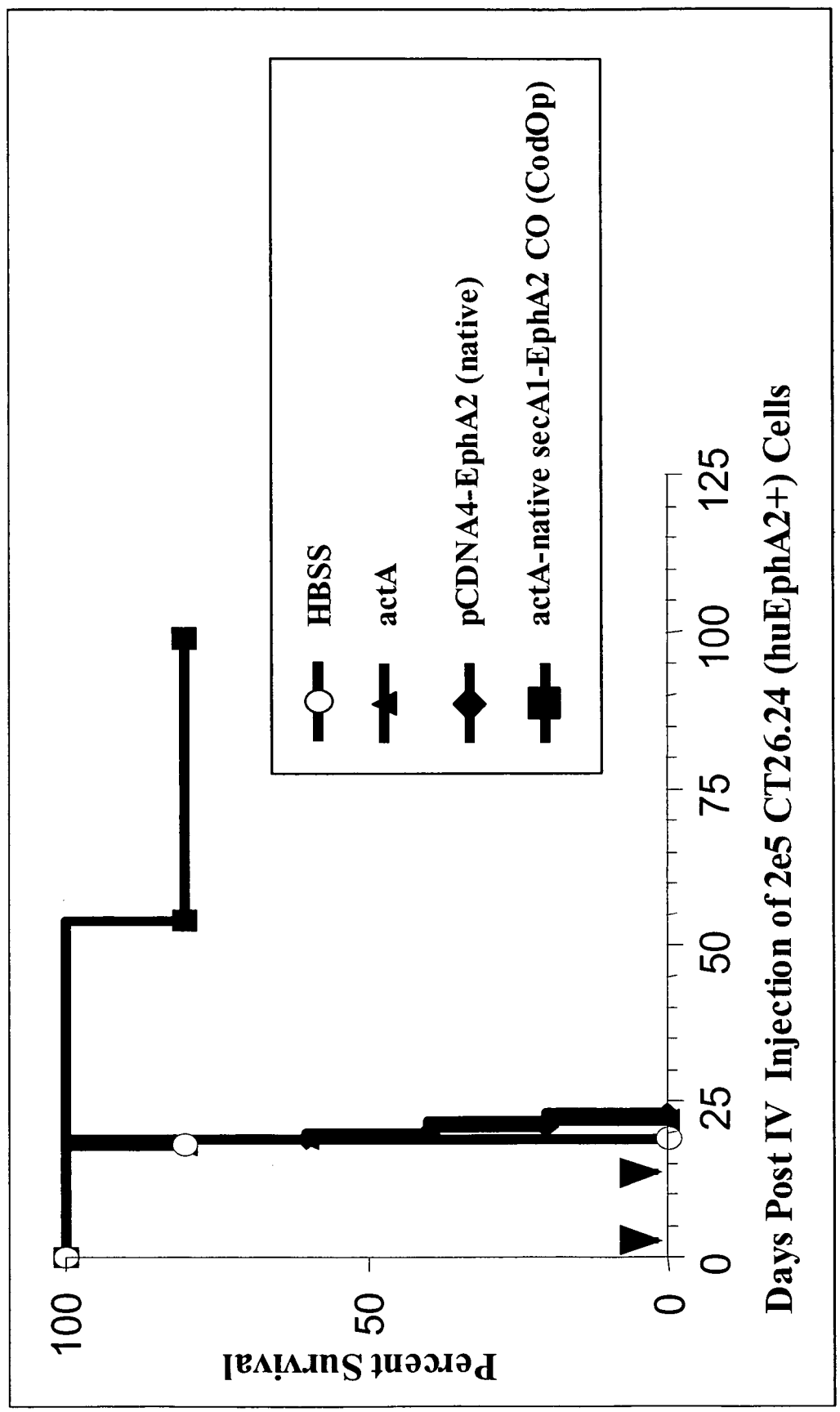

FIG. 44 is a graph showing that immunization of Balb/C mice bearing CT26.24 (huEphA2+) lung tumors with recombinant *Listeria* encoding EphA2 CO domain but not with plasmid DNA encoding full-length EphA2 confers long-term survival.

Figure 45:
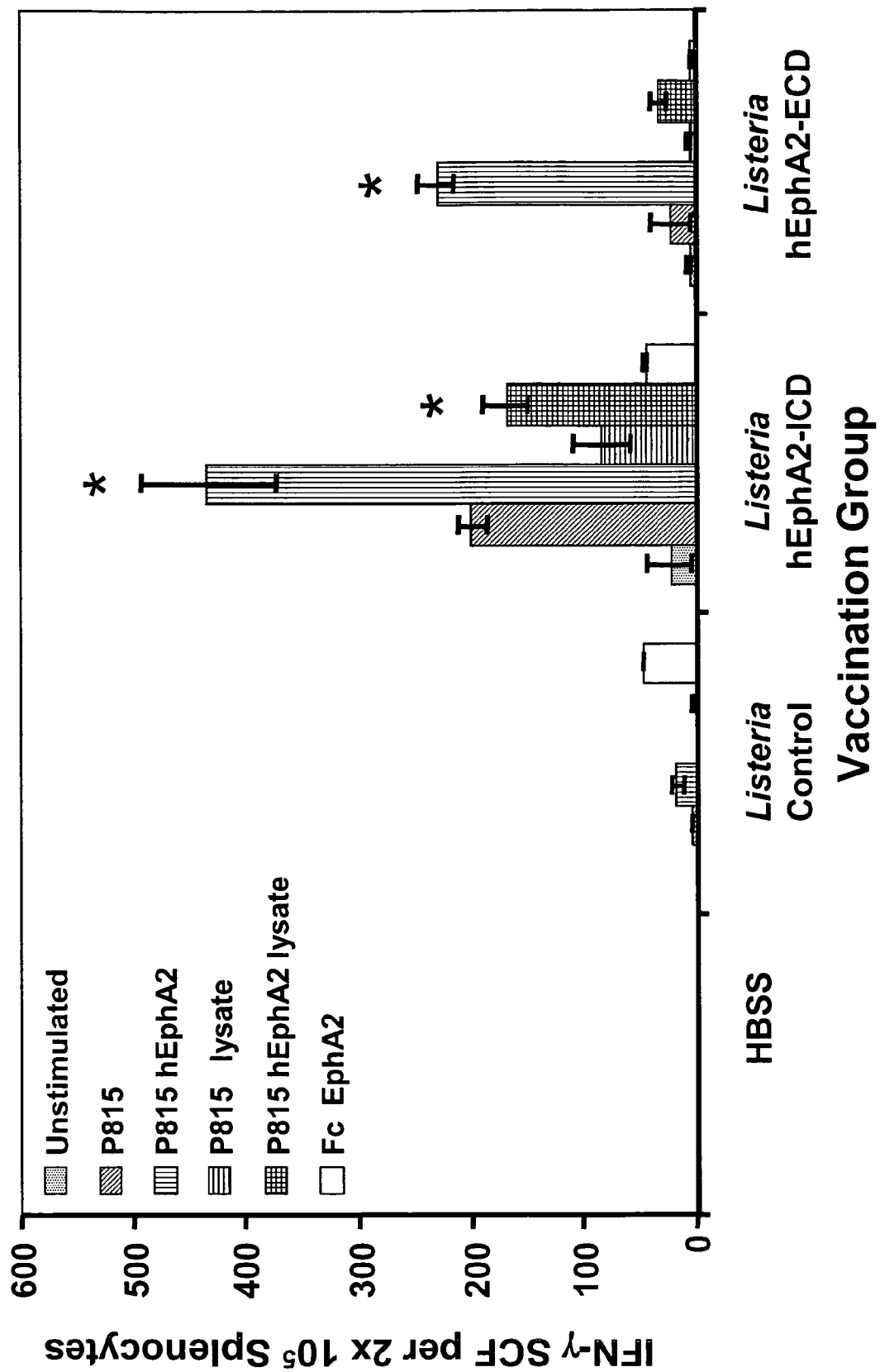

FIG. 45 is a graph showing that *Listeria* expressing hEphA2 elicits an EphA2 specific CD8+ T cell response.

Figure 46:
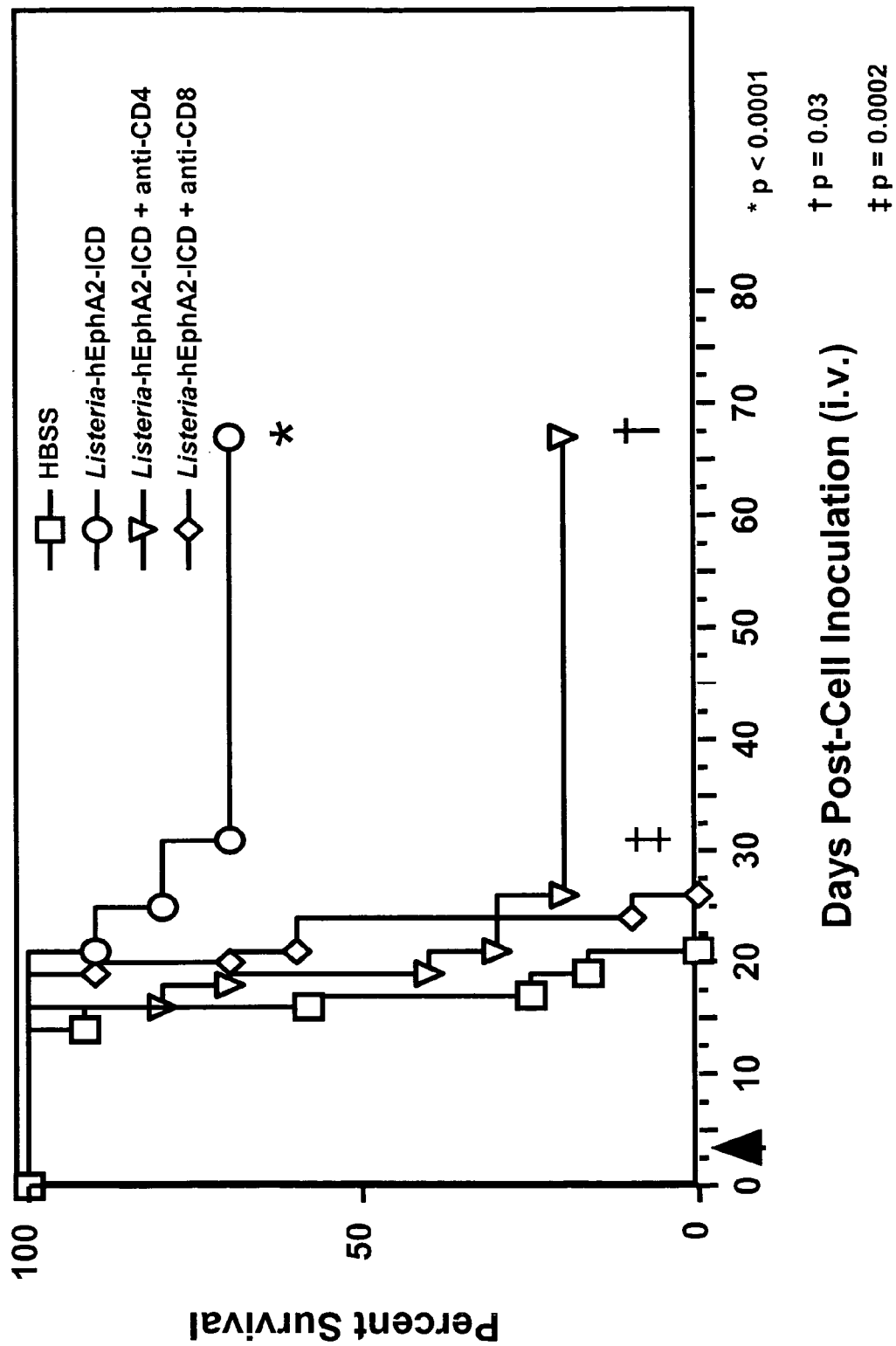

FIG. 46 is a graph showing that both CD4+ and CD8+ T cell responses contribute to the hEphA2-directed anti-tumor efficacy of *Listeria* expressing hEphA2.

FIG. 47 shows the sequence (SEQ ID NO:38) of the *Listeria monocytogenes* strain 10403S hly promoter operably linked to Protective Antigen signal peptide from *B. anthracis*, codon-optimized for secretion in *Listeria monocytogenes*. Six additional nucleotides (5'-GGATCC-3') corresponding to the Bam HI restriction enzyme recognition site were included at the carboxy terminus of the signal peptide sequence, facilitating operable in-frame linkage to any selected coding sequence. The 5' end of the hly promoter contains a unique Kpn I restriction enzyme recognition site.

FIG. 48 shows the efficient expression and secretion of full-length human tumor antigens from recombinant *Listeria*. FIG. 48A shows mesothelin expression/secretion with constructs consisting of LLO signal peptide fused with human mesothelin, using native codons. FIG. 48B shows mesothelin expression/secretion with constructs comprising various signal peptides fused with human mesothelin codon-optimized for expression in *Listeria*. FIG. 48C shows the expression/secretion of NY-ESO-1 with constructs comprising codon-optimized LLO signal peptide fused with human mesothelin codon-optimized NY-ESO-1.

FIG. 49 shows the coding sequences of phEphA2KD (SEQ ID NO:39).

FIG. 50 shows the Mlu I subfragment (SEQ ID NO:40) of codon-optimized human EphA2 containing the actA-plcB intergenic region.

FIG. 51 shows the sequence (SEQ ID NO:41) of the hly promoter-70 N-terminal p60 amino acids.

FIG. 52 shows the KpnI-BamHI sub-fragment (SEQ ID NO:42) of plasmid pPL2-hlyP-Np60 CodOp(1-77).

FIG. 53 shows the KpnI-BamHI sub-fragment (SEQ ID NO:43) of plasmid pPL2-hlyP-Np60 CodOp(1-77)-Mesothelin.

FIG. 54 shows the KpnI-BamHI sub-fragment (SEQ ID NO:44) of plasmid pPL2-hlyP-Np60 CodOp(1-77)-Mesothelin ΔSP/ΔGPI.

FIG. 55 shows the Western blot analysis of the expression and secretion of antigens from recombinant *Listeria* comprising antigen-bacterial protein chimeras.

FIG. 56 shows the Western blot analysis of the expression of the intracellular domain (ICD) of EphA2 from a bicistronic message.

Figure 57A:
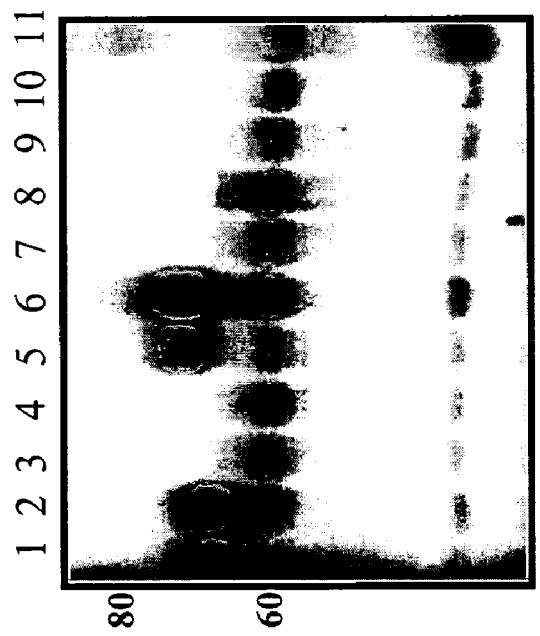
Figure 57B:
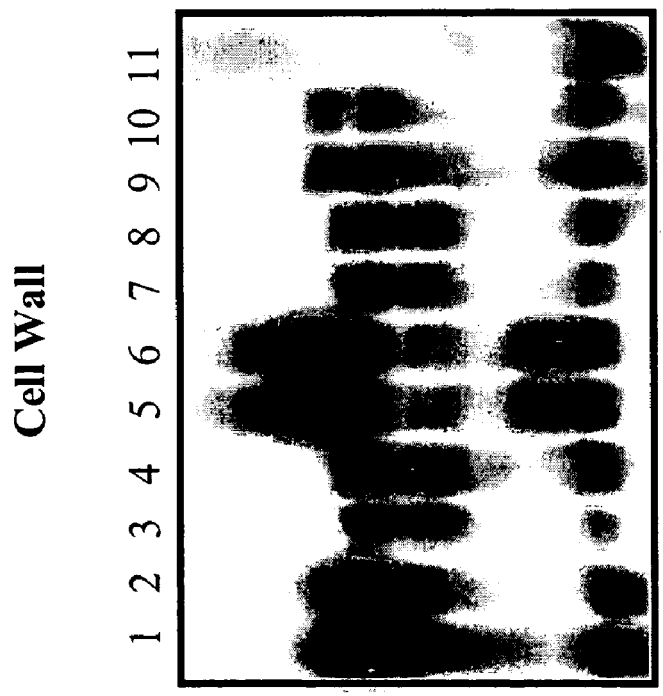

FIG. 57 shows the Western blot analysis of the plasmid based expression and secretion of murine mesothelin as a function of N-terminal fusion with various codon-optimized signal peptides as evidenced in different bacterial fractions: secreted protein (FIG. 57A); cell wall (FIG. 57B); and cell lysate (FIG. 57C).

Figure 58:
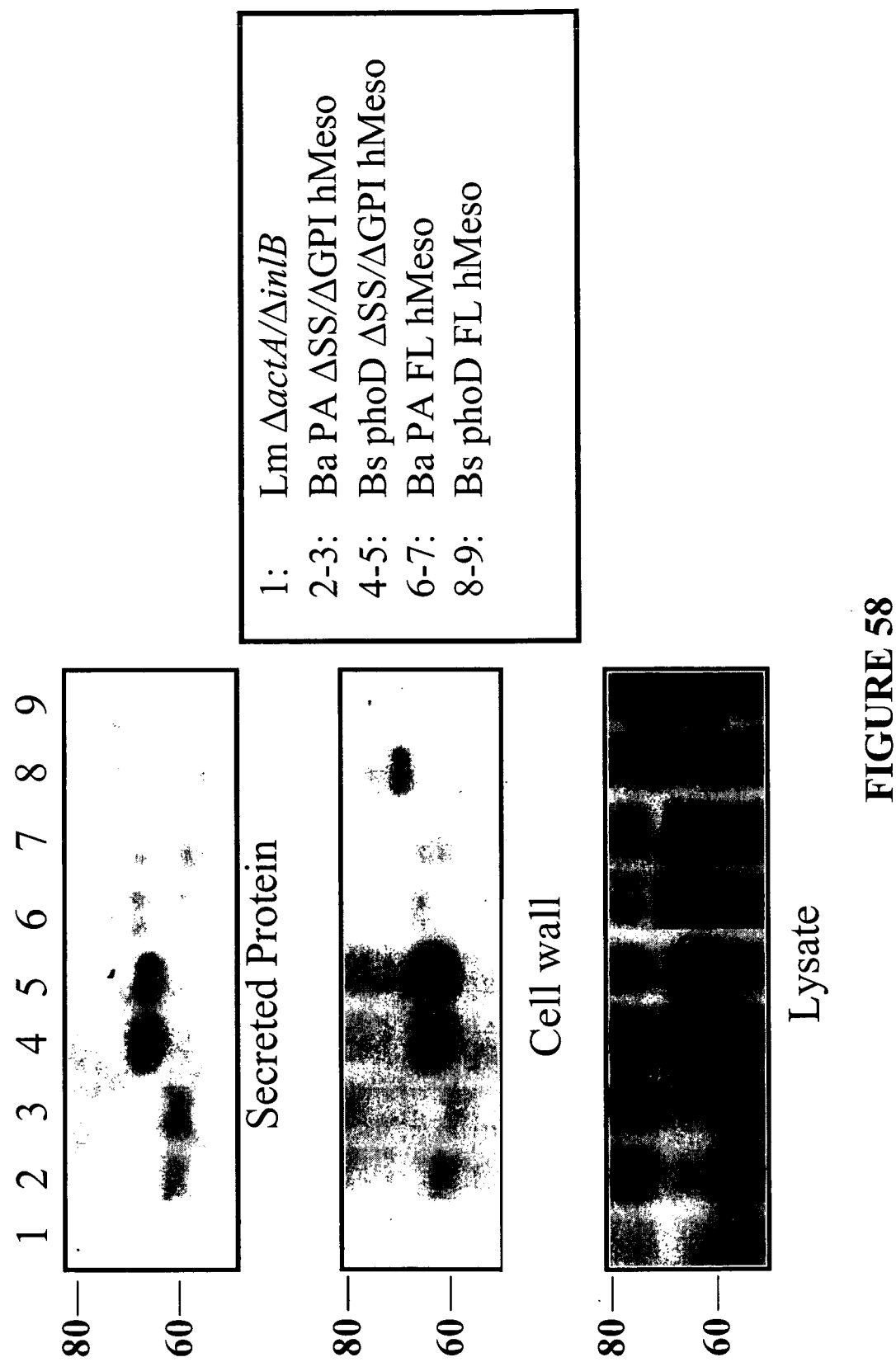

FIG. 58 shows the Western blot analysis of chromosomal-based expression and secretion of human mesothelin in *Listeria monocytogenes*. Western blot analysis of mesothelin expression in various bacterial cell fractions, with results from control *Listeria* (not encoding mesothelin) and *Listeria* encoding mesothelin expressed from the indicated signal sequences, is shown.

FIGS. 59A and 59B are graphs showing the delivery of a heterologous antigen (AH1-A5) to MHC Class I pathway by a *Listeria* vaccine. The *Listeria* vaccine comprised *Listeria* expressing a p60-AH1-A5 protein chimera (AH1-A5 embedded in p60) (FIG. 59A) or *Listeria* expressing a fusion protein comprising an LLO signal peptide and AH1-A5 (FIG. 59B).

Figure 60:
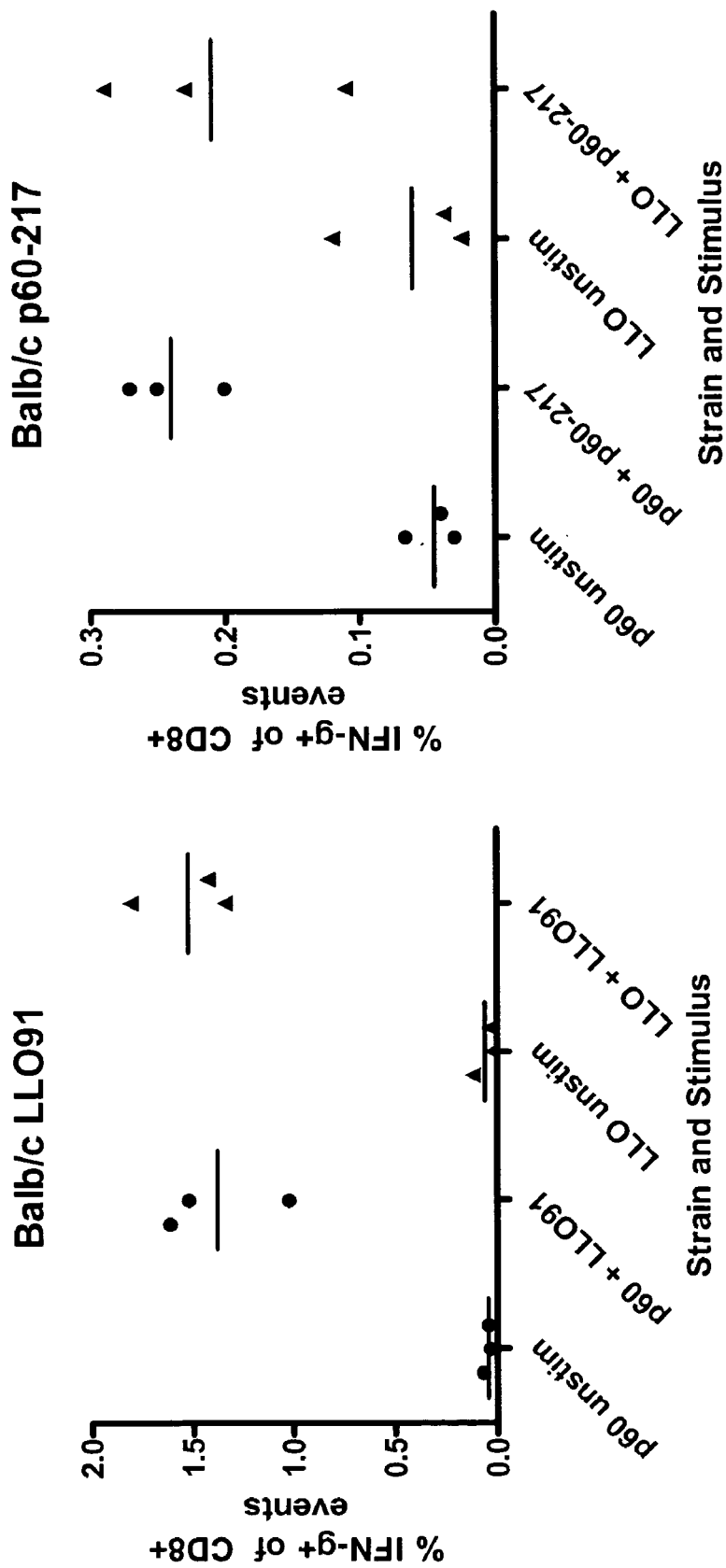

FIGS. 60A and 60B are graphs showing the *Listeria* vaccine mediated delivery of bacteria-specific antigens to MHC Class I pathway, where the vaccine comprised *Listeria* expressing a p60-AH1-A5 protein chimera (AH1-A5 embedded in p60) (FIG. 60A) or *Listeria* expressing a fusion protein comprising an LLO signal peptide and AH1-A5 (FIG. 60B), and where the test peptides added to the cell based assay were no test peptide (unstimulated) (FIG. 60A), $LLO_{91-99}$ (FIG. 60A), no test peptide (FIG. 60B), or $p60_{217-225}$ (FIG. 60B).

Figure 61:
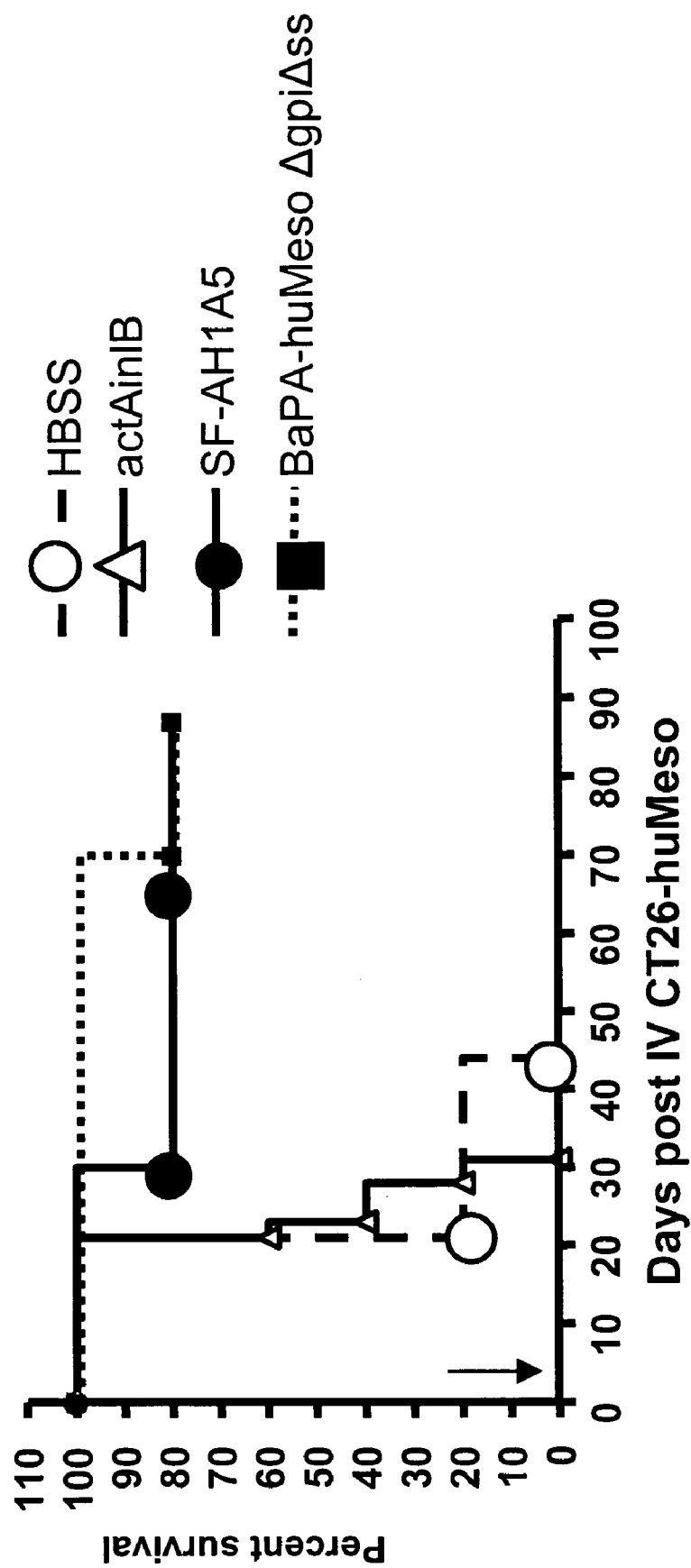

FIG. 61 is a graph showing the therapeutic efficacy of *Listeria* expressing human mesothelin in vaccinated tumor-bearing animals, where tumor cells were engineered to express human mesothelin.

Figure 62:
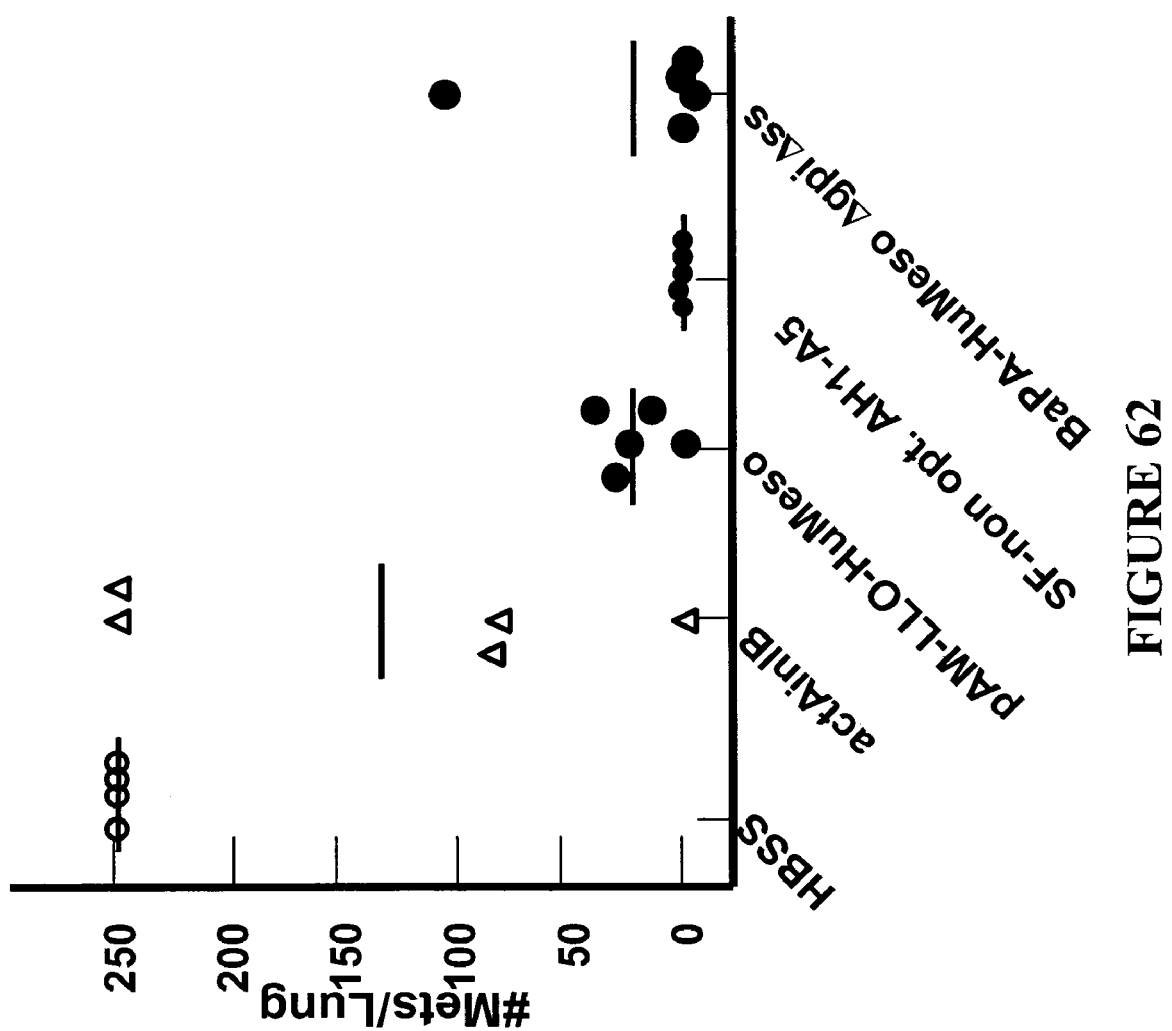

FIG. 62 is a graph showing the reduction in lung tumor nodule level in tumor-bearing mice vaccinated with *Listeria* expressing human mesothelin, where the tumor cells were engineered to express human mesothelin.

Figure 63:
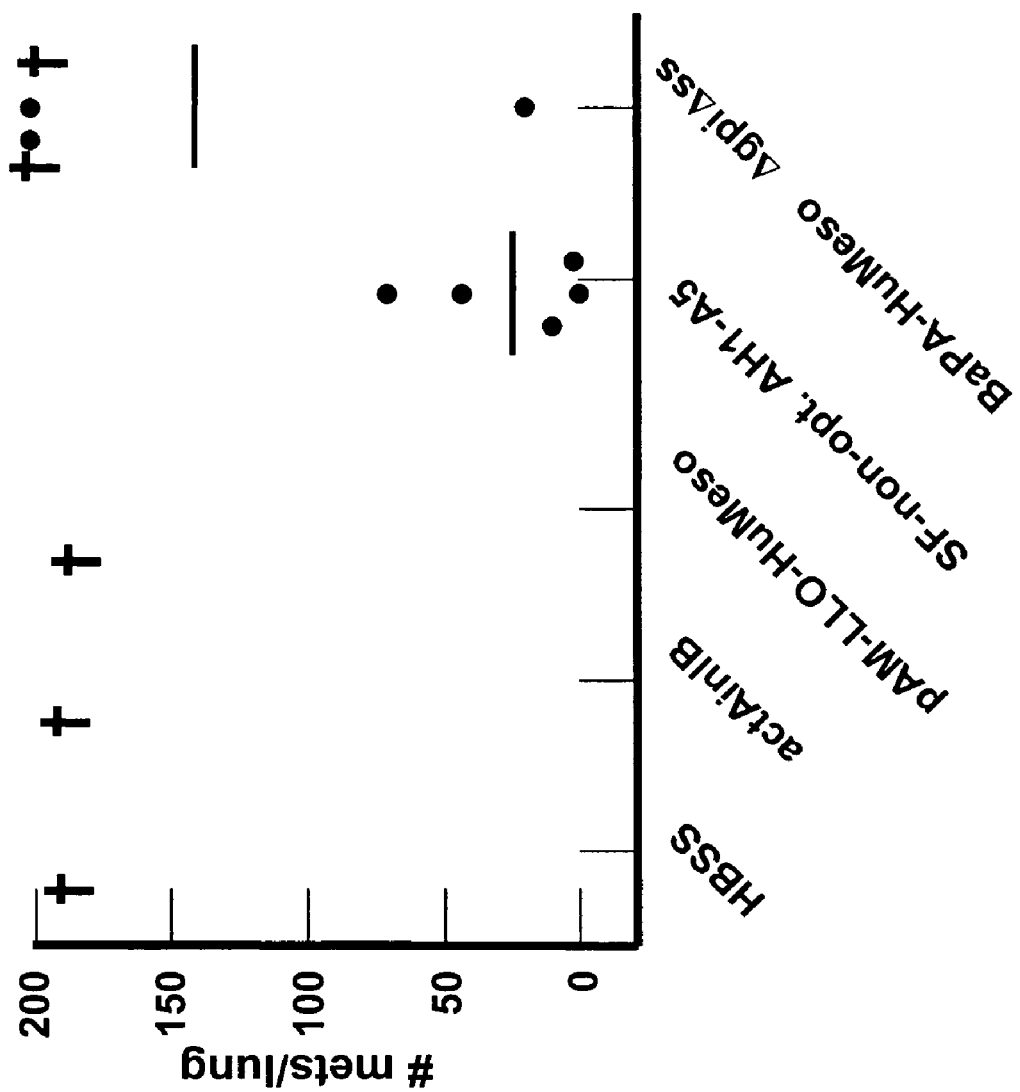

FIG. 63 is a graph showing a control study using CT.26 parental target cells, i.e., cells not engineered to express human mesothelin, that demonstrates the anti-tumor efficacy of Lm-Meso vaccination is mesothelin specific.

Figure 64:
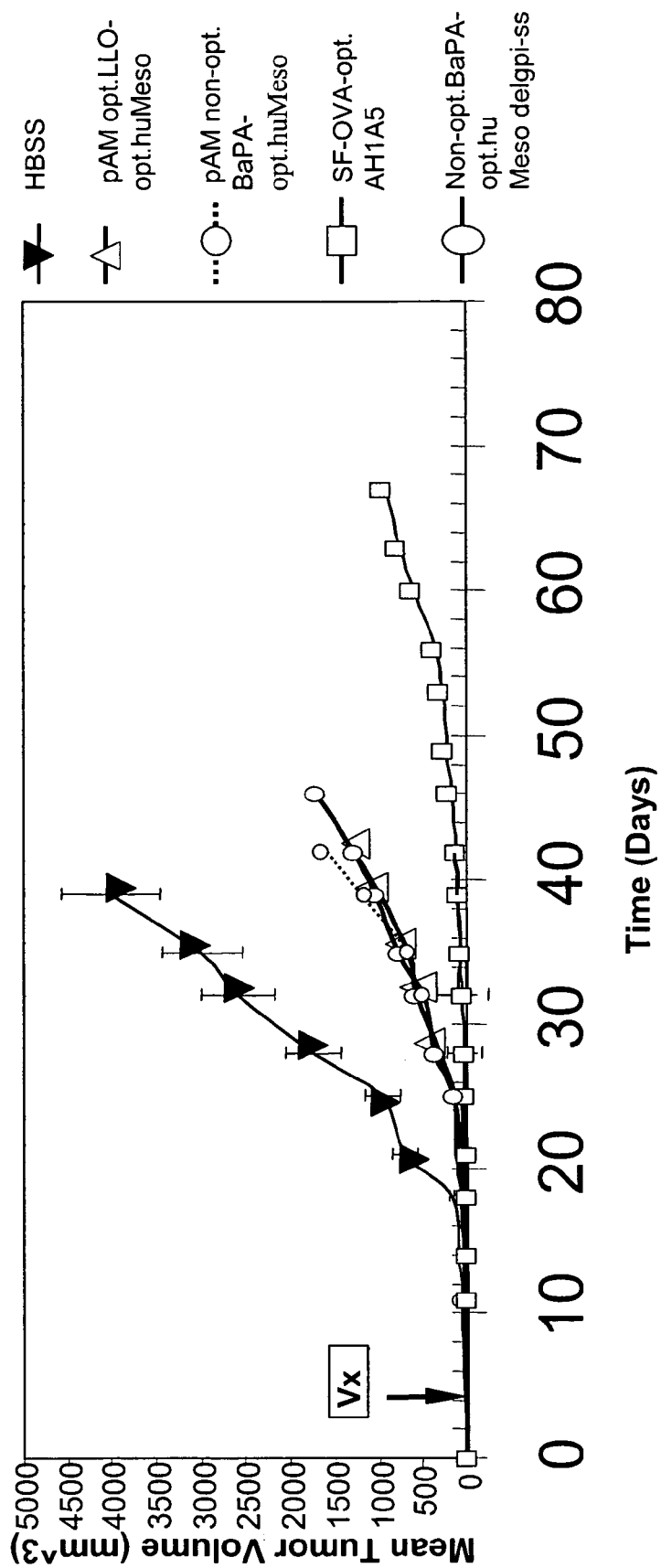

FIG. 64 is a graph showing that vaccination with *Listeria* expressing codon optimized human mesothelin reduces tumor volume.

Figure 65:
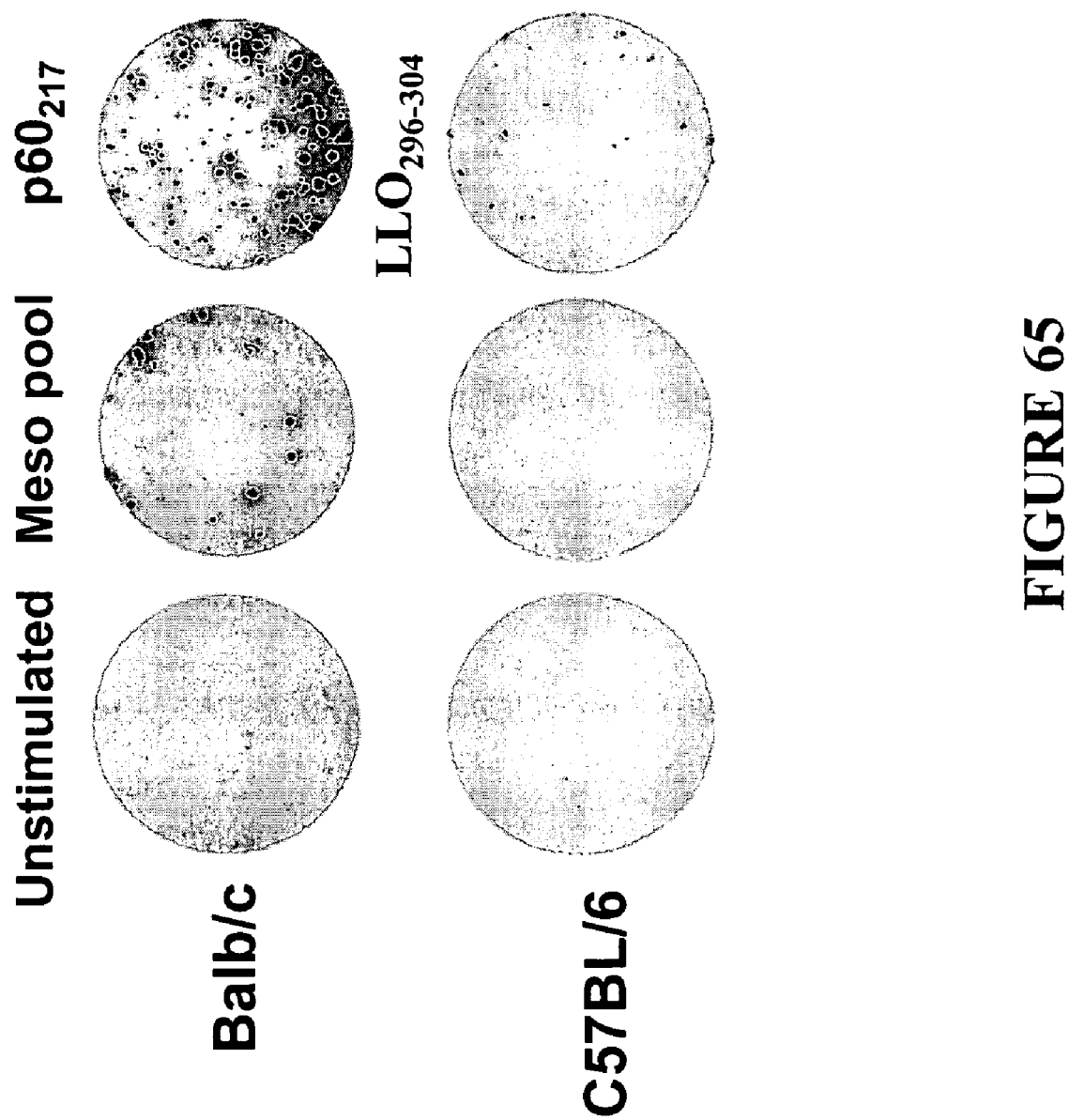

FIG. 65 shows the results of ELISPOT experiments which show the immunogenicity of a *Listeria* ΔactA/ΔinlB-hMesothelin strain where the nucleic acid encoding hMesothelin has been integrated into the *Listeria* genome.

DETAILED DESCRIPTION OF THE INVENTION

I. Introduction

The present invention provides a variety of polynucleotides including recombinant nucleic acid molecules, expression cassettes, and expression vectors useful for expression and/or secretion of polypeptides, including heterologous polypeptides (e.g. antigens and/or mammalian proteins), in bacteria, such as *Listeria*. In some embodiments, these polynucleotides can be used for enhanced expression and/or secretion of polypeptides in bacteria. Some of the expression cassettes comprise codon-optimized coding sequences for the polypeptide and/or for the signal peptide. In addition, some of the expression cassettes for use in bacteria contain signal peptide sequences derived from other bacterial sources and/or from a variety of different secretory pathways. Bacteria comprising the expression cassettes are also provided, as are compositions, such as vaccines, containing the bacteria. Methods of using the polynucleotides, bacteria, and compositions to induce an immune response and/or to prevent or treat a condition, such as a disease (e.g. cancer), in a host are also provided.

The invention is based, in part, on the discovery that codon-optimization of the signal peptide sequence in an expression cassette enhances the expression and/or secretion of a heterologous polypeptide (such as an antigen) from recombinant bacteria (particularly in combination with codon-optimization of the heterologous polypeptide), even when the signal peptide sequence is native to the bacteria (see, e.g., Examples 19 and 27, below). Additionally, it has been discovered that signal peptide sequences from non-secA1 secretory pathways and/or signal peptide sequences from non-Listerial bacterial sources can also be used to effect efficient expression and/or secretion of heterologous polypeptides from *Listeria* (see, e.g., Examples 19, 27, and 30 below). The invention is also based, in part, on the additional discovery that codon-optimization of the coding sequences of heterologous polypeptides enhances expression and/or secretion of the heterologous polypeptides in *Listeria* (see e.g., Example 19, below). Enhanced expression and/or secretion of the heterologous protein obtained through optimization of the expression cassette has also been shown to lead to enhanced immunogenicity of the bacteria comprising the optimized expression cassettes (see, e.g., Example 20, below). In addition, expression cassettes encoding protein chimeras comprising a heterologous antigen embedded within an autolysin have been shown to useful in effecting efficient expression and secretion of a heterologous antigen in *Listeria* (see, e.g., Example 29, below). The autolysin protein chimeras have also been shown to be immunogenic (see, e.g., Example 31A, below). In addition, *Listeria* comprising codon-optimized expression cassettes and/or expression cassettes comprising non-Listerial signal peptides have also been shown to be immunogenic, reduce tumor volume, and increase survival in a mouse model (see, e.g., Examples 31B-E, below).

Accordingly, in one aspect, the invention provides a recombinant nucleic acid molecule, comprising a first polynucleotide encoding a signal peptide, wherein the first polynucleotide is codon-optimized for expression in a bacterium, and a second polynucleotide encoding a polypeptide (e.g., an antigen), wherein the second polynucleotide is in the same translational reading frame as the first polynucleotide, and wherein the recombinant nucleic acid molecule encodes a fusion protein comprising the signal peptide and the polypeptide. In some embodiments, the second polynucleotide is codon-optimized as well (typically for expression in the same type of bacteria as the first polynucleotide). In some embodiments, the first polynucleotide or the first and second polynucleotides are codon-optimized for expression in *Listeria, Bacillus, Yersinia pestis, Salmonella, Shigella, Brucella*, mycobacteria or *E. coli*. In some embodiments, the polynucleotide(s) is codon-optimized for expression in *Listeria*, such as *Listeria monocytogenes*. In some embodiments, the polypeptide encoded by the second polynucleotide is (or comprises) an antigen, which, in some instances, may be a non-bacterial antigen. For instance, the antigen is, in some embodiments a tumor-associated antigen or is derived from such a tumor-associated antigen. For instance, in some embodiments, the antigen is K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA, or is derived from K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. For instance, in some embodiments, the antigen is mesothelin, or an antigenic fragment or antigenic variant of mesothelin. In some other embodiments, the antigen is NY-ESO-1, or an antigenic fragment or antigenic variant of NY-ESO-1. In some embodiments, the antigen is an infectious disease antigen or is derived from an infectious disease antigen. In some embodiments, the signal peptide is bacterial (Listerial or non-Listerial). In some embodiments, the signal peptide encoded by the codon-optimized first polynucleotide is native to the bacterium. In other embodiments, the signal peptide encoded by the codon-optimized first polynucleotide is foreign to the bacterium. In some embodiments, the signal peptide is a secA1 signal peptide, such as an LLO signal peptide from *Listeria monocytogenes*, a Usp45 signal peptide from *Lactococcus lactis*, or a Protective Antigen signal peptide from *Bacillus anthracis*. In some embodiments, the signal peptide is a secA2 signal peptide. For instance, the signal peptide may be the p60 signal peptide from *Listeria monocytogenes*. In addition, the recombinant nucleic acid molecule optionally comprises a third polynucleotide sequence encoding p60, or a fragment thereof, in the same translational reading frame as the first and second polynucleotides, wherein the second polynucleotide is positioned within the third polynucleotide or between the first and third polynucleotides. In still further embodiments, the signal peptide is a Tat signal peptide, such as a *B. subtilis* Tat signal peptide (e.g., PhoD). The invention also provides expression cassettes comprising the recombinant nucleic acid molecule and further comprising a promoter operably linked to the recombinant nucleic acid molecule (e.g., to the first and second polynucleotides (and third polynucleotide, if present)). Expression vectors and recombinant bacteria (e.g. *Listeria*) comprising the expression cassette are also provided, as are pharmaceutical compositions, immunogenic compositions, and vaccines, comprising the bacteria. Methods of using the bacteria or compositions comprising the bacteria to induce an immune response and/or prevent or treat a condition, such as a disease, are also provided. The use of the bacterium in the manufacture of a medicament for inducing an immune response in a host to an antigen, wherein the polypeptide encoded by the second polynucleotide comprises the antigen is also provided.

In a second aspect, the invention provides a recombinant nucleic acid molecule, comprising (a) a first polynucleotide encoding a signal peptide native to a bacterium, wherein the first polynucleotide is codon-optimized for expression in the bacterium, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the polypeptide encoded by the second polynucleotide is heterologous to the signal peptide. In some embodiments, the second polynucleotide is heterologous to the first polynucleotide. In some embodiments, the polypeptide is foreign to the bacterium to which the signal peptide is native. In some embodiments, the polypeptide encoded by the second polynucleotide is heterologous to the signal peptide, foreign to the bacterium, or both. In some embodiments, the bacterium from which the signal peptide is derived is an intracellular bacterium. In some embodiments, the bacterium is selected from the group consisting of *Listeria, Bacillus, Yersinia pestis, Salmonella, Shigella, Brucella*, mycobacteria and *E. coli*. In some embodiments the bacterium is a *Listeria* bacterium (e.g., *Listeria monocytogenes*). In some embodiments, second polynucleotide is codon-optimized for expression in the bacterium. In some embodiments, the codon-optimization of the first and/or second polynucleotide enhances expression in and/or secretion from the bacterium of the encoded fusion protein (relative to the non-codon-optimized sequence). In some embodiments, the polypeptide encoded by the second polynucleotide comprises an antigen. The polypeptide encoded by the second polynucleotide is an antigen. In some embodiments, the antigen is a non-bacterial antigen. In some embodiments, the antigen is a tumor-associated antigen or comprises an antigen derived from a tumor-associated antigen. In some embodiments, the antigen is selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA, or is derived from an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA. For instance, in some embodiments, the antigen is mesothelin, or an antigenic fragment or variant thereof, or is NY-ESO-1, or an antigenic fragment or variant thereof. In some alternative embodiments, the antigen is an infectious disease antigen or is derived from an infectious disease antigen. In some embodiments, the signal peptide is a secA1 signal peptide (e.g., LLO signal peptide from *Listeria monocytogenes*). In some embodiments, the signal peptide is a secA2 signal peptide (e.g., p60 signal peptide from *Listeria monocytogenes*). An expression cassette comprising the recombinant nucleic acid molecule and further comprising a promoter operably linked to the first and second polynucleotides of the recombinant nucleic acid molecule is also provided. An expression vector comprising the expression cassette is also provided. A recombinant bacterium comprising the recombinant nucleic acid molecule, wherein the first polynucleotide is codon-optimized for expression in the recombinant bacterium is also provided. In some embodiments, the recombinant bacterium is an intracellular bacterium. In some embodiments, the recombinant bacterium is selected from the group consisting of *Listeria, Bacillus, Yersinia pestis, Salmonella, Shigella, Brucella*, mycobacteria and *E. coli*. In some embodiments, the bacterium is a recombinant *Listeria* bacterium (e.g., a recombinant *Listeria monocytogenes* bacterium). An immunogenic composition comprising the recombinant bacterium, wherein the polypeptide encoded by the second polynucleotide is an antigen is further provided. Methods of inducing an immune response in a host to an antigen comprising administering to the host an effective amount of a composition comprising the recombinant bacterium, wherein the polypeptide encoded by the second polynucleotide is (or comprises) the antigen, are also provided. The use of the bacterium in the manufacture of a medicament for inducing an immune response in a host to an antigen, wherein the polypeptide encoded by the second polynucleotide comprises the antigen is also provided.

In a third aspect, the invention provides a recombinant *Listeria* bacterium (e.g., *Listeria monocytogenes*) comprising a recombinant nucleic acid molecule, wherein the recombinant nucleic acid molecule comprises (a) a first polynucleotide encoding a signal peptide, wherein the first polynucleotide is codon-optimized for expression in the *Listeria* bacterium, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the polypeptide encoded by the second polynucleotide is heterologous to the signal peptide. In some embodiments, the recombinant nucleic acid molecule is part of an expression cassette that further comprises a promoter operably linked to both the first and second polynucleotides. In other words, in some embodiments the recombinant *Listeria* bacterium comprises an expression cassette which comprises the recombinant nucleic acid molecule, wherein the expression cassette further comprises a promoter operably linked to both the first and second polynucleotides of the recombinant nucleic acid molecule. In some embodiments, the expression cassette is a polycistronic expression cassette. In some embodiments, the second polynucleotide is codon-optimized for expression in the *Listeria* bacterium. In some embodiments, the codon-optimization of the first and/or second polynucleotide enhances expression in and/or secretion from the *Listeria* bacterium of the encoded fusion protein (relative to the non-codon-optimized sequence). In some embodiments, the polypeptide encoded by the second polynucleotide is foreign to the *Listeria* bacterium (i.e., heterologous to the *Listeria* bacterium). In some embodiments, the polypeptide encoded by the second polynucleotide comprises an antigen (e.g., a non-Listerial or non-bacterial antigen). In some embodiments, the polypeptide encoded by the second polynucleotide is an antigen. In some embodiments, the antigen is a tumor-associated antigen or is derived from a tumor-associated antigen. In some embodiments, the antigen is selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA, or is derived from an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA. For instance, in some embodiments, the antigen is mesothelin, or an antigenic fragment or antigenic variant thereof. In some embodiments, the antigen is human mesothelin. In some embodiments, the antigen is human mesothelin deleted of its signal peptide and GPI linker domain. In some alternative embodiments, the antigen is NY-ESO-1, or an antigenic fragment or antigenic variant thereof. In some alternative embodiments, the antigen is an infectious disease antigen or is an antigen derived from an infectious disease antigen. In some embodiments, the signal peptide is non-Listerial. In some embodiments, the signal peptide is bacterial. In some embodiments, the signal peptide is foreign to the *Listeria* bacterium. In other embodiments, the signal peptide is native to the *Listeria* bacterium. In some embodiments, the signal peptide is a secA1 signal peptide (e.g., LLO signal peptide from *Listeria monocytogenes*, Usp45 signal peptide from *Lactococcus lactis*, and Protective Antigen signal peptide from *Bacillus anthracis*). In some embodiments, the signal peptide is a secA2 signal peptide (e.g., p60 signal peptide from *Listeria monocytogenes*). In some embodiments the signal peptide is a Tat signal peptide (e.g., PhoD signal peptide from *B. subtilis*). In some embodiments, the *Listeria* bacterium is attenuated. For instance, the *Listeria* may be attenuated for cell-to-cell spread, entry into non-phagocytic cells, or proliferation. In some embodiments, the recombinant *Listeria* bacterium is deficient with respect to ActA, Internalin B, or both Act A and Internalin B (e.g., an ΔactAΔ-inlB double deletion mutant). In some embodiments, the recombinant *Listeria* bacterium is deleted in functional ActA, Internalin B, or both Act A and Internalin B. In some embodiments, the nucleic acid of the recombinant bacterium has been modified by reaction with a nucleic acid targeting compound (e.g., a psoralen compound). The invention also provides a pharmaceutical composition comprising the recombinant *Listeria* bacterium and a pharmaceutically acceptable carrier, as well an immunogenic composition comprising the recombinant *Listeria* bacterium, wherein the polypeptide encoded by the second polynucleotide is an antigen. The invention also provides a vaccine comprising the recombinant *Listeria* bacterium. Methods of inducing an immune response in a host to an antigen comprising administering to the host an effective amount of a composition comprising the recombinant bacterium, wherein the polypeptide encoded by the second polynucleotide is (or comprises) an antigen are also provided. Also provided are methods of preventing or treating a condition (e.g., a disease such as cancer or an infectious disease) in a host comprising administering to the host an effective amount of a composition comprising the recombinant *Listeria* bacterium. The use of the bacterium in the manufacture of a medicament for inducing an immune response in a host to an antigen, wherein the polypeptide encoded by the second polynucleotide comprises the antigen is also provided.

In a fourth aspect, the invention provides a recombinant nucleic acid molecule, comprising a first polynucleotide encoding a non-secA1 bacterial signal peptide, and a second polynucleotide encoding a polypeptide (e.g., an antigen), wherein the second polynucleotide is in the same translational reading frame as the first polynucleotide, and wherein the recombinant nucleic acid molecule encodes a fusion protein comprising the signal peptide and the polypeptide. In some embodiments, the first polynucleotide and/or the second polynucleotide is codon-optimized for expression in a particular type of bacterium. In some embodiments, the codon-optimization of the first and/or second polynucleotide enhances expression in and/or secretion from the bacterium of the fusion protein (relative to the non-codon-optimized sequence). In some embodiments, the first polynucleotide and/or the second polynucleotide is codon-optimized for expression in *Listeria, Bacillus, Yersinia pestis, Salmonella, Shigella, Brucella*, mycobacteria or *E. coli*. In some embodiments, the polynucleotide(s) is codon-optimized for expression in *Listeria*, such as *Listeria monocytogenes*. In some embodiments, the signal peptide encoded by the codon-optimized first polynucleotide is native to the bacterium for which it is codon-optimized. In some embodiments, the first polynucleotide encoding the signal peptide is heterologous to the second polynucleotide. In some embodiments, the polypeptide encoded by the second polynucleotide is heterologous to the signal peptide. In some embodiments, the polypeptide encoded by the second polynucleotide comprises an antigen. In some embodiments, the polypeptide encoded by the second polynucleotide is an antigen, which, in some instances, may be a non-bacterial antigen. In some embodiments, the antigen is a tumor-associated antigen or is derived from such a tumor-associated antigen. For instance, in some embodiments, the antigen is K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA, or is derived from K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. For instance, in some embodiments, the antigen is mesothelin, or is an antigenic fragment or antigenic variant of mesothelin. In some other embodiments, the antigen is NY-ESO-1, or an antigenic fragment or antigenic variant of NY-ESO-1. In some embodiments, the antigen is an infectious disease antigen or is derived from an infectious disease antigen. In some embodiments, the signal peptide encoded by the first polynucleotide of the recombinant nucleic acid molecule is Listerial. In other embodiments, the signal peptide is non-Listerial. In some embodiments, the signal peptide is derived from a gram positive bacterium. In some embodiments, the signal peptide is derived from a bacterium belonging to the genus *Bacillus, Staphylococcus,* or *Lactococcus*. In some embodiments, the signal peptide is a secA2 signal peptide. For instance, the signal peptide may be the p60 signal peptide from *Listeria monocytogenes*. In addition, the recombinant nucleic acid molecule optionally comprises a third polynucleotide sequence encoding p60, or a fragment thereof, in the same translational reading frame as the first and second polynucleotides, wherein the second polynucleotide is positioned within the third polynucleotide or between the first and third polynucleotides. In still further embodiments, the signal peptide is a Tat signal peptide, such as a *B. subtilis* Tat signal peptide (e.g., a *B. subtilis* PhoD signal peptide). The invention also provides expression cassettes comprising the recombinant nucleic acid molecule and further comprising a promoter operably linked to the first and second polynucleotides of the recombinant nucleic acid molecule. Expression vectors and bacteria comprising the expression cassette and/or recombinant nucleic acid molecule are also provided, as are pharmaceutical compositions, immunogenic compositions, and vaccines, comprising the bacteria. In some embodiments, the recombinant bacterium comprising the expression cassette or recombinant nucleic acid molecule is an intracellular bacterium. In some embodiments, the bacterium is a bacterium selected from the group consisting of *Listeria, Bacillus, Yersinia pestis, Salmonella, Shigella, Brucella*, mycobacteria or *E. coli*. In some embodiments, the bacterium is a *Listeria* bacterium (e.g., a member of the species *Listeria monocytogenes*). In some embodiments, the polypeptide encoded by the second polynucleotide is foreign to the bacterium (i.e., heterologous to the bacterium). Methods of using the bacteria or compositions comprising the bacteria to induce an immune response and/or to prevent or treat a condition (e.g., a disease) in a host are also provided. In some embodiment, the condition is cancer. In other embodiments, the condition is an infectious disease. The use of the bacterium in the manufacture of a medicament for inducing an immune response in a host to an antigen, wherein the polypeptide encoded by the second polynucleotide comprises the antigen is also provided.

In another aspect, the invention provides a recombinant *Listeria* bacterium comprising a recombinant nucleic acid molecule, wherein the recombinant nucleic acid molecule comprises (a) a first polynucleotide encoding a non-secA1 bacterial signal peptide, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the polypeptide encoded by the second polynucleotide is heterologous to the signal peptide or is foreign to the bacterium, or both. In some embodiments, the *Listeria* bacterium belongs to the species *Listeria monocytogenes*. In some embodiments, the recombinant nucleic acid molecule is part of an expression cassette that further comprises a promoter operably linked to both the first and second polynucleotides. In other words, in some embodiments, the recombinant *Listeria* bacterium comprises an expression cassette which comprises the recombinant nucleic acid molecule, wherein the expression cassette further comprises a promoter operably linked to both the first and second polynucleotides of the recombinant nucleic acid molecule. In some embodiments, the expression cassette is a polycistronic expression cassette. In some embodiments, the first polynucleotide, the second polynucleotide, or both the first and second polynucleotide are codon-optimized for expression in the *Listeria* bacterium (e.g., *Listeria monocytogenes*). In some embodiments, the codon-optimization of the first and/or second polynucleotide enhances expression in and/or secretion from the bacterium of the fusion protein (relative to the non-codon-optimized sequence). In some embodiments, the first and second polynucleotides are heterologous to each other. In some embodiments, the polypeptide encoded by the second polynucleotide and the signal peptide are heterologous to each other. In some embodiments, the polypeptide encoded by the second polynucleotide is foreign to the *Listeria* bacterium (i.e., heterologous to the *Listeria* bacterium). In some embodiments, the polypeptide encoded by the second polynucleotide comprises an antigen. In some embodiments, the polypeptide encoded by the second polynucleotide is an antigen (e.g., a non-Listerial or non-bacterial antigen). In some embodiments, the antigen is a tumor-associated antigen or is derived from a tumor-associated antigen. In some embodiments, the antigen is selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA, or is derived from an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA. For instance, in some embodiments, the antigen is mesothelin, or an antigenic fragment or antigenic variant thereof. In some embodiments, the antigen is human mesothelin. In some embodiments, the antigen is human mesothelin deleted of its signal peptide and GPI linker domain. In some alternative embodiments, the antigen is an infectious disease antigen or is derived from an infectious disease antigen. In some embodiments, the signal peptide is non-Listerial. In some embodiments, the non-secA1 signal peptide is a Listerial signal peptide. In other embodiments, the non-secA1 signal peptide is a non-Listerial signal peptide. In some embodiments, the signal peptide is a secA2 signal peptide (e.g., p60 signal peptide from *Listeria monocytogenes*). In some embodiments, the recombinant nucleic acid molecule comprising a secA2 signal peptide, further comprises a third polynucleotide encoding a secA2 autolysin (e.g., p60 or N-acetylmuramidase), or a fragment thereof (e.g., a catalytically active fragment), in the same translational reading frame as the first and second polynucleotides, wherein the second polynucleotide is positioned within the third polynucleotide or between the first and third polynucleotides of the recombinant nucleic acid molecule. In some embodiments, the second polynucleotide is positioned within the third polynucleotide. In some embodiments the signal peptide is a Tat signal peptide. In some embodiments, the signal peptide is a Tat signal peptide derived *B. subtilis*. (e.g., PhoD signal peptide from *B. subtilis*). In some embodiments, the *Listeria* bacterium is attenuated. For instance, the *Listeria* may be attenuated for cell-to-cell spread, entry into non-phagocytic cells, or proliferation. In some embodiments, the recombinant *Listeria* bacterium is deficient with respect to ActA, Internalin B, or both Act A and Internalin B (e.g., an ΔactAΔinlB double deletion mutant). In some embodiments, the recombinant *Listeria* bacterium is deleted in functional ActA, Internalin B, or both Act A and Internalin B. In some embodiments, the nucleic acid of the recombinant bacterium has been modified by reaction with a nucleic acid targeting compound (e.g., a psoralen compound). The invention also provides a pharmaceutical composition comprising the recombinant *Listeria* bacterium and a pharmaceutically acceptable carrier. The invention also provides an immunogenic composition comprising the recombinant bacterium, wherein the polypeptide encoded by the second polynucleotide is an antigen. The invention also provides a vaccine comprising the recombinant *Listeria* bacterium. Methods of inducing an immune response in a host to an antigen comprising administering to the host an effective amount of a composition comprising the recombinant bacterium, wherein the polypeptide encoded by the second polynucleotide is (or comprises) an antigen are also provided. Also provided are methods of preventing or treating a condition (e.g., a disease such as cancer or an infectious disease) in a host comprising administering to the host an effective amount of a composition comprising the recombinant *Listeria* bacterium. The use of the bacterium in the manufacture of a medicament for inducing an immune response in a host to an antigen, wherein the polypeptide encoded by the second polynucleotide comprises the antigen is also provided.

In another aspect, the invention provides a recombinant nucleic acid molecule comprising a polynucleotide encoding a polypeptide foreign to a *Listeria* bacterium (such as an antigen like a cancer antigen or a non-Listerial bacterial antigen), wherein the polynucleotide is codon-optimized for expression in *Listeria*. In some embodiments, the codon-optimization of the polynucleotide enhances expression in and/or secretion from a *Listeria* bacterium of the polypeptide (relative to the non-codon-optimized sequence). In some embodiments, the foreign polypeptide comprises an antigen. In some embodiments, the foreign polypeptide is an antigen. In some embodiments, the antigen is a non-bacterial antigen. For instance, the antigen is, in some embodiments a tumor-associated antigen or is derived from such a tumor-associated antigen. For instance, in some embodiments, the polypeptide is K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA, or is derived from K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. In some embodiments, the antigen is mesothelin, or is an antigenic fragment or antigenic variant of mesothelin. In some other embodiments, the antigen is NY-ESO-1, or is an antigenic fragment or variant of NY-ESO-1. In some other embodiments, the antigen is an infectious disease antigen or is derived from an infectious disease antigen. In some embodiments, the recombinant nucleic acid molecule further comprises a polynucleotide encoding a signal peptide in the same translational frame as the foreign polypeptide so that the recombinant nucleic acid molecule encodes a fusion protein comprising the signal peptide and the foreign polypeptide. In some embodiments, the polynucleotide encoding the signal peptide (which may or may not be native to *Listeria*) is codon-optimized for expression in *Listeria monocytogenes*. The invention further provides an expression cassette comprising the recombinant nucleic acid molecule and further comprising a promoter operably linked to the first and second polynucleotides of the recombinant nucleic acid molecule. A vector (e.g., an expression vector) comprising the recombinant nucleic acid molecule and/or expression cassette is also provided. The invention also provides a recombinant *Listeria* bacterium comprising the recombinant nucleic acid molecule and/or expression cassette. In some embodiments, the *Listeria* bacterium belongs to the species *Listeria monocytogenes*. Pharmaceutical compositions, immunogenic compositions, and vaccines comprising the recombinant *Listeria* bacteria are also provided. The invention further provides a method of inducing an immune response in host to an antigen comprising administering to the host an effective amount of a composition comprising the recombinant *Listeria* bacterium, wherein the polypeptide is (or comprises) the antigen. In addition, the invention provides methods of using the recombinant *Listeria* bacteria to induce an immune response and/or prevent or treat a condition (e.g., a disease). The use of the bacterium in the manufacture of a medicament for inducing an immune response in a host to an antigen, wherein the foreign polypeptide comprises the antigen is also provided.

In another aspect, the invention provides a recombinant *Listeria* bacterium comprising an expression cassette, wherein the expression cassette comprises a polynucleotide encoding a polypeptide foreign to the *Listeria* bacterium (such as an antigen like a cancer antigen or a non-Listerial bacterial antigen), wherein the polynucleotide is codon-optimized for expression in *Listeria*, and a promoter, operably linked to the polynucleotide encoding the foreign polypeptide. In some embodiments, the *Listeria* bacterium belongs to the species *Listeria monocytogenes*. In some embodiments, the codon-optimization of the polynucleotide enhances expression in and/or of the polypeptide from a *Listeria* bacterium of the polypeptide (relative to the non-codon-optimized sequence). In some embodiments, the foreign polypeptide comprises an antigen. In some embodiments, the foreign polypeptide is an antigen, which, in some instances, may be a non-bacterial antigen. For instance, the antigen is, in some embodiments a tumor-associated antigen or is derived from such a tumor-associated antigen. For instance, in some embodiments, the polypeptide is K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA, or is derived from K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. In some embodiments, the antigen is mesothelin, or is an antigenic fragment or antigenic variant of mesothelin. In some other embodiments, the antigen is NY-ESO-1, or is an antigenic fragment or antigenic variant of NY-ESO-1. In some other embodiments, the antigen is an infectious disease antigen or is derived from an infectious disease antigen. In some embodiments, the expression cassette further comprises a polynucleotide encoding a signal peptide which is operably linked to the promoter and in the same translational frame as the foreign polypeptide so that the expression cassette encodes a fusion protein comprising the signal peptide and the foreign polypeptide. In some embodiments, the polynucleotide encoding the signal peptide (which may or may not be native to *Listeria*) is codon-optimized for expression in *Listeria monocytogenes*. Pharmaceutical compositions, immunogenic compositions, and vaccines comprising the recombinant *Listeria* bacteria are also provided. The invention further provides a method of inducing an immune response in host to an antigen comprising administering to the host an effective amount of a composition comprising the recombinant *Listeria* bacterium. In addition, the invention provides methods of using the recombinant *Listeria* bacteria to induce an immune response and/or prevent or treat a condition (e.g., a disease). The use of the bacterium in the manufacture of a medicament for inducing an immune response in a host to an antigen, wherein the foreign polypeptide comprises the antigen is also provided.

In a further aspect, the invention provides a recombinant *Listeria* bacterium (e.g., *Listeria monocytogenes*) comprising a recombinant nucleic acid molecule, wherein the recombinant nucleic acid molecule comprises (a) a first polynucleotide encoding a non-Listerial signal peptide; and (b) a second polynucleotide encoding a polypeptide that is in the same translational reading frame as the first polynucleotide, wherein the recombinant nucleic acid molecule encodes a fusion protein comprising both the non-Listerial signal peptide and the polypeptide. In some embodiments, the recombinant nucleic acid molecule is positioned in an expression cassette that further comprises a promoter operably linked to both the first and second polynucleotides. Thus, in some embodiments the recombinant *Listeria* bacterium comprises an expression cassette which comprises the recombinant nucleic acid molecule, wherein the expression cassette further comprises a promoter operably linked to both the first and second polynucleotides of the recombinant nucleic acid molecule. In some embodiments, the expression cassette is a polycistronic expression cassette (e.g., a bicistronic expression cassette). In some embodiments, the first polynucleotide, the second polynucleotide, or both the first and second polynucleotide are codon-optimized for expression in *Listeria* (e.g., *Listeria monocytogenes*). In some embodiments, the codon-optimization of the first and/or second polynucleotide enhances expression of the fusion protein in and/or secretion of the fusion protein from the bacterium (relative to the non-codon-optimized sequence). In some embodiments, the first and second polynucleotides are heterologous to each other. In some embodiments, the polypeptide encoded by the second polynucleotide and the signal peptide are heterologous to each other. In some embodiments, the polypeptide encoded by the second polynucleotide is foreign to the *Listeria* bacterium (i.e., heterologous to the *Listeria* bacterium). In some embodiments, the polypeptide encoded by the second polynucleotide comprises an antigen (e.g., a non-Listerial antigen). The polypeptide encoded by the second polynucleotide is, in some embodiments, an antigen. In some embodiments, the antigen is a tumor-associated antigen or is derived from a tumor-associated antigen. In some embodiments, the antigen is selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA, or is derived from an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA. For instance, in some embodiments, the antigen is mesothelin, or an antigenic fragment or antigenic variant thereof. In some embodiments, the antigen is human mesothelin. In some embodiments, the antigen is human mesothelin deleted of its signal peptide and GPI linker domain. In some alternative embodiments, the antigen is an infectious disease antigen or is derived from an infectious disease antigen. In some embodiments, the signal peptide is bacterial. In some embodiments, the signal peptide is derived from an intracellular bacterium. In some embodiments, the signal peptide is derived from a gram positive bacterium. In some embodiments, the signal peptide is from a bacterium belonging to the genus *Bacillus, Staphylococcus*, or *Lacotococcus* (e.g., *Bacillus anthracis, Bacillus subtilis, Staphylococcus aureus*, or *Lactococcus lactis*). In some embodiments, the signal peptide is a secA1 signal peptide (e.g., Usp45 signal peptide from *Lactococcus lactis* or Protective Antigen signal peptide from *Bacillus anthracis*). In some embodiments, the signal peptide is a secA2 signal peptide. In some embodiments the signal peptide is a Tat signal peptide (e.g., PhoD signal peptide from *B. subtilis*). In some embodiments, the *Listeria* bacterium is attenuated. For instance, in some embodiments, the *Listeria* are attenuated for cell-to-cell spread, entry into non-phagocytic cells, or proliferation. In some embodiments, the recombinant *Listeria* bacterium is deficient with respect to ActA, Internalin B, or both ActA and Internalin B (e.g., an ΔactAΔ-inlB double deletion mutant). In some embodiments, the recombinant *Listeria* bacterium is deleted in functional ActA, Internalin B, or both ActA and Internalin B. In some embodiments, the nucleic acid of the recombinant bacterium has been modified by reaction with a nucleic acid targeting compound (e.g., a psoralen compound). The invention also provides a pharmaceutical composition comprising the recombinant *Listeria* bacterium and a pharmaceutically acceptable carrier. The invention further provides an immunogenic composition comprising the recombinant bacterium, wherein the polypeptide encoded by the second polynucleotide is an antigen. The invention also provides a vaccine comprising the recombinant *Listeria* bacterium. Methods of inducing an immune response in a host to an antigen comprising administering to the host an effective amount of a composition comprising the recombinant *Listeria* bacterium, wherein the polypeptide encoded by the second polynucleotide is (or comprises) an antigen are also provided. Also provided are methods of preventing or treating a condition (e.g., a disease such as cancer or an infectious disease) in a host comprising administering to the host an effective amount of a composition comprising the recombinant *Listeria* bacterium. The use of the bacterium in the manufacture of a medicament for inducing an immune response in a host to an antigen, wherein the polypeptide encoded by the second polynucleotide comprises the antigen is also provided.

In still another aspect, the invention provides a recombinant *Listeria* bacterium (for instance, from the species *Listeria monocytogenes*) comprising an expression cassette which comprises a first polynucleotide encoding a non-Listerial signal peptide, a second polynucleotide encoding a polypeptide that is in the same translational reading frame as the first polynucleotide, and a promoter operably linked to both the first and second polynucleotides. The expression cassette encodes a fusion protein comprising both the non-Listerial signal peptide and the polypeptide. In some embodiments, the *Listeria* bacterium is attenuated for cell-to-cell spread, entry into non-phagocytic cells, or proliferation. In some embodiments, the first polynucleotide, the second polynucleotide, or both the first and second polynucleotides are codon-optimized for expression in *Listeria*. In some embodiments, the codon-optimization of the first and/or second polynucleotide enhances expression in and/or secretion from the bacterium of the encoded fusion protein (relative to the non-codon-optimized sequence). In some embodiments, the first polynucleotide and/or second polynucleotide is codon-optimized for expression in *Listeria monocytogenes*. In some embodiments, the polypeptide encoded by the second polynucleotide comprises an antigen. In some embodiments, the polypeptide encoded by the second polynucleotide is an antigen, which, in some instances, may be a non-bacterial antigen. For instance, the antigen is, in some embodiments a tumor-associated antigen or is derived from such a tumor-associated antigen. For instance, in some embodiments, the antigen is K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA, or is derived from K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. For instance, in some embodiments, the antigen is mesothelin, or is a antigenic fragment or antigenic variant of mesothelin. In some other embodiments, the antigen is NY-ESO-1, or an antigenic fragment or antigenic variant of NY-ESO-1. In some embodiments, the antigen is an infectious disease antigen or is derived from an infectious disease antigen. In preferred embodiments, the signal peptide is bacterial. In some embodiments, the signal peptide is from a bacterium belonging to the genus *Bacillus, Staphylococcus*, or *Lactococcus*. For instance, in some embodiments, the signal peptide is from *Bacillus anthracis, Bacillus subtilis, Staphylococcus aureus*, or *Lactococcus lactis*. In some embodiments, the signal peptide is a secA1 signal peptide, such as a Usp45 signal peptide from *Lactococcus lactis* or a Protective Antigen signal peptide from *Bacillus anthracis*. In some embodiments, the signal peptide is a secA2 signal peptide. In still further embodiments, the signal peptide is a Tat signal peptide, such as a *B. subtilis* Tat signal peptide (e.g., PhoD). Pharmaceutical compositions, immunogenic compositions, and vaccines comprising the recombinant *Listeria* bacteria described herein are also provided. In addition, the invention provides methods of using the recombinant *Listeria* bacteria to induce an immune response and/or to prevent or treat a condition such as a disease. The use of the bacterium in the manufacture of a medicament for inducing an immune response in a host to an antigen, wherein the polypeptide encoded by the second polynucleotide comprises the antigen is also provided.

The invention further provides a recombinant nucleic acid molecule, comprising (a) a first polynucleotide encoding a bacterial autolysin, or a catalytically active fragment or catalytically active variant thereof; and (b) a second polynucleotide encoding a polypeptide, wherein the second polynucleotide is in the same translational reading frame as the first polynucleotide, wherein the recombinant nucleic acid molecule encodes a protein chimera comprising the polypeptide encoded by the second polynucleotide and the autolysin, or catalytically active fragment or catalytically active variant thereof, wherein, in the protein chimera, the polypeptide is fused to the autolysin, or catalytically active fragment or catalytically active variant thereof, or is positioned within the autolysin, or catalytically active fragment or catalytically active variant thereof. In some embodiments, the first polynucleotide encodes a bacterial autolysin. In some embodiments, the protein chimera is catalytically active as an autolysin. In some embodiments, the bacterial autolysin is from an intracellular bacterium (e.g., *Listeria*). In some embodiments, the bacterial autolysin is a Listerial autolysin. In some embodiments, the second polynucleotide encoding the polypeptide is positioned within the first polynucleotide encoding the autolysin, or catalytically active fragment or catalytically active variant thereof, and the recombinant nucleic acid molecule encodes a protein chimera in which the polypeptide is positioned within the autolysin, or catalytically active fragment or catalytically active variant thereof (i.e., the polypeptide is embedded within the autolysin or catalytically active fragment or variant). In some alternative embodiments, the second polynucleotide is positioned outside of the first polynucleotide encoding the autolysin, or catalytically active fragment or catalytically active variant thereof, and the recombinant nucleic acid molecule encodes a protein chimera in which the polypeptide is fused to the autolysin, or catalytically active fragment or catalytically active variant thereof In some embodiments, the polypeptide is heterologous to the autolysin. In some embodiments, the first polynucleotide and the second polynucleotide are heterologous to each other. In some embodiments, the recombinant nucleic acid molecule further comprises (c) a third polynucleotide encoding a signal peptide in the same translational reading frame as the first and second polynucleotides, wherein the recombinant nucleic acid molecule encodes a protein chimera comprising the signal peptide, the polypeptide encoded by the second polynucleotide, and the autolysin, or catalytically active fragment or catalytically active variant thereof. In some embodiments, the signal peptide is a secA2 signal peptide (such as p60). In some embodiments, the signal peptide is the signal peptide associated with the autolysin in nature (e.g., the signal peptide is p60 and the autolysin is p60). In some embodiments, the autolysin is a secA2-dependent autolysin. In some embodiments, the autolysin is a peptidoglycan hydrolase (e.g., N-acetylmuramidase or p60). In some embodiments, the polypeptide encoded by the second polynucleotide comprises an antigen. In some embodiments, the polypeptide is an antigen (e.g., a tumor-associated antigen, an antigen derived from a tumor-associated antigen, an infectious disease antigen, or an antigen derived from an infectious disease antigen. In some embodiments, the antigen is selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA, or is derived from an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA. For instance, in some embodiments, the antigen is mesothelin, or an antigenic fragment or antigenic variant thereof. In some embodiments, the antigen is human mesothelin. In some embodiments, the antigen is human mesothelin deleted of its signal peptide and GPI anchor. The invention also provides an expression cassette comprising the recombinant nucleic acid molecule, further comprising a promoter operably linked to the first and second polynucleotides of the recombinant nucleic acid molecule, as well as an expression vector comprising the expression cassette. The invention further provides a recombinant bacterium comprising the recombinant nucleic acid molecule. In some embodiments, the recombinant bacterium is an intracellular bacterium, such as a *Listeria* bacterium (e.g., *Listeria monocytogenes*). In some embodiments, the polypeptide encoded by the second polynucleotide is foreign to the recombinant bacterium. A pharmaceutical composition comprising (a) the recombinant bacterium, and (b) a pharmaceutically acceptable carrier is also provided. In addition, an immunogenic composition comprising the recombinant bacterium, wherein the polypeptide encoded by the second polynucleotide is an antigen, is also provided. Also provided is a vaccine comprising the recombinant bacterium, wherein the polypeptide encoded by the second polynucleotide is an antigen. The invention also provides a method of inducing an immune response in a host to an antigen comprising administering to the host an effective amount of a composition comprising the recombinant bacterium, wherein the polypeptide encoded by the second polynucleotide is (or comprises) the antigen. A method of preventing or treating a condition in a host comprising administering to the host an effective amount of a composition comprising the recombinant bacterium is also provided. The use of the bacterium in the manufacture of a medicament for inducing an immune response in a host to an antigen, wherein the polypeptide encoded by the second polynucleotide comprises the antigen is also provided.

In yet another aspect, the invention provides a recombinant *Listeria* bacterium comprising a polycistronic expression cassette, wherein the polycistronic expression cassette encodes at least two discrete non-Listerial polypeptides. For instance, in some embodiments, the expression cassette comprises a first polynucleotide encoding the first non-Listerial polypeptide, a second polynucleotide encoding the second non-Listerial polypeptide, and a promoter operably linked to the first and second polynucleotides. In some embodiments, the expression cassette further comprises an intergenic sequence between the first and second polynucleotides. In some embodiments, the polycistronic expression cassette is a bicistronic expression cassette which encodes two discrete non-Listerial polypeptides. In some embodiments, the recombinant *Listeria* bacterium belongs to the species *Listeria monocytogenes*. In some embodiments, at least one of the non-Listerial polypeptides encoded by the polycistronic expression cassette comprises an antigen. In some embodiments, at least two of the non-Listerial polypeptides each comprise fragments of the same antigen. In some embodiments, the antigen is a tumor-associated antigen or is derived from a tumor-associated antigen. For instance, in some embodiments, the antigen is an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA, or is derived from an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA. In some embodiments, the antigen is mesothelin, or an antigenic fragment or antigenic variant thereof. In some embodiments, the antigen is human mesothelin. In some embodiments, the antigen is human mesothelin deleted of its signal peptide and GPI anchor. In some embodiments, the antigen is an infectious disease antigen or is derived from an infectious disease antigen. In some embodiments, at least one of the non-Listerial polypeptides encoded by the polycistronic expression cassette comprises a signal peptide (either a Listerial signal peptide or a non-Listerial signal peptide). In some embodiments, the signal peptide is a secA1 signal peptide. In some embodiments, the signal peptide is a secA2 signal peptide. In other embodiments, the signal peptide is a Tat signal peptide. In some embodiments, the expression cassette comprises a polynucleotide encoding the signal peptide, wherein the polynucleotide encoding the signal peptide is codon-optimized for expression in *Listeria*. The invention also provides a pharmaceutical composition comprising: (a) the recombinant *Listeria* bacterium, and (b) a pharmaceutically acceptable carrier. Also provided is an immunogenic composition comprising the recombinant *Listeria* bacterium. Also provided is a vaccine comprising the recombinant *Listeria* bacterium. A method of inducing an immune response in a host to an antigen comprising administering to the host an effective amount of a composition comprising the recombinant *Listeria* bacterium is also provided wherein at least one of the non-Listerial polypeptides comprises an antigen. A method of preventing or treating a condition in a host comprising administering to the host an effective amount of a composition comprising the recombinant *Listeria* bacterium is also provided. The use of the bacterium in the manufacture of a medicament for inducing an immune response in a host to an antigen, wherein at least one of the non-Listerial polypeptides encoded by the polycistronic expression cassette comprises the antigen is also provided.

In other aspects, the invention provides a recombinant nucleic acid molecule, comprising (a) a first polynucleotide encoding a signal peptide, (b) a second polynucleotide encoding a secreted protein, or a fragment thereof, wherein the second polynucleotide is in the same translational reading frame as the first polynucleotide, and (c) a third polynucleotide encoding a polypeptide heterologous to the secreted protein, or fragment thereof, wherein the third polynucleotide is in the same translational reading frame as the first and second polynucleotides, wherein the recombinant nucleic acid molecule encodes a protein chimera comprising the signal peptide, the polypeptide encoded by the third polynucleotide, and the secreted protein, or fragment thereof, and wherein the polypeptide encoded by the third polynucleotide is fused to the secreted protein, or fragment thereof, or is positioned within the secreted protein, or fragment thereof, in the protein chimera. In some embodiments, the secreted protein is a naturally secreted protein (i.e., a protein that is secreted from its native cell). In some embodiments, the third polynucleotide is positioned within the second polynucleotide in the recombinant nucleic acid molecule, and the polypeptide encoded by the third polynucleotide is positioned with the secreted protein, or fragment thereof, in the protein chimera encoded by the recombinant nucleic acid molecule. In some embodiments, the third polynucleotide is positioned outside of the second polynucleotide in the recombinant nucleic acid molecule and the polypeptide encoded by the third polynucleotide is fused to the secreted protein or fragment thereof, in the protein chimera. An expression cassette comprising the recombinant nucleic acid molecule and further comprising a promoter operably linked to the first, second, and third polynucleotides of the recombinant nucleic acid molecule is also provided. In some embodiments, the polypeptide encoded by the second polynucleotide comprises an antigen. In some embodiments, the polypeptide encoded by the second polynucleotide is an antigen. For instance, in some embodiments, the antigen is a tumor-associated antigen or is derived from a tumor-associated antigen. (e.g., an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA, or is derived from an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA). In some embodiments, the antigen is mesothelin, or an antigenic fragment or antigenic variant thereof. For instance, in some embodiments, the antigen is human mesothelin or is human mesothelin deleted of its signal peptide and GPI anchor. In alternative embodiments, the antigen is an infectious disease antigen or is derived from an infectious disease antigen. An expression vector comprising the expression cassette is also provided. Recombinant bacteria comprising the recombinant nucleic acid molecules are also provided. A recombinant *Listeria* bacterium (e.g., *Listeria monocytogenes*) is also provided and in some embodiments, the polypeptide encoded by the third nucleotide is foreign to the *Listeria* bacterium. The invention also provides an immunogenic composition comprising the recombinant bacterium, wherein the polypeptide encoded by the third polynucleotide is an antigen. Also provided is a method of inducing an immune response in a host to an antigen comprising administering to the host an effective amount of a composition comprising the recombinant bacterium, wherein the polypeptide encoded by the third polynucleotide is (or comprises) an antigen. Pharmaceutical compositions and vaccines, comprising the bacteria are also provided, as are methods of using the recombinant bacteria or compositions comprising the bacteria to prevent or treat a condition in a host. The use of the bacterium in the manufacture of a medicament for inducing an immune response in a host to an antigen, wherein the polypeptide encoded by the third polynucleotide comprises the antigen is also provided.

In further aspects, the invention provides improved methods of expressing and secreting heterologous proteins in host bacteria. The invention also provides methods of improving expression and secretion of heterologous proteins in bacteria. The invention further provides methods of making the recombinant nucleic acid molecule, expression cassettes, expression vectors, and recombinant bacteria described herein.

The invention also provides a variety of polynucleotides useful in optimizing expression of heterologous polynucleotides in bacteria such as *Listeria*.

It will be understood that embodiments set forth in a Markush group, Markush claim, or by way of "or language," encompass each separate embodiment, any combination of each of separate embodiments, as well as an invention consisting of or comprising all of each of the separate embodiments, unless dictated otherwise explicitly or by the context.

Further descriptions of the aspects and embodiments described above as well as additional embodiments and aspects of the invention are provided below.

II. Recombinant Nucleic Acid Molecules

The invention provides a variety of polynucleotides useful for expression of polynucleotides, such as heterologous polynucleotides, in bacteria such as *Listeria*. For instance, recombinant nucleic acid molecules comprising novel combinations of sequences encoding signal peptides (or polypeptides comprising signal peptides) with coding sequences of polypeptides such as heterologous antigens are provided. Recombinant nucleic acid molecules comprising codon-optimized polynucleotide sequences are provided. In some embodiments, these recombinant nucleic acid molecules are heterologous in that they comprise polynucleotides (i.e., polynucleotide sequences) which are not naturally found in combination with each other as part of the same nucleic acid molecule. In some embodiments, the recombinant nucleic acid molecules are isolated. In some embodiments, the recombinant nucleic acid molecules are positioned within the sequences of expression cassettes, expression vectors, plasmid DNA within bacteria, and/or even the genomic DNA of bacteria (following insertion). In some embodiments, the recombinant nucleic acid molecules provide enhanced expression and/or secretion of the polypeptide (e.g., a heterologous polypeptide) within a bacterium.

In some embodiments, the recombinant nucleic acid molecule is DNA. In some embodiments, the recombinant nucleic acid molecule is RNA. In some embodiments, the recombinant nucleic acid is single-stranded. In other embodiments, the recombinant nucleic acid is double-stranded.

In some embodiments, the recombinant nucleic acid molecules described herein encode a fusion protein such as fusion protein comprising a signal peptide and another polypeptide, such as a polypeptide heterologous to the signal peptide. In some embodiments, the signal peptide is a bacterial signal peptide. It is understood that the recited polypeptide components of a fusion protein may, but need not necessarily be, directly fused to each other. The polypeptide components of a fusion protein, may in some embodiments be separated on the polypeptide sequence by one or more intervening amino acid sequences. In some embodiments the other polypeptide is non-bacterial, for instance, mammalian or viral.

For instance, in one aspect, the invention provides a recombinant nucleic acid molecule, comprising: (a) a first polynucleotide encoding a signal peptide, wherein the first polynucleotide is codon-optimized for expression in a bacterium; and (b) a second polynucleotide encoding a polypeptide (e.g., an antigen), wherein the second polynucleotide is in the same translational reading frame as the first polynucleotide, wherein the recombinant nucleic acid molecule encodes a fusion protein comprising the signal peptide and the polypeptide. In additional embodiments, the second polynucleotide (the polynucleotide encoding the polypeptide, such as an antigen) is also codon-optimized for expression in a bacterium. The bacterium for which the first and/or second polynucleotide is codon-optimized should be the bacterium of a type in which the recombinant nucleic acid molecule is intended to be placed.

In another aspect, the invention provides a recombinant nucleic acid molecule, comprising (a) a first polynucleotide encoding a signal peptide native to a bacterium, wherein the first polynucleotide is codon-optimized for expression in the bacterium, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the polypeptide encoded by the second polynucleotide is heterologous to the signal peptide. In some embodiments, the second polynucleotide is heterologous to the first polynucleotide. In some embodiments, the polypeptide is heterologous to the bacterium to which the signal peptide is native (i.e., foreign to the bacterium). In some embodiments, the polypeptide encoded by the second polynucleotide is heterologous to the signal peptide, foreign to the bacterium, or both. In some embodiments, the bacterium from which the signal peptide is derived is an intracellular bacterium. In some embodiments, the bacterium is selected from the group consisting of *Listeria, Bacillus, Yersinia pestis, Salmonella, Shigella, Brucella,* mycobacteria and *E. coli*. In some embodiments, the signal peptide is native to a *Listeria* bacterium. In some embodiments, the signal peptide is native to a *Listeria* bacterium belonging to the species *Listeria monocytogenes*. In some embodiments, the second polynucleotide is codon-optimized for expression in the bacterium.

In another aspect, the invention provides a recombinant nucleic acid molecule, wherein the recombinant nucleic acid molecule comprises (a) a first polynucleotide encoding a signal peptide, wherein the first polynucleotide is codon-optimized for expression in a *Listeria* bacterium, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the signal peptide is native to the *Listeria* bacterium. In some other embodiments, the signal peptide is foreign to the *Listeria* bacterium. In some embodiments, the signal peptide is heterologous to the polypeptide encoded by the second polynucleotide. In some embodiments, the polypeptide encoded by the second polynucleotide is heterologous to the *Listeria* bacterium. In some embodiments, the *Listeria* bacterium belongs to the species *Listeria monocytogenes*.

The invention also provides a recombinant nucleic acid molecule comprising a polynucleotide encoding a polypeptide foreign to a *Listeria* bacterium (e.g., a cancer or non- Listerial infectious disease antigen), wherein the polynucleotide encoding the foreign polypeptide is codon-optimized for expression in the *Listeria* bacterium.

In another aspect, the invention provides a recombinant nucleic acid molecule, comprising: (a) a first polynucleotide encoding a non-secA1 bacterial signal peptide, and (b) a second polynucleotide encoding a polypeptide, such as an antigen, wherein the second polynucleotide is in the same translational reading frame as the first polynucleotide, wherein the recombinant nucleic acid molecule encodes a fusion protein comprising the signal peptide and the polypeptide. In some embodiments, the non-secA1 bacterial signal peptide is a secA2 signal peptide or a Tat signal peptide. In some embodiments, the first polynucleotide encoding the non-secA1 signal peptide is codon-optimized for expression in the bacteria in which the recombinant nucleic acid molecule is intended to be placed (e.g., *Listeria*). In some embodiments, the second polynucleotide encoding a polypeptide, such as an antigen, is codon-optimized for expression in the bacteria in which the recombinant nucleic acid molecule is intended to be placed. In some embodiments, the polypeptide encoded by the second polynucleotide is heterologous to the signal peptide. In some embodiments, the polypeptide encoded by the second polynucleotide is foreign to the bacterium in which the recombinant nucleic acid molecule is to be incorporated or has been incorporated. In some embodiments, the polypeptide encoded by the second polynucleotide is foreign to the bacterium in which the recombinant nucleic acid molecule is to be incorporated or has been incorporated and the polypeptide encoded by the second polynucleotide is also heterologous to the signal peptide.

The invention further provides a recombinant nucleic acid molecule, comprising a first polynucleotide encoding a non-secA1 bacterial signal peptide, a second polynucleotide encoding a polypeptide (e.g., heterologous protein and/or antigen), and a third polynucleotide encoding a SecA2 autolysin, or fragment thereof, in the same translational reading frame as the first and second polynucleotides, wherein the second polynucleotide is positioned within the third polynucleotide or between the first and third polynucleotides. In some embodiments, the recombinant nucleic acid molecule encodes a fusion protein comprising the signal peptide, the polypeptide, and the autolysin. In some embodiments, the fragment of the autolysin is catalytically active as an autolysin. In some embodiments, the autolysin is from an intracellular bacterium. In some embodiments, the autolysin is a peptidoglycan hydrolase. In some embodiments, the bacterial autolysin is a Listerial autolysin. In some embodiments, the autolysin is p60. In some embodiments, the autolysin is N-acetylmuramidase.

The invention also provides a recombinant nucleic acid molecule, wherein the recombinant nucleic acid molecule comprises (a) a first polynucleotide encoding a non-Listerial signal peptide; and (b) a second polynucleotide encoding a polypeptide that is in the same translational reading frame as the first polynucleotide, wherein the recombinant nucleic acid molecule encodes a fusion protein comprising both the non-Listerial signal peptide and the polypeptide. In some embodiments, the non-Listerial signal peptide is heterologous to the polypeptide encoded by the second polynucleotide. In some embodiments, the first polynucleotide, the second polynucleotide, or both the first and second polynucleotides are codon-optimized for expression in a *Listeria* bacterium.

The invention also provides a recombinant nucleic acid molecule, comprising (a) a first polynucleotide encoding a bacterial autolysin, or a catalytically active fragment or catalytically active variant thereof, and (b) a second polynucleotide encoding a polypeptide, wherein the second polynucleotide is in the same translational reading frame as the first polynucleotide, wherein the recombinant nucleic acid molecule encodes a protein chimera comprising the polypeptide encoded by the second polynucleotide and the autolysin, or catalytically active fragment or catalytically active variant thereof, wherein, in the protein chimera, the polypeptide is fused to the autolysin, or catalytically active fragment or catalytically active variant thereof, or is positioned within the autolysin, or catalytically active fragment or catalytically active variant thereof. In some embodiments, the second polynucleotide is positioned within the first polynucleotide, and the recombinant nucleic acid molecule encodes a protein chimera in which the polypeptide encoded by the second polynucleotide is positioned within the autolysin, or catalytically active fragment or catalytically active variant thereof. In some embodiments, the second polynucleotide is positioned outside the second polynucleotide, and the recombinant nucleic acid molecule encodes a protein chimera in which the polypeptide encoded by the second polynucleotide is fused to the autolysin, or catalytically active fragment or catalytically active variant thereof. In some embodiments, the first polynucleotide encodes an autolysin. In some embodiments, the recombinant nucleic acid molecule further comprises (c) a third polynucleotide encoding a signal peptide in the same translational reading frame as the first and second polynucleotides, wherein the recombinant nucleic acid molecule encodes a protein chimera comprising the signal peptide, the polypeptide encoded by the second polynucleotide, and the autolysin, or catalytically active fragment or catalytically active variant thereof. In some embodiments, the polypeptide encoded by the second polynucleotide is heterologous to the autolysin. In some embodiments, the fragments of the autolysin are at least about 30, at least about 40, at least about 50, or at least about 100 amino acids in length. In some embodiments, the autolysin is from an intracellular bacterium. In some embodiments, the bacterial autolysin is a Listerial autolysin. Catalytically active variants of an autolysin include variants that differ from the original autolysin in one or more substitutions, deletions, additions, and/or insertions. In some embodiments, the autolysin is a peptidoglycan hydrolase. In some embodiments, the autolysin is p60. In some embodiments, the autolysin is N-acetylmuramidase.

Additional autolysins can be identified and characterized by zymography, a technique known to those skilled in the art (see, e.g., Lenz, et al. (2003) Proc. Natl. Acad. Sci. USA 100:12432-12437). Zymography can also be used determine whether a given fragment and/or variant of an autolysin is catalytically active as an autolysin. The technique can also be used to assess whether or not a particular protein chimera is catalytically active as an autolysin.

In some embodiments, the catalytically active fragments and/or variants of the autolysin are at least about 10%, at least about 30%, at least about 50%, at least about 75%, at least about 90%, or at least about 95% as catalytically active as an autolysin as the native autolysin.

In some embodiments, the protein chimera is catalytically active as an autolysin. In some embodiments, the protein chimera is at least about 10%, at least about 30%, at least about 50%, at least about 75%, at least about 90%, or at least about 95% as catalytically active as an autolysin as the native autolysin.

Another option for heterologous protein expression is to utilize a protein "scaffold" into which a heterologous protein is functionally inserted "in-frame." In this composition, whole genes or components of the gene corresponding to, for example, MHC class I or MHC class II epitopes are inserted within and through a scaffold protein. The scaffold protein can be a highly expressed bacterial proteins (such as a *Listeria* protein, like LLO or p60), but in another embodiment can be a heterologous protein that is selected for its high expression, stability, secretion, and or (lack of) immunogenicity. Representative examples of scaffold proteins are chicken ovalbumin, or other human proteins, such as β-globin or albumin.

The invention also provides a recombinant nucleic acid molecule, comprising (a) a first polynucleotide encoding a signal peptide, (b) a second polynucleotide encoding a secreted protein, or a fragment thereof, wherein the second polynucleotide is in the same translational reading frame as the first polynucleotide, and (c) a third polynucleotide encoding a polypeptide heterologous to the secreted protein, or fragment thereof, wherein the third polynucleotide is in the same translational reading frame as the first and second polynucleotides, wherein the recombinant nucleic acid molecule encodes a protein chimera comprising the signal peptide, the polypeptide encoded by the second polynucleotide, and the secreted protein, or fragment thereof, and wherein the polypeptide is fused to the secreted protein, or fragment thereof, or is positioned within the secreted protein, or fragment thereof, in the protein chimera. In some embodiments, the second polynucleotide encodes a secreted protein. In some embodiments, the secreted protein is a protein that is secreted from its native cell. In some embodiments, the third polynucleotide is positioned within the second polynucleotide in the recombinant nucleic acid molecule, and the polypeptide encoded by the third polynucleotide is positioned with the secreted protein, or fragment thereof, in the protein chimera encoded by the recombinant nucleic acid molecule. In some embodiments, the third polynucleotide is positioned outside of the second polynucleotide in the nucleic acid molecule and the polypeptide encoded by the third polynucleotide is fused to the secreted protein or fragment thereof, in the protein chimera. In some embodiments, the secreted protein is ovalbumin. In some embodiments, a truncated form of ovalbumin is used. In some embodiments, the secreted protein is p60. In some embodiments, the secreted protein is N-acetylmuramidase. In some embodiments, the signal peptide is the signal peptide normally associated with the secreted protein. In some embodiments, the signal peptide is heterologous to the secreted protein. In some embodiments, the fragments of the secreted protein are at least about 30, at least about 40, at least about 50, or at least about 100 amino acids in length.

In some embodiments, the recombinant nucleic acid molecule, expression cassette, or expression vector comprises a coding sequence for a polypeptide that is foreign to the bacteria, embedded within part or a whole coding sequence of a protein that is highly expressed within the bacteria. In some embodiments, the highly expressed sequence is native to the bacteria in which the sequence is to be expressed. In other embodiments, the highly expressed sequence is not native to the bacteria in which it is to be expressed, but provides sufficient expression, nonetheless.

In another aspect, the invention provides a recombinant nucleic acid molecule, wherein the nucleic acid molecule encodes at least two discrete non-Listerial polypeptides. In some embodiments, the polynucleotides encoding the non-Listerial polypeptides are codon-optimized for expression in a *Listeria* bacterium.

Methods of preparing recombinant nucleic acid molecules, including those described above, are well known to those of ordinary skill in the art. For instance, recombinant nucleic acid molecules can be prepared by synthesizing long oligonucleotides on a DNA synthesizer which overlap with each other and then performing extension reaction and/or PCR to generate the desired quantity of double-stranded DNA. The double-stranded DNA can be cut with restriction enzymes and inserted into the desired expression or cloning vectors. Sequencing may be performed to verify that the correct sequence has been obtained. Also by way of non-limiting example, alternatively, one or more portions of the recombinant nucleic acid molecules may be obtained from plasmids containing the portions. PCR of the relevant portions of the plasmid and/or restriction enzyme excision of the relevant portions of the plasmid can be performed, followed by ligation and/or PCR to combine the relevant polynucleotides to generate the desired recombinant nucleic acid molecules. Such techniques are standard in the art. Standard cloning techniques may also be used to insert the recombinant nucleic acid sequence into a plasmid and replicate the recombinant nucleic acid within a host cell, such as bacteria. The recombinant nucleic acid can then be isolated from the host cell.

The invention also provides a method of using any of the recombinant nucleic acid molecules described herein to produce a recombinant bacterium (e.g. a recombinant *Listeria* bacterium). In some embodiments, the method of using a recombinant nucleic acid molecule described herein to make a recombinant bacterium comprises introducing the recombinant nucleic acid molecule into a bacterium. In some embodiments, the recombinant nucleic acid molecule is integrated into the genome of the bacterium. In some other embodiments, the recombinant nucleic acid molecule is on a plasmid which is incorporated within the bacterium. In some embodiments, incorporation of the recombinant nucleic acid molecule into the bacterium occurs by conjugation. The introduction into the bacterium can be effected by any of the standard techniques known in the art. For instance, incorporation of the recombinant nucleic acid molecule into the bacterium can occur by conjugation, transduction (transfection), or transformation.

III. Signal Peptides

In some embodiments, the recombinant nucleic acid molecules, expression cassettes, and/or vectors of the invention encode fusion proteins or protein chimeras which comprise signal peptides and are suitable for expression in and secretion from host cells such as bacteria. Thus, in some embodiments, the recombinant nucleic acid molecules, expression cassettes and/or vectors of the invention comprise polynucleotides encoding signal peptides.

The terms "signal peptide" and "signal sequence," are used interchangeably herein. In some embodiments, the signal peptide helps facilitate transportation of a polypeptide fused to the signal peptide across the cell membrane of a cell (e.g., a bacterial cell) so that the polypeptide is secreted from the cell. Accordingly, in some embodiments, the signal peptide is a "secretory signal peptide" or "secretory sequence". In some embodiments, the signal peptide is positioned at the N-terminal end of the polypeptide to be secreted.

In some embodiments, the sequence encoding the signal peptide in the recombinant nucleic acid molecule or expression cassette is positioned within the recombinant nucleic acid molecule or expression cassette such that the encoded signal peptide will effect secretion, of the polypeptide to which it is fused from the desired host cell (e.g., a bacterium). In some embodiments, in a recombinant nucleic acid molecule or an expression cassette, the polynucleotide encoding the signal peptide is positioned in frame (either directly or separated by intervening polynucleotides) at the 5' end of the polynucleotide that encodes the polypeptide to be secreted (e.g., a polypeptide comprising an antigen).

In some embodiments, the signal peptides that are a part of the fusion proteins and/or protein chimeras encoded by the recombinant nucleic acid molecules, expression cassettes and/or expression vectors, are heterologous to at least one other polypeptide sequence in the fusion protein and/or protein chimera. In some embodiments, the signal peptide encoded by the recombinant nucleic acid molecule, expression cassette and/or expression vector is heterologous (i.e., foreign) to the bacterium into which the recombinant nucleic acid molecule, expression cassette and/or expression vector is to be incorporated or has been incorporated. In some embodiments, the signal peptide is native to the bacterium in which the recombinant nucleic acid molecule, expression cassette and/or expression vector is to be incorporated.

In some embodiments, the polynucleotide encoding the signal peptide is codon-optimized for expression in a bacterium (e.g., *Listeria* such as *Listeria monocytogenes*). In some embodiments, the polynucleotide that is codon-optimized for a particular bacterium is foreign to the bacterium. In other embodiments, the polynucleotide that is codon-optimized for a particular bacterium is native to that bacterium.

A large variety of signal peptides are known in the art. In addition, a variety of algorithms and software programs, such as the "SignalP" algorithms, which can be used to predict signal peptide sequences are available in the art. For instance, see: Antelmann et al., Genome Res., 11:1484-502 (2001); Menne et al., Bioinformatics, 16:741-2 (2000); Nielsen et al., Protein Eng., 10:1-6 (1997); Zhang et al., Protein Sci., 13:2819-24 (2004); Bendtsen et al., J. Mol. Biol., 340:783-95 (2004) (regarding SignalP 3.0); Hiller et al., Nucleic Acids Res., 32:W375-9 (2004); Schneider et al., Proteomics 4:1571-80 (2004); Chou, Curr. Protein Pept. Sci., 3:615-22 (2002); Shah et al., Bioinformatics, 19:1985-96 (2003); and Yuan et al., Biochem. Biophys. Res. Commun. 312:1278-83 (2003).

In some embodiments the signal peptide is prokaryotic. In some alternative embodiments, the signal peptide is eukaryotic. The use of eukaryotic signal peptides for expression of proteins in *Escherichia coli* for example, is described in Humphreys et al., *Protein Expression and Purification*, 20:252-264 (2000).

In some embodiments, the signal peptide is a bacterial signal peptide. In some embodiments, the signal peptide is a non-Listerial signal peptide. In some embodiments, the signal peptide is a Listerial signal peptide. In some embodiments the signal peptide is derived from a gram-positive bacterium. In some embodiments, the signal peptide is derived from an intracellular bacterium.

In some embodiments, the signal peptide (e.g., a non-secA1 bacterial signal peptide) used in a recombinant nucleic acid molecule, expression cassette, or expression vector is derived from *Listeria*. In some embodiments, this signal peptide is derived from *Listeria monocytogenes*. In some embodiments, the signal peptide is a signal peptide from *Listeria monocytogenes*. In some embodiments, the signal peptide is not derived from *Listeria*, but is instead derived from a bacterium other than a bacterium belonging to the genus *Listeria*. In some embodiments, the bacterial signal peptide is derived from a *Bacillus* bacterium. In some embodiments, the bacterial signal peptide is derived from *Bacillus subtilis*. In some embodiments, the bacterial signal peptide is derived from a bacterium belonging to the genus *Staphylococcus*. In some embodiments, the bacterial signal peptide is derived from a *Lactococcus* bacterium. In some embodiments, the bacterial signal peptide is derived from a *Bacillus*, *Staphylococcus*, or *Lactococcus* bacterium. In some embodiments, the bacterial signal peptide is a signal peptide from a *Bacillus*, *Staphylococcus*, or *Lactococcus* bacterium. In some embodiments, the bacterial signal peptide is a signal peptide derived from *Bacillus anthracis*, *Bacillus subtilis*, *Staphylococcus aureus*, or *Lactococcus lactis*. In some embodiments, the bacterial signal peptide is a signal peptide from *Bacillus anthracis*. In some embodiments, the bacterial signal peptide is a signal peptide from *Bacillus subtilis*. In some embodiments, the bacterial signal peptide is a signal peptide from *Lactococcus lactis*. In some embodiments, the bacterial signal peptide is a signal peptide from *Staphylococcus aureus*.

In some embodiments of the polynucleotides described herein, the signal peptide that is derived from an organism, such as a bacterium, is identical to a naturally occurring signal peptide sequence obtained from the organism. In other embodiments, the signal peptide sequence encoded by the recombinant nucleic acid molecule, expression cassette, and/or expression vector is derived from a naturally occurring signal peptide sequence, i.e., a fragment and/or variant of a naturally occurring signal peptide sequence, wherein the fragment or variant still functions as a signal peptide. A variant includes polypeptides that differ from the original sequence by one or more substitutions, deletions, additions, and/or insertions. For instance, in some embodiments the signal peptide that is encoded by the polynucleotides contains one or more conservative mutations. Possible conservative amino acid changes are well known to those of ordinary skill in the art. See, e.g., Section IV of the Detailed Description, below, for additional information regarding conservative amino acid changes.

A signal peptide derived from another signal peptide (i.e., a fragment and/or variant of the other signal peptide) is preferably substantially equivalent to the original signal peptide. For instance, the ability of a signal peptide derived from another signal peptide to function as a signal peptide should be substantially unaffected by the variations (deletions, mutations, etc.) made to the original signal peptide sequence. In some embodiments, the derived signal peptide is at least about 70%, at least about 80%, at least about 90%, or at least about 95% able to function as a signal peptide as the native signal peptide sequence. In some embodiments, the signal peptide has at least about 70%, at least about 80%, at least about 90%, or at least about 95% identity in amino acid sequence to the original signal peptide. In some embodiments, the only alterations made in the sequence of the signal peptide are conservative amino acid substitutions. Fragments of signal peptides are preferably at least about 80% or at least about 90% of the length of the original signal peptides.

In some embodiments, the signal peptide encoded by a polynucleotide in the recombinant nucleic acid molecules, expression cassettes, or expression vectors is a secA1 signal peptide, a secA2 signal peptide, or a Twin-arginine translocation (Tat) signal peptide. In some embodiments, the signal peptide is a secA1 signal peptide signal peptide. In some embodiments, the signal peptide is a non-secA1 signal peptide. In some embodiments, the signal peptide is a secA2 signal peptide. In some embodiments, the signal peptide is a twin-arginine translocation (Tat) signal peptide. In some embodiments, these secA1, secA2, or Tat signal peptides are derived from *Listeria*. In some embodiments, these secA1, secA2, or Tat signal peptides are non-Listerial. For instance, in some embodiments, the secA1, secA2, and Tat signal peptides are derived from bacteria belonging to one of the following genera: *Bacillus*, *Staphylococcus*, or *Lactococcus*.

Bacteria utilize diverse pathways for protein secretion, including secA1, secA2, and Twin-Arg Translocation (Tat). Which pathway is utilized is largely determined by the type of signal sequence located at the N-terminal end of the pre-protein. The majority of secreted proteins utilize the Sec pathway, in which the protein translocates through the bacterial membrane-embedded proteinaceous Sec pore in an unfolded conformation. In contrast, the proteins utilizing the Tat pathway are secreted in a folded conformation. Nucleotide sequence encoding signal peptides corresponding to any of these protein secretion pathways can be fused genetically in-frame to a desired heterologous protein coding sequence. The signal peptides optimally contain a signal peptidase cleavage site at their carboxyl terminus for release of the authentic desired protein into the extra-cellular environment (Sharkov and Cai. 2002 *J. Biol. Chem.* 277:5796-5803; Nielsen et. al. 1997 *Protein Engineering* 10:1-6).

The signal peptides used in the polynucleotides of the invention can be derived not only from diverse secretion pathways, but also from diverse bacterial genera. Signal peptides generally have a common structural organization, having a charged N-terminus (N-domain), a hydrophobic core region (H-domain) and a more polar C-terminal region (C-domain), however, they do not show sequence conservation. In some embodiments, the C-domain of the signal peptide carries a type I signal peptidase (SPase I) cleavage site, having the consensus sequence A-X-A, at positions-1 and -3 relative to the cleavage site. Proteins secreted via the sec pathway have signal peptides that average 28 residues. The secA2 protein secretion pathway was first discovered in *Listeria monocytogenes*; mutants in the secA2 paralogue are characterized by a rough colony phenotype on agar media, and an attenuated virulence phenotype in mice (Lenz and Portnoy, 2002 *Mol. Microbiol.* 45:1043-1056; and, Lenz et. al 2003 *PNAS* 100:12432-12437). Signal peptides related to proteins secreted by the Tat pathway have a tripartite organization similar to Sec signal peptides, but are characterized by having an RR-motif (R—R—X-#-#, where # is a hydrophobic residue), located at the N-domain/H-domain boundary. Bacterial Tat signal peptides average 14 amino acids longer than sec signal peptides. The *Bacillus subtilis* secretome may contain as many as 69 putative proteins that utilize the Tat secretion pathway, 14 of which contain a SPase I cleavage site (Jongbloed et. al. 2002 *J. Biol. Chem.* 277:44068-44078; Thalsma et. al., 2000 *Microbiol. Mol. Biol. Rev.* 64:515-547).

Shown in Table 1 below are non-limiting examples of signal peptides that can be used in fusion compositions (including protein chimera compositions) with a selected other polypeptide such as a heterologous polypeptide, resulting in secretion from the bacterium of the encoded protein.

TABLE 1

Some exemplary signal peptides

| Secretion Pathway | Signal Peptide Amino Acid Sequence (NH$_2$—CO$_2$) | Signal peptidase Site (cleavage site represented by ') | Gene | Genus/species |
|---|---|---|---|---|
| secA1 | MKKIMLVFITLILVSLPIAQQ TEAKD (SEQ ID NO: 45) | TEA'KD (SEQ ID NO: 54) | hly (LLO) | *Listeria monocytogenes* |
|  | MKKKIISAILMSTVILSAAAP LSGVYADT (SEQ ID NO: 46) | VYA'DT (SEQ ID NO: 55) | Usp45 | *Lactococcus lactis* |
|  | MKKRKVLIPLMALSTILVSS TGNLEVIQAEV (SEQ ID NO: 47) | IQA'EV (SEQ ID NO: 56) | pag (Protective Antigen) | *Bacillus anthracis* |
| secA2 | MNMKKATIAATAGIAVTAF AAPTIASAST (SEQ ID NO: 48) | ASA'ST (SEQ ID NO: 57) | iap invasion-associated protein p60 | *Listeria monocytogenes* |
|  | MQKTRKERILEALQEEKKN KKSKKFKTGATIAGVTAIAT SITVPGIEVIVSADE (SEQ ID NO: 49) | VSA'DE (SEQ ID NO: 58) | NamA lmo2691 (autolysin) | *Listeria monocytogenes* |
|  | MKKLKMASCALVAGLMFS GLTPNAFAED (SEQ ID NO: 50) | AFA'ED (SEQ ID NO: 59) | * BA_0281 (NLP/P60 Family) | *Bacillus anthracis* |
|  | MAKKFNYKLPSMVALTLVG SAVTAHQVQAAE (SEQ ID NO: 51) | VQA'AE (SEQ ID NO: 60) | * atl (autolysin) | *Staphylococcus aureus* |
| Tat | MTDKKSENQTEKTETKENK GMTRREMLKLSAVAGTGIA VGATGLGTILNVVDQVDKA LT (SEQ ID NO: 52) | DKA'LT (SEQ ID NO: 61) | lmo0367 | *Listeria monocytogenes* |
|  | MAYDSRFDEWVQKLKEESF QNNTFDRRKFIQGAGKIAGL SLGLTIAQSVGAFG (SEQ ID NO: 53) | VGA'FG (SEQ ID NO: 62) | PhoD (alkaline phosphatase) | *Bacillus subtilis* |

* Bacterial autolysins secreted by sec pathway (not determined whether secA1 or secA2).

Accordingly, in some embodiments, the sequence that encodes the signal peptide encodes a secA1 signal peptide. An example of a secA1 signal peptide is the Listeriolysin O (LLO) signal peptide from *Listeria monocytogenes*. In some embodiments, the recombinant nucleic acid molecule or expression cassette comprising a polynucleotide encoding an LLO signal peptide further comprises a polynucleotide sequence encoding the LLO PEST sequence. Other examples of secA1 signal peptides suitable for use in the present invention include the signal peptides from the Usp45 gene in *Lactococcus lactis* (see Table 1, above, and Example 12 below) and Pag (Protective Antigen) gene from *Bacillus anthracis*. Thus, in some embodiments, the signal peptide is a protective antigen signal peptide from *Bacillus anthracis*. In some other embodiments, the signal peptide is a secA1 signal peptide other than the protective antigen signal peptide from *Bacillus anthracis*. Another example of a secA1 signal peptide is the SpsB signal peptide from *Staphylococcus aureus* (Sharkov et al., *J. of Biological Chemistry*, 277: 5796-5803 (2002)).

In some alternative embodiments, the heterologous coding sequences are genetically fused with signal peptides that are recognized by the secA2 pathway protein secretion complex. An auxiliary SecA paralog (SecA2) has been identified in nine Gram-positive bacteria that cause severe or lethal infections of humans. SecA2 is required for secretion of a subset of the exported proteomes (secretomes) of *Listeria*, Mycobacteria, and Streptococci (Braunstein et al., Mol. Microbiol. 48:453-64 (2003); Bensing et al., Mol. Microbiol., 44:1081-94 (2002); Lenz et al., Mol. Microbiol., 45:1043-1056 (2002); and Braunstein et al., J. Bacteriology, 183:6979-6990 (2001)). The *Listeria monocytogenes* SecA2 was identified through its association with bacterial smooth-rough variation, and mutations in secA2 reduced virulence of *L. monocytogenes* and *Mycobacterium tuberculosis*.

For example, the *Listeria* protein p60 is a peptidoglycan autolysin that is secreted by the secA2 pathway. As an example, the secA2 signal peptide and signal peptidase cleavage site from p60 can be linked genetically with the amino terminus of a desired protein (e.g. antigen)-encoding gene. In one embodiment, the pre-protein comprised of the secA2 signal peptide and signal peptidase-antigen fusion is translated from an expression cassette within a bacterium, transported through the Gram-positive cell wall, in which the authentic heterologous protein is released into the extracellular milieu.

Alternatively, a heterologous sequence can be incorporated "in-frame" within p60, such that the heterologous protein is secreted in the form of a chimeric p60-heterologous protein. Insertion of the heterologous protein coding sequence in-frame into p60 can occur, for example, at the junction between the signal peptidase cleavage site and the mature p60 protein. In this embodiment, the chimeric protein retains the appropriate secA2 secretion signals, and also its autolysin activity, meaning that the heterologous protein is secreted as a gratuitous passenger of p60. In-frame incorporation of the heterologous antigen into p60 can be engineered at any point within p60 that retains both the secretion and autolysin activities of the p60 protein. An example of a partial expression cassette suitable for insertion of the desired antigen or other heterologous polypeptide coding sequence is described in Example 13, below.

In some embodiments, the fusion protein encoded by the recombinant nucleic acid molecule is a chimera comprising a bacterial protein having a particular desirable property (in addition to the desired heterologous protein such as an antigen). In some embodiments the chimera comprises a hydrolase. In some embodiments, the recombinant nucleic acid molecule encodes a p60 chimera comprising the endopeptidase p60, a peptidoglycan hydrolase that degrades the bacterial cell wall. In some embodiments, the fusion protein encoded by the recombinant nucleic acid molecule comprises a *L. monocytogenes* hydrolase, for example, p60 (see, e.g., Genbank accession no. NP_464110) or N-acetylmuramidase (NamA) (Genbank accession no. NP_466213), both of which are secA2 dependent secreted proteins that degrade the cell wall. Such particular protein chimera compositions take advantage of not only molecular chaperones required for secretion of bacterial proteins, but also of the activity of the bacterial protein that can facilitate its secretion. Particular protein chimeras comprised of precise placement of a heterologous protein encoding sequence with a *L. monocytogenes* hydrolase result in the efficient expression and secretion of the heterologous protein. (See, e.g., the specific example, Example 29, below.) Accordingly, in some embodiments, the signal peptide encoded by the recombinant nucleic acid molecule as part of a fusion protein is p60 signal peptide. In some embodiments, the signal peptide encoded by the recombinant nucleic acid molecule as part of a fusion protein is a NamA signal peptide.

In some embodiments, the recombinant nucleic acid molecule comprises a third polynucleotide sequence encoding p60 protein, or a fragment thereof, in the same translational reading frame as both the first polynucleotide encoding the p60 signal peptide and the second polynucleotide encoding the other polypeptide (e.g., antigen). The recombinant nucleic acid molecule then encodes a fusion protein comprising the signal peptide, the polypeptide encoded by the second polynucleotide (e.g., an antigen), and the p60 protein, or a fragment thereof. In such embodiments, the second polynucleotide is preferably positioned either within the third polynucleotide or between the first and third polynucleotides.

In some embodiments, the secA2 signal peptide is a secA2 signal peptide derived from *Listeria*. For instance, in some embodiments, the signal peptide is a secA2 signal peptide such as the p60 signal peptide or the N-acetylmuramidase (NamA) signal peptide from *L. monocytogenes*. In addition, other *L. monocytogenes* proteins have been identified as not being secreted in the absence of secA2 (Lenz et al., Mol. Microbiology 45:1043-1056 (2002)) and polynucleotides encoding the signal peptides from these proteins can be used in some embodiments. Additionally, secA2 signal peptides from bacteria other than *Listeria* can be utilized for expression and secretion of heterologous proteins from recombinant *Listeria* or other bacteria. For instance, as an illustrative but non-limiting example, secA2 signal peptides from *B. anthracis* can be used in the recombinant nucleic acid molecules and/or expression cassettes. In other embodiments, a secA2 signal peptide from *S. aureus* is used. See Table 1. Proteins secreted via the SecA2 pathway in other bacteria have also been identified (see, e.g., Braunstein et al., Mol. Microbiol., 48:453-64 (2003) and Bensing et al., Mol. Microbiol. 44:1081-94 (2002)).

Additional proteins secreted via the secA2 pathway can be identified. SecA2 homologues have been identified in a number of bacterial species (see, e.g., Lenz et al., Mol. Microbiology 45:1043-1056 (2002) and Braunstein et al., J. Bacteriology, 183:6979-6990 (2001)). Additional secA2 homologues can be identified by further sequence comparison using techniques known to those skilled in the art. Once a homologue is identified, the homologue can be deleted from the bacterial organism to generate a ΔsecA2 mutant. The supernatant proteins of the wild-type and mutant bacterial cultures can be TCA-precipitated and analyzed by any of the proteomics techniques known in the art to determine which proteins are secreted by the wild-type bacteria, but not the ΔsecA2 mutant. For instance, the secreted proteins can be analyzed via SDS-PAGE and silver staining. The resulting bands can be compared to identify those proteins for which secretion did not occur in the absence of the SecA2. (See, e.g., Lenz et al., Mol. Microbiology 45:1043-1056 (2002)). The N-terminal sequences of these proteins can then be analyzed (e.g., with an algorithm to predict the signal peptide cleavage site) to determine the secA2 signal peptide sequence used by that protein. N-terminal sequencing by automated Edman degradation can also be performed to identify the sequence of the signal peptide.

In alternative embodiments, the polynucleotides encode polypeptides (e.g., heterologous polypeptide sequences) that are genetically fused with signal peptides that are recognized by the Tat pathway protein secretion complex. The Tat secretion pathway is utilized by bacteria, including *Listeria* spp., for secretion of proteins that are folded within the bacterium. For example, the *Listeria innocua* protein YwbN has a putative Tat motif at its amino terminus and thus uses the Tat pathway for secretion (Genbank Accession No. NP_469731 [gi|16799463|ref|NP_469731.1| conserved hypothetical protein similar to *B. subtilis* YwbN protein (*Listeria innocua*)], incorporated by reference herein). Another protein containing a Tat signal peptide is the YwbN protein from *Listeria monocytogenes* strain EGD(e) (Genbank Accession No. NP_463897 [gi|16802412|ref|NP_463897.1| conserved hypothetical protein similar to *B. subtilis* YwbN protein (*Listeria monocytogenes* EGD (e)]). As an example, the YwbN signal peptide and signal peptidase cleavage site from YwbN can be linked genetically with the amino terminus of a desired protein (e.g. antigen)-encoding gene. In this composition, the pre-protein comprised of the Tat signal peptide and signal peptidase-antigen fusion will be translated from an expression cassette within the bacterium, transported through the Gram-positive cell wall, in which the authentic heterologous protein is released into the extracellular milieu. Another protein predicted to be secreted from *Listeria innocua* via the Tat pathway is 3-oxoxacyl-acyl carrier protein synthase (Genbank Accession No. NP_471636 [gi|16801368|ref|NP_471636.1| similar to 3 (oxoacyl(acyl (carrier protein synthase (*Listeria innocua*)]). Polynucleotides encoding signal sequences from any of these proteins predicted to be secreted from *Listeria* via the Tat secretory pathway may be used in the polynucleotides, expression cassettes, and/or expression vectors described herein.

Tat signal sequences from other bacteria can also be used as signal peptides, including, but not restricted to, phoD from *B. subtilis*. Examples of Tat signal peptides from *Bacillus subtilis*, such as phoD, are described in Jongbloed et al., *J. of Biological Chemistry*, 277:44068-44078 (2002); Jongbloed et al., *J. of Biological Chemistry*, 275:41350-41357 (2000), Pop et al., *J. of Biological Chemistry*, 277:3268-3273 (2002); van Dijl et al., *J. of Biotechnology*, 98:243-254 (2002); and Tjalsma et al., Microbiology and *Molecular Biology Reviews*, 64: 515-547 (2000), all of which are incorporated by reference herein in their entirety. Other proteins identified in *B. subtilis* that have been predicted to be secreted by the Tat pathway include those sequences having the following Genbank/Embl Accession Nos.: CAB15017 [gi|2635523|emb|CAB15017.1| similar to two (component sensor histidine kinase (YtsA) (*Bacillus subtilis*)]; CAB12056 [gi|2632548|emb|CAB12056.1| phosphodiesterase/alkaline phosphatase D (*Bacillus subtilis*)]; CAB12081 [gi|2632573|emb|CAB12081.1| similar to hypothetical proteins (*Bacillus subtilis*)]; CAB13278 [gi|2633776|emb|CAB13278.1| similar to hypothetical proteins (*Bacillus subtilis*)]; CAB14172 [gi|2634674|emb|CAB14172.1| menaquinol:cytochrome c oxidoreductase (iron (sulfur subunit) (*Bacillus subtilis*)]; CAB15089 [gi|2635595|emb|CAB15089.1| yubF (*Bacillus subtilis*)]; and CAB15852 [gi|2636361|emb|CAB15852.1| alternate gene name: ipa (29d~similar to hypothetical proteins (*Bacillus subtilis*)], the sequences of which are all incorporated by reference herein. Thus, in some embodiments, the signal peptide encoded by the polynucleotide in the recombinant nucleic acid molecule and/or the expression cassettes is a Tat signal peptide derived from *B. subtilis*. Information on Tat signal peptides from *Pseudomonas aeruginosa* is provided in Ochsner et al., *PNAS*, 99: 8312-8317 (2002). Also, Tat signal peptides from a wide variety of other bacteria are described in Dilks et al., *J. of Bacteriology*, 185: 1478-1483 (2003) and Berks et al., *Molecular Microbiology*, 35:260-274 (2000), both of which are incorporated by reference herein in their entirety.

Additional Tat signal peptide may be identified and distinguished from Sec-type signal peptides by their "twin-arginine" consensus motif. As noted above, signal peptides related to proteins secreted by the Tat pathway have a tripartite organization similar to Sec signal peptides, but are characterized by having an RR-motif (R—R—X-#-#, where # is a hydrophobic residue) located at the N-domain/H-domain boundary. Tat signal peptides are also generally longer and less hydrophobic than the Sec-type signal peptides. See, e.g., Berks et al., Adv. *Microb. Physiol.*, 47:187-254 (2003) and Berks et al., *Mol. Microbiol.* 35:260-74 (2000).

In addition, techniques analogous to those described above for the identifying new proteins secreted by the SecA2 pathway and their corresponding SecA2 signal peptides can also be used to identify new proteins secreted via the Tat pathway and their signal peptides. The reference Jongbloed et al., *J. Biological Chem.*, 277:44068-44078 (2002) provides examples of techniques which can be used to identify a protein expressed by a type of bacteria as a protein secreted via the twin-arginine translocation pathway.

IV. Polypeptides

The recombinant nucleic acid molecules described herein, as well as the expression cassettes or expression vectors described herein, can be used to encode any desired polypeptide. In particular, the recombinant nucleic acid molecules, expression cassettes, and expression vectors are useful for expressing heterologous polypeptides in a bacterium.

In some embodiments (depending on the recombinant nucleic acid molecule, expression cassette or expression vector used), the polypeptide encoded by a polynucleotide of the recombinant nucleic acid molecule, expression cassette, and/or expression vector is encoded as part of a fusion protein with a signal peptide. In other embodiments, the encoded polypeptide is encoded as a discrete polypeptide by the recombinant nucleic acid molecule, expression cassette, or expression vector. In still other embodiments, the polypeptide encoded by a polynucleotide of the recombinant nucleic acid molecule, expression cassette, or expression vector is encoded as part of a fusion protein that does not include a signal peptide. In still other embodiments, the polypeptide encoded by a polynucleotide of the recombinant nucleic acid molecule, expression cassette, or expression vector of the invention is encoded as part of a fusion protein (also referred to herein as a protein chimera) in which the polypeptide is embedded within another polypeptide sequence.

Thus, it is understood that each of the polypeptides listed herein (below and elsewhere) which are encoded by polynucleotides of the recombinant nucleic acid molecules, expression cassettes, or expression vectors of the invention may be expressed as either fusion proteins (fused to signal peptides and/or to or in other polypeptides) or as discrete polypeptides by the recombinant nucleic acid molecule, expression cassette, or expression vector, depending on the particular recombinant nucleic acid molecule, expression cassette or expression vector used. For instance, in some embodiments, a recombinant nucleic acid molecule comprising a polynucleotide encoding the antigen CEA will encode CEA as a fusion protein with a signal peptide.

In some embodiments, the polypeptide is part of a fusion protein encoded by the recombinant nucleic acid molecule, expression cassette, or expression vector and is heterologous to the signal peptide of the fusion protein. In some embodiments, the polypeptide is positioned within another polypeptide sequence (e.g., a secreted protein or an autolysin, or fragments or variants thereof) to which it is heterologous.

In some embodiments, the polypeptide is bacterial (either Listerial or non-Listerial). In some embodiments, the polypeptide is not bacterial. In some embodiments, the polypeptide encoded by the polynucleotide is a mammalian polypeptide. For instance, the polypeptide may correspond to a polypeptide sequence found in humans (i.e., a human polypeptide). In some embodiments, the polypeptide is Listerial. In some embodiments, the polypeptide is non-Listerial. In some embodiments, the polypeptide is not native (i.e., is foreign) to the bacterium in which the recombinant nucleic acid molecule, expression cassette, and/or expression vector is to be incorporated or is incorporated.

In some embodiments, the polynucleotide encoding the polypeptide is codon-optimized for expression in a bacterium. In some embodiments, the polynucleotide encoding the polypeptide is fully codon-optimized for expression in a bacterium. In some embodiments, the polypeptide which is encoded by the codon-optimized polynucleotide is foreign to the bacterium (i.e., is heterologous to the bacterium).

The term "polypeptide" is used interchangeably herein with "peptide" and "protein" and no limitation with respect to the length or size of the amino acid sequence contained therein is intended. Typically, however, the polypeptide will comprise at least about 6 amino acids. In some embodiments, the polypeptide will comprise, at least about 9, at least about 12, at least about 20, at least about 30, or at least about 50 amino acids. In some embodiments, the polypeptide comprises at least about 100 amino acids. In some embodiments, the polypeptide is one particular domain of a protein (e.g., an extracellular domain, an intracellular domain, a catalytic domain, or a binding domain). In some embodiments, the polypeptide comprises an entire (i.e., full-length) protein.

In some embodiments, the polypeptide that is encoded by a polynucleotide of a recombinant nucleic acid molecule, expression cassette, and/or expression vector comprises an antigen or a protein that provides a palliative treatment for a disease. In some embodiments, the polypeptide that is encoded by a polynucleotide of a recombinant nucleic acid molecule, expression cassette, and/or expression vector is an antigen or a protein that provides a palliative treatment for a disease. In some embodiments, the polypeptide that is encoded is a therapeutic protein (or comprises a therapeutic protein).

In some embodiments, the polypeptide that is encoded by a polynucleotide of a recombinant nucleic acid molecule, expression cassette, and/or vector comprises an antigen (e.g., any of the antigens described herein). In some embodiments, the polypeptide that is encoded by a polynucleotide of a recombinant nucleic acid molecule, expression cassette, and/ or vector is an antigen. In some embodiments, the antigen is a bacterial antigen. In some embodiments, the antigen is a non-Listerial bacterial antigen. In some embodiments, however, the antigen is a non-Listerial antigen. In other embodiments, the antigen is a non-bacterial antigen. In some embodiments, the antigen is a mammalian antigen. In some embodiments, the antigen is a human antigen. In some embodiments, the polypeptide is (or comprises) an antigen comprising one or more immunogenic epitopes. In some embodiments, the antigen comprises one or more MHC class I epitopes. In other embodiments, the antigen comprises one or more MHC class II epitope. In some embodiments, the epitope is a CD4+ T-cell epitope. In other embodiments, the epitope is a CD8+ T-cell epitope.

The polynucleotide encoding an antigen is not limited to any exact nucleic acid sequence (e.g., that encoding a naturally occurring, full-length antigen) but can be of any sequence that encodes a polypeptide that is sufficient to elicit the desired immune response when administered to an individual within the bacteria or compositions of the invention. The term "antigen," as used herein, is also understood to include fragments of larger antigen proteins so long as the fragments are antigenic (i.e., immunogenic). In addition, in some embodiments, the antigen encoded by a polynucleotide of the recombinant nucleic acid, expression cassette, or expression vector may be a variant of a naturally occurring antigen sequence. (Similarly for polynucleotides encoding other, non-antigen proteins, the sequences of the polynucleotides encoding a given protein may vary so long as the desired protein that is expressed provides the desired effect (e.g. a palliative effect) when administered to an individual.)

An antigen that is derived from another antigen includes an antigen that is an antigenic (i.e., immunogenic) fragment of the other antigen, an antigenic variant of the other antigen, or an antigenic variant of a fragment of the other antigen. A variant of an antigen includes antigens that differ from the original antigen in one or more substitutions, deletions, additions, and/or insertions.

The antigenic fragment may be of any length, but is most typically at least about 6 amino acids, at least about 9 amino acids, at least about 12 amino acids, at least about 20 amino acids, at least about 30 amino acids, at least about 50 amino acids, or at least about 100 amino acids. An antigenic fragment of an antigen comprises at least one epitope from the antigen. In some embodiments, the epitope is a MHC class I epitope. In other embodiments, the epitope is a MHC class II epitope. In some embodiments, the epitope is a CD4+ T-cell epitope. In other embodiments, the epitope is a CD8+ T-cell epitope.

A variety of algorithms and software packages useful for predicting antigenic regions (including epitopes) within proteins are available to those skilled in the art. For instance, algorthims that can be used to select epitopes that bind to MHC class I and class II molecules are publicly available. For instance, the publicly available "SYFPEITHI" algorithm can be used to predict MHC-binding peptides (Rammensee et al. (1999) Immunogenetics 50:213-9). For other examples of publicly available algorithms, see the following references: Parker et al. (1994) J. Immunol 152:163-75; Singh and Raghava (2001) Bioinformatics 17:1236-1237; Singh and Raghava (2003) Bioinformatics 19:1009-1014; Mallios (2001) Bioinformatics 17:942-8; Nielsen et al. (2004) Bioinformatics 20:1388-97; Donnes et al. (2002) BMC Bioinformatics 3:25; Bhasin, et al. (2004) Vaccine 22:3195-204; Guan et al. (2003) Nucleic Acids Res 31:3621-4; Reche et al. (2002) Hum. Immunol. 63:701-9; Schirle et al. (2001) J. Immunol Methods 257:1-16; Nussbaum et al. (2001) Immunogenetics (2001) 53:87-94; Lu et al. (2000) Cancer Res. 60:5223-7. See also, e.g., Vector NTI® Suite (Informax, Inc, Bethesda, Md.), GCG Wisconsin Package (Accelrys, Inc., San Diego, Calif.), Welling, et al. (1985) FEBS Lett. 188:215-218, Parker, et al. (1986) Biochemistry 25:5425-5432, Van Regenmortel and Pellequer (1994) Pept. Res. 7:224-228, Hopp and Woods (1981) PNAS 78:3824-3828, and Hopp (1993) Pept. Res. 6:183-190. Some of the algorthims or software packages discussed in the references listed above in this paragraph are directed to the prediction of MHC class I and/or class II binding peptides or epitopes, others to identification of proteasomal cleavage sites, and still others to prediction of antigenicity based on hydrophilicity.

Once a candidate antigenic fragment believed to contain at least one epitope of the desired nature has been identified, the polynucleotide sequence encoding that sequence can be incorporated into an expression cassette and introduced into a Listeria vaccine vector or other bacterial vaccine vector. The immunogenicity of the antigenic fragment can then be confirmed by assessing the immune response generated by the *Listeria* or other bacteria expressing the fragments. Standard immunological assays such as ELISPOT assays, Intracellular Cytokine Staining (ICS) assay, cytotoxic T-cell activity assays, or the like, can be used to verify that the fragment of the antigen chosen maintains the desired imunogenicity. Examples of these types of assays are provided in the Examples below (see, e.g., Example 21). In addition, the anti-tumor efficacy of the *Listeria* and/or bacterial vaccines can also be assessed using the methods described below in the Examples (e.g., implantation of CT26 murine colon cells expressing the antigen fragment in mice, followed by vaccination of the mice with the candidate vaccine and observation of effect on tumor size, metastasis, survival, etc. relative to controls and/or the full-length antigen).

In addition, large databases containing epitope and/or MHC ligand information using for identifying antigenic fragments are publicly available. See, e.g., Brusic et al. (1998) Nucleic Acids Res. 26:368-371; Schonbach et al. (2002) Nucleic Acids Research 30:226-9; and Bhasin et al. (2003) Bioinformatics 19:665-666; and Rammensee et al. (1999) Immunogenetics 50:213-9.

The amino acid sequence of an antigenic variant has at least about 60%, at least about 70%, at least about 80%, at least about 90%, at least about 95%, or at least about 98% identity to the original antigen.

In some embodiments, the antigenic variant is a conservative variant that has at least about 80% identity to the original antigen and the substitutions between the sequence of the antigenic variant and the original antigen are conservative amino acid substitutions. The following substitutions are considered conservative amino acid substitutions: valine, isoleucine, or leucine are substituted for alanine; lysine, glutamine, or asparagine are substituted for arginine; glutamine, histidine, lysine, or arginine are substituted for asparagine; glutamic acid is substituted for aspartic acid; serine is substituted for cysteine; asparagine is substituted for glutamine; aspartic acid is substituted for glutamic acid; proline or alanine is substituted for glycine; asparagine, glutamine, lysine or arginine is substituted for histidine; leucine, valine, methionine, alanine, phenylalanine, or norleucine is substituted for isoleucine; norleucine, isoleucine, valine, methionine, alanine, or phenylalanine is substituted for leucine; arginine, glutamine, or asparagine is substituted for lysine; leucine, phenylalanine, or isoleucine is substituted for methionine; leucine, valine, isoleucine, alanine, or tyrosine is substituted for phenylalanine; alanine is substituted for proline; threonine is substituted for serine; serine is substituted for threonine; tyrosine or phenylalanine is substituted for tryptophan; tryptophan, phenylalanine, threonine, or serine is substituted for tyrosine; tryptophan, phenylalanine, threonine, or serine is substituted for tyrosine; isoleucine, leucine, methionine, phenylalanine, alanine, or norleucine is substituted for valine. In some embodiments, the antigenic variant is a convervative variant that has at least about 90% identity to the original antigen.

In some embodiments, an antigen derived from another antigen is substantially equivalent to the other antigen. An antigen derived from another antigen is substantially equivalent to the original antigen from which it is derived if the antigen if the derived antigen has at least about 70% identity in amino acid sequence to the original antigen and maintains at least about 70% of the immunogenicity of the original antigen. In some embodiments, the substantially equivalent antigen has at least about 80%, at least about 90%, at least about 95%, or at least about 98% identity in amino acid sequence to the original antigen. In some embodiments, the substantially equivalent antigen comprises only conservative substitutions relative to the original antigen. In some embodiments, the substantially equivalent antigen maintains at least about 80%, at least about 90%, or at least about 95% of the immunogenicity of the original antigen. To determine the immunogenicity of a particular derived antigen and compare to that of the original antigen to determine whether the derived antigen is substantially equivalent to the original antigen, one can test both the derived and original antigen in any of a number of immunogenicity assays known to those skilled in the art. For instance, *Listeria* expressing either the original antigen or the derived antigen can be prepared as described herein. The ability of those *Listeria* expressing the different antigens to produce an immune response can be measured by vaccinating mice with the *Listeria* and then assessing the immunogenic response using the standard techniques of ELISPOT assays, Intracellular Cytokine Staining (ICS) assay, cytotoxic T-cell activity assays, or the like. Examples of these types of assays are provided in the examples below (see, e.g., Example 21).

In some embodiments, the polypeptide encoded by a polynucleotide of the recombinant nucleic acid molecule, expression cassette, and/or vector comprises an antigen. In some embodiments, the antigen is selected from the group consisting of a tumor-associated antigen, a polypeptide derived from a tumor-associated antigen, an infectious disease antigen, and a polypeptide derived from an infectious disease antigen.

In some embodiments, the polypeptide encoded by a polynucleotide of the recombinant nucleic acid molecule, expression cassette, and/or vector comprises a tumor-associated antigen or comprises an antigen derived from a tumor-associated antigen. In some embodiments, the polypeptide comprises a tumor-associated antigen. In some embodiments, the encoded polypeptide comprises more than one antigen that is a tumor-associated antigen or an antigen derived from a tumor-associated antigen. For instance, in some embodiments, the encoded polypeptide comprises both mesothelin (or an antigenic fragment or antigenic variant thereof) and K-Ras, 12-K-Ras, or PSCA (or an antigenic fragment or antigenic variant of K-Ras, 12-K-Ras, or PSCA).

In some embodiments, the antigen encoded by a polynucleotide of the recombinant nucleic acid molecule, expression cassette, and/or expression vector is a tumor-associated antigen or is an antigen that is derived from a tumor-associated antigen. In some embodiments, the antigen is a tumor-associated antigen.

In some embodiments, a polynucleotide in a recombinant nucleic acid molecule, expression cassette, and/or expression vector encodes an antigen (or encodes a polypeptide comprising an antigen) that is not identical to a tumor-associated antigen, but rather is an antigen derived from a tumor-associated antigen. For instance, in some embodiments, the antigen encoded by a polynucleotide of a recombinant nucleic acid molecule, expression cassette, and/or expression vector may comprise a fragment of a tumor-associated antigen, a variant of a tumor-associated antigen, or a variant of a fragment of a tumor-associated antigen. In some cases, an antigen, such as a tumor antigen, is capable of inducing a more significant immune response in a vaccine when the amino acid sequence differs slightly from that endogenous to a host. In other cases, the derived antigen induces a less significant immune response than the original antigen, but is, for instance, more convenient for heterologous expression in a Listerial vaccine vector due to a smaller size. In some embodiments, the amino acid sequence of a variant of a tumor-associated antigen, or a variant of a fragment of a tumor-associated antigen, differs from that of the tumor-associated antigen, or its corresponding fragment, by one or more amino acids. The antigen derived from a tumor-associated antigen will comprise at least one epitope sequence capable of inducing the desired immune response upon expression of the polynucleotide encoding the antigen within a host.

Accordingly, in some embodiments, a polynucleotide in the recombinant nucleic acid molecule, expression cassette, or vector encodes a polypeptide that comprises an antigen derived from a tumor-associated antigen, wherein the antigen comprises at least one antigenic fragment of a tumor-associated antigen. In some embodiments, a polynucleotide in the recombinant nucleic acid molecule, expression cassette, or vector encodes an antigen that is derived from a tumor-associated antigen, wherein the antigen comprises at least one antigenic fragment of a tumor-associated antigen. The antigenic fragment comprises at least one epitope of the tumor-associated antigen. In some embodiments, the antigen that is derived from another antigen is an antigenic (i.e., immunogenic) fragment or an antigenic variant of the other antigen. In some embodiments, the antigen is an antigenic fragment of the other antigen. In some embodiments, the antigen is an antigenic variant of the other antigen.

A large number of tumor-associated antigens that are recognized by T cells have been identified (Renkvist et al., *Cancer Immunol Innumother* 50:3-15 (2001)). These tumor-associated antigens may be differentiation antigens (e.g., PSMA, Tyrosinase, gp100), tissue-specific antigens (e.g. PAP, PSA), developmental antigens, tumor-associated viral antigens (e.g. HPV 16 E7), cancer-testis antigens (e.g. MAGE, BAGE, NY-ESO-1), embryonic antigens (e.g. CEA, alpha-fetoprotein), oncoprotein antigens (e.g. Ras, p53), over-expressed protein antigens (e.g. ErbB2 (Her2/Neu), MUC1), or mutated protein antigens. The tumor-associated antigens that may be encoded by the heterologous nucleic acid sequence include, but are not limited to, 707-AP, Annexin II, AFP, ART-4, BAGE, β-catenin/m, BCL-2, bcr-abl, bcr-abl p190, bcr-abl p210, BRCA-1, BRCA-2, CAMEL, CAP-1, CASP-8, CDC27/m, CDK-4/m, CEA (Huang et al., *Exper Rev. Vaccines* (2002)1:49-63), CT9, CT10, Cyp-B, Dek-cain, DAM-6 (MAGE-B2), DAM-10 (MAGE-B1), EphA2 (Zantek et al., *Cell Growth Differ.* (1999) 10:629-38; Carles-Kinch et al., *Cancer Res.* (2002) 62:2840-7), ELF2M, EphA2 (Zantek et al., *Cell Growth Differ.* (1999) 10:629-38; Carles-Kinch et al., *Cancer Res.* (2002) 62:2840-7), ETV6-AML1, G250, GAGE-1, GAGE-2, GAGE-3, GAGE-4, GAGE-5, GAGE-6, GAGE-7B, GAGE-8, GnT-V, gp100, HAGE, HER2/neu, HLA-A*0201-R170I, HPV-E7, H-Ras, HSP70-2M, HST-2, hTERT, hTRT, iCE, inhibitors of apoptosis (e.g. survivin), KIAA0205, K-Ras, 12-K-Ras (K-Ras with codon 12 mutation), LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE-D, MART-1, MART-1/Melan-A, MC1R, MDM-2, mesothelin, Myosin/m, MUC1, MUC2, MUM-1, MUM-2, MUM-3, neo-polyA polymerase, NA88-A, N-Ras, NY-ESO-1, NY-ESO-1a (CAG-3), PAGE-4, PAP, Proteinase 3 (PR3) (Molldrem et al., *Blood* (1996) 88:2450-7; Molldrem et al., *Blood* (1997) 90:2529-34), P15, p190, Pm1/RARα, PRAME, PSA, PSM, PSMA, RAGE, RAS, RCAS1, RU1, RU2, SAGE, SART-1, SART-2, SART-3, SP17, SPAS-1, TEL/AML1, TPI/m, Tyrosinase, TARP, TRP-1 (gp75), TRP-2, TRP-2/INT2, WT-1, and alternatively translated NY-ESO-ORF2 and CAMEL proteins, derived from the NY-ESO-1 and LAGE-1 genes.

In some embodiments, the antigen encoded by the polynucleotide in the recombinant nucleic acid molecule, expression cassette, and/or vector may encompass any tumor-associated antigen that can elicit a tumor-specific immune response, including antigens yet to be identified. In some embodiments, the polynucleotide in the recombinant nucleic acid molecule, expression cassette, and/or vector encodes more than one tumor-associated antigen.

In some embodiments, the antigen is mesothelin (Argani et al., *Clin Cancer Res.* 7(12):3862-8 (2001)), Sp17 (Lim et al., *Blood* 97(5):1508-10 (2001)), gp100 (Kawakami et al., *Proc. Natl. Acad. Sci. USA* 91:6458 (1994)), PAGE-4 (Brinkmann et al., *Cancer Res.* 59(7):1445-8 (1999)), TARP (Wolfgang et al., *Proc. Natl. Acad. Sci. USA* 97(17):9437-42 (2000)), EphA2 (Tatsumi et al., *Cancer Res.* 63(15):4481-9 (2003)), PR3 (Muller-Berat et al., Clin. Immunol. Immunopath. 70(1): 51-9 (1994)), prostate stem cell antigen (PSCA) (Reiter et al., Proc. Natl. Acad. Sci., 95:1735-40 (1998); Kiessling et al., Int. J. Cancer, 102:390-7 (2002)), or SPAS-1 (U.S. patent application Publication No. 2002/0150588).

In some embodiments of the invention, the antigen encoded by the recombinant nucleic acid molecule or expression cassette is CEA. In other embodiments, the antigen is an antigenic fragment and/or antigenic variant of CEA. CEA is a 180-kDA membrane intercellular adhesion glycoprotein that is over-expressed in a significant proportion of human tumors, including 90% of colorectal, gastric, and pancreatic, 70% of non-small cell lung cancer, and 50% of breast cancer (Hammarstrom, *Semin. Cancer Biol.*, 9:67-81). A variety of immunotherapeutics such as anti-idiotype monoclonal antibody mimicking CEA (Foon et al., *Clin. Cancer Res.*, 87:982-90 (1995), or vaccination using a recombinant vaccinia virus expressing CEA (Tsang et al., *J. Natl. Cancer Inst.*, 87:982-90 (1995)) have been investigated, unfortunately, however, with limited success. Nonetheless, investigators have identified a HLA*0201-restricted epitope, CAP-1(CEA605-613), that is recognized by human T cell lines that were generated from vaccinated patients. Vaccination of patients with DC pulsed with this epitope failed to induce clinical responses (Morse et al., *Clin. Cancer Res.*, 5:1331-8 (1999)). Recently, a CEA605-613 peptide agonist was identified with a heteroclitic aspartate to asparagine substitution at position 610 (CAP1-6D). Although this amino acid substitution did not alter MHC binding affinity of this peptide, the use of the altered peptide ligand (APL) resulted in improved generation of CEA-specific cytotoxic T lymphocytes (CTL) in vitro. CAP1-6D-specific CTL maintained their ability to recognize and lyse tumor cells expressing native CEA (Zaremba et al., *Cancer Res.*, 57: 4570-7 (1997); Salazar et al., *Int. J. Cancer,* 85:829-38 (2000)). Fong et al. demonstrated induction of CEA-specific immunity in patients with colon cancer vaccinated with Flt3-ligand expanded DC incubated with this APL. Encouragingly, 2 of 12 patients after vaccination experienced dramatic tumor regressions that correlated with the induction of peptide-MHC tetramer$^+$ T cells (Fong et al., *Proc. Natl. Acad. Sci. U.S.A.*, 98:8809-14 (2001)).

In another embodiment, the antigen is proteinase-3 or is derived from proteinase-3. For instance, in one embodiment, the antigen comprises the HLA-A2.1-restricted peptide PR1 (aa 169-177; VLQELNVTV (SEQ ID NO:63)). Information on proteinase-3 and/or the PR1 epitope is available in the following references: U.S. Pat. No. 5,180,819, Molldrem, et al., *Blood,* 90:2529-2534 (1997); Molldrem et al., *Cancer Research,* 59:2675-2681 (1999); Molldrem, et al., *Nature Medicine,* 6:1018-1023 (2000); and Molldrem et al., *Oncogene,* 21: 8668-8673 (2002).

In some embodiments, the polypeptide encoded by a polynucleotide in the recombinant nucleic acid molecule, expression cassette, and/or vector comprises an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA, or comprises an antigen derived from an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, and CEA.

In some embodiments, the polypeptide encoded by a polynucleotide in the recombinant nucleic acid molecule, expression cassette, and/or vector comprises an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. In some embodiments, the polypeptide comprises K-Ras. In some embodiments, the polypeptide comprises H-Ras. In some embodiments, the polypeptide comprises N-Ras. In some embodiments, the polypeptide comprises K-Ras. In some embodiments, the polypeptide comprises mesothelin (e.g., human mesothelin). In some embodiments, the polypeptide comprises PSCA. In some embodiments, the polypeptide comprises NY-ESO-1. In some embodiments, the polypeptide comprises WT-1. In some embodiments, the polypeptide comprises survivin. In some embodiments, the polypeptide comprises gp100. In some embodiments, the polypeptide comprises PAP. In some embodiments, the polypeptide comprises proteinase 3. In some embodiments, the polypeptide comprises SPAS-1. In some embodiments, the polypeptide comprises SP-17. In some embodiments, the polypeptide comprises PAGE-4. In some embodiments, the polypeptide comprises TARP. In some embodiments, the polypeptide comprises CEA.

In some embodiments, the antigen encoded by a polynucleotide in the recombinant nucleic acid molecule, expression cassette, and/or vector is an antigen selected from the group consisting of K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. In some embodiments, the antigen is K-Ras. In some embodiments, the antigen is H-Ras. In some embodiments, the antigen is N-Ras. In some embodiments, the antigen is K-Ras. In some embodiments, the antigen is mesothelin. In some embodiments, the antigen is PSCA. In some embodiments, the antigen is NY-ESO-1. In some embodiments, the antigen is WT-1. In some embodiments, the antigen is survivin. In some embodiments, the antigen is gp100. In some embodiments, the antigen is PAP. In some embodiments, the antigen is proteinase 3. In some embodiments, the antigen is SPAS-1. In some embodiments, the antigen is SP-17. In some embodiments, the antigen is PAGE-4. In some embodiments, the antigen is TARP. In some embodiments, the antigen is CEA. In some embodiments, the antigen is human mesothelin.

In some embodiments, the antigen is mesothelin, SPAS-1, proteinase-3, EphA2, SP-17, gp100, PAGE-4, TARP, or CEA, or an antigen derived from one of those proteins. In some embodiments the antigen is mesothelin or is derived from mesothelin. In other embodiments, the antigen is EphA2 or is an antigen derived from EphA2. In some embodiments, the antigen encoded by a polynucleotide in a recombinant nucleic acid molecule, expression cassette, or expression vector described herein is not Epha2 (or an antigen derived from Epha2). In some embodiments, the antigen is a tumor-associated antigen other than Epha2. In some embodiments, the antigen is derived from a tumor-associated antigen other than Epha2. In some embodiments, the polypeptide encoded by a polynucleotide in the recombinant nucleic acid molecule, expression cassette, and/or expression vector comprises an antigen other than Epha2. In some embodiments, the polypeptide encoded by a polynucleotide in the recombinant nucleic acid molecule, expression cassette, and/or expression vector comprises an antigen other than Epha2 or an antigen derived from Epha2.

In some embodiments, a polynucleotide in the recombinant nucleic acid molecule, expression cassette, and/or expression vector encodes a polypeptide comprising an antigen derived from K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. In some embodiments, the polypeptide comprises an antigen derived from K-Ras. In some embodiments, the polypeptide comprises an antigen derived from H-Ras. In some embodiments, the polypeptide comprises an antigen derived from N-Ras. In some embodiments, the polypeptide comprises an antigen derived from 12-K-Ras. In some embodiments, the polypeptide comprises an antigen derived from mesothelin. In some embodiments, the polypeptide comprises an antigen derived from PSCA. In some embodiments, the polypeptide comprises an antigen derived from NY-ESO-1. In some embodiments, the polypeptide comprises an antigen derived from WT-1. In some embodiments, the polypeptide comprises an antigen derived from survivin. In some embodiments, the polypeptide comprises an antigen derived from gp100. In some embodiments, the polypeptide comprises an antigen derived from PAP. In some embodiments, the polypeptide comprises an antigen derived from proteinase 3. In some embodiments, the polypeptide comprises an antigen derived from SPAS-1. In some embodiments, the polypeptide comprises an antigen derived from SP-17. In some embodiments, the polypeptide comprises an antigen derived from PAGE-4. In some embodiments, the polypeptide comprises an antigen derived from TARP. In some embodiments, the polypeptide comprises an antigen derived from CEA.

In some embodiments, a polynucleotide in the recombinant nucleic acid molecule, expression cassette, and/or expression vector encodes an antigen derived from K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. In some embodiments, the antigen is derived from K-Ras. In some embodiments, the antigen is derived from H-Ras. In some embodiments, the antigen is derived from N-Ras. In some embodiments, the antigen is derived from 12-K-Ras. In some embodiments, the antigen is an antigen derived from mesothelin. In some embodiments, the antigen is an antigen derived from PSCA. In some embodiments, the antigen is an antigen derived from NY-ESO-1. In some embodiments, the antigen is an antigen derived from WT-1. In some embodiments, the antigen is an antigen derived from survivin. In some embodiments, the antigen is an antigen that is derived from gp100. In some embodiments, the antigen is an antigen that is derived from PAP. In some embodiments, the antigen is an antigen that is derived from proteinase 3. In some embodiments, the antigen is an antigen derived from SPAS-1. In some embodiments, the antigen is an antigen derived from SP-17. In some embodiments, the antigen is an antigen derived from PAGE-4. In some embodiments, the antigen is an antigen derived from TARP. In some embodiments, the antigen is an antigen derived from CEA.

In some embodiments, the antigen is mesothelin, or an antigenic fragment or antigenic variant thereof. Thus, in some embodiments, the polypeptide encoded by a polynucleotide in the recombinant nucleic acid molecule, expression cassette and/or vector comprises mesothelin, or an antigenic fragment or antigenic variant thereof. In some embodiments, the polypeptide encoded by the polynucleotide is mesothelin, or an antigenic fragment or antigenic variant thereof.

In some embodiments, the antigen is mesothelin (e.g., human mesothelin) in which the mesothelin signal peptide and/or GPI (glycosylphosphatidylinositol) anchor has been deleted. Accordingly, in some embodiments, the polypeptide encoded by the polynucleotide comprises mesothelin in which the mesothelin signal peptide and/or GPI anchor has been deleted. In some embodiments, the polypeptide encoded by the polynucleotide is mesothelin in which the mesothelin signal peptide and/or GPI anchor has been deleted. In some embodiments, the polypeptide encoded by the polynucleotide is human mesothelin in which the mesothelin signal peptide and/or GPI anchor has been deleted. In some embodiments, the polypeptide encoded by the polynucleotide is human mesothelin in which both the mesothelin signal peptide and GPI anchor have been deleted.

In some embodiments, the antigen is NY-ESO-1, or an antigenic fragment or antigenic variant thereof. Thus, in some embodiments, the polypeptide encoded by a polynucleotide in the recombinant nucleic acid molecule, expression cassette, or vector comprises an antigen which is NY-ESO-1, or an antigenic fragment or antigenic variant thereof. In some embodiments, the polypeptide is an antigen which is NY-ESO-1, or an antigenic fragment or antigenic variant thereof.

In some embodiments, a polypeptide encoded by polynucleotide in a recombinant nucleic acid molecule, expression cassette, or vector comprises at least one antigenic fragment of a tumor-associated antigen, e.g., human prostate stem cell antigen (PSCA; GenBank Acc. No. AF043498), human testes antigen (NY-ESO-1; GenBank Acc. No. NM_001327), human carcinoembryonic antigen (CEA; GenBank Acc. No. M29540), human Mesothelin (GenBank Acc. No. U40434), human survivin (GenBank Acc. No. U75285), human Proteinase 3 (GenBank No. X55668), human K-Ras (GenBank Acc. Nos. M54969 & P01116), human H-Ras (GenBank Acc. No. P01112), human N-Ras (GenBank Acc. No. P01111), and human 12-K-Ras (K-Ras comprising a Gly12Asp mutation) (see, e.g., GenBank Acc. No. K00654). In some embodiments, a polypeptide encoded by polynucleotide in a recombinant nucleic acid molecule, expression cassette, or expression vector comprises an antigenic fragment of a tumor-associated antigen with at least one conservatively substituted amino acid. In some embodiments, a polypeptide encoded by polynucleotide in a recombinant nucleic acid molecule, expression cassette, or expression vector comprises an antigenic fragment with at least one deleted amino acid residue. In some embodiments, a polypeptide encoded by polynucleotide in a recombinant nucleic acid molecule, expression cassette, or expression vector comprises combinations of antigenic sequences derived from more than one type of tumor-associated antigen, e.g., a combination of antigenic fragments derived from both mesothelin and Ras.

Exemplary regions of tumor antigens predicted to be antigenic include the following: amino acids 25-35; 70-80; and 90-118 of the PSCA amino acid sequence in GenBank Acc. No. AF043498; amino acids 40-55, 75-85, 100-115, and 128-146 of the NY-ESO-1 of GenBank Acc. No. NM_001327; amino acids 70-75, 150-155, 205-225, 330-340, and 510-520 of the CEA amino acid sequence of GenBank Acc. No. M29540; amino acids 90-110, 140-150, 205-225, 280-310, 390-410, 420-425, and 550-575; of the mesothelin polypeptide sequence of GenBank Acc. No. U40434; amino acids 12-20, 30-40, 45-55, 65-82, 90-95, 102-115, and 115-130 of the surviving polypeptide sequence of GenBank Acc. No. U75285; amino acids 10-20, 30-35, 65-75, 110-120, and 160-170, of the amino acid sequence of proteinase-3 found in GenBank Acc. No. X55668; amino acids 10-20, 30-50, 55-75, 85-110, 115-135, 145-155, and 160-185 of GenBank Acc. Nos. P01117 or M54968 (human K-Ras); amino acids 10-20, 25-30, 35-45, 50-70, 90-110, 115-135, and 145-175 of GenBank Acc. No. P01112 (human H-Ras); amino acids 10-20, 25-45, 50-75, 85-110, 115-135, 140-155, and 160-180 of GenBank Acc. No. P01111 (human N-Ras); and the first 25-amino acids of 12-K-Ras (sequence disclosed in GenBank Acc. No. K00654). These antigenic regions were predicted by Hopp-Woods and Welling antigenicity plots.

In some embodiments, the polypeptides encoded by the polynucleotides of the invention either as discrete polypeptides, as fusion proteins with the chosen signal peptide, or as a protein chimera in which the polypeptide has been inserted in another polypeptide, are polypeptides comprising one or more of the following peptides of human mesothelin: SLL-FLLFSL (amino acids 20-28; (SEQ ID NO:64)); VLPLT-VAEV (amino acids 530-538; (SEQ ID NO:65)); ELAVA-LAQK (amino acids 83-92; (SEQ ID NO:66)); ALQGGGPPY (amino acids 225-234; (SEQ ID NO:67)); FYPGYLCSL (amino acids 435-444; (SEQ ID NO:68)); and LYPKARLAF (amino acids 475-484; (SEQ ID NO:69)). For instance, in some embodiments, the antigen encoded by a polynucleotide of the invention is an (antigenic) fragment of human mesothelin comprising one or more of these peptides. Additional information regarding these mesothelin peptide sequences and their correlation with medically relevant immune responses can be found in the PCT Publication WO 2004/006837.

Alternatively, polynucleotides in the recombinant nucleic acid molecule, expression cassette, or expression vector can encode an autoimmune disease-specific antigen (or a polypeptide comprising an autoimmune disease-specific antigen). In a T cell mediated autoimmune disease, a T cell response to self antigens results in the autoimmune disease. The type of antigen for use in treating an autoimmune disease with the vaccines of the present invention might target the specific T cells responsible for the autoimmune response. For example, the antigen may be part of a T cell receptor, the idiotype, specific to those T cells causing an autoimmune response, wherein the antigen incorporated into a vaccine of the invention would elicit an immune response specific to those T cells causing the autoimmune response. Eliminating those T cells would be the therapeutic mechanism to alleviating the autoimmune disease. Another possibility would be to incorporate into the recombinant nucleic acid molecule a polynucleotide encoding an antigen that will result in an immune response targeting the antibodies that are generated to self antigens in an autoimmune disease or targeting the specific B cell clones that secrete the antibodies. For example, a polynucleotide encoding an idiotype antigen may be incorporated into the recombinant nucleic acid molecule that will result in an anti-idiotype immune response to such B cells and/or the antibodies reacting with self antigens in an autoimmune disease. Autoimmune diseases treatable with vaccines comprising bacteria comprising the expression cassettes and recombinant nucleic acid molecules of the present invention include, but are not limited to, rheumatoid arthritis, multiple sclerosis, Crohn's disease, lupus, myasthenia gravis, vitiligo, scleroderma, psoriasis, pemphigus vulgaris, fibromyalgia, colitis and diabetes. A similar approach may be taken for treating allergic responses, where the antigens incorporated into the vaccine bacterium target either T cells, B cells or antibodies that are effective in modulating the allergic reaction. In some autoimmune diseases, such as psoriasis, the disease results in hyperproliferative cell growth with expression of antigens that may be targeted as well. Such an antigen that will result in an immune response to the hyperproliferative cells is considered.

In some embodiments, the antigen is an antigen that targets unique disease associated protein structures. One example of this is the targeting of antibodies, B cells or T cells using idiotype antigens as discussed above. Another possibility is to target unique protein structures resulting from a particular disease. An example of this would be to incorporate an antigen that will generate an immune response to proteins that cause the amyloid plaques observed in diseases such as Alzheimer's disease, Creutzfeldt-Jakob disease (CJD) and Bovine Spongiform Encephalopathy (BSE). While this approach may only provide for a reduction in plaque formation, it may be possible to provide a curative vaccine in the case of diseases like CJD. This disease is caused by an infectious form of a prion protein. In some embodiments, the polynucleotides of the invention encode an antigen to the infectious form of the prion protein such that the immune response generated by the vaccine may eliminate, reduce, or control the infectious proteins that cause CJD.

In some embodiments, the polypeptide encoded by a polynucleotide of the recombinant nucleic acid molecule, expression cassette, and/or expression vector comprises an infectious disease antigen or an antigen derived from an infectious disease antigen. In some embodiments, the polypeptide comprises an infectious disease antigen. In some other embodiments, the polypeptide comprises an antigen derived from an infectious disease antigen. In some embodiments, the polypeptide encoded by a polynucleotide of the recombinant nucleic acid molecule, expression cassette, and/or expression vector is an infectious disease antigen or is an antigen derived from an infectious disease antigen. In some embodiments, the polypeptide encoded by the recombinant nucleic acid molecule, expression cassette, and/or expression vector is an infectious disease antigen. In some embodiments, the polypeptide encoded by the recombinant nucleic acid molecule, expression cassette, and/or expression vector is derived from an infectious disease antigen.

In other embodiments of the invention, the antigen is derived from a human or animal pathogen. The pathogen is optionally a virus, bacterium, fungus, or a protozoan. For instance, the antigen may be a viral or fungal or bacterial antigen. In one embodiment, the antigen encoded by the recombinant nucleic acid molecule, expression cassette, and/or expression vector that is derived from the pathogen is a protein produced by the pathogen, or is derived from a protein produced by the pathogen. For instance, in some embodiments, the polypeptide encoded by the recombinant nucleic acid molecules, expression cassette and/or expression vector is a fragment and/or variant of a protein produced by the pathogen.

For instance, in some embodiments, the antigen is derived from Human Immunodeficiency virus (such as gp 120, gp 160, gp41, gag antigens such as p24gag and p55gag, as well as proteins derived from the pol, env, tat, vif, rev, nef, vpr, vpu and LTR regions of HIV), Feline Immunodeficiency virus, or human or animal herpes viruses. For example, in some embodiments, the antigen is gp 120. In one embodiment, the antigen is derived from herpes simplex virus (HSV) types 1 and 2 (such as gD, gB, gH, Immediate Early protein such as ICP27), from cytomegalovirus (such as gB and gH), from metapneumovirus, from Epstein-Barr virus or from Varicella Zoster Virus (such as gpI, II or III). (See, e. g., Chee et al. (1990) *Cytomegaloviruses* (J. K. McDougall, ed., Springer Verlag, pp. 125-169; McGeoch et al. (1988) J. Gen. Virol. 69: 1531-1574; U.S. Pat. No. 5,171,568; Baer et al. (1984) *Nature* 310: 207-211; and Davison et al. (1986) *J. Gen. Virol.* 67: 1759-1816.)

In another embodiment, the antigen is derived from a hepatitis virus such as hepatitis B virus (for example, Hepatitis B Surface antigen), hepatitis A virus, hepatitis C virus, delta hepatitis virus, hepatitis E virus, or hepatitis G virus. See, e. g., WO 89/04669; WO 90/11089; and WO 90/14436. The hepatitis antigen can be a surface, core, or other associated antigen. The HCV genome encodes several viral proteins, including E1 and E2. See, e. g., Houghton et al., *Hepatology* 14: 381-388 (1991).

An antigen that is a viral antigen is optionally derived from a virus from any one of the families Picornaviridae (e. g., polioviruses, rhinoviruses, etc.); Caliciviridae; Togaviridae (e. g., rubella virus, dengue virus, etc.); Flaviviridae; Coronaviridae; Reoviridae (e. g., rotavirus, etc.); Birnaviridae; Rhabodoviridae (e. g., rabies virus, etc.); Orthomyxoviridae (e. g., influenza virus types A, B and C, etc.); Filoviridae; Paramyxoviridae (e. g., mumps virus, measles virus, respiratory syncytial virus, parainfluenza virus, etc.); Bunyaviridae; Arenaviridae; Retroviradae (e. g., HTLV-I; HTLV-11; HIV-1 (also known as HTLV-111, LAV, ARV, hTLR, etc.)), including but not limited to antigens from the isolates HIVI11b, HIVSF2, HTVLAV, HIVLAI, HIVMN); HIV-1CM235, HIV-1; HIV-2, among others; simian immunodeficiency virus (SIV)); Papillomavirus, the tick-borne encephalitis viruses; and the like. See, e. g. *Virology,* 3rd Edition (W. K. Joklik ed. 1988); *Fundamental Virology,* 3rd Edition (B. N. Fields, D. M. Knipe, and P. M. Howley, Eds. 1996), for a description of these and other viruses. In one embodiment, the antigen is Flu-HA (Morgan et al., J. Immunol. 160:643 (1998)).

In some alternative embodiments, the antigen is derived from bacterial pathogens such as *Mycobacterium, Bacillus, Yersinia, Salmonella, Neisseria, Borrelia* (for example, OspA or OspB or derivatives thereof), Chlamydia, or Bordetella (for example, P.69, PT and FHA), or derived from parasites such as plasmodium or Toxoplasma. In one embodiment, the antigen is derived from *Mycobacterium tuberculosis* (e.g. ESAT-6, 85A, 85B, 85C, 72F), *Bacillus anthracis* (e.g. PA), or *Yersinia pestis* (e.g. F1, V). In addition, antigens suitable for use in the present invention can be obtained or derived from known causative agents responsible for diseases including, but not limited to, Diptheria, Pertussis, Tetanus, Tuberculosis, Bacterial or Fungal Pneumonia, Otitis Media, Gonorrhea, Cholera, Typhoid, Meningitis, Mononucleosis, Plague, Shigellosis or Salmonellosis, Legionaire's Disease, Lyme Disease, Leprosy, Malaria, Hookworm, Onchocerciasis, Schistosomiasis, Trypanosomiasis, Leishmaniasis, Giardia, Amoebiasis, Filariasis, Borelia, and Trichinosis. Still further antigens can be obtained or derived from unconventional pathogens such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

In still other embodiments, the antigen is obtained or derived from a biological agent involved in the onset or progression of neurodegenerative diseases (such as Alzheimer's disease), metabolic diseases (such as Type I diabetes), and drug addictions (such as nicotine addiction). Alternatively, the antigen encoded by the recombinant nucleic acid molecule is used for pain management and the antigen is a pain receptor or other agent involved in the transmission of pain signals.

In some embodiments, the antigen is a human protein or is derived from a human protein. In other embodiments, the antigen is a non-human protein or is derived from a non-human protein (a fragment and/or variant thereof). In some embodiments, the antigen portion of the fusion protein encoded by the expression cassette is a protein from a non-human animal or is a protein derived from a non-human animal. For instance, even if the antigen is to be expressed in a *Listeria*-based vaccine that is to be used in humans, in some embodiments, the antigen can be murine mesothelin or derived from murine mesothelin.

V. Codon-Optimization

In some embodiments, one or more of the polynucleotides (i.e., polynucleotide sequences) within the recombinant nucleic acid molecule, expression cassette and/or expression vector are codon-optimized (relative to the native coding sequence). In some embodiments, a polynucleotide in the recombinant nucleic acid molecules (and/or in the expression cassette and/or expression vector) described herein that encodes a signal peptide is codon-optimized for expression in a bacterium. In some embodiments, a polynucleotide encoding a polypeptide other than a signal peptide, such as an antigen or other therapeutic protein, is codon-optimized for expression in a bacterium. In some embodiments, both a polynucleotide encoding a signal peptide and a polynucleotide encoding another polypeptide fused to the signal peptide are codon-optimized for expression in a bacterium. In some embodiments, a polynucleotide encoding a secreted protein (or fragment thereof) used as a scaffold or a polynucleotide encoding an autolysin (or fragment or variant thereof) is codon-optimized.

A polynucleotide comprising a coding sequence is "codon-optimized" if at least one codon of the native coding sequence of the polynucleotide has been replaced with a codon that is more frequently used by the organism in which the coding sequence is to be expressed (the "target organism") than the original codon of the native coding sequence. For instance, a polynucleotide encoding a non-bacterial antigen that is to be expressed in a particular species of bacteria is codon-optimized if at least one of the codons from the native bacterial polynucleotide sequence is replaced with a codon that is preferentially expressed in that particular species of bacteria in which the non-bacterial antigen is to be expressed. As another example, a polynucleotide encoding a human cancer antigen that is to be part of an expression cassette in recombinant *Listeria monocytogenes* is codon-optimized if at least one codon in the polynucleotide sequence is replaced with a codon that is more frequently used by *Listeria monocytogenes* for that amino acid than the codon in the original human sequence would be. Likewise, a polynucleotide encoding a signal peptide native to *Listeria monocytogenes* (such as the LLO signal peptide from *L. monocytogenes*) that is to be part of an expression cassette to encode a fusion protein comprising a human cancer antigen in recombinant *Listeria monocytogenes* is codon-optimized if at least one codon in the polynucleotide sequence encoding the signal peptide is replaced with a codon that is more frequently used by *Listeria monocytogenes* for that amino acid than the codon in the original (native) sequence is. In some embodiments, at least one codon that is replaced in the codon-optimized sequence is replaced with the codon most frequently used by the target organism to code for the same amino acid.

In some embodiments, at least two codons of the native coding sequence of the polynucleotide have been replaced with a codon that is more frequently used by the organism in which the coding sequence is to be expressed than the original codon of the native coding sequence. In some embodiments, at least about five codons, at least about 10 codons, or at least about 20 codons of the native coding sequence of the polynucleotide have been replaced with a codon that is more frequently used by the organism in which the coding sequence is to be expressed than the original codon of the native coding sequence.

In some embodiments, at least about 10% of the codons in the codon-optimized polynucleotide have been replaced with codons more frequently (or most frequently) used by the target organism (than the original codons of the native sequence). In other embodiments, at least about 25% of the codons in the codon-optimized polynucleotide have been replaced with codons more frequently used (or most frequently) used by the target organism. In other embodiments, at least about 50% of the codons in the codon-optimized polynucleotide have been replaced with codons more frequently used (or most frequently) used by the target organism. In still other embodiments, at least about 75% of the codons in the codon-optimized polynucleotide have been replaced with codons more frequently used (or most frequently used) by the target organism.

The codon preferences of different organisms have been widely studied by those skilled in the art. For instance, see Sharp et al., *Nucleic Acids Res.*, 15:1281-95 (1987) and Uchijima et al., *The Journal of Immunology*, 161:5594-9 (1998). As a result, codon usage tables are publicly available for a wide variety of organisms. For instance, codon usage tables can be found as described in Nakamura et al. (2000) *Nucleic Acids Research* 28:292. An exemplary codon usage table for *Listeria monocytogenes* is reproduced for convenience below in Table 2A. Exemplary codon usage tables for *Bacillus anthracis, Mycobacterium tuberculosis, Salmonella typhimurium, Mycobacterium bovis* BCG, and *Shigella flexneri* are also provided in Tables 2B, 2C, 2D, 2E, and 2F, respectively, below.

TABLE 2A

Codon Usage Table for *Listeria monocytogenes*.
*Listeria monocytogenes*: 3262 CDS's (1029006 codons)
fields: [triplet] [frequency: per thousand] ([number])

| | | | |
|---|---|---|---|
| UUU 29.4(30274) | UCU 13.2(13586) | UAU 22.9(23604) | UGU 3.8(3960) |
| UUC 14.1(14486) | UCC 6.5(6714) | UAC 10.7(11055) | UGC 1.9(1972) |
| UUA 36.8(37821) | UCA 10.4(10751) | UAA 2.2(2307) | UGA 0.6(583) |
| UUG 12.3(12704) | UCG 6.1(6278) | UAG 0.4(372) | UGG 9.3(9580) |
| CUU 21.0(21567) | CCU 8.4(8622) | CAU 12.0(12332) | CGU 12.6(12930) |
| CUC 5.4(5598) | CCC 1.7(1780) | CAC 5.2(5336) | CGC 7.0(7215) |
| CUA 12.9(13279) | CCA 18.5(18996) | CAA 29.9(30719) | CGA 5.6(5732) |
| CUG 5.0(5120) | CCG 7.0(7219) | CAG 5.1(5234) | CGG 2.8(2884) |
| AUU 49.3(50692) | ACU 17.1(17614) | AAU 33.0(33908) | AGU 14.1(14534) |

TABLE 2A-continued

Codon Usage Table for *Listeria monocytogenes*.
*Listeria monocytogenes*: 3262 CDS's (1029006 codons)
fields: [triplet] [frequency: per thousand] ([number])

| | | | |
|---|---|---|---|
| AUC 18.4(18894) | ACC 6.9(7089) | AAC 15.3(15790) | AGC 8.8(9031) |
| AUA 9.4(9642) | ACA 26.5(27318) | AAA 61.6(63379) | AGA 6.9(7111) |
| AUG 25.9(26651) | ACG 12.9(13285) | AAG 10.4(10734) | AGG 1.2(1254) |
| GUU 26.4(27202) | GCU 24.3(24978) | GAU 39.8(40953) | GGU 24.2(24871) |
| GUC 8.7(8990) | GCC 8.4(8612) | GAC 14.3(14751) | GGC 14.2(14581) |
| GUA 21.6(22247) | GCA 28.6(29401) | GAA 60.4(62167) | GGA 19.1(19612) |
| GUG 13.1(13518) | GCG 16.6(17077) | GAG 13.1(13507) | GGG 8.7(9003) |

TABLE 2B

Codon Usage Table for *Bacillus anthracis*.
*Bacillus anthracis* [gbbct]: 312 CDS's (90023 codons)
fields: [triplet] [frequency: per thousand] ([number])

| | | | |
|---|---|---|---|
| UUU 32.4(2916) | UCU 17.2(1547) | UAU 31.9(2876) | UGU 5.1(455) |
| UUC 10.4(934) | UCC 5.0(453) | UAC 9.5(853) | UGC 1.8(164) |
| UUA 43.7(3931) | UCA 14.8(1330) | UAA 2.2(199) | UGA 0.5(47) |
| UUG 11.4(1024) | UCG 4.2(375) | UAG 0.7(66) | UGG 9.3(835) |
| CUU 14.4(1300) | CCU 10.7(967) | CAU 15.5(1392) | CGU 9.8(883) |
| CUC 3.7(335) | CCC 2.7(242) | CAC 4.2(379) | CGC 2.5(223) |
| CUA 12.4(1117) | CCA 17.8(1599) | CAA 32.3(2912) | CGA 6.3(569) |
| CUG 4.4(392) | CCG 5.9(534) | CAG 9.5(859) | CGG 2.0(179) |
| AUU 44.5(4009) | ACU 21.0(1890) | AAU 44.0(3959) | AGU 17.4(1565) |
| AUC 11.9(1072) | ACC 5.0(453) | AAC 14.1(1268) | AGC 5.2(467) |
| AUA 22.7(2042) | ACA 26.8(2414) | AAA 64.3(5786) | AGA 13.7(1236) |
| AUG 23.3(2098) | ACG 9.4(844) | AAG 22.7(2047) | AGG 4.1(368) |
| GUU 20.3(1824) | GCU 17.8(1598) | GAU 39.3(3536) | GGU 17.9(1611) |
| GUC 4.6(414) | GCC 4.1(372) | GAC 9.0(811) | GGC 5.8(524) |
| GUA 26.4(2374) | GCA 23.5(2117) | GAA 53.9(4855) | GGA 24.5(2203) |
| GUG 10.8(973) | GCG 7.9(709) | GAG 17.9(1614) | GGG 12.0(1083) |

Coding GC 34.55% 1st letter GC 44.99% 2nd letter GC 33.16% 3rd letter GC 25.51%

TABLE 2C

Codon Usage Table for *Mycobacterium tuberculosis*.
*Mycobacterium tuberculosis* [gbbct]: 363 CDS's (131426 codons)
fields: [triplet] [frequency: per thousand] ([number])

| | | | |
|---|---|---|---|
| UUU 5.4(709) | UCU 2.0(265) | UAU 6.0(788) | UGU 2.5(326) |
| UUC 25.6(3359) | UCC 11.4(1499) | UAC 17.6(2307) | UGC 5.6(738) |
| UUA 1.8(231) | UCA 4.3(571) | UAA 0.4(52) | UGA 1.5(201) |
| UUG 14.8(1945) | UCG 19.2(2522) | UAG 0.8(103) | UGG 17.9(2352) |
| CUU 5.9(778) | CCU 3.9(511) | CAU 5.4(711) | CGU 8.0(1048) |
| CUC 17.7(2329) | CCC 18.3(2411) | CAC 14.7(1928) | CGC 26.7(3508) |
| CUA 4.0(521) | CCA 6.4(843) | CAA 7.8(1030) | CGA 5.8(764) |
| CUG 45.9(6032) | CCG 33.2(4359) | CAG 24.2(3176) | CGG 21.1(2772) |
| AUU 7.6(993) | ACU 4.1(545) | AAU 4.8(637) | AGU 4.0(531) |
| AUC 32.7(4300) | ACC 36.0(4735) | AAC 26.3(3451) | AGC 15.0(1976) |
| AUA 2.1(282) | ACA 4.7(616) | AAA 5.8(761) | AGA 1.5(192) |
| AUG 19.7(2591) | ACG 16.4(2158) | AAG 26.5(3485) | AGG 3.3(429) |
| GUU 8.3(1095) | GCU 11.2(1473) | GAU 15.6(2046) | GGU 18.7(2455) |
| GUC 32.3(4249) | GCC 51.5(6769) | GAC 44.6(5858) | GGC 48.6(6383) |
| GUA 4.7(622) | GCA 12.4(1625) | GAA 16.8(2211) | GGA 9.0(1183) |
| GUG 35.7(4687) | GCG 41.7(5482) | GAG 35.8(4702) | GGG 16.9(2215) |

Coding GC 64.43% 1st letter GC 65.27% 2nd letter GC 48.28% 3rd letter GC 79.75%

TABLE 2D

Codon Usage Table for *Salmonella typhimurium*.
*Salmonella typhimurium* [gbbct]: 1322 CDS's (416065 codons)
fields: [triplet] [frequency: per thousand] ([number])

| | | | |
|---|---|---|---|
| UUU 21.7(9041) | UCU 8.5(3518) | UAU 16.5(6853) | UGU 4.6(1920) |
| UUC 15.1(6265) | UCC 10.6(4430) | UAC 11.6(4826) | UGC 6.1(2524) |
| UUA 13.6(5650) | UCA 7.9(3286) | UAA 1.8(731) | UGA 1.1(465) |
| UUG 12.1(5025) | UCG 9.4(3924) | UAG 0.3(121) | UGG 14.1(5851) |

TABLE 2D-continued

Codon Usage Table for *Salmonella typhimurium*.
*Salmonella typhimurium* [gbbct]: 1322 CDS's (416065 codons)
fields: [triplet] [frequency: per thousand] ([number])

| | | | |
|---|---|---|---|
| CUU 12.1(5038) | CCU 7.9(3290) | CAU 12.1(5047) | CGU 18.1(7542) |
| CUC 10.6(4396) | CCC 7.0(2921) | CAC 9.2(3818) | CGC 20.8(8659) |
| CUA 4.7(1958) | CCA 6.5(2712) | CAA 12.8(5315) | CGA 4.1(1695) |
| CUG 49.3(20508) | CCG 22.7(9463) | CAG 30.8(12803) | CGG 7.2(3004) |
| AUU 28.1(11700) | ACU 8.2(3401) | AAU 19.5(8107) | AGU 8.6(3569) |
| AUC 23.9(9941) | ACC 24.0(9980) | AAC 21.4(8920) | AGC 18.0(7485) |
| AUA 6.7(2771) | ACA 8.0(3316) | AAA 33.0(13740) | AGA 3.2(1348) |
| AUG 26.1(10842) | ACG 18.6(7743) | AAG 12.4(5151) | AGG 2.3(959) |
| GUU 16.4(6831) | GCU 14.4(5985) | GAU 32.9(13700) | GGU 18.1(7541) |
| GUC 17.7(7367) | GCC 27.5(11462) | GAC 21.5(8949) | GGC 33.0(13730) |
| GUA 11.9(4935) | GCA 14.8(6156) | GAA 36.1(15021) | GGA 9.1(3788) |
| GUG 24.3(10092) | GCG 37.0(15387) | GAG 20.9(8715) | GGG 11.6(4834) |

Coding GC 52.45% 1st letter GC 58.32% 2nd letter GC 41.31% 3rd letter GC 57.71%

TABLE 2E

Codon Usage Table for *Mycobacterium bovis* BCG.
*Mycobacterium bovis* BCG [gbbct]: 51 CDS's (16528 codons)
fields: [triplet] [frequency: per thousand] ([number])

| | | | |
|---|---|---|---|
| UUU 4.7(77) | UCU 1.9(31) | UAU 6.6(109) | UGU 2.0(33) |
| UUC 27.4(453) | UCC 11.4(189) | UAC 17.0(281) | UGC 6.7(110) |
| UUA 1.6(26) | UCA 4.5(74) | UAA 0.9(15) | UGA 1.3(22) |
| UUG 14.7(243) | UCG 20.8(343) | UAG 0.8(14) | UGG 14.3(237) |
| CUU 5.6(92) | CCU 2.9(48) | CAU 4.9(81) | CGU 9.4(155) |
| CUC 14.8(244) | CCC 16.3(270) | CAC 17.2(285) | CGC 33.8(559) |
| CUA 5.1(85) | CCA 5.1(84) | CAA 7.3(120) | CGA 7.1(118) |
| CUG 51.5(852) | CCG 31.0(512) | CAG 25.5(421) | CGG 26.7(441) |
| AUU 6.1(100) | ACU 3.1(51) | AAU 4.8(80) | AGU 2.8(46) |
| AUC 39.6(654) | ACC 36.8(609) | AAC 22.3(369) | AGC 14.5(240) |
| AUA 2.2(37) | ACA 4.4(73) | AAA 6.2(102) | AGA 1.1(19) |
| AUG 20.2(334) | ACG 17.4(288) | AAG 24.5(405) | AGG 3.8(62) |
| GUU 7.8(129) | GCU 9.6(158) | GAU 13.4(222) | GGU 16.9(280) |
| GUC 30.1(497) | GCC 54.3(898) | GAC 45.6(754) | GGC 42.6(704) |
| GUA 4.1(67) | GCA 12.5(206) | GAA 16.5(273) | GGA 7.3(120) |
| GUG 37.6(621) | GCG 41.7(689) | GAG 32.7(541) | GGG 16.7(276) |

Coding GC 64.82% 1st letter GC 65.36% 2nd letter GC 48.07% 3rd letter GC 81.04%

TABLE 2F

Codon Usage Table for *Shigella flexneri*.
*Shigella flexneri* [gbbct]: 706 CDS's (180312 codons)
fields: [triplet] [frequency: per thousand] ([number])

| | | | |
|---|---|---|---|
| UUU 25.8(4658) | UCU 16.6(2986) | UAU 21.9(3945) | UGU 6.9(1252) |
| UUC 15.1(2714) | UCC 9.5(1717) | UAC 11.0(1992) | UGC 5.6(1011) |
| UUA 20.8(3756) | UCA 15.6(2821) | UAA 2.0(362) | UGA 1.4(254) |
| UUG 13.4(2424) | UCG 6.9(1241) | UAG 0.5(91) | UGG 13.1(2357) |
| CUU 17.6(3169) | CCU 9.2(1656) | CAU 15.1(2725) | CGU 15.0(2707) |
| GUC 10.4(1878) | CCC 5.9(1072) | CAC 8.2(1472) | CGC 12.6(2269) |
| CUA 7.2(1295) | CCA 9.7(1744) | CAA 15.9(2861) | CGA 5.8(1046) |
| CUG 33.5(6045) | CCG 12.2(2199) | CAG 23.6(4255) | CGG 9.0(1627) |
| AUU 30.0(5417) | ACU 13.8(2480) | AAU 33.5(6044) | AGU 15.3(2764) |
| AUC 16.7(3018) | ACC 13.4(2413) | AAC 18.6(3348) | AGC 12.7(2281) |
| AUA 18.9(3402) | ACA 16.2(2930) | AAA 41.6(7507) | AGA 10.3(1865) |
| AUG 23.3(4198) | ACG 10.0(1809) | AAG 16.4(2961) | AGG 5.7(1029) |
| GUU 19.8(3576) | GCU 19.6(3527) | GAU 34.0(6123) | GGU 19.2(3468) |
| GUC 11.8(2126) | GCC 18.5(3338) | GAC 16.3(2939) | GGC 15.3(2754) |
| GUA 13.1(2370) | GCA 22.2(4009) | GAA 37.5(6763) | GGA 15.1(2727) |
| GUG 16.1(2910) | GCG 15.2(2732) | GAG 21.7(3913) | GGG 10.9(1970) |

Coding GC 44.63% 1st letter GC 51.72% 2nd letter GC 38.85% 3rd letter GC 43.32%

In some embodiments of the invention, at least about 10%, at least about, 25%, at least about 50%, or at least about 75% of the codons in a codon-optimized coding sequence are the most preferred codon for that amino acid used in the target organism. In other embodiments, 100% of the codons in the codon-optimized coding sequence are the most preferred codon for that amino acid in the target organism (i.e., the sequence is "fully codon-optimized"). For instance, in the Examples shown below, all of the codons of the sequences characterized as codon-optimized were the most frequently used codons for the target organism; however, any codon substitution that results in a more frequently used codon than the original (native) sequence can be considered "codon-optimized". Table 3, below shows the optimal codon usage in *Listeria monocytogenes

TABLE 3

Optimal Codon Usage Table in *Listeria monocytogenes*.

| Amino Acid | One Letter Code | Optimal *Listeria* Codon |
| --- | --- | --- |
| Alanine | A | GCA |
| Arginine | R | CGU |
| Asparagine | N | AAU |
| Aspartate | D | GAU |
| Cysteine | C | UGU |
| Glutamine | Q | CAA |
| Glutamate | E | GAA |
| Glycine | G | GGU |
| Histidine | H | CAU |
| Isoleucine | I | AUU |
| Leucine | L | UUA |
| Lysine | K | AAA |
| Methionine | M | AUG |
| Phenylalanine | F | UUU |
| Proline | P | CCA |
| Serine | S | AGU |
| Threonine | T | ACA |
| Tryptophan | W | UGG |
| Tyrosine | Y | UAU |
| Valine | V | GUU |

In some embodiments, the codon-optimized polynucleotides encode a signal peptide. In some embodiments, the signal peptide is foreign to the bacterium for which the sequence is codon-optimized. In other embodiments, the signal peptide is native to the bacterium for which the sequence is codon-optimized. For instance, in some embodiments, the codon-optimized polynucleotide encodes a signal peptide selected from the group consisting of LLO signal peptide from *Listeria monocytogenes*, Usp45 signal peptide from *Lactococcus lactis*, Protective Antigen signal peptide from *Bacillus anthracis*, p60 signal peptide from *Listeria monocytogenes* and PhoD signal peptide from *B. subtilis* Tat signal peptide. In some embodiments, the codon-optimized polynucleotide encodes a signal peptide other than Protective Antigen signal peptide from *Bacillus anthracis*. In some embodiments, the polynucleotide encoding a signal peptide is codon-optimized for expression in *Listeria monocytogenes*.

In some embodiments, the codon-optimized polynucleotide encodes a (non-signal peptide) protein that is foreign to the bacterium for which the polynucleotide sequence has been codon-optimized. In some embodiments, the codon-optimized polynucleotide encodes a polypeptide comprising an antigen. For instance, in some embodiments, the codon-optimized polynucleotide encodes a polypeptide comprising an antigen that is a tumor-associated antigen or an antigen that is derived from a tumor-associated antigen.

In some embodiments, codon-optimization of a polynucleotide encoding a signal peptide and/or other polypeptide enhances expression of a polypeptide (such as a fusion protein, protein chimera and/or a foreign polypeptide encoded by a recombinant nucleic acid molecule, expression cassette, or expression vector) comprising the signal peptide and/or other polypeptide in a bacterium, relative to the corresponding polynucleotide without codon-optimization. In some embodiments, the codon-optimization of the polynucleotide enhances expression by at least about 2-fold, by at least about 5-fold, by at least about 10-fold, or by at least about 20 fold (relative to the corresponding polynucleotide without codon-optimization). In some embodiments, codon-optimization of a polynucleotide encoding a signal peptide and/or other polypeptide enhances secretion of a polypeptide (such as a fusion protein, protein chimera and/or a foreign polypeptide) comprising the signal peptide and/or other polypeptide from a bacterium, relative to the corresponding polynucleotide without codon-optimization. In some embodiments, the codon-optimization enhances secretion by at least about 2-fold, by at least about 5-fold, by at least about 10-fold, or by at least about 20 fold (relative to the corresponding polynucleotide without codon-optimization). In some embodiments, both the level of expression and secretion is enhanced. Levels of expression and/or secretion can be readily assessed using techniques standard to those in the art such as Western blots of the various relevant bacterial culture fractions.

VI. Expression Cassettes

Expression cassettes are also provided by the present invention. For instance, in some embodiments, the invention provides an expression cassette comprising any of the recombinant nucleic acid molecules described herein and further comprising promoter sequences operably linked to the coding sequences in the recombinant nucleic acid molecules (e.g., the first polynucleotide encoding a signal peptide and the second polynucleotide encoding the other polypeptide). In some embodiments, the expression cassette is isolated. In some other embodiments, the expression cassette is contained within an expression vector, which may be isolated or may be contained within a bacterium. In still further embodiments, the expression cassette is positioned in the chromosomal DNA of a bacterium. For instance, in some embodiments, the expression cassette has been integrated within the genome of a bacterium. In some embodiments, an expression cassette that is integrated within the genome of a bacterium comprises one or more elements from the genomic DNA. For instance, in some embodiments, a recombinant nucleic acid molecule is inserted in a site in the genomic DNA of a bacterium (e.g., via site-specific integration or homologous recombination) such that the recombinant nucleic acid is operably linked to a promoter already present in the genomic DNA, thereby generating a new expression cassette integrated within the genomic DNA. In some other embodiments, the expression cassette is integrated into the genomic DNA (e.g., via site-specific integration or homologous recombination) as an intact unit comprising both the promoter and the recombinant nucleic acid molecule.

In some embodiments, the expression cassettes are designed for expression of polypeptides in bacteria. In some embodiments, the expression cassettes are designed for the expression of heterologous polypeptides, such as heterologous antigens in bacteria. In some embodiments, the expression cassettes provide enhanced expression and/or secretion of the polypeptides.

Generally, an expression cassette comprises the following ordered elements: (1) a promoter and (2) a polynucleotide encoding a polypeptide. In some embodiments, an expression cassette comprises the following elements: (1) a promoter; (2) a polynucleotide encoding a signal peptide; and (3) a polynucleotide encoding a polypeptide (e.g., a heterologous protein). In still other embodiments, an expression cassette comprises the following elements: (1) prokaryotic promoter; (2) Shine-Dalgarno sequence; (3) a polynucleotide encoding a signal peptide; and, (4) a polynucleotide encoding a polypeptide (such as a heterologous protein). In some embodiments, an expression cassette comprises more than one promoter.

In some embodiments, the expression cassette may also contain a transcription termination sequence inserted downstream from the C-terminus of the translational stop codon related to the heterologous polypeptide. For instance, in some embodiments, a transcription termination sequence may be used in constructs designed for stable integration within the bacterial chromosome. While not required, inclusion of a transcription termination sequence as the final ordered element in a heterologous gene expression cassette may prevent polar effects on the regulation of expression of adjacent genes due to read-through transcription. Accordingly, in some embodiments, appropriate sequence elements known to those who are skilled in the art that promote either rho-dependent or rho-independent transcription termination can be placed in the heterologous protein expression cassette.

In one aspect, the invention provides an expression cassette comprising the following: (a) a first polynucleotide encoding a signal peptide, wherein the first polynucleotide is codon-optimized for expression in a bacterium; (b) a second polynucleotide encoding a polypeptide, wherein the second polynucleotide is in the same translational reading frame as the first polynucleotide; and (c) a promoter operably linked to the first and second polynucleotides, so that the expression cassette encodes a fusion protein comprising the signal peptide and the polypeptide.

In another aspect, the invention provides an expression cassette comprising (a) a first polynucleotide encoding a signal peptide native to a bacterium, wherein the first polynucleotide is codon-optimized for expression in the bacterium, (b) a second polynucleotide encoding a polypeptide, wherein the second polynucleotide is in the same translational reading frame as the first polynucleotide, and (c) a promoter operably linked to the first and second polynucleotides of the expression cassette, wherein the recombinant nucleic acid molecule encodes a fusion protein comprising the signal peptide and the polypeptide. In some embodiments, the polypeptide encoded by the second polynucleotide is heterologous to the signal peptide. In some embodiments, the second polynucleotide is heterologous to the first polynucleotide. In some embodiments, the polypeptide is heterologous to the bacterium to which the signal peptide is native (i.e., foreign to the bacterium). In some embodiments, the bacterium from which the signal peptide is derived is an intracellular bacterium. In some embodiments, the bacterium is selected from the group consisting of *Listeria, Bacillus, Yersinia pestis, Salmonella, Shigella, Brucella*, mycobacteria and *E. coli*. In some embodiments the bacterium is a *Listeria* bacterium (e.g., *Listeria monocytogenes*). In some embodiments, the second polynucleotide is codon-optimized for expression in the bacterium.

In another aspect, the invention provides an expression cassette, wherein the expression cassette comprises (a) a first polynucleotide encoding a signal peptide, wherein the first polynucleotide is codon-optimized for expression in a Listeria bacterium, (b) a second polynucleotide encoding a polypeptide, wherein the second polynucleotide is in the same translational reading frame as the first polynucleotide, and (c) a promoter operably linked to the first and second polynucleotides of the expression cassette, wherein the recombinant nucleic acid molecule encodes a fusion protein comprising the signal peptide and the polypeptide. In some embodiments, the expression cassette is a polycistronic expression cassette. In some embodiments, the second polynucleotide is codon-optimized for expression in the *Listeria* bacterium. In some embodiments, the polypeptide encoded by the second polynucleotide is foreign to the *Listeria* bacterium (i.e., heterologous to the *Listeria* bacterium). In some embodiments, the polypeptide encoded by the second polynucleotide is heterologous to the signal peptide. In some embodiments, the expression cassette comprises more than one promoter.

In another aspect, the invention provides an expression cassette comprising (a) a first polynucleotide encoding a non-secA1 bacterial signal peptide; (b) a second polynucleotide encoding a polypeptide in the same translational reading frame as the first polynucleotide; and (c) a promoter operably linked to the first and second polynucleotides, so that the expression cassette encodes a fusion protein comprising the signal peptide and the polypeptide. In some embodiments, the first polynucleotide and/or the second polynucleotide is codon-optimized for expression in a bacterium, such as *Listeria, Bacillus, Yersinia pestis, Salmonella, Shigella, Brucella*, mycobacteria or *E. coli*. In some embodiments, the polynucleotide(s) is codon-optimized for expression in *Listeria*, such as *Listeria monocytogenes*. In some embodiments, the signal peptide encoded by the codon-optimized first polynucleotide is native to the bacterium for which it is codon-optimized. In some embodiments, the first polynucleotide encoding the signal peptide is heterologous to the second polynucleotide. In some embodiments, the polypeptide encoded by the second polynucleotide is heterologous to the signal peptide. In some embodiments, the expression cassette is a polycistronic expression cassette. In some embodiments, the first polynucleotide, the second polynucleotide, or both the first and second polynucleotide is codon-optimized for expression in a *Listeria* bacterium (e.g., *Listeria monocytogenes*). In some embodiments, the first and second polynucleotides are heterologous to each other. In some embodiments, the polypeptide encoded by the second polynucleotide and the signal peptide are heterologous to each other. In some embodiments, the polypeptide encoded by the second polynucleotide is foreign to the *Listeria* bacterium (i.e., heterologous to the *Listeria* bacterium). In some embodiments, the expression cassette comprises more than one promoter.

The invention also provides an expression cassette comprising the following: (a) a polynucleotide encoding a polypeptide foreign to *Listeria*, wherein the polynucleotide is codon-optimized for expression in *Listeria*; and (b) a promoter, operably linked to the polynucleotide encoding the foreign polypeptide. In some embodiments, the polypeptide that is encoded by the expression cassette is an antigen (e.g., see description of some possible antigens above). In some embodiments, the expression cassette further comprises a polynucleotide encoding a signal peptide. The polynucleotide encoding the signal peptide is also operably linked with the promoter so that the expression cassette expresses a fusion protein comprising both the foreign polypeptide and the signal peptide. Polynucleotides encoding signal peptides suitable for use in the expression cassette include, but are not limited to, those described above. In some embodiments, the polynucleotide encoding a signal peptide that is included in the expression cassette is codon-optimized for expression in a bacterium such as *Listeria* (e.g., a *L. monocytogenes* bacterium) as described above.

The invention also provides an expression cassette comprising the following: (a) a first polynucleotide encoding a non-Listerial signal peptide; (b) a second polynucleotide encoding a polypeptide that is in the same translational reading frame as the first polynucleotide; and (c) a promoter operably linked to both the first and second polynucleotides, wherein the expression cassette encodes a fusion protein comprising both the non-Listerial signal peptide and the polypeptide. In some embodiments, the expression cassette is a polycistronic expression cassette. In some embodiments, the first polynucleotide, the second polynucleotide, or both the first and second polynucleotide is codon-optimized for expression in *Listeria* (e.g., *Listeria monocytogenes*). In some embodiments, the first and second polynucleotides are heterologous to each other. In some embodiments, the polypeptide encoded by the second polynucleotide and the signal peptide are heterologous to each other. In some embodiments, the polypeptide encoded by the second polynucleotide is foreign to the *Listeria* bacterium (i.e., heterologous to the *Listeria* bacterium). In some embodiments, the expression cassette comprises more than one promoter.

The invention further provides an expression cassette, wherein the expression cassette comprises (a) a first polynucleotide encoding a bacterial autolysin, or a catalytically active fragment or catalytically active variant thereof, and (b) a second polynucleotide encoding a polypeptide, wherein the second polynucleotide is in the same translational reading frame as the first polynucleotide, and (c) a promoter operably linked to the first and second polynucleotides, wherein the expression cassette encodes a protein chimera comprising the polypeptide encoded by the second polynucleotide and the autolysin, or catalytically active fragment or catalytically active variant thereof, wherein in the protein chimera the polypeptide is fused to the autolysin, or catalytically active fragment or catalytically active variant thereof, or is inserted within the autolysin, or catalytically active fragment or catalytically active variant thereof. In some embodiments, the protein chimera is catalytically active as an autolysin. In some embodiments, the polypeptide is heterologous to the autolysin. In some embodiments, the bacterial autolysin is from an intracellular bacterium (e.g., *Listeria*). In some embodiments, the second polynucleotide encoding the polypeptide is inserted within the first polynucleotide encoding the autolysin, or catalytically active fragment or catalytically active variant thereof, and the expression cassette encodes a protein chimera in which the polypeptide is inserted within the autolysin, or catalytically active fragment or catalytically active variant thereof (i.e., the polypeptide is embedded within the autolysin or catalytically active fragment or catalytically active variant thereof). In alternative embodiments, the second polynucleotide is positioned outside of the first polynucleotide encoding the autolysin, or catalytically active fragment or catalytically active variant thereof, and the expression cassette encodes a protein chimera in which the polypeptide is fused to the autolysin, or catalytically active fragment or catalytically active variant thereof. In some embodiments, the polypeptide is heterologous to the autolysin. In some embodiments, the first polynucleotide and the second polynucleotide are heterologous to each other. In some embodiments, the autolysin is a SecA2-dependent autolysin. In some embodiments, the autolysin is a peptidoglycan hydrolase (e.g., N-acetylmuramidase or p60). In some embodiments, the expression cassette further comprises a polynucleotide encoding a signal peptide (e.g., a signal peptide normally associated with the autolysin or a signal peptide heterologous to the signal peptide). For instance, in some embodiments, the expression cassette encodes a protein chimera comprising a p60 signal peptide, the p60 protein (or catalytically active fragment or catalytically active variant thereof), and a polypeptide heterologous to p60, embedded within the p60 sequence. In some embodiments, the polypeptide encoded by the second polynucleotide is a non-Listerial polypeptide.

In another aspect, the invention provides an expression cassette comprising (a) a first polynucleotide encoding a signal peptide, (b) a second polynucleotide encoding a secreted protein, or a fragment thereof, wherein the second polynucleotide is in the same translational reading frame as the first polynucleotide, (c) a third polynucleotide encoding a polypeptide heterologous to the secreted protein, or fragment thereof, wherein the third polynucleotide is in the same translational reading frame as the first and second polynucleotides, and (d) promoter operably linked to the first, second, and third polynucleotides, wherein the recombinant nucleic acid molecule encodes a protein chimera comprising the signal peptide, the polypeptide encoded by the second polynucleotide, and the secreted protein, or fragment thereof, and wherein the polypeptide encoded by the third polynucleotide is fused to the secreted protein, or fragment thereof, or is positioned within the secreted protein, or fragment thereof, in the protein chimera.

In some embodiments, the promoters in the expression cassettes described herein (or recombinant nucleic acid molecules described herein) are prokaryotic promoters. For instance, the prokaryotic promoters can be Listerial promoters. In some embodiments, the Listerial promoter is an hly promoter. In some embodiments, the promoters are prfA-dependent promoters (e.g., an actA promoter). In some embodiments, the promoters are constitutive promoters (e.g., ap60 promoter). In some embodiments, the expression cassette comprising a recombinant nucleic acid molecule described herein comprises an hly, actA, or p60 promoter operably linked to the polynucleotides of the recombinant nucleic acid molecule. One of ordinary skill in the art will be readily able to identify additional prokaryotic and/or Listerial promoters suitable for use in the expression cassettes in view of the intended use of the expression cassette and host bacteria into which the expression cassette will be placed.

For instance, a variety of mycobacterial promoters suitable for use in the recombinant expression cassettes within mycobacteria and other bacteria are known. These include the *Mycobacterium bovis* BCG promoters HSP60 and HSP70, and also include such promoters as the mycobactin promoters, α-antigen promoter and 45 KDa antigen promoter of *M. tuberculosis* and BCG, the superoxide dismutase promoter, MBP-70, the mycobacterial asd promoter, the mycobacterial 14 kDa and 12 kDa antigen promoters, mycobacteriophage promoters such as the Bxb1, Bxb2, and Bxb3 promoters, the L1 and L5 promoters, the D29 promoter and the TM4 promoters (see, e.g., U.S. Pat. No. 6,566,121). Promoters suitable for use in *Bacillus anthracis* include, but are not limited to, the pagA promoter, the alpha-amylase promoter (Pamy), and Pntr (see, e.g., Gat et al., *Infect. Immun.*, 71; 801-13 (2003)). Promoters suitable for use in recombinant Salmonella expression cassettes and vaccines are also known and include the nirB promoter, the osmC promoter, P(pagC), and P(tac) (see, e.g., Bumann, *Infect. Immun.* 69:7493-500 (2001); Wang et al., Vaccine, 17:1-12 (1999); McSorley et al., Infect. Immun. 65:171-8 (1997)). A variety of *E. coli* promoters are also known to those of ordinary skill in the art.

In some embodiments, the promoter used in an expression cassette described herein is a constitutive promoter. In other embodiments, the promoter used in an expression cassettes described herein is an inducible promoter. The inducible promoter can be induced by a molecule (e.g., a protein) endogenous to the bacteria in which the expression cassette is to be used. Alternatively, the inducible promoter can be induced by a molecule (e.g. a small molecule or protein) heterologous to the bacteria in which the expression cassette is to be used. A variety of inducible promoters are well-known to those of ordinary skill in the art.

In some embodiments of the expression cassettes, at the 3'-end of the promoter is a poly-purine Shine-Dalgarno sequence, the element required for engagement of the 30S ribosomal subunit (via 16S rRNA) to the heterologous gene RNA transcript and initiation of translation. The Shine-Dalgarno sequence has typically the following consensus sequence: 5'-NAGGAGGU-$N_{5-10}$-AUG (start codon)-3' (SEQ ID NO:85; SEQ ID NOS:125-129). There are variations of the poly-purine Shine-Dalgarno sequence. Notably, the *Listeria* hly gene that encodes listerolysin O (LLO) has the following Shine-Dalgarno sequence: AAGGAGAGT-GAAACCCATG (SEQ ID NO:70) (Shine-Dalgarno sequence is underlined, and the translation start codon is bolded).

The construction of expression cassettes for use in bacteria, and even the construction of expression cassettes specifically for use in recombinant bacterial vaccines, are known in the art. For instance, descriptions of the production and use of a variety of bacterial expression cassettes and/or recombinant bacterial vaccines can be found in the following references, each of which is hereby incorporated by reference herein in its entirety: Horwitz et al., *Proc. Natl. Acad. Sci. USA*, 97:13853-8 (2000); Garmory et al., *J. Drug Target*, 11:471-9 (2003); Kang et al., *FEMS Immunol. Med. Microbiol.*, 37:99-104 (2003); Garmory et al., *Vaccine*, 21:3051-7 (2003); Kang et al., *Infect. Immun.*, 1739-49 (2002); Russman, et al., *J. Immunol.*, 167:357-65 (2001); Harth et al., Microbiology, 150:2143-51 (2004); Varaldo et al., *Infect. Immun.*, 72:3336-43 (2004); Goonetilleke et al., *J. Immunol.*, 171:1602-9 (2003); Uno-Furuta et al., Vaccine, 21:3149-56 (2003); Biet et al., Infect. Immun., 71:2933-7 (2003); Bao et al., *Infect. Immun.*, 71:1656-61 (2003); Kawahara et al., *Clin. Immunol.*, 105:326-31 (2002); Anderson et al., *Vaccine*, 18:2193-202 (2000); Bumann, *Infect. Immun.*, 69:7493-500 (2001); Wang et al., *Vaccine*, 17:1-12 (1999); McSorley et al., *Infect. Immun.*, 65:171-8 (1997); Gat et al., *Infect. Immun.*, 71:801-13 (2003); U.S. Pat. No. 5,504,005; U.S. Pat. No. 5,830,702; U.S. Pat. No. 6,051,237; U.S. patent Publication No. 2002/0025323; U.S. patent Publication No. 2003/0202985; WO 04/062597; U.S. Pat. No. 6,566,121; and U.S. Pat. No. 6,270,776.

In some embodiments, it is desirable to construct expression cassettes that utilize bicistronic, polycistronic (also known as multicistronic) expression of heterologous coding sequences. Such expression cassettes can utilize, for example, a single promoter that is operably linked to two or more independent coding sequences. These coding sequences can, for example, correspond to individual genes or can, alternatively, correspond to desired and/or selected sub-fragments of a whole designated gene. In this later example, a gene might contain a sequence encoding a hydrophobic trans-membrane domain, which may potentially inhibit efficient secretion from *Listeria*. Thus, it may be desirable to segregate in two sub-fragments the coding sequence of this gene from the hydrophobic domain; in this instance the two sub-fragments are then expressed as a bicistronic message. Utilization of polycistronic expression requires that the 30s ribosome subunit stay on the polycistronic RNA message following translation termination of the first coding sequence and release of the 50s ribosome sub-unit, and subsequently "read-through" the RNA message to the next initiation codon, during which the 50s ribosome sub-unit binds to the RNA-bound 30s ribosome subunit, and re-initiating translation.

*Listeria monocytogenes*, like other bacteria, utilizes polycistronic expression of its genomic repertoire. By way of example, the sequence of a *Listeria monocytogenes* intergenic region from a selected polycistronic message can be used to construct polycistronic expression cassettes for expression of a selected heterologous protein from recombinant *Listeria* species. For example, several of the prfA-dependent virulence factors from *Listeria monocytogenes* are expressed from polycistronic message. For instance, the *Listeria monocytogenes* ActA and PlcB proteins are expressed as a bicistronic message. The DNA sequence corresponding to the *Listeria monocytogenes* actA-plcB intergenic sequence (5'-3') is shown below (SEQ ID NO: 71)
5'-TAAAAACACAGAACGAAAGAAAAAGTGAGGTGAATGA-3'

(The Shine-Dalgarno sequence for translation initiation of plcB is shown in bold. The first 3 nucleotides of the sequence correspond to an Ochre stop codon.) For a non-limiting example of a bicistronic expression vector, a bicistronic hEphA2 expression vector for use in *Listeria monocytogenes*, see Example 28, below.

Alternatively, other known intergenic or synthetic sequences can be used to construct polycistronic expression cassettes for use in *Listeria* or other bacteria. Construction of intergenic regions which lead to substantial secondary RNA structure should be prevented, to avoid unwanted transcription termination by a rho-independent mechanism.

Importantly, if secretion of any or all translated proteins expressed from the polycistronic message is desired, signal peptides must be functionally linked to each coding region. In some embodiments, these signal peptides differ from each other.

Thus, in some embodiments, the expression cassettes described herein for use in *Listeria* or other bacteria are polycistronic (e.g., bicistronic). Two or more polypeptides are encoded by the bicistronic or polycistronic expression cassettes as discrete polypeptides. In some embodiments, the bicistronic or polycistronic expression cassettes comprise an intergenic sequence (e.g., from a bicistronic or polycistronic gene) positioned between the coding sequences of the two polypeptides. In some embodiments, the intergenic sequence comprises a sequence which promotes ribosomal entry and initiation of translation. In some embodiments, the intergenic sequence comprises a Shine-Dalgarno sequence. In some embodiments, the intergenic sequence is the *Listeria monocytogenes* actA-plcB intergenic sequence. Typically, the intergenic sequence is positioned between a polynucleotide sequence encoding a first polypeptide (or a first fusion protein comprising a first polypeptide and a signal peptide) and a polynucleotide sequence encoding a second polypeptide (or a second fusion protein comprising a second polypeptide and signal peptide).

Accordingly, in one aspect, the invention provides an expression cassette comprising the following: (a) a first polynucleotide encoding a first polypeptide; (b) a second polynucleotide encoding a second polypeptide; (c) an intergenic sequence positioned between the first and second polynucleotides; and (f) a promoter operably linked to the first and second polynucleotides, wherein the expression cassette encodes the first and second polypeptides as two discrete polypeptides. In some embodiments, the first and second polypeptides are polypeptides selected from any of the polypeptides described herein (e.g., in Section IV, above). In some embodiments, at least one of the first or second polypeptides comprises an antigen. In some embodiments, the first and second polynucleotides each comprise a (different or the same) fragment of the same antigen. In some embodiments, the antigen is a tumor-associated antigen or is derived from a tumor-associated-antigen.

The invention further provides an expression cassette comprising the following: (a) a first polynucleotide encoding a first signal peptide; (b) a second polynucleotide encoding a first (non-signal) polypeptide, wherein the second polynucleotide is in the same translational reading frame as the first polynucleotide; (c) a third polynucleotide encoding a second signal peptide; (d) a fourth polynucleotide encoding a second (non-signal) polypeptide, wherein the fourth polynucleotide is in the same translational reading frame as the third polynucleotide; (e) an intergenic sequence (typically positioned between the second polynucleotide and the third polynucleotide); and (f) a promoter operably linked to the first polynucleotide, second polynucleotide, third polynucleotide, and fourth polynucleotide, so that the expression cassette encodes both a first fusion protein comprising the first signal peptide and the first polypeptide and a second fusion protein comprising the second signal peptide and second polypeptide. In some embodiments, the one or more of the polynucleotides encoding a signal peptide is codon-optimized for expression in a bacterium. In some embodiments, the third and/or fourth polynucleotides are codon-optimized for expression in a bacterium (preferably in addition to codon-optimization of the polynucleotides encoding the signal peptides). In some embodiments, the first and/or second signal peptide is a non-secA1 bacterial signal peptide. In some embodiments, the intergenic sequence is the *Listeria monocytogenes* actA-plcB intergenic sequence. In some embodiments, the second and third polypeptides are polypeptides selected from any of the polypeptides described herein (e.g., in Section IV, above), such as polypeptides comprising antigens. In some embodiments, the first and second polypeptides are polypeptides selected from any of the polypeptides described herein (e.g., in Section IV, above). In some embodiments, at least one of the first or second polypeptides comprises an antigen. In some embodiments, the first and second polynucleotides each comprise a fragment of the same antigen. In some embodiments, the antigen is a tumor-associated antigen or is derived from a tumor-associated-antigen.

For instance, the invention provides a polycistronic expression cassette for expression of heterologous polypeptides in *Listeria*, wherein the expression cassette encodes at least two discrete non-Listerial polypeptides. In some embodiments, the polycistronic expression cassette is a bicistronic expression cassette which encodes two discrete non-Listerial polypeptides. In some embodiments, the expression cassette comprises the following: (a) a first polynucleotide encoding a first non-Listerial polypeptide; (b) a second polynucleotide encoding a second non-Listerial polypeptide; (c) an intergenic sequence positioned between the first and second polynucleotides; and (d) a promoter operably linked to the first and second polynucleotides, wherein the expression cassette encodes the first and second polypeptides as two discrete polypeptides. If the expression cassette is a polycistronic expression cassette that encodes three polypeptides as discrete polypeptides, the expression cassette will comprise a third polynucleotide operably linked to the promoter and a second intergenic sequence positioned between the second and third polynucleotide. In some embodiments, at least one of the non-Listerial polypeptides comprises an antigen. In some embodiments, at least two of the non-Listerial polypeptides each comprises a fragment of the same antigen.

In some embodiments, the expression cassette comprises the following: (a) a first polynucleotide encoding a first signal peptide; (b) a second polynucleotide encoding a first (non-signal) non-Listerial polypeptide, wherein the second polynucleotide is in the same translational reading frame as the first polynucleotide; (c) a third polynucleotide encoding a second signal peptide; (d) a fourth polynucleotide encoding a second (non-signal) non-Listerial polypeptide, wherein the fourth polynucleotide is in the same translational reading frame as the third polynucleotide; (e) an intergenic sequence positioned between the second polynucleotide and the third polynucleotide; and (f) a promoter operably linked to the first polynucleotide, second polynucleotide, third polynucleotide, and fourth polynucleotide, so that the expression cassette encodes both a first fusion protein comprising the first signal peptide and the first polypeptide and a second fusion protein comprising the second signal peptide and second polypeptide. In some embodiments, at least one of the non-Listerial polypeptides is an antigen. In some embodiments, at least two of the non-Listerial polypeptides are each fragments of the same antigen.

The invention also provides a method of using any of the expression cassettes described herein to produce a recombinant bacterium (e.g. a recombinant *Listeria* bacterium). In some embodiments, the method of using an expression cassette described herein to make a recombinant bacterium comprises introducing the expression cassette into a bacterium. In some embodiments, the expression cassette is integrated into the genome of the bacterium. In some other embodiments, the expression cassette is on a plasmid which is incorporated within the bacterium. In some embodiments, incorporation of the expression cassette into the bacterium occurs by conjugation. The introduction of the expression cassette into the bacterium can be effected by any of the standard techniques known in the art. For instance, incorporation of the expression cassette into the bacterium can occur by conjugation, transduction (transfection), or transformation.

VII. Vectors

The invention further provides vectors, such as expression vectors, which comprise any one of the expression cassettes and/or recombinant nucleic acid molecules described herein. In some embodiments, the vector is a plasmid. In some embodiments, the vector is linear. In some embodiments, the vector is circular. In some embodiments, the vector is an integration or homologous recombinant vector. In some embodiments, the vector is pAM401. In some embodiments, the vector is pPL2. In some embodiments, the vector is isolated.

As indicated above, in some embodiments, an expression cassette described herein is contained within an expression vector. In some embodiments, the vector is a plasmid. In other embodiments the vector is linear. In alternative embodiments, the expression cassette is inserted (i.e. integrated) within genomic DNA of a bacterium using an expression vector. In some embodiments, the expression vector is linear. In other embodiments, the expression vector is circular.

Expression vectors suitable for use in bacteria such as *Listeria* are known to those skill in the art. There are a variety of suitable vectors suitable for use as a plasmid construct backbone for assembly of the expression cassettes. A particular plasmid construct backbone is selected based on whether expression of the polynucleotide (i.e., a polynucleotide encoding a heterologous antigen) from the bacterial chromosome or from an extra-chromosomal episome is desired.

In some embodiments, incorporation of the expression cassette (and/or recombinant nucleic acid molecule) into the bacterial chromosome of *Listeria monocytogenes* (*Listeria*) is accomplished with an integration vector that contains an expression cassette for a listeriophage integrase that catalyzes sequence-specific integration of the vector into the *Listeria* chromosome. For example, the integration vectors known as pPL1 and pPL2 program stable single-copy integration of a heterologous protein expression cassette within an innocuous region of the bacterial genome, and have been described in the literature (Lauer et. al. 2002 J. Bacteriol. 184:4177-4178; U.S. patent Publication No. 20030203472). The integration vectors are stable as plasmids in *E. coli* and are introduced via conjugation into the desired *Listeria* background. Each vector lacks a *Listeria*-specific origin of replication and encodes a phage integrase, such that the vectors are stable only upon integration into a chromosomal phage attachment site. Starting with a desired plasmid construct, the process of generating a recombinant *Listeria* strain expressing a desired protein(s) takes approximately one week. The pPL1 and pPL2 integration vectors are based, respectively, on the U153 and PSA listeriophages. The pPL1 vector integrates within the open reading frame of the comK gene, while pPL2 integrates within the tRNAArg gene in such a manner that the native sequence of the gene is restored upon successful integration, thus keeping its native expressed function intact. The pPL1 and pPL2 integration vectors contain a multiple cloning site sequence in order to facilitate construction of plasmids containing a recombinant nucleic acid molecule or an expression cassette such as the heterologous protein expression cassette. Some specific examples of the use of the pPL2 integration vector are described in Example 2 and Example 3, below.

Alternatively, incorporation of the expression cassette (and/or recombinant nucleic acid molecule) into the *Listeria* chromosome can be accomplished through allelic exchange methods, known to those skilled in the art. In particular, compositions in which it is desired to not incorporate a gene encoding an antibiotic resistance protein as part of the construct containing the expression cassette, methods of allelic exchange are desirable. For example, the pKSV7 vector (Camilli et. al. *Mol. Microbiol.* (1993) 8, 143-157), contains a temperature-sensitive *Listeria* Gram-positive replication origin which is exploited to select for recombinant clones at the non-permissive temperature that represent the pKSV7 plasmid recombined into the *Listeria* chromosome. The pKSV7 allelic exchange plasmid vector contains a multiple cloning site sequence in order to facilitate construction of plasmids containing the protein expression cassette, and also a chloramphenicol resistance gene. For insertion into the *Listeria* chromosome, the expression cassette construct may be flanked by approximately 1 kb of chromosomal DNA sequence that corresponds to the precise location of desired integration. The pKSV7-expression cassette plasmid may be introduced into a desired bacterial strain by electroporation, according to standard methods for electroporation of Gram positive bacteria. A non-limiting example of a method of effecting allelic exchange using the pKSV7 vector is provided in Example 16 below.

In other embodiments, it may be desired to express the polypeptide (including a fusion protein comprising a polypeptide) from a stable plasmid episome. Maintenance of the plasmid episome through passaging for multiple generations requires the co-expression of a protein that confers a selective advantage for the plasmid-containing bacterium. As non-limiting examples, the protein co-expressed from the plasmid in combination with the polypeptide may be an antibiotic resistance protein, for example chloramphenicol, or may be a bacterial protein (that is expressed from the chromosome in wild-type bacteria), that can also confer a selective advantage. Non-limiting examples of bacterial proteins include enzyme required for purine or amino acid biosynthesis (selected using defined media lacking relevant amino acids or other necessary precursor macromolecules), or a transcription factor required for the expression of genes that confer a selective advantage in vitro or in vivo (Gunn et. al. 2001 J. Immuol. 167:6471-6479). As a non-limiting example, pAM401 is a suitable plasmid for episomal expression of a selected polypeptide in diverse Gram-positive bacterial genera (Wirth et. al. 1986 J. Bacteriol 165:831-836). For further description of exemplary uses of pAM401, see Examples 3 and 13, below.

Incorporation of the expression cassette into the bacterial chromosome of *B. anthracis* can, for instance, be accomplished with an integration vector that contains an expression cassette for a phage integrase that catalyzes sequence-specific integration of the vector into the *B. anthracis* chromosome. The integrase and attachment site of a *B. anthracis* phage can be used to derive an integration vector, to incorporate desired antigen expression cassettes into the vaccine composition. As a non-limiting example, the integrase and attachment site from the *B. anthracis* temperate phage w-alpha is used to derive a *B. anthracis* specific integration vector (McCloy, E. W. 1951. Studies on a lysogenic *Bacillus* stain. I. A bacteriophage specific for *Bacillus anthracis*. J. Hyg. 49:114-125).

Alternatively, incorporation of an antigen expression cassette into the *B. anthracis* chromosome can be accomplished through allelic exchange methods, known to those skilled in the art. See, e.g., Gat et al., *Infect. Immun.*, 71:801-13 (2003). In particular, compositions in which it is desired to not incorporate a gene encoding an antibiotic resistance protein as part of the construct containing the expression cassette, methods of allelic exchange are desirable. For example, the pKSV7 vector (Camilli et. al. *Mol. Microbiol.* 1993 8, 143-157), contains a temperature-sensitive *Listeria*-derived Gram positive replication origin which is exploited to select for recombinant clones at the non-permissive temperature that represent the pKSV7 plasmid recombined into the bacterial chromosome. The pKSV7 allelic exchange plasmid vector contains a multiple cloning site sequence in order to facilitate construction of plasmids containing the expression cassette, and also a chloramphenicol resistance gene. For insertion into the *Bacillus anthracis* chromosome, the expression cassette construct may be flanked by approximately 1 kb of chromosomal DNA sequence that corresponds to the precise location of desired integration. The pKSV7-expression cassette plasmid may be introduced into a desired bacterial strain by electroporation, according to standard methods for electroporation of Gram positive bacteria. A non-limiting example of a method of effecting allelic exchange in *B. anthracis* is provided in U.S. patent application Ser. No. 10/883,599, incorporated by reference herein in its entirety. In particular, allelic exchange using the pKSV7 vector can be used in strains of *B. anthracis* to add a desired antigen expression cassette at any desired location within the bacterial chromosome.

The allelic exchange methods described above using pKSV7 are broadly applicable to use in gram positive bacteria. In addition, a variety of expression vectors useful in bacteria, including recombinant bacterial vectors, are known to those of ordinary skill in the art. Examples include those vectors described in the following references, each of which is incorporated by reference herein in its entirety: Horwitz et al., *Proc. Natl. Acad. Sci. USA*, 97:13853-8 (2000); Garmory et al., *J. Drug Target*, 11:471-9 (2003); Kang et al., *FEMS Immunol. Med. Microbiol.*, 37:99-104 (2003); Garmory et al., *Vaccine*, 21:3051-7 (2003); Kang et al., *Infect. Immun.*, 1739-49 (2002); Russman, et al., *J. Immunol.*, 167:357-65 (2001); Harth et al., *Microbiology*, 150:2143-51 (2004); Varaldo et al., *Infect. Immun.*, 72:3336-43 (2004); Goonetilleke et al., *J. Immunol.*, 171:1602-9 (2003); Uno-Furuta et al., *Vaccine*, 21:3149-56 (2003); Biet et al., Infect. Immun., 71:2933-7 (2003); Bao et al., *Infect. Immun.*, 71:1656-61 (2003); Kawahara et al., *Clin. Immunol.*, 105:326-31 (2002); Anderson et al., *Vaccine*, 18:2193-202 (2000); Bumann, *Infect. Immun.*, 69:7493-500 (2001); Wang et al., *Vaccine*, 17:1-12 (1999); McSorley et al., *Infect. Immun.*, 65:171-8 (1997); Gat et al., *Infect. Immun.*, 71:801-13 (2003); U.S. Pat. No. 5,504,005; U.S. Pat. No. 5,830,702; U.S. Pat. No. 6,051,237; U.S. patent Publication No. 2002/0025323; U.S. patent Publication No. 2003/0202985; WO 04/062597; U.S. Pat. No. 6,566,121; and U.S. Pat. No. 6,270,776.

The invention further provides expression vectors comprising expression cassettes comprising the following: (a) a first polynucleotide encoding a first signal peptide; (b) a second polynucleotide encoding a first polypeptide, wherein the second polynucleotide is in the same translational reading frame as the first polynucleotide; (c) an intergenic sequence; (d) a third polynucleotide encoding a second signal peptide; (e) a fourth polynucleotide encoding a second polypeptide, wherein the fourth polynucleotide is in the same translational reading frame as the third polynucleotide; and (f) a promoter operably linked to the first polynucleotide, second polynucleotide, third polynucleotide, fourth polynucleotide, and intergenic sequence, such that the expression cassette encodes both a first fusion protein comprising the first signal peptide and the first polypeptide and a second fusion protein comprising the second signal peptide and second polypeptide.

The invention further provides methods of using any of the expression vectors described herein to produce a recombinant bacterium (e.g. a recombinant *Listeria* bacterium). In some embodiments, the method of using an expression vector described herein to make a recombinant bacterium comprises introducing the expression vector into a bacterium.

VIII. Bacteria and Other Host Cells

The invention further provides host cells comprising the recombinant nucleic acid molecules, expression cassettes, and/or vectors described herein (see, e.g., the Summary of the Invention and Sections I, II, VI, and VII of the Detailed Description, above, as well as the specific Examples below). In some embodiments, the cells are prokaryotic. In some embodiments, the cells are eukaryotic. In some embodiments, the cells are mammalian. In some embodiments, the cells are antigen-presenting cells, such as dendritic cells. In some embodiments, the cells are bacterial cells. In some embodiments, the host cells are isolated.

For example, the invention provides bacteria comprising the recombinant nucleic acid molecules, expression cassettes, and/or the vectors described herein (see, e.g., Summary of the Invention and Sections I, II, VI, and VII of the Detailed Description, above, as well as the specific examples below). The bacteria comprising these polynucleotides are alternatively referred to herein as "recombinant bacteria," and a bacterium comprising a recombinant nucleic acid molecule, expression cassette, or vector described herein is alternatively referred to herein as "a recombinant bacterium." In some embodiments, the bacteria comprising the recombinant nucleic acid molecules, expression cassettes, and/or expression vectors are isolated. In some embodiments, the recombinant bacteria comprising the recombinant nucleic acid molecules, expression cassettes, and/or expression vectors express the polypeptides or fusion proteins encoded by the recombinant nucleic acid molecules, expression cassettes, and/or expression vectors contained therein. In some embodiments, the recombinant bacteria secrete the polypeptides or fusion proteins encoded by the recombinant nucleic acid molecules, expression cassettes, and/or expression vectors contained therein. In some embodiments, the recombinant bacteria express and secrete the polypeptides and/or fusion proteins in an amount sufficient to generate an immune response in a host upon administration of the bacteria (or a composition comprising the bacteria) to a host (e.g., a human subject).

In some embodiments, the bacteria are selected from the group consisting of gram positive bacteria, Gram negative bacteria, intracellular bacteria and mycobacteria. In some embodiments, the bacteria are gram positive bacteria. In some embodiments of the invention, the bacteria are intracellular bacteria (e.g., facultative intracellular bacteria). In some embodiments the bacteria belong to the genus *Listeria*. In other embodiments, the bacteria are members of the species *Listeria monocytogenes*. In some other embodiments the bacteria are members of the *Listeria ivanovii*, *Listeria seeligeri*, or *Listeria innocua* species. In some embodiments, the bacteria are members of the genus *Bacillus*. In another embodiment, the bacteria are *Bacillus anthracis*. In still another embodiment, the bacteria are *Yersinia pestis*. In other embodiments of the invention, the bacteria are from the genus Salmonella. In some embodiments, the bacteria are *Salmonella typhimurium*. In some embodiments, the bacteria belong to the genus *Shigella*. For instance, in some embodiments, the bacteria are *Shigella flexneri*. In some embodiments, the bacteria are members of the genus *Brucella*. In an alternative embodiment, the bacteria are mycobacteria. The mycobacteria is optionally a member of the species *Mycobacterium tuberculosis*. In some embodiments, the bacteria are Bacillus Calmette-Guerin (BCG). In some embodiments, the bacteria are *E. coli*, for instance, an *E. coli* which has been modified to express Listeriolysin O (LLO). Accordingly, in some embodiments, the bacteria comprising the recombinant nucleic acid molecules, expression cassettes, and/or vectors described herein are selected from the group consisting of *Listeria*, *Bacillus anthracis*, *Yersinia pestis*, *Salmonella*, and mycobacteria. In some other embodiments, the bacteria comprising the recombinant nucleic acid molecules, expression cassettes, and/or vectors described herein are selected from the group consisting of *Listeria*, *Bacillus*, *Yersinia pestis*, *Salmonella*, *Shigella*, *Brucella*, mycobacteria and *E. coli*.

In some embodiments, the bacteria of the invention that are modified through the insertion of the recombinant nucleic acid molecules, expression cassettes, and/or vectors described herein (e.g., see the Summary of the Invention, Sections I, II, VI, and VII of the Detailed Description, above, and the Examples, below) to express polypeptides, and, in at least some embodiments, secrete the polypeptides, are wild-type bacteria. For instance, in some embodiments, the recombinant bacterium is a wild-type *Listeria* bacterium, such as a *Listeria monocytogenes* bacterium, which comprises the recombinant nucleic acid molecule, expression cassette, and/or vector. However, in some embodiments of the invention, the bacteria comprising the expression cassettes and/or vectors is a mutant strain of the bacteria. In some embodiments, the bacteria are attenuated. In some embodiments, the bacteria are an attenuated mutant strain of bacteria. A mutant in which a gene "xyz" has been deleted is alternatively referred to herein as Δxyz⁻ or xyz or an xyz deletion mutant. For instance, a bacterial strain in which the uvrA gene has been deleted is alternatively referred to herein as uvrA mutant, ΔuvrA, or uvrA⁻. In addition, it will be understood by one of ordinary skill in the art that a reference to a particular mutant or strain as an "xyz" mutant or "xyz" strain will sometimes refer to a mutant or strain in which the xyz gene has been deleted.

The mutation in a mutant bacterium comprising the expression cassettes and/or expression vectors may be a mutation of any type. For instance, the mutation may constitute a point mutation, a frame-shift mutation, an insertion, a deletion of part or all of a gene. In addition, in some embodiments of the modified strains, a portion of the bacterial genome has been replaced with a heterologous polynucleotide. In some embodiments, the mutations are naturally-occurring. In other embodiments, the mutations are the results of artificial mutation pressure. In still other embodiments, the mutations in the bacterial genome are the result of genetic engineering.

In some embodiments, the bacteria comprising any one of the recombinant nucleic acid molecules, expression cassettes and/or vectors described herein are attenuated for cell-to-cell spread, entry into non-phagocytic cells, or proliferation (relative to the wild-type bacteria). The bacteria may be attenuated by mutation or by other modifications. In some embodiments, the bacteria comprising any one of the recombinant nucleic acid molecules, expression cassettes and/or expression vectors described herein are attenuated for cell-to-cell spread (e.g., *Listeria monocytogenes* actA mutants). In some embodiments, the bacteria comprising any one of the recombinant nucleic acid molecules, expression cassettes and/or expression vectors described herein are attenuated for entry into non-phagocytic cells (e.g., *Listeria monocytogenes* internalin mutants, such as in/B deletion mutants). In some embodiments, the bacteria comprising any one of the recombinant nucleic acid molecules, expression cassettes and/or expression vectors described herein are attenuated for proliferation. In some embodiments, the bacteria are attenuated both for cell-to-cell spread and for entry into non-phagocytic cells.

In some embodiments, the bacteria comprising the expression cassettes and/or expression vectors described herein are attenuated for cell-to-cell spread. In some embodiments, the bacteria (e.g., *Listeria*) are defective with respect to ActA (relative to the non-mutant or wildtype bacteria), or its equivalent (depending on the organism). In some embodiments, the bacteria comprise one or more mutation in actA. For instance, the bacterium (e.g., *Listeria*) may be an actA deletion mutant. ActA is the actin polymerase encoded by the actA gene (Kocks, et al., *Cell*, 68:521-531 (1992); Genbank accession no. AL591974, nts 9456-11389). The actin polymerase protein is involved in the recruitment and polymerization of host F-actin at one pole of the *Listeria* bacterium. Subsequent polymerization and dissolution of actin results in *Listeria* propulsion throughout the cytosol and into neighboring cells. This mobility enables the bacteria to spread directly from cell-to-cell without further exposure to the extracellular environment, thus escaping host defenses such as antibody development. In some embodiments, the attenuated *Listeria* optionally comprises both a mutation in an internalin gene, such as inlB, and in actA. The *Listeria* strain of this embodiment of the present invention is attenuated for entry into non-phagocytic cells as well as attenuated for cell-to-cell spreading.

In some embodiments, the capacity of the attenuated bacterium for cell-to-cell spread is reduced by at least about 10%, at least about 25%, at least about 50%, at least about 75%, or at least about 90%, relative to a bacterium without the attenuating mutation (e.g., the wild type bacterium). In some embodiments, the capacity of the attenuated bacterium for cell-to-cell spread is reduced by at least about 25% relative to a bacterium without the attenuating mutation. In some embodiments, the capacity of the attenuated bacterium attenuated for cell-to-cell spread is reduced by at least about 50% relative to a bacterium without the attenuating mutation.

In vitro assays for determining whether or not a bacterium such as a *Listeria* bacterium is attenuated for cell-to-cell spread are known to those of ordinary skill in the art. For example, the diameter of plaques formed over a time course after infection of selected cultured cell monolayers can be measured. Plaque assays within L2 cell monolayers can be performed as described previously in Sun, A., A. Camilli, and D. A. Portnoy. 1990, Isolation of *Listeria monocytogenes* small-plaque mutants defective for intracellular growth and cell-to-cell spread. *Infect. Immun.* 58:3770-3778, with modifications to the methods of measurement, as described by in Skoble, J., D. A. Portnoy, and M. D. Welch. 2000, Three regions within ActA promote Arp2/3 complex-mediated actin nucleation and *Listeria monocytogenes* motility. *J. Cell Biol.* 150:527-538. In brief, L2 cells are grown to confluency in six-well tissue culture dishes and then infected with bacteria for 1 h. Following infection, the cells are overlayed with media warmed to 40° C. that is comprised of DME containing 0.8% agarose, Fetal Bovine Serum (e.g., 2%), and a desired concentration of Gentamicin. The concentration of Gentamicin in the media dramatically affects plaque size, and is a measure of the ability of a selected *Listeria* strain to effect cell-to-cell spread (Glomski, I J., M. M. Gedde, A. W. Tsang, J. A. Swanson, and D. A. Portnoy. 2002. *J. Cell Biol.* 156: 1029-1038). For example, at 3 days following infection of the monolayer the plaque size of *Listeria* strains having a phenotype of defective cell-to-cell spread is reduced by at least 50% as compared to wild-type *Listeria*, when overlayed with media containing Gentamicin at a concentration of 50 µg/ml. On the otherhand, the plaque size between *Listeria* strains having a phenotype of defective cell-to-cell spread and wild-type *Listeria* is similar, when infected monolayers are overlayed with media+agarose containing only 5 µg/ml gentamicin. Thus, the relative ability of a selected strain to effect cell-to-cell spread in an infected cell monolayer relative to wild-type *Listeria* can be determined by varying the concentration of gentamicin in the media containing agarose. Optionally, visualization and measurement of plaque diameter can be facilitated by the addition of media containing Neutral Red (GIBCO BRL; 1:250 dilution in DME+agarose media) to the overlay at 48 h. post infection. Additionally, the plaque assay can be performed in monolayers derived from other primary cells or continuous cells. For example HepG2 cells, a hepatocyte-derived cell line, or primary human hepatocytes can be used to evaluate the ability of selected *Listeria* mutants to effect cell-to-cell spread, as compared to wild-type *Listeria*. In some embodiments, *Listeria* comprising mutations or other modifications that attenuate the *Listeria* for cell-to-cell spread produce "pinpoint" plaques at high concentrations of gentamicin (about 50 µg/ml).

In some embodiments, the bacteria comprising the expression cassettes and/or expression vectors described herein are mutant bacteria that are attenuated for nucleic acid repair (relative to wildtype such as bacteria without the attenuating genetic mutation). For instance, in some embodiments, the bacteria are defective with respect to at least one DNA repair enzyme (e.g., *Listeria monocytogenes* uvrAB mutants). In some embodiments, the bacteria are defective with respect to PhrB, UvrA, UvrB, UvrC, UvrD, and/or RecA, or one of their equivalents (depending on the genus and species of the bacteria). In some embodiments, the bacteria are defective with respect to UvrA, UvrB, and/or UvrC. In some embodiments, the bacteria comprise attenuating mutations in phrB, uvrA, uvrB, uvrC, uvrD, and/or recA genes. In some embodiments, the bacteria comprise one or more mutations in the uvrA, uvrB, and/or uvrC genes. In some embodiments, the bacteria are functionally deleted in UvrA, UvrB, and/or UvrC. In some embodiments, the bacteria are deleted in functional UvrA and UvrB. In some embodiments, the bacteria are uvrAB deletion mutants. In some embodiments, the bacteria are ΔuvrABΔactA mutants. In some embodiments, the nucleic acid of the bacteria which are attenuated for nucleic acid repair and/or are defective with respect to at least one DNA repair enzyme are modified by reaction with a nucleic acid targeting compound (see below). Nucleic acid repair mutants, such as ΔuvrAB *Listeria monocytogenes* mutants, and methods of making the mutants, are described in detail in U.S. patent Publication No. 2004/0197343 (see, e.g., Example 7 of U.S. 2004/0197343).

In some embodiments, the capacity of the attenuated bacterium for nucleic acid repair is reduced by at least about 10%, at least about 25%, at least about 50%, at least about 75%, or at least about 90%, relative to a bacterium without the attenuating mutation (e.g., the wild type bacterium). In some embodiments, the capacity of the attenuated bacterium for nucleic acid repair is reduced by at least about 25% relative a bacterium without the attenuating mutation. In some embodiments, the capacity of the attenuated bacterium attenuated for nucleic acid repair is reduced by at least about 50% relative a bacterium without the attenuating mutation.

Confirmation that a particular mutation is present in a bacterial strain can be obtained through a variety of methods known to those of ordinary skill in the art. For instance, the relevant portion of the strain's genome can be cloned and sequenced. Alternatively, specific mutations can be identified via PCR using paired primers that code for regions adjacent to a deletion or other mutation. Southern blots can also be used to detect changes in the bacterial genome. Also, one can analyze whether a particular protein is expressed by the strain using techniques standard to the art such as Western blotting. Confirmation that the strain contains a mutation in the desired gene may also be obtained through comparison of the phenotype of the strain with a previously reported phenotype. For example, the presence of a nucleotide excision repair mutation such as deletion of uvrAB can be assessed using an assay which tests the ability of the bacteria to repair its nucleic acid using the nucleotide excision repair (NER) machinery and comparing that ability against wild-type bacteria. Such functional assays are known in the art. For instance, cyclobutane dimer excision or the excision of UV-induced (6-4) products can be measured to determine a deficiency in an NER enzyme in the mutant (see, e.g., Franklin et al., *Proc. Natl. Acad. Sci. USA,* 81: 3821-3824 (1984)). Alternatively, survival measurements can be made to assess a deficiency in nucleic acid repair. For instance, the bacteria can be subjected to psoralen/UVA treatment and then assessed for their ability to proliferate and/or survive in comparison to wild-type.

In some embodiments, the bacterium is attenuated for entry into non-phagocytic cells (relative or a non-mutant or wild-type bacterium). In some embodiments, the bacterium (e.g., *Listeria*) is defective with respect to one or more internalins (or equivalents). In some embodiments, the bacterium is defective with respect to internalin A. In some embodiments, the bacterium is defective with respect to internalin B. In some embodiments, the bacterium comprises a mutation in inlA. In some embodiments, the bacterium comprises a mutation in inlB. In some embodiments, the bacterium comprises a mutation in both actA and inlb. In some embodiments, the bacterium is deleted in functional ActA and internalinB. In some embodiments, the bacterium is an ΔactAΔinlB double deletion mutant. In some embodiments, the bacterium is defective with respect to both ActA and internalin B.

In some embodiments, the capacity of the attenuated bacterium for entry into non-phagocytic cells is reduced by at least about 10%, at least about 25%, at least about 50%, at least about 75%, or at least about 90%, relative to a bacterium without the attenuating mutation (e.g., the wild type bacterium). In some embodiments, the capacity of the attenuated bacterium for entry into non-phagocytic cells is reduced by at least about 25% relative to a bacterium without the attenuating mutation. In some embodiments, the capacity of the attenuated bacterium for entry into non-phagocytic cells is reduced by at least about 50% relative to a bacterium without the attenuating mutation. In some embodiments, the capacity of the attenuated bacterium for entry into non-phagocytic cells is reduced by at least about 75% relative to a bacterium without the attenuating mutation.

In some embodiments, the attenuated bacteria, such as a mutant *Listeria* strain, are not attenuated for entry into more than one type of non-phagocytic cell. For instance, the attenuated strain may be attenuated for entry into hepatocytes, but not attenuated for entry into epithelial cells. As another example, the attenuated strain may be attenuated for entry into epithelial cells, but not hepatocytes. It is also understood that attenuation for entry into a non-phagocytic cell of particular modified bacteria is a result of mutating a designated gene, for example a deletion mutation, encoding an invasin protein which interacts with a particular cellular receptor, and as a result facilitates infection of a non-phagocytic cell. For example, *Listeria* ΔinlB mutant strains are attenuated for entry into non-phagocytic cells expressing the hepatocyte growth factor receptor (c-met), including hepatocyte cell lines (e.g., HepG2), and primary human hepatocytes.

In some embodiments, even though the bacteria (e.g., mutant *Listeria*) are attenuated for entry into non-phagocytic cells, the *Listeria* are still capable of uptake by phagocytic cells, such as at least dendritic cells and/or macrophages. In one embodiment the ability of the attenuated bacteria to enter phagocytic cells is not diminished by the modification made to the strain, such as the mutation of an invasin (i.e. approximately 95% or more of the measured ability of the strain to be taken up by phagocytic cells is maintained post-modification). In other embodiments, the ability of the attenuated bacteria to enter phagocytic cells is diminished by no more than about 10%, no more than about 25%, no more than about 50%, or no more than about 75%.

In some embodiments of the invention, the amount of attenuation in the ability of the bacterium (e.g., a *Listeria* bacterium) to enter non-phagocytic cells ranges from a twofold reduction to much greater levels of attenuation. In some embodiments, the attenuation in the ability of the bacteria to enter non-phagocytic cells is at least about 0.3 log, about 1 log, about 2 log, about 3 log, about 4 log, about 5 log, or at least about 6 log. In some embodiments, the attenuation is in the range of about 0.3 to >8 log, about 2 to >8 log, about 4 to >8 log, about 6 to >8 log, about 0.3-8 log, also about 0.3-7 log, also about 0.3-6 log, also about 0.3-5 log, also about 0.3-4 log, also about 0.3-3 log, also about 0.3-2 log, also about 0.3-1 log. In some embodiments, the attenuation is in the range of about 1 to >8 log, 1-7 log, 1-6 log, also about 2-6 log, also about 2-5 log, also about 3-5 log.

A number of internalins have been identified in *L. monocytogenes* (Boland, et al., *Clinical Microbiology Reviews,* 2001, 14: 584-640). These internalins include, but are not limited to, InlA, InlB, InlC, InlC2, InlD, InlE, InlF, InlG, and InlH (Dramsi, et al., Infection and Immunity, 65: 1615-1625 (1997); Raffelsbauer et al., Mol. Gen. Genet. 260:144-158 (1988)). The gene sequences encoding these proteins have been previously reported. For instance, the sequences for both inlA and inlB have been reported in Gaillard et al., *Cell,* 65:1127-1141 (1991) and as GenBank accession number M67471. Genes encoding additional members of the internalin-related protein family are identified in Web Table 2 of the Supplementary Web material of Glaser et al., *Science,* 294: 849-852 (2001), including lmo0327, lmo0331, lmo0514, lmo0610, lmo0732, lmo1136, lmo1289, lmo2396, lmo0171, lmo0333, lmo0801, lmo1290, lmo2026, and lmo2821. (The sequences of each member of the internalin-related protein family can be found in the *L. monocytogenes* strain EGD genome, GenBank Accession no. AL591824, and/or in the *L. monocytogenes* strain EGD-e genome, GenBank Accession no. NC_003210. Locations of the various internalin-related genes are indicated in Glaser et al.).

InlA (internalin A) (Gaillard et al., *Cell*, 65:1127-1141 (1991); Genbank accession no. NC_003210) directs the uptake of *Listeria* by epithelial cells such as those of the intestines.

InlB (internalin B) (Gaillard et al., *Cell*, 65:1127-1141 (1991); Genbank accession number AL591975 (*Listeria monocytogenes* strain EGD, complete genome, segment 3/12, inlB gene region: nts. 97008-98963); and Genbank accession number NC_003210 (*Listeria monocytogenes* strain EGD, complete genome, inlB gene region: nts. 457008-458963), each of which is incorporated by reference herein in its entirety) directs the uptake of *Listeria* by hepatocytes or by endothelial cells such as the vascular endothelial cells of the brain microvasculature that comprise the blood brain barrier. (For further descriptions of internalin B, see Ireton, et al., *J. of Biological Chemistry*, 274: 17025-17032 (1999); Dramsi, et al., *Molecular Microbiology* 16:251-261 (1995); Mansell et al., *J. of Biological Chemistry*, 276: 43597-43603 (2001); and Bierne et al., *J. of Cell Science* 115:3357-3367 (2002), all of which are incorporated by reference herein in their entirety.)

In some embodiments, the bacterium is deficient with respect to ActA, internalin B, or both Act A and internalin B. In some embodiments, the bacterium is deleted in functional ActA, internalin B, or both ActA and internalin B. In some embodiments, the bacterium is deleted in functional ActA. In some embodiments, the bacterium is deleted in functional internalin B. In some embodiments, the bacterium is deleted in functional ActA and internalin B.

In vitro assays for determining whether or not a bacterium (e.g., a mutant *Listeria* strain) is attenuated for entry into non-phagocytic cells are known to those of ordinary skill in the art. For instance, both Dramsi et al., *Molecular Microbiology* 16:251-261 (1995) and Gaillard et al., *Cell* 65:1127-1141 (1991) describe assays for screening the ability of mutant *L. monocytogenes* strains to enter certain cell lines. For instance, to determine whether a *Listeria* bacterium with a particular modification is attenuated for entry into a particular type of non-phagocytic cells, the ability of the attenuated *Listeria* bacterium to enter a particular type of non-phagocytic cell is determined and compared to the ability of the identical *Listeria* bacterium without the modification to enter non-phagocytic cells. Likewise, to determine whether a *Listeria* strain with a particular mutation is attenuated for entry into a particular type of non-phagocytic cells, the ability of the mutant *Listeria* strain to enter a particular type of non-phagocytic cell is determined and compared to the ability of the *Listeria* strain without the mutation to enter non-phagocytic cells. In addition, confirmation that the strain is defective with respect to internalin B may also be obtained through comparison of the phenotype of the strain with the previously reported phenotypes for internalin B mutants.

In some embodiments, the attenuation of bacteria can be measured in terms of biological effects of the *Listeria* on a host. The pathogenicity of a bacterial strain can be assessed by measurement of the $LD_{50}$ in mice or other vertebrates. The $LD_{50}$ is the amount, or dosage, of *Listeria* injected into vertebrates necessary to cause death in 50% of the vertebrates. The $LD_{50}$ values can be compared for bacteria having a particular modification (e.g., mutation) versus the bacteria without the particular modification as a measure of the level of attenuation. For example, if the bacterial strain without a particular mutation has an $LD_{50}$ of $10^3$ bacteria and the bacterial strain having the particular mutation has an $LD_{50}$ of $10^5$ bacteria, the strain has been attenuated so that is $LD_{50}$ is increased 100-fold or by 2 log.

Alternatively, the degree of attenuation of the ability of a bacterium (e.g., a *Listeria* bacterium) to infect non-phagocytic cells can be assessed much more directly in vitro. For instance, the ability of a modified *Listeria* bacterium to infect non-phagocytic cells, such as hepatocytes, can be compared to the ability of non-modified *Listeria* or wild type *Listeria* to infect phagocytic cells. In such an assay, the modified and non-modified *Listeria* are typically added to the non-phagocytic cells in vitro for a limited period of time (for instance, an hour), the cells are then washed with a gentamicin-containing solution to kill any extracellular bacteria, the cells are lysed and then plated to assess titer. Examples of such an assay are found in U.S. patent publication No. 2004/0228877.

As a further example, the degree of attenuation may also be measured qualitatively by other biological effects, such as the extent of tissue pathology or serum liver enzyme levels. Alanine aminotransferase (ALT), aspartate aminotransferase (AST), albumin and bilirubin levels in the serum are determined at a clinical laboratory for mice injected with *Listeria* (or other bacteria). Comparisons of these effects in mice or other vertebrates can be made for *Listeria* with and without particular modifications/mutations as a way to assess the attenuation of the *Listeria*. Attenuation of the *Listeria* may also be measured by tissue pathology. The amount of *Listeria* that can be recovered from various tissues of an infected vertebrate, such as the liver, spleen and nervous system, can also be used as a measure of the level of attenuation by comparing these values in vertebrates injected with mutant versus non-mutant *Listeria*. For instance, the amount of *Listeria* that can be recovered from infected tissues such as liver or spleen as a function of time can be used as a measure of attenuation by comparing these values in mice injected with mutant vs. non-mutant *Listeria*.

Accordingly, the attenuation of the *Listeria* can be measured in terms of bacterial load in particular selected organs in mice known to be targets by wild-type *Listeria*. For example, the attenuation of the Listeria can be measured by enumerating the colonies (Colony Forming Units; CFU) arising from plating dilutions of liver or spleen homogenates (homogenized in $H_2O+0.2\%$ NP40) on BHI agar media. The liver or spleen cfu can be measured, for example, over a time course following administration of the modified *Listeria* via any number of routes, including intravenous, intraperitoneal, intramuscular, and subcutaneous. Additionally, the *Listeria* can be measured and compared to a drug-resistant, wild type *Listeria* (or any other selected *Listeria* strain) in the liver and spleen (or any other selected organ) over a time course following administration by the competitive index assay, as described.

The degree of attenuation in uptake of the attenuated bacteria by non-phagocytic cells need not be an absolute attenuation in order to provide a safe and effective vaccine. In some embodiments, the degree of attenuation is one that provides for a reduction in toxicity sufficient to prevent or reduce the symptoms of toxicity to levels that are not life threatening.

In some embodiments of the invention, the bacterium that comprises a recombinant nucleic acid molecule, expression cassette and/or expression vector described herein is a mutant strain of *Listeria*. In further embodiments, the bacterium is an attenuated mutant strain of *Listeria monocytogenes*. A variety of exemplary mutant strains of *Listeria* that are attenuated are described in the U.S. Patent Application Nos. 60/446,051 (filed Feb. 6, 2003), 60/449,153 (filed Feb. 21, 2003), 60/511, 719 (filed Oct. 15, 2003), 60/511,919 (filed Oct. 15, 2003), 60/511,869 (filed Oct. 15, 2003), 60/541,515 (filed Feb. 2, 2004), and Ser. No. 10/883,599 (filed Jun. 30, 2004), as well as in U.S. patent Publication Nos. 2004/0197343 and US 2004/0228877, each of which is incorporated by reference herein in its entirety. Mutant strains of *Listeria* are also described in the International Application No. PCT/US2004/23881, filed Jul. 23, 2004, which is incorporated by reference herein in its entirety. For instance, the bacterium that comprise the expression cassette and/or vector is optionally a mutant strain of *Listeria monocytogenes* that is defective with respect to ActA or internalin B, or both ActA and internalin B. In some embodiments, the bacterium is a mutant strain of *Listeria monocytogenes* that is actA$^-$ (e.g., DP-L4029 (the DP-L3078 strain described in Skoble et al., *J. of Cell Biology*, 150: 527-537 (2000), incorporated by reference herein in its entirety, which has been cured of its prophage as described in (Lauer et al., *J. Bacteriol.* 184:4177 (2002); U.S. patent Publication No. 2003/0203472)), actA$^-$inlB$^-$ (e.g., DP-L4029inlB, deposited with the American Type Culture Collection (ATCC), 10801 University Blvd., Manassas, Va. 20110-2209, United States of America, on Oct. 3, 2003, under the provisions of the Budapest Treaty on the International Recognition of the Deposit of Microorganisms for the Purposes of Patent Procedure, and designated with accession number PTA-5562), actA$^-$uvrAB$^-$ (e.g., DP-L4029uvrAB, deposited with the American Type Culture Collection (ATCC), 10801 University Blvd., Manassas, Va. 20110-2209, United States of America, on Oct. 3, 2003, under the provisions of the Budapest Treaty on the International Recognition of the Deposit of Microorganisms for the Purposes of Patent Procedure, and designated with accession number PTA-5563), or actA$^-$inlB$^-$uvrAB$^-$. In some embodiments, the attenuated *Listeria* bacterium (e.g., a *Listeria monocytogenes* bacterium) is an ΔactAΔinlB double deletion mutant.

Bacterial mutations can be achieved through traditional mutagenic methods, such as mutagenic chemicals or radiation followed by selection of mutants. Bacterial mutations can also be achieved by one of skill in the art through recombinant DNA technology. For instance, the method of allelic exchange using the pKSV7 vector described in Camilli et al., *Molecular Micro.* 8:143-157 (1993) and described above with respect to the introduction of heterologous expression cassettes in bacterial genomes is suitable for use in generating mutants including deletion mutants. (Camilli et al. (1993) is incorporated by reference herein in its entirety.) One exemplary example of the production of a *Listeria monocytogenes* internalin B mutant using the pKSV7 vector is provided in Example 24, below. Alternatively, the gene replacement protocol described in Biswas et al., *J. Bacteriol.* 175:3628-3635 (1993), can be used. Other similar methods are known to those of ordinary skill in the art.

The construction of a variety of bacterial mutants is described in U.S. patent application Ser. No. 10/883,599, U.S. patent Publication No. 2004/0197343, and U.S. patent Publication No. 2004/0228877, each of which is incorporated by reference herein in its entirety.

In some embodiments of the invention, the bacterium that comprises the recombinant nucleic acid molecule, expression cassette and/or expression vector is a mutant strain of *Bacillus anthracis*. In some embodiments, the bacterium is the Sterne strain. In some embodiments, the bacterium is the Ames strain. In some embodiments, the *Bacillus anthracis* bacterium is a uvrAB mutant. In some embodiments, the *Bacillus anthracis* strain is a uvrC mutant. In some embodiments, the *Bacillus anthracis* mutant is a recA mutant. In some embodiments, the bacterium is a ΔuvrAB mutant of the *Bacillus anthracis* (e.g., the *Bacillus anthracis* Sterne ΔuvrAB mutant deposited with the American Type Culture Collection (ATCC), 108011 University Blvd., Manassas, Va. 20110-2209, United States of America, on Feb. 20, 2004, under the provisions of the Budapest Treaty on the International Recognition of the Deposit of Microorganisms for the Purposes of Patent Procedure, and designated with accession number PTA-5825).

Methods of altering the genome of *Bacillus anthracis* are known to those skilled in the art. One method of generating mutations in *Bacillus anthracis* is by allelic exchange using an allelic exchange vector known to those in the art. An exemplary allelic exchange plasmid is pKSV7 described in Camilli et al., Molecular Microbiology, 8:143-147 (1993). As a first step in generating a mutant *Bacillus anthracis*, the region of the genome to be deleted or otherwise mutated and approximately 1000 bps both upstream and downstream of the *B. anthracis* genome is PCR-amplified and then cloned into the pKSV7 plasmid vector (or an analogous vector). (A *Bacillus* genera-specific or *B. anthracis*-specific temperature (ts) replicon may be substituted for the *Listeria* ts replicon present in the pKSV7 allelic exchange plasmid vector.) Restriction endonuclease recognition sites in the region to be deleted or mutated may be used to delete the desired portion of the targeted gene in the region. Alternatively, a portion of the targeted gene within the region may be removed and replaced with sequences containing the desired mutation or other alteration. The region of the *B. anthracis* genome that is amplified can be altered, for instance, using restriction enzymes or a combination of restriction enzymes and synthetic gene sequences, before or after cloning into the allelic exchange plasmid. In some embodiments, the sequence may be altered as a PCR amplicon and then cloned into pKSV7. In alternative embodiments, the amplicon is first inserted into another plasmid first and then altered, excised, and inserted into pKSV7. Alternatively, the PCR amplicon is inserted directly into the pKSV7 plasmid and then altered, for instance, using convenient restriction enzymes. The pKSV7 plasmid containing the altered sequence is then introduced into *B. anthracis*. This can be done via electroporation. The bacteria are then selected on media at a permissive temperature in the presence of chloramphenicol. This is followed by selection for single cross-over integration into the bacterial chromosome by passaging for multiple generations at a non-permissive temperature in the presence of chloramphenicol. Lastly, colonies are passaged for multiple generations at the permissive temperature in media not containing the antibiotic to achieve plasmid excision and curing (double cross-over). The U.S. Provisional Application Ser. Nos. 60/584,886, and 60/599,522, and U.S. patent Publication No. 2004/0197343, incorporated by reference herein in their entirety, provide additional description regarding the construction of different types of *Bacillus anthracis* mutants.

In some embodiments of the invention, the bacterium that comprises the recombinant nucleic acid molecule, expression cassette, and/or expression vector is a bacterium that has been modified so that the bacterium is attenuated for proliferation (relative to the non-modified bacterium). Preferably, the modified bacterium maintains a sufficient level of gene expression despite the modification. For instance, in some embodiments the gene expression level is substantially unaffected by the modification so that an antigen is expressed at a level sufficient to stimulate an immune response to the antigen upon administration of the bacterium expressing the antigen to a host. In some embodiments, the nucleic acid of the bacterium has been modified by reaction with a nucleic acid targeting compound. In some embodiments, the nucleic acid of the modified bacterium has been modified by reaction with a nucleic acid targeting compound that reacts directly with the nucleic acid so that proliferation of the bacterium is attenuated. In some embodiments, the nucleic-acid targeting compound is a nucleic acid alkylator, such as β-alanine, N-(acridin-9-yl), 2-[bis(2-chloroethyl)amino]ethyl ester. In some embodiments, the nucleic acid targeting compound is activated by irradiation, such as UVA irradiation. In some embodiments, the bacterium has been treated with a psoralen compound. For instance, in some embodiments, the bacterium has been modified by treatment with a psoralen, such as 4'-(4-amino-2-oxa)butyl-4,5',8-trimethylpsoralen ("S-59"), and UVA light. In some embodiments, the nucleic acid of the bacterium has been modified by treatment with a psoralen compound and UVA irradiation. Descriptions of methods of modifying bacteria to attenuate them for proliferation using nucleic acid targeting compounds are described in each of the following U.S. patent applications or publications, each of which is incorporated by reference herein in its entirety: 60/446,051 (filed Feb. 6, 2003), 60/449,153 (filed Feb. 21, 2003), 60/490,089 (filed Jul. 24, 2003), 60/511,869 (filed Oct. 15, 2003), 60/541,515 (filed Feb. 2, 2004), 10/883,599 (filed Jun. 30, 2004), and US 2004/0197343. Modified bacteria and their uses are also described in International Application No. PCT/US2004/23881, filed Jul. 23, 2004, incorporated by reference herein in its entirety.

For example, for treatment of ΔactAΔuvrAB *L. monocytogenes*, in some embodiments, S-59 psoralen can be added to 200 nM in a log-phase culture of (approximately) $OD_{600}=0.5$, followed by inactivation with 6 $J/m^2$ of UVA light when the culture reaches an optical density of one. Inactivation conditions are optimized by varying concentrations of S-59, UVA dose, the time of S-59 exposure prior to UVA treatment as well as varying the time of treatment during bacterial growth of the *Listeria* actA/uvrAB strain. The parental *Listeria* strain is used as a control. Inactivation of *Listeria* (log-kill) is determined by the inability of the bacteria to form colonies on BHI (Brain heart infusion) agar plates. In addition, one can confirm the expression of a heterologous protein and virulence factors, such as LLO and p60, of the S-59/UVA inactivated *Listeria* using $^{35}$S-pulse-chase experiments to determine the synthesis and secretion of newly expressed proteins post S-59/UVA inactivation. Expression of LLO and p60 using $^{35}$S-metabolic labeling can be routinely determined. S-59/UVA inactivated *Listeria* actA/uvrAB can be incubated for 1 hour in the presence of $^{35}$S-Methionine. Antigen expression and secretion of the heterologous protein, endogenous LLO, and p60 can be determined of both whole cell lysates, and TCA precipitation of bacterial culture fluids. LLO-, p60- and heterologous protein-specific monoclonal antibodies can be used for immunoprecipitation to verify the continued expression and secretion from recombinant Listeria post inactivation.

In some embodiments, the bacteria attenuated for proliferation are also attenuated for nucleic acid repair and/or are defective with respect to at least one DNA repair enzyme. For instance, in some embodiments, the bacterium in which nucleic acid has been modified by a nucleic acid targeting compound such as a psoralen (combined with UVA treatment) is a uvrAB deletion mutant.

In some embodiments, the proliferation of the bacteria is attenuated by at least about 0.3 log, also at least about 1 log, about 2 log, about 3 log, about 4 log, about 6 log, or at least about 8 log. In another embodiment, the proliferation of the bacteria is attenuated by about 0.3 to >10 log, about 2 to >10 log, about 4 to >10 log, about 6 to >10 log, about 0.3-8 log, about 0.3-6 log, about 0.3-5 log, about 1-5 log, or about 2-5 log. In some embodiments, the expression of an antigen by the bacteria are at least about 10%, about 25%, about 50%, about 75%, or at least about 90% of the expression of the antigen by bacteria in which the bacterial nucleic acid is not modified.

In some embodiments, the nucleic acid of the bacterium has not been modified by reaction with a nucleic acid targeting compound. In some embodiments, the recombinant bacterium has not been attenuated for proliferation. In some embodiments, the recombinant bacterium is not attenuated in its ability for nucleic acid repair. In some embodiments, the recombinant bacterium is not deficient with respect to at least one DNA repair enzyme.

In some embodiments, the signal peptide encoded by first polynucleotide in the recombinant nucleic acid molecule, expression cassette, and/or expression vector contained within the recombinant bacterium is native to the recombinant bacterium. In some embodiments, the polynucleotide encoding the signal peptide that is native to the recombinant bacterium has been codon-optimized for expression in the recombinant bacterium. In some embodiments, the polynucleotide has been fully codon-optimized. In some embodiments, the signal peptide encoded by the first polynucleotide of the recombinant nucleic acid molecule, expression cassette, and/or expression vector contained within the recombinant bacterium is foreign to the host recombinant bacterium. In some embodiments, the polynucleotide encoding the signal peptide that is foreign to the host recombinant bacterium has been codon-optimized for expression in the recombinant bacterium.

In some embodiments, the second polynucleotide in the recombinant nucleic acid molecule, expression cassette, and/or expression vector within the recombinant bacterium has been codon-optimized for expression in the recombinant bacterium. In some embodiments, the second polynucleotide has been fully codon-optimized for expression in the recombinant bacterium. In some embodiments, both the first and second polynucleotides within the recombinant bacterium have been codon-optimized for expression in the recombinant bacterium. In some embodiments, both the first and second polynucleotides within the recombinant bacterium have been fully codon-optimized for expression in the recombinant bacterium.

In one aspect, the invention provides a bacterium comprising an expression cassette, wherein the expression cassette comprises (a) a first polynucleotide encoding a signal peptide, wherein the first polynucleotide is codon-optimized for expression in the bacterium; (b) a second polynucleotide encoding a polypeptide, wherein the second polynucleotide is in the same translational reading frame as the first polynucleotide; and (c) a promoter operably linked to the first and second polynucleotides, wherein the expression cassette encodes a fusion protein comprising the signal peptide and the polypeptide. As described herein, e.g., in Section III, in some embodiments, the signal peptide that is encoded is a derived from bacteria. In some embodiments, the bacterial signal peptide encoded by the expression cassette is derived from the bacteria of the same genus and/or species as the bacterium comprising the expression cassette. In some embodiments, the signal peptide is native to the host recombinant bacterium. In other embodiments, the bacterial signal peptide encoded by the expression cassette is derived from bacteria of a different genus and/or species as the bacterium comprising the expression cassette. In some embodiments, the signal peptide is foreign to the host recombinant bacterium. In some embodiments the signal peptide is a secA1, secA2, or a Tat signal peptide. In some embodiments the polypeptide encoded by the second polynucleotide is heterologous (i.e., foreign) to the bacterium.

In another aspect, the invention provides a bacterium comprising a recombinant nucleic acid molecule, comprising (a) a first polynucleotide encoding a signal peptide native to the bacterium, wherein the first polynucleotide is codon-optimized for expression in the bacterium, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the bacterium is an intracellular bacterium. In some embodiments, the recombinant nucleic acid molecule is part of an expression cassette that further comprises a promoter operably linked to both the first and second polynucleotides. In some embodiments, the bacterium is selected from the group consisting of *Listeria, Bacillus, Yersinia pestis, Salmonella, Shigella, Brucella*, mycobacteria and *E. coli*. In some embodiments, the bacterium is *Listeria* (e.g., *Listeria monocytogenes*).

In another aspect, the invention provides a recombinant *Listeria* bacterium (e.g., *Listeria monocytogenes*) comprising a recombinant nucleic acid molecule, wherein the recombinant nucleic acid molecule comprises (a) a first polynucleotide encoding a signal peptide, wherein the first polynucleotide is codon-optimized for expression in the *Listeria* bacterium, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the recombinant nucleic acid molecule is part of an expression cassette that further comprises a promoter operably linked to both the first and second polynucleotides. In some embodiments, the second polynucleotide is codon-optimized for expression in the *Listeria* bacterium. In some embodiments, the polypeptide encoded by the second polynucleotide is foreign to the *Listeria* bacterium (i.e., heterologous to the *Listeria* bacterium). In some embodiments, the *Listeria* bacterium is attenuated. For instance, the *Listeria* may be attenuated for cell-to-cell spread, entry into non-phagocytic cells, or proliferation. In some embodiments, the recombinant *Listeria* bacterium is deficient with respect to ActA, Internalin B, or both Act A and Internalin B (e.g., an ΔactAΔinlB double deletion mutant). In some embodiments, the nucleic acid of the recombinant bacterium has been modified by reaction with a nucleic acid targeting compound (e.g., a psoralen compound).

In another aspect, the invention provides a bacterium comprising a recombinant nucleic acid molecule, wherein the recombinant nucleic acid molecule comprises a first polynucleotide encoding a non-secA1 bacterial signal peptide, and a second polynucleotide encoding a polypeptide (e.g., an antigen), wherein the second polynucleotide is in the same translational reading frame as the first polynucleotide, and wherein the recombinant nucleic acid molecule encodes a fusion protein comprising the signal peptide and the polypeptide. In some embodiments, the polypeptide encoded by the second polynucleotide is heterologous to the signal peptide. In some embodiments, the recombinant nucleic acid molecule is part of an expression cassette that further comprises a promoter operably linked to both the first and second polynucleotides. In some embodiments, the bacterium is a bacterium selected from the group consisting of *Listeria, Bacillus, Yersinia pestis, Salmonella, Shigella, Brucella*, mycobacteria or *E. coli*. In some embodiments, the polypeptide encoded by the second polynucleotide is foreign to the bacterium (i.e., heterologous to the bacterium).

In another aspect, the invention provides a bacterium comprising an expression cassette, wherein the expression cassette comprises (a) a first polynucleotide encoding a non-secA1 bacterial signal peptide; (b) a second polynucleotide encoding a polypeptide (e.g., a polypeptide heterologous to the bacterium) in the same translational reading frame as the first polynucleotide; and (c) a promoter operably linked to the first and second polynucleotides, wherein the expression cassette encodes a fusion protein comprising the signal peptide and the polypeptide. As described herein, e.g., in Section III, above, in some embodiments, the non-secA1 bacterial signal peptide is a secA2 signal peptide. In some other embodiments, the non-secA1 bacterial signal peptide is a Tat signal peptide. In some embodiments, the bacterial signal peptide encoded by the expression cassette is derived from the bacteria of the same genus and/or species as the bacterium comprising the expression cassette. In other embodiments, the bacterial signal peptide encoded by the expression cassette is derived from bacteria of a different genus and/or species as the bacterium comprising the expression cassette.

In another aspect, the invention provides a recombinant *Listeria* bacterium comprising a recombinant nucleic acid molecule, wherein the recombinant nucleic acid molecule comprises (a) a first polynucleotide encoding a non-secA1 bacterial signal peptide, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide. In some embodiments, the recombinant nucleic acid molecule is part of an expression cassette that further comprises a promoter operably linked to both the first and second polynucleotides. In some embodiments, the *Listeria* bacterium is attenuated. In some embodiments, the *Listeria* bacterium is a *Listeria monocytogenes* bacterium. For instance, the *Listeria* may be attenuated for cell-to-cell spread, entry into non-phagocytic cells, or proliferation. In some embodiments, the recombinant *Listeria* bacterium is deficient with respect to ActA, Internalin B, or both Act A and Internalin B (e.g., an ΔactAΔinlB double deletion mutant). In some embodiments, the nucleic acid of the recombinant bacterium has been modified by reaction with a nucleic acid targeting compound (e.g., a psoralen compound).

In an another aspect, the invention provides a recombinant *Listeria* bacterium comprising a recombinant nucleic acid molecule, wherein the recombinant nucleic acid molecule comprises a polynucleotide encoding a polypeptide foreign to the *Listeria* bacterium, wherein the polynucleotide is codon-optimized for expression in *Listeria*.

In an additional aspect, the invention provides a recombinant *Listeria* bacterium comprising an expression cassette, wherein the expression cassette comprises the following: (a) a polynucleotide encoding a polypeptide foreign to the *Listeria* bacterium, wherein the polynucleotide is codon-optimized for expression in *Listeria*; and (b) a promoter, operably linked to the polynucleotide encoding the foreign polypeptide. Again, in some embodiments, the *Listeria* is *Listeria monocytogenes*. In other embodiments the *Listeria* bacterium belongs to the *Listeria ivanovii, Listeria seeligeri*, or *Listeria innocua* species. In some embodiments, the *Listeria* bacterium is an attenuated strain of *Listeria* bacterium as described above.

In a further aspect, the invention provides a recombinant *Listeria* bacterium (e.g., *Listeria monocytogenes*) comprising a recombinant nucleic acid molecule, wherein the recombinant nucleic acid molecule comprises (a) a first polynucleotide encoding a non-Listerial signal peptide; and (b) a second polynucleotide encoding a polypeptide that is in the same translational reading frame as the first polynucleotide, wherein the recombinant nucleic acid molecule encodes a fusion protein comprising both the non-Listerial signal peptide and the polypeptide. In some embodiments, the *Listeria* bacterium is attenuated. For instance, the *Listeria* may be attenuated for cell-to-cell spread, entry into non-phagocytic cells, or proliferation. In some embodiments, the recombinant *Listeria* bacterium is deficient with respect to ActA, Internalin B, or both Act A and Internalin B (e.g., an ΔactAΔ-inlB double deletion mutant). In some embodiments, the nucleic acid of the recombinant bacterium has been modified by reaction with a nucleic acid targeting compound (e.g., a psoralen compound).

In still another aspect, the invention provides a recombinant *Listeria* bacterium (for instance, from the species *Listeria monocytogenes*) comprising an expression cassette which comprises a first polynucleotide encoding a non-Listerial signal peptide, a second polynucleotide encoding a polypeptide (e.g., a non-Listerial polypeptide) that is in the same translational reading frame as the first polynucleotide, and a promoter operably linked to both the first and second polynucleotides. The expression cassette encodes a fusion protein comprising both the non-Listerial signal peptide and the polypeptide. In some embodiments, the *Listeria* bacterium is attenuated for cell-to-cell spread, entry into non-phagocytic cells, or proliferation. In some embodiments, the *Listeria* bacterium is deficient with respect to ActA, Internalin B, or both ActA and Internalin B. In some embodiments, the nucleic acid of the recombinant bacterium has been modified by reaction with a nucleic acid targeting compound (e.g., a psoralen compound). In some embodiments, the first polynucleotide, the second polynucleotide, or both the first and second polynucleotides are codon-optimized for expression in *Listeria*. In some embodiments, the first polynucleotide and/or second polynucleotide is codon-optimized for expression in *Listeria monocytogenes*. In some embodiments, the polypeptide encoded by the second polynucleotide is an antigen, which, in some instances, may be a non-bacterial antigen. For instance, the polypeptide is, in some embodiments a tumor-associated antigen or is derived from such a tumor-associated antigen. For instance, in some embodiments, the polypeptide is K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA, or is derived from K-Ras, H-Ras, N-Ras, 12-K-Ras, mesothelin, PSCA, NY-ESO-1, WT-1, survivin, gp100, PAP, proteinase 3, SPAS-1, SP-17, PAGE-4, TARP, or CEA. For instance, in some embodiments, the polypeptide is mesothelin, or is a fragment or variant of mesothelin. In some other embodiments, the polypeptide is NY-ESO-1, or a fragment or variant of mesothelin. In some embodiments, the antigen is an infectious disease antigen or is derived from an infectious disease antigen. In preferred embodiments, the signal peptide is bacterial. In some embodiments, the signal peptide is from a bacterium belonging to the genus *Bacillus, Staphylococcus*, or *Lactococcus*. For instance, in some embodiments, the signal peptide is from *Bacillus anthracis, Bacillus subtilis, Staphylococcus aureus*, or *Lactococcus lactis*. In some embodiments, the signal peptide is a secA1 signal peptide, such as a Usp45 signal peptide from Lactococcus lactis or a Protective Antigen signal peptide from Bacillus anthracis. In some embodiments, the signal peptide is a secA2 signal peptide. In still further embodiments, the signal peptide is a Tat signal peptide, such as a *B. subtilis* Tat signal peptide (e.g., PhoD).

The invention further provides a recombinant bacterium comprising a recombinant nucleic acid molecule, wherein the recombinant nucleic acid molecule comprises: (a) a first polynucleotide encoding a bacterial autolysin, or a catalytically active fragment or catalytically active variant thereof; and (b) a second polynucleotide encoding a polypeptide, wherein the second polynucleotide is in the same translational reading frame as the first polynucleotide, wherein the recombinant nucleic acid molecule encodes a protein chimera comprising the polypeptide encoded by the second polynucleotide and the autolysin, or catalytically active fragment or catalytically active variant thereof, wherein, in the protein chimera, the polypeptide is fused to the autolysin, or catalytically active fragment or catalytically active variant thereof, or is positioned within the autolysin, or catalytically active fragment or catalytically active variant thereof. In some embodiments, the recombinant bacterium is an intracellular bacterium, such as a *Listeria* bacterium (e.g., *Listeria monocytogenes*). In some embodiments, the polypeptide encoded by the second polynucleotide is foreign to the recombinant bacterium.

In yet another aspect, the invention provides a recombinant *Listeria* bacterium comprising a polycistronic expression cassette, wherein the polycistronic expression cassette encodes at least two discrete non-Listerial polypeptides. For instance, in some embodiments, the expression cassette comprises a first polynucleotide encoding the first non-Listerial polypeptide, a second polynculeotide encoding the second non-Listerial polypeptide, and a promoter operably linked to the first and second polynucleotides. In some embodiments, the recombinant *Listeria* bacterium belongs to the species *Listeria monocytogenes*. In some embodiments, the first and/or second non-Listerial polypeptides comprise antigens (or fragments thereof).

In some embodiments, the invention provides a recombinant bacterium (e.g., *Listeria*) comprising an expression cassette comprising the following: (a) a first polynucleotide encoding a first signal peptide; (b) a second polynucleotide encoding a first polypeptide, wherein the second polynucleotide is in the same translational reading frame as the first polynucleotide; (c) an intergenic sequence; (d) a third polynucleotide encoding a second signal peptide; (e) a fourth polynucleotide encoding a second polypeptide, wherein the fourth polynucleotide is in the same translational reading frame as the third polynucleotide; and (f) a promoter operably linked to the first polynucleotide, second polynucleotide, third polynucleotide, fourth polynucleotide, and intergenic sequence, such that the expression cassette encodes both a first fusion protein comprising the first signal peptide and the first polypeptide and a second fusion protein comprising the second signal peptide and second polypeptide. In some embodiments, the one or more of the polynucleotides encoding a signal peptide is codon-optimized for expression in the bacterium. In some embodiments, the third and/or fourth polynucleotides are codon-optimized for expression in the bacterium. In some embodiments, the first and/or second polypeptides are heterologous to the recombinant bacterium (e.g., heterologous antigens). In some embodiments, the first and/or second signal peptide is a non-secA1 bacterial signal peptide. The first and/or second signal peptide may be native or foreign to the recombinant bacterium. In some embodiments, the recombinant bacterium is a *Listeria* bacterium and the first and/or second signal peptide is non-Listerial. In some embodiments, the intergenic sequence is the *Listeria monocytogenes* actA-plcB intergenic sequence. In some embodiments, the bacterium is *Listeria monocytogenes.*

In other aspects, the invention provides a bacterium comprising a recombinant nucleic acid molecule, comprising (a)

a first polynucleotide encoding a signal peptide, (b) a second polynucleotide encoding a secreted protein, or a fragment thereof, wherein the second polynucleotide is in the same translational reading frame as the first polynucleotide, and (c) a third polynucleotide encoding a polypeptide heterologous to the secreted protein, or fragment thereof, wherein the third polynucleotide is in the same translational reading frame as the first and second polynucleotides, and wherein the recombinant nucleic acid molecule encodes a protein chimera comprising the signal peptide, the polypeptide encoded by the second polynucleotide, and the secreted protein, or fragment thereof, and wherein the polypeptide is fused to the secreted protein, or fragment thereof, or is positioned within the secreted protein, or fragment thereof, in the protein chimera. In some embodiments, the bacterium is a *Listeria* bacterium. In some embodiments, where the bacterium is a *Listeria* bacterium, the polypeptide encoded by the third polynucleotide is foreign to the *Listeria*. In some embodiments, the bacterium is *Listeria monocytogenes.*

In some embodiments (for instance, in some embodiments of each of the aforementioned aspects), the expression cassette contained within the bacterium is integrated into the genome of the bacterium. In other embodiments, the expression cassette contained within the bacterium is on a plasmid within the bacterium.

Generally, the promoter that is used in the expression cassette will be an expression cassette that is suitable for effecting heterologous expression with the particular bacterial host chosen. One of ordinary skill in the art can readily discern which promoters are suitable for use in which bacteria. In some embodiments, the promoter is a bacterial promoter. In additional embodiments, the promoter on the expression cassette in the bacterium is a promoter from bacteria belonging to the same genus as the bacterium which contains the expression cassette. In other embodiments, the promoter on the expression cassette in the bacterium is a promoter from bacteria belonging to the same species as the bacterium which contains the expression cassette. For instance, if the bacterium which contains the expression cassette belongs to the species *Listeria monocytogenes*, then the promoter that is used on the expression cassette is optionally derived from a Listerial gene such as hly. In other embodiments, the promoter is a constitutive promoter (e.g., a p60 promoter) or is prfA-dependent promoter (e.g. an actA promoter). Again, as described above, the promoter of the expression cassette is, in some embodiments, a constitutive promoter. In other embodiments, the promoter of the expression cassette is an inducible promoter, as also described above.

In some embodiments (for instance, in some embodiments of each of the aforementioned aspects), the polypeptides or fusion proteins comprising the polypeptides that are encoded by the expression cassettes in the bacteria are antigens or other proteins of therapeutic value, as described, for instance, above in Section IV. In some embodiments, the polypeptide or a protein comprising the polypeptide is secreted from the bacterium. In some embodiments the polypeptide that is expressed and/or secreted from the bacterium is heterologous to the bacterium.

In some embodiments, therefore, the invention provides recombinant Listeria comprising an expression cassette, wherein the expression cassette comprises (a) a first polynucleotide encoding a bacterial (either Listerial or non-Listerial) signal peptide, wherein the first polynucleotide is codon-optimized for expression in *Listeria*; (b) a second polynucleotide encoding a non-Listerial antigen, wherein the second polynucleotide is in the same translational reading frame as the first polynucleotide; and (c) a promoter operably linked to the first and second polynucleotides, wherein the expression cassette encodes a fusion protein comprising the signal peptide and the antigen. In further embodiments, the *Listeria* is a strain of *Listeria monocytogenes*, such as an $actA^-inlB^-$ strain. In some embodiments, the expression cassette has been integrated into the genome of the recombinant *Listeria*. In some embodiments, the second polynucleotide is codon-optimized for expression in *Listeria.*

The invention also provides Listeria comprising an expression cassette, wherein the expression cassette comprises (a) a first polynucleotide encoding a secA2 or Tat bacterial signal peptide; (b) a second polynucleotide encoding an antigen in the same translational reading frame as the first polynucleotide; and (c) a promoter operably linked to the first and second polynucleotides, wherein the expression cassette encodes a fusion protein comprising the signal peptide and the antigen. In some embodiments, the bacterial signal peptide is Listerial. In other embodiments, the bacterial signal peptide is non-Listerial. In further embodiments, the *Listeria* is a strain of *Listeria monocytogenes*, such as an $actA^-inlB^-$ strain. In some embodiments, the expression cassette has been integrated into the genome of the recombinant *Listeria*. In some embodiments, either the polynucleotide encoding the signal peptide (even if the signal peptide is a Listerial signal peptide) and/or the polynucleotide encoding the antigen is codon-optimized for expression in *Listeria.*

In further embodiments, the invention provides recombinant *Listeria* comprising an expression cassette, where the expression cassette comprises the following: (a) a polynucleotide encoding a non-Listerial antigen, wherein the polynucleotide is codon-optimized for expression in *Listeria*; and (b) a promoter, operably linked to the polynucleotide encoding the foreign polypeptide. In some embodiments, the expression cassette further comprises a polynucleotide encoding a bacterial signal peptide, which is also codon-optimized for expression in Listeria. In one embodiment, the bacterial signal peptide is Listerial. In another embodiment, the bacterial signal peptide is non-Listerial. In some embodiments the bacterial signal peptide is a secA1 signal peptide, a secA2 signal peptide, or a Tat signal peptide. In further embodiments, the *Listeria* is a strain of *Listeria monocytogenes*, such as an $actA^-inlB^-$ strain. In some embodiments, the expression cassette has been integrated into the genome of the recombinant *Listeria.*

In still another embodiment, the invention provides a recombinant *Listeria* bacterium, comprising (a) a first polynucleotide encoding a bacterial (either Listerial or non-Listerial) signal peptide, wherein the first polynucleotide is codon-optimized for expression in *Listeria*; (b) a second polynucleotide encoding an non-Listerial antigen, wherein the second polynucleotide is also codon-optimized for expression in *Listeria* and is in the same translational reading frame as the first polynucleotide; and (c) a promoter operably linked to the first and second polynucleotides, wherein the expression cassette encodes a fusion protein comprising the signal peptide and the antigen. In some embodiments, the *Listeria* bacterium belongs to the species *Listeria* monocytogenes. In some embodiments, the *Listeria* bacterium is an $actA^-inlB^-$ mutant strain of *Listeria monocytogenes.*

The present invention further provides bacteria such as *Listeria* comprising more than one expression cassette described herein. In particular compositions, the molecular mass of a given protein can inhibit its expression from recombinant bacteria, such as recombinant *Listeria*. One approach to address this problem is to molecularly "divide" the gene encoding a protein of interest and fuse each division functionally to a sequence that will program its secretion from the bacterium (e.g., secA1, secA2, or Tat elements). One approach is to individually derive recombinant *Listeria* expressing each division of the heterologous gene. Alternatively, the individually components of the molecularly divided gene (also including appropriate elements for secretion) can be introduced into intergenic regions throughout the bacterial chromosome, using methods well established in the art, for example by allelic exchange. Another example is to express the molecularly divided gene as a single polycistronic message. According to this composition, interspersed between the protein-encoding sequence of the molecularly divided gene would be the Shine-Dalgarno ribosome binding sequence, in order to re-initiate protein synthesis on the polycistronic message.

In additional aspects, the invention provides methods of improving expression and/or secretion of heterologous polypeptides in recombinant bacteria such as *Listeria*. Any of the polynucleotides, expression cassettes and/or expression vectors described herein may be used in these methods. For instance, the invention provides a method of improving expression and/or secretion of a heterologous polypeptide fused to a signal peptide in *Listeria*, comprising codon-optimizing either the polypeptide-encoding sequence on the expression cassette, the signal peptide-encoding sequence of the expression cassette, or both. The invention also provides a method of improving expression and/or secretion of a heterologous polypeptide fused to a signal peptide in *Listeria*, comprising using a signal peptide from a non-Listerial source and/or from a secretory pathway other than secA1.

The invention also provides a method of producing a recombinant bacterium (e.g. a recombinant *Listeria* bacterium) comprising introducing a recombinant nucleic acid molecule, expression cassette, and/or expression vector described herein into a bacterium to produce the recombinant bacterium. For instance, in some embodiments, a recombinant nucleic acid molecule comprising (a) a first polynucleotide encoding a signal peptide native to a bacterium, wherein the first polynucleotide is codon-optimized for expression in the bacterium, and (b) a second polynucleotide encoding a polypeptide, wherein the second polynucleotide is in the same translational reading frame as the first polynucleotide, wherein the recombinant nucleic acid molecule encodes a fusion protein comprising the signal peptide and the polypeptide, is introduced into a bacterium to produce the recombinant bacterium. In some embodiments, a recombinant nucleic acid molecule, comprising (a) a first polynucleotide encoding a non-secA1 bacterial signal peptide, and (b) a second polynucleotide encoding a polypeptide, wherein the second polynucleotide is in the same translational reading frame as the first polynucleotide, and wherein the recombinant nucleic acid molecule encodes a fusion protein comprising the signal peptide and the polypeptide, is introduced into a bacterium to produce the recombinant bacterium. In some embodiments, the recombinant nucleic acid molecule that is introduced into a bacterium to produce the recombinant bacterium is a recombinant nucleic acid molecule, wherein the recombinant nucleic acid molecule comprises (a) a first polynucleotide encoding a non-Listerial signal peptide, and (b) a second polynucleotide encoding a polypeptide that is in the same translational reading frame as the first polynucleotide, wherein the recombinant nucleic acid molecule encodes a fusion protein comprising both the non-Listerial signal peptide and the polypeptide. The recombinant nucleic acid molecule used to produce the recombinant bacterium is, in some embodiments, a recombinant nucleic acid molecule, comprising (a) a first polynucleotide encoding a bacterial autolysin, or catalytically active fragment or catalytically active variant thereof, and (b) a second polynucleotide encoding a polypeptide, wherein the second polynucleotide is in the same translational reading frame as the first polynucleotide, wherein the recombinant nucleic acid molecule encodes a protein chimera in which the non-Listerial polypeptide is fused to the autolysin, or catalytically active fragment or catalytically active variant thereof, or is inserted within the autolysin, or catalytically active fragment or catalytically active variant thereof. In some other embodiments, a method of producing a recombinant *Listeria* bacterium is provided, which comprises introducing a polycistronic expression cassette, wherein the expression cassette encodes at least two discrete non-Listerial polypeptides, into a *Listeria* bacterium to produce the recombinant *Listeria* bacterium.

IX. Pharmaceutical, Immunogenic, and/or Vaccine Compositions

A variety of different compositions such as pharmaceutical compositions, immunogenic compositions, and vaccines are also provided by the invention. These compositions comprise any of the recombinant bacteria described herein (see, e.g., the Summary of the Invention, Sections I and VIII of the Detailed Description, above, and elsewhere in the specification, including the Examples, below). In some embodiments, the compositions are isolated.

For instance, the invention provides a pharmaceutical composition comprising the following: (i) a pharmaceutically acceptable carrier; and (ii) a recombinant bacterium described herein.

For example, the invention provides a pharmaceutical composition comprising the following (i) a pharmaceutically acceptable carrier; and (ii) a recombinant bacterium comprising an expression cassette comprising a first polynucleotide encoding a signal peptide, wherein the first polynucleotide is codon-optimized for expression in a bacterium, a second polynucleotide encoding a polypeptide, wherein the second polynucleotide is in the same translational reading frame as the first polynucleotide, and a promoter operably linked to the first and second polynucleotides, so that the expression cassette encodes a fusion protein comprising the signal peptide and the polypeptide.

The invention also provides a pharmaceutical composition comprising: (i) a pharmaceutically acceptable carrier; and (ii) a recombinant bacterium comprising an expression cassette, where the expression cassette comprises a first polynucleotide encoding a non-secA1 bacterial signal peptide, a second polynucleotide encoding a polypeptide in the same translational reading frame as the first polynucleotide, and a promoter operably linked to the first and second polynucleotides, so that the expression cassette encodes a fusion protein comprising the signal peptide and the polypeptide.

The invention further provides a pharmaceutical composition comprising: (i) a pharmaceutically acceptable carrier; and (ii) a recombinant *Listeria* bacterium comprising an expression cassette, wherein the expression cassette comprises the following: (a) a polynucleotide encoding a polypeptide foreign to *Listeria*, wherein the polynucleotide is codon-optimized for expression in *Listeria*; and (b) a promoter, operably linked to the polynucleotide encoding the foreign polypeptide.

The invention also provides a pharmaceutical composition comprising: (i) a pharmaceutically acceptable carrier; and (ii) a recombinant *Listeria* bacterium comprising an expression cassette which comprises: (a) a first polynucleotide encoding a non-Listerial signal peptide; (b) a second polynucleotide encoding a polypeptide that is in the same translational reading frame as the first polynucleotide; and (c) a promoter operably linked to both the first and second polynucleotides, wherein the expression cassette encodes a fusion protein comprising both the non-Listerial signal peptide and the polypeptide.

As used herein, "carrier" includes any and all solvents, dispersion media, vehicles, coatings, diluents, antifungal agents, isotonic and absorption delaying agents, buffers, carrier solutions, suspensions, colloids, and the like. Pharmaceutically acceptable carriers are well known to those of ordinary skill in the art, and include any material which, when combined with an active ingredient, allows the ingredient to retain biological activity and is non-reactive with the subject's immune system. For instance, pharmaceutically acceptable carriers include, but are not limited to, water, buffered saline solutions (e.g., 0.9% saline), emulsions such as oil/water emulsions, and various types of wetting agents. Possible carriers also include, but are not limited to, oils (e.g., mineral oil), dextrose solutions, glycerol solutions, chalk, starch, salts, glycerol, and gelatin.

While any suitable carrier known to those of ordinary skill in the art may be employed in the pharmaceutical compositions, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. In some embodiments, for parenteral administration, such as subcutaneous injection, the carrier comprises water, saline, alcohol, a fat, a wax or a buffer. In some embodiments, any of the above carriers or a solid carrier, such as mannitol, lactose, starch, magnesium stearate, sodium saccharine, talcum, cellulose, glucose, sucrose, and magnesium carbonate, are employed for oral administration.

Compositions comprising such carriers are formulated by well known conventional methods (see, for example, *Remington's Pharmaceutical Sciences*, 18th edition, A. Gennaro, ed., Mack Publishing Co., Easton, Pa., 1990; and *Remington, The Science and Practice of Pharmacy* 20th Ed. Mack Publishing, 2000).

In addition to pharmaceutical compositions, immunogenic compositions are provided. For instance, the invention provides an immunogenic composition comprising a recombinant bacterium described herein (see, e.g., the recombinant bacteria described above in the Summary of the Invention, Sections I and VIII of the Detailed Description above, and elsewhere in the specification, including the Examples, below). In some embodiments, the immunogenic composition comprises a recombinant bacterium, wherein the polypeptide sequence that is part of the polypeptide expressed by the recombinant bacterium as a discrete protein, as part of a fusion protein, or embedded in a protein chimera (depending on the recombinant nucleic acid molecule or expression cassette used) is an antigen or comprises an antigen. In other words, in some embodiments, the immunogenic composition comprises a recombinant bacterium which comprises a recombinant nucleic acid molecule or expression cassette encoding a polypeptide that comprises an antigen. Suitable antigens include, but are not limited to, any of those described herein (e.g., above in Section IV). In some embodiments, the recombinant bacterium in the immunogenic composition expresses the polypeptide comprising the antigen at a level sufficient to induce an immune response to the antigen upon administration of the composition to a host (e.g., a mammal such as a human). In some embodiments, the immune response stimulated by the immunogenic composition is a cell-mediated immune response. In some embodiments, the immune response stimulated by the immunogenic composition is a humoral immune response. In some embodiments, the immune response stimulated by the immunogenic composition comprises both a humoral and cell-mediated immune response.

For instance, in one aspect, the invention provides an immunogenic composition comprising a recombinant bacterium, where the bacterium comprises an expression cassette comprising the following: (a) a first polynucleotide encoding a signal peptide, wherein the first polynucleotide is codon-optimized for expression in a bacterium; (b) a second polynucleotide encoding an antigen, wherein the second polynucleotide is in the same translational reading frame as the first polynucleotide; and (c) a promoter operably linked to the first and second polynucleotides, so that the expression cassette encodes a fusion protein comprising the signal peptide and the antigen.

In another aspect, the invention provides an immunogenic composition comprising a recombinant bacterium, where the bacterium comprises an expression cassette that comprises the following: (a) a first polynucleotide encoding a non-secA1 bacterial signal peptide; (b) a second polynucleotide encoding an antigen in the same translational reading frame as the first polynucleotide; and (c) a promoter operably linked to the first and second polynucleotides, so that the expression cassette encodes a fusion protein comprising the signal peptide and the antigen.

In still another aspect, the invention provides an immunogenic composition comprising a recombinant *Listeria* bacterium, wherein the recombinant *Listeria* bacterium comprises an expression cassette, wherein the expression cassette comprises the following: (a) a polynucleotide that encodes a non-Listerial antigen and that is codon-optimized for expression in *Listeria*; and (b) a promoter, operably linked to the polynucleotide encoding the antigen.

The invention also provides an immunogenic composition comprising a recombinant *Listeria* bacterium comprising an expression cassette which comprises: (a) a first polynucleotide encoding a non-Listerial signal peptide; (b) a second polynucleotide encoding an antigen that is in the same translational reading frame as the first polynucleotide; and (c) a promoter operably linked to both the first and second polynucleotides, wherein the expression cassette encodes a fusion protein comprising both the non-Listerial signal peptide and the antigen.

In another aspect, the invention provides an immunogenic composition (or vaccine) comprising a recombinant bacterium comprising a recombinant nucleic acid molecule, wherein the recombinant nucleic acid molecule comprises (a) a first polynucleotide encoding a signal peptide native to a bacterium, wherein the first polynucleotide is codon-optimized for expression in the bacterium, and (b) a second polynucleotide encoding a polypeptide comprising an antigen, wherein the second polynucleotide is in the same translational reading frame as the first polynucleotide, wherein the recombinant nucleic acid molecule encodes a fusion protein comprising the signal peptide and the polypeptide.

In another aspect, the invention provides an immunogenic composition (or vaccine) comprising a recombinant *Listeria* bacterium, wherein the recombinant bacterium comprises a recombinant nucleic acid molecule which comprises (a) a first polynucleotide encoding a signal peptide, wherein the first polynucleotide is codon-optimized for expression in *Listeria*, and (b) a second polynucleotide encoding a polypeptide comprising an antigen, wherein the second polynucleotide is in the same translational reading frame as the first polynucleotide, wherein the recombinant nucleic acid molecule encodes a fusion protein comprising the signal peptide and the polypeptide.

In another aspect, the invention provides an immunogenic composition (or vaccine) comprising a recombinant bacterium comprising a recombinant nucleic acid molecule, wherein the recombinant nucleic acid molecule comprises a first polynucleotide encoding a non-secA1 bacterial signal peptide, and a second polynucleotide encoding a polypeptide comprising an antigen, wherein the second polynucleotide is in the same translational reading frame as the first polynucleotide, and wherein the recombinant nucleic acid molecule encodes a fusion protein comprising the signal peptide and the polypeptide.

In still another aspect, the invention provides an immunogenic composition (or vaccine) comprising a recombinant Listeria bacterium comprising a recombinant nucleic acid molecule, wherein the recombinant nucleic acid molecule comprises (a) a first polynucleotide encoding a non-secA1 bacterial signal peptide, and (b) a second polynucleotide encoding a polypeptide either heterologous to the signal peptide or foreign to the bacterium, wherein the second polynucleotide is in the same translational reading frame as the first polynucleotide, and wherein the recombinant nucleic acid molecule encodes a fusion protein comprising the signal peptide and the polypeptide. In some embodiments, the polypeptide encoded by the first polynucleotide comprises an antigen.

In another aspect, the invention provides an immunogenic composition (or vaccine) comprising a recombinant Listeria bacterium, wherein the recombinant Listeria bacterium comprises a recombinant nucleic acid molecule, wherein the recombinant nucleic acid molecule comprises a polynucleotide encoding a polypeptide foreign to Listeria, wherein the polynucleotide encoding the foreign polypeptide is codon-optimized for expression in Listeria. In some embodiments, the foreign polypeptide comprises an antigen.

In another aspect, the invention provides an immunogenic composition (or vaccine) comprising a recombinant Listeria bacterium, wherein the recombinant bacterium comprises a recombinant nucleic acid molecule comprising (a) a first polynucleotide encoding a non-Listerial signal peptide, and (b) a second polynucleotide encoding a polypeptide comprising an antigen, wherein the second polynucleotide is in the same translational reading frame as the first polynucleotide, and wherein the recombinant nucleic acid molecule encodes a fusion protein comprising both the non-Listerial signal peptide and the polypeptide.

The invention also provides an immunogenic composition (or vaccine) comprising a recombinant bacterium, wherein the recombinant bacterium comprises a nucleic acid molecule comprising (a) a first polynucleotide encoding a bacterial autolysin, or a catalytically active fragment or catalytically active variant thereof, and (b) a second polynucleotide encoding a polypeptide, wherein the second polynucleotide is in the same translational reading frame as the first polynucleotide, wherein the recombinant nucleic acid molecule encodes a protein chimera comprising the polypeptide encoded by the second polynucleotide and the autolysin, or catalytically active fragment or catalytically active variant thereof, wherein, in the protein chimera, the polypeptide is fused to or is positioned within the autolysin, or catalytically active fragment or catalytically active variant thereof. In some embodiments, the polypeptide encoded by the second polynucleotide comprises an antigen.

In another aspect, the invention provides an immunogenic composition (or vaccine) comprising a recombinant Listeria bacterium, wherein the recombinant Listeria bacterium comprises a recombinant nucleic acid molecule, wherein the recombinant nucleic acid molecule encodes at least two discrete non-Listerial polypeptides, at least one of which comprises an antigen.

In other aspects, the invention provides an immunogenic composition (or vaccine) comprising a recombinant bacterium, which comprises a recombinant nucleic acid molecule comprising (a) a first polynucleotide encoding a signal peptide, (b) a second polynucleotide encoding a secreted protein, or a fragment thereof, wherein the second polynucleotide is in the same translational reading frame as the first polynucleotide, and (c) a third polynucleotide encoding a polypeptide heterologous to the secreted protein, or fragment thereof, wherein the third polynucleotide is in the same translational reading frame as the first and second polynucleotides, wherein the recombinant nucleic acid molecule encodes a protein chimera comprising the signal peptide, the polypeptide encoded by the third polynucleotide, and the secreted protein, or fragment thereof, and wherein the polypeptide encoded by the third polynucleotide is fused to the secreted protein, or fragment thereof, or is positioned within the secreted protein, or fragment thereof, in the protein chimera. In some embodiments, the heterologous polypeptide encoded by the third polynucleotide comprises an antigen.

It can be determined if a particular form of recombinant bacteria (and/or a particular expression cassette) is useful in an immunogenic composition (or as a vaccine) by testing the ability of the recombinant bacteria to stimulate an immune response in vitro or in a model system.

These immune cell responses can be measured by both in vitro and in vivo methods to determine if the immune response of a particular recombinant bacterium (and/or a particular expression cassette) is effective. One possibility is to measure the presentation of the protein or antigen of interest by an antigen-presenting cell that has been mixed with a population of the recombinant bacteria. The recombinant bacteria may be mixed with a suitable antigen presenting cell or cell line, for example a dendritic cell, and the antigen presentation by the dendritic cell to a T cell that recognizes the protein or antigen can be measured. If the recombinant bacteria are expressing the protein or antigen at a sufficient level, it will be processed into peptide fragments by the dendritic cells and presented in the context of MHC class I or class II to T cells. For the purpose of detecting the presented protein or antigen, a T cell clone or T cell line responsive to the particular protein or antigen may be used. The T cell may also be a T cell hybridoma, where the T cell is immortalized by fusion with a cancer cell line. Such T cell hybridomas, T cell clones, or T cell lines can comprise either CD8+ or CD4+ T cells. The dendritic cell can present to either CD8+ or CD4+ T cells, depending on the pathway by which the antigens are processed. CD8+ T cells recognize antigens in the context of MHC class I while CD4+ recognize antigens in the context of MHC class II. The T cell will be stimulated by the presented antigen through specific recognition by its T cell receptor, resulting in the production of certain proteins, such as IL-2, tumor necrosis factor-$\alpha$ (TNF-$\alpha$), or interferon-$\gamma$ (IFN-$\gamma$), that can be quantitatively measured (for example, using an ELISA assay, ELISPOT assay, or Intracellular Cytokine Staining (ICS)). These are techniques that are well known in the art and that are also exemplified below in the Examples (see, e.g., Example 21, below).

Alternatively, a hybridoma can be designed to include a reporter gene, such as $\beta$-galactosidase, that is activated upon stimulation of the T cell hybridoma by the presented antigens. The increase in the production of $\beta$-galactosidase can be readily measured by its activity on a substrate, such as chlorophenol red-B-galactoside, which results in a color change. The color change can be directly measured as an indicator of specific antigen presentation.

Additional in vitro and in vivo methods for assessing the antigen expression of recombinant bacteria vaccines of the present invention are known to those of ordinary skill in the art. It is also possible to directly measure the expression of a particular heterologous antigen by recombinant bacteria. For example, a radioactively labeled amino acid can be added to a cell population and the amount of radioactivity incorporated into a particular protein can be determined. The proteins synthesized by the cell population can be isolated, for example by gel electrophoresis or capillary electrophoresis, and the amount of radioactivity can be quantitatively measured to assess the expression level of the particular protein. Alternatively, the proteins can be expressed without radioactivity and visualized by various methods, such as an ELISA assay or by gel electrophoresis and Western blot with detection using an enzyme linked antibody or fluorescently labeled antibody.

Example 21, below, provides some specific exemplary examples of how some of the techniques known to those of ordinary skill in the art can be used to assess immunogenicity. For instance, Elispot assay, Intracellular Cytokine Staining Assay (ICS), measurement of cytokine expression of stimulated spleen cells, and assessment of cytotoxic T cell activity in vitro and in vivo are all techniques for assessing immunogenicity known to those in the art. Exemplary descriptions of these techniques with model antigens are provided in Example 21. Exemplary assays are also described in Examples 31A and 31E, below.

In addition, therapeutic efficacy of the vaccine composition can be assessed more directly by administration of the immunogenic composition or vaccine to an animal model such as a mouse model, followed by an assessment of survival or tumor growth. For instance, survival can be measured following administration and challenge (e.g., with a tumor or pathogen). See, e.g., the assays described in Examples 20 and 31B-D, below.)

Mouse models useful for testing the immunogenicity of an immunogenic composition or vaccine expressing a particular antigen can be produced by first modifying a tumor cell so that it expresses the antigen of interest or a model antigen and then implanting the tumor cells expressing the antigen of interest into mice. The mice can be vaccinated with the candidate immunogenic composition or vaccine comprising a recombinant bacterium expressing a polypeptide comprising the antigen of interest or a model antigen prior to implantation of the tumor cells (to test prophylactic efficacy of the candidate composition) or following implantation of the tumor cells in the mice (to test therapeutic efficacy of the candidate composition).

As an example, CT26 mouse murine colon carcinoma cells can be transfected with an appropriate vector comprising an expression cassette encoding the desired antigen or model antigen using techniques standard in the art. Standard techniques such as flow cytometry and Western blots can then be used to identify clones expressing the antigen or model antigen at sufficient levels for use in the immunogenicity and/or efficacy assays.

Alternatively, candidate compositions can be tested which comprise a recombinant bacterium expressing an antigen that corresponds to or is derived from an antigen endogenous to a tumor cell line (e.g., the retroviral gp70 tumor antigen AH1 endogenous to CT26 mouse murine colon carcinoma cells, or the heteroclitic epitope AH1-A5). In such assays, the tumor cells can be implanted in the animal model without further modification to express an additional antigen. Candidate vaccines comprising the antigen can then be tested.

As indicated, vaccine compositions comprising the bacteria described herein are also provided. For instance, the invention provides a vaccine comprising a recombinant bacterium described herein (see, e.g., the recombinant bacteria described above in the Summary of the Invention, Sections I and VIII of the Detailed Description above, and elsewhere in the specification, including the Examples, below) where the polypeptide sequence that is part of the polypeptide expressed by the recombinant bacterium as a discrete protein, as part of a fusion protein, or embedded in a protein chimera (depending on the recombinant nucleic acid molecule or expression cassette used) is an antigen. Suitable antigens include any of those described herein (e.g., above in Section IV).

In one aspect, the invention provides a vaccine that comprises a bacterium, wherein the bacterium comprises an expression cassette comprising the following: (a) a first polynucleotide encoding a signal peptide, wherein the first polynucleotide is codon-optimized for expression in a bacterium; (b) a second polynucleotide encoding an antigen, wherein the second polynucleotide is in the same translational reading frame as the first polynucleotide; and (c) a promoter operably linked to the first and second polynucleotides, so that the expression cassette encodes a fusion protein comprising the signal peptide and the antigen.

In another aspect, the invention provides a vaccine that comprises a bacterium, where the bacterium comprises an expression cassette that comprises the following: (a) a first polynucleotide encoding a non-secA1 bacterial signal peptide; (b) a second polynucleotide encoding an antigen in the same translational reading frame as the first polynucleotide; and (c) a promoter operably linked to the first and second polynucleotides, so that the expression cassette encodes a fusion protein comprising the signal peptide and the antigen.

In still another aspect, the invention provides a vaccine that comprises a recombinant *Listeria* bacterium comprising a nucleic acid molecule, wherein the nucleic acid molecule comprises the following: (a) a polynucleotide that encodes a non-Listerial antigen and that is codon-optimized for expression in *Listeria*; and (b) a promoter, operably linked to the polynucleotide encoding the antigen.

In another aspect, the invention provides a vaccine comprising a recombinant *Listeria* bacterium comprising an expression cassette which comprises: (a) a first polynucleotide encoding a non-Listerial signal peptide; (b) a second polynucleotide encoding an antigen that is in the same translational reading frame as the first polynucleotide; and (c) a promoter operably linked to both the first and second polynucleotides, wherein the expression cassette encodes a fusion protein comprising both the non-Listerial signal peptide and the antigen.

In some embodiments, the vaccine compositions comprise antigen-presenting cells (APC) which have been infected with any of the recombinant bacteria described herein. In some embodiments the vaccine (or immunogenic or pharmaceutical composition) does not comprise antigen-presenting cells (i.e., the vaccine or composition is a bacteria-based vaccine or composition, not an APC-based vaccine or composition).

Methods of administration suitable for administration of vaccine compositions (and pharmaceutical and immunogenic compositions) are known in the art, and include oral, intravenous, intradermal, intraperitoneal, intramuscular, intralymphatic, intranasal and subcutaneous routes of administration.

Vaccine formulations are known in the art and in some embodiments may include numerous additives, such as preservatives (e.g., thimerosal, 2-phenyoxy ethanol), stabilizers, adjuvants (e.g. aluminum hydroxide, aluminum phosphate, cytokines), antibiotics (e.g., neomycin, streptomycin), and other substances. In some embodiments, stabilizers, such as lactose or monosodium glutamate (MSG), are added to stabilize the vaccine formulation against a variety of conditions, such as temperature variations or a freeze-drying process. In some embodiments, vaccine formulations may also include a suspending fluid or diluent such as sterile water, saline, or isotonic buffered saline (e.g., phosphate buffered to physiological pH). Vaccine may also contain small amount of residual materials from the manufacturing process.

For instance, in some embodiments, the vaccine compositions are lyophilized (i.e., freeze-dried). The lyophilized preparation can be combined with a sterile solution (e.g., citrate-bicarbonate buffer, buffered water, 0.4% saline, or the like) prior to administration.

In some embodiments, the vaccine compositions may further comprise additional components known in the art to improve the immune response to a vaccine, such as adjuvants or co-stimulatory molecules. In addition to those listed above, possible adjuvants include chemokines and bacterial nucleic acid sequences, like CpG. In some embodiments, the vaccines comprise antibodies that improve the immune response to a vaccine, such as CTLA4. In some embodiments, co-stimulatory molecules comprise one or more factors selected from the group consisting of GM-CSF, IL-2, IL-12, IL-14, IL-15, IL-18, B7.1, B7.2, and B7-DC are optionally included in the vaccine compositions of the present invention. Other co-stimulatory molecules are known to those of ordinary skill in the art.

In additional aspects, the invention provides methods of improving a vaccine or immunogenic composition comprising *Listeria* that express an antigen. Any of the polynucleotides, expression cassettes and/or expression vectors described herein may be used in these methods. For instance, the invention provides a method of improving a vaccine or immunogenic composition comprising a *Listeria* bacterium, wherein the *Listeria* bacterium expresses a heterologous antigen fused to a signal peptide, comprising codon-optimizing either the polypeptide-encoding sequence on the expression cassette, the signal peptide-encoding sequence of the expression cassette, or both. The invention provides a method of improving a vaccine or immunogenic composition comprising *Listeria* bacterium, wherein the *Listeria* bacterium expresses a heterologous antigen fused to a signal peptide, comprising using a signal peptide from a non-Listerial source and/or from a secretory pathway other than secA1.

Methods of producing the vaccines of the present invention are also provided. For instance, in one embodiment, a method of producing a vaccine comprising a recombinant bacterium (e.g. a recombinant *Listeria* bacterium) comprises introducing a recombinant nucleic acid molecule into the bacterium, expression cassette, or expression vector described herein into a bacterium, wherein the recombinant nucleic acid molecule, expression cassette, or expression vector encodes an antigen. For instance, in some embodiments, a recombinant nucleic acid molecule comprising (a) a first polynucleotide encoding a signal peptide native to a bacterium, wherein the first polynucleotide is codon-optimized for expression in the bacterium, and (b) a second polynucleotide encoding an antigen, wherein the second polynucleotide is in the same translational reading frame as the first polynucleotide, wherein the recombinant nucleic acid molecule encodes a fusion protein comprising the signal peptide and the antigen, is introduced into a bacterium to produce the vaccine. In some embodiments, a recombinant nucleic acid molecule, comprising (a) a first polynucleotide encoding a non-secA1 bacterial signal peptide, and (b) a second polynucleotide encoding an antigen, wherein the second polynucleotide is in the same translational reading frame as the first polynucleotide, and wherein the recombinant nucleic acid molecule encodes a fusion protein comprising the signal peptide and the antigen, is introduced into the bacterium to produce the vaccine. In some embodiments, the recombinant nucleic acid molecule that is introduced into the bacterium to produce the vaccine is a recombinant nucleic acid molecule, wherein the recombinant nucleic acid molecule comprises (a) a first polynucleotide encoding a non-Listerial signal peptide, and (b) a second polynucleotide encoding an antigen that is in the same translational reading frame as the first polynucleotide, wherein the recombinant nucleic acid molecule encodes a fusion protein comprising both the non-Listerial signal peptide and the antigen. The recombinant nucleic acid molecule used to produce the vaccine is, in some embodiments, a recombinant nucleic acid molecule, comprising (a) a first polynucleotide encoding a bacterial autolysin, or a catalytically active fragment or catalytically active variant thereof, and (b) a second polynucleotide encoding a polypeptide, wherein the second polynucleotide is in the same translational reading frame as the first polynucleotide, wherein the recombinant nucleic acid molecule encodes a protein chimera in which the non-Listerial polypeptide is fused to the autolysin, or catalytically active fragment or catalytically active variant thereof, or is inserted within the autolysin, or catalytically active fragment or catalytically active variant thereof. In some other embodiments, a method of producing a vaccine comprising a recombinant *Listeria* bacterium is provided, which comprises introducing a polycistronic expression cassette, wherein the polycistronic expression cassette encodes at least two discrete non-Listerial polypeptides, where at least one of the polypeptides is an antigen, into a *Listeria* bacterium to produce vaccine.

Kits comprising any of the recombinant nucleic acid molecules, expression cassettes, vectors, bacteria and/or compositions of the invention are also provided.

X. Methods of Use

A variety of methods of using the recombinant bacteria or pharmaceutical, immunogenic, or vaccine compositions described herein for inducing immune responses, and/or preventing or treating conditions in a host are provided. In some embodiments, the condition that is treated or prevented is a disease. In some embodiments, the disease is cancer. In some embodiments, the disease is an infectious disease. In addition, the recombinant bacteria are also useful in the production and isolation of heterologous proteins, such as mammalian proteins.

As used herein, "treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival. For instance, in those embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer.

As used herein, the terms "preventing" disease or "protecting a host" from disease (used interchangeably herein) encompass, but are not limited to, one or more of the following: stopping, deferring, hindering, slowing, retarding, and/or postponing the onset or progression of a disease, stabilizing the progression of a disease, and/or delaying development of a disease. The terms "preventing" a condition or "protecting a host" from a condition (used interchangeably herein) encompass, but are not limited to, one or more of the following: stopping, deferring, hindering, slowing, retarding, and/or postponing the onset or progression of a condition, stabilizing the progression of a condition, and/or delaying development of a condition. The period of this prevention can be of varying lengths of time, depending on the history of the disease or condition and/or individual being treated. By way of example, where the vaccine is designed to prevent or protect against an infectious disease caused by a pathogen, the terms "preventing" disease or "protecting a host" from disease encompass, but are not limited to, one or more of the following: stopping, deferring, hindering, slowing, retarding, and/or postponing the infection by a pathogen of a host, progression of an infection by a pathogen of a host, or the onset or progression of a disease associated with infection of a host by a pathogen, and/or stabilizing the progression of a disease associated with infection of a host by a pathogen. Also, by way of example, where the vaccine is an anti-cancer vaccine, the terms "preventing" disease or "protecting the host" from disease encompass, but are not limited to, one or more of the following: stopping, deferring, hindering, slowing, retarding, and/or postponing the development of cancer or metastasis, progression of a cancer, or a reoccurrence of a cancer.

In one aspect, the invention provides a method of inducing an immune response in a host to an antigen, comprising administering to the host an effective amount of a recombinant bacterium described herein or an effective amount of a composition (e.g., a pharmaceutical composition, immunogenic composition, or vaccine) comprising a recombinant bacterium described herein (see, e.g., the Summary of the Invention, Sections I, VIII, and IX of the Detailed Description above, or the Examples below). In some embodiments, the polypeptide encoded by the recombinant nucleic acid, expression cassette, and/or expression vector in the recombinant bacterium comprises the antigen or is a fusion protein or protein chimera comprising the antigen.

For instance, in one aspect, the invention provides a method of inducing an immune response in a host to an antigen comprising administering to the host an effective amount of a composition comprising a recombinant bacterium, wherein the recombinant bacterium comprises an expression cassette comprising the following: (a) a first polynucleotide encoding a signal peptide, wherein the first polynucleotide is codon-optimized for expression in the bacterium; (b) a second polynucleotide encoding the antigen, wherein the second polynucleotide is in the same translational reading frame as the first polynucleotide; and (c) a promoter operably linked to the first and second polynucleotides, so that the expression cassette encodes a fusion protein comprising the signal peptide and the antigen.

In another aspect, the invention provides a method of inducing an immune response in a host to an antigen comprising administering to the host an effective amount of a composition comprising a recombinant bacterium comprising an expression cassette, where the expression cassette comprises the following: (a) a first polynucleotide encoding a non-secA1 bacterial signal peptide; (b) a second polynucleotide encoding the antigen in the same translational reading frame as the first polynucleotide; and (c) a promoter operably linked to the first and second polynucleotides, so that the expression cassette encodes a fusion protein comprising the signal peptide and the antigen.

In yet another aspect, the invention provides a method of inducing an immune response in a host to a non-Listerial antigen comprising administering to the host an effective amount of a compositions comprising a recombinant *Listeria* bacterium comprising a nucleic acid molecule, wherein the nucleic acid molecule comprises the following: (a) a polynucleotide which encodes the non-Listerial antigen and that is codon-optimized for expression in *Listeria*; and (b) a promoter, operably linked to the polynucleotide encoding the antigen.

In another aspect, the invention provides a method of inducing an immune response in a host to an antigen comprising administering to the host an effective amount of a recombinant *Listeria* bacterium comprising an expression cassette which comprises the following: (a) a first polynucleotide encoding a non-Listerial signal peptide; (b) a second polynucleotide encoding the antigen that is in the same translational reading frame as the first polynucleotide; and (c) a promoter operably linked to both the first and second polynucleotides, wherein the expression cassette encodes a fusion protein comprising both the non-Listerial signal peptide and the polypeptide.

In some embodiments of the methods of inducing immune responses described herein, the bacterium is administered in the form of a pharmaceutical composition, an immunogenic composition and/or vaccine composition.

In some embodiments, the immune response is an MHC Class I immune response. In other embodiments, the immune response is an MHC Class II immune response. In still other embodiments, the immune response that is induced by administration of the bacteria or compositions is both an MHC Class I and an MHC Class II response. Accordingly, in some embodiments, the immune response comprises a CD4+ T-cell response. In some embodiments, the immune response comprises a CD8+ T-cell response. In some embodiments, the immune response comprises both a CD4+ T-cell response and a CD8+ T-cell response. In some embodiments, the immune response comprises a B-cell response and/or a T-cell response. B-cell responses may be measured by determining the titer of an antibody directed against the antigen, using methods known to those of ordinary skill in the art. In some embodiments, the immune response which is induced by the compositions described herein is a humoral response. In other embodiments, the immune response which is induced is a cellular immune response. In some embodiments, the immune response comprises both cellular and humoral immune responses. In some embodiments, the immune response is antigen-specific. In some embodiments, the immune response is an antigen-specific T-cell response.

In addition to providing methods of inducing immune responses, the present invention also provides methods of preventing or treating a condition in a host (e.g., a subject such as human patient). In some embodiments, the condition is a disease. The methods comprise administration to the host of an effective amount of a recombinant bacterium described herein, or a composition comprising a recombinant bacterium described herein (see, e.g., the Summary of the Invention, Sections I, VIII, and IX of the Detailed Description above, or the Examples below). In some embodiments, the disease is cancer. In some embodiments, the disease is an infectious disease.

For instance, in one aspect, the invention provides a method of preventing or treating disease (or condition) in a host comprising administering to the host an effective amount of composition comprising a bacterium, wherein the bacterium comprises an expression cassette comprising the following: (a) a first polynucleotide encoding a signal peptide, wherein the first polynucleotide is codon-optimized for expression in a bacterium; (b) a second polynucleotide encoding a polypeptide (e.g., an antigen and/or a therapeutic mammalian protein), wherein the second polynucleotide is in the same translational reading frame as the first polynucleotide; and (c) a promoter operably linked to the first and second polynucleotides, so that the expression cassette encodes a fusion protein comprising the signal peptide and the antigen.

In another aspect, the invention provides a method of preventing or treating disease (or condition) in a host comprising administering to the host an effective amount of a composition comprising a recombinant bacterium, where the bacterium comprises an expression cassette, and where the expression cassette comprises the following: (a) a first polynucleotide encoding a non-secA1 bacterial signal peptide; (b) a second polynucleotide encoding a polypeptide (e.g., an antigen and/or mammalian protein) in the same translational reading frame as the first polynucleotide; and (c) a promoter operably linked to the first and second polynucleotides, so that the expression cassette encodes a fusion protein comprising the signal peptide and the antigen.

In still another aspect, the invention provides a method of preventing or treating disease (or a condition) in a host comprising administering to the host an effective amount of a composition comprising a recombinant *Listeria* bacterium comprising a nucleic acid molecule, wherein the nucleic acid molecule comprises the following: (a) a polynucleotide which encodes a non-Listerial polypeptide (e.g., an antigen and/or a therapeutic mammalian protein) and that is codon-optimized for expression in *Listeria*; and (b) a promoter, operably linked to the polynucleotide encoding the antigen.

In another aspect, the invention provides a method of preventing or treating disease (or a condition) in a host comprising administering to the host an effective amount of a composition comprising a recombinant *Listeria* bacterium comprising an expression cassette which comprises: (a) a first polynucleotide encoding a non-Listerial signal peptide; (b) a second polynucleotide encoding a polypeptide (e.g., an antigen and/or a therapeutic mammalian protein) that is in the same translational reading frame as the first polynucleotide; and (c) a promoter operably linked to both the first and second polynucleotides, wherein the expression cassette encodes a fusion protein comprising both the non-Listerial signal peptide and the polypeptide.

In some embodiments, the disease is cancer. In some embodiments, where the condition being treated or prevented is cancer, the disease is melanoma, breast cancer, pancreatic cancer, liver cancer, colon cancer, colorectal cancer, lung cancer, brain cancer, testicular cancer, ovarian cancer, squamous cell cancer, gastrointestinal cancer, cervical cancer, kidney cancer, thyroid cancer or prostate cancer. In some embodiments, the cancer is melanoma. In some embodiments, the cancer is pancreatic cancer. In some embodiments, the cancer is colon cancer. In some embodiments, the cancer is prostate cancer. In some embodiments, the cancer is metastatic.

In other embodiments, the disease is an autoimmune disease. In still other embodiments, the disease is an infectious disease or another disease caused by a pathogen such as a virus, bacterium, fungus, or protozoa. In some embodiments, the disease is an infectious disease.

In some embodiments, the use of the recombinant bacteria in the prophylaxis or treatment of a cancer comprises the delivery of the recombinant bacteria to cells of the immune system of an individual to prevent or treat a cancer present or to which the individual has increased risk factors, such as environmental exposure and/or familial disposition. In other embodiments, the use of the recombinant bacteria in the prophylaxis or treatment of a cancer comprises delivery of the recombinant bacteria to an individual who has had a tumor removed or has had cancer in the past, but is currently in remission.

In some embodiments, administration of composition comprising a recombinant bacterium described herein to a host elicits a CD4+T-cell response in the host. In some other embodiments, administration of a composition comprising a recombinant bacterium described herein to a host elicits a CD8+ T-cell response in the host. In some embodiments, administration of a composition comprising a recombinant bacterium described herein elicits both a CD4+ T-cell response and a CD8+ T-cell response in the host.

The efficacy of the vaccines or other compositions for the treatment of a condition can be evaluated in an individual, for example in mice. A mouse model is recognized as a model for efficacy in humans and is useful in assessing and defining the vaccines of the present invention. The mouse model is used to demonstrate the potential for the effectiveness of the vaccines in any individual. Vaccines can be evaluated for their ability to provide either a prophylactic or therapeutic effect against a particular disease. For example, in the case of infectious diseases, a population of mice can be vaccinated with a desired amount of the appropriate vaccine of the invention, where the recombinant bacterium expresses an infectious disease associated antigen. The mice can be subsequently infected with the infectious agent related to the vaccine antigen and assessed for protection against infection. The progression of the infectious disease can be observed relative to a control population (either non vaccinated or vaccinated with vehicle only or a bacterium that does not contain the appropriate antigen).

In the case of cancer vaccines, tumor cell models are available, where a tumor cell line expressing a desired tumor antigen can be injected into a population of mice either before (therapeutic model) or after (prophylactic model) vaccination with a composition comprising a bacterium of the invention containing the desired tumor antigen. Vaccination with a recombinant bacterium containing the tumor antigen can be compared to control populations that are either not vaccinated, vaccinated with vehicle, or with a recombinant bacterium that expresses an irrelevant antigen. The effectiveness of the vaccine in such models can be evaluated in terms of tumor volume as a function of time after tumor injection or in terms of survival populations as a function of time after tumor injection (e.g., Example 31D). In one embodiment, the tumor volume in mice vaccinated with a composition comprising the recombinant bacterium is about 5%, about 10%, about 25%, about 50%, about 75%, about 90% or about 100% less than the tumor volume in mice that are either not vaccinated or are vaccinated with vehicle or a bacterium that expresses an irrelevant antigen. In another embodiment, this differential in tumor volume is observed at least about 10, about 17, or about 24 days following the implant of the tumors into the mice. In one embodiment, the median survival time in the mice vaccinated with the composition comprising a recombinant bacterium is at least about 2, about 5, about 7 or at least about 10 days longer than in mice that are either not vaccinated or are vaccinated with vehicle or bacteria that express an irrelevant antigen.

The host (i.e., subject) in the methods described herein, is any vertebrate, preferably a mammal, including domestic animals, sport animals, and primates, including humans. In some embodiments, the host is a mammal. In some embodiments, the host is a human.

The delivery of the recombinant bacteria, or a composition comprising the strain, may be by any suitable method, such as intradermal, subcutaneous, intraperitoneal, intravenous, intramuscular, intralymphatic, oral or intranasal, as well as by any route that is relevant for any given malignant or infectious disease or other condition.

The compositions comprising the recombinant bacteria and an immunostimulatory agent may be administered to a host simultaneously, sequentially or separately. Examples of immunostimulatory agents include, but are not limited to IL-2, IL-12, GMCSF, IL-15, B7.1, B7.2, and B7-DC and IL-14. Additional examples of stimulatory agents are provided in Section IX, above.

As used herein, an "effective amount" of a bacterium or composition (such as a pharmaceutical composition or an immunogenic composition) is an amount sufficient to effect beneficial or desired results. For prophylactic use, beneficial or desired results includes results such as eliminating or reducing the risk, lessening the severity, or delaying the outset of the disease, including biochemical, histologic and/or behavioral symptoms of a disease, its complications and intermediate pathological phenotypes presenting during development of the disease. For therapeutic use, beneficial or desired results includes clinical results such as inhibiting or suppressing a disease, decreasing one or more symptoms resulting from a disease (biochemical, histologic and/or behavioral), including its complications and intermediate pathological phenotypes presenting during development of a disease, increasing the quality of life of those suffering from a disease, decreasing the dose of other medications required to treat the disease, enhancing effect of another medication, delaying the progression of the disease, and/or prolonging survival of patients. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an effective amount may be considered in the context of administering one or more therapeutic agents, and a single agent may be considered to be given in an effective amount if, in conjunction with one or more other agents, a desirable result may be or is achieved.

In some embodiments, for a therapeutic treatment of a cancer, an effective amount includes an amount that will result in the desired immune response, wherein the immune response either slows the growth of the targeted tumors, reduces the size of the tumors, or preferably eliminates the tumors completely. The administration of the vaccine may be repeated at appropriate intervals, and may be administered simultaneously at multiple distinct sites in the vaccinated individual. In some embodiments, for a prophylactic treatment of a cancer, an effective amount includes a dose that will result in a protective immune response such that the likelihood of an individual to develop the cancer is significantly reduced. The vaccination regimen may be comprised of a single dose, or may be repeated at suitable intervals until a protective immune response is established.

In some embodiments, the therapeutic treatment of an individual for cancer may be started on an individual who has been diagnosed with a cancer as an initial treatment, or may be used in combination with other treatments. For example, individuals who have had tumors surgically removed or who have been treated with radiation therapy or by chemotherapy may be treated with the vaccine in order to reduce or eliminate any residual tumors in the individual, or to reduce the risk of a recurrence of the cancer. In some embodiments, the prophylactic treatment of an individual for cancer, would be started on an individual who has an increased risk of contracting certain cancers, either due to environmental conditions or genetic predisposition.

The dosage of the pharmaceutical compositions or vaccines that are given to the host will vary depending on the species of the host, the size of the host, and the condition or disease of the host. The dosage of the compositions will also depend on the frequency of administration of the compositions and the route of administration. The exact dosage is chosen by the individual physician in view of the patient to be treated.

In some embodiments, the pharmaceutical compositions, immunogenic compositions, or vaccines used in the methods comprise recombinant bacteria which comprise the recombinant nucleic acid molecules, expression cassettes and/or expression vectors described herein. In some embodiments, the recombinant bacteria are modified and/or mutant bacteria such as those described in U.S. patent application Ser. No. 10/883,599, entitled "Modified Free-Living Microbes, Vaccine Compositions and Methods of Use Thereof," by Thomas W. Dubensky, Jr. et al., filed Jun. 30, 2004, U.S. patent Publication No. 2004/0228877 and U.S. patent Publication No. 2004/0197343, each of which is incorporated by reference herein in its entirety. In some embodiments, a single dose of the pharmaceutical composition or vaccine comprising such modified and/or mutant bacteria or any of the other recombinant bacteria described herein comprises from about $10^2$ to about $10^{12}$ of the bacterial organisms. In another embodiment, a single dose comprises from about $10^5$ to about $10^{11}$ of the bacterial organisms. In another embodiment, a single dose comprises from about $10^6$ to about $10^{11}$ of the bacterial organisms. In still another embodiment, a single dose of the pharmaceutical composition or vaccine comprises from about $10^7$ to about $10^{10}$ of the bacterial organisms. In still another embodiment, a single dose of the pharmaceutical composition or vaccine comprises from about $10^7$ to about $10^9$ of the bacterial organisms.

In some embodiments, a single dosage comprises at least about $1\times10^2$ bacterial organisms. In some embodiments, a single dose of the composition comprises at least about $1\times10^5$ organisms. In another embodiment, a single dose of the composition or vaccine comprises at least about $1\times10^6$ bacterial organisms. In still another embodiment, a single dose of the composition or vaccine comprises at least about $1\times10^7$ of the bacterial organisms.

In some embodiments, a single dose of the pharmaceutical composition, immunogenic composition, or vaccine comprising recombinant, modified and/or mutant bacteria described herein comprises from about 1 CFU/kg to about $1\times10^{10}$ CFU/kg (CFU=colony forming units). In some embodiments, a single dose of the composition comprises from about 10 CFU/kg to about $1\times10^9$ CFU/kg. In another embodiment, a single dose of the composition or vaccine comprises from about $1\times10^2$ CFU/kg to about $1\times10^8$ CFU/kg. In still another embodiment, a single dose of the composition or vaccine comprises from about $1\times10^3$ CFU/kg to about $1\times10^8$ CFU/kg. In still another embodiment, a single dose of the composition or vaccine comprises from about $1\times10^4$ CFU/kg to about $1\times10^7$ CFU/kg. In some embodiments, a single dose of the composition comprises at least about 1 CFU/kg. In some embodiments, a single dose of the composition comprises at least about 10 CFU/kg. In another embodiment, a single dose of the composition or vaccine comprises at least about $1\times10^2$ CFU/kg. In still another embodiment, a single dose of the composition or vaccine comprises at least about $1\times10^3$ CFU/kg. In still another embodiment, a single dose of the composition or vaccine comprises from at least about $1\times10^4$ CFU/kg.

In some embodiments, the proper (i.e., effective) dosage amount for one host, such as human, may be extrapolated from the $LD_{50}$ data for another host, such as a mouse, using methods known to those in the art.

In some embodiments, the pharmaceutical composition, immunogenic composition, or vaccine comprises antigen-presenting cells, such as dendritic cells, which have been infected with recombinant bacteria comprising the recombinant nucleic acid molecules, expression cassettes and/or expression vectors described herein. In some embodiments, the bacteria have been modified and/or are mutants such as those described in U.S. patent application Ser. No. 10/883,599, filed Jun. 30, 2004, and U.S. patent Publication Nos. 2004/0228877 and US 2004/0197343, each of which is incorporated by reference herein in its entirety. Such antigen-presenting cell based vaccines are described, for instance, in the following: International Application No. PCT/US2004/23881, entitled "Antigen-Presenting Cell Vaccines and Methods of Use Thereof," by Thomas W. Dubensky, Jr. et al., filed Jul. 23, 2004; U.S. patent application Ser. No. 10/883,599, filed Jun. 30, 2004; U.S. patent Publication No. 2004/0228877; and U.S. patent Publication No. US 2004/0197343, each of which is incorporated by reference herein in its entirety. In some embodiments, an individual dosage of an antigen-presenting cell based vaccine comprising bacteria such as those described herein comprises between about $1\times10^3$ to about $1\times10^{10}$ antigen-presenting cells. In some embodiments, an individual dosage of the vaccine comprises between about $1\times10^5$ to about $1\times10^9$ antigen-presenting cells. In some embodiments, an individual dosage of the vaccine comprises between about $1\times10^7$ to about $1\times10^9$ antigen-presenting cells.

In some embodiments, multiple administrations of the dosage unit are preferred, either in a single day or over the course of a week or month or year or years. In some embodiments, the dosage unit is administered every day for multiple days, or once a week for multiple weeks.

The invention further provides the use of any recombinant bacterium described herein (i.e., any bacterium comprising a recombinant nucleic acid molecule, expression cassette, or vector described herein) in the manufacture of a medicament for inducing an immune response in a host to an antigen, wherein a polypeptide encoded by the recombinant nucleic acid molecule, expression cassette, and/or vector in the bacterium comprises the antigen. In some embodiments, the antigen is a heterologous antigen. The invention also provides the use of a recombinant bacterium described herein in the manufacture of a medicament for preventing or treating a condition in a host (e.g., a disease such as cancer or an infectious disease). The invention further provides the recombinant bacteria described herein for use in inducing an immune response in a host to an antigen, wherein a polypeptide encoded by the recombinant nucleic acid molecule, expression cassette, and/or vector in the bacterium comprises the antigen. The invention further provides the recombinant bacteria described herein for use in the prevention or treatment of a condition (such as a disease) in a host.

The invention also provides a method of inducing MHC class I antigen presentation or MHC class II antigen presentation on an antigen-presenting cell comprising contacting a bacterium described herein with an antigen-presenting cell.

The invention further provides a method of inducing an immune response in a host to an antigen comprising, the following steps: (a) contacting a recombinant bacterium described herein with an antigen-presenting cell from the host, under suitable conditions and for a time sufficient to load the antigen-presenting cells; and (b) administering the antigen-presenting cell to the host.

Other possible uses of the recombinant nucleic acid molecules, expression cassettes, and bacteria will be recognized by those of ordinary skill in the art. For instance, the recombinant nucleic acid molecules, expression cassettes, vectors, and recombinant bacteria (and other host cells) described herein are useful for the production and isolation of heterologous polypeptides. Accordingly in an alternative aspect, the invention provides a method of expressing a polypeptide in a bacterium, comprising (a) introducing an expression cassette or vector described herein into bacteria (e.g., via transfection, transformation, or conjugation); and (b) growing the bacteria in culture under conditions suitable for protein expression. In another alternative aspect, the invention provides a method of producing an isolated polypeptide comprising the following: (a) introducing an expression cassette or vector described herein into bacteria (e.g., via transfection, transformation, or conjugation); (b) growing the bacteria in cell culture under conditions suitable for protein expression; and (c) isolating the protein from the bacterial cell culture. Suitable methods of transformation, transfection, and conjugation are well known to those of ordinary skill in the art, as are methods of culturing and growing bacteria and isolating secreted or non-secreted protein from cell culture.

EXAMPLES

The following examples are provided to illustrate, but not to limit, the invention.

Example 1

Preparation of Exemplary Mutant *Listeria* Strains

*Listeria* strains were derived from 10403S (Bishop et al., *J. Immunol.* 139:2005 (1987)). *Listeria* strains with in-frame deletions of the indicated genes were generated by SOE-PCR and allelic exchange with established methods (Camilli, et al, *Mol. Microbiol.* 8:143 (1993)). The mutant strain LLO L461T (DP-L4017) was described in Glomski, et al, *J. Cell. Biol.* 156: 1029 (2002), incorporated by reference herein. The actA⁻ mutant (DP-L4029) is the DP-L3078 strain described in Skoble et al., *J. of Cell Biology,* 150: 527-537 (2000), incorporated by reference herein in its entirety, which has been cured of its prophage. (Prophage curing is described in (Lauer et al., *J. Bacteriol.* 184:4177 (2002); U.S. patent Publication No. 2003/0203472).) Construction of an actA⁻/uvrAB⁻ strain is described in the U.S. provisional application 60/446,051, filed Feb. 6, 2003, as L4029/uvrAB (see, e.g. Example 7 of that application), as well as in U.S. patent Publication No. 2004/0197343. DP-L4029uvrAB (a *Listeria monocytogenes* actA⁻/uvrAB⁻ double deletion mutant) was deposited with the American Type Culture Collection (ATCC), at 10801 University Blvd, Manassas, Va., 20110-2209, United States of America, on Oct. 3, 2003, under the provisions of the Budapest Treaty on the International Recognition of the Deposit of Microorganisms for the Purposes of Patent Procedure, and designated PTA-5563. Additional descriptions regarding mutant *Listeria* are provided in the following applications or publications, each of which is incorporated by reference herein in its entirety: U.S. patent Publication No. 2004/0228877; U.S. patent Publication No. US 2004/0197343; the PCT International Application No. PCT/US2004/23881, filed Jul. 23, 2004; and U.S. patent application Ser. No. 10/883,599, filed Jun. 30, 2004. In addition, an exemplary *Listeria monocytogenes* ΔactAΔinlB double deletion mutant has been deposited with the American Type Culture Collection (ATCC), at 10801 University Blvd, Manassas, Va., 20110-2209, United States of America, on Oct. 3, 2003, under the provisions of the Budapest Treaty on the International Recognition of the Deposit of Microorganisms for the Purposes of Patent Procedure, and designated PTA-5562.

One non-limiting example of a method of deleting a gene in *Listeria monocytogenes* to generate an attenuated mutant is provided in Example 24, below.

Example 2

Construction of *Listeria* Strains Expressing AH1/OVA or AH1-A5/OVA

Mutant *Listeria* strains expressing a truncated form of a model antigen ovalbumin (OVA), the immunodominant epitope from mouse colorectal cancer (CT26) known as AH1 (SPSYVYHQF (SEQ ID NO:72)), and the altered epitope AH1-A5 (SPSYAYHQF (SEQ ID NO:73); Slansky et al., *Immunity*, 13:529-538 (2000)) were prepared. The pPL2 integrational vector (Lauer et al., *J. Bacteriol.* 184:4177 (2002); U.S. patent Publication No. 2003/0203472) was used to derive OVA and AH1-A5/OVA recombinant *Listeria* strains containing a single copy integrated into an innocuous site of the *Listeria* genome.

A. Construction of OVA-Expressing *Listeria* (DP-L4056).

An antigen expression cassette consisting of hemolysin-deleted LLO fused with truncated OVA and contained in the pPL2 integration vector (pPL2/LLO-OVA) is first prepared. The *Listeria*-OVA vaccine strain is derived by introducing pPL2/LLO-OVA into the phage-cured *L. monocytogenes* strain DP-L4056 at the PSA (Phage from ScottA) attachment site TRNA$^{Arg}$-attBB'.

PCR is used to amplify the hemolysin-deleted LLO using the following template and primers:
Source: DP-L4056 genomic DNA
Primers:

```
Forward (KpnI-LLO nts. 1257-1276):
                                     (SEQ ID NO: 74)
5'-CTCTGGTACCTCCTTTGATTAGTATATTC
(T_m: LLO-spec: 52° C. Overall: 80° C.)
```

```
Reverse (BamHI-XhoI-LLO nts. 2811-2792):
                                     (SEQ ID NO: 75)
5'-CAATGGATCCCTCGAGATCATAATTTACTTCATCCC
(T_m: LLO-spec: 52° C. Overall: 102° C.)
```

PCR is also used to amplify the truncated OVA using the following template and primers:
Source: pDP3616 plasmid DNA from DP-E3616 *E. coli* (Higgins et al., *Mol. Molbiol.* 31:1631-1641 (1999)).
Primers:

```
Forward (XhoI- NcoI OVA cDNA nts. 174-186):
                                     (SEQ ID NO: 76)
5'-ATTTCTCGAGTCCATGGGGGGTTCTCATCATC
(T_m: OVA-spec: 60° C. Overall: 88° C.)

Reverse (XhoI-NotI-HindIII):
                                     (SEQ ID NO: 77)
5'-GGTGCTCGAGTGCGGCCGCAAGCTT
(T_m: Overall: 82° C.)
```

One protocol for completing the construction process involves first cutting the LLO amplicon with KpnI and BamHI and inserting the KpnI/BamHI vector into the pPL2 vector (pPL2-LLO). The OVA amplicon is then cut with XhoI and NotI and inserted into the pPL2-LLO which has been cut with XhoI/NotI. (Note: The pPL2 vector does not contain any XhoI sites; pDP-3616 contains one XhoI site, that is exploited in the OVA reverse primer design.) The construct pPL2/LLO-OVA is verified by restriction analysis (KpnI-LLO-XhoI-OVA-NotI) and sequencing. The plasmid pPL2/LLO-OVA is introduced into *E. coli* by transformation, followed by introduction and integration into *Listeria* (DP-L4056) by conjugation, exactly as described by Lauer et al. (or into another desired strain of *Listeria*, such as an inlB⁻ mutant or an inlB⁻actA⁻ double mutant).

B. Construction of *Listeria* Strains Expressing AH1/OVA or AH1-A5/OVA.

To prepare *Listeria* expressing either the AH1/OVA or the AH1-A5/OVA antigen sequences, inserts bearing the antigen are first prepared from oligonucleotides and then ligated into the vector pPL2/LLO-OVA (prepared as described above).

The following oligonucleotides are used in preparation of the AH1 or AH1-A5 insert:
AH1 epitope insert (ClaI-PstI compatible ends):

```
Top strand oligo (AH1 Top):
                                     (SEQ ID NO: 78)
5'-CGATTCCCCTAGTTATGTTTACCACCAATTTGCTGCA Bottom strand oligo (AH1 Bottom):
                                     (SEQ ID NO: 79)
5'-GCAAATTGGTGGTAAACATAACTAGGGGAAT
```

AH1-A5 epitope insert (ClaI-AvaII compatible ends):

```
The sequence of the AH1-A5 epitope is SPSYAYHQF
                                     (SEQ ID NO: 73)
(5'-AGT CCA AGT TAT GCA TAT CAT CAA TTT-3'
(SEQ ID NO: 80))

(SEQ ID NO: 81)
Top: 5'-CGATAGTCCAAGTTATGCATATCATCAATTTGC (SEQ ID NO: 82)
Bottom: 5'-GTCGCAAATTGATGATATGCATAACTTGGACTAT
```

The oligonucletide pair for a given epitope are mixed together at an equimolar ratio, heated at 95° C. for 5 min. The oligonucleotide mixture is then allowed to slowly cool. The annealed oligonucleotide pairs are then ligated at a 200 to 1 molar ratio with pPL2-LLO/OVA plasmid prepared by digestion with the relevant restriction enzymes. The identity of the new construct can be verified by restriction analysis and/or sequencing.

The plasmid can then be introduced into E. coli by transformation, followed by introduction and integration into Listeria (DP-L4056) by conjugation, exactly as described by Lauer et al., or into another desired strain of Listeria, such as an actA⁻ mutant strain (DP-L0429), LLO L461T strain (DP-L4017), or actA⁻/uvrAB⁻ strain (DP-L4029uvrAB).

Example 3

Construction of Listeria Polynucleotides and Expression Cassette Elements

A. Cloning Vectors

Selected heterologous antigen expression cassette molecular constructs were inserted into pPL2 (Lauer et. al. J. Bacteriol. 2002), or pAM401 (Wirth et. al., J. Bacteriol. 165:831-836), modified to contain the multiple cloning sequence of pPL2 (Aat II small fragment, 171 bps), inserted between blunted Xba I and Nru I recognition sites, within the tetracycline resistance gene (pAM401-MCS, FIG. 32). In general, the hly promoter and (selected) signal peptide sequence was inserted between the unique Kpn I and Bam HI sites in the pPL2 or pAM401-MCS plasmid vectors. Selected EphA2 genes (sometimes modified to contain N-terminal and C-terminal epitope tags; see description below) were cloned subsequently into these constructs between unique Bam HI and Sac I sites. Molecular constructs based on the pAM401-MCS plasmid vector were introduced by electroporation into selected Listeria monocytogenes strains also treated with lysozyme, utilizing methods common to those skilled in the art. The expected plasmid structure in Listeria-transfectants was verified by isolating DNA from colonies that formed on chloramphenicol-containing BHI agar plates (10 µg/ml) by restriction enzyme analysis. Recombinant Listeria transformed with various pAM401-MCS based heterologous protein expression cassette constructs were utilized to measure heterologous protein expression and secretion, as described below.

The pPL2 based heterologous protein expression cassette constructs were incorporated into the tRNA$^{Arg}$ gene in the genome of selected Listeria strains, according to the methods as described previously [Lauer et. al., J. Bacteriol. 184, 4177-4186 (2002)]. Briefly, the pPL2 heterologous protein expression cassette constructs plasmid was first introduced into the E. coli host strain SM10 (Simon et. al., Bio/Technology 1:784-791 (1983)] by electroporation or by chemical means. Subsequently, the pPL2-based plasmid was transferred from transformed SM10 to the selected Listeria strains by conjugation. Following incubation on drug-selective BHI agar plates containing 7.5 µg of chloramphenicol per ml and 200 µg of streptomycin per ml as described, selected colonies are purified by passaging 3 times on plates with the same composition. To verify integration of the pPL2 vector at the phage attachment site, individual colonies are picked and screened by PCR using the primer pair of forward primer NC 16 (5'-gtcaaaacatacgctcttatc-3' (SEQ ID NO:94)) and reverse primer PL95 (5'-acataatcagtccaaagtagatgc-3' (SEQ ID NO:95)). Selected colonies having the pPL2-based plasmid incorporated into the TRNA$^{Arg}$ gene in the genome of selected Listeria strains yielded a diagnostic DNA amplicon of 499 bps.

B. Promoter

Heterologous protein expression cassettes contained the prfA-dependent hly promoter, which drives the transcription of the gene encoding Listeriolysin O (LLO), and is activated within the microenvironment of the infected cell. Nucleotides 205586-206000 (414 bps) were amplified by PCR from Listeria monocytogenes, strain DP-L4056, using the primer pair shown below. The region amplified includes the hly promoter and also the first 28 amino acids of LLO, comprising the secA1 signal peptide (see above) and PEST domain. The expected sequence of this region for Listeria monocytogenes, strain EGD can be found in GenBank (Accession number: gi|16802048|ref|NC_003210.1|[16802048]). The primers used in the PCR reaction are as follows:

Primer Pair:

```
Forward (KpnI-LLO nts. 1257-1276):
5'-CTCTGGTACCTCCTTTGATTAGTATATTC    (SEQ ID NO: 74)

Reverse (Barn HI-LLO nts.):
5'-CTCTGGATCCATCCGCGTGTTTCTTTTCG    (SEQ ID NO: 84)
```

(Restriction endonuclease recognition sites are underlined.)

The 422 bp PCR amplicon was cloned into the plasmid vector pCR-XL-TOPO (Invitrogen, Carlsbad, Calif.), according to the manufacturer's specifications. The nucleotide sequences of Listeria-specific bases in the pCR-XL-TOPO-hly promoter plasmid clone was determined. Listeria monocytogenes strain DP-L4056 contained eight nucleotide base changes flanking the prfA box in the hly promoter, as compared to the EGD strain. The hly promoter alignment for the Listeria monocytogenes DP-L4056 and EGD strains is shown in FIG. 1 below.

The 422 bp DNA corresponding to the hly promoter and secA1 LLO signal peptide were liberated from the pCR-XL-TOPO-hly promoter plasmid clone by digestion with Kpn I and Bam HI, and cloned into the pPL2 plasmid vector (Lauer et. al. 2002 J. Bact.), according to conventional methods well-known to those skilled in the art. This plasmid is known as pPL2-hlyP (native).

C. Shine-Dalgarno Sequence

At the 3' end of the promoter is contained a poly-purine Shine-Dalgarno sequence, the element required for engagement of the 30S ribosomal subunit (via 16S rRNA) to the heterologous gene RNA transcript and initiation of translation. The Shine-Dalgarno sequence has typically the following consensus sequence: 5'-NAGGAGGU-N$_{5-10}$-AUG (start codon)-3' (SEQ ID NO:85; SEQ ID NOS:125-129). There are variations of the poly-purine Shine-Dalgarno sequence, Notably, the Listeria hly gene that encodes listerolysin O (LLO) has the following Shine-Dalgarno sequence: AAG-GAGAGTGAAACCCATG (SEQ ID NO:70) (Shine-Dalgarno sequence is underlined, and the translation start codon is bolded).

Example 4

Polynucleotides Encoding a Fusion Protein Comprising a secA1 Signal Peptide (LLO) and Human EphA2

The sequence of an expression cassette encoding the full-length human EphA2 antigen fused to a secA1 signal peptide (LLO signal peptide), plus the LLO PEST sequence, is shown in FIG. 2. The amino acid sequence of the fusion protein encoded by this expression cassette is shown in FIG. 3.

Example 5

Codon-Optimization of the Extracellular Domain of Human EphA2 (EX2)

The sequence encoding the extracellular domain of human EphA2 (amino acids 25-526) has been codon-optimized for expression in *Listeria monocytogenes*. The native nucleotide sequence encoding the extracellular domain of human EphA2 is shown in FIG. 4. The nucleotide sequence for optimal codon usage in *Listeria* is shown in FIG. 5. The amino acid sequence of the extracellular domain of human EphA2 is shown in FIG. 6.

Example 6

Polynucleotides Encoding an Fusion Proteins Comprising a secA1 Signal Peptide (LLO) and the Extracellular Domain of huEphA2 (EX2)

A. Polynucleotide Without Codon-Optimization

The sequence of a polynucleotide encoding the extracellular domain of human EphA2 antigen fused to a secA1 signal peptide (LLO signal peptide), plus the LLO PEST sequence, is shown in FIG. 7. The amino acid sequence of the fusion protein encoded by this expression cassette is shown in FIG. 8.

B. Expression Cassette With Codon-Optimized Extracellular Domain of Human EphA2

The sequence of an expression cassette encoding the extracellular domain of human EphA2 antigen fused to a secA1 signal peptide (LLO signal peptide), plus the LLO PEST sequence, in which the sequence encoding the extracellular domain of EphA2 is codon-optimized for expression in *Listeria monocytogenes*, is shown in FIG. 9. The amino acid sequence of the fusion protein encoded by this expression cassette is shown in FIG. 10.

C. Expression Cassette With Codon-Optimized secA1 Signal Peptide and Codon-Optimized Extracellular Domain of Human EphA2

The sequence of an expression cassette encoding the extracellular domain of human EphA2 antigen fused to a secA1 signal peptide (LLO signal peptide), plus the LLO PEST sequence, where the sequences encoding the extracellular domain of EphA2, signal peptide and PEST sequence are all codon-optimized for expression in *Listeria monocytogenes*, is shown in FIG. 11. The amino acid sequence of the fusion protein encoded by this expression cassette is shown in FIG. 12.

Example 7

Codon-Optimized Expression Cassette Encoding a Fusion Protein Comprising a Tat Signal Peptide (*B. subtilis* phoD) and Extracellular Domain of huEphA2 (EX2)

The sequence of an expression cassette encoding the extracellular domain of EphA2 antigen fused to a Tat signal peptide (*B. subtilis* phoD) where the sequences encoding the extracellular domain of EphA2 and the signal peptide are all codon-optimized for expression in *Listeria monocytogenes*, is shown in FIG. 13. The amino acid sequence of the fusion protein encoded by this expression cassette is shown in FIG. 14.

Example 8

Codon-Optimization of the Intracellular Domain of Human EphA2 (CO)

The sequence encoding the intracellular domain of human EphA2 (amino acids 558-975) has been codon-optimized for expression in *Listeria monocytogenes*. The native nucleotide sequence encoding the extracellular domain of human EphA2 is shown in FIG. 15. The nucleotide sequence for optimal codon usage in *Listeria* is shown in FIG. 16. The amino acid sequence of the extracellular domain of human EphA2 is shown in FIG. 17.

Example 9

Polynucleotides Encoding Fusion Proteins Comprising a secA1 Signal Peptide (LLO) and Intracellular Domain of huEphA2 (CO)

A. Polynucleotide Without Codon-Optimization

The sequence of a polynucleotide encoding the intracellular domain of human EphA2 antigen fused to a secA1 signal peptide (LLO), plus the LLO PEST sequence, is shown in FIG. 18. The amino acid sequence of the fusion protein encoded by this expression cassette is shown in FIG. 19.

B. Expression Cassette With Codon-Optimized Intracellular Domain of Human EphA2

The sequence of an expression cassette encoding the intracellular domain of huEphA2 antigen fused to a secA1 signal peptide (LLO signal peptide), plus the LLO PEST sequence, in which the sequence encoding the intracellular domain of EphA2 is codon-optimized for expression in *Listeria monocytogenes*, is shown in FIG. 20. The amino acid sequence of the fusion protein encoded by this expression cassette is shown in FIG. 21.

C. Expression Cassette With Codon-Optimized secA1 Signal Peptide and Codon-Optimized Intracellular Domain of Human EphA2

The sequence of an expression cassette encoding the intracellular domain of EphA2 antigen fused to a secA1 signal peptide (LLO signal peptide), plus the LLO PEST sequence, where the sequences encoding the intracellular domain of EphA2, signal peptide and PEST sequence are all codon-optimized for expression in *Listeria monocytogenes*, is shown in FIG. 22. The amino acid sequence of the fusion protein encoded by this expression cassette is shown in FIG. 23.

Example 10

Codon-Optimized Expression Cassette Encoding a Fusion Protein Comprising *B. subtilis* phoD Signal Peptide and Intracellular Domain of huEphA2 (CO)

The sequence of an expression cassette encoding the intracellular domain of EphA2 antigen fused to a Tat signal peptide (*B. subtilis* phoD) where the sequences encoding the intracellular domain of EphA2 and the signal peptide are all codon-optimized for expression in *Listeria monocytogenes*, is shown in FIG. 24. The amino acid sequence of the fusion protein encoded by this expression cassette is shown in FIG. 25.

Example 11

Codon-Optimized Expression Cassette Encoding a Fusion Protein Comprising LLO Signal Peptide and NY-ESO-1

An expression cassette was designed for expression of the human testis cancer antigen NY-ESO-1 (Genbank Accession No. NM_001327) in *Listeria monocytogenes*. The sequence of the expression cassette encoding the NY-ESO-1 fused to a secA1 signal peptide (LLO), plus the LLO PEST sequence, is shown in FIG. 26. The sequences coding for the antigen as well as the signal peptide in the expression cassette were codon-optimized for expression in *Listeria monocytogenes*. The amino acid sequence of the fusion protein encoded by this expression cassette is shown in FIG. 27.

Example 12

Codon-Optimized Expression Cassette for Encoding Antigens Fused to a Non-Listerial secA1 Signal Peptide (*L. Lactis* usp45)

An expression cassette was designed for expression of heterologous antigens in *Listeria monocytogenes* using a non-Listerial secA1 signal peptide. The amino acid sequence of the usp45 signal peptide from *Lactococcus lactis* (Steidler et al., *Nature Biotechnology,* 21:785-9 (2003)), its native coding sequence, and the coding sequence optimized for expression in *Listeria monocytogenes* is shown below.

```
Amino acid sequence:
                                          (SEQ ID NO: 46)
MKKKIISAILMSTVILSAAAPLSGVYA'DT
                                          (SEQ ID NO: 55)
Signal peptidase recognition site: VYA-DT Native nucleotide sequence:
                                          (SEQ ID NO: 86)
5'ATGAAAAAAAAGATTATCTCAGCTATTTTAATGTCTACAGTGATACTT
TCTGCTGCAGCCCCGTTGTCAGGTGTTTACGCTGACACA3'

Codons optimized for expression in Listeria
monocytogenes:
                                          (SEQ ID NO: 87)
5'ATGAAAAAAAAAATTATTAGTGCAATTTTAATGAGTACAGTTATTTTA
AGTGCAGCAGCACCATTAAGTGGTGTTTATGCAGATACA3'
```

The sequence of a partial expression cassette comprising the hly promoter from *Listeria monocytogenes* operably linked to the codon-optimized sequence encoding the Usp45 signal peptide is shown in FIG. 28. This sequence can be combined with either a codon-optimized or non-codon-optimized antigen sequence for expression of a fusion protein comprising the Usp45 signal peptide and the desired antigen.

Example 13

Codon-Optimized Expression Cassette and Vector for Encoding Antigens Fused to a secA2 Signal Peptide (p60)

A. Design of Codon-Optimized Expression Cassette

An expression cassette was designed for expression of heterologous antigens in *Listeria monocytogenes* using the secA2 secretion pathway. The amino acid sequence of the p60 signal peptide from *Listeria monocytogenes*, its native coding sequence, and the coding sequence optimized for expression in *Listeria monocytogenes* is shown below.

```
Amino acid sequence:
                                          (SEQ ID NO: 48)
MNMKKATIAATAGIAVTAFAAPTIASA'ST
                                          (SEQ ID NO: 57)
Signal peptidase recognition site: ASA-ST Native nucleotide sequence:
                                          (SEQ ID NO: 90)
5'ATGAATATGAAAAAAGCAACTATCGCGGCTACAGCTGGGATTGCGGT
AACAGCATTTGCTGCGCCAACAATCGCATCCGCAAGCACT3'

Codons optimized for expression in Listeria
monocytogenes:
                                          (SEQ ID NO: 91)
5'ATGAATATGAAAAAAGCAACAATTGCAGCAACAGCAGGTATTGCAGT
TACAGCATTTGCAGCACCAACAATTGCAAGTGCAAGTACA3'
```

The sequence of a partial expression cassette comprising the hly promoter from *Listeria monocytogenes* operably linked to the native sequence encoding the p60 signal peptide is shown in FIG. 29. The sequence of a partial expression cassette comprising the hly promoter from *Listeria monocytogenes* operably linked to the codon-optimized sequence encoding the p60 signal peptide is shown in FIG. 30.

B. Construction of pPL2-hlypro_p60.

An expression cassette can also be constructed in which the antigen-encoding sequence is inserted in frame in one or more sites within the coding sequence of the p60 gene. A description of the construction of a partial expression cassette useful for inserting antigen sequences in frame within the p60 sequence is described below. This partial expression cassette contains an hly promoter.

Individual primary PCR reactions using Pfx or Vent polymerase are performed using the following primers and pPL2-hlyP-OVA (identical to pPL2/LLO-OVA described above in Example 2A) as a first template:

```
pPL2-5F:
                                          (SEQ ID NO: 92)
5'-GACGTCAATACGACTCACTATAG p60-hlyP-237R:
                                          (SEQ ID NO: 93)
5'-CTTTTTTCATATTCATGGGTTTCACTCTCCTTCTAC
```

The size of the resulting amplicon is 285 bps.

Individual primary PCR reactions using Pfx or Vent polymerase are also performed using the following primers and pCR-TOPO-p60 as a second template. (The vector pCR-TOPO-p60 is made from a pCR-TOPO vector obtained from Invitrogen, Carlsbad, Calif. in which the genomic p60 sequence from *Listeria monocytogenes* has been inserted. Any other of the many alternative sources of the p60 coding sequence that are available could be used as a template instead.) The primers used in this PCR reaction are as follows:

```
hlyP-p60-1F:
                                          (SEQ ID NO: 88)
5'-AAGGAGAGTGAAACCCATGAATATGAAAAAAGCAAC pCR-TOPO-2283R:
                                          (SEQ ID NO: 89)
5'-GTGTGATGGATATCTGCAGAATTC
```

The size of the resulting amplicon is 1510 bps. The PCR reactions are then cleaned with S6 columns (Bio-Rad Laboratories, Hercules, Calif.).

A secondary PCR reaction is then performed, using approximately 5 µl of each primary PCR reaction as template. The secondary PCR reaction uses the following primers: KpnI-LLO 1257F (primer used previously): 5'CTCTGG-TACCTCCTTTGATTAGTATATTC (SEQ ID NO:74) and pCR-TOPO-2258R: 5'-CCCTTGGGGATCCTTAAT-TATACG (SEQ ID NO:83). The size of the resulting amplicon is 1715 bps. The expected amplicon sizes in all PCR reactions are verified by agarose gel analysis. The secondary PCR reaction is cleaned, digested with BamHI, cleaned again, and digested with KpnI. The hlyP-p60 gene fragment (KpnI-BamHI) (FIG. 30) is then ligated between the BamHI and KpnI sites of both pPL2 and modified pAM401 (pAM401-MCS; FIG. 32) plasmids.

The construction of pPL2-p60 plasmid is then confirmed with BamH/KpnI (1697, 6024 bps) and HindIII (210, 424, 3460, 3634 bps) digests. The PstI site in pPL2-p60 plasmid is also confirmed as unique. (Also, KpnI/PstI digest will yield fragments of 736 and 6985 bps.) The construction of the pAM401-p60 plasmid (KpnI/PstI, and KpnI/BamHI fragments from p60 region is the same as that for the pPL2 construct.

Large prep isolations of each plasmid are then prepared using methods known to those of ordinary skill in the art.

The desired antigen-encoding sequences can then be inserted within the p60 sequence and in the same translational frame as the p60 sequence using techniques well known to those of ordinary skill in the art. Typically, the insertion or insertions should leave the N-terminal signal peptide sequence of p60 intact. The C-terminal autolysin sequence of p60 should also be left intact.

Example 14

Codon-Optimization of Human Mesothelin-Encoding Sequences for Expression in *Listeria monocytogenes*

A codon-optimized polynucleotide sequence encoding human mesothelin, a cancer antigen, is shown in FIG. 33. The sequence shown in FIG. 32 has been codon-optimized for expression in *Listeria monocytogenes*. The polypeptide sequence encoded by the sequence in FIG. 33 is shown in FIG. 34.

Example 15

Codon-Optimization of Murine Mesothelin-Encoding Sequences for Expression in *Listeria monocytogenes*

A codon-optimized polynucleotide sequence encoding human mesothelin, a cancer antigen, is shown in FIG. 35. The sequence shown in FIG. 35 has been codon-optimized for expression in *Listeria monocytogenes*. The polypeptide sequence encoded by the sequence in FIG. 35 is shown in FIG. 36.

Example 16

Integration of an Expression Cassette into the *Listeria* chromosome via Allelic Exchange As one possible alternative to using an integration vector such as pPL2 to insert the heterologous gene expression cassette into the chromosome of *Listeria*, allelic exchange may be used.

Briefly, bacteria electroporated with the pKSV7-heterologous protein expression cassette plasmid are selected by plating on BHI agar media containing chloramphenicol (10 µg/ml), and incubated at the permissive temperature of 30° C. Single cross-over integration into the bacterial chromosome is selected by passaging several individual colonies for multiple generations at the non-permissive temperature of 41° C. in media containing chloramphenicol. Finally, plasmid excision and curing (double cross-over) is achieved by passaging several individual colonies for multiple generations at the permissive temperature of 30° C. in BHI media not containing chloramphenicol. Verification of integration of the heterologous protein expression cassette into the bacteria chromosome is verified by PCR, utilizing a primer pair that amplifies a region defined from within the heterologous protein expression cassette to the bacterial chromosome targeting sequence not contained in the pKSV7 plasmid vector construct.

Example 17

Cloning and Insertion of EphA2 into pPL2 Vectors for Expression in Selected Recombinant *Listeria monocytogenes* Strains The external (EX2) and cytoplasmic (CO) domains of EphA2 which flank the EphA2 transmembrane helix were cloned separately for insertion into various pPL2-signal peptide expression constructs. Genes corresponding to the native mammalian sequence or codon-optimized for expression in *Listeria monocytogenes* of EphA2 EX2 and CO domains were used. The optimal codons in *Listeria* (see Table 3, above) for each of the 20 amino acids were utilized for codon-optimized EphA2 EX2 and EphA2 CO. The codon-optimized EphA2 EX2 and CO domains were synthesized by extension of overlapping oligonucleotides, using techniques common to those skilled in the art. The expected sequence of all synthesized EphA2 constructs was verified by nucleotide sequencing.

The primary amino acid sequences, together with the native and codon-optimized nucleotide sequences for the EX2 and CO domains of EphA2 are shown in FIGS. 4-6 (EX2 sequences) and FIGS. 15-17 (CO domain sequences).

Additonally, FLAG (Stratagene, La Jolla, Calif.) and myc epitope tags were inserted, respectively, in-frame at the amino and carboxy termini of synthesized EphA2 EX2 and CO genes for detection of expressed and secreted EphA2 by Western blot analysis using antibodies specific for the FLAG or proteins. Thus, the expressed protein had the following ordered elements: $NH_2$-Signal Peptide-FLAG-EphA2-myc-$CO_2$. Shown below are the FLAG and myc epitope tag amino acid and codon-optimized nucleotide sequences:

```
FLAG:
5'-GATTATAAAGATGATGATGATAAA      (SEQ ID NO: 96)

NH2-DYKDDDDK-CO2                  (SEQ ID NO: 97)

Myc:
5'-GAACAAAAATTAATTAGTGAAGAAGATTTA (SEQ ID NO: 98)

NH2-EQKLISEEDL-CO2                (SEQ ID NO: 99)
```

Example 18

Detection of Synthesized and Secreted Heterologous Proteins by Western Blot Analysis Synthesis of EphA2 protein and secretion from various selected recombinant *Listeria*-EphA2 strains was determined by Western blot analysis of trichloroacetic acid (TCA) precipitated bacterial culture fluids. Briefly, mid-log phase cultures of *Listeria* grown in BHI media were collected in a 50 mL conical centrifuge tube, the bacteria were pelleted, and ice-cold TCA was added to a final [6%] concentration to the bacterial culture supernatant and incubated on ice minimally for 90 min or overnight. The TCA-precipitated proteins were collected by centrifugation at 2400×g for 20 min at 4° C. The pellet was then resuspended in 300-600 µl volume of TE, pH 8.0 containing 15 µg/ml phenol red. Sample dissolution was facilitated by vortexing. Sample pH was adjusted by NH$_4$OH addition if necessary until color was pink. All samples were prepared for electrophoresis by addition of 100 µl of 4×SDS loading buffer and incubating for 10 min. at 90° C. The samples were then centrifuged from 5 min at 14,000 rpm in a micro-centrifuge, and the supernatants collected and stored at −20° C. For Western bolt analysis, 20 µl of prepared fractions (the equivalent of culture fluids from of 1-4×10$^9$ bacteria), were loaded on the 4-12% SDS-PAGE gel, electrophoresed, and the proteins were transferred to PDDF membrane, according to common methods used by those skilled in the art. Transferred membranes were prepared s for incubation with antibody, by incubating in 5% dry milk in PBS for 2 hr. at room temperature with agitation. Antibodies were used under the following dilutions in PBST buffer (0.1% Tween 20 in PBS): (1) Rabbit anti-Myc polyclonal antibody (ICL laboratories, Newberg, Oreg.) at 1:10,000; (2) murine anti-FLAG monoclonal antibody (Stratagene, La Jolla, Calif.) at 1:2,000; and, (3) Rabbit anti-EphA2 (carboxy terminus-specific) polyclonal antibody (sc-924, Santa Cruz Biotechnology, Inc., Santa Cruz, Calif.). Specific binding of antibody to protein targets was evaluated by secondary incubation with goat anti-rabbit or anti-mouse antibody conjugated with horseradish peroxidase and detection with the ECL chemilumenescence assay kit (Amersham), and exposure to film.

Example 19

Secretion of EphA2 Protein by Recombinant *Listeria* Encoding Various Forms of EphA2

A. *Listeria*: [Strains DP-L4029 (actA) or DP-L4017 (LLO L461T)]

Expression Cassette Construct: LLOss-PEST-CO-EphA2

The native sequence of the EphA2 CO domain was genetically fused to the native secA1 LLO sequence, and the heterologous antigen expression cassette under control of the *Listeria* hly promoter was inserted into the pPL2 plasmid between the Kpn I and Sac I sites as described above. The pPL2-EphA2 plasmid constructs were introduced by conjugation into the *Listeria* strains DP-L4029 (actA$^-$) and DP-L4017 (L461T LLO) as described above. FIG. 37 shows the results of a Western blot analysis of TCA-precipitated bacterial culture fluids of 4029-EphA2 CO and 4017-EphA2 CO. This analysis demonstrated that recombinant *Listeria* engineered to contain a heterologous protein expression cassette comprised of native sequences corresponding to the secA1 and EphA2 CO fusion protein secreted multiple EphA2-specific fragments that were lower than the 52 kDa expected molecular weight, demonstrating the need for modification of the expression cassette.

B. *Listeria*: [DP-L4029 (actA$^-$)]
  Expression Cassette Constructs:
  1. Native LLOss-PEST-FLA G-EX2_EphA2-myc-CodonOp
  2. (CodonOp) LLOss-PEST-(CodonOp)FLA G-EX2_EphA2-myc The native secA1 LLO signal peptide sequence or secA1 LLO signal peptide sequence codon-optimized for expression in *Listeria* was fused genetically with the EphA2 EX2 domain sequence codon-optimized for expression in *Listeria*, and the heterologous antigen expression cassette under control of the *Listeria* hly promoter was inserted into the pPL2 plasmid between the Kpn I and Sac I sites as described above. The pPL2-EphA2 plasmid constructs were introduced by conjugation into the *Listeria* strain DP-L4029 (actA) as described above. FIG. 38 shows the results of a Western blot analysis of TCA-precipitated bacterial culture fluids of *Listeria* actA encoding either the native or codon-optimized secA1 LLO signal peptide fused with the codon-optimized EphA2 EX2 domain. This analysis demonstrated that the combination of utilizing sequence for both signal peptide and heterologous protein optimized for the preferred codon usage in *Listeria monocytogenes* resulted in expression of the expected full-length EphA2 EX2 domain protein. Expression of full-length EphA2 EX2 domain protein was poor with codon-optimization of the EphA2 coding sequence alone. The level of heterologous protein expression (fragmented or full-length) was highest when utilizing the *Listeria monocytogenes* LLO secA1 signal peptide, codon-optimized for expression in *Listeria monocytogenes*.

C. Listeria: [DP-L4029 (actA)]
  Expression Cassette Constructs:
  3. Native LLOss-PEST-(CodonOp) FLAG-EphA2_CO-myc
  4. CodonOp LLOss-PEST-(CodonOp) FLAG-EphA2_CO-myc
  5. CodonOp PhoD-(CodonOp) FLAG-EphA2_CO-myc The native secA1 LLO signal peptide sequence or the secA1 LLO signal peptide sequence codon-optimized for expression in *Listeria*, or, alternatively, the Tat signal peptide of the phoD gene from *Bacillus subtilis* codon-optimized for expression in *Listeria*, was fused genetically with the EphA2 CO domain sequence codon-optimized for expression in *Listeria*, and the heterologous antigen expression cassette under control of the *Listeria* hly promoter was inserted into the pAM401-MCS plasmid between the Kpn I and Sac I sites as described above. The pAM401-EphA2 plasmid constructs were introduced by electroporation into the *Listeria* strain DP-L4029 (actA) as described above. FIG. 39 shows the results of a Western blot analysis of TCA-precipitated bacterial culture fluids of *Listeria* actA encoding either the native or codon-optimized secA1 LLO signal peptide, or codon-optimized *Bacillus subtilis* phoD Tat signal peptide fused with the codon-optimized EphA2 CO domain. This analysis demonstrated once again that the combination of utilizing sequence for both signal peptide and heterologous protein optimized for the preferred codon usage in *Listeria monocytogenes* resulted in expression of the expected full-length EphA2 CO domain protein. Furthermore, expression and secretion of the expected full-length EphA2 CO domain protein resulted from recombinant *Listeria* encoding codon-optimized *Bacillus subtilis* phoD Tat signal peptide fused with the codon-optimized EphA2 CO domain. This result demonstrates the novel and unexpected finding that signal peptides from distinct bacterial species can be utilized to program the secretion of heterologous proteins from recombinant *Listeria*. Expression of full-length EphA2 CO domain protein was poor with codon-optimization of just the EphA2 sequence. The level of heterologous protein expression was highest when utilizing signal peptides codon-optimized for expression in *Listeria monocytogenes*.

D. Transfection of 293 Cells With pCDNA4 Plasmids Encoding Full-Length EphA2

Expression Cassette Constructs:

6. pCDNA4-EphA2

The native full-length EphA2 gene was cloned into the eukaryotic CMV promoter-based expression plasmid pCDNA4 (Invitrogen, Carlsbad, Calif.). FIG. 40 shows the results of a Western blot analysis of lysates prepared from 293 cells transfected with the pCDNA4-EphA2 plasmid, and demonstrates the abundant expression in mammalian cells of full-length EphA2 protein.

Example 20

Therapeutic Efficacy in Balb/C Mice Bearing CT26 Tumors Encoding Human EphA2 Immunized With Recombinant *Listeria* Encoding Codon-Optimized EphA2

The following data presented in FIGS. 41-44 demonstrated the following:

Immunization of Balb/C mice bearing CT26.24 (huEphA2+) lung tumors with recombinant *Listeria* encoding OVA.AH1 (MMTV gp70 immunodominant epitope) or OVA.AH1-A5 (MMTV gp70 immunodominant epitope, with heteroclitic change for enhanced T-cell receptor binding) confers long-term survival (FIG. 41).

The EphA2 CO domain is strongly immunogenic, and a significant long term increase in survival of Balb/C mice bearing CT26.24 (huEphA2+) lung tumors was observed when immunized with recombinant *Listeria* encoding codon-optimized or native EphA2 CO domain sequence (FIG. 43).

The EphA2 EX2 domain is poorly immunogenic, and increased survival of Balb/C mice bearing CT26.24 (huEphA2+) lung tumors was observed only when immunized with recombinant *Listeria* encoding codon-optimized secA1 signal peptide fused with the codon-optimized EphA2 EX2 domain sequence. Therapeutic efficacy was not observed in mice when immunized with recombinant *Listeria* encoding native secA1 signal peptide fused with the codon-optimized EphA2 EX2 domain sequence (FIG. 42). The desirability of using both codon-optimized secA1 signal peptide and EphA2 EX2 domain sequences was supported by statistically significant therapeutic anti-tumor efficacy, as shown in Table 4, below.

TABLE 4

Comparison by log-rank test of survival curves shown in FIG. 42.

| Experimental Group | Median Survival (Days) | Significance versus HBSS cohort (p value) | Significance versus actA-native secA1/EphA2 EX2 cohort (p value) |
|---|---|---|---|
| HBSS | 19 | — | — |
| actA | 20 | NS | NS |
| actA-native secA1-EphA2 EX2 (native) | 19 | NS | — |
| actA-native secA1-EphA2 EX2 (CodOp) | 24 | 0.0035 | NS |
| actA-CodOp secA1-EphA2 EX2 (CodOp) | 37 | 0.0035 | 0.0162 |
| actA-native secA1-EphA2 CO (CodOp) | >99 | 0.0035 | 0.0015 |

Significantly, even though pCDNA4-EphA2 plasmid transfected 293 cells yielded very high levels of protein expression, immunization of Balb/C mice bearing CT26.24 (huEphA2+) lung tumors with the pCDNA4-EphA2 plasmid did not result in any observance of therapeutic anti-tumor efficacy (FIG. 44).

For therapeutic in vivo tumor studies, female Balb/C mice were implanted IV with $5 \times 10^5$ CT26 cells stably expressing EphA2. Three days later, mice were randomized and vaccinated IV with various recombinant *Listeria* strains encoding EphA2. In some cases (noted in figures) mice were vaccinated with 100 µg of pCDNA4 plasmid or pCDNA4-EphA2 plasmid in the tibialis anterior muscle. As a positive control, mice were vaccinated IV with recombinant *Listeria* strains encoding OVA.AHI or OVA.AH1-A5 protein chimeras. Mice were vaccinated on days 3 and 14 following tumor cell implantation. Mice injected with Hanks Balanced Salt Solution (HBSS) buffer or unmodified *Listeria* served as negative controls. All experimental cohorts contained 5 mice. For survival studies mice were sacrificed when they started to show any signs of stress or labored breathing.

Example 21

Assessment of Antigen-Specific Immune Responses After Vaccination

The vaccines of the present invention can be assessed using a variety of in vitro and in vivo methods. Some assays involve the analysis of antigen-specific T cells from the spleens of mice that have been vaccinated. Provided in this example are non-limiting examples of methods of assessing in vitro and in vivo immune responses. The antigens recited in these exemplary descriptions of assays are model antigens, not necessarily antigens produced using the recombinant nucleic acid molecules, expression cassettes, and/or expression vectors described herein. One of ordinary skill in the art will readily recognize that the assays described in this example can readily be applied for use in assessing the in vitro or in vivo immune responses of bacteria comprising the recombinant nucleic acid molecules, expression cassettes, and/or expression vectors described herein.

For example C57Bl/6 or Balb/c are vaccinated by intravenous injection of 0.1 $LD_{50}$ of a *Listeria* strain expressing OVA (or other appropriate antigen). Seven days after the vaccination, the spleen cells of the mice are harvested (typically 3 mice per group) by placing the spleens into ice cooled RPMI 1640 medium and preparing a single cell suspension from this. As an alternative, the lymph nodes of the mice could be similarly harvested, prepared as a single cell suspension and substituted for the spleen cells in the assays described below. Typically, spleen cells are assessed for intravenous or intraperitoneal administration of the vaccine while spleen cells and cells from lymph nodes are assessed for intramuscular, subcutaneous or intradermal administration of the vaccine.

Unless otherwise noted, all antibodies used in these examples can be obtained from Pharmingen, San Diego, Calif.

ELISPOT Assay: Using a *Listeria* strain having an OVA antigen as an example, the quantitative frequency of antigen-specific T cells generated upon immunization in a mouse model is assessed using an ELISPOT assay. The antigen-specific T cells evaluated are OVA specific CD8+ or LLO specific CD8+ or CD4+ T cells. This OVA antigen model assesses the immune response to a heterologous tumor antigen inserted into the vaccine and could be substituted with any antigen of interest. The LLO antigen is specific to *Listeria*. The specific T cells are assessed by detection of cytokine release (e.g. IFN-γ) upon recognition of the specific antigen. PVDF-based 96 well plates (BD Biosciences, San Jose, Calif.) are coated overnight at 4° C. with an anti-murine IFN-γ monoclonal antibody (mAb R4; 5 µg/ml). The plates are washed and blocked for 2 hours at room temperature with 200 µL of complete RPMI. Spleen cells from vaccinated mice (or non vaccinated control mice) are added at $2\times10^5$ cells per well and incubated for 20 to 22 hours at 37° C. in the presence of various concentrations of peptides ranging from 0.01 to 10 µM. The peptides used for OVA and LLO are either SL8, an MHC class I epitope for OVA, $LLO_{190}$ (NEKYAQAYPNVS (SEQ ID NO: 100) Invitrogen) an MHC class II epitope for listeriolysin O (*Listeria* antigen), $LLO_{296}$ (VAYGRQVYL (SEQ ID NO:101) an MHC class I epitope for listeriolysin O, or $LLO_{91}$ (GYKDGNEYI (SEQ ID NO:102)), an MHC class I epitope for listeriolysin O. $LLO_{190}$ and $LLO_{296}$ are used in a C57Bl/6 model, while $LLO_{91}$ is used in a Balb/c model. After washing, the plates are incubated with secondary biotinylated antibodies specific for IFN-γ (XMG1.2) diluted in PBS to 0.5 µg/ml. After incubation at room temperature for 2 hours, the plates are washed and incubated for 1 hour at 37° C. with a 1 nm gold goat anti-biotin conjugate (GAB-1; 1:200 dilution; Ted Pella, Redding, Calif.) diluted in PBS containing 1% BSA. After thorough washing, the plates are incubated at room temperature for 2 to 10 minutes with substrate (Silver Enhancing Kit; 30 ml/well; Ted Pella) for spot development. The plates are then rinsed with distilled water to stop the substrate reaction. After the plates have been air-dried, spots in each well are counted using an automated ELISPOT plate reader (CTL, Cleveland, Ohio). The cytokine response is expressed as the number of IFN-γ spot-forming cells (SFCs) per $2\times10^5$ spleen cells for either the OVA specific T cells or the *Listeria* specific T cells.

Intracellular Cytokine Staining Assay (ICS): In order to further assess the number of antigen-specific CD8+ or CD4+ T cells and correlate the results with those obtained from ELISPOT assays, ICS is performed and the cells evaluated by flow cytometry analysis. Spleen cells from vaccinated and control groups of mice are incubated with SL8 (stimulates OVA specific CD8+ cells) or $LLO_{190}$ (stimulates LLO specific CD4+ cells) for 5 hours in the presence of Brefeldin A (Pharmingen). The Brefeldin A inhibits secretion of the cytokines produced upon stimulation of the T cells. Spleen cells incubated with an irrelevant MHC class I peptide are used as controls. PMA (phorbol-12-myristate-13-acetate, Sigma) 20 ng/ml and ionomycin (Sigma) 2 µg/ml stimulated spleen cells are used as a positive control for IFN-γ and TNF-α intracellular cytokine staining. For detection of cytoplasmic cytokine expression, cells are stained with FITC-anti-CD4 mAb (RM 4-5) and PerCP-anti-CD8 mAb (53-6.7), fixed and permeabilized with Cytofix/CytoPerm solution (Pharmingen), and stained with PE-conjugated anti-TNF-α mAb (MP6-XT22) and APC-conjugated anti-IFN-γ mAb (XMG1.2) for 30 minutes on ice. The percentage of cells expressing intracellular IFN-γ and/or TNF-α was determined by flow cytometry (FACScalibur, Becton Dickinson, Mountain View, Calif.) and data analyzed using CELLQuest software (Becton Dickinson Immunocytometry System). As the fluorescent labels on the various antibodies can all be distinguished by the FACScalibur, the appropriate cells are identified by gating for those CD8+ and CD4+ that are stained with either or both of the anti-IFN-γ or anti-TNF-α.

*Cytokine Expression of Stimulated Spleen Cells*: The level of cytokine secretion by the spleen cells of mice can also be assessed for control and vaccinated C57Bl/6 mice. Spleen cells are stimulated for 24 hours with SL8 or $LLO_{190}$. Stimulation with irrelevant peptide HSV-gB2 (Invitrogen, SSIE-FARL, SEQ ID NO:124) is used as a control. The supernatants of the stimulated cells are collected and the levels of T helper-1 and T helper 2 cytokines are determined using an ELISA assay (eBiosciences, CO) or a Cytometric Bead Array Kit (Pharmingen).

Assessment of Cytotoxic T cell Activity: The OVA specific CD8+ T cells can be further evaluated by assessing their cytotoxic activity, either in vitro or directly in C57Bl/6 mouse in vivo. The CD8+ T cells recognize and lyse their respective target cells in an antigen-specific manner. In vitro cytotoxicity is determined using a chromium release assay. Spleen cells of naïve and *Listeria*-OVA (internal) vaccinated mice are stimulated at a 10:1 ratio with either irradiated EG7.OVA cells (EL-4 tumor cell line transfected to express OVA, ATCC, Manassas, Va.) or with 100 nM SL8, in order to expand the OVA specific T cells in the spleen cell population. After 7 days of culture, the cytotoxic activity of the effector cells is determined in a standard 4-hour 51Cr-release assay using EG7.OVA or SL8 pulsed EL-4 cells (ATCC, Manassas, Va.) as target cells and EL-4 cells alone as negative control. The YAC-1 cell line (ATCC, Manassas, Va.) is used as targets to determine NK cell activity, in order to distinguish the activity due to T cells from that due to NK cells. The percentage of specific cytotoxicity is calculated as 100× (experimental release−spontaneous release)/(maximal release−spontaneous release). Spontaneous release is determined by incubation of target cells without effector cells. Maximal release is determined by lysing cells with 0.1% Triton X-100. Experiments are considered valid for analysis if spontaneous release is <20% of maximal release.

For the assessment of cytotoxic activity of OVA-specific CD8+ T cells in vivo, spleen cells from naïve C57Bl/6 mice are split into two equivalent aliquots. Each group is pulsed with a specific peptide, either target (SL8) or control (HSV-gB2), at 0.5 µg/ml for 90 minutes at 37° C. Cells are then washed 3 times in medium, and twice in PBS+0.1% BSA. Cells are resuspended at $1\times10^7$ per ml in warm PBS+0.1% BSA (10 ml or less) for labeling with carboxyfluorescein diacetate succinimidyl ester (CFSE, Molecular Probes, Eugene, Oreg.). To the target cell suspension, 1.25 µL of a 5 mM stock of CFSE is added and the sample mixed by vortexing. To the control cell suspension, a ten-fold dilution of the CFSE stock is added and the sample mixed by vortexing. The cells are incubated at 37° C. for 10 minutes. Staining is stopped by addition of a large volume (>40 ml) of ice-cold PBS. The cells are washed twice at room temperature with PBS, then resuspended and counted. Each cell suspension is diluted to $50\times10^6$ per ml, and 100 µL of each population is mixed and injected via the tail vein of either naïve or vaccinated mice. After 12-24 hours, the spleens are harvested and a total of 5×10⁶ cells are analyzed by flow cytometry. The high (target) and low (control) fluorescent peaks are enumerated, and the ratio of the two is used to establish the percentage of target cell lysis. The in vivo cytotoxicity assay permits the assessment of lytic activity of antigen-specific T cells without the need of in vitro re-stimulation. Furthermore, this assays assesses the T cell function in their native environment.

Example 22

Human Epha2-Specific Immunity Induced by Vaccination of Balb/c Mice with *Listeria* Strains Expressing EphA2

Balb/c mice (n=3) were immunized with *Listeria* L461T expressing the intracellular domain of hEphA2 (*Listeria* hEphA2-ICD in FIG. 45) or an ΔactA (actA⁻) strain of *Listeria* expressing the extracellular domain of hEphA2 from a sequence codon-optimized for expression in *L. monocytogenes* (*Listeria* hEphA2-ECD in FIG. 45) two weeks apart. (The intracellular domain of hEphA2 is alternatively referred to herein as hEphA2-ICD, hEphA2 ICD, EphA2 CO, or CO. The extracellular domain of hEphA2 is alternatively referred to herein as hEphA2-ECD, hEphA2 ECD, EphA2 EX2, or EX2.) Mice were euthanized, and spleens harvested and pooled 6 days after the last immunization. For the ELISPOT assay, the cells were re-stimulated in vitro with P815 cells expressing full-length hEphA2 or cell lysates prepared from these cells. The parental P815 cells or cell lysates served as a negative control. Cells were also stimulated with recombinant hEphA2 Fc fusion protein. IFN-gamma positive spot forming colonies (SFCs) were measured using a 96 well spot reader. As shown in FIG. 45, increased IFN-gamma SFCs were observed with spleen cells derived from mice vaccinated with *Listeria*-hEphA2. Both hEphA2 expressing cells or cell lysates stimulation resulted in an increase in IFN-gamma SFC which suggests an EphA2-specific CD8+ as well as CD4+ T cell response. Spleen cells from mice vaccinated with the parental *Listeria* control did not demonstrate an increase in IFN-gamma SFC.

Example 23

CD4+ and CD8+ T Cell Responses are Required for EphA2 Specific Anti-Tumor Efficacy Balb/c mice (n=10) were inoculated i.v. with 2×10⁵ CT26-hEphA2 on day 0. CD4+ cells and CD8+ T-cells were depleted by injecting 200 μg anti-CD4 (ATCC hybridoma GK1.5) or anti-CD8 (ATCC hybridoma 2.4-3) on Days 1 and 3, which was confirmed by FACS analysis (data not shown). Mice were then immunized i.v. with 0.1 LD₅₀ *Listeria* L461T expressing hEphA2 ICD on Day 4 and monitored for survival.

As shown in FIG. 46, both CD4+ and CD8+ depleted groups failed to demonstrate the anti-tumor response seen in the non-T cell depleted animals. The data are summarized in Table 5 below:

TABLE 5

| Vaccination Group | Median Survival (Days) | P vs. HBSS | # Survivors (Day 67) |
|---|---|---|---|
| HBSS | 17 | — | 0 |
| *Listeria*-hEphA2-ICD | >67 | <0.0001 | 7 |
| *Listeria*-hEphA2-ICD + anti-CD4 | 19 | 0.03 | 2 |
| *Listeria*-hEphA2-ICD + anti-CD8 | 24 | 0.0002 | 0 |

The foregoing data indicate a requirement for both CD4+ and CD8+T cells in optimal suppression of tumor growth.

Example 24

Deletion of inlB from *Listeria* by Allelic Exchange

Bacteria comprising the recombinant nucleic acid molecules and expression cassettes described herein are, in some embodiments, mutant *Listeria*. For instance, in some embodiments, the bacteria comprising the recombinant nucleic acid molecules and expression cassettes are *Listeria monocytogenes* strains in which the actA gene, the inlB gene, or both, have been deleted. One exemplary method for generating a deletion mutant in *Listeria* is described below.

Deletion of the internalin B gene (inlB) from *Listeria* DP-L4029 (or from other selected mutant strains or from wild-type *Listeria*) can be effected by allelic exchange, as described by Camilli et al., *Mol. Microbiol.* 8:143-147 (1993). Splice Overlap Extension (SOE) PCR can be used to prepare the construct used in the allelic exchange procedure. The source of the internalin B gene is the sequence listed as Genbank accession number AL591975 (*Listeria monocytogenes* strain EGD, complete genome, segment 3/12; inlB gene region: nts. 97008-98963), incorporated by reference herein in its entirety, and/or the sequence listed as Genbank accession number NC_003210 (*Listeria monocytogenes* strain EGD, complete genome, inlB gene region: nts. 457008-458963), incorporated by reference herein in its entirety.

In the primary PCR reactions, approximately 1000 bps of sequence upstream and downstream from the *Listeria* inlB gene 5' and 3' ends, respectively, are amplified using the following template and primers:

Template: DP-L4056 or DP-L4029 genomic DNA

Primer pair 1 (For amplification of region upstream from 5' end of inlB):

```
Lm-96031F:
                                     (SEQ ID NO: 103)
5'-GTTAAGTTTCATGTGGACGGCAAAG
(T_m: 72° C.)

Lm-(3' inlB-R +) 97020R:
                                     (SEQ ID NO: 104)
5'-AGGTCTTTTTCAGTTAACTATCCTCTCCTTGATTCTAGTTAT
(T_m: 114° C.)
```

(The underlined sequence complementary to region downstream of InlB carboxy terminus.)

Amplicon Size (bps): 1007

Primer pair 2 (For amplification of region downstream from 3' end of inlB):

```
Lm-(5' inlB-F +) 98911F:
                                        (SEQ ID NO: 105)
5'-CAAGGAGAGGATAGTTAACTGAAAAAGACCTAAAAAAGAAGGC
(T_m: 118° C.)
```

(The underlined sequence complementary to region upstream of InlB amino terminus.)

```
Lm-99970R:
5'-TCCCCTGTTCCTATAATTGTTAGCTC    (SEQ ID NO: 106)
(T_m: 74° C.)
Amplicon size (bps): 1074
```

In the secondary PCR reaction, the primary PCR amplicons are fused through SOE PCR, taking advantage of complementarity between reverse primer from pair 1 and the forward primer of pair 2. This results in precise deletion of inlB coding sequence: nts. 97021-98910=1889 bps. The following template and primers were utilized in the secondary PCR reaction:
Template: Cleaned primary PCR reactions
Primer pair:

```
Lm-96043F:
5'-GTGGACGGCAAAGAAACAACCAAAG    (SEQ ID NO: 107)
(T_m: 74° C.)

Lm-99964R:
5'-GTTCCTATAATTGTTAGCTCATTTTTTTC (SEQ ID NO: 108)
(T_m: 74° C.)
(Amplicon size (bps): 2033)
```

A protocol for completing the construction process is as follows:

The primary PCR reactions (3 temperature cycle) are performed using Vent DNA polymerase (NEB) and 10 μl of a washed 30° C. *Listeria* DP-L4056 OR DP-L4029 overnight culture. The expected size of *Listeria* amplicons by 1% agarose gel (1007 bps and 1074 bps). The primary PCR reactions are gel purified and the DNA eluted with GeneClean (BIO 101).

A secondary PCR reaction is performed, utilizing approximately equal amounts of each primary reaction as template (ca. 5 μl). The expected size of the *Listeria* amplicon from the secondary PCR reaction is verified by 1% agarose gel (2033 bps). Adenosine residue are added at the 3' ends of *Listeria* dl inlB amplicon with Taq polymerase.

The *Listeria* dl inlB amplicon is then inserted into a pCR2.1-TOPO vector. The pCR2.1-TOPO-dl inlB plasmid DNA is digested with XhoI and KpnI and the 2123 bp fragment is gel purified. The KpnI/XhoI 2123 bp fragment is inserted into a pKSV7 vector that has been prepared by digestion with KpnI and XhoI and treatment with CIAP (pKSV7-dl inlB). The fidelity of dl inlB sequence in pKSV7-dl inlB is then verified. The inlB gene is deleted from desired *Listeria* strains by allelic exchange with pKSV7-dl inlB plasmid.

Example 25

Codon-Optimized Signal Peptides for Construction of Recombinant *Listeria*

Some exemplary codon-optimized signal peptides that can be used in the expression cassettes in the recombinant *Listeria* are provided in Table 6, below.

TABLE 6

Exemplary signal peptides for construction of recombinant *Listeria*

| Secretion Pathway | Signal Peptide Amino Acid Sequence | Signal peptidase Site (') | Native Sequence | Sequence codon-optimized for expression in Lm | Gene [Genus/species] |
|---|---|---|---|---|---|
| secA1 | MKKIMLV FITLILVSL PIAQQTEA KDASAFN KENSISSM APPASPPA SPKTPIEK KHAD (SEQ ID NO: 109)[1] | TEA'KD (SEQ ID NO: 54) | ATGAAAAAAATAATG CTAGTTTTTATTACAC TTATATTAGTTAGTCT ACCAATTGCGCAACA AACTGAAGCAAAGGA TGCATCTGCATTCAAT AAAGAAAATTCAATT TCATCCATGGCACCA CCAGCATCTCCGCCTG CAAGTCCTAAGACGC CAATCGAAAAGAAAC ACGCGGAT (SEQ ID NO: 110) | ATGAAAAAAATTATGTT AGTTTTTATTACATTAAT TTTAGTTAGTTTACCAAT TGCACAACAAACAGAAG CAAAAGATGCAAGTGCA TTTAATAAAGAAAATAG AAAGAAAATTCAATT TATTAGTAGTATGGCACC ACCAGCAAGTCCACCAG CAAGTCCAAAAACACCA ATTGAAAAAAAACATGC AGAT (SEQ ID NO: 113) | hly (LLO) [*Listeria monocytogenes*] |
| | MKKKIISA ILMSTVILS AAAPLSG VYADT (SEQ ID NO: 46) | VYA'DT (SEQ ID NO: 55) | ATGAAAAAAAGATT ATCTCAGCTATTTTAA TGTCTACAGTGATACT TTCTGCTGGAGCCCCG TTGTCAGGTGTTTACG CTGAGACA (SEQ ID NO: 86) | ATGAAAAAAAAATTAT TAGTGCAATTTTAATGAG TACAGTTATTTTAAGTGC AGCAGCACCATTAAGTG GTGTTTATGCAGATACA (SEQ ID NO: 87) | Usp45 [*Lactococcus lactis*] |
| | MKKRKVL IPLMALSTI LVSSTGNL EVIQAEV (SEQ ID NO: 47) | IQA'EV (SEQ ID NO: 56) | ATGAAAAAACGAAAA GTGTTAATACCATTAA TGGCATTGTCTACGAT ATTAGTTTCAAGCAC AGGTAATTTAGAGGT GATTCAGGCAGAAGT T(SEQ ID NO: 111) | ATGAAAAAACGTAAAGT TTTAATTCCATTAATGGC ATTAAGTACAATTTTAGT TAGTAGTACAGGTAATTT AGAAGTTATTCAAGCAG AAGTT (SEQ ID NO: 114) | pag (Protective Antigen) [*Bacillus anthracis*] |

TABLE 6-continued

Exemplary signal peptides for construction of recombinant *Listeria*

| Secretion Pathway | Signal Peptide Amino Acid Sequence | Signal peptidase Site (') | Native Sequence | Sequence codon-optimized for expression in Lm | Gene [Genus/species] |
|---|---|---|---|---|---|
| secA2 | MNMKKAT IAATAGIA VTAFAAPT IASAST (SEQ ID NO: 48) | ASA'ST (SEQ ID NO: 57) | ATGAATATGAAAAAA GCAACTATCGCGGCT ACAGCTGGGATTGCG GTAACAGCATTTGCT GCGCCAACAATCGCA TCCGCAAGCACT (SEQ ID NO: 90) | ATGAATATGAAAAAAGC AACAATTGCAGCAACAG CAGGTATTGCAGTTACAG CATTTGCAGCACCAACA ATTGCAAGTGCAAGTAC A (SEQ ID NO: 91) | iap invasion-associated protein p60 [*Listeria monocytogenes*] |
| Tat | MAYDSRF DEWVQKL KEESFQNN TFDRRKFI QGAGKIA GLSLGLTI AQSVGAF (SEQ ID NO: 53) | VGA'F (SEQ ID NO: 62) | ATGGCATACGACAGT CGTTTTGATGAATGG GTACAGAAACTGAAA GAGGAAAGCTTTCAA AACAATACGTTTGAC CGCCGCAAATTTATTC AAGGAGCGGGGAAGA TTGCAGGACTTTCTCT TGGATTAACGATTGC CCAGTCGGTTGGGGC CTTT (SEQ ID NO: 112) | ATGGCATATGATAGTCGT TTTGATGAATGGGTTCAA AAATTAAAAGAAGAAAG TTTTCAAAATAATACATT TGATCGTCGTAAATTTAT TCAAGGTGCAGGTAAAA TTGCAGGTTTAAGTTTAG GTTTAACAATTGCACAAA GTGTTGGTGCATTT (SEQ ID NO: 115) | PhoD alkaline phosphatase [*Bacillus subtilis*] |

¹The sequence shown includes the PEST sequence from LLO.

Example 26

Codon-Optimized Expression Cassette Comprising *Bacillus anthracis* Protective Antigen (PA) Signal Peptide An expression cassette was designed for expression of heterologous antigens in *Listeria monocytogenes* using a non-Listerial secA1 signal peptide. The amino acid sequence of the Protective Antigen (PA) signal peptide from *Bacillus anthracis* (Ba) (GenBank accession number NC_007322), its native coding sequence, and the coding sequence optimized for expression in *Listeria monocytogenes* are shown below.

Amino acid sequence:
(SEQ ID NO: 47)
MKKRKVLIPLMALSTILVSSTGNLEVIQAEV

Signal peptidase recognition site:
IQA'EV (SEQ ID NO: 56)

Native nucleotide sequence:
(SEQ ID NO: 111)
ATGAAAAAACGAAAAGTGTTAATACCATTAATGGCATTGTCTACGATATT

AGTTTCAAGCACAGGTAATTTAGAGGTGATTCAGGCAGAAGTT

Codons optimized for expression in *Listeria monocytogenes*:
(SEQ ID NO: 114)
ATGAAAAAACGTAAAGTTTTAATTCCATTAATGGCATTAAGTACAATTT

TAGTTAGTAGTACAGGTAATTTAGAAGTTATTCAAGCAGAAGTT

The sequence of a partial expression cassette comprising the hly promoter from *Listeria monocytogenes* operably linked to the codon-optimized sequence encoding the Ba PA signal peptide is shown in FIG. 47. This sequence can be combined with either a codon-optimized or non-codon-optimized antigen sequence for expression of a fusion protein comprising the *Bacillus anthracis* PA signal peptide and the desired antigen.

Example 27

Expression and Secretion of Antigens from Recombinant *Listeria* Comprising Codon-Optimized Expression Cassettes Codon optimization of both signal peptide and tumor antigen provides efficient expression and secretion from recombinant *Listeria*: Codon-optimization of both signal peptide- and heterologous protein-encoding genetic elements provides optimal secretion from recombinant *Listeria*-based vaccines of human tumor antigens that contain hydrophobic domains. Efficient antigen secretion from cytosolic bacteria is required for efficient presentation via the MHC class I pathway and CD8+ T-cell priming, and is thus linked directly to the potency of *Listeria*-based vaccines. Secretion from recombinant *Listeria* of two malignant cell membrane-bound human tumor antigens, mesothelin and NY-ESO-1, which are immune targets related to pancreatic and ovarian cancer (mesothelin), and melanoma (NY-ESO-1), among other solid tumors, has been optimized through codon-optimization of the combination of both the antigen and signal peptide coding sequences.

A variety of expression, cassettes were constructed comprising the hly promoter linked to either native or codon-optimized sequences encoding signal peptides related to secA1 or alternative secretion pathways including secA2 and Twin-Arg Translocation (Tat), fused in frame with a selected human tumor antigen—human NY-ESO-1 or human mesothelin. (See Examples 11-14 and 25, above, for the antigen sequences and/or signal sequences.) Western blot analysis of TCA-precipitated culture fluids of *Listeria* grown in BHI broth was used to assess the synthesis and secretion of the heterologous proteins from the recombinant *Listeria*.

(Methods analogous to those described in Example 18, above, were used for the Western blot analyses.)

Figure 48A:
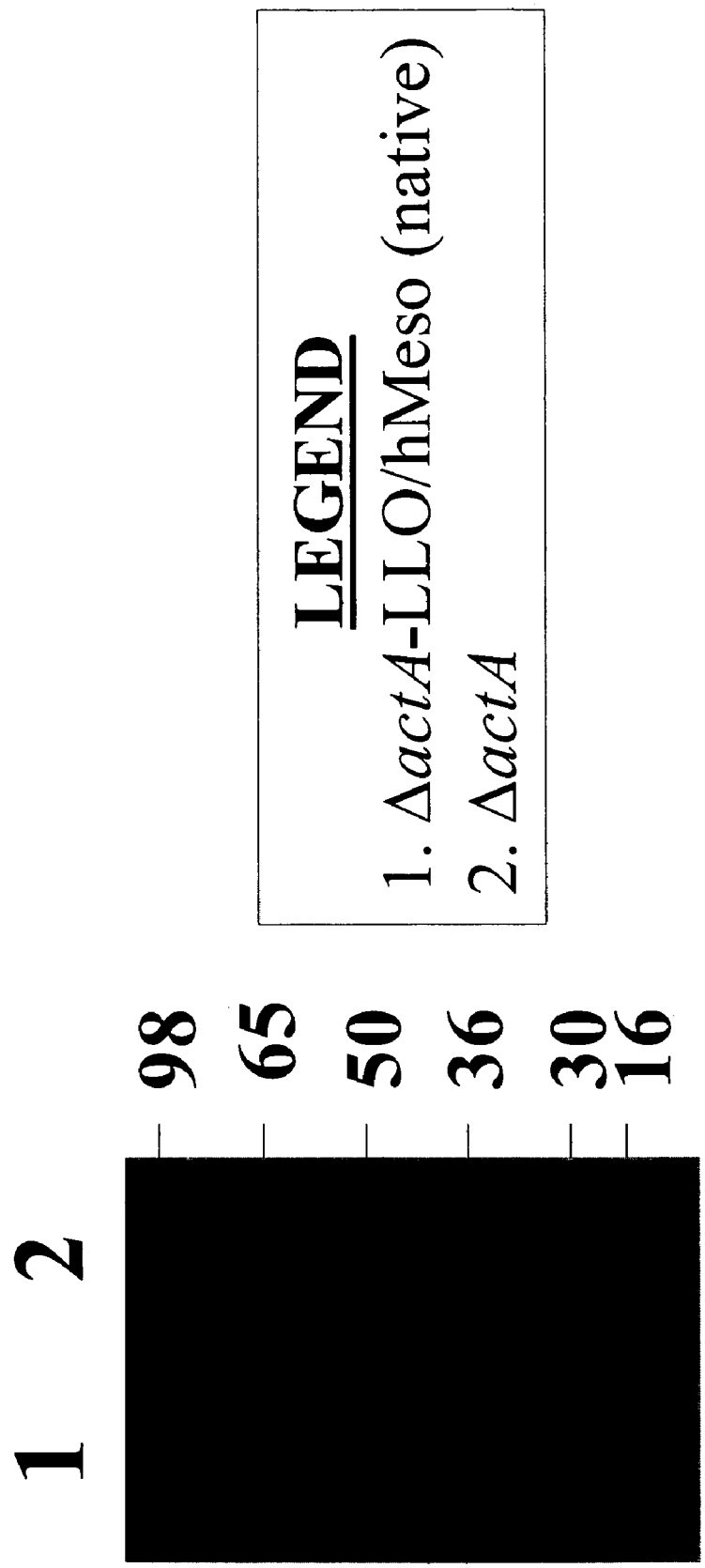
Figure 48B:
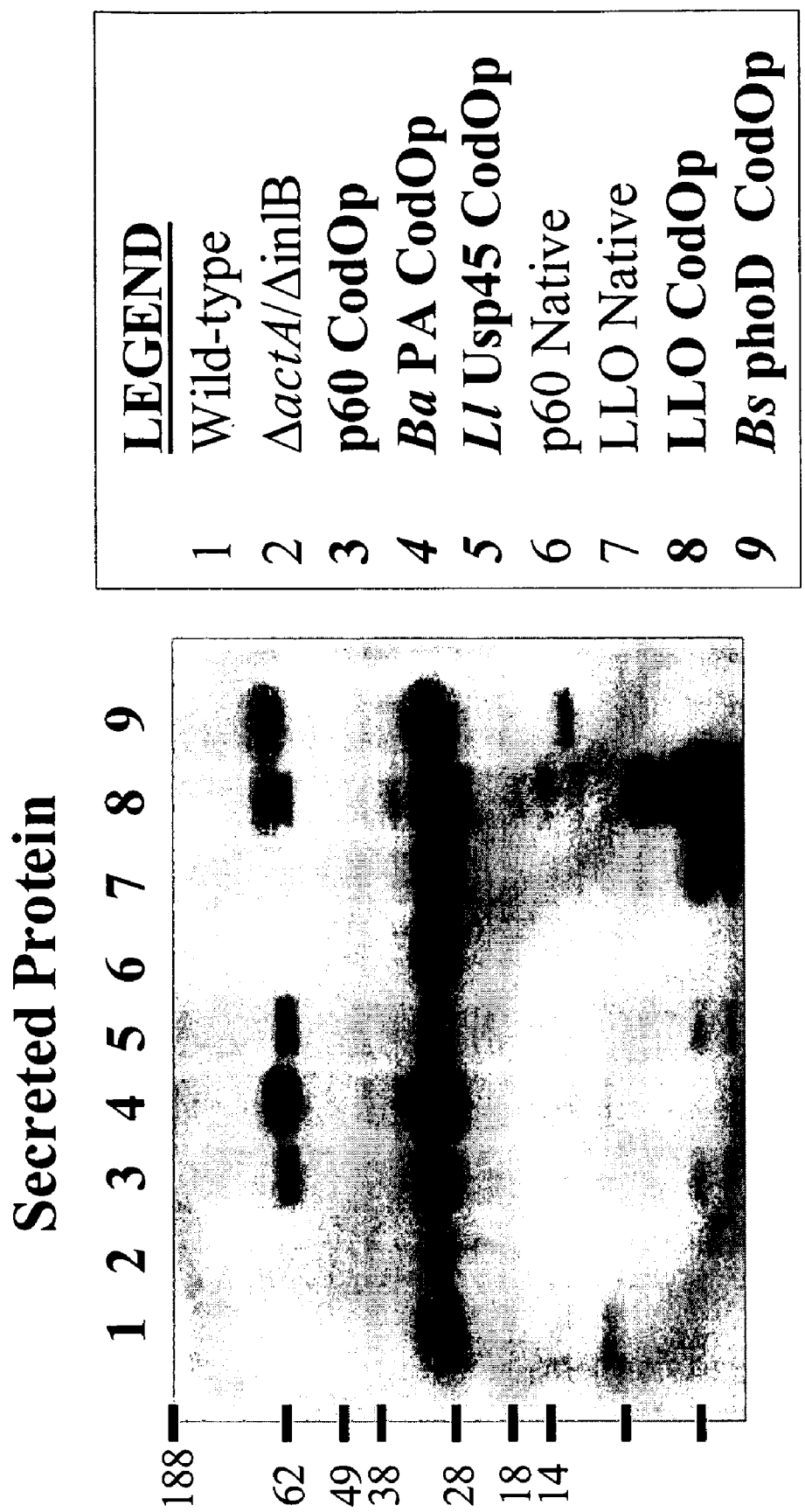
Figure 48C:
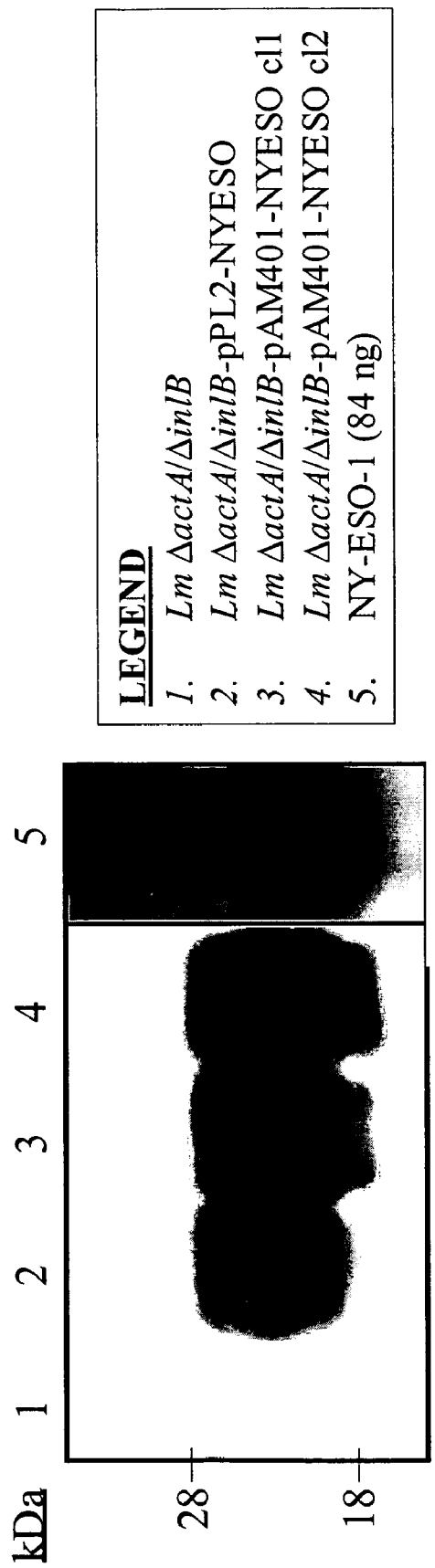

The results of these experiments are shown in FIG. 48A-C. Efficient expression and secretion of full-length tumor antigens from recombinant Listeria was observed when both signal peptide coding sequences, including when derived from Listeria monocytogenes, and operably linked foreign antigen coding sequences were optimized for codon usage in Listeria monocytogenes. FIG. 48A shows the expression/secretion of human mesothelin by ΔactA Listeria monocytogenes with a construct comprising an LLO signal peptide fused with human mesothelin, using native codons for both LLO and mesothelin. By Western analysis of TCA-precipitated bacterial culture fluids, secretion of expected full-length mesothelin (62 kDa) was not observed with these constructs, and only secretion of several small fragments was observed (FIG. 48A).

FIG. 48B shows a Western blot analysis of the expression/secretion of human mesothelin by Listeria monocytogenes ΔactA comprising plasmids (pAM401) containing constructs encoding various signal peptides fused with human mesothelin. In each construct, the mesothelin coding sequence was codon-optimized for expression in Listeria monocytogenes. Where indicated, the signal peptide coding sequences used contained either the native sequence ("native") or were codon-optimized ("CodOp") for expression in Listeria monocytogenes. Secreted mesothelin was detected using an affinity-purified polyclonal anti-human/mouse antibody, prepared by injection of rabbits with selected peptides together with IFA.

Significantly, as shown in lanes 3-5, and 8-9 of FIG. 48B, secretion of full-length mesothelin (62 kDa) was observed only when both signal peptide and mesothelin coding sequences were codon-optimized for expression in Listeria. This observation significantly also included the Listeria-derived signal peptides from the bacterial LLO and p60 proteins, related to the secA1 and secA2 secretion pathways, respectively, both of which contain infrequently-used codons. (The LLO PEST sequence is also included with the LLO signal peptide and its coding sequence is also codon-optimized.) Efficient secretion of full-length mesothelin (62 kDa) was observed when the codon-optimized Listeria LLO signal peptide was linked with codon-optimized mesothelin (Lane 8, FIG. 48B), but NOT when the native coding sequence of the Listeria LLO signal peptide was used (Lane 7, FIG. 48B). Furthermore, secretion of full-length mesothelin (62 kDa) was observed when the codon-optimized Listeria p60 signal peptide was linked with codon-optimized mesothelin (Lane 3, FIG. 48B), but NOT when the native coding sequence of the Listeria p60 signal peptide was used (Lane 6, FIG. 48B). Finally, secretion of full-length mesothelin (62 kDa) was observed when codon-optimized optimized signal peptides from bacterial species different from Listeria monocytogenes were operably linked to codon-optimized mesothelin (FIG. 48B). The signal peptide from Bacillus anthracis protective antigen (Ba PA), or the signal peptide from Lactococcus lactis Usp45 protein (Ll Usp45) programmed the efficient secretion of full-length mesothelin (62 kDa) from the recombinant Listeria strains (FIG. 48B, lanes 4 and 5). The Bacillus subtilis phoD signal peptide (Bs phoD) also programmed the efficient secretion of full-length mesothelin from Listeria (FIG. 48B, lane 9). The bands with a molecular weight of about 62,000 correspond to mesothelin and the pairs of double bands probably correspond to non-cleaved plus cleaved mesothelin polypeptides (i.e., to partial cleavage).

FIG. 48C shows the expression/secretion of NY-ESO-1 from Listeria monocytogenes ΔactAΔinlB with constructs comprising a sequence encoding LLO signal peptide which was fused with a sequence encoding human NY-ESO-1, both of which were codon-optimized for expression in Listeria. Secreted NY-ESO-1 was detected using a NY-ESO-1 monoclonal antibody.

In this example, signal peptide and tumor antigen domains were synthesized to utilize the most preferred codon for each amino acid, as defined by frequency of occurrence per 1000 codons in coding sequences from the Listeria genome (Table 2A). Signal peptides related to secA1, secA2, or twin-Arg translocation (Tat) secretion pathways from Listeria and other Gram-positive bacterial genera programmed the efficient secretion of human tumor antigens from recombinant Listeria. Surprisingly, the signal peptides from Listeria proteins LLO and p60 each contain rare codons (frequency of <10 per 1000 codons), and optimization of these sequences was required for efficient secretion of mesothelin and NY-ESO-1 from recombinant Listeria (FIG. 48B). Mesothelin secretion was also observed when linked to secA1 signal peptides from B. anthracis protective antigen (pagA) and Lactococcus lactis Usp45, and the Tat signal peptide from the phosphodiesterase/alkaline phosphatase D gene (PhoD) of B. subtilis.

Signal peptides from distinct secretion pathways were used to determine whether a particular pathway would be favored for optimal secretion of heterologous proteins. For example, the Tat pathway is utilized for secretion of proteins folded within the bacterium, and the B. subtilis phoD protein is secreted via this mechanism. It had originally been hypothesized that secretion of tumor antigens containing significant hydrophobic domains, such as NY-ESO-1, might be facilitated by folding prior to transport. However, these results indicated that codon-optimization of both the signal peptide and tumor antigen encoding sequences, and not secretion pathway, is the primary requirement for efficient secretion of mammalian proteins.

Importantly, the phenotype of recombinant vaccines utilizing any pathway for tumor antigen secretion was not significantly affected, as compared to the parental Listeria ΔactA/ΔinlB strain. The median lethality ($LD_{50}$) of Listeria ΔactA/ΔinlB is $1 \times 10^8$ cfu in C57BL/6 mice. Stable single copy site-specific incorporation of tumor antigen expression cassettes into an innocuous site on the chromosome of Listeria ΔactA/ΔinlB, was accomplished using the pPL2 integration vector. The $LD_{50}$ of tumor antigen encoding Listeria ΔactA/ΔinlB was within 5-fold of Listeria ΔactA/ΔinlB.

Example 28

Construction of Bicistronic hEphA2 Expression Vectors

As a non-limiting example, construction of an antigen expression cassette, in which expression of the external (EX2) and internal (CO; kinase dead) domains of hEphA2 occurs from a bicistronic message, is given. Secretion of the EX2 and CO domains is accomplished by functional linkage of the Ba PA and Bs PhoD signal peptides with the EX2 and CO domains, respectively.

A codon-optimized human EphA2 kinase dead plasmid, known as phEphA2KD, is used in the construction of a bicistronic hEphA2 expression vector. (EphA2 is a receptor tyrosine kinase, but the kinase activity is ablated by a mutation from K to M at the active site of the enzyme.) The coding sequences of phEphA2KD are shown in FIG. 49. The phEphA2KD sequence in FIG. 49 comprises the codon-optimized coding sequence for hEphA2 deleted of the transmembrane domain, and contains unique 5' and 3' Bam HI and Sac I restriction sites to facilitate construction of functional antigen expression cassettes. Mlu I recognition sequences are shown bolded in the sequence shown in FIG. 49.

A sub-fragment of the human EphA2 (trans-membrane domain deleted, kinase-dead) between the two Mlu I restriction enzyme recognition sequences is synthesized (by a gene synthesis method known in the art, e.g., by oligonucleotide synthesis, PCR, and/or Klenow fill-in, or the like). The actA-plcB intergenic region is inserted during the synthesis precisely at the junction between the EphA2 extracellular and intracellular domains, which are separated by the hydrophobic trans-membrane domain in the native protein. The sequence of the Mlu I sub-fragment of codon-optimized human EphA2 containing the actA-plcB intergenic region is shown in FIG. 50 (the intergenic region is shown in bold). Additionally, the codon-optimized Bs phoD signal peptide is placed at the 3' end of the actA-plcB intergenic sequence and is fused in-frame with the downstream EphA2 CO domain coding region.

The functional human EphA2 bicistronic cassette is assembled by substitution of the Mlu I fragment containing the actA-plcB intergenic region and Bs phoD signal peptide for the corresponding region in the trans-membrane deleted kinase dead human EphA2 sequence shown in FIG. 49. This resulting sequence contains unique Bam HI and Sac I restriction enzyme recognition sites at its 5' and 3' ends, respectively, to facilitate insertion and functional linkage to the hly promoter and initial signal peptide, for example Ba PA.

Thus, the seven ordered functional elements of the bicistronic human EphA2 antigen expression cassette are the following: hly promoter-Ba PA signal peptide-EX domain EphA2-termination codon-actA-plcB intergenic region (with Shine-Dalgarno sequence)-Bs PhoD signal peptide-CO domain EphA2-termination codon. All EphA2 and signal peptide coding sequences are preferably codon-optimized.

Recombinant Listeria strains that express and secrete the EphA2 EX and CO domains can be derived by methods illustrated in this application, utilizing the pAM401, pKSV7, or pPL1 and pPL2 integration vectors. Expression and secretion of the EphA2 proteins is detected by Western analysis of desired bacterial fractions, using methods described herein and/or known to those skilled in the art.

Example 29

Expression and Secretion of Antigens from Recombinant Listeria Comprising Antigen-Bacterial Protein Chimeras In some embodiments of the invention, both the sequences encoding the signal peptide and its heterologous protein fusion partner are codon-optimized. In some embodiments, it is desirable to place the codon-optimized heterologous protein sequence within a defined region of a protein, whose native form is secreted from Listeria. The heterologous protein sequence is functionally placed within a defined sequence of the selected secreted Listeria protein sequence such that a protein chimera is synthesized and secreted that corresponds to the combined molecular weights of the secreted proteins. Secretion of the heterologous protein can be facilitated by exploiting the machinery of the host Listeria bacterium that is required for optimal secretion of autologous bacterial proteins. Molecular chaperones facilitate secretion of selected bacterial proteins.

As a non-limiting example, protein chimeras between the L. monocytogene protein p60 and the human tumor antigen, mesothelin, were generated. The protein chimeras were generated by precise placement of the human tumor antigen, mesothelin, into L. monocytogenes protein p60 at amino acid position 70 (although it is understood that any desired heterologous protein encoding sequence can be selected to generate a protein chimera). The protein chimera contained optimal codons for expression in Listeria in the p60 amino acids 1-70 and the entire mesothelin coding sequence. Furthermore, the p60-human mesothelin protein chimeria was functionally linked to the L. monocytogenes hly promoter, incorporated into the pPL2 vector, which was used subsequently as described herein to generate recombinant L. monocytogenes strains expressing and secreting human mesothelin. The experimental methods used to construct a recombinant Listeria strain that optimally expresses and secretes a p60-human mesothelin protein chimera are described below.

In some embodiments, an important feature of protein chimeras between a selected L. monocytogenes gene and a selected heterologous protein sequence is appropriate functional placement of the selected heterologous protein sequence within the selected L. monocytogenes gene to retain optimal secretion of the protein chimera through interaction of the L. monocytogenes expressed protein with the bacterial chaperones and secretion apparatus, as well as to retain functional activity of the L. monocytogenes protein in the context of the protein chimera. In some embodiments, functional placement of a heterologous sequence within the L. monocytogenes secA2-dependent proteins NamA and p60 is desired to retain the peptidoglycan cell wall hydrolase activites of these said proteins. (See Lenz et. al. (2003 PNAS, 100:12432-12437), for instance, for descriptions of the SecA2-dependent NamA and p60 proteins.) In some embodiments, the functional placement of the heterologous protein coding sequence is desired between the signal sequence (SS) and the cell wall binding domains (LySM) and catalytic domains Lyz-2 (NamA) and p60-dom (p60) (Lenz et. al. (2003)).

In some embodiments, expression of antigens or heterologous proteins is functionally linked to a prfA-dependent promoter. As such, expression of the heterologous protein is induced within the microenvironment of the recombinant Listeria infected cell.

The first step in the construction of a p60-Mesothelin protein chimera involved the DNA synthesis of the prfA-dependent hly promoter linked functionally to a DNA sequence encoding the first 70 amino acids of p60, with codons for optimal secretion in Listeria. (In some embodiments, the codon usage can be modified further to avoid regions of excessive RNA secondary structure, which may inhibit protein translation efficiency.) The DNA sub-fragment corresponding to the hly promoter-70 N-terminal p60 amino acids was synthesized. (This can generally be done by a gene synthesis method known in the art, e.g., by oligonucleotide synthesis, PCR, and/or Klenow fill-in, or the like.)

The sequence of the first 70 amino acids of p60 from L. monocytogenes, strain 10403S, is shown below:

(SEQ ID NO: 116)
M N M K K A T I A A T A G I A V T A F A A P T I A

S A S T V V V E A G D T L W G I A Q S K G T T V D

A I K K A N N L T T D K I V P G Q K L Q

It can be appreciated to those skilled in the art that there exists multiple laboratory and field isolates of L. monocytogenes encoding genes, including p60, that may contain variability at both the nucleotide sequence and amino acid level, but are nevertheless essentially the same gene and protein. Furthermore, it can be appreciated by those skilled in the art that protein chimeras can be constructed utilizing genes from any laboratory or field isolate (including food-borne or clinical strain) of *L. monocytogenes*.

The synthesized DNA sequence corresponding to the hly promoter-70 N-terminal p60 amino acids is shown in FIG. 51. Furthermore, the codons encoding p60 amino acid residues 69 (L) and 70 (Q), were modified to contain a unique Pst I enzyme recognition sequence, to facilitate functional insertion of a heterologous sequence. Furthermore, the 5' end of the synthesized sub-fragment contains a unique KpnI enzyme recognition sequence.

The 447 bp KpnI and PstI digested sub-fragment fragment was ligated into the corresponding KpnI and PstI sites of the pPL2 vector, and treated by digestion with KpnI and PstI enzymes and digestion with calf intestinal alkaline phosphatase (CIAP). This plasmid is known as pPL2-hlyP-Np60 CodOp. Subsequently, the remainder of the native p60 gene was cloned into the pPL2-hlyP-Np60 CodOp plasmid, between the unique Pst I and BamHI sites. The remainder of the p60 gene was cloned by PCR, using a proof-reading containing thermostable polymerase, and the following primer pair:

```
Forward primer:
5'- CGC CTGCAGGTAAATAATGAGGTTGCTG  (SEQ ID NO: 117)

Reverse primer:
5'-CGCGGATCCTTAATTATACGCGACCGAAG   (SEQ ID NO: 118)
```

The 1241 bp amplicon was digested with PstI and BamHI, and the purified 1235 bp was ligated into the pPL2-hlyP-Np60 CodOp plasmid, digested with PstI and BamHI, and treated with CIA-P. This plasmid contains the full *L. monocytogenes* p60 gene with optimal codons corresponding to amino acids 1-77, and native codons corresponding to amino acids 78-478, and is linked functional to the *L. monocytogenes* hly promoter. This plasmid is known as pPL2-hlyP-Np60 CodOp(1-77), and the sequence of the KpnI-BamHI sub-fragment that contains the hlyP linked functionally to the p60 encoding sequence is shown in FIG. 52. The expected sequence of the pPL2-hlyP-Np60 CodOp(1-77) plasmid was confirmed by sequencing.

The next step in the construction was the functional insertion of a heterologous protein encoding sequence at the unique PstI site of plasmid as pPL2-hlyP-Np60 CodOp(1-77), which is between the N-terminal signal sequence and the first LysM cell wall binding domain of p60, thus retaining the normal biological function of the *L. monocytogenes* protein.

As a non-limiting example, human mesothelin that was codon-optimized for optimal expression in *L. monocytogenes* protein was inserted into the unique PstI site of plasmid as pPL2-hlyP-Np60 CodOp(1-77). Specifically, full-length mesothelin, or mesothelin that was deleted of the signal peptide and GPI linker domains (Mesothelin ΔSP/ΔGPI) was cloned from the plasmid described in Example 27 that contains the full-length human mesothelin, containing optimal codons for expression in *L. monocytogenes*, using a thermostable polymerase with proof-reading activity, and the following primer pair:

1. Full Length

```
Forward Primer (huMeso 3F):
                                              (SEQ ID NO: 119)
5'-AAACTGCAGGCATTGCCAACTGCACGTCC Reverse Primer (hMeso 1935R):
                                              (SEQ ID NO: 120)
5'-AAACTGCAGAGCTAATGTACTGGCTAATAATAATGCTAAC
```

2. ΔSignal Peptide, ΔGPI Anchor

```
Forward Primer (huMeso 133F):
5'-CGCCTGCAGCGTACATTAGCAG       (SEQ ID NO: 121)

GTGAAACAGG

Reverse Primer (huMeso 1770R):
5'-CGCCTGCAGGCCTTGTAAACCTAAAC   (SEQ ID NO:122)

CTAATGTATC
```

The PCR amplicons of 1932 bps (full-length mesothelin) and 1637 bps (Mesothelin ΔSP/ΔGPI) were purified, digested with PstI, purified, and ligated into the unique PstI site of plasmid pPL2-hlyP-Np60 CodOp(1-77), treated by digestion with PstI, and treatment with CIAP. The consistent N—CO orientation of the p60 and mesothelin domains was confirmed by restriction endonuclease mapping. These plasmids are known as pPL2-hlyP-Np60 CodOp(1-77)-Mesothelin and pPL2-hlyP-Np60 CodOp(1-77)-Mesothelin ΔSP/ΔGPI, and were introduced into selected *L. monocytogenes* strains (such as ΔactAΔinlB double deletion mutants), as described throughout the examples contained herein.

The sequence of the KpnI-BamHI sub-fragment of plasmid pPL2-hlyP-Np60 CodOp(1-77)-Mesothelin containing the hly promoter linked functionally to the p60-human Mesothelin protein chimera encoding gene is shown in FIG. 53.

The sequence of the KpnI-BamHI sub-fragment of plasmid pPL2-hlyP-Np60 CodOp(1-77)-Mesothelin ΔSP/ΔGPI containing the hly promoter linked functionally to the p60-human mesothelin ΔSP/ΔGPI protein chimera encoding gene is shown in FIG. 54.

Western Analysis of Expression and Secretion of p60-Mesothelin Protein Chimeras:

As discussed throughout the examples, expression and secretion of a selected heterologous antigen results in potent priming of MHC class I-restricted CD8+ T cell responses. The expression and secretion of the protein chimeras into the media by recombinant *L. monocytogenes* ΔactAΔinlB double deletion mutants containing tRNA-Arg chromosomal insertions of the pPL2-hlyP-Np60 CodOp(1-77)-Mesothelin or pPL2-hlyP-Np60 CodOp(1-77)-Mesothelin ΔSP/ΔGPI plasmids, generated by methods described herein, were tested by Western analysis by methods described in the Examples contained herein, using a mesothelin-specific polyclonal antibody.

The indicated engineered deletions in hMesothelin (ΔSP-ΔGPI, also referred to herein as ΔSSΔGPI, ΔSP/ΔGPI, ΔSS/ΔGPI, etc.) for the proteins shown in some of the lanes were as follows: The deleted signal sequence (ΔSP) corresponds to the N-terminal 34 amino acids of hMesothelin (for sequences of human mesothelin, see, e.g., FIG. 34 or GenBank Acc. No. BC009272). The deleted GPI (ΔGPI) domain corresponds to the C-terminal 42 amino acids, beginning with the amino acid residues Gly-Ile-Pro and ending with the amino acid residues Thr-Leu-Ala (see, e.g., FIG. 34).

The results of this analysis demonstrated that protein chimeras comprised of p60 with precise insertion of human mesothelin or human mesothelin ΔSP/ΔGPI (inserted in frame at amino acid 70 of p60 between the N-terminal signal sequence and the first of two LysM cell wall binding domains) were efficiently expressed and secreted from the recombinant *L. monocytogenes*. See FIG. 55. (The Y-axis of FIG. 55 shows the molecular weight (in kDa) of proteins in the ladder run in the far left lane.) Specifically, lanes 1-4 in FIG. 55 demonstrate the expression and secretion of the expected protein chimeras containing human mesothelin or human mesothelin ΔSP/ΔGPI. The increased efficiency of expression and secretion of human mesothelin ΔSP/ΔGPI relative to the full-length mesothelin is evident in lanes 2 and 4. In the protein chimeras shown in lanes 3 and 4, the authentic N-terminal p60 amino acids were used. In the chimeras run in lanes 1 and 2 in the FIG. 55, the nucleotides encoding amino acids T and V at positions 29 and 64, respectively, were deleted. Lane 5 shows expression and secretion of *Bacillus anthracis* PA signal peptide fused to human ΔSPΔGPI-mesothelin (where both the signal peptide and the mesothelin coding sequences were codon-optimized for expression in *L. monocytogenes*), and lane 6 shows the expression and secretion of LLO fused to full-length human mesothelin (where both the signal peptide and the mesothelin coding sequences were codon-optimized for expression in *L. monocytogenes*). Lane 8 shows protein expression by J293, a human cell line, while lane 7 shows protein expressed and secreted by J293 containing a plasmid encoding full-length human mesothelin ("J293/Full Length"). Lane 10 shows protein expression and secretion from *Listeria* which has been deleted of endogenous p60. The lower panel in FIG. 55 shows the Western analysis of *L. monocytogenes* p60 secretion using a polyclonal α-p60 antibody. The results demonstrate that equivalent amounts of Lm-secreted protein were loaded on the gel.

The results demonstrate that p60 can be used as a molecular chaperone to secrete heterologous proteins and facilitate presentation to the MHC class I pathway.

Example 30

Additional Examples of Antigen Expression and Secretion by Recombinant *Listeria monocytogenes*

A. Expression of the Intracellular Domain (ICD) of EphA2 from a Bicistronic Construct Using a Non-Listerial Signal Peptide.

FIG. 56 shows the Western blot analysis of the expression and secretion of the intracellular domain (ICD) of EphA2 from bicistronic messages using a non-Listerial, non-secA1 signal sequence.

EphA2 is a protein comprised of an extracellular domain (ECD) and an intracellular domain (ICD). Listeria ΔactAΔinlB were engineered to express a bicistronic mRNAs, where the bicistronic mRNAs encoded the extracellular domain and intracellular domain of Epha2 as discrete polypeptides. All of the sequences encoding the signal sequences used in the constructs (*B. subtilis* phoD signal peptide, *B. anthracis* Protective Antigen signal peptide, and *L. lactis* Usp45 signal peptide) were codon-optimized for expression in *L. monocytogenes*. The sequences encoding the ECD and ICD domains were also codon-optimized for expression in *L. monocytogenes*. The Listerial promoter hly from the LLO gene was used as the promoter in these constructs.

The expression cassettes encoding the bicistronic mRNA were integrated into the *Listeria* genome using the integration vector pPL2. Western blot analysis of various bacterial fractions using standard techniques was used to detect and measure the accumulated intracellular EphA2 domain. The results demonstrated that the intracellular domain of Epha2 was expressed and secreted from bicistronic constructs using non-Listerial signal peptides encoded by codon-optimized sequences.

The expression constructs comprised: (1) a codon-optimized sequence encoding the *L. lactis* Usp45 secretory sequence operably (functionally) linked with the coding sequence for the extracellular domain of EphA2 (first polypeptide) and a codon-optimized sequence encoding the *B. subtilis* phoD secretory signal operably linked with an intracellular domain of EphA2 (second polypeptide) (lane 1); and (2) a codon-optimized sequence encoding the *B. anthracis* Protective Antigen secretory sequence operably linked with the coding sequence for the extracellular domain of EphA2 (first polypeptide) and a codon-optimized sequence encoding the *B. subtilis* phoD secretory sequence operably linked with the coding sequence for the intracellular domain of EphA2 (second polypeptide) (lanes 2-3 (two different clones); see description of construction of this expression cassette in Example 28, above). Control studies (lane 4) with the attenuated parent Listeria ΔactAΔinlB strain demonstrated a variable amount of detectable cross reactivity in some control blots. Lanes 1-3 show a slow migrating band and a fast moving band, where the fast moving band corresponds to the intracellular domain (ICD). Expressed intracellular domain of EphA2 from all of the constructs (lanes 1-3) was observed in all three bacterial fractions. Lane 4 (control) shows only the slow migrating band. Because no antibody was available for the extracellular domain, expression/secretion of the extracellular domain was not assayed.

B. Plasmid Based Expression and Secretion of Murine Mesothelin as a Function of N-Terminal Fusion With Various Codon-Optimized Signal Peptides.

FIG. 57 shows plasmid based expression and secretion of murine mesothelin expressed from a codon-optimized mesothelin coding sequence using various signal peptides, including non-Listerial signal sequences and non-secA1 signal sequences. Plasmid based expression and secretion of murine mesothelin is shown as a function of N-terminal fusion with various signal peptides encoded by codon-optimized sequences. In all cases, the sequences encoding the signal peptides of the mesothelin fusion proteins were codon-optimized as well as the murine mesothelin coding sequence was codon-optimized for expression in *L. monocytogenes*. Expression and secretion of murine mesothelin from *L. monocytogenes* was measured, where the *Listeria* harbored a pAM401 plasmid, and where the plasmid encoded the mesothelin. Various plasmid-based constructs where tested, where the signal sequence was varied. Western blots were performed with proteins recovered from the various fractions of secreted proteins (A), the cell wall (B), and the cell lysate (C). For each fraction, lanes 1-2 show murine mesothelin expressed as a fusion with the *B. anthracis* Protective Antigen signal sequence, lanes 3-4 show murine mesothelin expressed as a fusion with the *Lactococcus lactis* Usp45 signal sequence, lanes 5-6 show murine mesothelin expressed as a fusion with the *B. subtilis* phoD signal sequence, lanes 7-8 show murine mesothelin expressed as a fusion with the p60 signal sequence, lanes 9-10 show murine mesothelin expressed as a fusion with the LLO signal sequence, and lane 11 shows protein expressed by the control host Listeria ΔactAΔinlB. The results demonstrate that the highest expression and secretion was found where the signal sequence comprised *B. anthracis* Protective Antigen signal sequence (lanes 1-2) and *B. subtilis* phoD signal sequence (lanes 5-6).

C. *Listeria monocytogenes* Chromosomal-Based Expression and Secretion of Human Mesothelin FIG. 58 shows the Western blot analysis of *Listeria monocytogenes* chromosomal-based expression and secretion of human mesothelin in various bacterial cell fractions (i.e., secreted protein, cell wall, and lysate). Expression and secretion of human mesothelin was tested when fused to a non-Listerial secA1 and non-secA1 signal peptides. The *Listeria* bacteria tested were all ΔactA/ΔinlB *Listeria* and were as follows: *Listeria* ΔactA/ΔinlB (control *Listeria* that was not engineered to express mesothelin) (Lane 1); *Listeria* encoding *B. anthracis* Protective Antigen signal sequence fused to ΔSS/ΔGPI hMesothelin (Lanes 2-3); Listeria encoding *B. subtilis* phoD signal sequence fused to ΔSS/ΔGPI hMesothelin (Lanes 4-5); Listeria encoding *B. anthracis* Protective Antigen signal sequence fused with full-length hMesothelin (Lanes 6-7); *Listeria* encoding *B. subtilis* phoD signal sequence fused to full-length hMesothelin (Lanes 8-9).

The sequences encoding the signal sequences fused to mesothelin in all of the above *Listeria* were codon-optimized for expression in *L. monocytogenes*. In addition, the mesothelin coding sequences (ΔSS/ΔGPI and full-length) were codon-optimized for expression in *L. monocytogenes* in each of the constructs. In each of the above *Listeria* expressing mesothelin, the mesothelin expression cassettes were inserted in the *Listeria* chromosome via integration with pPL2.

Highest expression occurred with the *B. subtilis* phoD secretory sequence where human mesothelin was engineered to delete its signal sequence and to delete a hydrophobic region (gpi region) (Lanes 4-5).

Example 31

Additional Examples of Immunogenicity and Anti-Tumor Efficacy of Recombinant *Listeria monocytogenes* Vaccines The following examples disclose results of vaccination with the *Listeria* of the present invention, e.g., vaccine-dependent stimulation of cytokine expression, vaccine-dependent survival of an animal with tumors, vaccine-dependent reduction in tumor metastasis, and vaccine-dependent reduction in tumor volume.

A. Immunogenicity of *Listeria* Vaccine Comprising P-60-Model Antigen Chimera

FIGS. 59A and B show delivery of a heterologous antigen to the MHC Class I pathway by *Listeria* expressing either a p60-antigen chimera or an LLO signal peptide-antigen fusion protein. The heterologous antigen used in this experiment was AH1-A5. Vaccination was with *Listeria* engineered to comprise a p60 protein chimera expression cassette encoding AH1-A5 (fused to the OVA SL8 peptide) inserted within the p60 polypeptide sequence including the N-terminal p60 signal peptide sequence ("p60-based construct"), or *Listeria* engineered to encode an LLO signal peptide linked to a nucleic acid encoding the same antigen, AH1-A5 embedded within OVA ("LLO-based construct"). Both of these constructs used the Listerial promoter hly. p60 is a Listerial peptidoglycan autolysin that is secreted by a secA2 pathway, while LLO is listeriolysin.

To generate the p60-based construct, the nucleic acid encoding p60 was engineered to contain a PstI cloning site, where the PstI cloning site represented a silent mutation, i.e., resulting in no change in the encoded amino acid sequence. The PstI site was located between the N-terminal signal sequence and the first of two LysM cell wall binding domains in the p60 sequence. A polynucleotide encoding a heterologous polypeptide comprising the AH1-A5 epitope (SPSYAYHQF (SEQ ID NO:73)) and SL8 epitope (SIINFEKL (SEQ ID NO:123)) was inserted in frame into the PstI cloning site. The coding sequences for these epitopes were separated by a unique XhoI site and codon-optimized for expression in *L. monocytogenes*. The insertion into the PstI site occurred at the equivalent of nucleotide base number 199 of p60. The first 1-70 amino acids of the p60 coding sequence were codon-optimized for expression in *L. monocytogenes*. Accordingly, the first 27 amino acids corresponding to the signal peptide were expressed from optimal codons for expression in *L. monocytogenes*. The antigen expression cassette further contained unique 5' and 3' KpnI and SacI sites, respectively for insertion into the MCS of the pPL2 plasmid, for site-specific integration adjacent to the tRNA$^{Arg}$ gene of the *L. monocytogenes* genome. The LLO-based construct comprised a sequence encoding an LLO signal sequence operably linked to a nucleic acid encoding AH1-A5 within OVA (without use of any codon-optimization). Thus, in the present study, the signal peptide was either from *Listeria* LLO or from *Listeria* p60.

The constructs were placed into pPL2, a vector that mediates site-specific recombination with *Listeria* genome, and inserted into the *Listeria* genome.

FIGS. 59A and B show the immune response to a vaccination (tail vein) of *Listeria* expressing the AH1-A5 antigen with p60 signal sequence/autolysin as a p60 chimera, and immune response to vaccination of *Listeria* expressing AH1-A5 antigen linked with the LLO signal sequence. In the x-axis of the figure, "Unstim" means that no peptide was added to the wells (i.e., the cells were unstimulated), while "AH1" means that the AH1 nonapeptide was added to the wells, and "AH1-A5" means that the AH1-A5 nonapeptide was added to the wells. All bacterial vaccines were engineered to contain an integrated nucleic acid encoding AH1-A5 (the bacterial vaccines did not encode AH1) (see, e.g., Slansky, et al. (2000) Immunity. 13:529-538). Where the vaccination was done with the *Listeria* comprising the p60-based constructs, the strain is indicated on the x-axis of the figure as "p60." Where the vaccination was done with *Listeria* comprising the LLO-based constructs, the strain is indicated on the x-axis of the figure as "LLO."

The overall protocol for vaccination with *Listeria* expressing the P60-based construct was as follows: (1) Mice were vaccinated with *Listeria* (tail vein (i.v.)) containing an integrated nucleic acid, where the integrated nucleic acid encoded p60 containing a nucleic acid encoding AH1-A5 inserted at nucleotide 199 of p60. In other words, the nucleic acid encoding AH1-A5 antigen was in frame with and operably linked with p60 signal sequence and with p60 autolysin. The nucleic acid encoding AH1-A5 was codon optimized for expression in *L. monocytogenes*; (2) Seven days post infection, the spleens were removed; (3) Spleen cells were dissociated, placed in wells, and the spleen cells were incubated with either no added peptide (FIGS. 59A and 59B), with added AH1 (FIG. 59A), or with added AH1-A5 (FIG. 59B), as indicated on the x-axis; (4) After adding the peptide, cells were incubated for five hours, followed by assessment of the percent of IFNgamma expressing CD8+ T cells by FACS analysis. An analogous protocol was used for vaccination with *Listeria* expressing the LLO-based construct.

The results demonstrate that the *Listeria* vaccines stimulated CD8+ T cell expression of IFNgamma, where the added peptide was AH1 (FIG. 59A) or where the added peptide was AH1-A5 (FIG. 59B). Stimulation was somewhat higher where integrated AH1-A5 was operably linked with LLO signal sequence, and stimulation was somewhat lower when integrated AH1-A5 was operably linked with p60 signal sequence (FIGS. 59A and B).

FIGS. 60A and B show experiments conducted with the same two *Listeria* vaccines as described above, i.e., as shown in FIGS. 59A and B. FIG. 60A shows results where mice were vaccinated with the *Listeria* engineered to contain the p60-based construct ("p60") or with the *Listeria* engineered to contain the LLO-based construct ("LLO"). As indicated on the x-axis of FIG. 60A, the cell based assays were supplemented with no peptide (unstimulated; "unstim") or with $LLO_{91-99}$ peptide ("LLO91"; Badovinac and Harty (2000) J. Immunol. 164:6444-6452). The results demonstrated a similar immune response (IFNgamma expression) where the *Listeria* vaccine contained the p-60 based construct or the LLO-based construct. The stimulated immune response in FIG. 60A, as reflected in the results from the cell-based assay, is due to the *Listeria*'s endogenous expression of native LLO.

FIG. 60B shows results where mice were vaccinated with *Listeria* engineered to contain the p60-based construct, where the hly promoter and signal peptide sequences were operably linked with a nucleic acid encoding AH1-A5, or with *Listeria* engineered to contain the LLO-based construct, where the hly promoter and signal peptide were operably linked with a nucleic acid encoding AH1-A5. The added peptides were either no peptide (unstimulated; "unstim") or $p60_{217-225}$ ("p60-217"; Sijts, et al. (1997) J. Biol. Chem. 272:19261-19268), as indicated on the x-axis. The stimulated immune response in FIG. 60B, as reflected in the results from the cell based assay, is due to the *Listeria*'s expression of endogenous p60 for the LLO-based construct and the combination of endogenous p60 and the expressed p60 protein chimera sequence for the p60-based construct.

B. Therapeutic Efficacy of *Listeria* Expressing Human Mesothelin

The results depicted in FIG. 61 reveal that vaccination with *Listeria* expressing human mesothelin (huMesothelin) prolongs survival in tumor-bearing mice, where the tumor cells in the mice had been engineered to express human mesothelin. The tumor cells were CT26 cells expressing human mesothelin and the mice were Balb/c mice. (All CT26 tumor studies described herein involved Balb/c mice.) In one of the expression cassettes, a sequence encoding a non-Listerial signal sequence was operably linked in frame with a codon-optimized sequence encoding human mesothelin (deleted of its signal sequence and GPI anchor). The expression cassette encoding a signal peptide fused with human mesothelin (ΔGPIΔSS) was administered to tumor-bearing mice in a *Listeria* vaccine in studies on the effect of the fusion protein on immune response to tumors. The expression cassette encoding the mesothelin fusion protein had been integrated into the *Listeria* chromosome. On Day 0, $2 \times 10^5$ CT26 cells expressing human mesothelin (CT.26 huMeso+) were injected intravenously into the Balb/c mice. Vaccination of the mice was in the tail vein (i.v.). Inoculation with 1e7 colony forming units (CFU) *Listeria* (i.v.) occurred at day 3.

FIG. 61 shows the percent survival (shown on y-axis) of the mice to CT26 tumor expressing human mesothelin, where the vaccine comprises Hank's Balanced Salt Solution (HBSS) (a sham vaccine; "HBSS"); *Listeria* ΔactAΔinlB expressing SF-AH1A5 from an integrated expression cassette (positive control vaccine; "SF-AH1A5"); or *Listeria* ΔactAΔinlB comprising an expression cassette encoding *B. anthracis* Protective Antigen signal sequence (encoded by a non-codon optimized sequence) fused with huMesothelin (encoded by a codon-optimized sequence), where the huMesothelin had a deleted signal sequence and a deleted region encoding the hydrophobic gpi-anchoring peptide ("BaPA-huMeso ΔgpiΔss"). *Listeria* bearing the SF-AH1A5 construct and the BaPA-huMeso ΔgpiΔss construct contained these constructs as chromosomally integrated constructs. The nucleic acid molecule encoding SF-AH1A5 and the nucleic acid molecule encoding the BaPA-huMeso ΔgpiΔss construct had been integrated into the *Listeria* genome using pPL2. SF is shorthand for an eight amino acid peptide derived from ovalbumin, also known as SL8 (see, e.g., Shastri and Ganzalez (1993) J. Immunol. 150:2724-2736). The abbreviations "SF-AH1A5," "SF-AH1-A5," and "OVA/AH1-A5" refer to AH1-A5 connected to an ovalbumin scaffold. "SF AH1-A5" refers to the AH1-A5 (SPSYAYHQF (SEQ ID NO:73)) and the SF peptide fused to the N-terminus of amino acids 138 to 386 of GenBank Accession. No. P01012 (ovalbumin). The polynucleotides encoding "SF-AH1A5," in this example, comprised a codon-optimized nucleic acid encoding AH1-A5 and a non-codon optimized nucleic acid encoding the ovalbumin-derived sequence.

The results demonstrate that a single immunization with *Listeria* expressing huMesothelin prolongs survival of mice containing huMesothelin-expressing tumors. The survival percentage was highest with the chromosomally integrated *B. anthracis* Protective Antigen signal sequence fused with the Δsignal sequence/Δgpi huMesothelin (BaPA-huMeso ΔgpiΔss; closed squares). Survival was lowest where "vaccination" was with the control salt solution.

C. Reduction in Lung Tumor Nodule Level in Tumor-Bearing Mice Vaccinated With *Listeria* Expressing Human Mesothelin Due to Mesothelin-Specific Anti-Tumor Efficacy The data in FIG. 62 demonstrate that the level of lung tumor nodules is reduced by vaccination with *Listeria* ΔactAΔinlB expressing human mesothelin, where the tumor cells were engineered to express human mesothelin. The mouse strain was Balb/c and the lung tumor cells were CT26 cells harboring a vector expressing human mesothelin. On Day 0, $2 \times 10^5$ CT26 cells expressing human mesothelin were administered intravenously to the Balb/c mice. Sequences encoding various signal sequences were operably linked in frame with codon-optimized sequences encoding human mesothelin in expression cassettes. The expression cassettes encoding various signal peptides fused with human mesothelin were administered to the tumor-bearing mice via *Listeria* vaccines comprising the expression cassettes. On Day 3, $1 \times 10^7$ CFU/ 100 μL of the *Listeria* vaccines were administered to the tumor-bearing mice intravenously. Negative control vaccinations were with HBSS or *Listeria* ΔactAΔinlB. Positive control vaccinations were with *Listeria* expressing an OVA fusion protein comprising AH1A5 (in frame with the OVA sequence). (The OVA fusion protein comprising AH1A5 was encoded by a non-codon optimized expression cassette.) On Day 19, the mice were sacrificed, their lungs harvested, and the lung tumor nodules counted.

The *Listeria* vaccines reduced the number of metastases in the lungs. Control vaccines involving only HBBS or *Listeria* ΔactAΔinlB resulted in a detected consistent 250 metastases per lung and an average of 135 metastasis per lung, respectively. *Listeria* bearing plasmid (pAM401) encoding LLO signal peptide fused to human mesothelin ("pAM-LLO-HuMeso") showed about 25 metastases per lung. The polynucleotide sequences of the pAM-LLO-HuMeso plasmid that encoded the LLO signal peptide and the human mesothelin sequence were codon-optimized for expression in *L. monocytogenes*. *Listeria* bearing integrated sequences encoding *B. anthracis* Protective Antigen signal sequence (BaPA) fused with huMesothelin (Δgpi/Δsignal sequence) ("BaPA-HuMeso ΔgpiΔss") also showed on the average about 25 metastases per lung on average. The polynucleotide in BaPA-HuMeso ΔgpiΔss that encoded the *B. anthracis* Protective Antigen signal sequence was not codon-optimized, whereas the polynucleotide that encoded the human mesothelin sequence deleted of the mesothelin signal peptide and GPI anchor was codon-optimized for expression in *L. monocytogenes*.

FIG. 63 shows the results of a control study using mice comprising lung tumor nodules generated using CT.26 parental target cells. Balb/c mice were used, but wt CT26 was instead injected ($2 \times 10^5$ cells (i.v.) on Day 0). The study demonstrates that the anti-tumor efficacy of vaccination with the *Listeria* vaccine expressing mesothelin fusion proteins is mesothelin specific. Sequences encoding various signal sequences were operably linked in frame with codon-optimized sequences encoding human mesothelin in expression cassettes. (The constructs used in this experiment were identical to those used in the experiments above to generate the data shown in FIG. 62.) The expression cassettes encoding various signal peptides fused with human mesothelin were administered to the tumor-bearing mice via *Listeria* vaccines comprising the expression cassettes. Vaccination was in the tail vein ($1 \times 10^7$ CFU/100 µL i.v. on Day 3). In this particular study, the tumor cells did not express human mesothelin. Survival was determined. Where the data was available, the number of lung metastases was also measured. There were a total of five mice in each vaccination group. Negative control inoculation involved HBSS or *Listeria* ΔactAΔinlB. Positive control inoculation involved *Listeria* expressing an OVA fusion comprising AH1A5 (not codon-optimized).

The results are shown in FIG. 63. Crosses indicate failure to survive and each vaccination group contained 5 mice. With the positive control inoculation, the mice survived, and the number of detected metastases in the lung was on the average about 25 per lung. As the tumor cells were not engineered to express human mesothelin, the mice inoculated with *Listeria* harboring a plasmid expressing LLO signal peptide fused with human mesothelin ("pAM-LLO-HuMeso") did not survive. Where mice were inoculated with *Listeria* bearing chromosomally integrated *B. anthracis* Protective Antigen secretory sequence (BaPA; encoded by a non-codon optimized nucleotide sequence) fused with with human mesothelin (Δgpi/Δsignal sequence) ("BaPA-HuMeso ΔgpiΔss"), some survived but others failed to survive.

D. Vaccination With *Listeria* Expressing Codon-Optimized Human Mesothelin Reduces Tumor Volume FIG. 64 shows vaccination with *Listeria* (ΔactAΔinlB) expressing human mesothelin from expression cassettes comprising codon-optimized mesothelin codon sequences reduces tumor volume.

Sequences encoding various signal sequences were operably linked in frame with codon-optimized sequences encoding human mesothelin in expression cassettes. The expression cassettes encoding various signal peptides fused with human mesothelin were administered to tumor-bearing mice via *Listeria* vaccines comprising the expression cassettes. The *Listeria* vaccines expressing human mesothelin that were used for vaccination of the tumor-bearing mice in this study include the following: *Listeria* (ΔactAΔinlB *L. monocytogenes*) bearing a pAM401 plasmid expressing and secreting LLO signal peptide (encoded by a sequence codon-optimized for expression in *L. monocytogenes*) fused with human mesothelin ("pAM opt.LLO-opt.huMeso"); *Listeria* bearing a pAM401 plasmid expressing *B. anthracis* Protective Antigen signal sequence (encoded by a non-codon optimized expression cassette) fused with huMesothelin ("pAM non-opt.BaPA-opt.huMeso"); and *Listeria* comprising an integrated expression cassette encoding *B. anthracis* Protective Antigen signal peptide (encoded by a non-codon optimized sequence) fused with huMesothelin, where the huMesothelin had a deleted signal sequence and a deleted region encoding the hydrophobic gpi-anchoring peptide ("Non-opt.BaPA-opt.huMeso delgpi-ss").

In the study, Balb/c mice were implanted subcutaneously with $2 \times 10^5$ cells of CT26 murine colon tumor cells engineered to expression human mesothelin (Day 0). Five mice were included in each vaccination group. On Day 3 following injection with the CT26 cells, the mice were vaccinated with non-Listerial control or $1 \times 10^7$ colony forming units (CFU) of the *Listeria* vaccine intravenously. Negative control inoculation involved HBSS. Positive control inoculation involved *Listeria* expressing SF-AH1A5 (codon optimized). (SF is an eight amino acid peptide derived from ovalbumin, also known as SL8 (see, e.g., Shastri and Ganzalez (1993) J. Immunol. 150:2724-2736).) At various time points, the mean tumor volume was determined.

The results of this study are shown in FIG. 64. The results demonstrated that vaccination with *Listeria* expressing human mesothelin fused to various signal peptides reduces tumor volume. Vaccination with *Listeria* expressing a *B. anthracis* Protective Antigen signal peptide fused with human mesothelin was protective (open circles with dotted line). Vaccination with *Listeria* expressing plasmid-encoded human mesothelin fused to LLO signal peptide was protective (open triangles). Vaccination with *Listeria* comprising a chromosomally integrated expression cassette encoding *B. anthracis* Protective Antigen (non-codon optimized nucleic acid) signal peptide fused with human mesothelin (Δgpi/Δsignal sequence) (open ovals with solid line) was also protective. Regarding the positive controls, *Listeria* expressing chromosomally integrated SF-AH1A5 (open squares) were also protective. The highest tumor volume, and earliest time of tumor growth onset, occurred in mice receiving the sham vaccine (HBSS).

E. Immunogenicity of a *Listeria* Vaccine Expressing Human Mesothelin Fused to a Non-Listerial Signal Sequence FIG. 65 depicts the immunogenicity of a *Listeria* ΔactA/ΔinlB-hMesothelin strain, where the *Listeria* contained a chromosomally integrated nucleic acid encoding hMesothelin fused to a *Bacillus anthracis* signal peptide (optimized BaPA hMeso ΔGPIΔSS). ELISPOT assays were used to assess immune response, where the assays were sensitive to expression of interferon-gamma.

The study comprised the following steps: (1) Mice (Balb/c mice or C57BL/6 mice) were vaccinated (i.v.) with the *Listeria* comprising an integrated expression cassette encoding *B. anthracis* Protective Antigen signal peptide (encoded by a non-codon optimized sequence) fused with huMesothelin (encoded by a codon-optimized sequences in which the mesothelin signal sequence and hydrophobic gpi-anchoring sequences had been deleted); (2) After 7 days, the spleens were removed; (3) The cells removed from the spleens were dispersed in wells. Each well received about 200,000 spleen cells; (4) One of three kinds of medium were added to the wells, as indicated. Spleen cells from studies with Balb/c mice received medium only ("Unstimulated"), mesothelin peptide pool ("Meso pool"), or $p60_{217\text{-}225}$ ("$p60_{217}$"). Spleen cells from studies with C57BL/6 received medium only ("Unstimulated"), mesothelin peptide pool ("Meso pool"), or LLO$_{296-304}$ ("LLO$_{296-304}$"); (5) ELISPOT assays were performed to determine number of immune cells responding to the added peptide(s). The mesothelin peptide pool comprised 153 different peptides, where these peptides spanned the entire sequence of hMesothelin, where each peptide was 15 amino acids long, overlapping the adjacent peptides by 11 amino acids.

The results of the ELISPOT assays are shown in FIG. 65. The results indicated that the *Listeria* vaccine expressing human mesothelin fused to *B. anthracis* signal peptide was capable of inducing an immune response to mesothelin in Balb/c mice. A higher IFN-gamma response to *Listeria*-expressed hMesothelin was observed with the Balb/c mouse immune system than with the C57BL/6 immune system. ELISPOT signal to p60 or LLO was in response to the *Listeria*'s naturally occurring p60 and LLO proteins.

All publications, patents, patent applications, internet sites, and accession numbers/database sequences (including both polynucleotide and polypeptide sequences) cited herein are hereby incorporated by reference herein in their entirety for all purposes to the same extent as if each individual publication, patent, patent application, internet site, or accession number/database sequence were specifically and individually indicated to be so incorporated by reference.

We claim:

1. A recombinant nucleic acid molecule, comprising:
   (a) a first polynucleotide sequence encoding a signal peptide native to a *Listeria monocytogenes* bacterium, wherein the first polynucleotide sequence is codon-optimized to replace at least one codon of the native coding sequence of the polynucleotide with a codon that is more frequently used by *Listeria monocytogenes*, for expression in the *Listeria monocytogenes* bacterium; and
   (b) a second polynucleotide sequence encoding a polypeptide heterologous to the signal peptide, wherein the second polynucleotide sequence is in the same translational reading frame as the first polynucleotide sequence, wherein the recombinant nucleic acid molecule encodes a fusion protein comprising the signal peptide and the polypeptide.

2. The recombinant nucleic acid molecule of claim 1, wherein the signal peptide is an LLO signal peptide from *Listeria monocytogenes* or is a p60 signal peptide from *Listeria monocytogenes*.

3. An expression cassette comprising the recombinant nucleic acid molecule of claim 1, further comprising a promoter operably linked to the first and second polynucleotide sequences of the recombinant nucleic acid molecule.

4. A recombinant *Listeria monocytogenes* bacterium comprising a recombinant nucleic acid molecule, wherein the recombinant nucleic acid molecule comprises:
   (a) a first polynucleotide sequence encoding a signal peptide native to a *Listeria monocytogenes* bacterium, wherein the first polynucleotide is codon-optimized to replace at least one codon of the native coding sequence of the polynucleotide with a codon that is more frequently used by *Listeria monocytogenes*, for expression in the *Listeria* bacterium; and
   (b) a second polynucleotide sequence encoding a polypeptide heterologous to the signal peptide, wherein the second polynucleotide sequence is in the same translational reading frame as the first polynucleotide sequence, wherein the recombinant nucleic acid molecule encodes a fusion protein comprising the signal peptide and the polypeptide.

5. The recombinant *Listeria monocytogenes* bacterium of claim 4, which comprises an expression cassette comprising the recombinant nucleic acid molecule, wherein the expression cassette further comprises a promoter operably linked to both the first and second polynucleotide sequences of the recombinant nucleic acid molecule.

6. The recombinant *Listeria monocytogenes* bacterium of claim 4, wherein the polypeptide encoded by the second polynucleotide sequence comprises an antigen selected from the group consisting of a tumor-associated antigen, a polypeptide derived from a tumor-associated antigen, an infectious disease antigen, and a polypeptide derived from an infectious disease antigen.

7. The recombinant *Listeria monocytogenes* bacterium of claim 6, wherein the polypeptide encoded by the second polynucleotide sequence comprises an antigen selected from the group consisting of K-Ras, H-Ras, N-Ras, 12-K-Ras, mesothelin, PSCA, NY-ESO-1, WT-1, survivin, gp 100, PAP, proteinase 3, SPAS-1, SP-17, PAGE-4, TARP, and CEA, or comprises a polypeptide derived from an antigen selected from the group consisting of K-Ras, H-Ras, N-Ras, 12-K-Ras, mesothelin, PSCA, NY-ESO-1, WT-1, survivin, gp 100, PAP, proteinase 3, SPAS-1, SP-17, PAGE-4, TARP, and CEA.

8. The recombinant *Listeria monocytogenes* bacterium of claim 7, wherein the polypeptide encoded by the second polynucleotide sequence comprises mesothelin, or an antigenic fragment or antigenic variant thereof, or comprises NY-ESO-1, or an antigenic fragment or antigenic variant thereof.

9. The recombinant *Listeria monocytogenes* bacterium of claim 8, wherein the polypeptide encoded by the second polynucleotide sequence comprises human mesothelin deleted of its signal peptide and GPI linker domain.

10. The recombinant *Listeria monocytogenes* bacterium of claim 4, wherein the polypeptide encoded by the second polynucleotide sequence is heterologous to the signal peptide.

11. The recombinant *Listeria monocytogenes* bacterium of claim 4, wherein the signal peptide is a signal peptide selected from the group consisting of an LLO signal peptide from *Listeria monocytogenes* and a p60 signal peptide from *Listeria monocytogenes*.

12. The recombinant *Listeria monocytogenes* bacterium of claim 4, which is attenuated for cell-to-cell spread, entry into non-phagocytic cells, or proliferation.

13. The recombinant *Listeria monocytogenes* bacterium of claim 4, which is deficient with respect to ActA, Internalin B, or both ActA and Internalin B.

14. The recombinant *Listeria monocytogenes* bacterium of claim 4, wherein the nucleic acid of the recombinant bacterium has been modified by reaction with a nucleic acid targeting compound.

15. A recombinant nucleic acid molecule, comprising:
   (a) a first polynucleotide sequence encoding a signal peptide native to a *Listeria monocytogenes* bacterium, wherein said first polynucleotide sequence is codon-optimized to replace at least one codon of the native coding sequence of the polynucleotide with a codon that is more frequently used by *Listeria monocytogenes*, for expression in the *Listeria monocytogenes* bacterium; and
   (b) a second polynucleotide sequence encoding a polypeptide heterologous to the signal peptide, wherein the second polynucleotide sequence is in the same translational reading frame as the first polynucleotide sequence, wherein the second polynucleotide sequence is codon-optimized to replace at least one codon of the native coding sequence of the polynucleotide with a codon that is more frequently used by *Listeria monocytogenes*, for expression in the *Listeria monocytogenes* bacterium, and
      wherein the recombinant nucleic acid molecule encodes a fusion protein comprising the signal peptide and the polypeptide.

16. The recombinant nucleic acid molecule of claim 15, wherein the signal peptide is a secA2 signal peptide.

17. The recombinant nucleic acid molecule of claim 15, wherein the signal peptide is a p60 signal peptide from *Listeria monocytogenes*.

18. The recombinant nucleic acid molecule of claim 15, wherein the polypeptide encoded by the second polynucleotide sequence comprises an antigen selected from the group consisting of a tumor-associated antigen, a polypeptide derived from a tumor-associated antigen, an infectious disease antigen, and a polypeptide derived from an infectious disease antigen.

19. An expression cassette comprising the recombinant nucleic acid molecule of claim 15, further comprising a promoter operably linked to the first and second polynucleotide sequences of the recombinant nucleic acid molecule.

20. A recombinant *Listeria monocytogenes* bacterium comprising the recombinant nucleic acid molecule of claim 15.

21. A recombinant *Listeria monocytogenes* bacterium comprising a recombinant nucleic acid molecule, wherein the recombinant nucleic acid molecule comprises:
   (a) a first polynucleotide sequence encoding signal peptide native to said *Listeria monocytogenes*, wherein said first polynucleotide sequence is codon-optimized to replace at least one codon of the native coding sequence of the polynucleotide with a codon that is more frequently used by *Listeria monocytogenes* for expression in said *Listeria monocytogenes*; and
   (b) a second polynucleotide sequence encoding a polypeptide which is heterologous to the signal peptide or is foreign to the bacterium, or both, wherein the second polynucleotide sequence is in the same translational reading frame as the first polynucleotide sequence;
      wherein the recombinant nucleic acid molecule encodes a fusion protein comprising the signal peptide and the polypeptide.

22. The recombinant *Listeria monocytogenes* bacterium of claim 21, which comprises an expression cassette comprising the recombinant nucleic acid molecule, wherein the expression cassette further comprises a promoter operably linked to both the first and second polynucleotide sequences of the recombinant nucleic acid molecule.

23. The recombinant *Listeria monocytogenes* bacterium of claim 21, wherein the first and second polynucleotide sequences are codon-optimized to replace at least one codon of the native coding sequence of the polynucleotide with a codon that is more frequently used by *Listeria monocytogenes* for expression in the *Listeria monocytogenes* bacterium.

24. The recombinant *Listeria monocytogenes* bacterium of claim 21, wherein the signal peptide is a secA2 signal peptide.

25. The recombinant *Listeria monocytogenes* bacterium of claim 24, wherein the recombinant nucleic acid molecule further comprises:
   (c) a third polynucleotide sequence encoding a secA2 autolysin, or a fragment thereof, in the same translational reading frame as the first and second polynucleotide sequences, wherein the second polynucleotide sequence is positioned within the third polynucleotide sequence or between the first and third polynucleotide sequences.

26. The recombinant *Listeria monocytogenes* bacterium of claim 21, wherein the polypeptide encoded by the second polynucleotide sequence comprises an antigen selected from the group consisting of a tumor-associated antigen, a polypeptide derived from a tumor-associated antigen, an infectious disease antigen, and a polypeptide derived from an infectious disease antigen.

27. The recombinant *Listeria monocytogenes* bacterium of claim 26, wherein the polypeptide encoded by the second polynucleotide sequence comprises an antigen selected from the group consisting of K-Ras, H-Ras, N-Ras, 12-K-Ras, mesothelin, PSCA, NY-ESO-1, WT-1, survivin, gp 100, PAP, proteinase 3, SPAS-1, SP-17, PAGE-4, TARP, and CEA, or comprises a polypeptide derived from an antigen selected from the group consisting of K-Ras, H-Ras, N-Ras, 12-K-Ras, mesothelin, PSCA, NY-ESO-1, WT-1, survivin, gp 100, PAP, proteinase 3, SPAS-1, SP-17, PAGE-4, TARP, and CEA.

28. The recombinant *Listeria monocytogenes* bacterium of claim 27, wherein the polypeptide encoded by the second polynucleotide sequence comprises mesothelin, or an antigenic fragment or antigenic variant thereof.

29. The recombinant *Listeria monocytogenes* bacterium of claim 28, wherein the polypeptide encoded by the second polynucleotide sequence comprises human mesothelin deleted of its signal peptide and GPI anchor.

30. The recombinant *Listeria monocytogenes* bacterium of claim 21, which is attenuated for cell-to-cell spread, entry into non-phagocytic cells, or proliferation.

31. The recombinant *Listeria monocytogenes* bacterium of claim 21, which is deficient with respect to ActA, Internalin B, or both ActA and Internalin B.

32. The recombinant *Listeria monocytogenes* bacterium of claim 21, wherein the nucleic acid of the recombinant bacterium has been modified by reaction with a nucleic acid targeting compound.

33. A recombinant nucleic acid molecule, comprising:
   (a) a first polynucleotide sequence encoding a signal peptide native to a *Listeria monocytogenes* bacterium, wherein the first polynucleotide sequence is codon-optimized to replace at least one codon of the native coding sequence of the polynucleotide with a codon that is more frequently used by *Listeria monocytogenes* for expression in the *Listeria monocytogenes* bacterium;

(b) a second polynucleotide sequence encoding a secreted protein, or a fragment thereof, heterologous to the signal peptide wherein the second polynucleotide sequence is in the same translational reading frame as the first polynucleotide sequence; and (c) a third polynucleotide sequence encoding a polypeptide heterologous to the secreted protein, or fragment thereof, wherein the third polynucleotide sequence is in the same translational reading frame as the first and second polynucleotide sequences, wherein the recombinant nucleic acid molecule encodes a protein chimera comprising the signal peptide, the polypeptide encoded by the third polynucleotide sequence, and the secreted protein, or fragment thereof, and wherein the polypeptide encoded by the third polynucleotide sequence is fused to the secreted protein, or fragment thereof, or is positioned within the secreted protein, or fragment thereof, in the protein chimera.

34. A recombinant *Listeria monocytogenes* bacterium comprising the recombinant nucleic acid molecule of claim 33.

35. The recombinant *Listeria monocytogenes* bacterium of claim 6, wherein the infectious disease antigen is from a virus selected from the group consisting of a hepatitis virus, an influenza virus, and a papillomavirus.

36. The recombinant *Listeria monocytogenes* bacterium of claim 35, wherein the infectious disease antigen is from a hepatitis A virus, a hepatitis B virus, or a hepatitis C virus.

* * * * *

(12) EX PARTE REEXAMINATION CERTIFICATE (8653rd)
United States Patent
Dubensky, Jr. et al.

(10) Number: US 7,842,289 C1
(45) Certificate Issued: Nov. 1, 2011

(54) RECOMBINANT NUCLEIC ACID MOLECULES, EXPRESSION CASSETTES, AND BACTERIA, AND METHODS OF USE THEREOF

(75) Inventors: Thomas W. Dubensky, Jr., Piedmont, CA (US); Daniel A. Portnoy, Albany, CA (US); William S. Luckett, Jr., Richmond, CA (US); David N. Cook, Lafayette, CA (US)

(73) Assignee: Aduro Biotech, Berkeley, CA (US)

Reexamination Request:
No. 90/011,781, Jul. 1, 2011

Reexamination Certificate for:
Patent No.: 7,842,289
Issued: Nov. 30, 2010
Appl. No.: 11/021,441
Filed: Dec. 23, 2004

Related U.S. Application Data

(63) Continuation-in-part of application No. PCT/US2004/23881, filed on Jul. 23, 2004, and a continuation-in-part of application No. 10/883,599, filed on Jun. 30, 2004, now Pat. No. 7,695,725, and a continuation-in-part of application No. 10/773,618, filed on Feb. 6, 2004, now Pat. No. 7,833,775, and a continuation-in-part of application No. 10/773,792, filed on Feb. 6, 2004, now Pat. No. 7,691,393.

(60) Provisional application No. 60/616,750, filed on Oct. 6, 2004, provisional application No. 60/615,287, filed on Oct. 1, 2004, provisional application No. 60/599,377, filed on Aug. 5, 2004, provisional application No. 60/556,744, filed on Mar. 26, 2004, provisional application No. 60/541,515, filed on Feb. 2, 2004, and provisional application No. 60/532,598, filed on Dec. 24, 2003.

(51) Int. Cl.
*A61K 48/00* (2006.01)
*A61K 39/00* (2006.01)
*A61K 39/29* (2006.01)
*C07H 21/04* (2006.01)
*C07H 21/02* (2006.01)
*C12N 15/00* (2006.01)
*C12N 1/20* (2006.01)

(52) U.S. Cl. .......... 424/93.2; 424/225.1; 424/277.1; 424/234.1; 424/235.1; 424/93.1; 424/184.1; 424/93.4; 435/440; 435/441; 435/320.1; 435/443; 435/252.1; 435/252.3; 536/23.1; 536/23.4; 536/23.7

(58) Field of Classification Search .................. None
See application file for complete search history.

(56) References Cited

To view the complete listing of prior art documents cited during the proceeding for Reexamination Control Number 90/011,781, please refer to the USPTO's public Patent Application Information Retrieval (PAIR) system under the Display References tab.

*Primary Examiner*—Bruce Campell

(57) ABSTRACT

The present invention provides recombinant nucleic acid molecules, expression cassettes, and vectors useful for expression of polypeptides, including heterologous polypeptides, such as antigens, in bacteria. Some of the recombinant nucleic acid molecules, expression cassettes and vectors comprise codon-optimized sequences encoding the polypeptides and/or signal peptides. Some of the recombinant nucleic acid molecules, expression cassettes, and expression vectors comprise sequences encoding non-Listerial and/or non-secA1 signal peptides for secretion of the polypeptides. The invention also provides bacteria comprising the nucleic acid molecules, expression cassettes, and expression vectors, as well as compositions such as vaccines comprising the bacteria. Methods of making and using the bacteria, recombinant nucleic acid molecules, and expression cassettes are also provided.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1-8 and 10-36 is confirmed.
Claim 9 was not reexamined.

\* \* \* \* \*

SEQUENCE LISTING

<160> NUMBER OF SEQ ID NOS: 129

<210> SEQ ID NO 1
<211> LENGTH: 240
<212> TYPE: DNA
<213> ORGANISM: Listeria monocytogenes

<400> SEQUENCE: 1
ggtacctcct tgattagta tattcctatc ttaaagttac ttttatgtgg aggcattaac      60
atttgttaat gacgtcaaaa ggatagcaag actagaataa agctataaag caagcatata     120
atattgcgtt tcatctttag aagcgaattt cgccaatatt ataattatca aaagagaggg     180
gtggcaaacg gtatttggca ttattaggtt aaaaaatgta gaaggagagt gaaacccatg     240

<210> SEQ ID NO 2
<211> LENGTH: 240
<212> TYPE: DNA
<213> ORGANISM: Listeria monocytogenes

<400> SEQUENCE: 2
ggtacctcct tgattagta tattcctatc ttaaagtgac ttttatgttg aggcattaac      60
atttgttaac gacgataaag ggacagcagg actagaataa agctataaag caagcatata     120
atattgcgtt tcatctttag aagcgaattt cgccaatatt ataattatca aaagagaggg     180
gtggcaaacg gtatttggca ttattaggtt aaaaaatgta gaaggagagt gaaacccatg     240

<210> SEQ ID NO 3
<211> LENGTH: 3105
<212> TYPE: DNA
<213> ORGANISM: Artificial Sequence
<220> FEATURE:
<223> OTHER INFORMATION: Fusion protein coding sequence

<400> SEQUENCE: 3
atgaaaaaaa taatgctagt ttttattaca cttatattag ttagtctacc aattgcgcaa      60
caaactgaag caaaggatgc atctgcattc aataaagaaa attcaatttc atccatggca     120
ccaccagcat ctccgcctgc aagtcctaag acgccaatcg aaaagaaaca cgcggatctc     180
gagctccagg cagcccgcgc ctgcttcgcc ctgctgtggg gctgtgcgct ggccgcggcc     240
gcggcggcgc agggcaagga agtggtactg ctggactttg ctgcagctgg aggggagctc     300
ggctggctca cacacccgta tggcaaaggg tgggacctga tgcagaacat catgaatgac     360
atgccgatct acatgtactc cgtgtgcaac gtgatgtctg gcgaccagga caactggctc     420
cgcaccaact gggtgtaccg aggagaggct gagcgtatct tcattgagct caagtttact     480

-continued

```
gtacgtgact gcaacagctt ccctggtggc gccagctcct gcaaggagac tttcaacctc     540
tactatgccg agtcggacct ggactacggc accaacttcc agaagcgcct gttcaccaag     600
attgacacca ttgcgcccga tgagatcacc gtcagcagcg acttcgaggc acgccacgtg     660
aagctgaacg tggaggagcg ctccgtgggg ccgctcaccc gcaaaggctt ctacctggcc     720
ttccaggata tcggtgcctg tgtggcgctg ctctccgtcc gtgtctacta caagaagtgc     780
cccgagctgc tgcagggcct ggcccacttc cctgagacca tcgccggctc tgatgcacct     840
tccctggcca ctgtggccgg cacctgtgtg gaccatgccg tggtgccacc gggggtgaa      900 gagcccgta tgcactgtgc agtggatggc gagtggctgg tgcccattgg gcagtgcctg     960
tgccaggcag gctacgagaa ggtggaggat gcctgccagg cctgctcgcc tggattttt     1020 aagtttgagg catctgagag ccctgcttg gagtgccctg agcacacgct gccatcccct     1080
gagggtgcca cctcctgcga gtgtgaggaa ggcttcttcc gggcacctca ggacccagcg     1140
tcgatgcctt gcacacgacc cccctccgcc ccacactacc tcacagccgt gggcatgggt     1200
gccaaggtgg agctgcgctg gacgccccct caggacagcg ggggccgcga ggacattgtc     1260
tacagcgtca cctgcgaaca gtgctggccc gagtctgggg aatgcgggcc gtgtgaggcc     1320
agtgtgcgct actcggagcc tcctcacgga ctgacccgca ccagtgtgac agtgagcgac     1380
ctggagcccc acatgaacta caccttcacc gtggaggccc gcaatggcgt ctcaggcctg     1440
gtaaccagcc gcagcttccg tactgccagt gtcagcatca ccagacaga gccccccaag      1500 gtgaggctgg agggccgcag caccacctcg cttagcgtct cctggagcat ccccccgccg     1560
cagcagagcc gagtgtggaa gtacgaggtc acttaccgca agaagggaga ctccaacagc     1620
tacaatgtgc ccgcaccga gggtttctcc gtgaccctgg acgacctggc cccagacacc     1680
acctacctgg tccaggtgca ggcactgacg caggagggcc agggggccgg cagcagggtg     1740
cacgaattcc agacgctgtc cccggaggga tctggcaact ggcggtgat  tggcggcgtg     1800 gctgtcggtg tggtcctgct tctggtgctg gcaggagttg gcttctttat ccaccgcagg     1860
aggaagaacc agcgtgcccg ccagtccccg gaggacgttt acttctccaa gtcagaacaa     1920
ctgaagcccc tgaagacata cgtggacccc cacacatatg aggaccccaa ccaggctgtg     1980
ttgaagttca ctaccgagat ccatccatcc tgtgtcactc ggcagaaggt gatcggagca     2040
ggagagtttg gggaggtgta caagggcatg ctgaagacat cctcggggaa gaaggaggtg     2100
ccggtggcca tcaagacgct gaaagccggc tacacagaga agcagcgagt ggacttcctc     2160
ggcgaggccg gcatcatggg ccagttcagc caccacaaca tcatccgcct agagggcgtc     2220
atctccaaat acaagcccat gatgatcatc actgagtaca tggagaatgg ggccctggac     2280
aagttccttc gggagaagga tggcgagttc agcgtgctgc agctggtggg catgctgcgg     2340
ggcatcgcag ctggcatgaa gtacctggcc aacatgaact atgtgcaccg tgacctggct     2400
gcccgcaaca tcctcgtcaa cagcaacctg gtctgcaagg tgtctgactt ggcctgtcc      2460 cgcgtgctgg aggacgaccc cgaggccacc tacaccacca gtggcggcaa gatccccatc     2520
cgctggaccg ccccggaggc catttcctac cggaagttca cctctgccag cgacgtgtgg     2580
agctttggca ttgtcatgtg ggaggtgatg acctatggcg agcggcccta ctgggagttg     2640
tccaaccacg aggtgatgaa agccatcaat gatggcttcc ggctcccac  acccatggac     2700 tgccccctccg ccatctacca gctcatgatg cagtgctggc agcaggagcg tgcccgccgc     2760
cccaagttcg ctgacatcgt cagcatcctg gacaagctca ttcgtgcccc tgactccctc     2820
aagaccctgg ctgactttga ccccgcgtg tctatccggc tccccagcac gagcggctcg     2880
```

```
gagggggtgc ccttccgcac ggtgtccgag tggctggagt ccatcaagat gcagcagtat    2940
acggagcact tcatggcggc cggctacact gccatcgaga aggtggtgca gatgaccaac    3000
gacgacatca agaggattgg ggtgcggctg cccggccacc agaagcgcat cgcctacagc    3060
ctgctgggac tcaaggacca ggtgaacact gtggggatcc ccatc                    3105
```

<210> SEQ ID NO 4
<211> LENGTH: 1035
<212> TYPE: PRT
<213> ORGANISM: Artificial Sequence
<220> FEATURE:
<223> OTHER INFORMATION: Fusion protein

<400> SEQUENCE: 4

```
Met Lys Lys Ile Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Ala Ser
        35                  40                  45

Pro Lys Thr Pro Ile Glu Lys Lys His Ala Asp Leu Glu Leu Gln Ala
    50                  55                  60

Ala Arg Ala Cys Phe Ala Leu Leu Trp Gly Cys Ala Leu Ala Ala Ala
65                  70                  75                  80

Ala Ala Ala Gln Gly Lys Glu Val Val Leu Leu Asp Phe Ala Ala Ala
                85                  90                  95

Gly Gly Glu Leu Gly Trp Leu Thr His Pro Tyr Gly Lys Gly Trp Asp
           100                 105                 110

Leu Met Gln Asn Ile Met Asn Asp Met Pro Ile Tyr Met Tyr Ser Val
       115                 120                 125

Cys Asn Val Met Ser Gly Asp Gln Asp Asn Trp Leu Arg Thr Asn Trp
   130                 135                 140

Val Tyr Arg Gly Glu Ala Glu Arg Ile Phe Ile Glu Leu Lys Phe Thr
145                 150                 155                 160

Val Arg Asp Cys Asn Ser Phe Pro Gly Gly Ala Ser Ser Cys Lys Glu
                165                 170                 175

Thr Phe Asn Leu Tyr Tyr Ala Glu Ser Asp Leu Asp Tyr Gly Thr Asn
            180                 185                 190

Phe Gln Lys Arg Leu Phe Thr Lys Ile Asp Thr Ile Ala Pro Asp Glu
        195                 200                 205

Ile Thr Val Ser Ser Asp Phe Glu Ala Arg His Val Lys Leu Asn Val
    210                 215                 220

Glu Glu Arg Ser Val Gly Pro Leu Thr Arg Lys Gly Phe Tyr Leu Ala
225                 230                 235                 240

Phe Gln Asp Ile Gly Ala Cys Val Ala Leu Leu Ser Val Arg Val Tyr
                245                 250                 255

Tyr Lys Lys Cys Pro Glu Leu Leu Gln Gly Leu Ala His Phe Pro Glu
            260                 265                 270

Thr Ile Ala Gly Ser Asp Ala Pro Ser Leu Ala Thr Val Ala Gly Thr
        275                 280                 285

Cys Val Asp His Ala Val Pro Pro Gly Gly Glu Glu Pro Arg Met
    290                 295                 300

His Cys Ala Val Asp Gly Glu Trp Leu Val Pro Ile Gly Gln Cys Leu
305                 310                 315                 320
```

```
Cys Gln Ala Gly Tyr Glu Lys Val Glu Asp Ala Cys Gln Ala Cys Ser
            325                 330                 335
Pro Gly Phe Phe Lys Phe Glu Ala Ser Glu Ser Pro Cys Leu Glu Cys
            340                 345                 350
Pro Glu His Thr Leu Pro Ser Pro Glu Gly Ala Thr Ser Cys Glu Cys
            355                 360                 365
Glu Glu Gly Phe Phe Arg Ala Pro Gln Asp Pro Ala Ser Met Pro Cys
            370                 375                 380
Thr Arg Pro Pro Ser Ala Pro His Tyr Leu Thr Ala Val Gly Met Gly
385                 390                 395                 400
Ala Lys Val Glu Leu Arg Trp Thr Pro Pro Gln Asp Ser Gly Gly Arg
            405                 410                 415
Glu Asp Ile Val Tyr Ser Val Thr Cys Glu Gln Cys Trp Pro Glu Ser
            420                 425                 430
Gly Glu Cys Gly Pro Cys Glu Ala Ser Val Arg Tyr Ser Glu Pro Pro
            435                 440                 445
His Gly Leu Thr Arg Thr Ser Val Thr Val Ser Asp Leu Glu Pro His
            450                 455                 460
Met Asn Tyr Thr Phe Thr Val Glu Ala Arg Asn Gly Val Ser Gly Leu
465                 470                 475                 480
Val Thr Ser Arg Ser Phe Arg Thr Ala Ser Val Ser Ile Asn Gln Thr
            485                 490                 495
Glu Pro Pro Lys Val Arg Leu Glu Gly Arg Ser Thr Thr Ser Leu Ser
            500                 505                 510
Val Ser Trp Ser Ile Pro Pro Pro Gln Gln Ser Arg Val Trp Lys Tyr
            515                 520                 525
Glu Val Thr Tyr Arg Lys Lys Gly Asp Ser Asn Ser Tyr Asn Val Arg
            530                 535                 540
Arg Thr Glu Gly Phe Ser Val Thr Leu Asp Asp Leu Ala Pro Asp Thr
545                 550                 555                 560
Thr Tyr Leu Val Gln Val Gln Ala Leu Thr Gln Glu Gly Gln Gly Ala
            565                 570                 575
Gly Ser Arg Val His Glu Phe Gln Thr Leu Ser Pro Glu Gly Ser Gly
            580                 585                 590
Asn Leu Ala Val Ile Gly Gly Val Ala Val Gly Val Val Leu Leu Leu
            595                 600                 605
Val Leu Ala Gly Val Gly Phe Phe Ile His Arg Arg Arg Lys Asn Gln
            610                 615                 620
Arg Ala Arg Gln Ser Pro Glu Asp Val Tyr Phe Ser Lys Ser Glu Gln
625                 630                 635                 640
Leu Lys Pro Leu Lys Thr Tyr Val Asp Pro His Thr Tyr Glu Asp Pro
            645                 650                 655
Asn Gln Ala Val Leu Lys Phe Thr Thr Glu Ile His Pro Ser Cys Val
            660                 665                 670
Thr Arg Gln Lys Val Ile Gly Ala Gly Glu Phe Gly Glu Val Tyr Lys
            675                 680                 685
Gly Met Leu Lys Thr Ser Ser Gly Lys Lys Glu Val Pro Val Ala Ile
            690                 695                 700
Lys Thr Leu Lys Ala Gly Tyr Thr Glu Lys Gln Arg Val Asp Phe Leu
705                 710                 715                 720
Gly Glu Ala Gly Ile Met Gly Gln Phe Ser His His Asn Ile Ile Arg
            725                 730                 735
Leu Glu Gly Val Ile Ser Lys Tyr Lys Pro Met Met Ile Ile Thr Glu
```

```
                740                 745                 750
Tyr Met Glu Asn Gly Ala Leu Asp Lys Phe Leu Arg Glu Lys Asp Gly
                755                 760                 765

Glu Phe Ser Val Leu Gln Leu Val Gly Met Leu Arg Gly Ile Ala Ala
            770                 775                 780

Gly Met Lys Tyr Leu Ala Asn Met Asn Tyr Val His Arg Asp Leu Ala
785                 790                 795                 800

Ala Arg Asn Ile Leu Val Asn Ser Asn Leu Val Cys Lys Val Ser Asp
                805                 810                 815

Phe Gly Leu Ser Arg Val Leu Glu Asp Asp Pro Glu Ala Thr Tyr Thr
            820                 825                 830

Thr Ser Gly Gly Lys Ile Pro Ile Arg Trp Thr Ala Pro Glu Ala Ile
            835                 840                 845

Ser Tyr Arg Lys Phe Thr Ser Ala Ser Asp Val Trp Ser Phe Gly Ile
            850                 855                 860

Val Met Trp Glu Val Met Thr Tyr Gly Glu Arg Pro Tyr Trp Glu Leu
865                 870                 875                 880

Ser Asn His Glu Val Met Lys Ala Ile Asn Asp Gly Phe Arg Leu Pro
                885                 890                 895

Thr Pro Met Asp Cys Pro Ser Ala Ile Tyr Gln Leu Met Met Gln Cys
            900                 905                 910

Trp Gln Gln Glu Arg Ala Arg Arg Pro Lys Phe Ala Asp Ile Val Ser
        915                 920                 925

Ile Leu Asp Lys Leu Ile Arg Ala Pro Asp Ser Leu Lys Thr Leu Ala
        930                 935                 940

Asp Phe Asp Pro Arg Val Ser Ile Arg Leu Pro Ser Thr Ser Gly Ser
945                 950                 955                 960

Glu Gly Val Pro Phe Arg Thr Val Ser Glu Trp Leu Glu Ser Ile Lys
                965                 970                 975

Met Gln Gln Tyr Thr Glu His Phe Met Ala Ala Gly Tyr Thr Ala Ile
            980                 985                 990

Glu Lys Val Val Gln Met Thr Asn Asp Asp Ile Lys Arg Ile Gly Val
        995                 1000                1005

Arg Leu Pro Gly His Gln Lys Arg Ile Ala Tyr Ser Leu Leu Gly Leu
    1010                1015                1020

Lys Asp Gln Val Asn Thr Val Gly Ile Pro Ile
1025                1030                1035
```

<210> SEQ ID NO 5
<211> LENGTH: 1506
<212> TYPE: DNA
<213> ORGANISM: Homo sapiens

<400> SEQUENCE: 5

```
cagggcaagg aagtggtact gctggacttt gctgcagctg aggggagct cggctggctc      60 acacaccgt atggcaaagg gtgggacctg atgcagaaca tcatgaatga catgccgatc    120
tacatgtact ccgtgtgcaa cgtgatgtct ggcgaccagg acaactggct ccgcaccaac    180
tgggtgtacc gaggagaggc tgagcgtatc ttcattgagc tcaagtttac tgtacgtgac    240
tgcaacagct ccctggtgg cgccagctcc tgcaaggaga ctttcaacct ctactatgcc    300
gagtcggacc tggactacgg caccaacttc agaagcgcc tgttcaccaa gattgacacc    360 attgcgccg atgagatcac cgtcagcagc gacttcgagg cacgccacgt gaagctgaac    420
gtggaggagc gctccgtggg gccgctcacc cgcaaaggct tctacctggc cttccaggat    480
```

| | |
|---|---|
| atcggtgcct gtgtggcgct gctctccgtc cgtgtctact acaagaagtg ccccgagctg | 540 |
| ctgcagggcc tggcccactt ccctgagacc atcgccggct ctgatgcacc ttccctggcc | 600 |
| actgtggccg gcacctgtgt ggaccatgcc gtggtgccac cggggggtga agagccccgt | 660 |
| atgcactgtg cagtggatgg cgagtggctg gtgcccattg ggcagtgcct gtgccaggca | 720 |
| ggctacgaga aggtggagga tgcctgccag gcctgctcgc ctggattttt taagtttgag | 780 |
| gcatctgaga gcccctgctt ggagtgccct gagcacacgc tgccatcccc tgagggtgcc | 840 |
| acctcctgcg agtgtgagga aggcttcttc cgggcacctc aggacccagc gtcgatgcct | 900 |
| tgcacacgac ccccctccgc cccacactac ctcacagccg tgggcatggg tgccaaggtg | 960 |
| gagctgcgct ggacgccccc tcaggacagc gggggccgcg aggacattgt ctacagcgtc | 1020 |
| acctgcgaac agtgctggcc cgagtctggg gaatgcgggc cgtgtgaggc cagtgtgcgc | 1080 |
| tactcggagc ctcctcacgg actgacccgc accagtgtga cagtgagcga cctggagccc | 1140 |
| cacatgaact acaccttcac cgtggaggcc cgcaatggcg tctcaggcct ggtaaccagc | 1200 |
| cgcagcttcc gtactgccag tgtcagcatc aaccagacag agcccccaa ggtgaggctg | 1260 |
| gagggccgca gcaccacctc gcttagcgtc tcctggagca tccccccgcc gcagcagagc | 1320 |
| cgagtgtgga agtacgaggt cacttaccgc aagaagggag actccaacag ctacaatgtg | 1380 |
| cgccgcaccg agggtttctc cgtgaccctg gacgacctgg ccccagacac cacctacctg | 1440 |
| gtccaggtgc aggcactgac gcaggagggc caggggccg gcagcagggt gcacgaattc | 1500 |
| cagacg | 1506 |

<210> SEQ ID NO 6
<211> LENGTH: 1506
<212> TYPE: DNA
<213> ORGANISM: Artificial Sequence
<220> FEATURE:
<223> OTHER INFORMATION: Codon-optimized sequence

<400> SEQUENCE: 6

| | |
|---|---|
| caaggtaaag aagttgtttt attagatttt gcagcagcag gtggtgaatt aggttggtta | 60 |
| acacatccat atggtaaagg ttgggattta atgcaaaata ttatgaatga tatgccaatt | 120 |
| tatatgtata gtgtttgtaa tgttatgagt ggtgatcaag ataattggtt acgtacaaat | 180 |
| tgggtttatc gtggtgaagc agaacgtatt tttattgaat taaaatttac agttcgtgat | 240 |
| tgtaatagtt ttccaggtgg tgcaagtagt tgtaaagaaa catttaattt atattatgca | 300 |
| gaaagtgatt tagattatgg tacaaatttt caaaaacgtt tatttacaaa aattgataca | 360 |
| attgcaccag atgaaattac agttagtagt gattttgaag cacgtcatgt taaattaaat | 420 |
| gttgaagaac gtagtgttgg tccattaaca cgtaaaggtt tttatttagc atttcaagat | 480 |
| attggtgcat gtgttgcatt attaagtgtt cgtgtttatt ataaaaaatg tccagaatta | 540 |
| ttacaaggtt tagcacattt tccagaaaca attgcaggta gtgatgcacc aagtttagca | 600 |
| acagttgcag gtacatgtgt tgatcatgca gttgttccac caggtggtga agaaccacgt | 660 |
| atgcattgtg cagttgatgg tgaatggtta gttccaattg gtcaatgttt atgtcaagca | 720 |
| ggttatgaaa aagttgaaga tgcatgtcaa gcatgtagtc caggtttttt taaatttgaa | 780 |
| gcaagtgaaa gtccatgttt agaatgtcca gaacatacat accaagtcc agaaggtgca | 840 |
| acaagttgtg aatgtgaaga aggttttttt cgtgcaccac aagatccagc aagtatgcca | 900 |
| tgtacacgtc caccaagtgc accacattat ttaacagcag ttggtatggg tgcaaaagtt | 960 |

-continued

```
gaattacgtt ggacaccacc acaagatagt ggtggtcgtg aagatattgt ttatagtgtt    1020
acatgtgaac aatgttggcc agaaagtggt gaatgtggtc catgtgaagc aagtgttcgt    1080
tatagtgaac caccacatgg tttaacacgt acaagtgtta cagttagtga tttagaacca    1140
catatgaatt atacatttac agttgaagca cgtaatggtg ttagtggttt agttacaagt    1200
cgtagttttc gtacagcaag tgttagtatt aatcaaacag aaccaccaaa agttcgttta    1260
gaaggtcgta gtacaacaag tttaagtgtt agttggagta ttccaccacc acaacaaagt    1320
cgtgtttgga aatatgaagt tacatatcgt aaaaaggtg atagtaatag ttataatgtt    1380
cgtcgtacag aaggttttag tgttacatta gatgatttag caccagatac aacatattta    1440
gttcaagttc aagcattaac acaagaaggt caaggtgcag gtagtcgtgt tcatgaattt    1500
caaaca                                                                1506
```

<210> SEQ ID NO 7
<211> LENGTH: 502
<212> TYPE: PRT
<213> ORGANISM: Homo sapiens

<400> SEQUENCE: 7

```
Gln Gly Lys Glu Val Leu Leu Asp Phe Ala Ala Gly Gly Glu
 1               5                  10                  15

Leu Gly Trp Leu Thr His Pro Tyr Gly Lys Gly Trp Asp Leu Met Gln
            20                  25                  30

Asn Ile Met Asn Asp Met Pro Ile Tyr Met Tyr Ser Val Cys Asn Val
        35                  40                  45

Met Ser Gly Asp Gln Asp Asn Trp Leu Arg Thr Asn Trp Val Tyr Arg
    50                  55                  60

Gly Glu Ala Glu Arg Ile Phe Ile Glu Leu Lys Phe Thr Val Arg Asp
65                  70                  75                  80

Cys Asn Ser Phe Pro Gly Gly Ala Ser Ser Cys Lys Glu Thr Phe Asn
                85                  90                  95

Leu Tyr Tyr Ala Glu Ser Asp Leu Asp Tyr Gly Thr Asn Phe Gln Lys
            100                 105                 110

Arg Leu Phe Thr Lys Ile Asp Thr Ile Ala Pro Asp Glu Ile Thr Val
        115                 120                 125

Ser Ser Asp Phe Glu Ala Arg His Val Lys Leu Asn Val Glu Glu Arg
    130                 135                 140

Ser Val Gly Pro Leu Thr Arg Lys Gly Phe Tyr Leu Ala Phe Gln Asp
145                 150                 155                 160

Ile Gly Ala Cys Val Ala Leu Leu Ser Val Arg Val Tyr Tyr Lys Lys
                165                 170                 175

Cys Pro Glu Leu Leu Gln Gly Leu Ala His Phe Pro Glu Thr Ile Ala
            180                 185                 190

Gly Ser Asp Ala Pro Ser Leu Ala Thr Val Ala Gly Thr Cys Val Asp
        195                 200                 205

His Ala Val Val Pro Gly Gly Glu Glu Pro Arg Met His Cys Ala
    210                 215                 220

Val Asp Gly Glu Trp Leu Val Pro Ile Gly Gln Cys Leu Cys Gln Ala
225                 230                 235                 240

Gly Tyr Glu Lys Val Glu Asp Ala Cys Gln Ala Cys Ser Pro Gly Phe
                245                 250                 255

Phe Lys Phe Glu Ala Ser Glu Ser Pro Cys Leu Glu Cys Pro Glu His
            260                 265                 270
```

```
Thr Leu Pro Ser Pro Glu Gly Ala Thr Ser Cys Glu Cys Glu Glu Gly
        275                 280                 285

Phe Phe Arg Ala Pro Gln Asp Pro Ala Ser Met Pro Cys Thr Arg Pro
    290                 295                 300

Pro Ser Ala Pro His Tyr Leu Thr Ala Val Gly Met Gly Ala Lys Val
305                 310                 315                 320

Glu Leu Arg Trp Thr Pro Pro Gln Asp Ser Gly Arg Glu Asp Ile
                325                 330                 335

Val Tyr Ser Val Thr Cys Glu Gln Cys Trp Pro Glu Ser Gly Glu Cys
            340                 345                 350

Gly Pro Cys Glu Ala Ser Val Arg Tyr Ser Glu Pro His Gly Leu
        355                 360                 365

Thr Arg Thr Ser Val Thr Val Ser Asp Leu Glu Pro His Met Asn Tyr
    370                 375                 380

Thr Phe Thr Val Glu Ala Arg Asn Gly Val Ser Gly Leu Val Thr Ser
385                 390                 395                 400

Arg Ser Phe Arg Thr Ala Ser Val Ser Ile Asn Gln Thr Glu Pro Pro
                405                 410                 415

Lys Val Arg Leu Glu Gly Arg Ser Thr Thr Ser Leu Ser Val Ser Trp
            420                 425                 430

Ser Ile Pro Pro Pro Gln Gln Ser Arg Val Trp Lys Tyr Glu Val Thr
        435                 440                 445

Tyr Arg Lys Lys Gly Asp Ser Asn Ser Tyr Asn Val Arg Arg Thr Glu
    450                 455                 460

Gly Phe Ser Val Thr Leu Asp Asp Leu Ala Pro Asp Thr Thr Tyr Leu
465                 470                 475                 480

Val Gln Val Gln Ala Leu Thr Gln Glu Gly Gln Gly Ala Gly Ser Arg
                485                 490                 495

Val His Glu Phe Gln Thr
            500

<210> SEQ ID NO 8
<211> LENGTH: 1689
<212> TYPE: DNA
<213> ORGANISM: Artificial Sequence
<220> FEATURE:
<223> OTHER INFORMATION: Fusion protein coding sequence

<400> SEQUENCE: 8
atgaaaaaaa taatgctagt ttttattaca cttatattag ttagtctacc aattgcgcaa    60
caaactgaag caaaggatgc atctgcattc aataaagaaa ttcaatttc atccatggca    120 ccaccagcat ctccgcctgc aagtcctaag acgccaatcg aaagaaaaca cgcggatctc    180
gagcagggca aggaagtggt actgctggac tttgctgcag ctggagggga gctcggctgg    240
ctcacacacc gtatggcaa agggtgggac ctgatgcaga acatcatgaa tgacatgccg    300
atctacatgt actccgtgtg caacgtgatg tctggcgacc aggacaactg gctccgcacc    360
aactgggtgt accgaggaga ggctgagcgt atcttcattg agctcaagtt tactgtacgt    420
gactgcaaca gcttccctgg tggcgccagc tcctgcaagg agactttcaa cctctactat    480
gccgagtcgg aactggacta cggcaccaac ttccagaagc gcctgttcac caagattgac    540
accattgcgc ccgatgagat caccgtcagc agcgacttcg aggcacgcca cgtgaagctg    600
aacgtggagg agcgctccgt ggggccgctc acccgcaaag gcttctacct ggccttccag    660
gatatcggtg cctgtgtggc gctgctctcc gtccgtgtct actacaagaa gtgccccgag    720
```

```
ctgctgcagg gcctggccca cttccctgag accatcgccg gctctgatgc accttccctg      780
gccactgtgg ccggcacctg tgtggaccat gccgtggtgc accggggggg tgaagagccc      840
cgtatgcact gtgcagtgga tggcgagtgg ctggtgccca ttgggcagtg cctgtgccag      900
gcaggctacg agaaggtgga ggatgcctgc caggcctgct cgcctggatt ttttaagttt      960
gaggcatctg agagccctg cttggagtgc cctgagcaca cgctgccatc ccctgagggt      1020
gccacctcct gcgagtgtga ggaaggcttc ttccgggcac ctcaggaccc agcgtcgatg      1080
ccttgcacac dacccccctc cgccccacac tacctcacag ccgtgggcat gggtgccaag      1140
gtggagctgc gctggacgcc ccctcaggac agcgggggcc gcgaggacat tgtctacagc      1200
gtcacctgcg aacagtgctg gcccgagtct ggggaatgcg gccgtgtgag gccagtgtg      1260 cgctactcgg agcctcctca cggactgacc cgcaccagtg tgacagtgag cgacctggag      1320
ccccacatga actacaccttt caccgtggag gcccgcaatg gcgtctcagg cctggtaacc      1380
agccgcagct tccgtactgc cagtgtcagc atcaaccaga cagagccccc caaggtgagg      1440
ctggagggcc gcagcaccac ctcgcttagc gtctcctgga gcatccccc gccgcagcag      1500 agccgagtgt ggaagtacga ggtcacttac cgcaagaagg gagactccaa cagctacaat      1560
gtgcgccgca ccgagggttt ctccgtgacc ctggacgacc tggccccaga caccacctac      1620
ctggtccagg tgcaggcact gacgcaggag ggccagggg ccggcagcag ggtgcacgaa      1680
ttccagacg                                                              1689

<210> SEQ ID NO 9
<211> LENGTH: 563
<212> TYPE: PRT
<213> ORGANISM: Artificial Sequence
<220> FEATURE:
<223> OTHER INFORMATION: Fusion protein

<400> SEQUENCE: 9

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Leu Glu Gln Gly Lys
    50                  55                  60

Glu Val Val Leu Leu Asp Phe Ala Ala Gly Gly Glu Leu Gly Trp
65                  70                  75                  80

Leu Thr His Pro Tyr Gly Lys Gly Trp Asp Leu Met Gln Asn Ile Met
                85                  90                  95

Asn Asp Met Pro Ile Tyr Met Tyr Ser Val Cys Asn Val Met Ser Gly
            100                 105                 110

Asp Gln Asp Asn Trp Leu Arg Thr Asn Trp Val Tyr Arg Gly Glu Ala
        115                 120                 125

Glu Arg Ile Phe Ile Glu Leu Lys Phe Thr Val Arg Asp Cys Asn Ser
    130                 135                 140

Phe Pro Gly Gly Ala Ser Ser Cys Lys Glu Thr Phe Asn Leu Tyr Tyr
145                 150                 155                 160

Ala Glu Ser Asp Leu Asp Tyr Gly Thr Asn Phe Gln Lys Arg Leu Phe
                165                 170                 175

Thr Lys Ile Asp Thr Ile Ala Pro Asp Glu Ile Thr Val Ser Ser Asp
            180                 185                 190
```

```
Phe Glu Ala Arg His Val Lys Leu Asn Val Glu Glu Arg Ser Val Gly
            195                 200                 205

Pro Leu Thr Arg Lys Gly Phe Tyr Leu Ala Phe Gln Asp Ile Gly Ala
            210                 215                 220

Cys Val Ala Leu Leu Ser Val Arg Val Tyr Tyr Lys Lys Cys Pro Glu
225                 230                 235                 240

Leu Leu Gln Gly Leu Ala His Phe Pro Glu Thr Ile Ala Gly Ser Asp
            245                 250                 255

Ala Pro Ser Leu Ala Thr Val Ala Gly Thr Cys Val Asp His Ala Val
            260                 265                 270

Val Pro Pro Gly Gly Glu Glu Pro Arg Met His Cys Ala Val Asp Gly
            275                 280                 285

Glu Trp Leu Val Pro Ile Gly Gln Cys Leu Cys Gln Ala Gly Tyr Glu
            290                 295                 300

Lys Val Glu Asp Ala Cys Gln Ala Cys Ser Pro Gly Phe Phe Lys Phe
305                 310                 315                 320

Glu Ala Ser Glu Ser Pro Cys Leu Glu Cys Pro Glu His Thr Leu Pro
            325                 330                 335

Ser Pro Glu Gly Ala Thr Ser Cys Glu Cys Glu Glu Gly Phe Phe Arg
            340                 345                 350

Ala Pro Gln Asp Pro Ala Ser Met Pro Cys Thr Arg Pro Pro Ser Ala
            355                 360                 365

Pro His Tyr Leu Thr Ala Val Gly Met Gly Ala Lys Val Glu Leu Arg
            370                 375                 380

Trp Thr Pro Pro Gln Asp Ser Gly Gly Arg Glu Asp Ile Val Tyr Ser
385                 390                 395                 400

Val Thr Cys Glu Gln Cys Trp Pro Glu Ser Gly Glu Cys Gly Pro Cys
            405                 410                 415

Glu Ala Ser Val Arg Tyr Ser Glu Pro Pro His Gly Leu Thr Arg Thr
            420                 425                 430

Ser Val Thr Val Ser Asp Leu Glu Pro His Met Asn Tyr Thr Phe Thr
            435                 440                 445

Val Glu Ala Arg Asn Gly Val Ser Gly Leu Val Thr Ser Arg Ser Phe
            450                 455                 460

Arg Thr Ala Ser Val Ser Ile Asn Gln Thr Glu Pro Pro Lys Val Arg
465                 470                 475                 480

Leu Glu Gly Arg Ser Thr Thr Ser Leu Ser Val Ser Trp Ser Ile Pro
            485                 490                 495

Pro Pro Gln Gln Ser Arg Val Trp Lys Tyr Glu Val Thr Tyr Arg Lys
            500                 505                 510

Lys Gly Asp Ser Asn Ser Tyr Asn Val Arg Arg Thr Glu Gly Phe Ser
            515                 520                 525

Val Thr Leu Asp Asp Leu Ala Pro Asp Thr Thr Tyr Leu Val Gln Val
            530                 535                 540

Gln Ala Leu Thr Gln Glu Gly Gln Gly Ala Gly Ser Arg Val His Glu
545                 550                 555                 560

Phe Gln Thr

<210> SEQ ID NO 10
<211> LENGTH: 1989
<212> TYPE: DNA
<213> ORGANISM: Artificial Sequence
<220> FEATURE:
<223> OTHER INFORMATION: Expression cassette, encodes fusion protein
```

<400> SEQUENCE: 10

```
ggtacctcct ttgattagta tattcctatc ttaaagttac ttttatgtgg aggcattaac      60
atttgttaat gacgtcaaaa ggatagcaag actagaataa agctataaag caagcatata     120
atattgcgtt tcatctttag aagcgaattt cgccaatatt ataattatca aaagagaggg     180
gtggcaaacg gtatttggca ttattaggtt aaaaaatgta aaggagagt gaaacccatg      240
aaaaaaataa tgctagtttt tattacactt atattagtta gtctaccaat tgcgcaacaa     300
actgaagcaa aggatgcatc tgcattcaat aaagaaaatt caatttcatc catggcacca     360
ccagcatctc cgcctgcaag tcctaagacg ccaatcgaaa agaaacacgc ggatggatcc     420
gattataaag atgatgatga taaacaaggt aaagaagttg ttttattaga ttttgcagca     480
gcaggtggtg aattaggttg gttaacacat ccatatggta aaggttggga tttaatgcaa     540
aatattatga atgatatgcc aatttatatg tatagtgttt gtaatgttat gagtggtgat     600
caagataatt ggttacgtac aaattgggtt tatcgtggtg aagcagaacg tatttttatt     660
gaattaaaat ttacagttcg tgattgtaat agttttccag gtggtgcaag tagttgtaaa     720
gaaacattta atttatatta tgcagaaagt gatttagatt atggtacaaa ttttcaaaaa     780
cgtttattta caaaaattga tacaattgca ccagatgaaa ttacagttag tagtgatttt     840
gaagcacgtc atgttaaatt aaatgttgaa gaacgtagtg ttggtccatt aacacgtaaa     900
ggttttatt tagcatttca agatattggt gcatgtgttg cattattaag tgttcgtgtt     960
tattataaaa aatgtccaga attattacaa ggtttagcac attttccaga aacaattgca    1020
ggtagtgatg caccaagttt agcaacagtt gcaggtacat gtgttgatca tgcagttgtt    1080
ccaccaggtg gtgaagaacc acgtatgcat tgtgcagttg atggtgaatg gttagttcca    1140
attggtcaat gtttatgtca agcaggttat gaaaaagttg aagatgcatg tcaagcatgt    1200
agtccaggtt ttttttaaatt tgaagcaagt gaaagtccat gtttagaatg tccagaacat    1260
acattaccaa gtccagaagg tgcaacaagt tgtgaatgtg aagaaggttt ttttcgtgca    1320
ccacaagatc cagcaagtat gccatgtaca cgtccaccaa gtgcaccaca ttatttaaca    1380
gcagttggta tgggtgcaaa agttgaatta cgttggacac caccacaaga tagtggtggt    1440
cgtgaagata ttgtttatag tgttacatgt gaacaatgtt ggccagaaag tggtgaatgt    1500
ggtccatgtg aagcaagtgt tcgttatagt gaaccaccac atggtttaac acgtacaagt    1560
gttacagtta gtgatttaga accacatatg aattatacat ttacagttga agcacgtaat    1620
ggtgttagtg gtttagttac aagtcgtagt tttcgtacag caagtgttag tattaatcaa    1680
acagaaccac caaagttcg tttagaaggt cgtagtacaa caagtttaag tgttagttgg    1740
agtattccac caccacaaca aagtcgtgtt tggaaatatg aagttacata tcgtaaaaaa    1800
ggtgatagta atagttataa tgttcgtcgt acagaaggtt ttagtgttac attagatgat    1860
ttagcaccag atacaacata tttagttcaa gttcaagcat taacacaaga aggtcaaggt    1920
gcaggtagtc gtgttcatga atttcaaaca gaacaaaaat taattagtga agaagattta    1980
tgagagctc                                                            1989
```

<210> SEQ ID NO 11
<211> LENGTH: 581
<212> TYPE: PRT
<213> ORGANISM: Artificial Sequence
<220> FEATURE:
<223> OTHER INFORMATION: Fusion protein

<400> SEQUENCE: 11

```
Met Lys Lys Ile Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Pro Ala Ser Pro Pro Ala Ser
         35                  40                  45

Pro Lys Thr Pro Ile Glu Lys Lys His Ala Asp Gly Ser Asp Tyr Lys
     50                  55                  60

Asp Asp Asp Asp Lys Gln Gly Lys Glu Val Val Leu Leu Asp Phe Ala
65                  70                  75                  80

Ala Ala Gly Gly Glu Leu Gly Trp Leu Thr His Pro Tyr Gly Lys Gly
                 85                  90                  95

Trp Asp Leu Met Gln Asn Ile Met Asn Asp Met Pro Ile Tyr Met Tyr
            100                 105                 110

Ser Val Cys Asn Val Met Ser Gly Asp Gln Asp Asn Trp Leu Arg Thr
        115                 120                 125

Asn Trp Val Tyr Arg Gly Glu Ala Glu Arg Ile Phe Ile Glu Leu Lys
    130                 135                 140

Phe Thr Val Arg Asp Cys Asn Ser Phe Pro Gly Gly Ala Ser Ser Cys
145                 150                 155                 160

Lys Glu Thr Phe Asn Leu Tyr Tyr Ala Glu Ser Asp Leu Asp Tyr Gly
                165                 170                 175

Thr Asn Phe Gln Lys Arg Leu Phe Thr Lys Ile Asp Thr Ile Ala Pro
            180                 185                 190

Asp Glu Ile Thr Val Ser Ser Asp Phe Glu Ala Arg His Val Lys Leu
        195                 200                 205

Asn Val Glu Glu Arg Ser Val Gly Pro Leu Thr Arg Lys Gly Phe Tyr
    210                 215                 220

Leu Ala Phe Gln Asp Ile Gly Ala Cys Val Ala Leu Leu Ser Val Arg
225                 230                 235                 240

Val Tyr Tyr Lys Lys Cys Pro Glu Leu Leu Gln Gly Leu Ala His Phe
                245                 250                 255

Pro Glu Thr Ile Ala Gly Ser Asp Ala Pro Ser Leu Ala Thr Val Ala
            260                 265                 270

Gly Thr Cys Val Asp His Ala Val Val Pro Pro Gly Gly Glu Glu Pro
        275                 280                 285

Arg Met His Cys Ala Val Asp Gly Glu Trp Leu Val Pro Ile Gly Gln
    290                 295                 300

Cys Leu Cys Gln Ala Gly Tyr Glu Lys Val Glu Asp Ala Cys Gln Ala
305                 310                 315                 320

Cys Ser Pro Gly Phe Phe Lys Phe Glu Ala Ser Glu Ser Pro Cys Leu
                325                 330                 335

Glu Cys Pro Glu His Thr Leu Pro Ser Pro Glu Gly Ala Thr Ser Cys
            340                 345                 350

Glu Cys Glu Glu Gly Phe Phe Arg Ala Pro Gln Asp Pro Ala Ser Met
        355                 360                 365

Pro Cys Thr Arg Pro Pro Ser Ala Pro His Tyr Leu Thr Ala Val Gly
    370                 375                 380

Met Gly Ala Lys Val Glu Leu Arg Trp Thr Pro Pro Gln Asp Ser Gly
385                 390                 395                 400

Gly Arg Glu Asp Ile Val Tyr Ser Val Thr Cys Glu Gln Cys Trp Pro
                405                 410                 415
```

```
Glu Ser Gly Glu Cys Gly Pro Cys Glu Ala Ser Val Arg Tyr Ser Glu
            420                 425                 430

Pro Pro His Gly Leu Thr Arg Thr Ser Val Thr Val Ser Asp Leu Glu
            435                 440                 445

Pro His Met Asn Tyr Thr Phe Thr Val Glu Ala Arg Asn Gly Val Ser
            450                 455                 460

Gly Leu Val Thr Ser Arg Ser Phe Arg Thr Ala Ser Val Ser Ile Asn
465                 470                 475                 480

Gln Thr Glu Pro Pro Lys Val Arg Leu Glu Gly Arg Ser Thr Thr Ser
                485                 490                 495

Leu Ser Val Ser Trp Ser Ile Pro Pro Gln Gln Ser Arg Val Trp
            500                 505                 510

Lys Tyr Glu Val Thr Tyr Arg Lys Lys Gly Asp Ser Asn Ser Tyr Asn
            515                 520                 525

Val Arg Arg Thr Glu Gly Phe Ser Val Thr Leu Asp Asp Leu Ala Pro
            530                 535                 540

Asp Thr Thr Tyr Leu Val Gln Val Gln Ala Leu Thr Gln Glu Gly Gln
545                 550                 555                 560

Gly Ala Gly Ser Arg Val His Glu Phe Gln Thr Glu Gln Lys Leu Ile
                565                 570                 575

Ser Glu Glu Asp Leu
            580

<210> SEQ ID NO 12
<211> LENGTH: 1989
<212> TYPE: DNA
<213> ORGANISM: Artificial Sequence
<220> FEATURE:
<223> OTHER INFORMATION: Expression cassette, encodes fusion protein

<400> SEQUENCE: 12
ggtacctcct ttgattagta tattcctatc ttaaagttac ttttatgtgg aggcattaac      60
atttgttaat gacgtcaaaa ggatagcaag actagaataa agctataaag caagcatata     120
atattgcgtt tcatctttag aagcgaattt cgccaatatt ataattatca aaagagaggg     180
gtggcaaacg gtatttggca ttattaggtt aaaaaatgta gaaggagagt gaaacccatg     240
aaaaaaatta tgttagtttt tattacatta atttttagtta gtttaccaat tgcacaacaa     300
acagaagcaa aagatgcaag tgcatttaat aaagaaaata gtattagtag tatggcacca     360
ccagcaagtc caccagcaag tccaaaaaca ccaattgaaa aaaacatgc agatggatcc     420 gattataaag atgatgatga taaacaaggt aaagaagttg ttttattaga ttttgcagca     480
gcaggtggtg aattaggttg gttaacacat ccatatggta aaggttggga tttaatgcaa     540
aatattatga atgatatgcc aatttatatg tatagtgttt gtaatgttat gagtggtgat     600
caagataatt ggttacgtac aaattgggtt tatcgtggtg aagcagaacg tatttttatt     660 gaattaaaaat ttacagttcg tgattgtaat agtttcccag gtggtgcaag tagttgtaaa     720
gaaacattta attatatta tgcagaaagt gatttagatt atggtacaaa ttttcaaaaa     780
cgtttattta caaaaattga tacaattgca ccagatgaaa ttacagttag tagtgatttt     840
gaagcacgtc atgttaaatt aaatgttgaa gaacgtagtc ttggtccatt aacacgtaaa     900 ggttttatt tagcatttca agatattggt gcatgtgttg cattattaag tgttcgtgtt     960
tattataaaa aatgtccaga attattacaa ggtttagcac atttccaga aacaattgca    1020 ggtagtgatg caccaagttt agcaacagtt gcaggtacat gtgttgatca tgcagttgtt    1080
```

-continued

```
ccaccaggtg gtgaagaacc acgtatgcat tgtgcagttg atggtgaatg gttagttcca    1140
attggtcaat gtttatgtca agcaggttat gaaaaagttg aagatgcatg tcaagcatgt    1200
agtccaggtt tttttaaatt tgaagcaagt gaaagtccat gtttagaatg tccagaacat    1260
acattaccaa gtccagaagg tgcaacaagt tgtgaatgtg aagaaggttt ttttcgtgca    1320
ccacaagatc cagcaagtat gccatgtaca cgtccaccaa gtgcaccaca ttatttaaca    1380
gcagttggta tgggtgcaaa agttgaatta cgttggacac caccacaaga tagtggtggt    1440
cgtgaagata ttgtttatag tgttacatgt gaacaatgtt ggccagaaag tggtgaatgt    1500
ggtccatgtg aagcaagtgt tcgttatagt gaaccaccac atggtttaac acgtacaagt    1560
gttacagtta gtgatttaga accacatatg aattatacat ttacagttga agcacgtaat    1620
ggtgttagtg gtttagttac aagtcgtagt tttcgtacag caagtgttag tattaatcaa    1680
acagaaccac caaagttcg tttagaaggt cgtagtacaa caagtttaag tgttagttgg    1740
agtattccac caccacaaca aagtcgtgtt tggaaatatg aagttacata tcgtaaaaaa    1800
ggtgatagta atagttataa tgttcgtcgt acagaaggtt ttagtgttac attagatgat    1860
ttagcaccag atacaacata tttagttcaa gttcaagcat taacacaaga aggtcaaggt    1920
gcaggtagtc gtgttcatga atttcaaaca gaacaaaaat taattagtga agaagattta    1980
tgagagctc                                                              1989
```

<210> SEQ ID NO 13
<211> LENGTH: 581
<212> TYPE: PRT
<213> ORGANISM: Artificial Sequence
<220> FEATURE:
<223> OTHER INFORMATION: Fusion protein

<400> SEQUENCE: 13

```
Met Lys Lys Ile Met Leu Val Phe Ile Thr Leu Ile Leu Val Ser Leu
  1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Pro Ala Ser Pro Ala Ser
         35                  40                  45

Pro Lys Thr Pro Ile Glu Lys Lys His Ala Asp Gly Ser Asp Tyr Lys
     50                  55                  60

Asp Asp Asp Asp Lys Gln Gly Lys Glu Val Val Leu Leu Asp Phe Ala
 65                  70                  75                  80

Ala Ala Gly Gly Glu Leu Gly Trp Leu Thr His Pro Tyr Gly Lys Gly
                 85                  90                  95

Trp Asp Leu Met Gln Asn Ile Met Asn Asp Met Pro Ile Tyr Met Tyr
            100                 105                 110

Ser Val Cys Asn Val Met Ser Gly Asp Gln Asp Asn Trp Leu Arg Thr
        115                 120                 125

Asn Trp Val Tyr Arg Gly Glu Ala Glu Arg Ile Phe Ile Glu Leu Lys
    130                 135                 140

Phe Thr Val Arg Asp Cys Asn Ser Phe Pro Gly Gly Ala Ser Ser Cys
145                 150                 155                 160

Lys Glu Thr Phe Asn Leu Tyr Tyr Ala Glu Ser Asp Leu Asp Tyr Gly
                165                 170                 175

Thr Asn Phe Gln Lys Arg Leu Phe Thr Lys Ile Asp Thr Ile Ala Pro
            180                 185                 190
```

```
Asp Glu Ile Thr Val Ser Ser Asp Phe Glu Ala Arg His Val Lys Leu
        195                 200                 205

Asn Val Glu Glu Arg Ser Val Gly Pro Leu Thr Arg Lys Gly Phe Tyr
    210                 215                 220

Leu Ala Phe Gln Asp Ile Gly Ala Cys Val Ala Leu Leu Ser Val Arg
225                 230                 235                 240

Val Tyr Tyr Lys Lys Cys Pro Glu Leu Leu Gln Gly Leu Ala His Phe
                245                 250                 255

Pro Glu Thr Ile Ala Gly Ser Asp Ala Pro Ser Leu Ala Thr Val Ala
                260                 265                 270

Gly Thr Cys Val Asp His Ala Val Pro Pro Gly Glu Glu Pro
            275                 280                 285

Arg Met His Cys Ala Val Asp Gly Glu Trp Leu Val Pro Ile Gly Gln
        290                 295                 300

Cys Leu Cys Gln Ala Gly Tyr Glu Lys Val Glu Asp Ala Cys Gln Ala
305                 310                 315                 320

Cys Ser Pro Gly Phe Phe Lys Phe Glu Ala Ser Glu Ser Pro Cys Leu
                325                 330                 335

Glu Cys Pro Glu His Thr Leu Pro Ser Pro Gly Ala Thr Ser Cys
                340                 345                 350

Glu Cys Glu Glu Gly Phe Phe Arg Ala Pro Gln Asp Pro Ala Ser Met
            355                 360                 365

Pro Cys Thr Arg Pro Pro Ser Ala Pro His Tyr Leu Thr Ala Val Gly
        370                 375                 380

Met Gly Ala Lys Val Glu Leu Arg Trp Thr Pro Pro Gln Asp Ser Gly
385                 390                 395                 400

Gly Arg Glu Asp Ile Val Tyr Ser Val Thr Cys Glu Gln Cys Trp Pro
                405                 410                 415

Glu Ser Gly Glu Cys Gly Pro Cys Glu Ala Ser Val Arg Tyr Ser Glu
                420                 425                 430

Pro Pro His Gly Leu Thr Arg Thr Ser Val Thr Val Ser Asp Leu Glu
            435                 440                 445

Pro His Met Asn Tyr Thr Phe Thr Val Glu Ala Arg Asn Gly Val Ser
        450                 455                 460

Gly Leu Val Thr Ser Arg Ser Phe Arg Thr Ala Ser Val Ser Ile Asn
465                 470                 475                 480

Gln Thr Glu Pro Pro Lys Val Arg Leu Glu Gly Arg Ser Thr Thr Ser
                485                 490                 495

Leu Ser Val Ser Trp Ser Ile Pro Pro Pro Gln Gln Ser Arg Val Trp
            500                 505                 510

Lys Tyr Glu Val Thr Tyr Arg Lys Lys Gly Asp Ser Asn Ser Tyr Asn
        515                 520                 525

Val Arg Arg Thr Glu Gly Phe Ser Val Thr Leu Asp Asp Leu Ala Pro
    530                 535                 540

Asp Thr Thr Tyr Leu Val Gln Val Gln Ala Leu Thr Gln Glu Gly Gln
545                 550                 555                 560

Gly Ala Gly Ser Arg Val His Glu Phe Gln Thr Glu Gln Lys Leu Ile
                565                 570                 575

Ser Glu Glu Asp Leu
            580

<210> SEQ ID NO 14
<211> LENGTH: 1968
<212> TYPE: DNA
```

<213> ORGANISM: Artificial Sequence
<220> FEATURE:
<223> OTHER INFORMATION: Expression cassette, encodes fusion protein

<400> SEQUENCE: 14

```
ggtacctcct tgattagta tattcctatc ttaaagttac ttttatgtgg aggcattaac      60
atttgttaat gacgtcaaaa ggatagcaag actagaataa agctataaag caagcatata     120
atattgcgtt tcatctttag aagcgaattt cgccaatatt ataattatca aaagagaggg     180
gtggcaaacg tatttggca ttattaggtt aaaaaatgta aaggagagt gaaacccatg       240
gcatacgaca gtcgttttga tgaatgggta cagaaactga agaggaaag ctttcaaaac     300
aatacgtttg accgccgcaa atttattcaa ggagcgggga agattgcagg actttctctt    360
ggattaacga ttgcccagtc ggttggggcc tttggatccg attataaaga tgatgatgat    420
aaacaaggta agaagttgt tttattagat tttgcagcag caggtggtga attaggttgg     480
ttaacacatc catatggtaa aggttgggat ttaatgcaaa atattatgaa tgatatgcca    540
atttatatgt atagtgtttg taatgttatg agtggtgatc aagataattg gttacgtaca    600
aattgggttt atcgtggtga agcagaacgt attttttattg aattaaaatt tacagttcgt  660
gattgtaata gttttccagg tggtgcaagt agttgtaaag aaacatttaa tttatattat    720
gcagaaagtg atttagatta tggtacaaat tttcaaaaac gtttatttac aaaaattgat    780
acaattgcac cagatgaaat tacagttagt agtgattttg aagcacgtca tgttaaatta    840
aatgttgaag aacgtagtgt tggtccatta cacgtaaag gttttttattt agcatttcaa   900
gatattggtg catgtgttgc attattaagt gttcgtgttt attataaaaa atgtccagaa    960
ttattacaag gttagcaca ttttccagaa acaattgcag gtagtgatgc accaagttta    1020
gcaacagttg caggtacatg tgttgatcat gcagttgttc caccaggtgg tgaagaacca   1080
cgtatgcatt gtgcagttga tggtgaatgg ttagttccaa ttggtcaatg tttatgtcaa  1140
gcaggttatg aaaaagttga agatgcatgt caagcatgta gtccaggttt tttaaatttt  1200
gaagcaagtg aaagtccatg tttagaatgt ccagaacata cattaccaag tccagaaggt  1260
gcaacaagtt gtgaatgtga agaaggtttt tttcgtgcac cacaagatcc agcaagtatg  1320
ccatgtacac gtccaccaag tgcaccacat tatttaacag cagttggtat gggtgcaaaa   1380
gttgaattac gttggacacc accacaagat agtggtggtc gtgaagatat tgtttatagt  1440
gttacatgtg aacaatgttg gccagaaagt ggtgaatgtg gtccatgtga agcaagtgtt  1500
cgttatagtg aaccaccaca tggtttaaca cgttacaagtt ttacagttag tgatttagaa  1560
ccacatatga attatacatt tcacagttgaa gcacgtaatg gtttagtgg tttagttaca  1620
agtcgtagtt tcgtacagc aagtgttagt attaatcaaa cagaaccacc aaaagttcgt  1680
ttagaaggtc gtagtacaac aagtttaagt gttagttgga gtattccacc accacaacaa  1740
agtcgtgttt ggaaatatga agttacatat cgtaaaaaag gtgatagtaa tagttatatt  1800
gttcgtcgta cagaaggttt tagtgttaca ttagatgatt tagcaccaga tacaacatat  1860
ttagttcaag ttcaagcatt aacacaagaa ggtcaaggtg caggtagtcg tgttcatgaa  1920
tttcaaacag aacaaaaatt aattagtgaa gaagatttat gagagctc                 1968
```

<210> SEQ ID NO 15
<211> LENGTH: 574
<212> TYPE: PRT
<213> ORGANISM: Artificial Sequence
<220> FEATURE:
<223> OTHER INFORMATION: Fusion protein

<400> SEQUENCE: 15

```
Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
            20                  25                  30

Ala Gly Lys Ile Ala Gly Leu Ser Leu Gly Leu Thr Ile Ala Gln Ser
        35                  40                  45

Val Gly Ala Phe Gly Ser Asp Tyr Lys Asp Asp Asp Lys Gln Gly
    50                  55                  60

Lys Glu Val Val Leu Leu Asp Phe Ala Ala Gly Gly Glu Leu Gly
65                  70                  75                  80

Trp Leu Thr His Pro Tyr Gly Lys Gly Trp Asp Leu Met Gln Asn Ile
                85                  90                  95

Met Asn Asp Met Pro Ile Tyr Met Tyr Ser Val Cys Asn Val Met Ser
            100                 105                 110

Gly Asp Gln Asp Asn Trp Leu Arg Thr Asn Trp Val Tyr Arg Gly Glu
            115                 120                 125

Ala Glu Arg Ile Phe Ile Glu Leu Lys Phe Thr Val Arg Asp Cys Asn
        130                 135                 140

Ser Phe Pro Gly Gly Ala Ser Ser Cys Lys Glu Thr Phe Asn Leu Tyr
145                 150                 155                 160

Tyr Ala Glu Ser Asp Leu Asp Tyr Gly Thr Asn Phe Gln Lys Arg Leu
                165                 170                 175

Phe Thr Lys Ile Asp Thr Ile Ala Pro Asp Glu Ile Thr Val Ser Ser
            180                 185                 190

Asp Phe Glu Ala Arg His Val Lys Leu Asn Val Glu Glu Arg Ser Val
        195                 200                 205

Gly Pro Leu Thr Arg Lys Gly Phe Tyr Leu Ala Phe Gln Asp Ile Gly
    210                 215                 220

Ala Cys Val Ala Leu Leu Ser Val Arg Val Tyr Tyr Lys Lys Cys Pro
225                 230                 235                 240

Glu Leu Leu Gln Gly Leu Ala His Phe Pro Glu Thr Ile Ala Gly Ser
                245                 250                 255

Asp Ala Pro Ser Leu Ala Thr Val Ala Gly Thr Cys Val Asp His Ala
            260                 265                 270

Val Val Pro Pro Gly Gly Glu Glu Pro Arg Met His Cys Ala Val Asp
        275                 280                 285

Gly Glu Trp Leu Val Pro Ile Gly Gln Cys Leu Cys Gln Ala Gly Tyr
    290                 295                 300

Glu Lys Val Glu Asp Ala Cys Gln Ala Cys Ser Pro Gly Phe Lys
305                 310                 315                 320

Phe Glu Ala Ser Glu Ser Pro Cys Leu Glu Cys Pro Glu His Thr Leu
                325                 330                 335

Pro Ser Pro Glu Gly Ala Thr Ser Cys Glu Cys Glu Glu Gly Phe Phe
            340                 345                 350

Arg Ala Pro Gln Asp Pro Ala Ser Met Pro Cys Thr Arg Pro Pro Ser
        355                 360                 365

Ala Pro His Tyr Leu Thr Ala Val Gly Met Gly Ala Lys Val Glu Leu
    370                 375                 380

Arg Trp Thr Pro Pro Gln Asp Ser Gly Gly Arg Glu Asp Ile Val Tyr
385                 390                 395                 400

Ser Val Thr Cys Glu Gln Cys Trp Pro Glu Ser Gly Glu Cys Gly Pro
```

```
                405                 410                 415
Cys Glu Ala Ser Val Arg Tyr Ser Glu Pro Pro His Gly Leu Thr Arg
            420                 425                 430

Thr Ser Val Thr Val Ser Asp Leu Glu Pro His Met Asn Tyr Thr Phe
        435                 440                 445

Thr Val Glu Ala Arg Asn Gly Val Ser Gly Leu Val Thr Ser Arg Ser
    450                 455                 460

Phe Arg Thr Ala Ser Val Ser Ile Asn Gln Thr Glu Pro Pro Lys Val
465                 470                 475                 480

Arg Leu Glu Gly Arg Ser Thr Thr Ser Leu Ser Val Ser Trp Ser Ile
                485                 490                 495

Pro Pro Pro Gln Gln Ser Arg Val Trp Lys Tyr Glu Val Thr Tyr Arg
            500                 505                 510

Lys Lys Gly Asp Ser Asn Ser Tyr Asn Val Arg Arg Thr Glu Gly Phe
        515                 520                 525

Ser Val Thr Leu Asp Asp Leu Ala Pro Asp Thr Thr Tyr Leu Val Gln
    530                 535                 540

Val Gln Ala Leu Thr Gln Glu Gly Gln Gly Ala Gly Ser Arg Val His
545                 550                 555                 560

Glu Phe Gln Thr Glu Gln Lys Leu Ile Ser Glu Glu Asp Leu
                565                 570

<210> SEQ ID NO 16
<211> LENGTH: 1254
<212> TYPE: DNA
<213> ORGANISM: Homo sapiens
<400> SEQUENCE: 16
caccgcagga ggaagaacca gcgtgcccgc cagtccccgg aggacgttta cttctccaag    60
tcagaacaac tgaagcccct gaagacatac gtggaccccc acacatatga ggaccccaac   120
caggctgtgt tgaagttcac taccgagatc catccatcct gtgtcactcg gcagaaggtg   180
atcggagcag agagtttggg gaggtgtac aagggcatgc tgaagacatc ctcggggaag   240
aaggaggtgc cggtggccat caagacgctg aaagccggct acacagagaa gcagcgagtg   300
gacttcctcg gcgaggccgg catcatgggc cagttcagcc accacaacat catccgccta   360
gagggcgtca tctccaaata caagcccatg atgatcatca ctgagtacat ggagaatggg   420
gccctggaca gttccttcg ggagaaggat ggcgagttca gcgtgctgca gctggtgggc   480
atgctgcggg gcatcgcagc tggcatgaag tacctggcca acatgaacta tgtgcaccgt   540
gacctggctg cccgcaacat cctcgtcaac agcaacctgg tctgcaaggt gtctgacttt   600
ggcctgtccc gcgtgctgga ggacgacccc gaggccacct acaccaccag tggcggcaag   660
atccccatcc gctggaccgc cccggaggcc atttcctacc ggaagttcac ctctgccagc   720
gacgtgtgga gctttggcat tgtcatgtgg gaggtgatga cctatggcga gcggccctac   780
tgggagttgt ccaaccacga ggtgatgaaa gccatcaatg atggcttccg gctccccaca   840
cccatggact gccctccgc catctaccag ctcatgatgc agtgctggca gcaggagcgt   900
gcccgccgcc caagttcgc tgacatcgtc agcatcctgg acaagctcat tcgtgcccct   960
gactccctca gaccctggc tgactttgac cccgcgtgt ctatccggct ccccagcacg  1020
agcggctcgg agggggtgcc cttccgcacg gtgtccgagt ggctggagtc catcaagatg  1080
cagcagtata cggagcactt catggcggcc ggctacactg ccatcgagaa ggtggtgcag  1140
atgaccaacg acgacatcaa gaggattggg gtgcggctgc ccggccacca gaagcgcatc  1200
```

-continued gcctacagcc tgctgggact caaggaccag gtgaacactg tggggatccc catc    1254

<210> SEQ ID NO 17
<211> LENGTH: 1254
<212> TYPE: DNA
<213> ORGANISM: Artificial Sequence
<220> FEATURE:
<223> OTHER INFORMATION: Codon-optimized sequence

<400> SEQUENCE: 17
cacagacgta gaaaaaatca acgtgctcga caatccccag aagatgtgta tttttcgaaa      60
agtgaacaat taaaaccatt aaaaacttat gttgatccgc atacgtacga agacccaaat     120
caagcagtat taaaatttac aacagaaata cacccaagtt gtgttacaag acaaaaagtt     180
attggagcag gtgaattcgg agaggtatat aaaggtatgt taaaaacatc atcaggtaaa     240
aaagaagttc cggttgcaat taaaaccttc aaggcaggat atacagaaaa acagcgagtt     300 gatttttttag gtgaagcagg aattatgggt caatttagcc atcataatat tattcgtttg     360
gaaggagtaa taagtaaata taaaccaatg atgattatta cagaatacat ggaaaacggt     420
gctttagata aattttttacg tgaaaaggat ggtgaattta gtgtttttaca attggttggt     480 atgttaagag gaattgctgc aggtatgaaa tatttagcta atatgaatta tgttcaccgt     540
gatttggcag caagaaatat cctagtcaat tccaatttag tatgtaaagt tagtgatttt     600
ggtttaagca gagtattaga agacgatcca gaggcaacct atacaacatc gggaggtaaa     660
attcctattc gttggacagc accagaagct atcagttacc gtaaatttac aagtgcatca     720
gacgtgtgga gttttgggat tgtaatgtgg gaagttatga catatggaga aagaccatat     780
tgggaattaa gtaatcatga agttatgaaa gcaattaacg atggatttag attaccaact     840
ccgatggatt gtccatctgc catttatcaa ctaatgatgc aatgttggca acaagaaaga     900
gcacgacgtc caaaatttgc agatattgtt agtatttttag acaaattaat tcgtgcacca     960 gatagttttaa aaactttagc agactttgat cctcgtgtta gtattcgatt accaagtacg    1020
tcaggttccg aaggagttcc atttcgcaca gtctccgaat ggttggaatc aattaaaatg    1080
caacaataca ccgaacactt tatggcagca ggttacacag caatcgaaaa agttgttcaa    1140
atgacaaatg atgatattaa acgtattgga gttagattac caggccacca gaaacgtatt    1200
gcatattctt tattaggttt aaaagatcaa gttaataccg tgggaattcc aatt          1254

<210> SEQ ID NO 18
<211> LENGTH: 456
<212> TYPE: PRT
<213> ORGANISM: Homo sapiens

<400> SEQUENCE: 18

Val His Glu Phe Gln Thr Leu Ser Pro Glu Gly Ser Gly Asn Leu Ala
  1               5                  10                  15

Val Ile Gly Gly Val Ala Val Gly Val Val Leu Leu Val Leu Ala
                 20                  25                  30

Gly Val Gly Phe Phe Ile His Arg Arg Arg Lys Asn Gln Arg Ala Arg
             35                  40                  45

Gln Ser Pro Glu Asp Val Tyr Phe Ser Lys Ser Glu Gln Leu Lys Pro
         50                  55                  60

Leu Lys Thr Tyr Val Asp Pro His Thr Tyr Glu Asp Pro Asn Gln Ala
 65                  70                  75                  80

Val Leu Lys Phe Thr Thr Glu Ile His Pro Ser Cys Val Thr Arg Gln

```
                85                  90                  95
Lys Val Ile Gly Ala Gly Glu Phe Gly Val Tyr Lys Gly Met Leu
            100                 105                 110
Lys Thr Ser Ser Gly Lys Lys Glu Val Pro Val Ala Ile Lys Thr Leu
            115                 120                 125
Lys Ala Gly Tyr Thr Glu Lys Gln Arg Val Asp Phe Leu Gly Glu Ala
130                 135                 140
Gly Ile Met Gly Gln Phe Ser His His Asn Ile Ile Arg Leu Glu Gly
145                 150                 155                 160
Val Ile Ser Lys Tyr Lys Pro Met Met Ile Ile Thr Glu Tyr Met Glu
                165                 170                 175
Asn Gly Ala Leu Asp Lys Phe Leu Arg Glu Lys Asp Gly Glu Phe Ser
            180                 185                 190
Val Leu Gln Leu Val Gly Met Leu Arg Gly Ile Ala Ala Gly Met Lys
            195                 200                 205
Tyr Leu Ala Asn Met Asn Tyr Val His Arg Asp Leu Ala Ala Arg Asn
            210                 215                 220
Ile Leu Val Asn Ser Asn Leu Val Cys Lys Val Ser Asp Phe Gly Leu
225                 230                 235                 240
Ser Arg Val Leu Glu Asp Asp Pro Glu Ala Thr Tyr Thr Thr Ser Gly
                245                 250                 255
Gly Lys Ile Pro Ile Arg Trp Thr Ala Pro Glu Ala Ile Ser Tyr Arg
            260                 265                 270
Lys Phe Thr Ser Ala Ser Asp Val Trp Ser Phe Gly Ile Val Met Trp
            275                 280                 285
Glu Val Met Thr Tyr Gly Glu Arg Pro Tyr Trp Glu Leu Ser Asn His
            290                 295                 300
Glu Val Met Lys Ala Ile Asn Asp Gly Phe Arg Leu Pro Thr Pro Met
305                 310                 315                 320
Asp Cys Pro Ser Ala Ile Tyr Gln Leu Met Met Gln Cys Trp Gln Gln
                325                 330                 335
Glu Arg Ala Arg Arg Pro Lys Phe Ala Asp Ile Val Ser Ile Leu Asp
            340                 345                 350
Lys Leu Ile Arg Ala Pro Asp Ser Leu Lys Thr Leu Ala Asp Phe Asp
            355                 360                 365
Pro Arg Val Ser Ile Arg Leu Pro Ser Thr Ser Gly Ser Glu Gly Val
            370                 375                 380
Pro Phe Arg Thr Val Ser Glu Trp Leu Glu Ser Ile Lys Met Gln Gln
385                 390                 395                 400
Tyr Thr Glu His Phe Met Ala Ala Gly Tyr Thr Ala Ile Glu Lys Val
                405                 410                 415
Val Gln Met Thr Asn Asp Asp Ile Lys Arg Ile Gly Val Arg Leu Pro
            420                 425                 430
Gly His Gln Lys Arg Ile Ala Tyr Ser Leu Leu Gly Leu Lys Asp Gln
            435                 440                 445
Val Asn Thr Val Gly Ile Pro Ile
            450                 455

<210> SEQ ID NO 19
<211> LENGTH: 1437
<212> TYPE: DNA
<213> ORGANISM: Artificial Sequence
<220> FEATURE:
<223> OTHER INFORMATION: Fusion protein coding sequence
```

```
<400> SEQUENCE: 19
atgaaaaaaa taatgctagt ttttattaca cttatattag ttagtctacc aattgcgcaa      60
caaactgaag caaaggatgc atctgcattc aataaagaaa attcaatttc atccatggca     120
ccaccagcat ctccgcctgc aagtcctaag acgccaatcg aaaagaaaca cgcggatctc     180
gagcaccgca ggaggaagaa ccagcgtgcc cgccagtccc cggaggacgt ttacttctcc     240
aagtcagaac aactgaagcc cctgaagaca tacgtggacc cccacacata tgaggacccc     300
aaccaggctg tgttgaagtt cactaccgag atccatccat cctgtgtcac tcggcagaag     360
gtgatcggag caggagagtt tggggaggtg tacaagggca tgctgaagac atcctcgggg     420
aagaaggagg tgccggtggc catcaagacg ctgaaagccg gctacacaga aagcagcga      480 gtggacttcc tcggcgaggc cggcatcatg gccagttca gccaccacaa catcatccgc      540
ctagagggcg tcatctccaa atacaagccc atgatgatca tcactgagta catggagaat    600
ggggccctgg acaagttcct tcgggagaag gatggcgagt tcagcgtgct gcagctggtg    660
ggcatgctgc ggggcatcgc agctggcatg aagtacctgg ccaacatgaa ctatgtgcac   720
cgtgacctgc tgcccgcaa catcctcgtc aacagcaacc tggtctgcaa ggtgtctgac     780
tttggcctgt cccgcgtgct ggaggacgac cccgaggcca cctacaccac cagtggcggc    840
aagatcccca tccgctggac cgccccggag gccatttcct accggaagtt cacctctgcc    900
agcgacgtgt ggagctttgg cattgtcatg tgggaggtga tgacctatgg cgagcggccc   960
tactgggagt tgtccaacca cgaggtgatg aaagccatca tgatggcttc ccggctcccc  1020
acacccatgg actgcccctc cgccatctac cagctcatga tgcagtgctg gcagcaggag  1080
cgtgcccgcc gccccaagtt cgctgacatc gtcagcatcc tggacaagct cattcgtgcc  1140
cctgactccc tcaagaccct ggctgacttt gaccccgcg tgtctatccg gctccccagc    1200
acgagcggct cggaggggt gcccttccgc acggtgtccg agtggctgga gtccatcaag   1260
atgcagcagt atacggagca cttcatggcg gccggctaca ctgccatcga aaggtggtg    1320 cagatgacca cgacgacat caagaggatt ggggtgcggc tgcccggcca ccagaagcgc  1380
atcgcctaca gcctgctggg actcaaggac caggtgaaca ctgtggggat ccccatc       1437

<210> SEQ ID NO 20
<211> LENGTH: 479
<212> TYPE: PRT
<213> ORGANISM: Artificial Sequence
<220> FEATURE:
<223> OTHER INFORMATION: Fusion protein

<400> SEQUENCE: 20

Met Lys Lys Ile Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Lys
                20                  25                  30

Glu Asn Ser Ile Ser Ser Met Ala Pro Pro Ala Ser Pro Pro Ala Ser
            35                  40                  45

Pro Lys Thr Pro Ile Glu Lys Lys His Ala Asp Leu Glu His Arg Arg
        50                  55                  60

Arg Lys Asn Gln Arg Ala Arg Gln Ser Pro Glu Asp Val Tyr Phe Ser
 65                  70                  75                  80

Lys Ser Glu Gln Leu Lys Pro Leu Lys Thr Tyr Val Asp Pro His Thr
                85                  90                  95

Tyr Glu Asp Pro Asn Gln Ala Val Leu Lys Phe Thr Thr Glu Ile His
```

```
                100                 105                 110
Pro Ser Cys Val Thr Arg Gln Lys Val Ile Gly Ala Gly Glu Phe Gly
            115                 120                 125

Glu Val Tyr Lys Gly Met Leu Lys Thr Ser Ser Gly Lys Lys Glu Val
        130                 135                 140

Pro Val Ala Ile Lys Thr Leu Lys Ala Gly Tyr Thr Glu Lys Gln Arg
145                 150                 155                 160

Val Asp Phe Leu Gly Glu Ala Gly Ile Met Gly Gln Phe Ser His His
                    165                 170                 175

Asn Ile Ile Arg Leu Glu Gly Val Ile Ser Lys Tyr Lys Pro Met Met
                180                 185                 190

Ile Ile Thr Glu Tyr Met Glu Asn Gly Ala Leu Asp Lys Phe Leu Arg
            195                 200                 205

Glu Lys Asp Gly Glu Phe Ser Val Leu Gln Leu Val Gly Met Leu Arg
        210                 215                 220

Gly Ile Ala Ala Gly Met Lys Tyr Leu Ala Asn Met Asn Tyr Val His
225                 230                 235                 240

Arg Asp Leu Ala Ala Arg Asn Ile Leu Val Asn Ser Asn Leu Val Cys
                    245                 250                 255

Lys Val Ser Asp Phe Gly Leu Ser Arg Val Leu Glu Asp Asp Pro Glu
                260                 265                 270

Ala Thr Tyr Thr Thr Ser Gly Gly Lys Ile Pro Ile Arg Trp Thr Ala
            275                 280                 285

Pro Glu Ala Ile Ser Tyr Arg Lys Phe Thr Ser Ala Ser Asp Val Trp
        290                 295                 300

Ser Phe Gly Ile Val Met Trp Glu Val Met Thr Tyr Gly Glu Arg Pro
305                 310                 315                 320

Tyr Trp Glu Leu Ser Asn His Glu Val Met Lys Ala Ile Asn Asp Gly
                    325                 330                 335

Phe Arg Leu Pro Thr Pro Met Asp Cys Pro Ser Ala Ile Tyr Gln Leu
                340                 345                 350

Met Met Gln Cys Trp Gln Gln Glu Arg Ala Arg Arg Pro Lys Phe Ala
            355                 360                 365

Asp Ile Val Ser Ile Leu Asp Lys Leu Ile Arg Ala Pro Asp Ser Leu
        370                 375                 380

Lys Thr Leu Ala Asp Phe Asp Pro Arg Val Ser Ile Arg Leu Pro Ser
385                 390                 395                 400

Thr Ser Gly Ser Glu Gly Val Pro Phe Arg Thr Val Ser Glu Trp Leu
                    405                 410                 415

Glu Ser Ile Lys Met Gln Gln Tyr Thr Glu His Phe Met Ala Ala Gly
                420                 425                 430

Tyr Thr Ala Ile Glu Lys Val Val Gln Met Thr Asn Asp Asp Ile Lys
            435                 440                 445

Arg Ile Gly Val Arg Leu Pro Gly His Gln Lys Arg Ile Ala Tyr Ser
        450                 455                 460

Leu Leu Gly Leu Lys Asp Gln Val Asn Thr Val Gly Ile Pro Ile
465                 470                 475

<210> SEQ ID NO 21
<211> LENGTH: 1737
<212> TYPE: DNA
<213> ORGANISM: Artificial Sequence
<220> FEATURE:
<223> OTHER INFORMATION: Expression cassette, encodes fusion protein
```

<400> SEQUENCE: 21

```
ggtacctcct tgattagta tattcctatc ttaaagttac ttttatgtgg aggcattaac        60
atttgttaat gacgtcaaaa ggatagcaag actagaataa agctataaag caagcatata       120
atattgcgtt tcatctttag aagcgaattt cgccaatatt ataattatca aaagagaggg       180
gtggcaaacg gtatttggca ttattaggtt aaaaaatgta aaggagagt gaaacccatg        240
aaaaaaataa tgctagtttt tattacactt atattagtta gtctaccaat tgcgcaacaa       300
actgaagcaa aggatgcatc tgcattcaat aaagaaaatt caatttcatc catggcacca      360
ccagcatctc cgcctgcaag tcctaagacg ccaatcgaaa gaaacacgc ggatggatcc       420
gattataaag atgatgatga taaacacaga cgtagaaaaa atcaacgtgc tcgacaatcc      480
ccagaagatg tgtattttc gaaaagtgaa caattaaaac cattaaaaac ttatgttgat      540
ccgcatacgt acgaagaccc aaatcaagca gtattaaaat ttacaacaga aatacaccca      600
agttgtgtta caagacaaaa agttattgga gcaggtgaat tcggagaggt atataaaggt     660
atgttaaaaa catcatcagg taaaaagaa gttccggttg caattaaaac cttaaaggca      720
ggatatacag aaaaacagcg agttgattt ttaggtgaag caggaattat gggtcaattt      780
agccatcata atattattcg tttggaagga gtaataagta aatataaacc aatgatgatt      840
attacagaat acatggaaaa cggtgcttta gataaatttt tacgtgaaaa ggatggtgaa      900
tttagtgttt tacaattggt tggtatgtta agaggaattg ctgcaggtat gaaatattta      960
gctaatatga attatgttca ccgtgatttg gcagcaagaa atatcctagt caattccaat    1020
ttagtatgta aagttagtga ttttggttta agcagagtat tagaagacga tccagaggca    1080
acctatacaa catcgggagg taaaattcct attcgttgga cagcaccaga agctatcagt    1140
taccgtaaat ttacaagtgc atcagacgtg tggagttttg ggattgtaat gtgggaagtt    1200
atgacatatg gagaaagacc atattgggaa ttaagtaatc atgaagttat gaaagcaatt    1260
aacgatggat ttagattacc aactccgatg gattgtccat ctgccattta tcaactaatg    1320
atgcaatgtt ggcaacaaga aagagcacga cgtccaaaat ttgcagatat tgttagtatt    1380
ttagacaaat taattcgtgc accagatagt ttaaaaactt tagcagactt tgatcctcgt    1440
gttagtattc gattaccaag tacgtcaggt tccgaaggag ttccatttcg cacagtctcc    1500
gaatggttgg aatcaattaa aatgcaacaa tacaccgaac actttatggc agcaggttac    1560
acagcaatcg aaaagttgt tcaaatgaca aatgatgata ttaaacgtat tggagttaga    1620
ttaccaggcc accagaaacg tattgcatat tctttattag gtttaaaaga tcaagttaat    1680
accgtgggaa ttccaattga acaaaaatta atttccgaag aagacttata agagctc       1737
```

<210> SEQ ID NO 22
<211> LENGTH: 497
<212> TYPE: PRT
<213> ORGANISM: Artificial Sequence
<220> FEATURE:
<223> OTHER INFORMATION: Fusion protein

<400> SEQUENCE: 22

```
Met Lys Lys Ile Met Leu Val Phe Ile Thr Leu Ile Leu Val Ser Leu
  1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Pro Ala Ser Pro Pro Ala Ser
         35                  40                  45
```

-continued

```
Pro Lys Thr Pro Ile Glu Lys Lys His Ala Asp Gly Ser Asp Tyr Lys
     50                  55                  60

Asp Asp Asp Asp Lys His Arg Arg Arg Lys Asn Gln Arg Ala Arg Gln
 65                  70                  75                  80

Ser Pro Glu Asp Val Tyr Phe Ser Lys Ser Glu Gln Leu Lys Pro Leu
                 85                  90                  95

Lys Thr Tyr Val Asp Pro His Thr Tyr Glu Asp Pro Asn Gln Ala Val
            100                 105                 110

Leu Lys Phe Thr Thr Glu Ile His Pro Ser Cys Val Thr Arg Gln Lys
        115                 120                 125

Val Ile Gly Ala Gly Glu Phe Gly Glu Val Tyr Lys Gly Met Leu Lys
    130                 135                 140

Thr Ser Ser Gly Lys Lys Glu Val Pro Val Ala Ile Lys Thr Leu Lys
145                 150                 155                 160

Ala Gly Tyr Thr Glu Lys Gln Arg Val Asp Phe Leu Gly Glu Ala Gly
                165                 170                 175

Ile Met Gly Gln Phe Ser His His Asn Ile Ile Arg Leu Glu Gly Val
            180                 185                 190

Ile Ser Lys Tyr Lys Pro Met Met Ile Ile Thr Glu Tyr Met Glu Asn
        195                 200                 205

Gly Ala Leu Asp Lys Phe Leu Arg Glu Lys Asp Gly Glu Phe Ser Val
    210                 215                 220

Leu Gln Leu Val Gly Met Leu Arg Gly Ile Ala Ala Gly Met Lys Tyr
225                 230                 235                 240

Leu Ala Asn Met Asn Tyr Val His Arg Asp Leu Ala Ala Arg Asn Ile
                245                 250                 255

Leu Val Asn Ser Asn Leu Val Cys Lys Val Ser Asp Phe Gly Leu Ser
            260                 265                 270

Arg Val Leu Glu Asp Asp Pro Glu Ala Thr Tyr Thr Thr Ser Gly Gly
        275                 280                 285

Lys Ile Pro Ile Arg Trp Thr Ala Pro Glu Ala Ile Ser Tyr Arg Lys
    290                 295                 300

Phe Thr Ser Ala Ser Asp Val Trp Ser Phe Gly Ile Val Met Trp Glu
305                 310                 315                 320

Val Met Thr Tyr Gly Glu Arg Pro Tyr Trp Glu Leu Ser Asn His Glu
                325                 330                 335

Val Met Lys Ala Ile Asn Asp Gly Phe Arg Leu Pro Thr Pro Met Asp
            340                 345                 350

Cys Pro Ser Ala Ile Tyr Gln Leu Met Met Gln Cys Trp Gln Gln Glu
        355                 360                 365

Arg Ala Arg Arg Pro Lys Phe Ala Asp Ile Val Ser Ile Leu Asp Lys
    370                 375                 380

Leu Ile Arg Ala Pro Asp Ser Leu Lys Thr Leu Ala Asp Phe Asp Pro
385                 390                 395                 400

Arg Val Ser Ile Arg Leu Pro Ser Thr Ser Gly Ser Glu Gly Val Pro
                405                 410                 415

Phe Arg Thr Val Ser Glu Trp Leu Glu Ser Ile Lys Met Gln Gln Tyr
            420                 425                 430

Thr Glu His Phe Met Ala Ala Gly Tyr Thr Ala Ile Glu Lys Val Val
        435                 440                 445

Gln Met Thr Asn Asp Asp Ile Lys Arg Ile Gly Val Arg Leu Pro Gly
    450                 455                 460

His Gln Lys Arg Ile Ala Tyr Ser Leu Leu Gly Leu Lys Asp Gln Val
```

465                 470                 475                 480
Asn Thr Val Gly Ile Pro Ile Glu Gln Lys Leu Ile Ser Glu Glu Asp
            485                 490                 495
Leu

<210> SEQ ID NO 23
<211> LENGTH: 1737
<212> TYPE: DNA
<213> ORGANISM: Artificial Sequence
<220> FEATURE:
<223> OTHER INFORMATION: Expression cassette, encodes fusion protein

<400> SEQUENCE: 23

```
ggtacctcct tgattagta tattcctatc ttaaagttac ttttatgtgg aggcattaac      60
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta aaggagagt gaaacccatg     240
aaaaaaatta tgttagtttt tattacatta attttagtta gtttaccaat tgcacaacaa    300
acagaagcaa aagatgcaag tgcatttaat aaagaaaata gtattagtag tatggcacca    360
ccagcaagtc caccagcaag tccaaaaaca ccaattgaaa aaaaacatgc agatggatcc    420
gattataaag acgatgatga taaacacaga cgtagaaaaa atcaacgtgc tcgacaatcc    480
ccagaagatg tgtattttc gaaaagtgaa caattaaaac cattaaaaac ttatgttgat    540
ccgcatacgt acgaagaccc aaatcaagca gtattaaat ttacaacaga aatacaccca     600
agttgtgtta caagacaaaa agttattgga gcaggtgaat tcggagaggt atataaaggt    660
atgttaaaaa catcatcagg taaaaaagaa gttccggttg caattaaaac cttaaaggca    720
ggatatacag aaaaacagcg agttgatttt ttaggtgaag caggaattat gggtcaattt    780
agccatcata atattattcg tttggaagga gtaataagta aatataaacc aatgatgatt    840
attacagaat acatggaaaa cggtgcttta gataaatttt acgtgaaaaa ggatggtgaa    900
tttagtgttt tacaattggt tggtatgtta agagaattg ctgcaggtat gaaatattta     960
gctaatatga attatgttca ccgtgatttg gcagcaagaa atatcctagt caattccaat   1020
ttagtatgta agttagtga ttttggttta agcagagtat tagaagacga tccagaggca    1080
acctatacaa catcgggagg taaaattcct attcgttgga cagcaccaga agctatcagt   1140
taccgtaaat ttacaagtgc atcagacgtg tggagttttg ggattgtaat gtgggaagtt   1200
atgacatatg gagaaagacc atattgggaa ttaagtaatc atgaagttat gaaagcaatt   1260
aacgatggat ttagattacc aactccgatg gattgtccat ctgccatta tcaactaatg   1320
atgcaatgtt ggcaacaaga aagagcacga cgtccaaaat ttgcagatat tgttagtatt   1380
ttagacaaat taattcgtgc accagatagt ttaaaaactt agcagactt tgatcctcgt    1440
gttagtattc gattaccaag tacgtcaggt tccgaaggag ttccatttcg cacagtctcc   1500
gaatggttgg aatcaattaa aatgcaacaa tacaccgaac actttatggc agcaggttac   1560
acagcaatcg aaaaagttgt tcaaatgaca aatgatgata ttaaacgtat tggagttaga   1620
ttaccaggcc accagaaacg tattgcatat tctttattag gttaaaagaa tcaagttaat   1680
accgtgggaa ttccaattga acaaaaatta atttccgaag aagacttata agagctc     1737
```

<210> SEQ ID NO 24
<211> LENGTH: 497
<212> TYPE: PRT

<213> ORGANISM: Artificial Sequence
<220> FEATURE:
<223> OTHER INFORMATION: Fusion protein

<400> SEQUENCE: 24

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Gly Ser Asp Tyr Lys
    50                  55                  60

Asp Asp Asp Asp Lys His Arg Arg Arg Lys Asn Gln Arg Ala Arg Gln
65                  70                  75                  80

Ser Pro Glu Asp Val Tyr Phe Ser Lys Ser Glu Gln Leu Lys Pro Leu
                85                  90                  95

Lys Thr Tyr Val Asp Pro His Thr Tyr Glu Asp Pro Asn Gln Ala Val
            100                 105                 110

Leu Lys Phe Thr Thr Glu Ile His Pro Ser Cys Val Thr Arg Gln Lys
        115                 120                 125

Val Ile Gly Ala Gly Glu Phe Gly Glu Val Tyr Lys Gly Met Leu Lys
    130                 135                 140

Thr Ser Ser Gly Lys Lys Glu Val Pro Val Ala Ile Lys Thr Leu Lys
145                 150                 155                 160

Ala Gly Tyr Thr Glu Lys Gln Arg Val Asp Phe Leu Gly Glu Ala Gly
                165                 170                 175

Ile Met Gly Gln Phe Ser His His Asn Ile Ile Arg Leu Glu Gly Val
            180                 185                 190

Ile Ser Lys Tyr Lys Pro Met Met Ile Ile Thr Glu Tyr Met Glu Asn
        195                 200                 205

Gly Ala Leu Asp Lys Phe Leu Arg Glu Lys Asp Gly Glu Phe Ser Val
    210                 215                 220

Leu Gln Leu Val Gly Met Leu Arg Gly Ile Ala Ala Gly Met Lys Tyr
225                 230                 235                 240

Leu Ala Asn Met Asn Tyr Val His Arg Asp Leu Ala Ala Arg Asn Ile
                245                 250                 255

Leu Val Asn Ser Asn Leu Val Cys Lys Val Ser Asp Phe Gly Leu Ser
            260                 265                 270

Arg Val Leu Glu Asp Asp Pro Glu Ala Thr Tyr Thr Thr Ser Gly Gly
        275                 280                 285

Lys Ile Pro Ile Arg Trp Thr Ala Pro Glu Ala Ile Ser Tyr Arg Lys
    290                 295                 300

Phe Thr Ser Ala Ser Asp Val Trp Ser Phe Gly Ile Val Met Trp Glu
305                 310                 315                 320

Val Met Thr Tyr Gly Glu Arg Pro Tyr Trp Glu Leu Ser Asn His Glu
                325                 330                 335

Val Met Lys Ala Ile Asn Asp Gly Phe Arg Leu Pro Thr Pro Met Asp
            340                 345                 350

Cys Pro Ser Ala Ile Tyr Gln Leu Met Met Gln Cys Trp Gln Gln Glu
        355                 360                 365

Arg Ala Arg Arg Pro Lys Phe Ala Asp Ile Val Ser Ile Leu Asp Lys
    370                 375                 380

Leu Ile Arg Ala Pro Asp Ser Leu Lys Thr Leu Ala Asp Phe Asp Pro

|  |  |  |  |  |  |  |  |  |  |  |
|--|--|--|--|--|--|--|--|--|--|--|
| 385 | | | | 390 | | | | 395 | | 400 |
| Arg | Val | Ser | Ile | Arg | Leu | Pro | Ser | Thr | Ser | Gly | Ser | Glu | Gly | Val | Pro |
| | | | | 405 | | | | 410 | | | | | 415 | | |

Arg Val Ser Ile Arg Leu Pro Ser Thr Ser Gly Ser Glu Gly Val Pro
            405                 410                415

Phe Arg Thr Val Ser Glu Trp Leu Glu Ser Ile Lys Met Gln Gln Tyr
        420                 425                 430

Thr Glu His Phe Met Ala Ala Gly Tyr Thr Ala Ile Glu Lys Val Val
            435                 440                 445

Gln Met Thr Asn Asp Asp Ile Lys Arg Ile Gly Val Arg Leu Pro Gly
        450                 455                 460

His Gln Lys Arg Ile Ala Tyr Ser Leu Leu Gly Leu Lys Asp Gln Val
465                 470                 475                 480

Asn Thr Val Gly Ile Pro Ile Glu Gln Lys Leu Ile Ser Glu Glu Asp
            485                 490                 495

Leu

<210> SEQ ID NO 25
<211> LENGTH: 1716
<212> TYPE: DNA
<213> ORGANISM: Artificial Sequence
<220> FEATURE:
<223> OTHER INFORMATION: Expression cassette, encodes fusion protein

<400> SEQUENCE: 25

```
ggtacctcct tgattagta tattcctatc ttaaagttac ttttatgtgg aggcattaac     60
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta gaaggagagt gaaacccatg    240
gcatacgaca gtcgttttga tgaatgggta cagaaactga agaggaaag cttcaaaac     300
aatacgtttg accgccgcaa atttattcaa ggagcgggga agattgcagg actttctctt    360
ggattaacga ttgcccagtc ggttgggcc tttggatccg attataaaga tgatgatgat     420
aaacacagac gtagaaaaaa tcaacgtgct cgacaatccc cagaagatgt gtattttcg     480
aaaagtgaac aattaaaacc attaaaaact tatgttgatc cgcatacgta cgaagaccca    540
aatcaagcag tattaaaatt tacaacagaa atacacccaa gttgtgttac aagcaaaaaa    600
gttattggag caggtgaatt cggagaggta tataaggta tgttaaaaac atcatcaggt    660
aaaaagaag ttccggttgc aattaaaacc ttaaaggcag gatatacaga aaaacagcga    720
gttgatttt taggtgaagc aggaattatg ggtcaattta gccatcataa tattattcgt    780
ttggaaggag taataagtaa atataaacca atgatgatta ttacagaata catggaaaac    840
ggtgctttag ataaatttt acgtgaaaag gatggtgaat ttagtgttt acaattggtt    900
ggtatgttaa gaggaattgc tgcaggtatg aaatatttag ctaatatgaa ttatgttcac    960
cgtgatttgg cagcaagaaa tatcctagtc aattccaatt agtatgtaa agttagtgat   1020
tttggtttaa gcagagtatt agaagacgat ccagaggcaa cctatacaac atcgggaggt    1080
aaaattccta ttcgttggac agcaccagaa gctatcagtt accgtaaatt tacaagtgca    1140
tcagacgtgt ggagttttgg gattgtaatg tgggaagtta tgacatatgg agaaagacca    1200
tattgggaat taagtaatca tgaagttatg aaagcaatta cgatggatt tagattacca    1260
actccgatgg attgtccatc tgccatttat caactaatga tgcaatgttg gcaacaagaa    1320
agagcacgac gtccaaaatt tgcagatatt gttagtattt tagacaaatt aattcgtgca    1380
ccagatagtt taaaaacttt agcagacttt gatcctcgtg ttagtattcg attaccaagt    1440
```

-continued

```
acgtcaggtt ccgaaggagt tccatttcgc acagtctccg aatggttgga atcaattaaa   1500
atgcaacaat acaccgaaca ctttatggca gcaggttaca cagcaatcga aaagttgtt    1560 caaatgacaa atgatgatat taaacgtatt ggagttagat taccaggcca ccagaaacgt   1620
attgcatatt ctttattagg tttaaaagat caagttaata ccgtgggaat tccaattgaa   1680
caaaaattaa tttccgaaga agacttataa gagctc                              1716
```

<210> SEQ ID NO 26
<211> LENGTH: 490
<212> TYPE: PRT
<213> ORGANISM: Artificial Sequence
<220> FEATURE:
<223> OTHER INFORMATION: Fusion protein

<400> SEQUENCE: 26

```
Met Ala Tyr Asp Ser Arg Phe Asp Glu Trp Val Gln Lys Leu Lys Glu
  1               5                  10                  15

Glu Ser Phe Gln Asn Asn Thr Phe Asp Arg Arg Lys Phe Ile Gln Gly
             20                  25                  30

Ala Gly Lys Ile Ala Gly Leu Ser Leu Gly Leu Thr Ile Ala Gln Ser
         35                  40                  45

Val Gly Ala Phe Gly Ser Asp Tyr Lys Asp Asp Asp Lys His Arg
 50                  55                  60

Arg Arg Lys Asn Gln Arg Ala Arg Gln Ser Pro Glu Asp Val Tyr Phe
 65                  70                  75                  80

Ser Lys Ser Glu Gln Leu Lys Pro Leu Lys Thr Tyr Val Asp Pro His
                 85                  90                  95

Thr Tyr Glu Asp Pro Asn Gln Ala Val Leu Lys Phe Thr Thr Glu Ile
            100                 105                 110

His Pro Ser Cys Val Thr Arg Gln Lys Val Ile Gly Ala Gly Glu Phe
        115                 120                 125

Gly Glu Val Tyr Lys Gly Met Leu Lys Thr Ser Ser Gly Lys Lys Glu
    130                 135                 140

Val Pro Val Ala Ile Lys Thr Leu Lys Ala Gly Tyr Thr Glu Lys Gln
145                 150                 155                 160

Arg Val Asp Phe Leu Gly Glu Ala Gly Ile Met Gly Gln Phe Ser His
                165                 170                 175

His Asn Ile Ile Arg Leu Glu Gly Val Ile Ser Lys Tyr Lys Pro Met
            180                 185                 190

Met Ile Ile Thr Glu Tyr Met Glu Asn Gly Ala Leu Asp Lys Phe Leu
        195                 200                 205

Arg Glu Lys Asp Gly Glu Phe Ser Val Leu Gln Leu Val Gly Met Leu
    210                 215                 220

Arg Gly Ile Ala Ala Gly Met Lys Tyr Leu Ala Asn Met Asn Tyr Val
225                 230                 235                 240

His Arg Asp Leu Ala Ala Arg Asn Ile Leu Val Asn Ser Asn Leu Val
                245                 250                 255

Cys Lys Val Ser Asp Phe Gly Leu Ser Arg Val Leu Glu Asp Asp Pro
            260                 265                 270

Glu Ala Thr Tyr Thr Thr Ser Gly Gly Lys Ile Pro Ile Arg Trp Thr
        275                 280                 285

Ala Pro Glu Ala Ile Ser Tyr Arg Lys Phe Thr Ser Ala Ser Asp Val
    290                 295                 300

Trp Ser Phe Gly Ile Val Met Trp Glu Val Met Thr Tyr Gly Glu Arg
```

```
            305                 310                 315                 320
Pro Tyr Trp Glu Leu Ser Asn His Glu Val Met Lys Ala Ile Asn Asp
                    325                 330                 335
Gly Phe Arg Leu Pro Thr Pro Met Asp Cys Pro Ser Ala Ile Tyr Gln
                340                 345                 350
Leu Met Met Gln Cys Trp Gln Gln Glu Arg Ala Arg Arg Pro Lys Phe
            355                 360                 365
Ala Asp Ile Val Ser Ile Leu Asp Lys Leu Ile Arg Ala Pro Asp Ser
        370                 375                 380
Leu Lys Thr Leu Ala Asp Phe Asp Pro Arg Val Ser Ile Arg Leu Pro
385                 390                 395                 400
Ser Thr Ser Gly Ser Glu Gly Val Pro Phe Arg Thr Val Ser Glu Trp
                405                 410                 415
Leu Glu Ser Ile Lys Met Gln Gln Tyr Thr Glu His Phe Met Ala Ala
            420                 425                 430
Gly Tyr Thr Ala Ile Glu Lys Val Val Gln Met Thr Asn Asp Asp Ile
        435                 440                 445
Lys Arg Ile Gly Val Arg Leu Pro Gly His Gln Lys Arg Ile Ala Tyr
    450                 455                 460
Ser Leu Leu Gly Leu Lys Asp Gln Val Asn Thr Val Gly Ile Pro Ile
465                 470                 475                 480
Glu Gln Lys Leu Ile Ser Glu Glu Asp Leu
                485                 490

<210> SEQ ID NO 27
<211> LENGTH: 966
<212> TYPE: DNA
<213> ORGANISM: Artificial Sequence
<220> FEATURE:
<223> OTHER INFORMATION: Expression cassette, encodes fusion protein

<400> SEQUENCE: 27
ggtacctcct tgattagta tattcctatc ttaaagttac ttttatgtgg aggcattaac      60
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta gaaggagagt gaaacccatg    240
aaaaaaatta tgttagtttt tattacatta attttagtta gtttaccaat gcacaacaa     300
acagaagcaa aagatgcaag tgcatttaat aaagaaaata gtattagtag tatggcacca    360
ccagcaagtc caccagcaag tccaaaaaca ccaattgaaa aaaacatgc agatggatcc     420
caagcagaag gtcgcggaac aggaggaagt acaggagatg cagacggacc aggaggacca    480
ggaataccag acggaccagg aggaaatgca ggaggcccag gcgaagcagg cgcaacagga    540
ggaagaggac caagaggagc aggagcagca cgagcatcag gaccaggagg cggagcacca    600
agaggaccac atggcggagc ggcaagcgga ttaaatggat gttgtagatg tggagcacgc    660
ggaccagaat caagactttt agaatttat ttagccatgc catttgcaac cccaatggaa     720
gcagaattag cacgaagatc attagcacaa gatgccccac cattaccagt accaggagtt    780
ttattaaaag agtttacagt atcaggcaat attttaacaa tacgtttaac agcagcagac    840
catcgtcaat tacaactatc tatcagttca tgtttacaac aattatcctt attaatgtgg    900
attacacaat gttttttacc agtttttta gcacaaccac catcaggaca aagaagataa    960
gagctc                                                                966
```

<210> SEQ ID NO 28
<211> LENGTH: 240
<212> TYPE: PRT
<213> ORGANISM: Artificial Sequence
<220> FEATURE:
<223> OTHER INFORMATION: Fusion protein

<400> SEQUENCE: 28

```
Met Lys Lys Ile Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Gly Ser Gln Ala Glu
    50                  55                  60

Gly Arg Gly Thr Gly Gly Ser Thr Gly Asp Ala Asp Gly Pro Gly Gly
65                  70                  75                  80

Pro Gly Ile Pro Asp Gly Pro Gly Asn Ala Gly Gly Pro Gly Glu
                85                  90                  95

Ala Gly Ala Thr Gly Gly Arg Gly Pro Arg Gly Ala Gly Ala Ala Arg
               100                 105                 110

Ala Ser Gly Pro Gly Gly Ala Pro Arg Gly Pro His Gly Gly Ala
               115                 120                 125

Ala Ser Gly Leu Asn Gly Cys Cys Arg Cys Gly Ala Arg Gly Pro Glu
           130                 135                 140

Ser Arg Leu Leu Glu Phe Tyr Leu Ala Met Pro Phe Ala Thr Pro Met
145                 150                 155                 160

Glu Ala Glu Leu Ala Arg Arg Ser Leu Ala Gln Asp Ala Pro Pro Leu
               165                 170                 175

Pro Val Pro Gly Val Leu Leu Lys Glu Phe Thr Val Ser Gly Asn Ile
               180                 185                 190

Leu Thr Ile Arg Leu Thr Ala Ala Asp His Arg Gln Leu Gln Leu Ser
           195                 200                 205

Ile Ser Ser Cys Leu Gln Gln Leu Ser Leu Leu Met Trp Ile Thr Gln
        210                 215                 220

Cys Phe Leu Pro Val Phe Leu Ala Gln Pro Pro Ser Gly Gln Arg Arg
225                 230                 235                 240
```

<210> SEQ ID NO 29
<211> LENGTH: 330
<212> TYPE: DNA
<213> ORGANISM: Artificial Sequence
<220> FEATURE:
<223> OTHER INFORMATION: Partial expression cassette comprising
     codon-optimized sequence

<400> SEQUENCE: 29

```
ggtacctcct ttgattagta tattcctatc ttaaagttac ttttatgtgg aggcattaac      60
atttgttaat gacgtcaaaa ggatagcaag actagaataa agctataaag caagcatata     120
atattgcgtt tcatctttag aagcgaattt cgccaatatt ataattatca aaagagaggg     180
gtggcaaacg gtatttggca ttattaggtt aaaaaatgta gaggagagt gaaacccatg      240 aaaaaaaaaa ttattagtgc aattttaatg agtacagtta ttttaagtgc agcagcacca     300
ttaagtggtg tttatgcaga tacaggatcc                                      330
```

<210> SEQ ID NO 30
<211> LENGTH: 330
<212> TYPE: DNA
<213> ORGANISM: Artificial Sequence
<220> FEATURE:
<223> OTHER INFORMATION: Partial expression cassette

<400> SEQUENCE: 30

```
ggtacctcct tgattagta tattcctatc ttaaagttac ttttatgtgg aggcattaac      60
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta gaggagagt gaaacccatg     240 aatatgaaaa agcaactat cgcggctaca gctgggattg cggtaacagc atttgctgcg     300
ccaacaatcg catccgcaag cactggatcc                                      330
```

<210> SEQ ID NO 31
<211> LENGTH: 330
<212> TYPE: DNA
<213> ORGANISM: Artificial Sequence
<220> FEATURE:
<223> OTHER INFORMATION: Partial expression cassette comprising
      codon-optimized sequence

<400> SEQUENCE: 31

```
ggtacctcct tgattagta tattcctatc ttaaagttac ttttatgtgg aggcattaac      60
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta gaggagagt gaaacccatg     240 aatatgaaaa agcaacaat tgcagcaaca gcaggtattg cagttacagc atttgcagca    300
ccaacaattg caagtgcaag tacaggatcc                                      330
```

<210> SEQ ID NO 32
<211> LENGTH: 1702
<212> TYPE: DNA
<213> ORGANISM: Artificial Sequence
<220> FEATURE:
<223> OTHER INFORMATION: hlyP-p60 gene fragment

<400> SEQUENCE: 32

```
ggtacctcct tgattagta tattcctatc ttaaagttac ttttatgtgg aggcattaac      60
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta gaggagagt gaaacccatg     240 aatatgaaaa agcaactat cgcggctaca gctgggattg cggtaacagc atttgctgcg     300
ccaacaatcg catccgcaag cactgtagta gtcgaagctg tgatactct tggggtatc     360 gcacaaagta aagggactac tgttgacgca attaaaaag caaacaattt aacaacagat    420
aaaatcgtac caggtcaaaa attacaagta ataatgagg ttgctgctgc tgaaaaaaca    480
gagaaatctg ttagcgcaac ttggttaaac gtccgtagtg gcgctggtgt tgataacagt    540
attattacgt ccatcaaagg tggaacaaaa gtaactgttg aaacaaccga atctaacggc    600
tggcacaaaa ttacttacaa cgatggaaaa actggtttcg ttaacggtaa atacttaact    660
gacaaagcag taagcactcc agttgcacca acacaagaag tgaaaaaaga aactactact    720
caacaagctg cacctgctgc agaaacaaaa actgaagtaa aacaaactac acaagcaact    780
```

| | |
|---|---|
| acacctgcgc ctaaagtagc agaaacgaaa gaaactccag tagtagatca aaatgctact | 840 |
| acacacgctg ttaaaagcgg tgacactatt tgggctttat ccgtaaaata cggtgtttct | 900 |
| gttcaagaca ttatgtcatg gaataattta tcttcttctt ctatttatgt aggtcaaaag | 960 |
| cttgctatta aacaaactgc taacacagct actccaaaag cagaagtgaa aacggaagct | 1020 |
| ccagcagctg aaaacaagc agctccagta gttaaagaaa atactaacac aaatactgct | 1080 |
| actacagaga aaaagaaac agcaacgcaa caacaaacag cacctaaagc accaacagaa | 1140 |
| gctgcaaaac cagctcctgc accatctaca aacacaaatg ctaataaaac aaatacaaat | 1200 |
| acaaatacaa atacaaatac aaacaatact aatacaaata caccatctaa aaatactaat | 1260 |
| acaaactcaa atactaatac gaatacaaac tcaaatacga atgctaatca aggttcttcc | 1320 |
| aacaataaca gcaattcaag tgcaagtgct attattgctg aagctcaaaa acaccttgga | 1380 |
| aaagcttatt catggggtgg taacggacca actacatttg attgctctgg ttacactaaa | 1440 |
| tatgtatttg ctaaagcggg aatctcccct ccacgtactt ctggcgcaca atacgctagc | 1500 |
| actacaagaa tctctgaatc tcaagcaaaa cctggtgatt tagtattctt tgactatggt | 1560 |
| agcggaattt ctcacgttgg tatctacgtt ggtaatggtc aaatgattaa cgcgcaagac | 1620 |
| aatggcgtta aatacgataa catccacggc tctggctggg gtaaatatct agttggcttc | 1680 |
| ggtcgcgtat aattaaggat cc | 1702 |

<210> SEQ ID NO 33
<211> LENGTH: 9808
<212> TYPE: DNA
<213> ORGANISM: Artificial Sequence
<220> FEATURE:
<223> OTHER INFORMATION: pAM401-MCS plasmid

<400> SEQUENCE: 33

| | |
|---|---|
| ctttaaacgt ggatcatttt ctttaaattt atgctgacga cctttgaatt tgcctttttt | 60 |
| cttagcaatt tcgattcctt gtgcctgacg ttccttaatt ttttttcgtt ctgattctgc | 120 |
| ttgatacttg tacaattcaa tgacaaggct attaatcaaa cgcctaaaat tttcatcttc | 180 |
| aataccattc attgagggta aatttaagac ttccagggtt gccccttaa tttgaatttg | 240 |
| attcatcaat tctgttaatt ctttattatt tcgtcctaat cgatctaatt cagtaacaat | 300 |
| aacaatatcc ccttcacgaa tatagttaag catagcttgt aattgtgggc gttcgaccga | 360 |
| ttgaccgctt aatttgtctg aaaagacctt agaaacgccc tgtaacgctt gtaattgccg | 420 |
| atctaagttc tgttctttgc tactgacacg tgcataacca atttagcca ttttcaacca | 480 |
| acctctaaaa ttctctcggt tgcaataacc aatcagcaat atctactttt tcaatttcaa | 540 |
| attgcttatc agaaattgtc ttttcgtaag cgataaaatc ttgcgcatat tgttgctcat | 600 |
| taaaaatagc caccacttcg tcattttcta aactcgata aataaatttt ttcatttac | 660 |
| tcctcctatt atgcccaact aaatgacct attccacaag tcaattatac tgctaaaatc | 720 |
| atattaggac aaataggtat actctattga cctataaatg atagcaactt aaaagatcaa | 780 |
| gtgttcgctt cgctctcact gccctcgac gttttagtag cctttccctc acttcgttca | 840 |
| gtccaagcca actaaaagtt tcgggctac tctctccttc tcccctaat aattaattaa | 900 |
| aatcttactc tgtatatttc tgctaatcat tcactaaaca gcaaagaaaa acaaacacgt | 960 |
| atcatagata taaatgtaat ggcatagtgc gggtttatt ttcagcctgt atcgtagcta | 1020 |
| aacaaatcga gttgtgggtc cgttttgggg cgttctgcca atttgtttag agtttcttga | 1080 |

```
ataaatgtac gttctaaatt aaacgaagct gtcagcgcct ttatatagct ttctcgttct     1140 tctttttta  atttaatgat cgatagcaac aatgatttaa cactagcaag ttgaatgcca     1200
ccatttcttc ctggtttaat cttaaagaaa atttcctgat tcgccttcag taccttcagc     1260
aatttatcta atgtccgttc aggaatgcct agcacttctc taatctcttt tttggtcgtc     1320
gctaaataag gcttgtatac atcgcttttt tcgctaatat aagccattaa atcttctttc     1380
cattctgaca aatgaacacg ttgacgttcg cttcttttt  tcttgaattt aaaccaccct     1440
tgacggacaa ataaatcttt actggttaaa tcacttgata cccaagcttt gcaaagaatg     1500
gtaatgtatt ccctattagc cccttgatag ttttctgaat aggcacttct aacaattttg     1560
attacttctt tttcttctaa gggttgatct aatcgattat taaactcaaa catattatat     1620
tcgcacgttt cgattgaata gcctgaacta aagtaggcta aagagagggt aaacataacg     1680
ctattgcgcc ctactaaacc ctttctcct  gaaaatttcg tttcgtgcaa taagagatta     1740
aaccagggtt catctacttg ttttttgcct tctgtaccgc ttaaaaccgt tagacttgaa     1800
cgagtaaagc ccttattatc tgtttgtttg aaagaccaat cttgccattc tttgaaagaa     1860
taacggtaat tgggatcaaa aaattctaca ttgtccgttc ttggtatacg agcaatccca     1920
aaatgattgc acgttagatc aactggcaaa gactttccaa aatattctcg gatattttgc     1980
gagattattt tggctgcttt gacagattta aattctgatt tgaagtcac  atagactggc     2040 gtttctaaaa caaaatatgc ttgataacct ttatcagatt tgataattaa cgtaggcata     2100
aaacctaaat caatagctgt tgttaaaata tcgcttgctg aaatagtttc ttttccgtg     2160 tgaatatcaa atcaataaa  gaaggtattg atttgtctta aattgttttc agaatgtcct     2220
ttagtgtatg aacggttttc gtctgcatac gtaccataac gataaacgtt tggtgtccaa     2280
tgcgtaaatg tatcttgatt ttcgtgaatc gcttcttcgg aagtcagaac aacgccacgt     2340
ccgccaatca tgctttttt  tgagcgatac gcaaaaatag cccctttact tttacctggc     2400
ttggtagtga ttgagcgaat tttactattt ttaaatttgt actttaacaa gccgtcatga     2460
agcacagttt ctacaacaaa agggatattc attcagctgt tctcctttct tacgaaaatt     2520
aattagttag aagctacgat caaagttgaa tcacaacaaa aaaggcaatc aactaagttt     2580
ttcttaattg attgcctggt atcttcttaa agacttgaaa tcccctcaaa aacccgatat     2640
aatgggttta cagatattta agtatctgat taataaagta attaaatact ttaccaaatt     2700
ttgggtctcg acttctttaa ttgattggtg gtaatcaatt aaggctcgca gttaaaattt     2760
ctcaggcttt aactggtcgt ggctcttttt ttgtattctt tattcagttc gttgtttcgt     2820
tatatctagt atatcgcttt ttaaaaaaat aagcaatgat ttcgtgcatt attcacacga     2880
aatcattgct ttttcttct  tccatttcta actccaatgt tacttgttct gtttctggtt     2940
ctggttctgt tggctcattt gggattaaat ccactactag cgttgagtta gttccgtctc     3000
taatagccgg ttaagtaata gccggttaag tggtcaaact ttgggaaaat ctcaacccgc     3060
attaagtttt gatgccatga caatcgttgg aaatttgaac aaaactaatg ctaaaaagct     3120
atctgacttt atgagtgtag agccacaaat acgactttgg gatatacttc aaacaaagtt     3180
taaagctaag gcacttcaag aaaaagttta tatcgaatat gacaaagtaa aagcagatac     3240
ttgggataga cgtaatatgc gtgttgaatt taatcccaat aaactcacac atgaagaaat     3300
gatttggtta aaacaaaata ttatcgacta catggaagat gacggtttta caagattaga     3360
cttagctttt gattttgaag atgatttgag cgattactat gcaatgactg ataaagcagt     3420
taagaaaact gttttttatg gtcgtaatgg caagccagaa acaaaatatt tggtgtccg      3480
```

```
tgatagtgat agatttatta gaatttataa taaaaaacaa gaacgtaaag ataacgcaga    3540
tgttgaagtt gtgtttgaac atttatggcg tgtagaagtt gaattaaaaa gagatatggt    3600
tgattactgg aatgattgtt ttaatgattt acacatcttt gaaacctgcg tgggctactt    3660
tagaaaaaat taatgagcaa gctatggttt atactttgtt gcatgaagaa agtatgtggg    3720
gaaagctaag taagaatact aagactaaat ttaaaaaatt gattagagaa atatctccaa    3780
ttgatttaac ggaattaatg aaatcgactt taaaagcgaa cgaaaaacaa ttgcaaaagc    3840
agattgattt ttggcaacgt gaatttaggt tttggaagta aaataagttt tatttgataa    3900
aaattgctaa ttcagtataa ttaatattta cgaggtgaca taacgtatga aaaaatcaga    3960
ggattattcc tcctaaatat aaaaatttaa aatttaggag gaagttatat atgactttta    4020
atattattga attagaaaat tgggatagaa aagaatattt tgaacactat tttaatcagc    4080
aaactactta tagcattact aaagaaattg atattacttt gtttaaagat atgataaaaa    4140
agaaaggata tgaaatttat ccctctttaa tttatgcaat tatggaagtt gtaaataaaa    4200
ataaagtgtt tagaacagga attaatagtg agaataaatt aggttattgg gataagttaa    4260
atcctttgta tacagttttt aataagcaaa ctgaaaaatt tactaacatt tggactgaat    4320
ctgataaaaa cttcatttct ttttataata attataaaaa tgacttgctt gaatataaag    4380
ataaagaaga aatgtttcct aaaaaaccga tacctgaaaa caccataccg atttcaatga    4440
ttccttggat tgattttagt tcatttaatt taaatattgg taacaatagc agctttttat    4500
tgcctattat tacgataggt aaattttata gtgagaataa taaaatttat ataccagttg    4560
ctctgcaact tcatcattct gtatgtgatg gttaccatgc ttcactattt atgaatgaat    4620
ttcaagatat aattcatagg gtagatgatt ggatttagtt tttagatttt gaaagtgaat    4680
ttaattttat acacgtaagt gatcataaaa tttatgaacg tataacaacc acatttttg    4740
gttgcttgtg gttttgattt tgaatttggt tttgaactta tggactgatt tattcagtcc    4800
attttttgtg cttgcacaaa aactagcctc gcagagcaca cgcattaatg acttatgaaa    4860
cgtagtaaat aagtctagtg tgttatactt tacttggaag atgcaccgaa taaaaaatat    4920
tgaagaacaa ctagcaaaag atttaaaga gttatttat tttaagtctt tataacatga    4980
gtgaagcgaa ttttaaatt tcgatagaaa ttttcatc aaaagcccc ctgtcaaat    5040
tgacgaaggg ggtttttgg cgcacgcttt tcgttagaaa tatacaagat tgaaaatcgt    5100
gtataagtgc gcccttttgtt ttgaacttag cacgttacat caatttttta aaatgatgta    5160
taagtgcgcc ctttaaatt ttgagtgatt atatttttg agttagaaaa agggattggg    5220
aaaatttccc aaaataattt aaaaaataag caaaaatttt cgatagagaa tgtgctattt    5280
tttgtcaaag gtgtatacct tgactgtgct tgctgttaca ttaagtttat ttttaagtta    5340
ttaaaaaaga aatagctttt aaagtttggc tcgctgtcgc tttataaagc tgattgactt    5400
ttgattgcaa actacttaaa gaaacaaac tcggactatt cgttttcttc tctttggttt    5460
gaacatcagc aattatcccc tcttgattgc ctattttagc ttgtttagaa gaaacaaaag    5520
ctaaaagctc ctcttgggtt ttaaaacgct gtgtggggct tagaacgccc ttaaacgacc    5580
cttggtttac ttttatacta gcttccacct cgaaaaaagg ttctttttta aaattctcta    5640
tggcttcctg gcgctgaaaa aataaggtat aaggtgggcg tttgaacacg tcctagtgaa    5700
aatgtacctt gtacgcccct tctgttgtaa atttaacgta tacaagggc ttgcgttcat    5760
gccgatcaac caatcggcaa tttggcgtgt ttgcgcttct tgataaaagg gatagtaatt    5820
```

```
cattccaggt tgcaaatttt gaaaaccgct tcggattaca tcttttttcta agctattgat    5880 ccatagtctt ttaaatgttt tatcttttga aaaggcattt gctttatgga taatcgacca    5940
ggcgatattt tcaccttctc tgtcgctatc tgttgcaaca ataattgtat ttgccttttt    6000
gagaagttct gcaacaattt taaactgctt tcccttatct tttgcaactt caaaatcgta    6060
tcgatcagga aaaatcggca aagattcaag tttccaattt tgccactttt cgtcataatg    6120
acctggttct gctaattcca ctaaatgccc aaaaccaaag gtgataaacg tttcatctgt    6180
aaatagtggg tctttgatct caaaataacc gtcttttttg gtgctttgtt ttaaagcact    6240
tgcgtaggct aatgcctggc ttggttttc agctaaaata accgtactca ttaactatcc    6300
ctcttttcat tgttttttct tgatcgact gtcacgttat atcttgctcg ataccttcta    6360
aacgttcggc gattgattcc agtttgttct tcaacttctt tatcggataa accattcaaa    6420
aacaaatcga agcatggat gcgccgcgtg cggctgctgg agatggcgga cgcgatggat    6480
atgttctgcc aagggttggt tgcgcattc acagttctcc gcaagaattg attggctcca    6540
attcttggag tggtgaatcc gttagcgagg tgccgccggc ttccattcag gtcgaggtgg    6600
cccggctcca tgcaccgcga cgcaacgcgg ggaggcagac aaggtatagg gcggcgccta    6660
caatccatgc caacccgttc catgtgctcg ccgaggcggc ataaatcgcc gtgacgatca    6720
gcggtccagt gatcgaagtt aggctggtaa gagccgcgag cgatccttga agctgtccct    6780
gatggtcgtc atctacctgc ctggacagca tggcctgcaa cgcgggcatc ccgatgccgc    6840
cggaagcgag aagaatcata atggggaagg ccatccagcc tcgcgtcgca atacgactca    6900
ctatagggcg aattgggtac cgggccccc ctcgaggtcg acggtatcga taagcttgat    6960
atcgaattcc tgcagcccgg gggatccact agttctagag cggccgccac cgcggtggag    7020
ctccagcttt tgttcccttt agtgagggtt aatgctagaa atatttatc tgattaataa    7080 gatgatcttc ttgagatcgt tttggtctgc gcgtaatctc ttgctctgaa acgaaaaaa    7140 ccgccttgca gggcggtttt tcgaaggttc tctgagctac caactctttg aaccgaggta    7200
actggcttgg aggagcgcag tcaccaaaac ttgtcctttc agtttagcct taaccggcgc    7260
atgacttcaa gactaactcc tctaaatcaa ttaccagtgg ctgctgccag tggtgctttt    7320
gcatgtcttt ccgggttgga ctcaagacga tagttaccgg ataaggcgca gcggtcggac    7380
tgaacggggg gttcgtgcat acagtccagc ttggagcgaa ctgcctaccc ggaactgagt    7440
gtcaggcgtg gaatgagaca aacgcggcca taacagcgga atgacaccgg taaaccgaaa    7500
ggcaggaaca ggagagcgca cgagggagcc gccaggggga aacgcctggt atctttatag    7560
tcctgtcggg tttcgccacc actgatttga gcgtcagatt tcgtgatgct tgtcaggggg    7620
gcggagccta tggaaaaacg ctttgccgc ggccctctca cttccctgtt aagtatcttc    7680
ctggcatctt ccaggaaatc tccgccccgt tcgtaagcca tttccgctcg ccgcagtcga    7740
acgaccgagc gtagcgagtc agtgagcgag gaagcggaat atatcctgta tcacatattc    7800
tgctgacgca ccggtgcagc cttttttctc ctgccacatg aagcacttca ctgacaccct    7860
catcagtgcc aacatagtaa gccagtatac actccgctag cgctgatgtc cggcggtgct    7920
tttgccgtta cgcaccaccc cgtcagtagc tgaacaggag ggacagctga tagaaacaga    7980
agccactgga gcacctcaaa aacaccatca tacactaaat cagtaagttg gcagcatcac    8040
ccgacgcact ttgcgccgaa taaatacctg tgacggaaga tcacttcgca gaataaataa    8100
atcctggtgt ccctgttgat accgggaagc cctgggccaa cttttggcga aaatgagacg    8160
ttgatcggca cgtaagaggt tccaactttc accataatga aataagatca ctaccgggcg    8220
```

```
tatttttga gttatcgaga ttttcaggag ctaaggaagc taaaatggag aaaaaaatca    8280
ctggatatac caccgttgat atatcccaat ggcatcgtaa agaacatttt gaggcatttc    8340
agtcagttgc tcaatgtacc tataaccaga ccgttcagct ggatattacg gccttttaa     8400 agaccgtaaa gaaaaataag cacaagtttt atccggcctt tattcacatt cttgcccgcc    8460
tgatgaatgc tcatccggaa ttccgtatgg caatgaaaga cggtgagctg gtgatatggg    8520
atagtgttca cccttgttac accgttttcc atgagcaaac tgaaacgttt tcatcgctct    8580
ggagtgaata ccacgacgat ttccggcagt ttctacacat atattcgcaa gatgtggcgt    8640
gttacggtga aaacctggcc tatttcccta aagggtttat tgagaatatg ttttcgtct     8700 cagccaatcc ctgggtgagt ttcaccagtt ttgatttaaa cgtggccaat atggacaact    8760
tcttcgcccc cgttttcacc atgggcaaat attatacgca aggcgacaag gtgctgatgc    8820
cgctggcgat tcaggttcat catgccgtct gtgatggctt ccatgtcggc agaatgctta    8880
atgaattaca acagtactgc gatgagtggc agggcggggc gtaatttttt taaggcagtt    8940
attggtgccc ttaaacgcct ggtgctacgc ctgaataagt gataataagc ggatgaatgg    9000
cagaaattcg aaagcaaatt cgacccggtc gtcggttcag ggcagggtcg ttaaatagcc    9060
gcttatgtct attgctggtt taccggttta ttgactaccg aagcagtgt gaccgtgtgc     9120 ttctcaaatg cctgaggcca gtttgctcag gctctccccg tggaggtaat aattgacgat    9180
atgatcattt attctgcctc ccagagcctg ataaaaacgg ttagcgcttc gttaatacag    9240
atgtaggtgt tccacagggt agccagcagc atcctgcgat gcagatccgg aacataatgg    9300
tgcagggcgc ttgtttcggc gtgggtatgg tggcaggccc cgtggccggg ggactgttgg    9360
gcgctgccgg cacctgtcct acgagttgca tgataaagaa gacagtcata agtgcggcga    9420
cgatagtcat gccccgcgcc caccggaagg agctaccgga cagcggtgcg gactgttgta    9480
actcagaata gaaatgagg ccgctcatgg cgttgactct cagtcatagt atcgtggtat     9540
caccggttgg ttccactctc tgttgcgggc aacttcagca gcacgtaggg gacttccgcg    9600
tttccagact ttacgaaaca cggaaaccga agaccattca tgttgttgct caggtcgcag    9660
acgttttgca gcagcagtcg cttcacgttc gctcgcgtat cggtgattca ttctgctaac    9720
cagtaaggca accccgccag cctagccggg tcctcaacga caggagcacg atcatgcgca    9780
cccgtggcca ggacccaacg ctgcccga                                       9808
```

<210> SEQ ID NO 34
<211> LENGTH: 1869
<212> TYPE: DNA
<213> ORGANISM: Artificial Sequence
<220> FEATURE:
<223> OTHER INFORMATION: Codon-optimized sequence

<400> SEQUENCE: 34

```
atggcattgc caactgcacg tccattacta ggtagttgcg gtacaccagc actaggttct      60
ttattatttt tgttatttc tctaggttgg gttcaaccaa gtcgtacatt agcaggtgaa      120
acaggtcaag aagcagcacc acttgacggt gtattaacga atccaccaaa tatatcaagt     180
ttaagtccac gtcaattatt aggttttcca tgtgcagaag tttcaggttt aagtacagaa     240
cgtgtccgtg agttagcagt tgcattagca caaaaaaacg ttaaattatc tacagaacag     300
ttacgttgtt tagcccatag attaagcgaa ccaccagaag acttgatgca acttcctttg     360
gaccttcttt tattcttaaa tccagatgca ttttcaggac cacaagcatg tacacgtttt     420
```

```
tttagtcgaa ttacaaaagc caatgttgat ttattacctc gtggggctcc tgaaagacaa    480
cgtttattac ctgctgcatt agcatgctgg ggtgttcgcg gtagcttatt aagtgaagcc    540
gatgttcgtg ctttaggggg tttagcatgt gatttacctg gtcgtttcgt tgcagaatca    600
gcagaagtgt tattaccgag attagtttca tgcccaggac ctttagatca agatcaacaa    660
gaggcagcta gagcagctct tcaaggagga ggcccaccat atggcccacc aagtacatgg    720 agtgttttcta caatggatgc gttaagaggt ttattaccgg ttttaggaca accaattatt    780
cgtagtattc cacaaggcat tgtagcagca tggcgtcaac gtagttctcg tgatccgtct    840
tggcgacaac cagaacgtac aattctacgt ccaagatttc gtagagaagt agaaaaaacg    900
gcgtgtccta gtggcaaaaa agcacgtgaa attgatgaaa gtttaatttt ttataaaaaa    960
tgggaattag aagcatgtgt cgatgcagca ttactagcta cacaaatgga tcgtgttaat    1020
gctattccat tcacatatga acaattagat gttttaaagc ataaattaga cgaattatat    1080
ccacaaggtt atccgaatc agttattcaa catttaggtt acttattttt aaaaatgagt    1140
ccagaagaca tacgcaaatg gaatgttaca agtttagaaa cattaaaagc gcttttagaa    1200
gttaacaaag gtcatgaaat gagtccacaa gttgctacgt taattgatag attcgttaaa    1260
ggccgtggtc aattagataa agatacttta gatacattaa cagcatttta tcctggctac    1320
ttatgcagtt tatcaccaga agaattaagt tccgttccac cgagtagtat ctgggcagtt    1380
cgtccgcaag atttagatac atgcgaccca cgtcaattag atgttttata tccaaaagca    1440
agattagctt tccaaaatat gaacggtagt gaatatttcg taaaaattca atcctttta    1500 ggtggtgcac caactgaaga tctaaaagca ttaagccaac aaaatgtaag tatggattta    1560
gctacgttta tgaaattacg tacagatgca gttctaccat taacagttgc agaagttcaa    1620
aaattattag gtccacacgt agaaggatta aaagcagaag aacgtcaccg tccagttcgc    1680
gattggattt tacgtcaacg tcaagatgat ttagatacat taggtttagg tttacaaggc    1740
ggtattccga atggatattt agtgttagat ttatctgttc aagaagcatt aagtggtaca    1800
ccgtgtttat taggtccagg tccagttta acagtgttag cattattatt agccagtaca    1860
ttagcttaa    1869
```

<210> SEQ ID NO 35
<211> LENGTH: 622
<212> TYPE: PRT
<213> ORGANISM: Homo sapiens

<400> SEQUENCE: 35

```
Met Ala Leu Pro Thr Ala Arg Pro Leu Leu Gly Ser Cys Gly Thr Pro
 1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Thr Asn Pro Pro Asn Ile Ser Ser Leu Ser Pro Arg
        50                  55                  60

Gln Leu Leu Gly Phe Pro Cys Ala Glu Val Ser Gly Leu Ser Thr Glu
 65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110
```

-continued

```
Glu Asp Leu Asp Ala Leu Pro Leu Asp Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
```

```
                530                 535                 540
Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620

<210> SEQ ID NO 36
<211> LENGTH: 1878
<212> TYPE: DNA
<213> ORGANISM: Artificial Sequence
<220> FEATURE:
<223> OTHER INFORMATION: Codon-optimized sequence

<400> SEQUENCE: 36
atggcattac caacggctcg cccattatta ggttcttgtg gttcaccaat ttgtagtcgc      60
agttttttat tattattact atctttaggt tggattccgc gtttacaaac acaaaccact     120
aaaacaagtc aagaagctac attattgcat gcagtcaatg cgcagcagaa ttttgcaagt     180
ttaccaacag gcttatttct tggtcttaca tgtgaagaag ttagtgattt aagtatggaa     240
caagcaaaag gtttagcgat ggcggttcgc caaaaaaata ttacattacg tggtcatcaa     300
ttacgttgtt tagcacgtcg tttaccacga catttaacag atgaagaatt aaatgctcta     360
ccattagact tattattatt tttaaatcca gcaatgtttc aggtcaaca agcatgtgcc     420 cattttttca gtttaatttc gaaagcaaat gtagatgttt accgagacg tagcttagaa     480 cgtcaacgtc ttttaatgga agcattaaaa tgtcaaggtg tttatggttt ccaagttagt     540
gaagcagatg ttcgtgcact tggtggttta gcttgtgatt taccagggaa atttgtagca     600
cgttctagtg aagtattatt accatggtta gcaggttgtc aaggtccatt agatcaaagt     660
caagaaaaag cagttcgtga agtcttacgt agtggtcgta ctcaatatgg cccacctagc     720
aaatggagtg ttagtacgtt agatgcatta caaagtttag tagctgtttt agatgaaagt     780
attgttcaga gtattccaaa agatgtgaaa gcagagtggt tacaacatat ttcccgtgac     840
ccatctcgtt taggtagtaa attaacagtt attcatccac gttttcgccg cgacgcagaa     900
caaaaagcat gtccaccagg taagaaccca tataagtag atgaagattt aattttttat     960
cagaattggg aattgaagc ctgtgttgat ggtacaatgt tagcacgtca atgggattta    1020
gttaatgaaa ttccatttac atatgaacaa ttaagtatct ttaaacataa attagataaa    1080
acatatccac aaggttatcc agaatcgtta attcaacaat taggtcattt ttttcgttat    1140
gttagtccag aagacattca tcaatggaat gttacaagtc cagatacagt taaaacttta    1200
ttaaaagtta gtaaaggtca aaaaatgaat gctcaagcaa ttgcattagt cgcatgttat    1260
ttacgtggag gtggtcaatt agatgaagat atggttaaag cattagggga tattccatta    1320
tcatatttat gtgatttctc cccacaagac ttacattcag ttccaagtag tgttatgtgg    1380
ttagttggtc cacaaggttt agataaatgt agtcaacgtc atttaggttt actttatcaa    1440
aaagcatgta gtgcgtttca aaatgttagt ggtttagaat attttgaaaa aatcaaaaca    1500
tttttaggag gtgcatctgt aaaagattta cgcgcattaa gtcaacataa tgtaagtatg    1560
```

```
gatatcgcaa catttaaacg tttacaagtc gatagtctag ttggtcttag tgtagcagaa      1620
gttcaaaaat tattagggcc gaatattgta gatttaaaaa cagaagaaga taaaagtcca      1680
gttcgtgact ggttatttcg acaacatcag aaagacttag atcgtcttgg attaggttta      1740
caaggtggta ttccaaatgg ttatttagtt ttagatttta atgtacgtga agcatttagt      1800
tcaagagcga gtttattagg tccaggtttt gtgttaattt ggattccagc attactacca      1860
gcacttcgtt tatcataa                                                   1878
```

<210> SEQ ID NO 37
<211> LENGTH: 625
<212> TYPE: PRT
<213> ORGANISM: Mus musculus

<400> SEQUENCE: 37

```
Met Ala Leu Pro Thr Ala Arg Pro Leu Leu Gly Ser Cys Gly Ser Pro
 1               5                  10                  15

Ile Cys Ser Arg Ser Phe Leu Leu Leu Leu Ser Leu Gly Trp Ile
                20                  25                  30

Pro Arg Leu Gln Thr Gln Thr Thr Lys Thr Ser Gln Glu Ala Thr Leu
            35                  40                  45

Leu His Ala Val Asn Gly Ala Ala Asp Phe Ala Ser Leu Pro Thr Gly
        50                  55                  60

Leu Phe Leu Gly Leu Thr Cys Glu Glu Val Ser Asp Leu Ser Met Glu
65                  70                  75                  80

Gln Ala Lys Gly Leu Ala Met Ala Val Arg Gln Lys Asn Ile Thr Leu
                85                  90                  95

Arg Gly His Gln Leu Arg Cys Leu Ala Arg Arg Leu Pro Arg His Leu
            100                 105                 110

Thr Asp Glu Glu Leu Asn Ala Leu Pro Leu Asp Leu Leu Leu Phe Leu
        115                 120                 125

Asn Pro Ala Met Phe Pro Gly Gln Gln Ala Cys His Phe Phe Ser
    130                 135                 140

Leu Ile Ser Lys Ala Asn Val Asp Val Leu Pro Arg Arg Ser Leu Glu
145                 150                 155                 160

Arg Gln Arg Leu Leu Met Glu Ala Leu Lys Cys Gln Gly Val Tyr Gly
                165                 170                 175

Phe Gln Val Ser Glu Ala Asp Val Arg Ala Leu Gly Gly Leu Ala Cys
            180                 185                 190

Asp Leu Pro Gly Lys Phe Val Ala Arg Ser Ser Glu Val Leu Leu Pro
        195                 200                 205

Trp Leu Ala Gly Cys Gln Gly Pro Leu Asp Gln Ser Gln Glu Lys Ala
    210                 215                 220

Val Arg Glu Val Leu Arg Ser Gly Arg Thr Gln Tyr Gly Pro Pro Ser
225                 230                 235                 240

Lys Trp Ser Val Ser Thr Leu Asp Ala Leu Gln Ser Leu Val Ala Val
                245                 250                 255

Leu Asp Glu Ser Ile Val Gln Ser Ile Pro Lys Asp Val Lys Ala Glu
            260                 265                 270

Trp Leu Gln His Ile Ser Arg Asp Pro Ser Arg Leu Gly Ser Lys Leu
        275                 280                 285

Thr Val Ile His Pro Arg Phe Arg Arg Asp Ala Glu Gln Lys Ala Cys
    290                 295                 300

Pro Pro Gly Lys Glu Pro Tyr Lys Val Asp Glu Asp Leu Ile Phe Tyr
305                 310                 315                 320
```

```
Gln Asn Trp Glu Leu Glu Ala Cys Val Asp Gly Thr Met Leu Ala Arg
                325                 330                 335
Gln Met Asp Leu Val Asn Glu Ile Pro Phe Thr Tyr Glu Gln Leu Ser
            340                 345                 350
Ile Phe Lys His Lys Leu Asp Lys Thr Tyr Pro Gln Gly Tyr Pro Glu
        355                 360                 365
Ser Leu Ile Gln Gln Leu Gly His Phe Phe Arg Tyr Val Ser Pro Glu
    370                 375                 380
Asp Ile His Gln Trp Asn Val Thr Ser Pro Asp Thr Val Lys Thr Leu
385                 390                 395                 400
Leu Lys Val Ser Lys Gly Gln Lys Met Asn Ala Gln Ala Ile Ala Leu
                405                 410                 415
Val Ala Cys Tyr Leu Arg Gly Gly Gln Leu Asp Glu Asp Met Val
            420                 425                 430
Lys Ala Leu Gly Asp Ile Pro Leu Ser Tyr Leu Cys Asp Phe Ser Pro
            435                 440                 445
Gln Asp Leu His Ser Val Pro Ser Ser Val Met Trp Leu Val Gly Pro
    450                 455                 460
Gln Gly Leu Asp Lys Cys Ser Gln Arg His Leu Gly Leu Leu Tyr Gln
465                 470                 475                 480
Lys Ala Cys Ser Ala Phe Gln Asn Val Ser Gly Leu Glu Tyr Phe Glu
                485                 490                 495
Lys Ile Lys Thr Phe Leu Gly Gly Ala Ser Val Lys Asp Leu Arg Ala
            500                 505                 510
Leu Ser Gln His Asn Val Ser Met Asp Ile Ala Thr Phe Lys Arg Leu
        515                 520                 525
Gln Val Asp Ser Leu Val Gly Leu Ser Val Ala Glu Val Gln Lys Leu
    530                 535                 540
Leu Gly Pro Asn Ile Val Asp Leu Lys Thr Glu Glu Asp Lys Ser Pro
545                 550                 555                 560
Val Arg Asp Trp Leu Phe Arg Gln His Gln Lys Asp Leu Asp Arg Leu
                565                 570                 575
Gly Leu Gly Leu Gln Gly Gly Ile Pro Asn Gly Tyr Leu Val Leu Asp
            580                 585                 590
Phe Asn Val Arg Glu Ala Phe Ser Ser Arg Ala Ser Leu Leu Gly Pro
        595                 600                 605
Gly Phe Val Leu Ile Trp Ile Pro Ala Leu Leu Pro Ala Leu Arg Leu
    610                 615                 620
Ser
625

<210> SEQ ID NO 38
<211> LENGTH: 335
<212> TYPE: DNA
<213> ORGANISM: Artificial Sequence
<220> FEATURE:
<223> OTHER INFORMATION: Partial expression cassette comprising
      codon-optimized sequence

<400> SEQUENCE: 38
gtacctcctt tgattagtat attcctatct taaagttact tttatgtgga ggcattaaca    60
tttgttaatg acgtcaaaag gatagcaaga ctagaataaa gctataaagc aagcatataa   120
tattgcgttt catctttaga agcgaatttc gccaatatta taattatcaa agagaggggg   180
tggcaaacgg tatttggcat tattaggtta aaaaatgtag aaggagagtg aaacccatga   240
```

| aaaaacgtaa agttttaatt ccattaatgg cattaagtac aatttagtt agtagtacag | 300 |
| gtaatttaga agttattcaa gcagaagttg gatcc | 335 |

<210> SEQ ID NO 39
<211> LENGTH: 2778
<212> TYPE: DNA
<213> ORGANISM: Artificial Sequence
<220> FEATURE:
<223> OTHER INFORMATION: Coding sequences of plasmid comprising codon-optimized sequence

<400> SEQUENCE: 39

| ggatcccaag gaaagaagt cgtactttta gatttcgcag cagcaggagg agaattagga | 60 |
| tggttaactc atccatatgg caaggctgg gatttaatgc aaaacattat gaacgatatg | 120 |
| ccaatttata tgtactccgt atgtaatgta atgagcggtg atcaagataa ctggttacgt | 180 |
| actaattggg tttatcgagg tgaagcagaa agaattttta ttgaacttaa atttactgtt | 240 |
| cgtgactgta atagttttcc aggaggggcc tcatcatgta agaaacatt caatctatat | 300 |
| tatgccgaaa gcgatcttga ttatggtaca aatttccaaa aacgtttatt tactaaaatt | 360 |
| gatacaatag ctccagatga aatcactgta agttccgatt ttgaagctcg tcatgtaaaa | 420 |
| ttaaatgtag aagaacgcag tgttggtcca ctaactagaa aaggatttta tcttgctttc | 480 |
| caagatatag ggcttgcgt agcattgtta tccgttcgtg tatactataa aaaatgtcca | 540 |
| gaactacttc aaggcttagc acattttcca gaaacaattg cgggctcaga tgcgccatca | 600 |
| cttgcaactg tggcgggtac atgtgttgat catgctgttg tgccaccagg aggagaggaa | 660 |
| cctcgcatgc actgtgcagt agatggtgaa tggttagttc ctattggtca atgtttatgt | 720 |
| caagccggtt atgaaaaagt tgaagatgct tgtcaagcat gctccccagg ttttttaaa | 780 |
| ttcgaagcta gtgaatctcc atgcttagaa tgtccagaac acacattacc aagtccagaa | 840 |
| ggtgcaacgt cctgtgaatg cgaagaaggt ttttttcgtg ccccacaaga tccagcctca | 900 |
| atgccttgta cacgaccgcc ttctgctcca cactatttaa cagccgtagg aatgggcgct | 960 |
| aaagtagagt tacgatggac accgcctcaa gatagtggag gccgtgaaga tattgtttat | 1020 |
| tccgttactt gtgaacaatg ctggccagaa agtggtgaat gcgggccttg cgaagcatca | 1080 |
| gttagatatt cggaaccacc acacgggtta actagaacta gtgtcacagt atcagactta | 1140 |
| gaaccacaca tgaattatac atttacagtt gaggcacgta atggagtatc tggtttagtt | 1200 |
| acatcacgct cttttcgcac agcatcggtc tctattaacc aaactgaacc gccaaaagta | 1260 |
| agattagaag gcgttcgac aacatcactt tccgtaagtt ggtcaattcc accaccacaa | 1320 |
| caatcacgcg tttggaaata tgaagttaca tacgaaaaaa aaggagattc gaatagttat | 1380 |
| aatgttagac gtacagaagg attcagcgta accctagatg atttagctcc agatacaaca | 1440 |
| tatttagtac aggtgcaagc attaacacaa gaaggacaag gggcgggctc acgagttcat | 1500 |
| gaatttcaaa cattacatag aagaagaaag aatcaaagag cacgtcaatc accagaagat | 1560 |
| gtttattttt caagtctga acagttgaaa ccattgaaaa cctatgttga tccacacaca | 1620 |
| tacgaagacc caaaccaagc ggtccttaaa tttacaaccg aaattcatcc atcatgcgta | 1680 |
| actcgtcaaa agtgatcgg agctggagaa ttcggggagg tatacaaagg catgttgaaa | 1740 |
| acctcaagtg gtaaaaaga agttcctgta gcaattatga ctcttaaagc agggtataca | 1800 |
| gaaaaacaac gagttgattt tttaggcgaa gctggtatca tgggacaatt ttcgcatcat | 1860 |
| aatataatta gacttgaagg tgttatctct aaatataaac caatgatgat tattactgaa | 1920 |

```
tatatggaaa acggtgcttt agataaattt ctacgcgaaa aagatggtga attttctgtc  1980
cttcaattag ttggtatgtt acgtggcatc gctgcaggta tgaaatatct tgccaacatg  2040
aattatgtac atagagattt agcggctcga atattcttg taaattccaa tttagtgtgc   2100
aaagttagtg atttcggttt aagtcgagta ttagaagatg atccagaagc aacctatact  2160
acttcggggg gtaaaattcc gatccgttgg acagcaccgg aagcaatttc atatcgtaaa  2220
tttacatctg caagcgatgt ttggagtttc ggaattgtga tgtgggaagt aatgacatac  2280
ggcgaacgtc catattggga attgtcaaac catgaagtaa tgaaagcgat taacgatggt  2340
ttcagattac caaccccaat ggactgtcca tcagcaattt atcaactaat gatgcaatgc  2400
tggcaacaag aaagagctag aagacctaaa tttgcagaca ttgtttcaat tttagacaaa  2460
ctaattcgtg cgccagatag tcttaaaacc ctagctgatt cgatccacg cgtatcaatt   2520
cgtcttccat caacatcggg atctgaaggt gttccttta gaacagtaag cgagtggtta   2580
gaatcgatta aaatgcaaca gtatacagaa cattttatgg cagccggata cacagcaatt  2640
gaaaagttg tgcaaatgac aaatgatgat attaaacgta ttggagtgcg tctacctggc   2700
caccaaaaac gtattgctta ctccctttta ggtttaaaag accaagtaaa tacagtcgga  2760
attccaatat gagagctc                                                2778

<210> SEQ ID NO 40
<211> LENGTH: 1382
<212> TYPE: DNA
<213> ORGANISM: Artificial Sequence
<220> FEATURE:
<223> OTHER INFORMATION: Subfragment of codon-optimized sequence
      containing intergenic region

<400> SEQUENCE: 40
acgcgtttgg aaatatgaag ttacatacag aaaaaaagga gattcgaata gttataatgt    60
tagacgtaca gaaggattca gcgtaaccct agatgattta gctccagata caacatattt   120
agtacaggtg caagcattaa cacaagaagg acaaggggcg ggctcacgag ttcatgaatt   180
tcaaacatta taaaaacaca gaacgaaaga aaaagtgagg tgaatgatat ggcatatgat   240
agtcgttttg atgaatgggt tcaaaaatta aagaagaaa gttttcaaaa taatacattt    300
gatcgtcgta aatttattca aggtgcaggt aaaattgcag gtttaagttt aggtttaaca   360
attgcacaaa gtgttggtgc atttcataga agaagaaaga atcaaagagc acgtcaatca   420
ccagaagatg tttattttc aaagtctgaa cagttgaaac cattgaaaac ctatgttgat   480
ccacacacat acgaagaccc aaaccaagcg gtccttaaat ttacaaccga aattcatcca   540
tcatgcgtaa ctcgtcaaaa agtgatcgga gctggagaat tcggggaggt atacaaaggc   600
atgttgaaaa cctcaagtgg taaaaagaa gttcctgtag caattatgac tcttaaagca   660
gggtatacag aaaaacaacg agttgatttt ttaggcgaag ctggtatcat gggacaatttt  720
tcgcatcata atataattag acttgaaggt gttatctcta aatataaacc aatgatgatt   780
attactgaat atatggaaaa cggtgctta gataaatttc tacgcgaaaa agatggtgaa    840
ttttctgtcc ttcaattagt tggtatgtta cgtggcatcg ctgcaggtat gaaatatctt   900
gccaacatga attatgtaca tagagattta gcggctcgaa atattcttgt aaattccaat   960
ttagtgtgca aagttagtga tttcggttta agtcgagtat tagaagatga tccagaagca  1020
acctatacta cttcgggggg taaaattccg atccgttgga cagcaccgga agcaatttca  1080
tatcgtaaat ttacatctgc aagcgatgtt tggagtttcg gaattgtgat gtgggaagta  1140
```

```
atgacatacg gcgaacgtcc atattgggaa ttgtcaaacc atgaagtaat gaaagcgatt      1200
aacgatggtt tcagattacc aaccccaatg gactgtccat cagcaattta tcaactaatg      1260
atgcaatgct ggcaacaaga aagagctaga agacctaaat ttgcagacat tgtttcaatt      1320
ttagacaaac taattcgtgc gccagatagt cttaaaaccc tagctgattt cgatccacgc      1380
gt                                                                    1382

<210> SEQ ID NO 41
<211> LENGTH: 447
<212> TYPE: DNA
<213> ORGANISM: Artificial Sequence
<220> FEATURE:
<223> OTHER INFORMATION: Synthetic construct

<400> SEQUENCE: 41
ggtacctcct ttgattagta tattcctatc ttaaagttac ttttatgtgg aggcattaac        60
atttgttaat gacgtcaaaa ggatagcaag actagaataa agctataaag caagcatata       120
atattgcgtt tcatctttag aagcgaattt cgccaatatt ataattatca aaagagaggg       180
gtggcaaacg gtatttggca ttattaggtt aaaaaatgta aaggagagt gaaacccatg        240 aatatgaaaa aagctacgat tgcagctaca gccggcattg ccgtaacagc ttttgcagca       300
ccaactattg cctcagcctc tacagttgtt gtcgaagcag gagacacatt atggggaatc       360
gcacaatcaa aagtacaac ggttgatgct attaaaaaag cgaataattt aacaacagat        420
aaaatcgtgc aggtcaaaa actgcag                                           447

<210> SEQ ID NO 42
<211> LENGTH: 1683
<212> TYPE: DNA
<213> ORGANISM: Artificial Sequence
<220> FEATURE:
<223> OTHER INFORMATION: Plasmid subfragment

<400> SEQUENCE: 42
ggtacctcct ttgattagta tattcctatc ttaaagttac ttttatgtgg aggcattaac        60
atttgttaat gacgtcaaaa ggatagcaag actagaataa agctataaag caagcatata       120
atattgcgtt tcatctttag aagcgaattt cgccaatatt ataattatca aaagagaggg       180
gtggcaaacg gtatttggca ttattaggtt aaaaaatgta aaggagagt gaaacccatg        240 aatatgaaaa aagctacgat tgcagctaca gccggcattg ccgtaacagc ttttgcagca       300
ccaactattg cctcagcctc tacagttgtt gtcgaagcag gagacacatt atggggaatc       360
gcacaatcaa aagtacaac ggttgatgct attaaaaaag cgaataattt aacaacagat        420
aaaatcgtgc aggtcaaaa actgcaggta ataatgagg ttgctgctgc tgaaaaaaca         480
gagaaatctg ttagcgcaac ttggttaaac gtccgtactg gcgctggtgt tgataacagt       540
attattacgt ccatcaaagg tggaacaaaa gtaactgttg aaacaaccga atctaacggc       600
tggcacaaaa ttacttacaa cgatggaaaa actggtttcg ttaacggtaa atacttaact       660
gacaaagcag taagcactcc agttgcacca acacaagaag tgaaaaaaga aactactact       720
caacaagctg cacctgttgc agaaacaaaa actgaagtaa acaaactac acaagcaact        780 acacctgcgc ctaaagtagc agaaacgaaa gaaactccag taatagatca aaatgctact       840
acacacgctg tcaaaagcgg tgacactatt tgggctttat ccgtaaaata cggtgtttct       900
gttcaagaca ttatgtcatg gaataattta tcttcttctt ctatttatgt aggtcaaaag       960
```

```
cttgctatta aacaaactgc taacacagct actccaaaag cagaagtgaa aacggaagct    1020
ccagcagctg aaaacaagc agctccagta gttaaagaaa atactaacac aaatactgct    1080
actacagaga aaaagaaac agcaacgcaa caacaaacag cacctaaagc accaacagaa    1140
gctgcaaaac cagctcctgc accatctaca aacacaaatg ctaataaaac gaatacaaat    1200
acaaatacaa acaatactaa tacaccatct aaaaatacta atacaaactc aaatactaat    1260
acgaatacaa actcaaatac gaatgctaat caaggttctt ccaacaataa cagcaattca    1320
agtgcaagtg ctattattgc tgaagctcaa aaacaccttg aaaagctta ttcatggggt    1380 ggtaacggac caactacatt tgattgctct ggttacacta aatatgtatt tgctaaagcg    1440
ggtatctccc ttccacgtac atctggcgca caatatgcta gcactacaag aatttctgaa    1500
tctcaagcaa aacctggtga tttagtattc ttcgactatg gtagcggaat ttctcacatt    1560
ggtatttatg ttggtaatgg tcaaatgatt aacgcgcaag acaatggcgt taaatacgat    1620
aacatccacg gctctggctg gggtaaatat ctagttggct tcggtcgcgt ataataagga    1680
tcc                                                                 1683

<210> SEQ ID NO 43
<211> LENGTH: 3552
<212> TYPE: DNA
<213> ORGANISM: Artificial Sequence
<220> FEATURE:
<223> OTHER INFORMATION: Plasmid subfragment

<400> SEQUENCE: 43
ggtacctcct ttgattagta tattcctatc ttaaagttac ttttatgtgg aggcattaac      60
atttgttaat gacgtcaaaa ggatagcaag actagaataa agctataaag caagcatata     120
atattgcgtt tcatctttag aagcgaattt cgccaatatt ataattatca aaagagaggg     180
gtggcaaacg gtatttggca ttattaggtt aaaaaatgta gaaggagagt gaaacccatg     240
aatatgaaaa aagctacgat tgcagctaca gccggcattg ccgtaacagc ttttgcagca     300
ccaactattg cctcagcctc tacagttgtt gtcgaagcag gagacacatt atggggaatc     360
gcacaatcaa aaggtacaac ggttgatgct attaaaaaag cgaataattt aacaacagat     420
aaaatcgtgc caggtcaaaa actgcaggca ttgccaactg cacgtccatt actaggtagt     480
tgcggtacac cagcactagg ttctttatta tttttgttat tttctctagg ttgggttcaa     540
ccaagtcgta cattagcagg tgaaacaggt caagaagcag caccacttga cggtgtatta     600
acgaatccac caaatatatc aagtttaagt ccacgtcaat tattaggttt tccatgtgca     660
gaagtttcag gtttaagtac agaacgtgtc cgtgagttag cagttgcatt agcacaaaaa     720
aacgttaaat tatctacaga acagttacgt tgtttagccc atagattaag cgaaccacca     780
gaagacttag atgcacttcc tttagacctt cttttattct taaatccaga tgcattttca     840
ggaccacaag catgtacacg ttttttagt cgaattacaa aagccaatgt tgatttatta     900
cctcgtgggg ctcctgaaag acaacgttta ttacctgctg cattagcatg ctggggtgtt     960
cgcggtagct tattaagtga agccgatgtt cgtgctttag ggggtttagc atgtgattta    1020
cctggtcgtt tcgttgcaga atcagcagaa gtgttattac cgagattagt ttcatgccca    1080
ggacctttag atcaagatca acaagaggca gctagcagca ctcttcaagg aggagcccca    1140
ccatatggcc caccaagtac atggagtgtt tctacaatgg atgcgttaag aggtttatta    1200
ccggttttag acaaccaat tattcgtagt attccacaag gcattgtagc agcatggcgt    1260
caacgtagtt ctcgtgatcc gtcttggcga caaccagaac gtacaattct acgtccaaga    1320
```

```
tttcgtagag aagtagaaaa aacggcgtgt cctagtggca aaaaagcacg tgaaattgat    1380
gaaagtttaa ttttttataa aaaatgggaa ttagaagcat gtgtcgatgc agcattacta    1440
gctacacaaa tggatcgtgt taatgctatt ccattcacat atgaacaatt agatgtttta    1500
aagcataaat tagacgaatt atatccacaa ggttatccag aatcagttat tcaacattta    1560
ggttacttat ttttaaaaat gagtccagaa gacatacgca aatggaatgt tacaagttta    1620
gaaacattaa aagcgctttt agaagttaac aaaggtcatg aaatgagtcc acaagttgct    1680
acgttaattg atagattcgt taaaggccgt ggtcaattag ataaagatac tttagataca    1740
ttaacagcat tttatcctgg ctacttatgc agtttatcac cagaagaatt aagttccgtt    1800
ccaccgagta gtatctgggc agttcgtccg caagatttag atacatgcga cccacgtcaa    1860
ttagatgttt tatatccaaa agcaagatta gctttccaaa atatgaacgg tagtgaatat    1920
ttcgtaaaaa ttcaatcctt tttaggtggt gcaccaactg aagatctaaa agcattaagc    1980
caacaaaatg taagtatgga tttagctacg tttatgaaat tacgtacaga tgcagttcta    2040
ccattaacag ttgcagaagt tcaaaaatta ttaggtccac acgtagaagg attaaaagca    2100
gaagaacgtc accgtccagt tcgcgattgg attttacgtc aacgtcaaga tgatttagat    2160
acattaggtt taggtttaca aggcggtatt ccgaatggat atttagtgtt agatttatct    2220
gttcaagaag cattaagtgg tacaccgtgt ttattaggtc caggtccagt tttaacagtg    2280
ttagcattat tattagccag tacattagct ctgcaggtaa ataatgaggt tgctgctgct    2340
gaaaaaacag agaaatctgt tagcgcaact tggttaaacg tccgtactgg cgctggtgtt    2400
gataacagta ttattacgtc catcaaaggt ggaacaaaag taactgttga aacaaccgaa    2460
tctaacggct ggcacaaaat tacttacaac gatggaaaaa ctggtttcgt taacggtaaa    2520
tacttaactg acaaagcagt aagcactcca gttgcaccaa cacaagaagt gaaaaaagaa    2580
actactactc aacaagctgc acctgttgca gaaacaaaaa ctgaagtaaa acaaactaca    2640
caagcaacta cacctgcgcc taaagtagca gaaacgaaag aaactccagt aatagatcaa    2700
aatgctacta cacacgctgt caaaagcggt gacactattt gggctttatc cgtaaaaatac   2760
ggtgtttctg ttcaagacat tatgtcatgg aataatttat cttcttcttc tatttatgta    2820
ggtcaaaagc ttgctattaa acaaactgct aacacagcta ctccaaaagc agaagtgaaa    2880
acggaagctc cagcagctga aaaacaagca gctccagtag ttaaagaaaa tactaacaca    2940
aatactgcta ctacagagaa aaaagaaaca gcaacgcaac aacaaacagc acctaaagca    3000
ccaacagaag ctgcaaaacc agctcctgca ccatctacaa acacaaatgc taataaaacg    3060
aatacaaata caaatacaaa caatactaat acaccatcta aaaatactaa tacaaactca    3120
aatactaata cgaatacaaa ctcaaatacg aatgctaatc aaggttcttc caacaataac    3180
agcaattcaa gtgcaagtgc tattattgct gaagctcaaa acacccttgg aaaagcttat    3240
tcatggggtg gtaacggacc aactacattt gattgctctg gttacactaa atatgtattt    3300
gctaaagcgg gtatctccct tccacgtaca tctggcgcac aatatgctag cactacaaga    3360
atttctgaat ctcaagcaaa acctggtgat ttagtattct tcgactatgg tagcggaatt    3420
tctcacattg gtatttatgt tggtaatggt caaatgatta acgcgcaaga caatggcgtt    3480
aaatacgata acatccacgg ctctggctgg ggtaaatatc tagttggctt cggtcgcgta    3540
taataaggat cc                                                       3552
```

<210> SEQ ID NO 44

<211> LENGTH: 3327
<212> TYPE: DNA
<213> ORGANISM: Artificial Sequence
<220> FEATURE:
<223> OTHER INFORMATION: Plasmid subfragment

<400> SEQUENCE: 44

```
ggtacctcct tgattagta tattcctatc ttaaagttac tttttatgtgg aggcattaac       60 atttgttaat gacgtcaaaa ggatagcaag actagaataa agctataaag caagcatata      120
atattgcgtt tcatctttag aagcgaattt cgccaatatt ataattatca aaagagaggg      180
gtggcaaacg gtatttggca ttattaggtt aaaaaatgta aaggagagt gaaacccatg       240 aatatgaaaa aagctacgat tgcagctaca gccggcattg ccgtaacagc ttttgcagca      300
ccaactattg cctcagcctc tacagttgtt gtcgaagcag agacacatt atggggaatc       360 gcacaatcaa aaggtacaac ggttgatgct attaaaaaag cgaataattt aacaacagat      420
aaaatcgtgc caggtcaaaa actgcagcgt acattagcg gtgaaacagg tcaagaagca      480
gcaccacttg acggtgtatt aacgaatcca ccaaatatat caagtttaag tccacgtcaa      540
ttattaggtt ttccatgtgc agaagtttca ggtttaagta cagaacgtgt ccgtgagtta      600
gcagttgcat tagcacaaaa aaacgttaaa ttatctacag aacagttacg ttgtttagcc      660
catagattaa gcgaaccacc agaagactta gatgcacttc ctttagacct tcttttattc      720
ttaaatccag atgcattttc aggaccacaa gcatgtacac gtttttttag tcgaattaca      780
aaagccaatg ttgatttatt acctcgtggg gctcctgaaa gacaacgttt attacctgct      840
gcattagcat gctggggtgt tcgcggtagc ttattaagtg aagccgatgt tcgtgctta      900 gggggtttag catgtgattt acctggtcgt ttcgttgcag aatcagcaga agtgttatta      960
ccgagattag tttcatgccc aggaccttta gatcaagatc aacaagaggc agctagagca     1020
gctcttcaag gaggaggccc accatatggc ccaccaagta catggagtgt ttctacaatg     1080
gatgcgttaa gaggtttatt accggtttta ggacaaccaa ttattcgtag tattccacaa     1140
ggcattgtag cagcatggcg tcaacgtagt tctcgtgatc cgtcttggcg acaaccagaa     1200
cgtacaattc tacgtccaag atttcgtaga gaagtagaaa aaacggcgtg tcctagtggc     1260
aaaaaagcac gtgaaattga tgaaagttta attttttata aaaatgggaa attagaagca     1320
tgtgtcgatg cagcattact agctacacaa atggatcgtg ttaatgctat tccattcaca     1380
tatgaacaat tagatgtttt aaagcataaa ttagacgaat tatatccaca aggttatcca     1440
gaatcagtta tcaacattt aggttactta ttttaaaaa tgagtccaga agacatacgc      1500
aaatggaatg ttacaagttt agaaacatta aaagcgcttt tagaagttaa caaaggtcat     1560
gaaatgagtc cacaagttgc tacgttaatt gatagattcg ttaaaggccg tggtcaatta     1620
gataaagata ctttagatac attaacagca ttttatcctg gctacttatg cagtttatca     1680
ccagaagaat taagttccgt tccaccgagt agtatctggg cagttcgtcc gcaagattta     1740
gatacatgcg acccacgtca attagatgtt ttatatccaa aagcaagatt agctttccaa     1800
aatatgaacg gtagtgaata tttcgtaaaa attcaatcct ttttaggtgg tgcaccaact     1860
gaagatctaa aagcattaag ccaacaaaat gtaagtatgg atttagctac gtttatgaaa     1920
ttacgtacag atgcagttct accattaaca gttgcagaag ttcaaaaatt attaggtcca     1980
cacgtagaag gattaaaagc agaagaacgt caccgtccag ttcgcgattg gatttttacgt    2040 caacgtcaag atgatttaga tacattaggt ttaggtttac aaggcctgca ggtaaataat     2100
gaggttgctg ctgctgaaaa aacagagaaa tctgttagcg caacttggtt aaacgtccgt     2160
```

-continued

```
actggcgctg gtgttgataa cagtattatt acgtccatca aaggtggaac aaaagtaact    2220
gttgaaacaa ccgaatctaa cggctggcac aaaattactt acaacgatgg aaaaactggt    2280
ttcgttaacg gtaaatactt aactgacaaa gcagtaagca ctccagttgc accaacacaa    2340
gaagtgaaaa agaaactac tactcaacaa gctgcacctg ttgcagaaac aaaaactgaa     2400
gtaaaacaaa ctacacaagc aactacacct gcgcctaaag tagcagaaac gaaagaaact    2460
ccagtaatag atcaaaatgc tactacacac gctgtcaaaa gcggtgacac tatttgggct    2520
ttatccgtaa atacggtgt ttctgttcaa gacattatgt catggaataa tttatcttct     2580
tcttctattt atgtaggtca aaagcttgct attaaacaaa ctgctaacac agctactcca    2640
aaagcagaag tgaaaacgga agctccagca gctgaaaaac aagcagctcc agtagttaaa    2700
gaaaatacta acacaaatac tgctactaca gagaaaaaag aaacagcaac gcaacaacaa    2760
acagcaccta agcaccaac agaagctgca aaaccagctc ctgcaccatc tacaaacaca    2820
aatgctaata aaacgaatac aaatacaaat acaaacaata ctaatacacc atctaaaaat    2880
actaatacaa actcaaatac taatacgaat acaaactcaa atacgaatgc taatcaaggt    2940
tcttccaaca ataacagcaa ttcaagtgca agtgctatta ttgctgaagc tcaaaaacac    3000
cttggaaaag cttattcatg gggtggtaac ggaccaacta catttgattg ctctggttac    3060
actaaatatg tatttgctaa agcgggtatc tcccttccac gtacatctgg cgcacaatat    3120
gctagcacta caagaatttc tgaatctcaa gcaaaacctg gtgatttagt attcttcgac    3180
tatggtagcg gaatttctca cattggtatt tatgttggta atggtcaaat gattaacgcg    3240
caagacaatg gcgttaaata cgataacatc cacggctctg ctggggtaa atatctagtt     3300 ggcttcggtc gcgtataata aggatcc                                        3327
```

<210> SEQ ID NO 45
<211> LENGTH: 26
<212> TYPE: PRT
<213> ORGANISM: Listeria monocytogenes

<400> SEQUENCE: 45

Met Lys Lys Ile Met Leu Val Phe Ile Thr Leu Ile Leu Val Ser Leu
1               5                   10                  15

Pro Ile Ala Gln Gln Thr Glu Ala Lys Asp
            20                  25

<210> SEQ ID NO 46
<211> LENGTH: 29
<212> TYPE: PRT
<213> ORGANISM: Lactococcus lactis

<400> SEQUENCE: 46

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr
            20                  25

<210> SEQ ID NO 47
<211> LENGTH: 31
<212> TYPE: PRT
<213> ORGANISM: Bacillus anthracis

<400> SEQUENCE: 47

Met Lys Lys Arg Lys Val Leu Ile Pro Leu Met Ala Leu Ser Thr Ile
1               5                   10                  15

-continued

```
Leu Val Ser Ser Thr Gly Asn Leu Glu Val Ile Gln Ala Glu Val
            20                  25                  30

<210> SEQ ID NO 48
<211> LENGTH: 29
<212> TYPE: PRT
<213> ORGANISM: Listeria monocytogenes

<400> SEQUENCE: 48

Met Asn Met Lys Lys Ala Thr Ile Ala Ala Thr Ala Gly Ile Ala Val
1               5                   10                  15

Thr Ala Phe Ala Ala Pro Thr Ile Ala Ser Ala Ser Thr
            20                  25

<210> SEQ ID NO 49
<211> LENGTH: 54
<212> TYPE: PRT
<213> ORGANISM: Listeria monocytogenes

<400> SEQUENCE: 49

Met Gln Lys Thr Arg Lys Glu Arg Ile Leu Glu Ala Leu Gln Glu Glu
1               5                   10                  15

Lys Lys Asn Lys Lys Ser Lys Lys Phe Lys Thr Gly Ala Thr Ile Ala
            20                  25                  30

Gly Val Thr Ala Ile Ala Thr Ser Ile Thr Val Pro Gly Ile Glu Val
        35                  40                  45

Ile Val Ser Ala Asp Glu
    50

<210> SEQ ID NO 50
<211> LENGTH: 28
<212> TYPE: PRT
<213> ORGANISM: Bacillus anthracis

<400> SEQUENCE: 50

Met Lys Lys Leu Lys Met Ala Ser Cys Ala Leu Val Ala Gly Leu Met
1               5                   10                  15

Phe Ser Gly Leu Thr Pro Asn Ala Phe Ala Glu Asp
            20                  25

<210> SEQ ID NO 51
<211> LENGTH: 31
<212> TYPE: PRT
<213> ORGANISM: Staphylococcus aureus

<400> SEQUENCE: 51

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu
            20                  25                  30

<210> SEQ ID NO 52
<211> LENGTH: 59
<212> TYPE: PRT
<213> ORGANISM: Listeria monocytogenes

<400> SEQUENCE: 52

Met Thr Asp Lys Lys Ser Glu Asn Gln Thr Glu Lys Thr Glu Thr Lys
1               5                   10                  15

Glu Asn Lys Gly Met Thr Arg Arg Glu Met Leu Lys Leu Ser Ala Val
            20                  25                  30
```

```
Ala Gly Thr Gly Ile Ala Val Gly Ala Thr Gly Leu Gly Thr Ile Leu
        35                  40                  45

Asn Val Val Asp Gln Val Asp Lys Ala Leu Thr
 50                  55
```

<210> SEQ ID NO 53
<211> LENGTH: 53
<212> TYPE: PRT
<213> ORGANISM: Bacillus subtilis

<400> SEQUENCE: 53

```
Met Ala Tyr Asp Ser Arg Phe Asp Glu Trp Val Gln Lys Leu Lys Glu
 1               5                  10                  15

Glu Ser Phe Gln Asn Asn Thr Phe Asp Arg Arg Lys Phe Ile Gln Gly
            20                  25                  30

Ala Gly Lys Ile Ala Gly Leu Ser Leu Gly Leu Thr Ile Ala Gln Ser
        35                  40                  45

Val Gly Ala Phe Gly
 50
```

<210> SEQ ID NO 54
<211> LENGTH: 5
<212> TYPE: PRT
<213> ORGANISM: Listeria monocytogenes

<400> SEQUENCE: 54

```
Thr Glu Ala Lys Asp
 1               5
```

<210> SEQ ID NO 55
<211> LENGTH: 5
<212> TYPE: PRT
<213> ORGANISM: Lactococcus lactis

<400> SEQUENCE: 55

```
Val Tyr Ala Asp Thr
 1               5
```

<210> SEQ ID NO 56
<211> LENGTH: 5
<212> TYPE: PRT
<213> ORGANISM: Bacillus anthracis

<400> SEQUENCE: 56

```
Ile Gln Ala Glu Val
 1               5
```

<210> SEQ ID NO 57
<211> LENGTH: 5
<212> TYPE: PRT
<213> ORGANISM: Listeria monocytogenes

<400> SEQUENCE: 57

```
Ala Ser Ala Ser Thr
 1               5
```

<210> SEQ ID NO 58
<211> LENGTH: 5
<212> TYPE: PRT
<213> ORGANISM: Listeria monocytogenes

<400> SEQUENCE: 58

Val Ser Ala Asp Glu
1               5

<210> SEQ ID NO 59
<211> LENGTH: 5
<212> TYPE: PRT
<213> ORGANISM: Bacillus anthracis

<400> SEQUENCE: 59

Ala Phe Ala Glu Asp
1               5

<210> SEQ ID NO 60
<211> LENGTH: 5
<212> TYPE: PRT
<213> ORGANISM: Staphylococcus aureus

<400> SEQUENCE: 60

Val Gln Ala Ala Glu
1               5

<210> SEQ ID NO 61
<211> LENGTH: 5
<212> TYPE: PRT
<213> ORGANISM: Listeria monocytogenes

<400> SEQUENCE: 61

Asp Lys Ala Leu Thr
1               5

<210> SEQ ID NO 62
<211> LENGTH: 5
<212> TYPE: PRT
<213> ORGANISM: Bacillus subtilis

<400> SEQUENCE: 62

Val Gly Ala Phe Gly
1               5

<210> SEQ ID NO 63
<211> LENGTH: 9
<212> TYPE: PRT
<213> ORGANISM: Homo sapiens

<400> SEQUENCE: 63

Val Leu Gln Glu Leu Asn Val Thr Val
1               5

<210> SEQ ID NO 64
<211> LENGTH: 9
<212> TYPE: PRT
<213> ORGANISM: Homo sapiens

<400> SEQUENCE: 64

Ser Leu Leu Phe Leu Leu Phe Ser Leu
1               5

<210> SEQ ID NO 65
<211> LENGTH: 9
<212> TYPE: PRT
<213> ORGANISM: Homo sapiens

<400> SEQUENCE: 65

Val Leu Pro Leu Thr Val Ala Glu Val
1               5

```
<210> SEQ ID NO 66
<211> LENGTH: 9
<212> TYPE: PRT
<213> ORGANISM: Homo sapiens

<400> SEQUENCE: 66

Glu Leu Ala Val Ala Leu Ala Gln Lys
 1               5

<210> SEQ ID NO 67
<211> LENGTH: 9
<212> TYPE: PRT
<213> ORGANISM: Homo sapiens

<400> SEQUENCE: 67

Ala Leu Gln Gly Gly Gly Pro Pro Tyr
 1               5

<210> SEQ ID NO 68
<211> LENGTH: 9
<212> TYPE: PRT
<213> ORGANISM: Homo sapiens

<400> SEQUENCE: 68

Phe Tyr Pro Gly Tyr Leu Cys Ser Leu
 1               5

<210> SEQ ID NO 69
<211> LENGTH: 9
<212> TYPE: PRT
<213> ORGANISM: Homo sapiens

<400> SEQUENCE: 69

Leu Tyr Pro Lys Ala Arg Leu Ala Phe
 1               5

<210> SEQ ID NO 70
<211> LENGTH: 19
<212> TYPE: DNA
<213> ORGANISM: Listeria monocytogenes

<400> SEQUENCE: 70
aaggagagtg aaacccatg                                                  19

<210> SEQ ID NO 71
<211> LENGTH: 37
<212> TYPE: DNA
<213> ORGANISM: Listeria monocytogenes

<400> SEQUENCE: 71
taaaaacaca gaacgaaaga aaaagtgagg tgaatga                              37

<210> SEQ ID NO 72
<211> LENGTH: 9
<212> TYPE: PRT
<213> ORGANISM: Mus musculus

<400> SEQUENCE: 72

Ser Pro Ser Tyr Val Tyr His Gln Phe
 1               5

<210> SEQ ID NO 73
<211> LENGTH: 9
```

```
<212> TYPE: PRT
<213> ORGANISM: Artificial Sequence
<220> FEATURE:
<223> OTHER INFORMATION: Altered epitope

<400> SEQUENCE: 73

Ser Pro Ser Tyr Ala Tyr His Gln Phe
 1               5

<210> SEQ ID NO 74
<211> LENGTH: 29
<212> TYPE: DNA
<213> ORGANISM: Artificial Sequence
<220> FEATURE:
<223> OTHER INFORMATION: PCR primer

<400> SEQUENCE: 74
ctctggtacc tcctttgatt agtatattc                                       29

<210> SEQ ID NO 75
<211> LENGTH: 36
<212> TYPE: DNA
<213> ORGANISM: Artificial Sequence
<220> FEATURE:
<223> OTHER INFORMATION: PCR primer

<400> SEQUENCE: 75
caatggatcc ctcgagatca taatttactt catccc                               36

<210> SEQ ID NO 76
<211> LENGTH: 32
<212> TYPE: DNA
<213> ORGANISM: Artificial Sequence
<220> FEATURE:
<223> OTHER INFORMATION: PCR primer

<400> SEQUENCE: 76
atttctcgag tccatggggg gttctcatca tc                                   32

<210> SEQ ID NO 77
<211> LENGTH: 25
<212> TYPE: DNA
<213> ORGANISM: Artificial Sequence
<220> FEATURE:
<223> OTHER INFORMATION: PCR primer

<400> SEQUENCE: 77
ggtgctcgag tgcggccgca agctt                                           25

<210> SEQ ID NO 78
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 78
cgattcccct agttatgttt accaccaatt tgctgca                              37

<210> SEQ ID NO 79
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 79
```

```
gcaaattggt ggtaaacata actaggggaa t                              31
```

<210> SE

<210> SEQ ID NO 86
<211> LENGTH: 87
<212> TYPE: DNA
<213> ORGANISM: Lactococcus lactis

<400> SEQUENCE: 86
atgaaaaaaa agattatctc agctatttta atgtctacag tgatactttc tgctgcagcc    60
ccgttgtcag gtgtttacgc tgacaca    87

<210> SEQ ID NO 87
<211> LENGTH: 87
<212> TYPE: DNA
<213> ORGANISM: Artificial Sequence
<220> FEATURE:
<223> OTHER INFORMATION: Codon-optimized sequence

<400> SEQUENCE: 87
atgaaaaaaa aaattattag tgcaattta atgagtacag ttattttaag tgcagcagca    60
ccattaagtg gtgtttatgc agataca    87

<210> SEQ ID NO 88
<211> LENGTH: 36
<212> TYPE: DNA
<213> ORGANISM: Artificial Sequence
<220> FEATURE:
<223> OTHER INFORMATION: PCR primer

<400> SEQUENCE: 88
aaggagagtg aaacccatga atatgaaaaa agcaac    36

<210> SEQ ID NO 89
<211> LENGTH: 24
<212> TYPE: DNA
<213> ORGANISM: Artificial Sequence
<220> FEATURE:
<223> OTHER INFORMATION: PCR primer

<400> SEQUENCE: 89
gtgtgatgga tatctgcaga attc    24

<210> SEQ ID NO 90
<211> LENGTH: 87
<212> TYPE: DNA
<213> ORGANISM: Listeria monocytogenes

<400> SEQUENCE: 90
atgaatatga aaaagcaac tatcgcggct acagctggga ttgcggtaac agcatttgct    60
gcgccaacaa tcgcatccgc aagcact    87

<210> SEQ ID NO 91
<211> LENGTH: 87
<212> TYPE: DNA
<213> ORGANISM: Artificial Sequence
<220> FEATURE:
<223> OTHER INFORMATION: Codon-optimized sequence

<400> SEQUENCE: 91
atgaatatga aaaagcaac aattgcagca acagcaggta ttgcagttac agcatttgca    60
gcaccaacaa ttgcaagtgc aagtaca    87

<210> SEQ ID NO 92
<211> LENGTH: 23

```
<212> TYPE: DNA
<213> ORGANISM: Artificial Sequence
<220> FEATURE:
<223> OTHER INFORMATION: PCR primer

<400> SEQUENCE: 92
gacgtcaata cgactcacta tag                                             23

<210> SEQ ID NO 93
<211> LENGTH: 36
<212> TYPE: DNA
<213> ORGANISM: Artificial Sequence
<220> FEATURE:
<223> OTHER INFORMATION: PCR primer

<400> SEQUENCE: 93
cttttttcat attcatgggt ttcactctcc ttctac                               36

<210> SEQ ID NO 94
<211> LENGTH: 21
<212> TYPE: DNA
<213> ORGANISM: Artificial Sequence
<220> FEATURE:
<223> OTHER INFORMATION: PCR primer

<400> SEQUENCE: 94
gtcaaaacat acgctcttat c                                               21

<210> SEQ ID NO 95
<211> LENGTH: 24
<212> TYPE: DNA
<213> ORGANISM: Artificial Sequence
<220> FEATURE:
<223> OTHER INFORMATION: PCR primer

<400> SEQUENCE: 95
acataatcag tccaaagtag atgc                                            24

<210> SEQ ID NO 96
<211> LENGTH: 24
<212> TYPE: DNA
<213> ORGANISM: Artificial Sequence
<220> FEATURE:
<223> OTHER INFORMATION: Codon-optimized sequence

<400> SEQUENCE: 96
gattataaag atgatgatga taaa                                            24

<210> SEQ ID NO 97
<211> LENGTH: 8
<212> TYPE: PRT
<213> ORGANISM: Artificial Sequence
<220> FEATURE:
<223> OTHER INFORMATION: Synthetic epitope tag

<400> SEQUENCE: 97

Asp Tyr Lys Asp Asp Asp Asp Lys
 1               5

<210> SEQ ID NO 98
<211> LENGTH: 30
<212> TYPE: DNA
<213> ORGANISM: Artificial Sequence
<220> FEATURE:
<223> OTHER INFORMATION: Codon-optimized sequence

<400> SEQUENCE: 98
```
gaacaaaaat taattagtga agaagattta                                                30

<210> SEQ ID NO 99
<211> LENGTH: 10
<212> TYPE: PRT
<213> ORGANISM: Homo sapiens

<400> SEQUENCE: 99

Glu Gln Lys Leu Ile Ser Glu Glu Asp Leu
 1               5                  10

<210> SEQ ID NO 100
<211> LENGTH: 12
<212> TYPE: PRT
<213> ORGANISM: Listeria monocytogenes

<400> SEQUENCE: 100

Asn Glu Lys Tyr Ala Gln Ala Tyr Pro Asn Val Ser
 1               5                  10

<210> SEQ ID NO 101
<211> LENGTH: 9
<212> TYPE: PRT
<213> ORGANISM: Listeria monocytogenes

<400> SEQUENCE: 101

Val Ala Tyr Gly Arg Gln Val Tyr Leu
 1               5

<210> SEQ ID NO 102
<211> LENGTH: 9
<212> TYPE: PRT
<213> ORGANISM: Listeria monocytogenes

<400> SEQUENCE: 102

Gly Tyr Lys Asp Gly Asn Glu Tyr Ile
 1               5

<210> SEQ ID NO 103
<211> LENGTH: 25
<212> TYPE: DNA
<213> ORGANISM: Artificial Sequence
<220> FEATURE:
<223> OTHER INFORMATION: PCR primer

<400> SEQUENCE: 103
gttaagtttc atgtggacgg caaag                                                     25

<210> SEQ ID NO 104
<211> LENGTH: 42
<212> TYPE: DNA
<213> ORGANISM: Artificial Sequence
<220> FEATURE:
<223> OTHER INFORMATION: PCR primer

<400> SEQUENCE: 104 aggtctttttt cagttaacta tcctctcctt gattctagtt at                                 42

<210> SEQ ID NO 105
<211> LENGTH: 43
<212> TYPE: DNA
<213> ORGANISM: Artificial Sequence
<220> FEATURE:
<223> OTHER INFORMATION: PCR primer

```
<400> SEQUENCE: 105
caaggagagg atagttaact gaaaaagacc taaaaaagaa ggc                    43

<210> SEQ ID NO 106
<211> LENGTH: 26
<212> TYPE: DNA
<213> ORGANISM: Artificial Sequence
<220> FEATURE:
<223> OTHER INFORMATION: PCR primer

<400> SEQUENCE: 106
tcccctgttc ctataattgt tagctc                                      26

<210> SEQ ID NO 107
<211> LENGTH: 25
<212> TYPE: DNA
<213> ORGANISM: Artificial Sequence
<220> FEATURE:
<223> OTHER INFORMATION: PCR primer

<400> SEQUENCE: 107
gtggacggca agaaacaac caaag                                        25

<210> SEQ ID NO 108
<211> LENGTH: 29
<212> TYPE: DNA
<213> ORGANISM: Artificial Sequence
<220> FEATURE:
<223> OTHER INFORMATION: PCR primer

<400> SEQUENCE: 108
gttcctataa ttgttagctc attttttttc                                  29

<210> SEQ ID NO 109
<211> LENGTH: 59
<212> TYPE: PRT
<213> ORGANISM: Listeria monocytogenes

<400> SEQUENCE: 109

Met Lys Lys Ile Met Leu Val Phe Ile Thr Leu Ile Leu Val Ser Leu
  1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Pro Ala Ser Pro Pro Ala Ser
         35                  40                  45

Pro Lys Thr Pro Ile Glu Lys Lys His Ala Asp
     50                  55

<210> SEQ ID NO 110
<211> LENGTH: 177
<212> TYPE: DNA
<213> ORGANISM: Listeria monocytogenes

<400> SEQUENCE: 110
atgaaaaaaa taatgctagt ttttattaca cttatattag ttagtctacc aattgcgcaa   60
caaactgaag caaaggatgc atctgcattc aataaagaaa attcaatttc atccatggca   120
ccaccagcat ctccgcctgc aagtcctaag acgccaatcg aaaagaaaca cgcggat      177

<210> SEQ ID NO 111
<211> LENGTH: 93
<212> TYPE: DNA
<213> ORGANISM: Bacillus anthracis
```

<400> SEQUENCE: 111
atgaaaaaac gaaaagtgtt aataccatta atggcattgt ctacgatatt agtttcaagc     60
acaggtaatt tagaggtgat tcaggcagaa gtt                                  93

<210> SEQ ID NO 112
<211> LENGTH: 156
<212> TYPE: DNA
<213> ORGANISM: Bacillus subtilis

<400> SEQUENCE: 112
atggcatacg acagtcgttt tgatgaatgg gtacagaaac tgaaagagga aagctttcaa     60
aacaatacgt tgaccgccg caaatttatt caaggagcgg ggaagattgc aggactttct    120
cttggattaa cgattgccca gtcggttggg gccttt                             156

<210> SEQ ID NO 113
<211> LENGTH: 177
<212> TYPE: DNA
<213> ORGANISM: Artificial Sequence
<220> FEATURE:
<223> OTHER INFORMATION: Codon-optimized sequence

<400> SEQUENCE: 113
atgaaaaaaa ttatgttagt ttttattaca ttaattttag ttagtttacc aattgcacaa     60
caaacagaag caaaagatgc aagtgcattt aataagaaa atagtattag tagtatggca    120
ccaccagcaa gtccaccagc aagtccaaaa acaccaattg aaaaaaaaca tgcagat      177

<210> SEQ ID NO 114
<211> LENGTH: 93
<212> TYPE: DNA
<213> ORGANISM: Artificial Sequence
<220> FEATURE:
<223> OTHER INFORMATION: Codon-optimized sequence

<400> SEQUENCE: 114
atgaaaaaac gtaaagtttt aattccatta atggcattaa gtacaatttt agttagtagt     60
acaggtaatt tagaagttat tcaagcagaa gtt                                  93

<210> SEQ ID NO 115
<211> LENGTH: 156
<212> TYPE: DNA
<213> ORGANISM: Artificial Sequence
<220> FEATURE:
<223> OTHER INFORMATION: Codon-optimized sequence

<400> SEQUENCE: 115
atggcatatg atagtcgttt tgatgaatgg gttcaaaaat taaagaaga aagttttcaa     60 aataatacat tgatcgtcg taaatttatt caaggtgcag gtaaaattgc aggtttaagt    120
ttaggtttaa caattgcaca aagtgttggt gcattt                             156

<210> SEQ ID NO 116
<211> LENGTH: 70
<212> TYPE: PRT
<213> ORGANISM: Listeria monocytogenes

<400> SEQUENCE: 116

Met Asn Met Lys Lys Ala Thr Ile Ala Ala Thr Ala Gly Ile Ala Val
1               5                   10                  15

Thr Ala Phe Ala Ala Pro Thr Ile Ala Ser Ala Ser Thr Val Val Val

```
            20                  25                  30
Glu Ala Gly Asp Thr Leu Trp Gly Ile Ala Gln Ser Lys Gly Thr Thr
         35                  40                  45

Val Asp Ala Ile Lys Lys Ala Asn Asn Leu Thr Thr Asp Lys Ile Val
     50                  55                  60

Pro Gly Gln Lys Leu Gln
65                  70

<210> SEQ ID NO 117
<211> LENGTH: 28
<212> TYPE: DNA
<213> ORGANISM: Artificial Sequence
<220> FEATURE:
<223> OTHER INFORMATION: PCR primer

<400> SEQUENCE: 117
cgcctgcagg taaataatga ggttgctg                                      28

<210> SEQ ID NO 118
<211> LENGTH: 29
<212> TYPE: DNA
<213> ORGANISM: Artificial Sequence
<220> FEATURE:
<223> OTHER INFORMATION: PCR primer

<400> SEQUENCE: 118
cgcggatcct taattatacg cgaccgaag                                     29

<210> SEQ ID NO 119
<211> LENGTH: 29
<212> TYPE: DNA
<213> ORGANISM: Artificial Sequence
<220> FEATURE:
<223> OTHER INFORMATION: PCR primer

<400> SEQUENCE: 119
aaactgcagg cattgccaac tgcacgtcc                                     29

<210> SEQ ID NO 120
<211> LENGTH: 40
<212> TYPE: DNA
<213> ORGANISM: Artificial Sequence
<220> FEATURE:
<223> OTHER INFORMATION: PCR primer

<400> SEQUENCE: 120
aaactgcaga gctaatgtac tggctaataa taatgctaac                         40

<210> SEQ ID NO 121
<211> LENGTH: 32
<212> TYPE: DNA
<213> ORGANISM: Artificial Sequence
<220> FEATURE:
<223> OTHER INFORMATION: PCR primer

<400> SEQUENCE: 121
cgcctgcagc gtacattagc aggtgaaaca gg                                 32

<210> SEQ ID NO 122
<211> LENGTH: 36
<212> TYPE: DNA
<213> ORGANISM: Artificial Sequence
<220> FEATURE:
<223> OTHER INFORMATION: PCR primer
```

-continued

```
<400> SEQUENCE: 122
cgcctgcagg ccttgtaaac ctaaacctaa tgtatc                              36

<210> SEQ ID NO 123
<211> LENGTH: 8
<212> TYPE: PRT
<213> ORGANISM: Gallus gallus

<400> SEQUENCE: 123

Ser Ile Ile Asn Phe Glu Lys Leu
 1               5

<210> SEQ ID NO 124
<211> LENGTH: 8
<212> TYPE: PRT
<213> ORGANISM: Herpes simplex virus

<400> SEQUENCE: 124

Ser Ser Ile Glu Phe Ala Arg Leu
 1               5

<210> SEQ ID NO 125
<211> LENGTH: 17
<212> TYPE: RNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: 1, 9, 10, 11, 12, 13, 14
<223> OTHER INFORMATION: n = A,U,C or G

<400> SEQUENCE: 125
naggaggunn nnnnaug                                                  17

<210> SEQ ID NO 126
<211> LENGTH: 18
<212> TYPE: RNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: 1, 9, 10, 11, 12, 13, 14, 15
<223> OTHER INFORMATION: n = A,U,C or G

<400> SEQUENCE: 126
naggaggunn nnnnnaug                                                 18

<210> SEQ ID NO 127
<211> LENGTH: 19
<212> TYPE: RNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: 1, 9, 10, 11, 12, 13, 14, 15, 16
<223> OTHER INFORMATION: n = A,U,C or G

<400> SEQUENCE: 127
naggaggunn nnnnnnaug                                                19

<210> SEQ ID NO 128
<211> LENGTH: 20
<212> TYPE: RNA
<213> ORGANISM: Artificial Sequence
```

```
-continued

<220> FEATURE:
<223> OTHER INFORMATION: Consensus sequence
<220> FEATURE:
<221> NAME/KEY: misc_feature
<222> LOCATION: 1, 9, 10, 11, 12, 13, 14, 15, 16, 17
<223> OTHER INFORMATION: n = A,U,C or G

<400> SEQUENCE: 128
naggaggunn nnnnnnnaug                                              20

<210> SEQ ID NO 129
<211> LENGTH: 21
<212> TYPE: RNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: 1, 9, 10, 11, 12, 13, 14, 15, 16, 17, 18
<223> OTHER INFORMATION: n = A,U,C or G

<400> SEQUENCE: 129
naggaggunn nnnnnnnnau g                                            21
```